(12) United States Patent
Bates et al.

(10) Patent No.: US 11,020,398 B2
(45) Date of Patent: Jun. 1, 2021

(54) AMINO-PYRROLOPYRIMIDINONE COMPOUNDS AND METHODS OF USE THEREOF

(71) Applicant: ArQule, Inc., Burlington, MA (US)

(72) Inventors: Craig Bates, Pelham, NH (US); Sudharshan Eathiraj, Shrewsbury, MA (US); Hiroaki Inagaki, Tokyo (JP); Jean-Marc Lapierre, Pelham, NH (US); Takayuki Momose, Tokyo (JP); Kiyoshi Nakayama, Tokyo (JP); Takashi Odagiri, Tokyo (JP); Masahiro Ota, Tokyo (JP); Yusuke Ota, Tokyo (JP); Yoshihiro Shibata, Tokyo (JP); Manish Tandon, Framingham, MA (US); Tomoyuki Tsunemi, Tokyo (JP)

(73) Assignee: ArQule, Inc., Burlington, MA (US)

( * ) Notice: Subject to any disclaimer, the term of this patent is extended or adjusted under 35 U.S.C. 154(b) by 0 days.

(21) Appl. No.: 15/683,913

(22) Filed: Aug. 23, 2017

(65) Prior Publication Data
US 2018/0055846 A1    Mar. 1, 2018

Related U.S. Application Data

(60) Provisional application No. 62/378,868, filed on Aug. 24, 2016, provisional application No. 62/378,871, filed on Aug. 24, 2016, provisional application No. 62/378,872, filed on Aug. 24, 2016.

(51) Int. Cl.

| | | |
|---|---|---|
| C07D 487/04 | (2006.01) |
| A61K 31/519 | (2006.01) |
| A61K 31/4188 | (2006.01) |
| C12N 9/12 | (2006.01) |
| A61K 31/03 | (2006.01) |
| A61K 31/341 | (2006.01) |
| A61P 9/00 | (2006.01) |
| A61P 7/04 | (2006.01) |
| A61P 43/00 | (2006.01) |
| A61P 37/08 | (2006.01) |
| A61P 37/00 | (2006.01) |
| A61P 37/06 | (2006.01) |
| A61P 35/02 | (2006.01) |
| A61P 35/00 | (2006.01) |
| A61P 29/00 | (2006.01) |
| A61P 25/00 | (2006.01) |
| A61P 19/02 | (2006.01) |
| A61P 17/00 | (2006.01) |
| A61P 11/06 | (2006.01) |
| A61P 1/04 | (2006.01) |

(52) U.S. Cl.
CPC ........ A61K 31/519 (2013.01); A61K 31/4188 (2013.01); C07D 487/04 (2013.01); C12N 9/12 (2013.01); A61K 31/03 (2013.01); A61K 31/341 (2013.01)

(58) Field of Classification Search
CPC ............................ C07D 487/04; A61K 31/519
See application file for complete search history.

(56) References Cited

U.S. PATENT DOCUMENTS

| | | |
|---|---|---|
| 7,504,509 B2 | 3/2009 | Ibrahim et al. |
| 8,067,434 B2 | 11/2011 | Ibrahim et al. |
| 8,377,946 B1 | 2/2013 | Chen et al. |
| 8,673,928 B2 | 3/2014 | Ibrahim et al. |
| 8,940,893 B2 | 1/2015 | Bosanac et al. |
| 9,630,968 B1 | 4/2017 | Lapierre et al. |
| 10,245,263 B2 | 4/2019 | Lapierre et al. |
| 2005/0113395 A1 | 5/2005 | Changelian |
| 2007/0004675 A1 | 1/2007 | Saavedra et al. |
| 2007/0066641 A1 | 3/2007 | Ibrahim et al. |
| 2007/0135461 A1 | 6/2007 | Rodgers et al. |
| 2007/0275984 A1 | 11/2007 | Imogai et al. |
| 2008/0161254 A1 | 7/2008 | Green et al. |

(Continued)

FOREIGN PATENT DOCUMENTS

| | | |
|---|---|---|
| CN | 103664996 | 3/2014 |
| JP | 2003/321472 | 11/2003 |

(Continued)

OTHER PUBLICATIONS

Stella (J. Pharmaceutical Sciences, 2010, 99(12), pp. 4755-4765).*
Anastassiadis T, et al., "Comprehensive assay of kinase catalytic activity reveals features of kinase inhibitor selectivity ", Nat. Biotechnol. 29(11):1039-45 (2011).

(Continued)

*Primary Examiner* — Susanna Moore
(74) *Attorney, Agent, or Firm* — Cooley LLP; Matthew Pavao; Chen Chen

(57) ABSTRACT

The application relates to a compound of Formula (I):

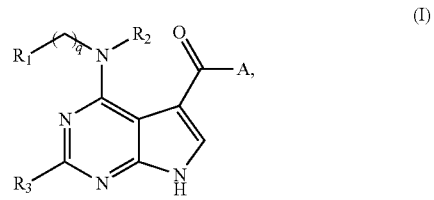

or a pharmaceutically acceptable salt, hydrate, solvate, prodrug, stereoisomer, or tautomer thereof, which modulates the activity of BTK, a pharmaceutical composition comprising a compound of Formula (I), and a method of treating or preventing a disease in which BTK plays a role.

38 Claims, No Drawings

(56) References Cited

U.S. PATENT DOCUMENTS

| | | |
|---|---|---|
| 2009/0181959 A1 | 7/2009 | Rodgers et al. |
| 2009/0286782 A1 | 11/2009 | Ibrahim et al. |
| 2009/0286783 A1 | 11/2009 | Ibrahim et al. |
| 2010/0063047 A1 | 3/2010 | Borchardt et al. |
| 2011/0152258 A1 | 6/2011 | Ibrahim et al. |
| 2011/0160203 A1 | 6/2011 | Liu et al. |
| 2011/0166137 A1 | 7/2011 | Ashwell et al. |
| 2011/0263595 A1 | 10/2011 | Zhang et al. |
| 2013/0096136 A1 | 4/2013 | Hata et al. |
| 2014/0128390 A1 | 5/2014 | Lin et al. |
| 2014/0357612 A1 | 12/2014 | Zhang et al. |
| 2015/0158864 A1 | 6/2015 | Thorarensen et al. |
| 2015/0239891 A1 | 8/2015 | Klar et al. |
| 2015/0252047 A1 | 9/2015 | Klar et al. |
| 2015/0291593 A1 | 10/2015 | Su et al. |
| 2017/0182053 A1 | 6/2017 | Lapierre et al. |
| 2018/0055846 A1 | 3/2018 | Bates et al. |
| 2019/0192520 A1 | 6/2019 | Lapierre et al. |

FOREIGN PATENT DOCUMENTS

| | | |
|---|---|---|
| WO | WO 1993/020078 | 10/1993 |
| WO | WO 1998/007726 | 2/1998 |
| WO | WO 2002/050306 A1 | 6/2002 |
| WO | WO 2002/051849 A1 | 7/2002 |
| WO | WO 2004/007479 A1 | 1/2004 |
| WO | WO 2005/080377 A1 | 9/2005 |
| WO | WO 2005/117909 A2 | 12/2005 |
| WO | WO 2006/030031 A1 | 3/2006 |
| WO | WO 2006/032631 A1 | 3/2006 |
| WO | WO 2006/042102 A2 | 4/2006 |
| WO | WO 2006/069080 A2 | 6/2006 |
| WO | WO 2007/013896 A2 | 2/2007 |
| WO | WO 2007/107545 A1 | 9/2007 |
| WO | WO 2007/125405 A2 | 11/2007 |
| WO | WO 2007/126841 A2 | 11/2007 |
| WO | WO 2008/006547 A2 | 1/2008 |
| WO | WO 2008/070908 A1 | 6/2008 |
| WO | WO 2008/075007 A1 | 6/2008 |
| WO | WO 2008/132155 A2 | 11/2008 |
| WO | WO 2008/135232 A1 | 11/2008 |
| WO | WO 2009/062118 A2 | 5/2009 |
| WO | WO 2009/134658 A2 | 11/2009 |
| WO | WO 2010/002954 A1 | 1/2010 |
| WO | WO 2010/039939 A1 | 4/2010 |
| WO | WO 2010/080996 A1 | 7/2010 |
| WO | WO 2011/044157 A1 | 4/2011 |
| WO | WO 2011/063159 A1 | 5/2011 |
| WO | WO 2011/082268 A2 | 7/2011 |
| WO | WO 2011/130628 A1 | 10/2011 |
| WO | WO 2011/133637 A2 | 10/2011 |
| WO | WO 2011/146882 A1 | 11/2011 |
| WO | WO 2011/149827 A1 | 12/2011 |
| WO | WO 2011/153553 A2 | 12/2011 |
| WO | WO 2012/027495 A1 | 3/2012 |
| WO | WO 2012/048058 A2 | 4/2012 |
| WO | WO 2012/109075 A1 | 8/2012 |
| WO | WO 2013/082275 A1 | 6/2013 |
| WO | WO 2013/082476 A1 | 6/2013 |
| WO | WO 2013/173506 A2 | 11/2013 |
| WO | WO 2013/182612 A1 | 12/2013 |
| WO | WO 2014/011911 A2 | 1/2014 |
| WO | WO 2014/015523 A1 | 1/2014 |
| WO | WO 2014/015675 A1 | 1/2014 |
| WO | WO 2014/015830 A1 | 1/2014 |
| WO | WO 2014/019908 A2 | 2/2014 |
| WO | WO 2014/039714 A2 | 3/2014 |
| WO | WO 2014/044691 A1 | 3/2014 |
| WO | WO 2014/047648 A1 | 3/2014 |
| WO | WO 2014/048869 A1 | 4/2014 |
| WO | WO 2014/048894 A1 | 4/2014 |
| WO | WO 2014/060432 A1 | 4/2014 |
| WO | WO 2014/144455 A1 | 9/2014 |
| WO | WO 2014/188173 A1 | 11/2014 |
| WO | WO 2014/194127 A1 | 12/2014 |
| WO | WO 2015/004024 A1 | 1/2015 |
| WO | WO 2015/083028 A1 | 6/2015 |
| WO | WO 2015/189620 A1 | 12/2015 |
| WO | WO 2016/004305 A2 | 1/2016 |
| WO | WO 2016/044650 A1 | 3/2016 |
| WO | WO 2016/063080 A1 | 4/2016 |
| WO | WO 2017/111787 A1 | 6/2017 |

OTHER PUBLICATIONS

DiPaolo et al., "Specific Btk inhibition suppresses B cell- and myeloid cell-mediated arthritis", *Nature Chemical Biology* 2011, vol. 7, No. 1, p. 41-50.

Liu et al. "Antiarthritis Effect of a Novel Bruton's Tyrosine Kinase (BTK) Inhibitor in Rat Collagen-Induced Arthritis and Mechanism-Based Pharmacokinetic/Pharmacodynamic Modeling: Relationships between Inhibition of BTK Phosphorylation and Efficacy", *The Journal of Pharmacology and Experimental Therapeutics*, 2011, vol. 338, No. 1, p. 154-163.

Dorwald, F.Z. *Side Reactions in Organic Synthesis. A Guide to Successful Synthesis Design.* Weinheim:Wiley-VCH, 2005, Preface, 4 pages.

Hunter, T. (Sep. 11, 1987) "A Thousand and One Protein Kinases" *Cell*, 50:823-829.

Johnson, J. et al.(2001) "Relationships between drug activity in NCI preclinical in vitro and in vivo models and early clinical trials" *British Journal of Cancer*, 84(10):1424-1431.

Kriek, N. et al. (2003) "Synthesis of Novel Tetrahydropyran-Based Dipeptide Isosters by Overman Rearrangement of 2,3-Didehydroglycosides" *Eur. J. Org. Chem.* 2003:2418-2427.

Sausville, E.A. (2006) "Contributions of human tumor xenografts to anticancer drug development" *Cancer Res*, 66(7):3351-3354.

Stella. "Prodrugs: Some thoughts and current issues," *J Pharm Sci*, 2010, 99(12): p. 4755-4765.

\* cited by examiner

AMINO-PYRROLOPYRIMIDINONE COMPOUNDS AND METHODS OF USE THEREOF

CROSS-REFERENCE TO RELATED APPLICATIONS

This application claims priority to, and the benefit of, U.S. Ser. Nos. 62/378,868, 62/378,871, and 62/378,872, each filed on Aug. 24, 2016, the contents of each of which are incorporated herein by reference in their entirety.

FIELD OF THE APPLICATION

The present application is directed to inhibitors of Bruton's Tyrosine Kinase (BTK), including mutant BTK, useful in the treatment of diseases or disorders associated with BTK kinase, including immune disorders, cancer, cardiovascular diseases, viral infections, inflammation, metabolism/endocrine function disorders, and neurological disorders. Specifically, the application is concerned with compounds and compositions thereof, which inhibit BTK, methods of treating diseases or disorders associated with BTK and methods of synthesis of these compounds.

BACKGROUND

BTK is a member of the Tec family of tyrosine kinases and plays an important role in the regulation of early B-cell development and mature B-cell activation and survival (Hunter, Cell, 1987 50, 823-829). Functioning downstream of multiple receptors, such as growth factors, B-cell antigen, chemokine, and innate immune receptors, BTK initiates a number of cellular processes including cell proliferation, survival, differentiation, motility, angiogenesis, cytokine production, and antigen presentation.

BTK-deficient mouse models have shown the role BTK plays in allergic disorders and/or autoimmune disease and/or inflammatory disease. For instance, BTK deficiency in standard murine preclinical models of systemic lupus erythematosus (SLE) has been shown to result in a marked amelioration of disease progression. Furthermore, BTK-deficient mice can be resistant to developing collagen-induced arthritis and less susceptible to *Staphylococcus*-induced arthritis. Due to BTK's role in B-cell activation, BTK inhibitors can also be useful as inhibitors of B-cell mediated pathogenic activity (such as autoantibody production). Expression of BTK in osteoclasts, mast cells and monocytes has been shown to be important for the function of these cells. For example, impaired IgE-mediated mast cell activation and reduced TNF-alpha production by activated monocytes has been associated with BTK deficiency in mice and humans. Thus, BTK inhibition can be useful for the treatment of allergic disorders and/or autoimmune and/or inflammatory diseases such as: SLE, rheumatoid arthritis, multiple vasculitides, idiopathic thrombocytopenic purpura (ITP), myasthenia gravis, allergic rhinitis, and asthma (DiPaolo et al., *Nature Chem. Biol.* 2011, 7(1):41-50; Liu et al., *Jour. Pharmacol. and Exp. Ther.* 2011, 338(1):154-163).

Moreover, BTK's role in apoptosis demonstrates the utility of inhibition of BTK activity for the treatment of cancers, B-cell lymphoma, leukemia, and other hematological malignancies. In addition, given the role of BTK in osteoclast function, inhibition of BTK activity can be useful for the treatment of bone disorders such as osteoporosis.

Inhibition of BTK with small molecule inhibitors therefore has the potential to be a treatment for immune disorders, cancer, cardiovascular diseases, viral infections, inflammation, metabolism/endocrine function disorders, and neurological disorders. Thus, there remains a considerable need for potent small molecule inhibitors of BTK.

SUMMARY

A first aspect of the application relates to a compound of Formula (I):

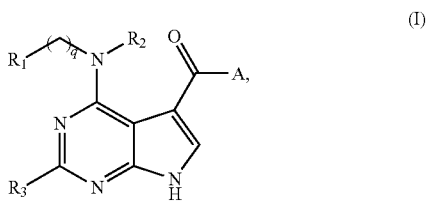

or a pharmaceutically acceptable salt, solvate, prodrug, stereoisomer, or tautomer thereof, wherein $R_1$, $R_2$, $R_3$, A, and q are as described in detail below.

Another aspect of the application relates to a pharmaceutical composition comprising a compound of Formula (I), or a pharmaceutically acceptable salt, solvate, prodrug, stereoisomer, or tautomer thereof, and a pharmaceutically acceptable diluent, excipient or carrier.

Another aspect of the application relates to a method of treating a BTK-mediated disorder. The method comprises administering to a subject in need of a treatment for a disease or disorder associated with modulation of BTK kinase a therapeutically effective amount of a compound of Formula (I), or a pharmaceutically acceptable salt, solvate, prodrug, stereoisomer, or tautomer thereof.

Another aspect of the application relates to a method of treating a BTK-mediated disorder. The method comprises administering to a subject in need of a treatment for a disease or disorder associated with modulation of BTK kinase a therapeutically effective amount of a pharmaceutical composition comprising a compound of Formula (I), or a pharmaceutically acceptable salt, solvate, prodrug, stereoisomer, or tautomer thereof, and a pharmaceutically acceptable diluent, excipient or carrier.

Another aspect of the application relates to a method of treating a cell proliferative disorder. The method comprises administering to a subject in need thereof a therapeutically effective amount of a compound of Formula (I), or a pharmaceutically acceptable salt, solvate, prodrug, stereoisomer, or tautomer thereof.

Another aspect of the application relates to a method of treating a cell proliferative disorder. The method comprises administering to a subject in need thereof a therapeutically effective amount of a pharmaceutical composition comprising a compound of Formula (I), or a pharmaceutically acceptable salt, solvate, prodrug, stereoisomer, or tautomer thereof, and a pharmaceutically acceptable diluent, excipient or carrier.

Another aspect of the application relates to a method of treating cancer. The method comprises administering to a subject in need thereof a therapeutically effective amount of a compound of Formula (I), or a pharmaceutically acceptable salt, solvate, prodrug, stereoisomer, or tautomer thereof.

Another aspect of the application relates to a method of treating cancer. The method comprises administering to a subject in need thereof a therapeutically effective amount of a pharmaceutical composition comprising a compound of Formula (I), or a pharmaceutically acceptable salt, solvate, prodrug, stereoisomer, or tautomer thereof, and a pharmaceutically acceptable diluent, excipient or carrier.

Another aspect of the application relates to a method of modulating (e.g., inhibiting) BTK. The method comprises administering to a subject in need thereof a therapeutically effective amount of a compound of Formula (I), or a pharmaceutically acceptable salt, solvate, prodrug, stereoisomer, or tautomer thereof.

Another aspect of the application relates to a method of modulating (e.g., inhibiting) BTK. The method comprises administering to a subject in need thereof a therapeutically effective amount of a pharmaceutical composition comprising a compound of Formula (I), or a pharmaceutically acceptable salt, solvate, prodrug, stereoisomer, or tautomer thereof, and a pharmaceutically acceptable diluent, excipient or carrier.

Another aspect of the application relates to a compound of Formula (I), or a pharmaceutically acceptable salt, solvate, prodrug, stereoisomer, or tautomer thereof, for use in a method of treating a BTK-mediated disorder, a cell proliferative disorder, or cancer, or of modulating (e.g., inhibiting) BTK. The compound of Formula (I), or a pharmaceutically acceptable salt, solvate, prodrug, stereoisomer, or tautomer thereof, is administered in a therapeutically effective amount to a subject in need thereof.

Another aspect of the application relates to a pharmaceutical composition comprising a compound of Formula (I), or a pharmaceutically acceptable salt, solvate, prodrug, stereoisomer, or tautomer thereof, and a pharmaceutically acceptable diluent, excipient or carrier for use in a method of treating a BTK-mediated disorder, a cell proliferative disorder, or cancer, or of modulating (e.g., inhibiting) BTK. The composition is administered in a therapeutically effective amount to a subject in need thereof.

Another aspect of the application relates to the use of a compound of Formula (I), or a pharmaceutically acceptable salt, solvate, prodrug, stereoisomer, or tautomer thereof, in the manufacture of a medicament for treating a BTK-mediated disorder, a cell proliferative disorder, or cancer, or for modulating (e.g., inhibiting) BTK. The compound of Formula (I), or a pharmaceutically acceptable salt, solvate, prodrug, stereoisomer, or tautomer thereof, is administered in a therapeutically effective amount to a subject in need thereof.

Another aspect of the application relates to the use of a pharmaceutical composition comprising a compound of Formula (I), or a pharmaceutically acceptable salt, solvate, prodrug, stereoisomer, or tautomer thereof, and a pharmaceutically acceptable diluent, excipient or carrier in the manufacture of a medicament for treating a BTK-mediated disorder, a cell proliferative disorder, or cancer, or for modulating (e.g., inhibiting) BTK. The composition is administered in a therapeutically effective amount to a subject in need thereof.

The present application further provides methods of treating a disease or disorder associated with modulation of BTK kinase including, but not limited to, immune disorders, cancer, cardiovascular diseases, viral infections, inflammation, metabolism/endocrine function disorders, and neurological disorders comprising, administering to a subject suffering from at least one of the diseases or disorders a compound of Formula (I), or a pharmaceutically acceptable salt, solvate, prodrug, stereoisomer, or tautomer thereof.

The present application provides inhibitors of BTK that are therapeutic agents in the treatment of diseases such as immune disorders, cancer, cardiovascular diseases, viral infections, inflammation, metabolism/endocrine function disorders, neurological disorders and other disease associated with the modulation of BTK kinase.

The present application further provides compounds and compositions with an improved efficacy and safety profile relative to known BTK inhibitors. The present application also provides agents with novel mechanisms of action toward BTK kinase in the treatment of various types of diseases including immune disorders, cancer, cardiovascular diseases, viral infections, inflammation, metabolism/endocrine function disorders, and neurological disorders. Ultimately the present application provides the medical community with a novel pharmacological strategy for the treatment of diseases and disorders associated with BTK kinase.

DETAILED DESCRIPTION

Compounds of the Application

The present application relates to compounds and compositions thereof that are capable of modulating the activity Bruton's Tyrosine Kinase (BTK). The application features methods of treating, preventing or ameliorating a disease or disorder in which BTK plays a role by administering to a subject in need thereof a therapeutically effective amount of a compound of Formula (I), or a pharmaceutically acceptable salt, solvate, prodrug, stereoisomer, or tautomer thereof. The methods of the present application can be used in the treatment of a variety of BTK-mediated diseases and disorders by inhibiting the activity of BTK kinase. Inhibition of BTK provides treatment, prevention, or amelioration of diseases including, but not limited to, immune disorders, cancer, cardiovascular diseases, viral infections, inflammation, metabolism/endocrine function disorders and neurological disorders.

In a first aspect of the application, a compound of Formula (I) is described:

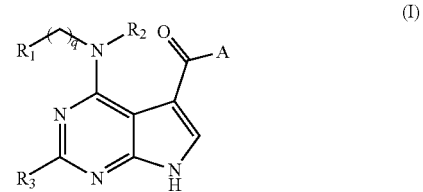

or a pharmaceutically acceptable salt, solvate, prodrug, stereoisomer, or tautomer thereof, wherein:

A is $(C_6-C_{10})$ aryl or 5- or 6-membered heteroaryl comprising 1 to 3 heteroatoms selected from N, O, and S, wherein the aryl and heteroaryl are optionally substituted with one or more $R_4$;

$R_1$ is $(C_3-C_7)$ cycloalkyl or 4- to 9-membered heterocyclyl comprising 1 to 3 heteroatoms selected from N, O, and S, wherein the cycloalkyl and heterocyclyl are optionally substituted with one or more $R_5$;

$R_2$ is H or $(C_1-C_4)$ alkyl; or when q is 0, $R_1$ and $R_2$ together with the nitrogen atom to which they are attached form a 5- or 6-membered heterocyclyl ring comprising 0 to 1 additional heteroatoms selected from N, O, and S and optionally substituted with one or more $NR_6R_7$;

$R_3$ is H or $N(R_8)_2$;

each $R_4$ is independently (i) $(C_1-C_4)$ alkyl, (ii) $(C_1-C_4)$ alkoxy optionally substituted with one or more $(C_1-C_4)$ alkoxy, (iii) (C$_1$-C$_4$) haloalkyl, (iv) (C$_1$-C$_4$) haloalkoxy, (v) halogen, (vi) NR$_9$S(O)$_p$R$_{10}$, (vii) O(CH$_2$)$_n$R$_{11}$, (viii) NH(CH$_2$)$_n$R$_{11}$, (ix) (CH$_2$)$_n$C(=O)NHR$_{25}$, (x) (CH$_2$)$_n$NHC(=O)R$_{25}$, (xi) (CH$_2$)$_n$NHC(=O)NHR$_{25}$, (xii) C(=O)R$_{25}$, or (xiii) heterocyclyl comprising one or two 4- to 6-membered rings and 1 to 3 heteroatoms selected from N, O, and S and optionally substituted with one or more substituents selected from (C$_1$-C$_4$) alkyl, (C$_1$-C$_4$) haloalkyl, C(=O)(C$_1$-C$_4$) alkyl, and halogen;

each R$_5$ is independently (i) (C$_1$-C$_6$) alkyl optionally substituted with one or more (C$_1$-C$_4$) alkoxy or phenyl, (ii) (C$_2$-C$_4$) alkenyl optionally substituted with one or more C(=O)(C$_1$-C$_4$) alkyl, (iii) (C(R$_{12}$)$_2$)$_r$OH, (iv) (C(R$_{12}$)$_2$)$_r$NR$_{13}$R$_{14}$, (v) C(=O)OH, (vi) C(=O)O(C$_1$-C$_4$) alkyl, (vii) C(=O)NR$_{13}$R$_{15}$, (viii) C(=O)R$_{16}$, (ix) S(O)$_p$R$_{16}$, or (x) 5- or 6-membered heteroaryl comprising 1 to 3 heteroatoms selected from N, O, and S and optionally substituted with one or more (C$_1$-C$_4$) alkyl, (xi) or two R$_5$ together with the carbon atom to which they are attached form (=O), or (xii) two R$_5$ together with the atoms to which they are attached form a bridged 3- to 6-membered heterocyclyl ring comprising 1 to 3 heteroatoms selected from N, O, and S;

R$_6$ is H or (C$_1$-C$_4$) alkyl;
R$_7$ is H, (C$_1$-C$_4$) alkyl, or C(=O)R$_{24}$;
each R$_8$ is independently (i) H, (ii) (C$_1$-C$_4$) alkyl, or (iii) 5- or 6-membered heterocyclyl comprising 1 to 3 heteroatoms selected from N, O, and S and optionally substituted with one or more (C$_1$-C$_4$) alkyl, or (iv) two R$_8$ together with the nitrogen atom to which they are attached form a 5- or 6-membered heterocyclyl ring comprising 0 to 1 additional heteroatoms selected from N, O, and S and optionally substituted with one or more (C$_1$-C$_4$) alkyl;

R$_9$ is H or (C$_1$-C$_4$) alkyl;
R$_{10}$ is (C$_1$-C$_4$) alkyl or (C$_6$-C$_{10}$) aryl;
R$_{11}$ is (C$_3$-C$_7$) cycloalkyl, (C$_4$-C$_7$) cycloalkenyl, (C$_6$-C$_{10}$) aryl, or 5- or 6-membered heteroaryl comprising 1 to 3 heteroatoms selected from N, O, and S, wherein the aryl and heteroaryl are optionally substituted with one or more R$_{17}$;

each R$_{12}$ is independently H or (C$_1$-C$_6$) alkyl;
R$_{13}$ is H or (C$_1$-C$_4$) alkyl;
R$_{14}$ is (i) H, (ii) (C$_1$-C$_4$) alkyl, (iii) (C(R$_{18}$)$_2$)$_r$C(=O)NR$_{19}$R$_{20}$, (iv) (CH$_2$)$_n$(C$_6$-C$_{10}$) aryl optionally substituted with one or more (C$_1$-C$_4$) alkyl or halogen, (v) C(=O)R$_{21}$, (vi) C(=O)O(C$_1$-C$_4$) alkyl, (vii) S(O)$_2$(C$_1$-C$_8$) alkyl, (viii) S(O)$_2$NH(C$_1$-C$_8$) alkyl, (ix) S(O)$_2$N((C$_1$-C$_8$) alkyl)$_2$, or (x) C(=O)(C$_1$-C$_8$) alkyl optionally substituted with one or more R$_{22}$; or R$_{13}$ and R$_{14}$ together with the nitrogen atom to which they are attached form a 4- to 6-membered heterocyclyl ring comprising 1 to 3 heteroatoms selected from N, O, and S and optionally substituted with one or more substituents selected from (C$_1$-C$_4$) alkyl, (C$_1$-C$_4$) alkoxy, OH, NH$_2$, and (=O);

R$_{15}$ is (i) H, (ii) 5- or 6-membered heterocyclyl comprising 1 to 3 heteroatoms selected from N, O, and S, or (iii) (C$_1$-C$_4$) alkyl optionally substituted with one or more substituents selected from OH, 5- or 6-membered heterocyclyl comprising 1 to 3 heteroatoms selected from N, O, and S, and 5- or 6-membered heteroaryl comprising 1 to 3 heteroatoms selected from N, O, and S; or R$_{13}$ and R$_{15}$ together with the nitrogen atom to which they are attached form a 4- to 6-membered heterocyclyl ring comprising 1 to 3 heteroatoms selected from N, O, and S and optionally substituted with one or more substituents selected from (C$_1$-C$_4$) alkyl, (C$_1$-C$_4$) alkoxy, and OH, or form a 5- to 8-membered bicyclic heterocyclyl ring comprising 1 to 3 heteroatoms selected from N, O, and S and optionally substituted with one or more substituents selected from (C$_1$-C$_4$) alkyl, (C$_1$-C$_4$) alkoxy, and OH;

R$_{16}$ is (C$_1$-C$_4$) alkyl, (C$_2$-C$_4$) alkenyl, (C$_2$-C$_4$) alkynyl, or 3- to 6-membered heterocyclyl comprising 1 to 3 heteroatoms selected from N, O, and S, wherein the alkyl, alkenyl, and alkynyl are optionally substituted with one or more substituents selected from (C$_1$-C$_4$) alkoxy, O-phenyl, halogen, CN, NH$_2$, (C$_1$-C$_4$) alkylamino, di-(C$_1$-C$_4$) alkylamino, and OS(O)$_2$(C$_1$-C$_4$) alkyl, and wherein the heterocyclyl is optionally substituted with one or more R$_{23}$;

each R$_{17}$ is independently (C$_1$-C$_4$) alkyl, (C$_1$-C$_4$) alkoxy, (C$_1$-C$_4$) haloalkyl, (C$_1$-C$_4$) haloalkoxy, halogen, C(=O)NH$_2$, C(=O)NH(C$_1$-C$_4$) alkyl, or C(=O)N((C$_1$-C$_4$) alkyl)$_2$;

each R$_{18}$ is independently H or (C$_1$-C$_4$) alkyl;
R$_{19}$ is H or (C$_1$-C$_4$) alkyl;
R$_{20}$ is H or (CH$_2$)$_n$(C$_6$-C$_{10}$) aryl optionally substituted with one or more (C$_1$-C$_4$) alkyl;
R$_{21}$ is (C$_3$-C$_7$) cycloalkyl, 5- or 6-membered heterocyclyl comprising 1 to 3 heteroatoms selected from N, O, and S, (C$_6$-C$_{10}$) aryl, or 5- or 6-membered heteroaryl comprising 1 to 3 heteroatoms selected from N, O, and S, wherein the aryl, heteroaryl, cycloalkyl, and heterocyclyl are optionally substituted with one or more substituents selected from (C$_1$-C$_4$) alkyl, (C$_1$-C$_4$) alkoxy, (C$_1$-C$_4$) haloalkyl, (C$_1$-C$_4$) haloalkoxy, OH, and halogen;

each R$_{22}$ is independently (i) (C$_1$-C$_4$) alkoxy, (ii) OH, (iii) NH$_2$, (iv) (C$_1$-C$_4$) alkylamino, (v) di-(C$_1$-C$_4$) alkylamino, or (vi) 5- or 6-membered heterocyclyl comprising 1 to 3 heteroatoms selected from N, O, and S and optionally substituted with one or more substituents selected from (a) (C$_1$-C$_4$) alkyl, (b) (CH$_2$)$_x$(C$_6$-C$_{10}$) aryl, and (c) C(=O)(C$_6$-C$_{10}$)aryl optionally substituted with one or more (C$_1$-C$_4$) alkyl;

each R$_{23}$ is independently (C$_1$-C$_4$) alkyl or C(=O)(C$_1$-C$_4$) alkyl, or two R$_{23}$ together with the atoms to which they are attached form a 5- or 6-membered heterocyclyl ring comprising 1 to 3 heteroatoms selected from N, O, and S;

R$_{24}$ is (C$_1$-C$_4$) alkyl optionally substituted with one or more substituents selected from (C$_1$-C$_4$) alkoxy and 5- or 6-membered heterocyclyl comprising 1 to 3 heteroatoms selected from N, O, and S;

R$_{25}$ is (C$_1$-C$_4$) alkyl optionally substituted with one or more (C$_1$-C$_4$) alkoxy, (C(R$_{26}$)$_2$)$_x$(C$_6$-C$_{10}$) aryl, (C(R$_{26}$)$_2$)$_x$-heteroaryl, wherein the heteroaryl comprises one or two 5- or 6-membered rings and 1 to 3 heteroatoms selected from N, O, and S, or (C(R$_{26}$)$_2$)$_x$-heterocyclyl, wherein the heterocyclyl comprises one or two 4- to 6-membered rings and 1 to 3 heteroatoms selected from N, O, and S, wherein the alkyl, alkoxy, aryl, heteroaryl, and heterocyclyl are optionally substituted with one or more substituents selected from (C$_1$-C$_4$) alkyl, (C$_1$-C$_4$) alkoxy, (C$_1$-C$_4$) haloalkyl, (C$_1$-C$_4$) haloalkoxy, cyano, halogen, OH, NH$_2$, (C$_6$-C$_{10}$) aryl, and 5- or 6-membered heteroaryl comprising 1 to 3 heteroatoms selected from N, O, and S;

each R$_{26}$ is independently H or (C$_1$-C$_4$) alkyl, or two R$_{26}$ together with the atom to which they are attached form a (C$_3$-C$_6$) cycloalkyl ring or 3- or 6-membered heterocyclyl ring comprising 1 to 3 heteroatoms selected from N, O, and S;

each n and each p is independently 0, 1, or 2;
each r is independently 0, 1, 2, or 3;
each q and each x is independently 0, 1, 2, or 3; and
provided that when R$_4$ is NR$_9$S(O)$_p$R$_{10}$, A is optionally substituted with one additional R$_4$; and provided that the compound is not (2-chloro-4-phenoxyphenyl)(4-(((3R,6S)-6-(hydroxymethyl)tetrahydro-2H-pyran-3-yl)amino)-7H-pyrrolo[2,3-d]pyrimidin-5-yl)methanone.

In some embodiments, the compounds of Formula (I) have the structure of Formula (Ia) or (Ia'):

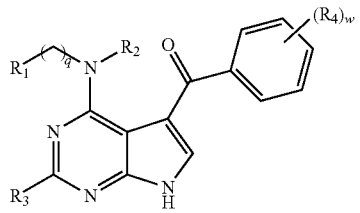
(Ia)

or

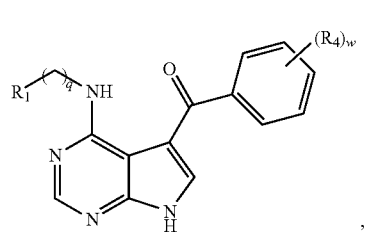
(Ia')

or a pharmaceutically acceptable salt, solvate, prodrug, stereoisomer, or tautomer thereof.

In some embodiments, the compounds of Formula (I) have the structure of Formula (Ib) or (Ib'):

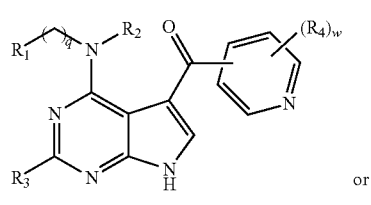
(Ib)

or

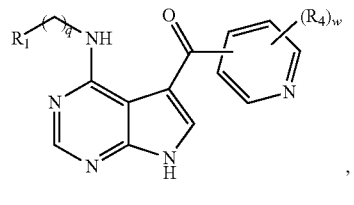
(Ib')

or a pharmaceutically acceptable salt, solvate, prodrug, stereoisomer, or tautomer thereof.

In some embodiments, the compounds of Formula (I) have the structure of Formula (Ic) or (Ic'):

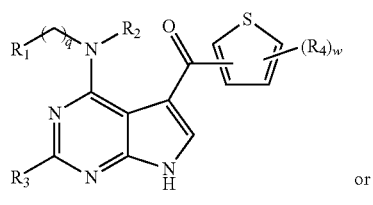
(Ic)

or

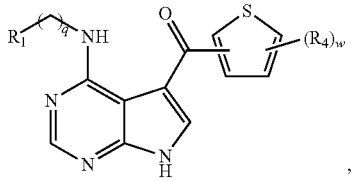
(Ic')

or a pharmaceutically acceptable salt, solvate, prodrug, stereoisomer, or tautomer thereof.

In some embodiments, the compounds of Formula (I) have the structure of Formula (Id) or (Id'):

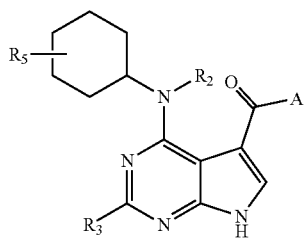
(Id)

or

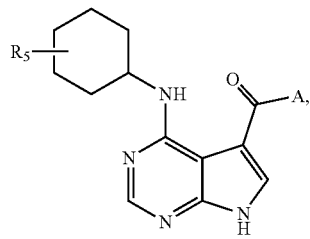
(Id')

or a pharmaceutically acceptable salt, solvate, prodrug, stereoisomer, or tautomer thereof.

In some embodiments, the compounds of Formula (I) have the structure of Formula (Ie) or (Ie'):

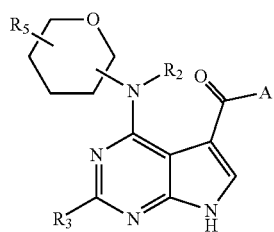
(Ie)

or

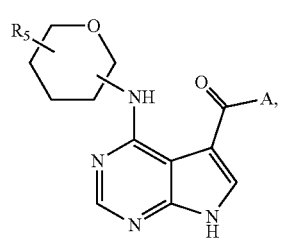
(Ie')

and pharmaceutically acceptable salts, solvates, prodrugs, stereoisomers, and tautomers thereof.

In some embodiments, the compounds of Formula (I) have the structure of Formula (If) or (If'):
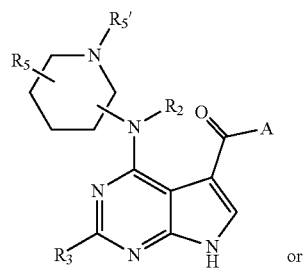
(If)
or
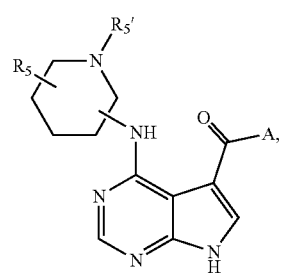
(If')
and pharmaceutically acceptable salts, solvates, prodrugs, stereoisomers, and tautomers thereof.
In some embodiments, the compounds of Formula (I) have the structure any of Formulae (Ig1) and (Ig12):
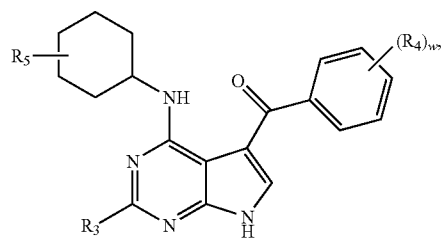
(Ig1)
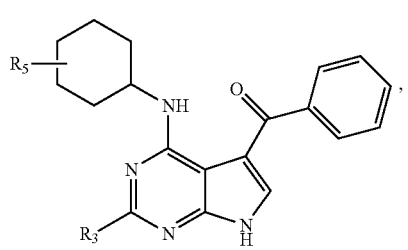
(Ig2)
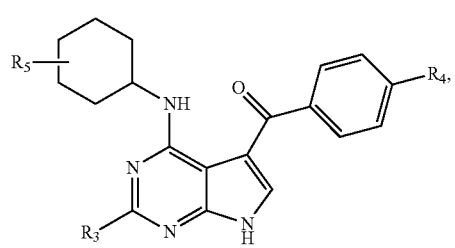
(Ig3)
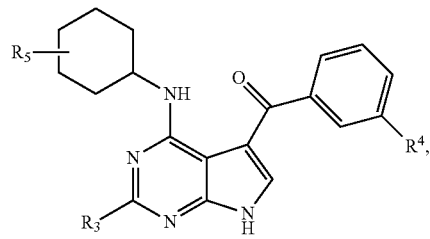
(Ig4)
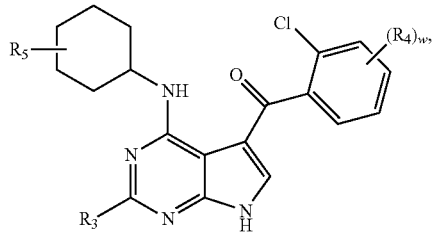
(Ig5)
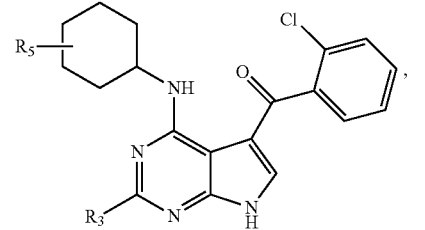
(Ig6)
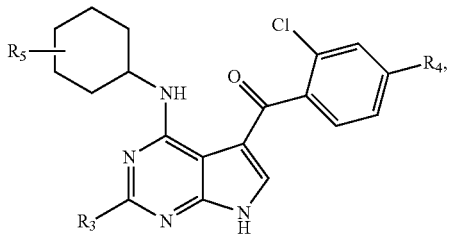
(Ig7)
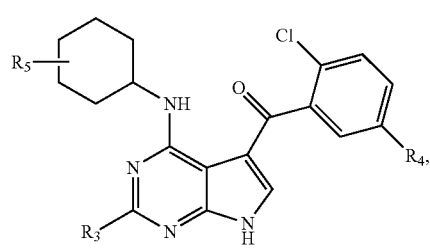
(Ig8)
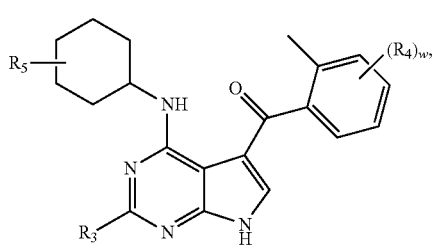
(Ig9)

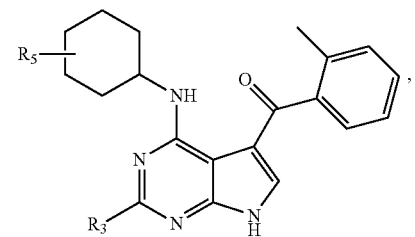
(Ig10)
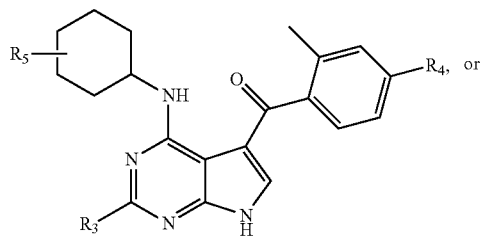
(Ig11), or
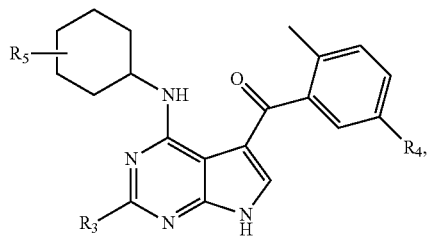
(Ig12)
and pharmaceutically acceptable salts, solvates, prodrugs, stereoisomers, and tautomers thereof.
In some embodiments, the compounds of Formula (I) have the structure any of Formulae (Ih1) and (Ih12):
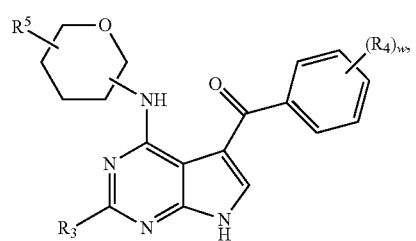
(Ih1)
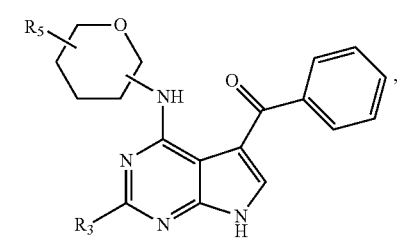
(Ih2)
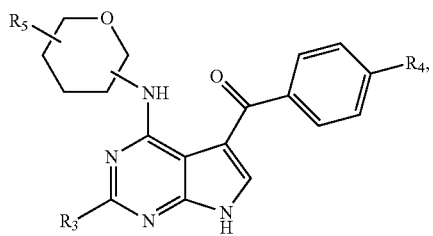
(Ih3)
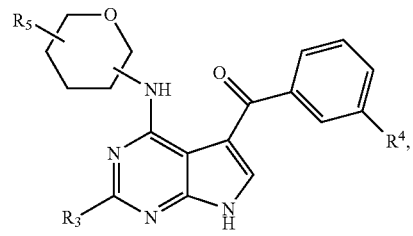
(Ih4)
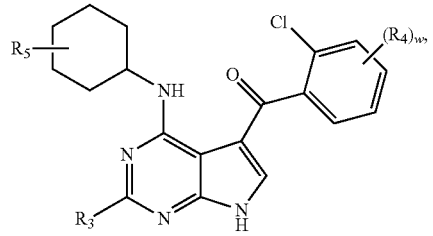
(Ih5)
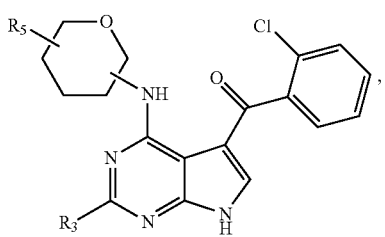
(Ih6)
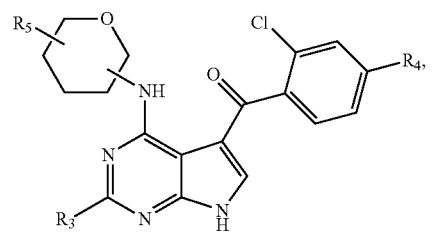
(Ih7)
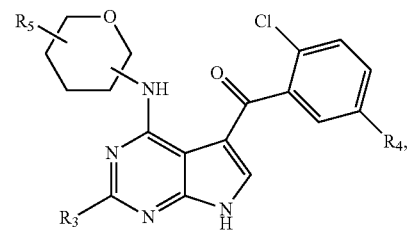
(Ih8)

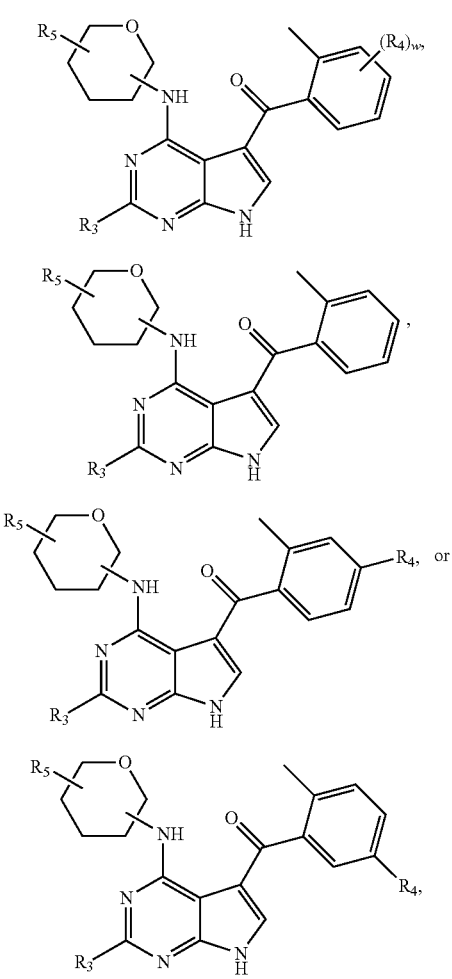
and pharmaceutically acceptable salts, solvates, prodrugs, stereoisomers, and tautomers thereof.
In some embodiments, the compounds of Formula (I) have the structure any of Formulae (Ii1) and (Ii12):
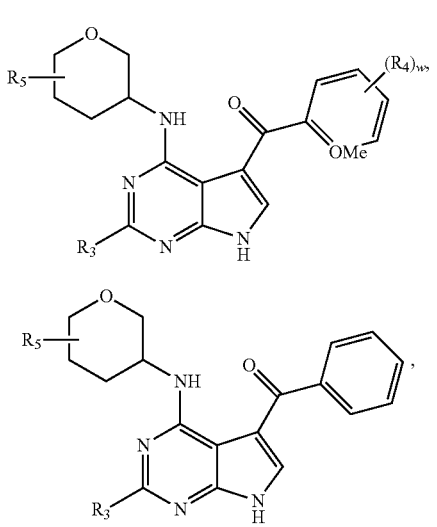
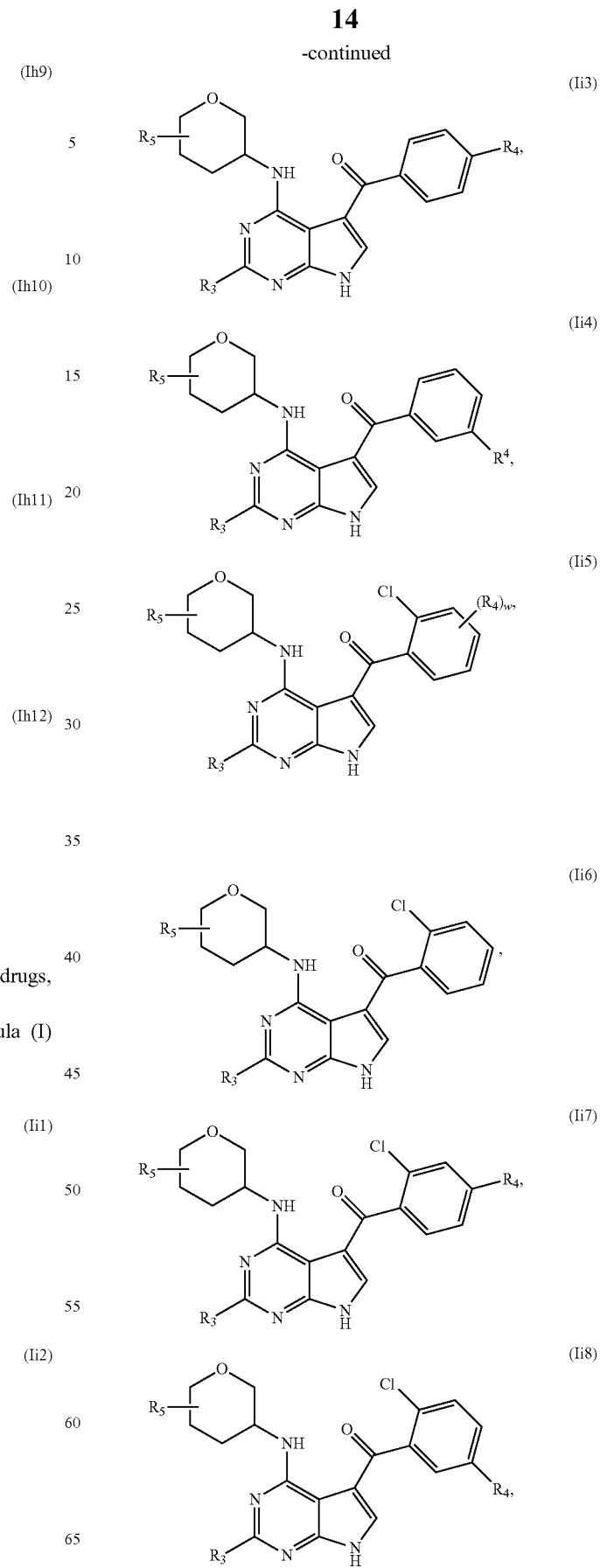

-continued

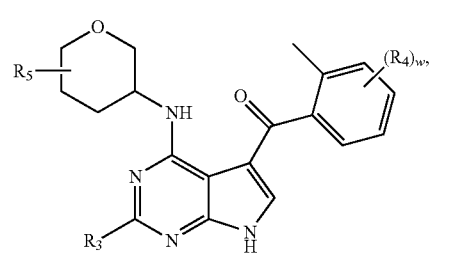
(Ii9)

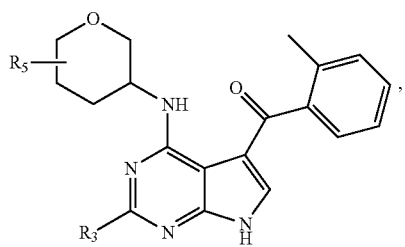
(Ii10)

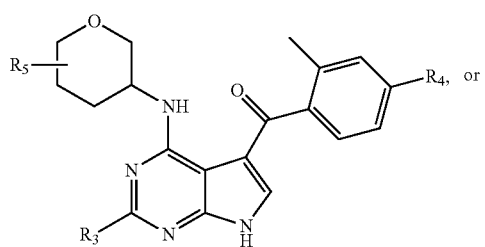
(Ii11)

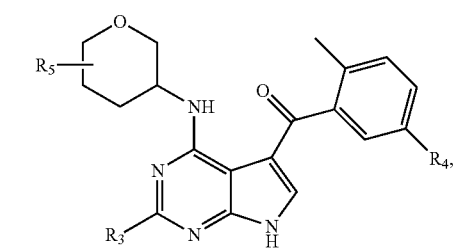
(Ii12)

and pharmaceutically acceptable salts, solvates, prodrugs, stereoisomers, and tautomers thereof.

In some embodiments of the formulae above, A is ($C_6$-$C_{10}$) aryl optionally substituted with one or more $R_4$. In one embodiment, A is 5- or 6-membered heteroaryl comprising 1 to 3 heteroatoms selected from N, O, and S (e.g., pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, and furanyl), optionally substituted with one or more $R_4$. In another embodiment, A is 5-membered heteroaryl comprising 1 to 3 heteroatoms selected from N, O, and S (e.g., pyrrolyl, pyrazolyl, imidazolyl, thiazolyl, oxazolyl, isooxazolyl, thiadiazolyl, oxadiazolyl, thiophenyl, and furanyl), optionally substituted with one or more $R_4$. In another embodiment, A is 6-membered heteroaryl comprising 1 to 3 heteroatoms selected from N, O, and S (e.g., pyridinyl, pyrazinyl, and pyrimidinyl), optionally substituted with one or more $R_4$. In another embodiment, A is ($C_6$-$C_{10}$) aryl or 5-membered heteroaryl comprising 1 to 3 heteroatoms selected from N, O, and S, wherein each is optionally substituted with one or more $R_4$. In another embodiment, A is ($C_6$-$C_{10}$) aryl or 6-membered heteroaryl comprising 1 to 3 heteroatoms selected from N, O, and S, wherein each is optionally substituted with one or more $R_4$.

In another embodiment, A is phenyl, thiophenyl, or pyridinyl wherein each is optionally substituted with one or more $R_4$. In another embodiment, A is phenyl, thiophenyl, or pyridinyl wherein each is substituted with one or more $R_4$. In another embodiment, A is phenyl, thiophenyl, or pyridinyl. In another embodiment, A is phenyl optionally substituted with one to two $R_4$. In another embodiment, A is phenyl substituted with one to two $R_4$. In another embodiment, A is phenyl. In another embodiment, A is thiophenyl optionally substituted with one to two $R_4$. In another embodiment, A is thiophenyl substituted with one to two $R_4$. In another embodiment, A is thiophenyl. In another embodiment, A is pyridinyl optionally substituted with one to two $R_4$. In another embodiment, A is pyridinyl substituted with one to two $R_4$. In another embodiment, A is pyridinyl. In a further embodiment, A is phenyl, thiophenyl, or pyridinyl wherein each is optionally substituted with one to two $R_4$. In another further embodiment, A is phenyl, thiophenyl, or pyridinyl wherein each is substituted with one to two $R_4$.

In some embodiments of the formulae above, each $R_4$ is independently ($C_1$-$C_4$) alkyl, ($C_1$-$C_4$) alkoxy optionally substituted with one or more ($C_1$-$C_4$) alkoxy, ($C_1$-$C_4$) haloalkyl, ($C_1$-$C_4$) haloalkoxy, halogen, $NR_9S(O)_pR_{10}$, $O(CH_2)_nR_{11}$, $C(=O)NHR_{25}$, $NHC(=O)R_{25}$, or heterocyclyl comprising one or two 4- to 6-membered rings and 1 to 3 heteroatoms selected from N, O, and S and optionally substituted with one or more substituents selected from ($C_1$-$C_4$) alkyl, ($C_1$-$C_4$) haloalkyl, $C(=O)(C_1$-$C_4)$ alkyl, and halogen.

In some embodiments of the formulae above, each $R_4$ is independently ($C_1$-$C_4$) alkyl, ($C_1$-$C_4$) alkoxy, ($C_1$-$C_4$) haloalkyl, ($C_1$-$C_4$) haloalkoxy, halogen, or $O(CH_2)_nR_{11}$ wherein the alkoxy is optionally substituted with one or more ($C_1$-$C_4$) alkoxy.

In some embodiments of the formulae above, at least one $R_4$ is ($C_1$-$C_4$) alkyl (e.g., methyl, ethyl, n-propyl, i-propyl, n-butyl, i-butyl, or t-butyl). In another embodiment, at least one $R_4$ is methyl, ethyl, n-propyl, or i-propyl. In another embodiment, at least one $R_4$ is methyl or ethyl. In another embodiment, at least one $R_4$ is methyl.

In some embodiments of the formulae above, at least one $R_4$ is ($C_1$-$C_4$) alkoxy (e.g., methoxy, ethoxy, n-propoxy, i-propoxy, n-butoxy, i-butoxy, or t-butoxy) optionally substituted with one or more ($C_1$-$C_4$) alkoxy (e.g., methoxy, ethoxy, n-propoxy, i-propoxy, n-butoxy, i-butoxy, or t-butoxy). In another embodiment, at least one $R_4$ is methoxy or ethoxy, wherein each is optionally substituted with one or more ($C_1$-$C_4$) alkoxy (e.g., methoxy, ethoxy, n-propoxy, i-propoxy, n-butoxy, i-butoxy, or t-butoxy). In another embodiment, at least one $R_4$ is methoxy or ethoxy, wherein each is optionally substituted with one or more methoxy or ethoxy. In another embodiment, at least one $R_4$ is methoxy or ethoxy, wherein each is optionally substituted with one to two methoxy. In a further embodiment, at least one $R_4$ is methoxy or ethoxy, wherein each is optionally substituted with one methoxy.

In some embodiments of the formulae above, at least one $R_4$ is ($C_1$-$C_4$) haloalkyl (e.g., $CF_3$, $CHF_2$, $CH_2F$, $CH_2CF_3$, $CF_2CF_3$, $CCl_3$, $CHCl_2$, $CH_2Cl$, etc.). In a further embodiment, at least one $R_4$ is $CF_3$.

In some embodiments of the formulae above, at least one $R_4$ is ($C_1$-$C_4$) haloalkoxy (e.g., $OCF_3$, $OCHF_2$, $OCH_2F$, $OCH_2CF_3$, $OCF_2CF_3$, $OCCl_3$, $OCHCl_2$, $OCH_2Cl$, etc.).

In some embodiments of the formulae above, at least one $R_4$ is halogen (e.g., F, Cl, Br, or I). In another embodiment, at least one $R_4$ is F or Cl. In another embodiment, at least one $R_4$ is F. In another embodiment, at least one $R_4$ is Cl.

In some embodiments of the formulae above, at least one $R_4$ is $OR_{11}$, $O(CH_2)R_{11}$, or $O(CH_2)_2R_{11}$. In another embodiment, at least one $R_4$ is $OR_{11}$ or $O(CH_2)R_{11}$.

In some embodiments of the formulae above, at least one $R_4$ is $NHR_{11}$, $NH(CH_2)R_1$, or $NH(CH_2)_2R_{11}$. In another embodiment, at least one $R_4$ is $NHR_{11}$ or $NH(CH_2)R_{11}$.

In some embodiments of the formulae above, at least one $R_4$ is $C(=O)NHR_{25}$, $(CH_2)C(=O)NHR_{25}$, or $(CH_2)_2C(=O)NHR_{25}$. In another embodiment, at least one $R_4$ is $C(=O)NHR_{25}$ or $(CH_2)C(=O)NHR_{25}$.

In some embodiments of the formulae above, at least one $R_4$ is $NHC(=O)R_{25}$, $(CH_2)NHC(=O)R_{25}$, or $(CH_2)_2NHC(=O)R_{25}$. In another embodiment, at least one $R_4$ is $NHC(=O)R_{25}$ or $(CH_2)NHC(=O)R_{25}$.

In some embodiments of the formulae above, at least one $R_4$ is $NHC(=O)NHR_{25}$, $(CH_2)NHC(=O)NHR_{25}$, or $(CH_2)_2NHC(=O)NHR_{25}$. In another embodiment, at least one $R_4$ is $NHC(=O)NHR_{25}$ or $(CH_2)NHC(=O)NHR_{25}$.

In some embodiments of the formulae above, at least one $R_4$ is $(CH_2)C(=O)NHR_{25}$, $(CH_2)NHC(=O)NHR_{25}$, or $(CH_2)NHC(=O)NHR_{25}$.

In some embodiments of the formulae above, at least one $R_4$ is $CH_2C(=O)NHR_{25}$ or $(CH_2)NHC(=O)NHR_{25}$.

In some embodiments of the formulae above, at least one $R_4$ is $CH_2NHC(=O)NHR_{25}$.

In some embodiments of the formulae above, at least one $R_4$ is (i) $(C_1-C_4)$ alkyl (e.g., methyl, ethyl, n-propyl, i-propyl, n-butyl, i-butyl, or t-butyl), (ii) $(C_1-C_4)$ alkoxy (e.g., methoxy, ethoxy, n-propoxy, i-propoxy, n-butoxy, i-butoxy, or t-butoxy) optionally substituted with one or more $(C_1-C_4)$ alkoxy (e.g., methoxy, ethoxy, n-propoxy, i-propoxy, n-butoxy, i-butoxy, or t-butoxy), (iii) $(C_1-C_4)$ haloalkyl (e.g., $CF_3$, $CHF_2$, $CH_2F$, $CH_2CF_3$, $CF_2CF_3$, $CCl_3$, $CHCl_2$, $CH_2Cl$, etc.), (iv) $(C_1-C_4)$ haloalkoxy (e.g., $OCF_3$, $OCHF_2$, $OCH_2F$, $OCH_2CF_3$, $OCF_2CF_3$, $OCCl_3$, $OCHCl_2$, $OCH_2Cl$, etc.), (v) halogen (e.g., F, Cl, Br, or I), (vi) $NR_9S(O)_pR_{10}$, (vii) $O(CH_2)_nR_{11}$, (viii) $NH(CH_2)_nR_{11}$, (ix) $(CH_2)_nC(=O)NHR_{25}$, (x) $(CH_2)_nNHC(=O)R_{25}$, (xi) $(CH_2)_nNHC(=O)NHR_{25}$, (xii) $C(=O)R_{25}$, or (xiii) heterocyclyl comprising one or two 4- to 6-membered rings and 1 to 3 heteroatoms selected from N, O, and S (e.g., pyrrolidinyl, pyrazolidinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, dioxanyl, and a spiroheterocyclyl such as oxaazaspiro[3.3]heptanyl) and optionally substituted with one to three substituents selected from $(C_1-C_4)$ alkyl (e.g., methyl, ethyl, n-propyl, i-propyl, n-butyl, i-butyl, or t-butyl), $(C_1-C_4)$ haloalkyl (e.g., $CF_3$, $CHF_2$, $CH_2F$, $CH_2CF_3$, $CF_2CF_3$, $CCl_3$, $CHCl_2$, $CH_2Cl$, etc.), $C(=O)(C_1-C_4)$ alkyl (wherein $(C_1-C_4)$ alkyl is methyl, ethyl, n-propyl, i-propyl, n-butyl, i-butyl, or t-butyl), and halogen (e.g., F, Cl, Br, or I). In another embodiment, at least one $R_4$ is (i) $O(CH_2)_nR_{11}$, (ii) $NH(CH_2)_nR_{11}$, (iii) $(CH_2)_nC(=O)NHR_{25}$, (iv) $(CH_2)_nNHC(=O)R_{25}$, (v) $(CH_2)_nNHC(=O)NHR_{25}$, (vi) $C(=O)R_{25}$, or (vii) heterocyclyl comprising one or two 4- to 6-membered rings and 1 to 3 heteroatoms selected from N, O, and S and optionally substituted with one to three substituents selected from $(C_1-C_4)$ alkyl, $(C_1-C_4)$ haloalkyl, $C(=O)(C_1-C_4)$ alkyl, and halogen. In another embodiment, at least one $R_4$ is heterocyclyl comprising one or two 4- to 6-membered rings and 1 to 3 heteroatoms selected from N, O, and S and optionally substituted with one to three substituents selected from $(C_1-C_4)$ alkyl, $(C_1-C_4)$ haloalkyl, $C(=O)(C_1-C_4)$ alkyl, and halogen.

In some embodiments of the formulae above, at least one $R_4$ is $(C_1-C_4)$ alkyl (e.g., methyl, ethyl, n-propyl, i-propyl, n-butyl, i-butyl, or t-butyl), $(C_1-C_4)$ alkoxy (e.g., methoxy, ethoxy, n-propoxy, i-propoxy, n-butoxy, i-butoxy, or t-butoxy) optionally substituted with one to two $(C_1-C_4)$ alkoxy (e.g., methoxy, ethoxy, n-propoxy, i-propoxy, n-butoxy, i-butoxy, or t-butoxy), $(C_1-C_4)$ haloalkyl (e.g., $CF_3$, $CHF_2$, $CH_2F$, $CH_2CF_3$, $CF_2CF_3$, $CCl_3$, $CHCl_2$, $CH_2Cl$, etc.), $(C_1-C_4)$ haloalkoxy (e.g., $OCF_3$, $OCHF_2$, $OCH_2F$, $OCH_2CF_3$, $OCF_2CF_3$, $OCCl_3$, $OCHCl_2$, $OCH_2Cl$, etc.), halogen (e.g., F, Cl, Br, or I), $NR_9S(O)_pR_{10}$, $O(CH_2)_nR_{11}$, $NH(CH_2)_nR_{11}$, $(CH_2)_nC(=O)NHR_{25}$, $(CH_2)_nNHC(=O)R_{25}$, $(CH_2)_nNHC(=O)NHR_{25}$, $C(=O)R_{25}$, or heterocyclyl comprising one or two 4- to 6-membered rings and 1 to 3 heteroatoms selected from N, O, and S (e.g., pyrrolidinyl, pyrazolidinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, dioxanyl, and spiroheterocyclyl such as oxaazaspiro[3.3]heptanyl) and optionally substituted with one or more substituents selected from $(C_1-C_4)$ alkyl (e.g., methyl, ethyl, n-propyl, i-propyl, n-butyl, i-butyl, or t-butyl). In another embodiment, at least one $R_4$ is $(C_1-C_4)$ alkyl, $(C_1-C_4)$ alkoxy optionally substituted with one to two $(C_1-C_4)$ alkoxy, $(C_1-C_4)$ haloalkyl, $(C_1-C_4)$ haloalkoxy, halogen, or $O(CH_2)_nR_{11}$, $NH(CH_2)_nR_{11}$, $(CH_2)_nC(=O)NHR_{25}$, $(CH_2)_nNHC(=O)R_{25}$, $(CH_2)_nNHC(=O)NHR_{25}$, $C(=O)R_{25}$, or 5- or 6-membered heterocyclyl comprising 1 to 3 heteroatoms selected from N, O, and S and optionally substituted with one or more $(C_1-C_4)$ alkyl.

In some embodiments of the formulae above, at least one $R_4$ is $(C_1-C_4)$ alkyl (e.g., methyl, ethyl, n-propyl, i-propyl, n-butyl, i-butyl, or t-butyl), $(C_1-C_4)$ alkoxy (e.g., methoxy, ethoxy, n-propoxy, i-propoxy, n-butoxy, i-butoxy, or t-butoxy), $(C_1-C_4)$ haloalkyl (e.g., $CF_3$, $CHF_2$, $CH_2F$, $CH_2CF_3$, $CF_2CF_3$, $CCl_3$, $CHCl_2$, $CH_2Cl$, etc.), $(C_1-C_4)$ haloalkoxy (e.g., $OCF_3$, $OCHF_2$, $OCH_2F$, $OCH_2CF_3$, $OCF_2CF_3$, $OCCl_3$, $OCHCl_2$, $OCH_2Cl$, etc.), halogen (e.g., F, Cl, Br, or I), $O(CH_2)_nR_{11}$, $NH(CH_2)_nR_{11}$, $(CH_2)_nC(=O)NHR_{25}$, $(CH_2)_nNHC(=O)R_{25}$, $(CH_2)_nNHC(=O)NHR_{25}$, or $C(=O)R_{25}$, wherein the alkoxy is optionally substituted with one or more $(C_1-C_4)$ alkoxy (e.g., methoxy, ethoxy, n-propoxy, i-propoxy, n-butoxy, i-butoxy, or t-butoxy). In another embodiment, at least one $R_4$ is $(C_1-C_2)$ alkyl (i.e., methyl or ethyl), $(C_1-C_2)$ alkoxy (i.e., methoxy or ethoxy), $(C_1-C_2)$ haloalkyl (e.g., $CF_3$, $CHF_2$, $CH_2F$, $CH_2CF_3$, $CF_2CF_3$, $CCl_3$, $CHCl_2$, $CH_2Cl$, etc.), $(C_1-C_2)$ haloalkoxy (e.g., $OCF_3$, $OCHF_2$, $OCH_2F$, $OCH_2CF_3$, $OCF_2CF_3$, $OCCl_3$, $OCHCl_2$, $OCH_2Cl$, etc.), halogen (e.g., F, Cl, Br, or I), $NR_9S(O)_pR_{10}$, $O(CH_2)_nR_{11}$, $NH(CH_2)_nR_{11}$, $(CH_2)_nC(=O)NHR_{25}$, $(CH_2)_nNHC(=O)R_{25}$, $(CH_2)_nNHC(=O)NHR_{25}$, or $C(=O)R_{25}$, wherein the alkoxy is optionally substituted with one or more $(C_1-C_4)$ alkoxy (e.g., methoxy, ethoxy, n-propoxy, i-propoxy, n-butoxy, i-butoxy, or t-butoxy). In another embodiment, at least one $R_4$ is $(C_1-C_2)$ alkyl, $(C_1-C_2)$ alkoxy, $(C_1-C_2)$ haloalkyl, $(C_1-C_2)$ haloalkoxy, halogen, $O(CH_2)_nR_{11}$, $NH(CH_2)_nR_{11}$, $(CH_2)_nC(=O)NHR_{25}$, $(CH_2)_nNHC(=O)R_{25}$, $(CH_2)_nNHC(=O)NHR_{25}$, or $C(=O)R_{25}$, wherein the alkoxy is optionally substituted with one or more $(C_1-C_4)$ alkoxy. In another embodiment, at least one $R_4$ is methyl, F, Cl, methoxy, $OCH_2CH_2OCH_3$, $NR_9S(O)_pR_{10}$, $O(CH_2)_nR_{11}$, $NH(CH_2)_nR_{11}$, $(CH_2)_nC(=O)NHR_{25}$, $(CH_2)_nNHC(=O)R_{25}$, $(CH_2)_nNHC(=O)NHR_{25}$, or $C(=O)R_{25}$. In another embodiment, at least one $R_4$ is methyl, F, Cl, methoxy, $OCH_2CH_2OCH_3$, $O(CH_2)_nR_{11}$, $NH(CH_2)_nR_{11}$, $(CH_2)_nC(=O)NHR_{25}$, $(CH_2)_nNHC(=O)R_{25}$, $(CH_2)_nNHC(=O)NHR_{25}$, $C(=O)R_{25}$. In a further embodiment, at least one $R_4$ is methyl, fluoro, chloro, methoxy, $OCH_2CH_2OCH_3$, $OR_{11}$, or $O(CH_2)R_{11}$, $NHR_{11}$, $NH(CH_2)R_{11}$, $C(=O)NHR_{25}$, $(CH_2)C(=O)NHR_{25}$, $NHC(=O)R_{25}$, $(CH_2)NHC(=O)R_{25}$, $NHC(=O)NHR_{25}$, $(CH_2)NHC(=O)NHR_{25}$, or $C(=O)R_{25}$.

In some embodiments of the formulae above, $R_9$ is $(C_1$-$C_4)$ alkyl (e.g., methyl, ethyl, n-propyl, i-propyl, n-butyl, i-butyl, or t-butyl). In another embodiment, $R_9$ is H or $(C_1$-$C_3)$ alkyl (e.g., methyl, ethyl, n-propyl, or i-propyl). In another embodiment, $R_9$ is H, methyl, or ethyl. In another embodiment, $R_9$ is H or methyl. In a further embodiment, $R_9$ is H.

In some embodiments of the formulae above, $R_{10}$ is $(C_1$-$C_3)$ alkyl (e.g., methyl, ethyl, n-propyl, or i-propyl) or $(C_6$-$C_{10})$ aryl. In another embodiment, $R_{10}$ is $(C_1$-$C_3)$ alkyl (e.g., methyl, ethyl, n-propyl, or i-propyl) or phenyl. In another embodiment, $R_{10}$ is methyl, ethyl, or phenyl. In a further embodiment, $R_{10}$ is methyl or phenyl In some embodiments of the formulae above, $R_{11}$ is $(C_3$-$C_7)$ cycloalkyl (e.g., cyclopropyl, cyclobutyl, cyclopentyl, cyclohexyl, or cycloheptyl) or $(C_4$-$C_7)$ cycloalkenyl (e.g., cyclobutenyl, cyclopentenyl, cyclohexenyl, or cycloheptenyl). In another embodiment, $R_{11}$ is $(C_6$-$C_{10})$ aryl or 5- or 6-membered heteroaryl comprising 1 to 3 heteroatoms selected from N, O, and S (e.g., pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, and furanyl), wherein the aryl and heteroaryl are optionally substituted with one or more $R_{17}$. In another embodiment, $R_{11}$ is $(C_6$-$C_{10})$ aryl or 5- or 6-membered heteroaryl comprising 1 to 3 heteroatoms selected from N, O, and S, wherein the aryl and heteroaryl are optionally substituted with one to three $R_{17}$. In another embodiment, $R_{11}$ is $(C_4$-$C_7)$ cycloalkenyl, $(C_6$-$C_{10})$ aryl, or 5- or 6-membered heteroaryl comprising 1 to 3 heteroatoms selected from N, O, and S, wherein the aryl and heteroaryl are optionally substituted with one to three $R_{17}$. In another embodiment, $R_{11}$ is $(C_4$-$C_7)$ cycloalkenyl, phenyl, or 5- or 6-membered heteroaryl comprising 1 to 3 heteroatoms selected from N, O, and S, wherein the phenyl and heteroaryl are optionally substituted with one to three $R_{17}$.

In another embodiment, $R_{11}$ is $(C_4$-$C_7)$ cycloalkenyl (e.g., cyclobutenyl, cyclopentenyl, cyclohexenyl, or cycloheptenyl), phenyl, or 5-membered heteroaryl comprising 1 to 3 heteroatoms selected from N, O, and S (e.g., pyrrolyl, pyrazolyl, imidazolyl, thiazolyl, oxazolyl, isooxazolyl, thiadiazolyl, oxadiazolyl, thiophenyl, and furanyl), wherein the phenyl and heteroaryl are optionally substituted with one to three $R_{17}$. In another embodiment, $R_{11}$ is $(C_4$-$C_7)$ cycloalkenyl, phenyl, or 6-membered heteroaryl comprising 1 to 3 heteroatoms selected from N, O, and S (e.g., pyridinyl, pyrazinyl, and pyrimidinyl), wherein the phenyl and heteroaryl are optionally substituted with one to three $R_{17}$. In another embodiment, $R_{11}$ is phenyl or 5-membered heteroaryl comprising 1 to 3 heteroatoms selected from N, O, and S, wherein the phenyl and heteroaryl are optionally substituted with one to three $R_{17}$. In another embodiment, $R_{11}$ is phenyl or 6-membered heteroaryl comprising 1 to 3 heteroatoms selected from N, O, and S, wherein the phenyl and heteroaryl are optionally substituted with one to three $R_{17}$. In another embodiment, $R_{11}$ is phenyl optionally substituted with one to three $R_{17}$. In another embodiment, $R_{11}$ is $(C_4$-$C_7)$ cycloalkenyl, phenyl, or pyridinyl, wherein the phenyl and pyridinyl are optionally substituted with one to three $R_{17}$. In a further embodiment, $R_{11}$ is cycloalkenyl, phenyl, or pyridinyl, wherein the phenyl and pyridinyl are optionally substituted with one to three $R_{17}$. In another embodiment, $R_{11}$ is phenyl or pyridinyl, wherein the phenyl and pyridinyl are optionally substituted with one to three $R_{17}$.

In some embodiments of the formulae above, each $R_{17}$ is independently $C(=O)NH_2$, $C(=O)NH(C_1$-$C_4)$ alkyl (wherein $(C_1$-$C_4)$ alkyl is methyl, ethyl, n-propyl, i-propyl, n-butyl, i-butyl, or t-butyl), or $C(=O)N((C_1$-$C_4)$ alkyl$)_2$ (wherein $(C_1$-$C_4)$ alkyl is methyl, ethyl, n-propyl, i-propyl, n-butyl, i-butyl, or t-butyl).

In some embodiments of the formulae above, at least one $R_{17}$ is $(C_1$-$C_3)$ alkyl (e.g., methyl, ethyl, n-propyl, or i-propyl), $(C_1$-$C_3)$ alkoxy (e.g., methoxy, ethoxy, n-propoxy, or i-propoxy), $(C_1$-$C_3)$ haloalkyl (e.g., $CF_3$, $CHF_2$, $CH_2F$, $CH_2CF_3$, $CF_2CF_3$, $CCl_3$, $CHCl_2$, $CH_2Cl$, etc.), $(C_1$-$C_3)$ haloalkoxy (e.g., $OCF_3$, $OCHF_2$, $OCH_2F$, $OCH_2CF_3$, $OCF_2CF_3$, $OCCl_3$, $OCHCl_2$, $OCH_2Cl$, etc.), or halogen (e.g., F, Cl, Br, or I). In another embodiment, at least one $R_{17}$ is $(C_1$-$C_3)$ alkyl or $(C_1$-$C_3)$ alkoxy. In another embodiment, at least one $R_{17}$ is $(C_1$-$C_3)$ haloalkyl, $(C_1$-$C_3)$ haloalkoxy, or halogen. In another embodiment, at least one $R_{17}$ is $(C_1$-$C_3)$ alkyl, $(C_1$-$C_3)$ haloalkyl, or halogen. In another embodiment, at least one $R_{17}$ is methyl, ethyl, F, Cl, methoxy, ethoxy, $CF_3$, or $OCF_3$. In another embodiment, at least one $R_{17}$ is methyl, ethyl, F, Cl, or $CF_3$. In a further embodiment, at least one $R_{17}$ is methyl, F, Cl, or $CF_3$.

In some embodiments of the formulae above, $R_{25}$ is $(C_1$-$C_4)$ alkyl (e.g., methyl, ethyl, n-propyl, i-propyl, n-butyl, i-butyl, or t-butyl) optionally substituted with one or more $(C_1$-$C_4)$ alkoxy (e.g., methoxy, ethoxy, n-propoxy, i-propoxy, n-butoxy, i-butoxy, or t-butoxy), wherein the alkyl and alkoxy are optionally substituted with one or more substituents selected from $(C_1$-$C_4)$ alkoxy (e.g., methoxy, ethoxy, n-propoxy, i-propoxy, n-butoxy, i-butoxy, or t-butoxy), $(C_1$-$C_4)$ haloalkyl (e.g., $CF_3$, $CHF_2$, $CH_2F$, $CH_2CF_3$, $CF_2CF_3$, $CCl_3$, $CHCl_2$, $CH_2Cl$, etc.), $(C_1$-$C_4)$ alkoxy (e.g., methoxy, ethoxy, n-propoxy, i-propoxy, n-butoxy, i-butoxy, or t-butoxy), $(C_1$-$C_4)$ haloalkyl (e.g., $CF_3$, $CHF_2$, $CH_2F$, $CH_2CF_3$, $CF_2CF_3$, $CCl_3$, $CHCl_2$, $CH_2Cl$, etc.), $(C_1$-$C_4)$ haloalkoxy (e.g., $OCF_3$, $OCHF_2$, $OCH_2F$, $OCH_2CF_3$, $OCF_2CF_3$, $OCCl_3$, $OCHCl_2$, $OCH_2Cl$, etc.), cyano, halogen (e.g., F, Cl, Br, or I), OH, $NH_2$, $(C_6$-$C_{10})$ aryl, and 5- or 6-membered heteroaryl comprising 1 to 3 heteroatoms selected from N, O, and S (e.g., pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, and furanyl). In some embodiments of the formulae above, $R_{25}$ is methyl or ethyl optionally substituted with methoxy or ethoxy, each of which is optionally substituted.

In some embodiments of the formulae above, $R_{25}$ is $(C(R_{26})_2)_x(C_6$-$C_{10})$ aryl, $(C(R_{26})_2)_x$-heteroaryl, wherein the heteroaryl comprises one or two 5- or 6-membered rings and 1 to 3 heteroatoms selected from N, O, and S (e.g., pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, and isoquinolinyl), or $(C(R_{26})_2)_x$-heterocyclyl, wherein the heterocyclyl comprises one or two 4- to 6-membered rings and 1 to 3 heteroatoms selected from N, O, and S (e.g., pyrrolidinyl, pyrazolidinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, dioxanyl, tetrahydroisoquinolinyl, and a spiroheterocyclyl such as oxaazaspiro[3.3]heptanyl), wherein the aryl, heteroaryl, and heterocyclyl are optionally substituted with one to three substituents selected from $(C_1$-$C_4)$ alkyl (e.g., methyl, ethyl, n-propyl, i-propyl, n-butyl, i-butyl, or t-butyl), $(C_1$-$C_4)$ alkoxy (e.g., methoxy, ethoxy, n-propoxy, i-propoxy, n-butoxy, i-butoxy, or t-butoxy), $(C_1$-$C_4)$ haloalkyl (e.g., $CF_3$, $CHF_2$, $CH_2F$, $CH_2CF_3$, $CF_2CF_3$, $CCl_3$, $CHCl_2$, $CH_2Cl$, etc.), $(C_1$-$C_4)$ haloalkoxy (e.g., $OCF_3$, $OCHF_2$, $OCH_2F$, $OCH_2CF_3$, $OCF_2CF_3$, $OCCl_3$, $OCHCl_2$, $OCH_2Cl$, etc.), cyano, halogen (e.g., F, Cl, Br, or I), OH, $NH_2$, $(C_6$-$C_{10})$ aryl, and 5- or 6-membered heteroaryl comprising 1 to 3 heteroatoms selected from N, O, and S (e.g., pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, and furanyl).

In another embodiment, $R_{25}$ is $(C_6-C_{10})$ aryl, $(C(R_{26})_2)(C_6-C_{10})$ aryl, or $(C(R_{26})_2)_2(C_6-C_{10})$ aryl, wherein the aryl is optionally substituted with one to three substituents selected from $(C_1-C_4)$ alkyl, $(C_1-C_4)$ alkoxy, $(C_1-C_4)$ haloalkyl, $(C_1-C_4)$ haloalkoxy, cyano, halogen, OH, and $NH_2$. In another embodiment, $R_{25}$ is $(C_6-C_{10})$-heteroaryl, $(C(R_{26})_2)$-heteroaryl, or $(C(R_{26})_2)_2$-heteroaryl, wherein the heteroaryl is optionally substituted with one to three substituents selected from $(C_1-C_4)$ alkyl, $(C_1-C_4)$ alkoxy, $(C_1-C_4)$ haloalkyl, $(C_1-C_4)$ haloalkoxy, cyano, halogen, OH, and $NH_2$. In another embodiment, $R_{25}$ is $(C_6-C_{10})$-heteroaryl, $(C(R_{26})_2)$-heteroaryl, or $(C(R_{26})_2)_2$-heteroaryl, wherein the heteroaryl is 5-membered heteroaryl comprising 1 to 3 heteroatoms selected from N, O, and S (e.g., pyrrolyl, pyrazolyl, imidazolyl, thiazolyl, oxazolyl, isooxazolyl, thiadiazolyl, oxadiazolyl, thiophenyl, and furanyl) and optionally substituted with one to three substituents selected from $(C_1-C_4)$ alkyl, $(C_1-C_4)$ alkoxy, $(C_1-C_4)$ haloalkyl, $(C_1-C_4)$ haloalkoxy, cyano, halogen, OH, and $NH_2$. In another embodiment, $R_{25}$ is $(C_6-C_{10})$-heteroaryl, $(C(R_{26})_2)$-heteroaryl, or $(C(R_{26})_2)_2$-heteroaryl, wherein the heteroaryl is 6-membered heteroaryl comprising 1 to 3 heteroatoms selected from N, O, and S (e.g., pyridinyl, pyrazinyl, and pyrimidinyl) and optionally substituted with one to three substituents selected from $(C_1-C_4)$ alkyl, $(C_1-C_4)$ alkoxy, $(C_1-C_4)$ haloalkyl, $(C_1-C_4)$ haloalkoxy, cyano, halogen, OH, and $NH_2$. In another embodiment, $R_{25}$ is $(C_6-C_{10})$-heterocyclyl, $(C(R_{26})_2)$-heterocyclyl, or $(C(R_{26})_2)_2$-heterocyclyl optionally substituted with one to three substituents selected from $(C_1-C_4)$ alkyl, $(C_1-C_4)$ alkoxy, $(C_1-C_4)$ haloalkyl, $(C_1-C_4)$ haloalkoxy, cyano, halogen, OH, and $NH_2$. In another embodiment, $R_{25}$ is phenyl or pyridinyl comprising 1 to 3 heteroatoms selected from N, O, and S, and optionally substituted with one to three substituents selected from $(C_1-C_4)$ alkyl, $(C_1-C_4)$ alkoxy, $(C_1-C_4)$ haloalkyl, $(C_1-C_4)$ haloalkoxy, cyano, halogen, OH, and $NH_2$. In another embodiment, $R_{25}$ is phenyl or pyridinyl comprising 1 to 3 heteroatoms selected from N, O, and S, and optionally substituted with one to three halogen.

In some embodiments of the formulae above, each $R_{26}$ is H.

In some embodiments of the formulae above, at least one $R_{26}$ is $(C_1-C_4)$ alkyl (e.g., methyl, ethyl, n-propyl, i-propyl, n-butyl, i-butyl, or t-butyl).

In some embodiments of the formulae above, two $R_{26}$ together with the atom to which they are attached form a $(C_3-C_6)$ cycloalkyl ring (e.g., cyclopropyl, cyclobutyl, cyclopentyl, or cyclohexyl) or 3- or 6-membered heterocyclyl ring comprising 1 to 3 heteroatoms selected from N, O, and S (e.g., [1,3]dioxolanyl, pyrrolidinyl, pyrazolinyl, pyrazolidinyl, imidazolinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, dioxanyl, oxiranyl, aziridinyl, oxetanyl, azetidinyl, and thietanyl). In another embodiment, two $R_{26}$ together with the atom to which they are attached form a cyclopropyl or cyclobutyl ring, or 3- or 4-membered heterocyclyl ring comprising 1 or 2 heteroatoms selected from N, O, and S (e.g., oxiranyl, aziridinyl, oxetanyl, azetidinyl, and thietanyl).

In some embodiments of the formulae above, $R_1$ is $(C_3-C_7)$ cycloalkyl optionally substituted with one or more $R_5$. In another embodiment, $R_1$ is cyclopropyl, cyclobutyl, cyclopentyl, cyclohexyl, or cycloheptyl optionally substituted with one to three $R_5$. In another embodiment, $R_1$ is cyclobutyl, cyclopentyl, cyclohexyl, or cycloheptyl optionally substituted with one to three $R_5$. In another embodiment, $R_1$ is cyclobutyl, cyclopentyl, cyclohexyl, or cycloheptyl substituted with one to three $R_5$. In another embodiment, $R_1$ is cyclopropyl optionally substituted with one to three $R_5$. In another embodiment, $R_1$ is cyclopropyl substituted with one to three $R_5$. In another embodiment, $R_1$ is cyclobutyl optionally substituted with one to three $R_5$. In another embodiment, $R_1$ is cyclobutyl substituted with one to three $R_5$. In another embodiment, $R_1$ is cyclopentyl optionally substituted with one to three $R_5$. In another embodiment, $R_1$ is cyclopentyl substituted with one to three $R_5$. In another embodiment, $R_1$ is cyclohexyl optionally substituted with one to three $R_5$. In another embodiment, $R_1$ is cyclohexyl substituted with one to three $R_5$. In another embodiment, $R_1$ is cycloheptyl optionally substituted with one to three $R_5$. In another embodiment, $R_1$ is cycloheptyl substituted with one to three $R_5$.

In another embodiment, $R_1$ is 4- to 6-membered heterocyclyl comprising 1 to 3 heteroatoms selected from N, O, and S (e.g., [1,3]dioxolanyl, pyrrolidinyl, pyrazolinyl, pyrazolidinyl, imidazolinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, dioxanyl, oxetanyl, azetidinyl, and thietanyl), optionally substituted with one or more $R_5$. In another embodiment, $R_1$ is 4-membered heterocyclyl comprising 1 to 3 heteroatoms selected from N, O, and S (e.g., oxetanyl, azetidinyl, and thietanyl), optionally substituted with one or more $R_5$. In another embodiment, $R_1$ is 5-membered heterocyclyl comprising 1 to 3 heteroatoms selected from N, O, and S (e.g., [1,3]dioxolanyl, pyrrolidinyl, pyrazolinyl, pyrazolidinyl, imidazolinyl, imidazolidinyl, oxazolidinyl, isoxazolidinyl, thiazolidinyl, isothiazolidinyl, and tetrahydrofuryl), optionally substituted with one or more $R_5$. In another embodiment, $R_1$ is 6-membered heterocyclyl comprising 1 to 3 heteroatoms selected from N, O, and S (e.g., piperidinyl, piperazinyl, morpholinyl, tetrahydropyranyl, and dioxanyl), optionally substituted with one or more $R_5$. In another embodiment, $R_1$ is piperidinyl, tetrahydrofuranyl, tetrahydropyranyl, pyrrolidinyl, or 1,4-dioxanyl optionally substituted with one or more $R_5$. In another embodiment, $R_1$ is piperidinyl, tetrahydrofuranyl, tetrahydropyranyl, pyrrolidinyl, or 1,4-dioxanyl optionally substituted with one to three $R_5$. In another embodiment, $R_1$ is piperidinyl, tetrahydrofuranyl, tetrahydropyranyl, pyrrolidinyl, or 1,4-dioxanyl substituted with one to three $R_5$. In another embodiment, $R_1$ is piperidinyl optionally substituted with one to three $R_5$. In another embodiment, $R_1$ is tetrahydrofuranyl optionally substituted with one to three $R_5$. In another embodiment, $R_1$ is tetrahydropyranyl optionally substituted with one to three $R_5$. In another embodiment, $R_1$ is pyrrolidinyl optionally substituted with one to three $R_5$. In another embodiment, $R_1$ is 1,4-dioxanyl optionally substituted with one to three $R_5$. In a further embodiment, $R_1$ is cyclohexyl, cyclopentyl, cyclobutyl, tetrahydropyran, tetrahydrofuran, piperidinyl, 1,4-dioxane, pyrrolyl, or cyclohexanone wherein each substituted with one to two $R_5$.

In some embodiments of the formulae above, at least one $R_5$ is (i) $(C_1-C_6)$ alkyl (e.g., methyl, ethyl, n-propyl, i-propyl, n-butyl, i-butyl, t-butyl, pentyl, or hexyl) optionally substituted with one to three $(C_1-C_4)$ alkoxy (e.g., methoxy, ethoxy, n-propoxy, i-propoxy, n-butoxy, i-butoxy, or t-butoxy) or phenyl, (ii) $(C_2-C_4)$ alkenyl (e.g., ethenyl, propenyl, or butenyl) optionally substituted with one or more $C(=O)$ $(C_1-C_4)$ alkyl (wherein $(C_1-C_4)$ alkyl is methyl, ethyl, n-propyl, i-propyl, n-butyl, i-butyl, or t-butyl), (iii) $(C(R_{12})_2)_rOH$, (iv) $(C(R_{12})_2)_rNR_{13}R_{14}$, (v) $C(=O)OH$, (vi) $C(=O)O(C_1-C_4)$ alkyl (wherein $(C_1-C_4)$ alkyl is methyl, ethyl, n-propyl, i-propyl, n-butyl, i-butyl, or t-butyl), (vii) $C(=O)NR_{13}R_{15}$, (viii) $C(=O)R_{16}$, (ix) $S(O)_pR_{16}$, or (x) 5- or 6-membered heteroaryl comprising 1 to 3 heteroatoms selected from N, O, and S (e.g., pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, and furanyl) and optionally substituted with one to three $(C_1-C_4)$ alkyl (e.g., methyl, ethyl, n-propyl, i-propyl, n-butyl, i-butyl, or t-butyl), (xi) or two $R_5$ together with the carbon atom to which they are attached form (=O), or (xii) two $R_5$ together with the atoms to which they are attached form a bridged 3- to 6-membered heterocyclyl ring comprising 1 to 3 heteroatoms selected from N, O, and S (e.g., pyrrolidinyl, pyrazolidinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, dioxanyl, oxetanyl, azetidinyl, thietanyl, oxiranyl, aziridinyl, and thiiranyl). In another embodiment, at least one $R_5$ is (i) $(C_1-C_6)$ alkyl optionally substituted with one to three $(C_1-C_4)$ alkoxy or phenyl, (ii) $(C_2-C_4)$ alkenyl optionally substituted with one or more $C(=O)(C_1-C_4)$ alkyl, (iii) $(C(R_{12})_2)_rOH$, (iv) $(C(R_{12})_2)_rNR_{13}R_{14}$, (v) $C(=O)OH$, (vi) $C(=O)O(C_1-C_4)$ alkyl, (vii) $C(=O)NR_{13}R_{15}$, (viii) $C(=O)R_{16}$, (ix) $S(O)_pR_{16}$, or (x) 5- or 6-membered heteroaryl comprising 1 to 3 heteroatoms selected from N, O, and S and optionally substituted with one to three $(C_1-C_4)$ alkyl, (xi) or two $R_5$ together with the carbon atom to which they are attached form (=O). In another embodiment, at least one $R_5$ is (i) $(C_2-C_4)$ alkenyl optionally substituted with one or more $C(=O)(C_1-C_4)$ alkyl, (ii) $(C(R_{12})_2)_rOH$, (iii) $(C(R_{12})_2)_rNR_{13}R_{14}$, (iv) $C(=O)O(C_1-C_4)$ alkyl, (v) $C(=O)NR_{13}R_{15}$, (vi) $C(=O)R_{16}$, or (vii) $S(O)_pR_{16}$. In another embodiment, at least one $R_5$ is (i) $(C_2-C_4)$ alkenyl optionally substituted with one or more $C(=O)(C_1-C_4)$ alkyl or (ii) $S(O)_pR_{16}$.

In some embodiments of the formulae above, at least one $R_5$ is (i) $(C_1-C_4)$ alkyl (e.g., methyl, ethyl, n-propyl, i-propyl, n-butyl, i-butyl, or t-butyl) optionally substituted with one to two $(C_1-C_4)$ alkoxy (e.g., methoxy, ethoxy, n-propoxy, i-propoxy, n-butoxy, i-butoxy, or t-butoxy) or phenyl, (ii) $(C(R_{12})_2)_rOH$, (iii) $(C(R_{12})_2)_rNR_{13}R_{14}$, (iv) $C(=O)OH$, (v) $C(=O)O(C_1-C_4)$ alkyl (wherein $(C_1-C_4)$ alkyl is methyl, ethyl, n-propyl, i-propyl, n-butyl, i-butyl, or t-butyl), (vi) $C(=O)NR_{13}R_{15}$, (vii) $C(=O)R_{16}$, (viii) $S(O)_pR_{16}$, or (ix) 5- or 6-membered heteroaryl comprising 1 to 3 heteroatoms selected from N, O, and S (e.g., pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, and furanyl) and optionally substituted with one or more $(C_1-C_4)$ alkyl (e.g., methyl, ethyl, n-propyl, i-propyl, n-butyl, i-butyl, or t-butyl), or (x) two $R_5$ together with the carbon atom to which they are attached form (=O), or (xi) two $R_5$ together with the atoms to which they are attached form a bridged 3- to 6-membered heterocyclyl ring comprising 1 to 3 heteroatoms selected from N, O, and S (e.g., pyrrolidinyl, pyrazolidinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, dioxanyl, oxetanyl, azetidinyl, thietanyl, oxiranyl, aziridinyl, and thiiranyl). In another embodiment, $R_5$ is independently (i) $(C_1-C_4)$ alkyl optionally substituted with one to two $(C_1-C_4)$ alkoxy or phenyl, (ii) $(C(R_{12})_2)_rOH$, (iii) $(C(R_{12})_2)_rNR_{13}R_{14}$, (iv) $C(=O)O(C_1-C_4)$ alkyl, (v) $C(=O)NR_{13}R_{15}$, (vi) $C(=O)R_{16}$, or (vii) $S(O)_pR_{16}$. In another embodiment, (i) two $R_5$ together with the carbon atom to which they are attached form (=O), or (ii) two $R_5$ together with the atoms to which they are attached form a bridged 3- to 6-membered heterocyclyl ring comprising 1 to 3 heteroatoms selected from N, O, and S.

In some embodiments of the formulae above, at least one $R_5$ is (i) $(C_1-C_3)$ alkyl (e.g., methyl, ethyl, n-propyl, or i-propyl) optionally substituted with one to three $(C_1-C_4)$ alkoxy (e.g., methoxy, ethoxy, n-propoxy, i-propoxy, n-butoxy, i-butoxy, or t-butoxy) or phenyl, (ii) $(C(R_{12})_2)_rOH$, (iii) $(C(R_{12})_2)_rNR_{13}R_{14}$, (iv) $C(=O)OH$, (v) $C(=O)O(C_1-C_4)$ alkyl (wherein $(C_1-C_4)$ alkyl is methyl, ethyl, n-propyl, i-propyl, n-butyl, i-butyl, or t-butyl), (vi) $C(=O)NR_{13}R_{15}$, (vii) $C(=O)R_{16}$, or (viii) 5- or 6-membered heteroaryl comprising 1 to 3 heteroatoms selected from N, O, and S (e.g., pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, and furanyl), and optionally substituted with one or more $(C_1-C_4)$ alkyl (e.g., methyl, ethyl, n-propyl, i-propyl, n-butyl, i-butyl, or t-butyl). In another embodiment, at least one $R_5$ is (i) $(C_1-C_3)$ alkyl optionally substituted with one to three $(C_1-C_4)$ alkoxy or phenyl, (ii) $(C(R_{12})_2)_rOH$, (iii) $(C(R_{12})_2)_rNR_{13}R_{14}$, (iv) $C(=O)OH$, (v) $C(=O)O(C_1-C_4)$ alkyl, (vi) $C(=O)NR_{13}R_{15}$, (vii) $C(=O)R_{16}$, (viii) 5- or 6-membered heteroaryl comprising 1 to 3 heteroatoms selected from N, O, and S and optionally substituted with one or more $(C_1-C_4)$ alkyl, or (ix) two $R_5$ together with the carbon atom to which they are attached form (=O). In another embodiment, at least one $R_5$ is (i) $(C_1-C_2)$ alkyl (i.e., methyl or ethyl) optionally substituted with one to three $(C_1-C_4)$ alkoxy (e.g., methoxy, ethoxy, n-propoxy, i-propoxy, n-butoxy, i-butoxy, or t-butoxy) or phenyl, (ii) $(C(R_{12})_2)_rOH$, or (iii) $(C(R_{12})_2)_rNR_{13}R_{14}$. In another embodiment, at least one $R_5$ is (i) $C(=O)OH$, (ii) $C(=O)O(C_1-C_4)$ alkyl, (iii) $C(=O)NR_{13}R_{15}$, or (iv) $C(=O)R_{16}$. In another embodiment, at least one $R_5$ is (i) $(C(R_{12})_2)_rOH$, (ii) $(C(R_{12})_2)_rNR_{13}R_{14}$, (iii) $C(=O)NR_{13}R_{15}$, or (iv) $C(=O)R_{16}$. In another embodiment, at least one $R_5$ is (i) $(C_1-C_2)$ alkyl optionally substituted with one to three $(C_1-C_4)$ alkoxy or phenyl, (ii) $(C(R_{12})_2)_rOH$, (iii) $(C(R_{12})_2)_rNR_{13}R_{14}$, (iv) $C(=O)O(C_1-C_4)$ alkyl, or (v) $C(=O)NR_{13}R_{15}$. In another embodiment, at least one $R_5$ is (i) $(C_1-C_2)$ alkyl optionally substituted with one to three $(C_1-C_4)$ alkoxy or phenyl, (ii) $(C(R_{12})_2)_rOH$, (iii) $(C(R_{12})_2)_rNR_{13}R_{14}$, (iv) $C(=O)NR_{13}R_{15}$, (v) $C(=O)R_{16}$.

In another embodiment, at least one $R_5$ is (i) $C(=O)OH$, (ii) $C(=O)O(C_1-C_4)$ alkyl (wherein $(C_1-C_4)$ alkyl is methyl, ethyl, n-propyl, i-propyl, n-butyl, i-butyl, or t-butyl), (iii) $C(=O)NR_{13}R_{15}$, or (iv) $C(=O)R_{16}$. In another embodiment, at least one $R_5$ is (i) $(C(R_{12})_2)_rOH$, (ii) $(C(R_{12})_2)_rNR_{13}R_{14}$, (iii) $C(=O)NR_{13}R_{15}$, or (iv) $C(=O)R_{16}$. In another embodiment, at least one $R_5$ is (i) $(C(R_{12})_2)_rOH$, (ii) $(C(R_{12})_2)_rNR_{13}R_{14}$, (iii) $C(=O)NR_{13}R_{15}$, (iv) $C(=O)R_{16}$, or (v) two $R_5$ together with the carbon atom to which they are attached form (=O). In another embodiment, at least one $R_5$ is (i) $(C_1-C_2)$ alkyl (i.e., methyl or ethyl) optionally substituted with one to three $(C_1-C_4)$ alkoxy (e.g., methoxy, ethoxy, n-propoxy, i-propoxy, n-butoxy, i-butoxy, or t-butoxy) or phenyl, (ii) $(C(R_{12})_2)_rOH$, (iii) $(C(R_{12})_2)_rNR_{13}R_{14}$, (iv) $C(=O)O(C_1-C_4)$ alkyl, or (v) $C(=O)NR_{13}R_{15}$. In another embodiment, at least one $R_5$ is (i) $(C_1-C_2)$ alkyl (i.e., methyl or ethyl) optionally substituted with one to three $(C_1-C_4)$ alkoxy (e.g., methoxy, ethoxy, n-propoxy, i-propoxy, n-butoxy, i-butoxy, or t-butoxy) or phenyl, (ii) $(C(R_{12})_2)_rOH$, (iii) $(C(R_{12})_2)_rNR_{13}R_{14}$, (iv) $C(=O)NR_{13}R_{15}$, or (v) $C(=O)R_{16}$.

In some embodiments of the formulae above, two $R_5$ together with the carbon atom to which they are attached form (=O). In another embodiment, at least one $R_5$ is (i) $(C_1-C_2)$ alkyl (i.e., methyl or ethyl) optionally substituted with one to three $(C_1-C_4)$ alkoxy (e.g., methoxy, ethoxy, n-propoxy, i-propoxy, n-butoxy, i-butoxy, or t-butoxy) or phenyl, (ii) $(C(R_{12})_2)_rOH$, (iii) $(C(R_{12})_2)_rNR_{13}R_{14}$, (iv) $C(=O)NR_{13}R_{15}$, (v) $C(=O)R_{16}$, or (vi) two $R_5$ together with the carbon atom to which they are attached form (=O).

In some embodiments of the formulae above, at least one $R_{12}$ is $(C_1-C_4)$ alkyl (e.g., methyl, ethyl, n-propyl, i-propyl, n-butyl, i-butyl, or t-butyl). In another embodiment, at least one $R_{12}$ is H or $(C_1-C_3)$ alkyl (e.g., methyl, ethyl, n-propyl, or i-propyl). In another embodiment, at least one $R_{12}$ is H, methyl, or ethyl. In another embodiment, at least one $R_{12}$ is H. In a further embodiment, at least one $R_{12}$ is H or methyl. In another embodiment, each $R_{12}$ is H.

In some embodiments of the formulae above, $R_{13}$ is $(C_1-C_4)$ alkyl (e.g., methyl, ethyl, n-propyl, i-propyl, n-butyl, i-butyl, or t-butyl). In another embodiment, $R_{13}$ is H or $(C_1-C_3)$ alkyl (e.g., methyl, ethyl, n-propyl, or i-propyl). In another embodiment, $R_{13}$ is H, methyl, or ethyl. In another embodiment, $R_{13}$ is H or methyl. In another embodiment, $R_{13}$ is H.

In some embodiments of the formulae above, $R_{14}$ is (i) H, (ii) $(C_1-C_4)$ alkyl (e.g., methyl, ethyl, n-propyl, i-propyl, n-butyl, i-butyl, or t-butyl), (iii) $(C(R_{18})_2)_rC(=O)NR_{19}R_{20}$, (iv) $(CH_2)_n(C_6-C_{10})$ aryl optionally substituted with one to three $(C_1-C_4)$ alkyl (e.g., methyl, ethyl, n-propyl, i-propyl, n-butyl, i-butyl, or t-butyl) or halogen (e.g., F, Cl, Br, or I), (v) $C(=O)R_{21}$, (vi) $C(=O)O(C_1-C_4)$ alkyl (wherein $(C_1-C_4)$ alkyl is methyl, ethyl, n-propyl, i-propyl, n-butyl, i-butyl, or t-butyl), (vii) $S(O)_2(C_1-C_8)$ alkyl (wherein $(C_1-C_8)$ alkyl is methyl, ethyl, n-propyl, i-propyl, n-butyl, i-butyl, t-butyl, hexyl, heptyl, octyl), (viii) $S(O)_2NH(C_1-C_8)$ alkyl (wherein $(C_1-C_8)$ alkyl is methyl, ethyl, n-propyl, i-propyl, n-butyl, i-butyl, t-butyl, hexyl, heptyl, octyl), (ix) $S(O)_2N((C_1-C_8)\;alkyl)_2$, or (x) $C(=O)(C_1-C_8)$ alkyl (wherein $(C_1-C_8)$ alkyl is methyl, ethyl, n-propyl, i-propyl, n-butyl, i-butyl, t-butyl, hexyl, heptyl, octyl) optionally substituted with one or more $R_{22}$. In another embodiment, $R_{14}$ is (i) $S(O)_2(C_1-C_8)$ alkyl, (ii) $S(O)_2NH(C_1-C_8)$ alkyl, (iii) $S(O)_2N((C_1-C_8)\;alkyl)_2$, or (iv) $C(=O)(C_1-C_8)$ alkyl optionally substituted with one or more $R_{22}$.

In some embodiments of the formulae above, $R_{14}$ is (i) H, (ii) $(C_1-C_2)$ alkyl (i.e., methyl or ethyl), (iii) $(C(R_{18})_2)_rC(=O)NR_{19}R_{20}$, (iv) $(CH_2)_n(C_6-C_{10})$ aryl optionally substituted with one to three $(C_1-C_4)$ alkyl (e.g., methyl, ethyl, n-propyl, i-propyl, n-butyl, i-butyl, or t-butyl) or halogen (e.g., F, Cl, Br, or I), (v) $C(=O)R_{21}$, (vi) $C(=O)O(C_1-C_4)$ alkyl (wherein $(C_1-C_4)$ alkyl is methyl, ethyl, n-propyl, i-propyl, n-butyl, i-butyl, or t-butyl), or (viii) $C(=O)(C_1-C_8)$ alkyl (wherein $(C_1-C_8)$ alkyl is methyl, ethyl, n-propyl, i-propyl, n-butyl, i-butyl, t-butyl, hexyl, heptyl, octyl) optionally substituted with one or more $R_{22}$. In another embodiment, $R_{14}$ is (i) H, (ii) $(C_1-C_2)$ alkyl, (iii) $(C(R_{18})_2)_rC(=O)NR_{19}R_{20}$, (iv) $(CH_2)_n(C_6-C_{10})$ aryl optionally substituted with one to three $(C_1-C_4)$ alkyl or halogen. In another embodiment, $R_{14}$ is (i) H, (ii) $(C_1-C_2)$ alkyl, (iii) $C(=O)R_{21}$, (iv) $C(=O)O(C_1-C_4)$ alkyl, or (v) $C(=O)(C_1-C_8)$ alkyl optionally substituted with one or more $R_{22}$. In another embodiment, $R_{14}$ is (i) $(C(R_{18})_2)_rC(=O)NR_{19}R_{20}$, (ii) $(CH_2)_n(C_6-C_{10})$ aryl optionally substituted with one to three $(C_1-C_4)$ alkyl or halogen, (iii) $C(=O)R_{21}$, (iv) $C(=O)O(C_1-C_4)$ alkyl, or (v) $C(=O)(C_1-C_8)$ alkyl optionally substituted with one or more $R_{22}$. In another embodiment, $R_{14}$ is (i) H, (ii) $(C_1-C_2)$ alkyl, (iii) $(CH_2)_n(C_6-C_{10})$ aryl optionally substituted with one to three $(C_1-C_4)$ alkyl or halogen, (iv) $C(=O)R_{21}$, (v) $C(=O)O(C_1-C_4)$ alkyl, or (v) $C(=O)(C_1-C_8)$ alkyl optionally substituted with one or more $R_{22}$. In another embodiment, $R_{14}$ is (i) $C(=O)R_{21}$, (ii) $C(=O)O(C_1-C_4)$ alkyl, or (iii) $C(=O)(C_1-C_8)$ alkyl optionally substituted with one or more $R_{22}$.

In some embodiments of the formulae above, at least one $R_{22}$ is (i) $(C_1-C_2)$ alkoxy (i.e., methoxy or ethoxy), (ii) OH, (iii) $NH_2$, (iv) $(C_1-C_2)$ alkylamino (i.e., methylamino or ethylamino), (v) di-$(C_1-C_2)$ alkylamino (i.e., dimethylamino, methylethylamino or diethylamino), or (vi) 5- or 6-membered heterocyclyl comprising 1 to 3 heteroatoms selected from N, O, and S (e.g., pyrrolidinyl, pyrazolidinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, and dioxanyl) and optionally substituted with one or more substituents selected from (a) $(C_1-C_4)$ alkyl (e.g., methyl, ethyl, n-propyl, i-propyl, n-butyl, i-butyl, or t-butyl), (b) $(CH_2)_x(C_6-C_{10})$ aryl, and (c) $C(=O)(C_6-C_{10})$aryl optionally substituted with one or more $(C_1-C_4)$ alkyl (e.g., methyl, ethyl, n-propyl, i-propyl, n-butyl, i-butyl, or t-butyl). In another embodiment, at least one $R_{22}$ is (i) $(C_1-C_4)$ alkoxy (e.g., methoxy, ethoxy, n-propoxy, i-propoxy, n-butoxy, i-butoxy, or t-butoxy), (ii) OH, (iii) $NH_2$, (iv) $(C_1-C_4)$ alkylamino (e.g., methylamino, ethylamino, propylamino, or butylamino), or (v) di-$(C_1-C_4)$ alkylamino (e.g., dimethylamino, diethylamino, dipropylamino, or dibutylamino). In another embodiment, at least one $R_{22}$ is 5- or 6-membered heterocyclyl comprising 1 to 3 heteroatoms selected from N, O, and S and optionally substituted with one or more substituents selected from (a) $(C_1-C_4)$ alkyl, (b) $(CH_2)_x(C_6-C_{10})$ aryl, and (c) $C(=O)(C_6-C_{10})$aryl optionally substituted with one or more $(C_1-C_4)$ alkyl.

In another embodiment, at least one $R_{22}$ is (i) $(C_1-C_2)$ alkoxy (i.e., methoxy or ethoxy), (ii) OH, (iii) di-$(C_1-C_2)$ alkylamino (i.e., dimethylamino, methylethylamino or diethylamino), or (iv) 5- or 6-membered heterocyclyl comprising 1 to 3 heteroatoms selected from N, O, and S (e.g., pyrrolidinyl, pyrazolidinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, and dioxanyl) and optionally substituted with one to two substituents selected from (a) $(C_1-C_4)$ alkyl (e.g., methyl, ethyl, n-propyl, i-propyl, n-butyl, i-butyl, or t-butyl), (b) $(CH_2)_x(C_6-C_{10})$ aryl, and (c) $C(=O)(C_6-C_{10})$aryl optionally substituted with one or more $(C_1-C_4)$ alkyl (e.g., methyl, ethyl, n-propyl, i-propyl, n-butyl, i-butyl, or t-butyl). In another embodiment, at least one $R_{22}$ is (i) $(C_1-C_2)$ alkoxy, (ii) OH, (iii) di-$(C_1-C_2)$ alkylamino, or (iv) 6-membered heterocyclyl comprising 1 to 3 heteroatoms selected from N, O, and S (e.g., piperidinyl, piperazinyl, morpholinyl, tetrahydropyranyl, and dioxanyl) and optionally substituted with one to two substituents selected from (a) $(C_1-C_4)$ alkyl, (b) $(CH_2)_x(C_6-C_{10})$ aryl, and (c) $C(=O)(C_6-C_{10})$ aryl optionally substituted with one or more $(C_1-C_4)$ alkyl.

In some embodiments of the formulae above, at least one $R_{18}$ is $(C_1-C_4)$ alkyl (e.g., methyl, ethyl, n-propyl, i-propyl, n-butyl, i-butyl, or t-butyl). In another embodiment, at least one $R_{18}$ is H or $(C_1-C_3)$ alkyl (e.g., methyl, ethyl, n-propyl, or i-propyl). In another embodiment, at least one $R_{18}$ is H, methyl, or ethyl. In another embodiment, at least one $R_{18}$ is H or methyl. In another embodiment, each $R_{18}$ is H.

In some embodiments of the formulae above, $R_{19}$ is $(C_1-C_4)$ alkyl (e.g., methyl, ethyl, n-propyl, i-propyl, n-butyl, i-butyl, or t-butyl). In another embodiment, $R_{19}$ is H or $(C_1-C_3)$ alkyl (e.g., methyl, ethyl, n-propyl, or i-propyl). In another embodiment, $R_{19}$ is H, methyl, or ethyl. In another embodiment, $R_{19}$ is H or methyl. In another embodiment, $R_{19}$ is H.

In some embodiments of the formulae above, $R_{20}$ is H or $(CH_2)_n(C_6-C_{10})$ aryl optionally substituted with one to three $(C_1-C_4)$ alkyl (e.g., methyl, ethyl, n-propyl, i-propyl, n-butyl, i-butyl, or t-butyl). In another embodiment, $R_{20}$ is H. In another embodiment, $R_{20}$ is $(CH_2)_n$phenyl optionally substituted with one to three $(C_1-C_4)$ alkyl (e.g., methyl, ethyl, n-propyl, i-propyl, n-butyl, i-butyl, or t-butyl). In another embodiment, $R_{20}$ is H or $(CH_2)_n$phenyl optionally substituted with one to three $(C_1-C_4)$ alkyl.

In some embodiments of the formulae above, $R_{21}$ is $(C_3-C_7)$ cycloalkyl (e.g., cyclopropyl, cyclobutyl, cyclopentyl, cyclohexyl, or cycloheptyl), 5- or 6-membered heterocyclyl comprising 1 to 3 heteroatoms selected from N, O, and S (e.g., pyrrolidinyl, pyrazolidinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, and dioxanyl), $(C_6-C_{10})$ aryl, or 5- or 6-membered heteroaryl comprising 1 to 3 heteroatoms selected from N, O, and S (e.g., pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, and furanyl), wherein the aryl, heteroaryl, cycloalkyl, and heterocyclyl are optionally substituted with one to three substituents selected from $(C_1-C_4)$ alkyl (e.g., methyl, ethyl, n-propyl, i-propyl, n-butyl, i-butyl, or t-butyl), $(C_1-C_4)$ alkoxy (e.g., methoxy, ethoxy, n-propoxy, i-propoxy, n-butoxy, i-butoxy, or t-butoxy), $(C_1-C_4)$ haloalkyl (e.g., $CF_3$, $CHF_2$, $CH_2F$, $CH_2CF_3$, $CF_2CF_3$, $CCl_3$, $CHCl_2$, $CH_2Cl$, etc.), $(C_1-C_4)$ haloalkoxy (e.g., $OCF_3$, $OCHF_2$, $OCH_2F$, $OCH_2CF_3$, $OCF_2CF_3$, $OCCl_3$, $OCHCl_2$, $OCH_2Cl$, etc.), OH, and halogen (e.g., F, Cl, Br, or I). In another embodiment, $R_{21}$ is $(C_3-C_7)$ cycloalkyl or 5- or 6-membered heterocyclyl comprising 1 to 3 heteroatoms selected from N, O, and S, wherein the cycloalkyl and heterocyclyl are optionally substituted with one to three substituents selected from $(C_1-C_4)$ alkyl, $(C_1-C_4)$ alkoxy, $(C_1-C_4)$ haloalkyl, $(C_1-C_4)$ haloalkoxy, OH, and halogen. In another embodiment, $R_{21}$ is $(C_6-C_{10})$ aryl or 5- or 6-membered heteroaryl comprising 1 to 3 heteroatoms selected from N, O, and S, wherein the aryl and heteroaryl are optionally substituted with one to three substituents selected from $(C_1-C_4)$ alkyl, $(C_1-C_4)$ alkoxy, $(C_1-C_4)$ haloalkyl, $(C_1-C_4)$ haloalkoxy, OH, and halogen.

In some embodiments of the formulae above, $R_{16}$ is (i) $(C_1-C_4)$ alkyl (e.g., methyl, ethyl, n-propyl, i-propyl, n-butyl, i-butyl, or t-butyl), (ii) $(C_2-C_4)$ alkenyl (e.g., ethenyl, propenyl, butenyl), (iii) $(C_2-C_4)$ alkynyl (e.g., ethynyl, propynyl, butynyl), or (iv) 3- to 6-membered heterocyclyl comprising 1 to 3 heteroatoms selected from N, O, and S (e.g., pyrrolidinyl, pyrazolidinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, dioxanyl, oxetanyl, azetidinyl, thietanyl, oxiranyl, aziridinyl, and thiiranyl), wherein the alkyl, alkenyl, and alkynyl are optionally substituted with one to three substituents selected from $(C_1-C_4)$ alkoxy (e.g., methoxy, ethoxy, n-propoxy, i-propoxy, n-butoxy, i-butoxy, or t-butoxy), O-phenyl, halogen (e.g., F, Cl, Br, or I), CN, $NH_2$, $(C_1-C_4)$ alkylamino (e.g., methylamino, ethylamino, propylamino, or butylamino), di-$(C_1-C_4)$ alkylamino (e.g., dimethylamino, diethylamino, dipropylamino, or dibutylamino), and $OS(O)_2(C_1-C_4)$ alkyl (wherein $(C_1-C_4)$ alkyl is methyl, ethyl, n-propyl, i-propyl, n-butyl, i-butyl, or t-butyl), and wherein the heterocyclyl is optionally substituted with one or more $R_{23}$. In another embodiment, $R_{16}$ is (ii) $(C_2-C_4)$ alkenyl, (iii) $(C_2-C_4)$ alkynyl, or (iv) 3- to 6-membered heterocyclyl comprising 1 to 3 heteroatoms selected from N, O, and S, wherein the alkenyl and alkynyl are optionally substituted with one to three substituents selected from $(C_1-C_4)$ alkoxy, O-phenyl, halogen, CN, $NH_2$, $(C_1-C_4)$ alkylamino, di-$(C_1-C_4)$ alkylamino, and $OS(O)_2(C_1-C_4)$ alkyl, and wherein the heterocyclyl is optionally substituted with one or more $R_{23}$. In another embodiment, $R_{16}$ is (ii) $(C_2-C_4)$ alkenyl, (iii) $(C_2-C_4)$ alkynyl, or (iv) 3- to 6-membered heterocyclyl comprising 1 to 3 heteroatoms selected from N, O, and S, wherein the alkenyl, and alkynyl are optionally substituted with one to three substituents selected from O-phenyl, halogen, CN, and $OS(O)_2(C_1-C_4)$ alkyl, and wherein the heterocyclyl is optionally substituted with one or more $R_{23}$.

In some embodiments of the formulae above, $R_{16}$ is $(C_1-C_4)$ alkyl (e.g., methyl, ethyl, n-propyl, i-propyl, n-butyl, i-butyl, or t-butyl) or 5- or 6-membered heterocyclyl (e.g., pyrrolidinyl, pyrazolidinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, and dioxanyl) comprising 1 to 3 heteroatoms selected from N, O, and S, wherein the alkyl is optionally substituted with one to three substituents selected from $(C_1-C_4)$ alkoxy (e.g., methoxy, ethoxy, n-propoxy, i-propoxy, n-butoxy, i-butoxy, or t-butoxy), $NH_2$, $(C_1-C_4)$ alkylamino (e.g., methylamino, ethylamino, propylamino, or butylamino), and di-$(C_1-C_4)$ alkylamino (e.g., dimethylamino, diethylamino, dipropylamino, or dibutylamino), and wherein the heterocyclyl is optionally substituted with one to three $R_{23}$. In another embodiment, $R_{16}$ is $(C_1-C_4)$ alkyl optionally substituted with one to three substituents selected from $(C_1-C_4)$ alkoxy, $NH_2$, $(C_1-C_4)$ alkylamino, and di-$(C_1-C_4)$ alkylamino. In another embodiment, $R_{16}$ is 5- or 6-membered heterocyclyl comprising 1 to 3 heteroatoms selected from N, O, and S and optionally substituted with one to three $R_{23}$. In another embodiment, $R_{16}$ is 5-membered heterocyclyl comprising 1 to 3 heteroatoms selected from N, O, and S (e.g., pyrrolidinyl, pyrazolidinyl, imidazolidinyl, oxazolidinyl, isoxazolidinyl, thiazolidinyl, isothiazolidinyl, and tetrahydrofuryl) and optionally substituted with one to three $R_{23}$. In another embodiment, $R_{16}$ is 6-membered heterocyclyl comprising 1 to 3 heteroatoms selected from N, O, and S (e.g., piperidinyl, piperazinyl, morpholinyl, tetrahydropyranyl, and dioxanyl) and optionally substituted with one to three $R_{23}$.

In another embodiment, $R_{16}$ is $(C_1-C_4)$ alkyl (e.g., methyl, ethyl, n-propyl, i-propyl, n-butyl, i-butyl, or t-butyl) optionally substituted with one to three substituents selected from $(C_1-C_4)$ alkoxy (e.g., methoxy, ethoxy, n-propoxy, i-propoxy, n-butoxy, i-butoxy, or t-butoxy) and di-$(C_1-C_4)$ alkylamino (e.g., dimethylamino, diethylamino, dipropylamino, or dibutylamino). In another embodiment, $R_{16}$ is $(C_1-C_4)$ alkyl optionally substituted with one to three substituents selected from $(C_1-C_4)$ alkoxy and di-$(C_1-C_4)$ alkylamino, or 5- or 6-membered heterocyclyl comprising 1 to 3 heteroatoms selected from N, O, and S (e.g., pyrrolidinyl, pyrazolidinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, and dioxanyl) and optionally substituted with one to three $R_{23}$. In another embodiment, $R_{16}$ is $(C_1-C_4)$ alkyl optionally substituted with one to three substituents selected from $(C_1-C_4)$ alkoxy and di-($C_1$-$C_4$) alkylamino, or 6-membered heterocyclyl comprising 1 to 3 heteroatoms selected from N, O, and S (e.g., piperidinyl, piperazinyl, morpholinyl, tetrahydropyranyl, and dioxanyl) and optionally substituted with one to three $R_{23}$. In another embodiment, $R_{16}$ is ($C_1$-$C_4$) alkyl optionally substituted with one to three substituents selected from ($C_1$-$C_4$) alkoxy, and di-($C_1$-$C_4$) alkylamino or 5-membered heterocyclyl comprising 1 to 3 heteroatoms selected from N, O, and S (e.g., pyrrolidinyl, pyrazolidinyl, imidazolidinyl, oxazolidinyl, isoxazolidinyl, thiazolidinyl, isothiazolidinyl, and tetrahydrofuryl) and optionally substituted with one to three $R_{23}$.

In another embodiment, $R_{16}$ is (i) ($C_1$-$C_4$) alkyl (e.g., methyl, ethyl, n-propyl, i-propyl, n-butyl, i-butyl, or t-butyl), (ii) ($C_2$-$C_4$) alkenyl (e.g., ethenyl, propenyl, butenyl), (iii) ($C_2$-$C_4$) alkynyl (e.g., ethynyl, propynyl, butynyl), or (iv) 5- or 6-membered heterocyclyl comprising 1 to 3 heteroatoms selected from N, O, and S (e.g., pyrrolidinyl, pyrazolidinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, and dioxanyl), wherein the alkyl, alkenyl, and alkynyl are optionally substituted with one to three substituents selected from ($C_1$-$C_4$) alkoxy (e.g., methoxy, ethoxy, n-propoxy, i-propoxy, n-butoxy, i-butoxy, or t-butoxy), CN, $NH_2$, ($C_1$-$C_4$) alkylamino (e.g., methylamino, ethylamino, propylamino, or butylamino), and di-($C_1$-$C_4$) alkylamino (e.g., dimethylamino, diethylamino, dipropylamino, or dibutylamino), and wherein the heterocyclyl is optionally substituted with one or more $R_{23}$. In another embodiment, $R_{16}$ is (i) ($C_1$-$C_4$) alkyl, (ii) ($C_2$-$C_4$) alkenyl, or (iii) ($C_2$-$C_4$) alkynyl, wherein the alkyl, alkenyl, and alkynyl are optionally substituted with one to three substituents selected from ($C_1$-$C_4$) alkoxy, CN, $NH_2$, ($C_1$-$C_4$) alkylamino, and di-($C_1$-$C_4$) alkylamino. In another embodiment, $R_{16}$ is (i) ($C_2$-$C_4$) alkenyl or (ii) ($C_2$-$C_4$) alkynyl, wherein the alkenyl and alkynyl are optionally substituted with one to three substituents selected from ($C_1$-$C_4$) alkoxy, CN, $NH_2$, ($C_1$-$C_4$) alkylamino, and di-($C_1$-$C_4$) alkylamino.

In some embodiments of the formulae above, at least one $R_{23}$ is ($C_1$-$C_4$) alkyl (e.g., methyl, ethyl, n-propyl, i-propyl, n-butyl, i-butyl, or t-butyl) or C(=O)($C_1$-$C_4$) alkyl (wherein ($C_1$-$C_4$) alkyl is methyl, ethyl, n-propyl, i-propyl, n-butyl, i-butyl, or t-butyl). In another embodiment, at least one $R_{23}$ is ($C_1$-$C_3$) alkyl (e.g., methyl, ethyl, n-propyl, or i-propyl). In another embodiment, at least one $R_{23}$ is methyl or ethyl. In another embodiment, each $R_{23}$ is independently C(=O)($C_1$-$C_4$) alkyl or two $R_{23}$ together with the atoms to which they are attached form a 5- or 6-membered heterocyclyl ring comprising 1 to 3 heteroatoms selected from N, O, and S (e.g., pyrrolidinyl, pyrazolidinyl, imidazolidinyl, oxazolidinyl, isoxazolidinyl, thiazolidinyl, isothiazolidinyl, and tetrahydrofuryl). In another embodiment, each $R_{23}$ is independently C(=O)($C_1$-$C_4$) alkyl.

In some embodiments of the formulae above, two $R_{23}$ together with the atoms to which they are attached form a 5-membered heterocyclyl ring comprising 1 to 3 heteroatoms selected from N, O, and S (e.g., pyrrolidinyl, pyrazolidinyl, imidazolidinyl, oxazolidinyl, isoxazolidinyl, thiazolidinyl, isothiazolidinyl, and tetrahydrofuryl). In another embodiment, two $R_{23}$ together with the atoms to which they are attached form a 6-membered heterocyclyl ring comprising 1 to 3 heteroatoms selected from N, O, and S (e.g., piperidinyl, piperazinyl, morpholinyl, tetrahydropyranyl, and dioxanyl).

In some embodiments of the formulae above, $R_{13}$ and $R_{14}$ together with the nitrogen atom to which they are attached form a 4- to 6-membered heterocyclyl ring comprising 1 to 3 heteroatoms selected from N, O, and S (e.g., pyrrolidinyl, pyrazolidinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, dioxanyl, oxetanyl, azetidinyl, and thietanyl) optionally substituted with one to three substituents selected from ($C_1$-$C_4$) alkyl (e.g., methyl, ethyl, n-propyl, i-propyl, n-butyl, i-butyl, or t-butyl), ($C_1$-$C_4$) alkoxy (e.g., methoxy, ethoxy, n-propoxy, i-propoxy, n-butoxy, i-butoxy, or t-butoxy), OH, $NH_2$, and (=O). In another embodiment, $R_{13}$ and $R_{14}$ together with the nitrogen atom to which they are attached form a 4- or 5-membered heterocyclyl ring comprising 1 to 3 heteroatoms selected from N, O, and S (e.g., pyrrolidinyl, pyrazolidinyl, imidazolidinyl, oxazolidinyl, isoxazolidinyl, thiazolidinyl, isothiazolidinyl, tetrahydrofuryl, oxetanyl, azetidinyl, and thietanyl) optionally substituted with one to three substituents selected from ($C_1$-$C_4$) alkyl (e.g., methyl, ethyl, n-propyl, i-propyl, n-butyl, i-butyl, or t-butyl), ($C_1$-$C_4$) alkoxy (e.g., methoxy, ethoxy, n-propoxy, i-propoxy, n-butoxy, i-butoxy, or t-butoxy), OH, $NH_2$, and (=O). In another embodiment, $R_{13}$ and $R_{14}$ together with the nitrogen atom to which they are attached form a 5- or 6-membered heterocyclyl ring comprising 1 to 3 heteroatoms selected from N, O, and S (e.g., pyrrolidinyl, pyrazolidinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, and dioxanyl) optionally substituted with one to three substituents selected from ($C_1$-$C_4$) alkyl (e.g., methyl, ethyl, n-propyl, i-propyl, n-butyl, i-butyl, or t-butyl), ($C_1$-$C_4$) alkoxy (e.g., methoxy, ethoxy, n-propoxy, i-propoxy, n-butoxy, i-butoxy, or t-butoxy), OH, $NH_2$, and (=O). In another embodiment, $R_{13}$ and $R_{14}$ together with the nitrogen atom to which they are attached form a 4-membered heterocyclyl ring comprising 1 to 3 heteroatoms selected from N, O, and S (e.g., oxetanyl, azetidinyl, and thietanyl) optionally substituted with one to three substituents selected from ($C_1$-$C_4$) alkyl (e.g., methyl, ethyl, n-propyl, i-propyl, n-butyl, i-butyl, or t-butyl), ($C_1$-$C_4$) alkoxy (e.g., methoxy, ethoxy, n-propoxy, i-propoxy, n-butoxy, i-butoxy, or t-butoxy), OH, $NH_2$, and (=O). In another embodiment, $R_{13}$ and $R_{14}$ together with the nitrogen atom to which they are attached form a 5-membered heterocyclyl ring comprising 1 to 3 heteroatoms selected from N, O, and S (e.g., pyrrolidinyl, pyrazolidinyl, imidazolidinyl, oxazolidinyl, isoxazolidinyl, thiazolidinyl, isothiazolidinyl, and tetrahydrofuryl) optionally substituted with one to three substituents selected from ($C_1$-$C_4$) alkyl (e.g., methyl, ethyl, n-propyl, i-propyl, n-butyl, i-butyl, or t-butyl), ($C_1$-$C_4$) alkoxy (e.g., methoxy, ethoxy, n-propoxy, i-propoxy, n-butoxy, i-butoxy, or t-butoxy), OH, $NH_2$, and (=O). In another embodiment, $R_{13}$ and $R_{14}$ together with the nitrogen atom to which they are attached form a 6-membered heterocyclyl ring comprising 1 to 3 heteroatoms selected from N, O, and S (e.g., piperidinyl, piperazinyl, morpholinyl, tetrahydropyranyl, and dioxanyl) optionally substituted with one to three substituents selected from ($C_1$-$C_4$) alkyl (e.g., methyl, ethyl, n-propyl, i-propyl, n-butyl, i-butyl, or t-butyl), ($C_1$-$C_4$) alkoxy (e.g., methoxy, ethoxy, n-propoxy, i-propoxy, n-butoxy, i-butoxy, or t-butoxy), OH, $NH_2$, and (=O).

In some embodiments of the formulae above, $R_{15}$ is (i) H or (ii) ($C_1$-$C_4$) alkyl (e.g., methyl, ethyl, n-propyl, i-propyl, n-butyl, i-butyl, or t-butyl) optionally substituted with one or more substituents selected from OH, 5- or 6-membered heterocyclyl comprising 1 to 3 heteroatoms selected from N, O, and S (e.g., pyrrolidinyl, pyrazolidinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, and dioxanyl), and 5- or 6-membered heteroaryl comprising 1 to 3 heteroatoms selected from N, O, and S (e.g., pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, and furanyl). In another embodiment, $R_{15}$ is (i) 5- or 6-membered heterocyclyl comprising 1 to 3 heteroatoms selected from N, O, and S (e.g., pyrrolidinyl, pyrazolidinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, and dioxanyl) or (ii) ($C_1$-$C_4$) alkyl (e.g., methyl, ethyl, n-propyl, i-propyl, n-butyl, i-butyl, or t-butyl) optionally substituted with one or more substituents selected from OH, 5- or 6-membered heterocyclyl comprising 1 to 3 heteroatoms selected from N, O, and S (e.g., pyrrolidinyl, pyrazolidinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, and dioxanyl), and 5- or 6-membered heteroaryl comprising 1 to 3 heteroatoms selected from N, O, and S (e.g., pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, and furanyl). In another embodiment, $R_{15}$ is (i) H, (ii) 6-membered heterocyclyl comprising 1 to 3 heteroatoms selected from N, O, and S (e.g., piperidinyl, piperazinyl, morpholinyl, tetrahydropyranyl, and dioxanyl), or (iii) ($C_1$-$C_4$) alkyl (e.g., methyl, ethyl, n-propyl, i-propyl, n-butyl, i-butyl, or t-butyl) optionally substituted with one or more substituents selected from OH, 5- or 6-membered heterocyclyl comprising 1 to 3 heteroatoms selected from N, O, and S (e.g., pyrrolidinyl, pyrazolidinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, and dioxanyl), and 5- or 6-membered heteroaryl comprising 1 to 3 heteroatoms selected from N, O, and S (e.g., pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, and furanyl). In another embodiment, $R_{15}$ is (i) H, (ii) 5-membered heterocyclyl comprising 1 to 3 heteroatoms selected from N, O, and S (e.g., pyrrolidinyl, pyrazolidinyl, imidazolidinyl, oxazolidinyl, isoxazolidinyl, thiazolidinyl, isothiazolidinyl, and tetrahydrofuryl), or (iii) ($C_1$-$C_4$) alkyl (e.g., methyl, ethyl, n-propyl, i-propyl, n-butyl, i-butyl, or t-butyl) optionally substituted with one or more substituents selected from OH, 5- or 6-membered heterocyclyl comprising 1 to 3 heteroatoms selected from N, O, and S (e.g., pyrrolidinyl, pyrazolidinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, and dioxanyl), and 5- or 6-membered heteroaryl comprising 1 to 3 heteroatoms selected from N, O, and S (e.g., pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, and furanyl). In another embodiment, $R_{15}$ is H. In another embodiment, $R_{15}$ is 5- or 6-membered heterocyclyl comprising 1 to 3 heteroatoms selected from N, O, and S. In another embodiment, $R_{15}$ is 5-membered heterocyclyl comprising 1 to 3 heteroatoms selected from N, O, and S. In another embodiment, $R_{15}$ is 6-membered heterocyclyl comprising 1 to 3 heteroatoms selected from N, O, and S. In another embodiment, $R_{15}$ is ($C_1$-$C_4$) alkyl optionally substituted with one or more substituents selected from OH, 5- or 6-membered heterocyclyl comprising 1 to 3 heteroatoms selected from N, O, and S, and 5- or 6-membered heteroaryl comprising 1 to 3 heteroatoms selected from N, O, and S. In another embodiment, $R_{15}$ is ($C_1$-$C_4$) alkyl optionally substituted with one or more substituents selected from OH, 6-membered heterocyclyl comprising 1 to 3 heteroatoms selected from N, O, and S, and 6-membered heteroaryl comprising 1 to 3 heteroatoms selected from N, O, and S. In another embodiment, $R_{15}$ is ($C_1$-$C_4$) alkyl optionally substituted with one or more substituents selected from OH, 5-membered heterocyclyl comprising 1 to 3 heteroatoms selected from N, O, and S, and 5-membered heteroaryl comprising 1 to 3 heteroatoms selected from N, O, and S.

In some embodiments of the formulae above, $R_{13}$ and $R_{15}$ together with the nitrogen atom to which they are attached form a 4- to 6-membered heterocyclyl ring comprising 1 to 3 heteroatoms selected from N, O, and S (e.g., [1,3]dioxolanyl, pyrrolidinyl, pyrazolinyl, pyrazolidinyl, imidazolinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, dioxanyl, oxetanyl, azetidinyl, and thietanyl) and optionally substituted with one to three substituents selected from ($C_1$-$C_4$) alkyl (e.g., methyl, ethyl, n-propyl, i-propyl, n-butyl, i-butyl, or t-butyl), ($C_1$-$C_4$) alkoxy (e.g., methoxy, ethoxy, n-propoxy, i-propoxy, n-butoxy, i-butoxy, or t-butoxy), and OH, or form a 5- to 8-membered bicyclic heterocyclyl ring comprising 1 to 3 heteroatoms selected from N, O, and S and optionally substituted with one to three substituents selected from ($C_1$-$C_4$) alkyl (e.g., methyl, ethyl, n-propyl, i-propyl, n-butyl, i-butyl, or t-butyl), ($C_1$-$C_4$) alkoxy (e.g., methoxy, ethoxy, n-propoxy, i-propoxy, n-butoxy, i-butoxy, or t-butoxy), and OH. In another embodiment, $R_{13}$ and $R_{15}$ together with the nitrogen atom to which they are attached form a 4- to 6-membered heterocyclyl ring comprising 1 to 3 heteroatoms selected from N, O, and S and optionally substituted with one to three substituents selected from ($C_1$-$C_4$) alkyl, ($C_1$-$C_4$) alkoxy, and OH. In another embodiment, $R_{13}$ and $R_{15}$ together with the nitrogen atom to which they are attached form a 5- to 8-membered bicyclic heterocyclyl ring comprising 1 to 3 heteroatoms selected from N, O, and S and optionally substituted with one to three substituents selected from ($C_1$-$C_4$) alkyl, ($C_1$-$C_4$) alkoxy, and OH. In another embodiment, $R_{13}$ and $R_{15}$ together with the nitrogen atom to which they are attached form a 4- to 6-membered heterocyclyl ring comprising 1 to 3 heteroatoms selected from N, O, and S and optionally substituted with one to three substituents selected from ($C_1$-$C_4$) alkyl, ($C_1$-$C_4$) alkoxy, and OH, or form a 7- to 8-membered bicyclic heterocyclyl ring comprising 1 to 3 heteroatoms selected from N, O, and S and optionally substituted with one to three substituents selected from ($C_1$-$C_4$) alkyl, ($C_1$-$C_4$) alkoxy, and OH.

In some embodiments of the formulae above, $R_2$ is ($C_1$-$C_4$) alkyl (e.g., methyl, ethyl, n-propyl, i-propyl, n-butyl, i-butyl, or t-butyl). In another embodiment, $R_2$ is H or ($C_1$-$C_3$) alkyl (e.g., methyl, ethyl, n-propyl, or i-propyl). In another embodiment, $R_2$ is H, methyl, or ethyl. In another embodiment, $R_2$ is H or methyl. In a further embodiment, $R_2$ is H.

In some embodiments of the formulae above, when q is 0, $R_1$ and $R_2$ together with the nitrogen atom to which they are attached form a 5- or 6-membered heterocyclyl ring comprising 0 to 1 additional heteroatoms selected from N, O, and S (e.g., pyrrolidinyl, pyrazolidinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, and dioxanyl) and optionally substituted with one to two $NR_6R_7$. In another embodiment, when q is 0, $R_1$ and $R_2$ together with the nitrogen atom to which they are attached form a 5- or 6-membered heterocyclyl ring comprising 0 to 1 additional heteroatoms selected from N, O, and S and substituted with one to two $NR_6R_7$. In another embodiment, when q is 0, $R_1$ and $R_2$ together with the nitrogen atom to which they are attached form a 5-membered heterocyclyl ring comprising 0 to 1 additional heteroatoms selected from N, O, and S (e.g., pyrrolidinyl, pyrazolidinyl, imidazolidinyl, oxazolidinyl, isoxazolidinyl, thiazolidinyl, isothiazolidinyl, and tetrahydrofuryl) and optionally substituted with one or more $NR_6R_7$. In another embodiment, when q is 0, $R_1$ and $R_2$ together with the nitrogen atom to which they are attached form a 5-membered heterocyclyl ring comprising 0 to 1 additional heteroatoms selected from N, O, and S and optionally substituted with one to two $NR_6R_7$. In another embodiment, when q is 0, $R_1$ and $R_2$ together with the nitrogen atom to which they are attached form a 5-membered heterocyclyl ring comprising 0 to 1 additional heteroatoms selected from N, O, and S and substituted with one to two $NR_6R_7$. In another embodiment, when q is 0, $R_1$ and $R_2$ together with the nitrogen atom to which they are attached form a 6-membered heterocyclyl ring comprising 0 to 1 additional heteroatoms selected from N, O, and S (e.g., piperidinyl, piperazinyl, morpholinyl, tetrahydropyranyl, and dioxanyl) and optionally substituted with one or more $NR_6R_7$. In another embodiment, when q is 0, $R_1$ and $R_2$ together with the nitrogen atom to which they are attached form a 6-membered heterocyclyl ring comprising 0 to 1 additional heteroatoms selected from N, O, and S and optionally substituted with one to two $NR_6R_7$. In another embodiment, when q is 0, $R_1$ and $R_2$ together with the nitrogen atom to which they are attached form a 6-membered heterocyclyl ring comprising 0 to 1 additional heteroatoms selected from N, O, and S and substituted with one to two $NR_6R_7$.

In some embodiments of the formulae above, $R_6$ is $(C_1-C_4)$ alkyl (e.g., methyl, ethyl, n-propyl, i-propyl, n-butyl, i-butyl, or t-butyl). In another embodiment, $R_6$ is H or $(C_1-C_3)$ alkyl (e.g., methyl, ethyl, n-propyl, or i-propyl). In another embodiment, $R_6$ is H, methyl, or ethyl. In another embodiment, $R_6$ is H or methyl. In another embodiment, $R_6$ is H.

In some embodiments of the formulae above, $R_7$ is H or $(C_1-C_4)$ alkyl (e.g., methyl, ethyl, n-propyl, i-propyl, n-butyl, i-butyl, or t-butyl). In another embodiment, $R_7$ is $(C_1-C_4)$ alkyl (e.g., methyl, ethyl, n-propyl, i-propyl, n-butyl, i-butyl, or t-butyl) or $C(=O)R_{24}$. In another embodiment, $R_7$ is H, $(C_1-C_3)$ alkyl (e.g., methyl, ethyl, n-propyl, or i-propyl), or $C(=O)R_{24}$. In another embodiment, $R_7$ is H, methyl, ethyl, or $C(=O)R_{24}$. In another embodiment, $R_7$ is methyl, ethyl, or $C(=O)R_{24}$. In another embodiment, $R_7$ is H or $C(=O)R_{24}$.

In some embodiments of the formulae above, $R_{24}$ is $(C_1-C_4)$ alkyl (e.g., methyl, ethyl, n-propyl, i-propyl, n-butyl, i-butyl, or t-butyl) optionally substituted with one to three $(C_1-C_4)$ alkoxy (e.g., methoxy, ethoxy, n-propoxy, i-propoxy, n-butoxy, i-butoxy, or t-butoxy). In another embodiment, $R_{24}$ is $(C_1-C_4)$ alkyl (e.g., methyl, ethyl, n-propyl, i-propyl, n-butyl, i-butyl, or t-butyl) optionally substituted with one to three 5- or 6-membered heterocyclyl comprising 1 to 3 heteroatoms selected from N, O, and S (e.g., pyrrolidinyl, pyrazolidinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, and dioxanyl). In another embodiment, $R_{24}$ is $(C_1-C_4)$ alkyl substituted with one to three substituents selected from $(C_1-C_4)$ alkoxy and 5- or 6-membered heterocyclyl comprising 1 to 3 heteroatoms selected from N, O, and S. In another embodiment, $R_{24}$ is $(C_1-C_2)$ alkyl (i.e., methyl or ethyl) optionally substituted with one to three substituents selected from $(C_1-C_4)$ alkoxy (e.g., methoxy, ethoxy, n-propoxy, i-propoxy, n-butoxy, i-butoxy, or t-butoxy) and 5- or 6-membered heterocyclyl comprising 1 to 3 heteroatoms selected from N, O, and S (e.g., pyrrolidinyl, pyrazolidinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, and dioxanyl). In another embodiment, $R_{24}$ is $(C_1-C_2)$ alkyl optionally substituted with one to three substituents selected from $(C_1-C_2)$ alkoxy (i.e., methoxy or ethoxy) and 6-membered heterocyclyl comprising 1 to 3 heteroatoms selected from N, O, and S (e.g., piperidinyl, piperazinyl, morpholinyl, tetrahydropyranyl, tetrahydrofuryl, and dioxanyl).

In some embodiments of the formulae above, $R_3$ is $N(R_8)_2$. In another embodiment, $R_3$ is $NH_2$, $NHCH_3$, $N(CH_3)_2$, or 4-methylpiperzinyl. In another embodiment, $R_3$ is H, $NH_2$, $NHCH_3$, $N(CH_3)_2$, or 4-methylpiperzinyl. In another embodiment, $R_3$ is H, $NH_2$, $NHCH_3$, or 4-methylpiperzinyl. In a further embodiment, $R_3$ is H.

In some embodiments of the formulae above, at least one $R_8$ is (i) H, (ii) $(C_1-C_4)$ alkyl (e.g., methyl, ethyl, n-propyl, i-propyl, n-butyl, i-butyl, or t-butyl), or (iii) 5- or 6-membered heterocyclyl comprising 1 to 3 heteroatoms selected from N, O, and S (e.g., pyrrolidinyl, pyrazolidinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, and dioxanyl) and optionally substituted with one or more $(C_1-C_4)$ alkyl (e.g., methyl, ethyl, n-propyl, i-propyl, n-butyl, i-butyl, or t-butyl). In another embodiment, at least one $R_8$ is (i) H, (ii) $(C_1-C_2)$ alkyl (i.e., methyl or ethyl), or (iii) 5- or 6-membered heterocyclyl comprising 1 to 3 heteroatoms selected from N, O, and S and optionally substituted with one to three $(C_1-C_4)$ alkyl (e.g., methyl, ethyl, n-propyl, i-propyl, n-butyl, i-butyl, or t-butyl). In another embodiment, at least one $R_8$ is (i) H, (ii) $(C_1-C_2)$ alkyl, or (iii) 5-membered heterocyclyl comprising 1 to 3 heteroatoms selected from N, O, and S (e.g., pyrrolidinyl, pyrazolidinyl, imidazolidinyl, oxazolidinyl, isoxazolidinyl, thiazolidinyl, isothiazolidinyl, and tetrahydrofuryl) and optionally substituted with one to three $(C_1-C_4)$ alkyl (e.g., methyl, ethyl, n-propyl, i-propyl, n-butyl, i-butyl, or t-butyl). In another embodiment, at least one $R_8$ is (i) H, (ii) $(C_1-C_2)$ alkyl, or (iii) 6-membered heterocyclyl comprising 1 to 3 heteroatoms selected from N, O, and S (e.g., piperidinyl, piperazinyl, morpholinyl, tetrahydropyranyl, and dioxanyl) and optionally substituted with one to three $(C_1-C_4)$ alkyl (e.g., methyl, ethyl, n-propyl, i-propyl, n-butyl, i-butyl, or t-butyl). In another embodiment, at least one $R_8$ is (i) H or (ii) $(C_1-C_2)$ alkyl.

In some embodiments of the formulae above, two $R_8$ together with the nitrogen atom to which they are attached form a 5- or 6-membered heterocyclyl ring comprising 0 to 1 additional heteroatoms selected from N, O, and S (e.g., pyrrolidinyl, pyrazolidinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, and dioxanyl) and optionally substituted with one to three $(C_1-C_4)$ alkyl (e.g., methyl, ethyl, n-propyl, i-propyl, n-butyl, i-butyl, or t-butyl). In another embodiment, two $R_8$ together with the nitrogen atom to which they are attached form a 5-membered heterocyclyl ring comprising 0 to 1 additional heteroatoms selected from N, O, and S (e.g., pyrrolidinyl, pyrazolidinyl, imidazolidinyl, oxazolidinyl, isoxazolidinyl, thiazolidinyl, isothiazolidinyl, and tetrahydrofuryl) and optionally substituted with one or more $(C_1-$ $C_4$) alkyl (e.g., methyl, ethyl, n-propyl, i-propyl, n-butyl, i-butyl, or t-butyl). In another embodiment, two $R_8$ together with the nitrogen atom to which they are attached form a 6-membered heterocyclyl ring comprising 0 to 1 additional heteroatoms selected from N, O, and S (e.g., piperidinyl, piperazinyl, morpholinyl, tetrahydropyranyl, and dioxanyl) and optionally substituted with one or more ($C_1$-$C_4$) alkyl (e.g., methyl, ethyl, n-propyl, i-propyl, n-butyl, i-butyl, or t-butyl). In another embodiment, two $R_8$ together with the nitrogen atom to which they are attached form a 5-membered heterocyclyl ring comprising 0 to 1 additional heteroatoms selected from N, O, and S and optionally substituted with one to three ($C_1$-$C_4$) alkyl. In another embodiment, two $R_8$ together with the nitrogen atom to which they are attached form a 6-membered heterocyclyl ring comprising 0 to 1 additional heteroatoms selected from N, O, and S and optionally substituted with one to three ($C_1$-$C_4$) alkyl. In another embodiment, two $R_8$ together with the nitrogen atom to which they are attached form a 5-membered heterocyclyl ring comprising 0 to 1 additional heteroatoms selected from N, O, and S and substituted with one to three ($C_1$-$C_4$) alkyl. In another embodiment, two $R_8$ together with the nitrogen atom to which they are attached form a 6-membered heterocyclyl ring comprising 0 to 1 additional heteroatoms selected from N, O, and S and substituted with one to three ($C_1$-$C_4$) alkyl.

In another embodiment, at least one $R_8$ is (i) H, (ii) ($C_1$-$C_2$) alkyl (i.e., methyl or ethyl), (iii) 6-membered heterocyclyl comprising 1 to 3 heteroatoms selected from N, O, and S (e.g., piperidinyl, piperazinyl, morpholinyl, tetrahydropyranyl, and dioxanyl) and optionally substituted with one to three ($C_1$-$C_4$) alkyl (e.g., methyl, ethyl, n-propyl, i-propyl, n-butyl, i-butyl, or t-butyl), or (iv) two $R_8$ together with the nitrogen atom to which they are attached form a 5- or 6-membered heterocyclyl ring comprising 0 to 1 additional heteroatoms selected from N, O, and S (e.g., pyrrolidinyl, pyrazolidinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, and dioxanyl) and optionally substituted with one to three ($C_1$-$C_4$) alkyl (e.g., methyl, ethyl, n-propyl, i-propyl, n-butyl, i-butyl, or t-butyl). In a further embodiment, at least one $R_8$ is (i) H, (ii) ($C_1$-$C_2$) alkyl (i.e., methyl or ethyl), or (iii) two $R_8$ together with the nitrogen atom to which they are attached form a 6-membered heterocyclyl ring (e.g., piperidinyl, piperazinyl, morpholinyl, tetrahydropyranyl, and dioxanyl) comprising 0 to 1 additional heteroatoms selected from N, O, and S and substituted with one to three ($C_1$-$C_4$) alkyl (e.g., methyl, ethyl, n-propyl, i-propyl, n-butyl, i-butyl, or t-butyl).

In some embodiments of the formulae above, n is 0 or 1. In another embodiment, n is 1 or 2. In another embodiment, n is 0. In another embodiment, n is 1. In another embodiment, n is 2.

In some embodiments of the formulae above, p is 0 or 1. In another embodiment, p is 1 or 2. In another embodiment, p is 0. In another embodiment, p is 1. In another embodiment, p is 2.

In some embodiments of the formulae above, r is 0, 1 or 2. In another embodiment, r is 1, 2, or 3. In another embodiment, r is 0 or 1. In another embodiment, r is 1 or 2. In another embodiment, r is 2 or 3. In another embodiment, r is 0. In another embodiment, r is 1. In another embodiment, r is 2. In another embodiment, r is 3.

In some embodiments of the formulae above, q is 0, 1 or 2. In another embodiment, q is 1, 2, or 3. In another embodiment, q is 0 or 1. In another embodiment, q is 1 or 2. In another embodiment, q is 2 or 3. In another embodiment, q is 0. In another embodiment, q is 1. In another embodiment, q is 2. In another embodiment, q is 3.

In some embodiments of the formulae above, x is 0, 1 or 2. In another embodiment, x is 1, 2, or 3. In another embodiment, x is 0 or 1. In another embodiment, x is 1 or 2. In another embodiment, x is 2 or 3. In another embodiment, x is 0. In another embodiment, x is 1. In another embodiment, x is 2. In another embodiment, x is 3.

In some embodiments of the formulae above, when $R_4$ is $NR_9S(O)_pR_{10}$, $O(CH_2)_nR_{11}$, $NH(CH_2)_nR_{11}$, $(CH_2)_nC(=O)NHR_{25}$, $(CH_2)_nNHC(=O)R_{25}$, $(CH_2)_nNHC(=O)NHR_{25}$, $C(=O)R_{25}$, or heterocyclyl comprising one or two 4- to 6-membered rings and 1 to 3 heteroatoms selected from N, O, and S and optionally substituted with one or more substituents selected from ($C_1$-$C_4$) alkyl, ($C_1$-$C_4$) haloalkyl, $C(=O)(C_1$-$C_4)$ alkyl, and halogen, A is optionally substituted with one additional $R_4$. In some embodiments of the formulae above, when $R_4$ is $NR_9S(O)_pR_{10}$, $O(CH_2)_nR_{11}$, $NH(CH_2)_nR_{11}$, $(CH_2)_nC(=O)NHR_{25}$, $(CH_2)_nNHC(=O)R_{25}$, $(CH_2)_nNHC(=O)NHR_{25}$, or $C(=O)R_{25}$, A is optionally substituted with one additional $R_4$. In some embodiments of the formulae above, when $R_4$ is $(CH_2)_nC(=O)NHR_{25}$, $(CH_2)_nNHC(=O)R_{25}$, $(CH_2)_nNHC(=O)NHR_{25}$, or $C(=O)R_{25}$, A is optionally substituted with one additional $R_4$. In some embodiments of the formulae above, when $R_4$ is $(CH_2)_nC(=O)NHR_{25}$ or $(CH_2)_nNHC(=O)R_{25}$, A is optionally substituted with one additional $R_4$. In some embodiments of the formulae above, when $R_4$ is $O(CH_2)_nR_{11}$ or $NH(CH_2)_nR_{11}$, A is optionally substituted with one additional $R_4$.

In some embodiments of the formulae above, when $R_4$ is $(CH_2)_nC(=O)NHR_{25}$, $(CH_2)_nNHC(=O)R_{25}$, or $NR_9S(O)_pR_{10}$, A is optionally substituted with one additional $R_4$.

In some embodiments of the formulae above, A is substituted with one to two $R_4$ and $R_4$ is ($C_1$-$C_4$) alkyl (e.g., methyl, ethyl, n-propyl, i-propyl, n-butyl, i-butyl, or t-butyl), ($C_1$-$C_4$) alkoxy (e.g., methoxy, ethoxy, n-propoxy, i-propoxy, n-butoxy, i-butoxy, or t-butoxy), ($C_1$-$C_4$) haloalkyl (e.g., $CF_3$, $CHF_2$, $CH_2F$, $CH_2CF_3$, $CF_2CF_3$, $CCl_3$, $CHCl_2$, $CH_2Cl$, etc.), ($C_1$-$C_4$) haloalkoxy (e.g., $OCF_3$, $OCHF_2$, $OCH_2F$, $OCH_2CF_3$, $OCF_2CF_3$, $OCCl_3$, $OCHCl_2$, $OCH_2Cl$, etc.), halogen (e.g., F, Cl, Br, or I), $NR_9S(O)_pR_{10}$, $O(CH_2)_nR_{11}$, $NH(CH_2)_nR_{11}$, $(CH_2)_nC(=O)NHR_{25}$, $(CH_2)_nNHC(=O)R_{25}$, $(CH_2)_nNHC(=O)NHR_{25}$, or $C(=O)R_{25}$. In another embodiment, A is substituted with one or more $R_4$ and $R_4$ is ($C_1$-$C_4$) alkyl (e.g., methyl, ethyl, n-propyl, i-propyl, n-butyl, i-butyl, or t-butyl), ($C_1$-$C_4$) alkoxy (e.g., methoxy, ethoxy, n-propoxy, i-propoxy, n-butoxy, i-butoxy, or t-butoxy), ($C_1$-$C_4$) haloalkyl (e.g., $CF_3$, $CHF_2$, $CH_2F$, $CH_2CF_3$, $CF_2CF_3$, $CCl_3$, $CHCl_2$, $CH_2Cl$, etc.), ($C_1$-$C_4$) haloalkoxy (e.g., $OCF_3$, $OCHF_2$, $OCH_2F$, $OCH_2CF_3$, $OCF_2CF_3$, $OCCl_3$, $OCHCl_2$, $OCH_2Cl$, etc.), halogen (e.g., F, Cl, Br, or I), $O(CH_2)_nR_{11}$, $NH(CH_2)_nR_{11}$, $(CH_2)_nC(=O)NHR_{25}$, $(CH_2)_nNHC(=O)R_{25}$, $(CH_2)_nNHC(=O)NHR_{25}$, or $C(=O)R_{25}$.

In some embodiments of the formulae above, the compounds of Formula (I) is not (2-chloro-4-phenoxyphenyl) (4-(((3R,6S)-6-(hydroxymethyl)tetrahydro-2H-pyran-3-yl) amino)-7H-pyrrolo[2,3-d]pyrimidin-5-yl)methanone.

In some embodiments of the formulae above, A is phenyl, thiophenyl, or pyridinyl optionally substituted with one or more $R_4$.

In some embodiments of the formulae above, A is phenyl, thiophenyl, or pyridinyl substituted with one to two $R_4$.

In some embodiments of the formulae above, A is phenyl substituted with one to two $R_4$.

In some embodiments of the formulae above, $R_3$ is H, $NH_2$, $NHCH_3$, or 4-methylpiperazine.

In some embodiments of the formulae above, at least one $R_4$ is $(C_1-C_4)$ alkyl (e.g., methyl, ethyl, n-propyl, i-propyl, n-butyl, i-butyl, or t-butyl), $(C_1-C_4)$ alkoxy (e.g., methoxy, ethoxy, n-propoxy, i-propoxy, n-butoxy, i-butoxy, or t-butoxy), halogen (e.g., F, Cl, Br, or I), $NR_9S(O)_pR_{10}$, $O(CH_2)_nR_{11}$, $NH(CH_2)_nR_{11}$, $C(=O)NHR_{25}$, $NHC(=O)R_{25}$, $NHC(=O)NHR_{25}$, $(CH_2)C(=O)NHR_{25}$, $(CH_2)NHC(=O)R_{25}$, $(CH_2)NHC(=O)NHR_{25}$, or $C(=O)R_{25}$.

In some embodiments of the formulae above, at least one $R_4$ is $(C_1-C_4)$ alkyl (e.g., methyl, ethyl, n-propyl, i-propyl, n-butyl, i-butyl, or t-butyl), $(C_1-C_4)$ alkoxy (e.g., methoxy, ethoxy, n-propoxy, i-propoxy, n-butoxy, i-butoxy, or t-butoxy), halogen (e.g., F, Cl, Br, or I), or $O(CH_2)_nR_{11}$, $C(=O)NHR_{25}$, $NHC(=O)R_{25}$, $NHC(=O)NHR_{25}$, $(CH_2)C(=O)NHR_{25}$, $(CH_2)NHC(=O)R_{25}$, $(CH_2)NHC(=O)NHR_{25}$, or $C(=O)R_{25}$.

In some embodiments of the formulae above, $R_{11}$ is $(C_6-C_{10})$ aryl or 5- or 6-membered heteroaryl comprising 1 to 3 heteroatoms selected from N, O, and S, wherein the aryl and heteroaryl are optionally substituted with one to three $R_{17}$.

In some embodiments of the formulae above, $R_{11}$ is phenyl or pyridinyl, and is optionally substituted with one to three $R_{17}$.

In some embodiments of the formulae above, $R_1$ is $(C_4-C_6)$ cycloalkyl (e.g., cyclobutyl, cyclopentyl, cyclohexyl) substituted with one to three $R_5$.

In some embodiments of the formulae above, $R_1$ is cyclohexyl substituted with one to three $R_5$.

In some embodiments of the formulae above, $R_1$ is 4- to 6-membered heterocyclyl comprising 1 to 3 heteroatoms selected from N, O, and S optionally substituted with one to three $R_5$.

In some embodiments of the formulae above, $R_1$ is piperidinyl, tetrahydrofuranyl, tetrahydropyranyl, pyrrolidinyl, or 1,4-dioxanyl optionally substituted with one to three $R_5$.

In some embodiments of the formulae above, $R_1$ is tetrahydropyranyl optionally substituted with one to three $R_5$.

In some embodiments of the formulae above, each $R_4$ is independently $(C_1-C_4)$ alkyl, $(C_1-C_4)$ alkoxy optionally substituted with one or more $(C_1-C_4)$ alkoxy, halogen, $NR_9(O)_pR_{10}$, $O(CH_2)_nR_{11}$, $NH(CH_2)_nR_{11}$, $C(=O)NHR_{25}$, $NHC(=O)R_{25}$, $NHC(=O)NHR_{25}$, $(CH_2)C(=O)NHR_{25}$, $(CH_2)NHC(=O)R_{25}$, $(CH_2)NHC(=O)NHR_{25}$, $C(=O)R_{25}$, or 5- or 6-membered heterocyclyl comprising 1 to 3 heteroatoms selected from N, O, and S and optionally substituted with one or more $(C_1-C_4)$ alkyl.

In some embodiments of the formulae above, each $R_4$ is independently $(C_1-C_4)$ alkyl, $(C_1-C_4)$ alkoxy, halogen, $O(CH_2)_nR_{11}$, $NH(CH_2)_nR_{11}$, $C(=O)NHR_{25}$, $NHC(=O)R_{25}$, $NHC(=O)NHR_{25}$, $(CH_2)C(=O)NHR_{25}$, $(CH_2)NHC(=O)R_{25}$, $(CH_2)NHC(=O)NHR_{25}$, $C(=O)R_{25}$, or 5- or 6-membered heterocyclyl comprising 1 to 3 heteroatoms selected from N, O, and S and optionally substituted with one or more $(C_1-C_4)$ alkyl.

In some embodiments of the formulae above, $R_1$ is $(C_4-C_7)$ cycloalkyl substituted with one to three $R_5$.

In some embodiments of the formulae above, $R_1$ is 4- to 7-membered heterocyclyl comprising 1 to 3 heteroatoms selected from N, O, and S optionally substituted with one to three $R_5$.

In some embodiments of the formulae above, $R_5$ is $C(=O)R_{16}$ or $S(O)_pR_{16}$ and $R_{16}$ is $(C_2-C_4)$ alkenyl or $(C_2-C_4)$ alkynyl, wherein the alkenyl and alkynyl are optionally substituted with one or more CN.

In some embodiments of the formulae above, two $R_5$ together with the atoms to which they are attached form a bridged 3- to 6-membered heterocyclyl ring comprising 1 to 3 heteroatoms selected from N, O, and S.

In some embodiments of the formulae above, $R_2$ is H. In another embodiment, $R_2$ is H and $R_3$ is H. In another embodiment, $R_2$ is H, $R_3$ is H, and A is $(C_6-C_{10})$ aryl optionally substituted with one to two $R_4$. In another embodiment, $R_2$ is H, $R_3$ is H, and A is $(C_6-C_{10})$ aryl optionally substituted with one to two $R_4$, and $R_1$ is $(C_3-C_7)$ cycloalkyl (e.g., cyclopropyl, cyclobutyl, cyclopentyl, cyclohexyl, or cycloheptyl) or 4- to 6-membered heterocyclyl comprising 1 to 3 heteroatoms selected from N, O, and S, wherein the cycloalkyl and heterocyclyl are optionally substituted with one to three $R_5$.

In some embodiments of the formulae above, $R_2$ is H. In another embodiment, $R_2$ is H and $R_3$ is H. In another embodiment, $R_2$ is H, $R_3$ is H, and A is $(C_6-C_{10})$ aryl substituted with one to two $R_4$. In another embodiment, $R_2$ is H, $R_3$ is H, and A is $(C_6-C_{10})$ aryl substituted with one to two $R_4$, and $R_1$ is $(C_3-C_7)$ cycloalkyl (e.g., cyclopropyl, cyclobutyl, cyclopentyl, cyclohexyl, or cycloheptyl) or 4- to 6-membered heterocyclyl comprising 1 to 3 heteroatoms selected from N, O, and S, wherein the cycloalkyl and heterocyclyl are optionally substituted with one to three $R_5$.

In some embodiments of the formulae above, $R_2$ is H. In another embodiment, $R_2$ is H and $R_3$ is H. In another embodiment, $R_2$ is H, $R_3$ is H, and A is phenyl optionally substituted with one to two $R_4$. In another embodiment, $R_2$ is H, $R_3$ is H, and A is phenyl optionally substituted with one to two $R_4$, and $R_1$ is $(C_3-C_7)$ cycloalkyl (e.g., cyclopropyl, cyclobutyl, cyclopentyl, cyclohexyl, or cycloheptyl) or 4- to 6-membered heterocyclyl comprising 1 to 3 heteroatoms selected from N, O, and S, wherein the cycloalkyl and heterocyclyl are optionally substituted with one to three $R_5$.

In some embodiments of the formulae above, $R_2$ is H. In another embodiment, $R_2$ is H and $R_3$ is H. In another embodiment, $R_2$ is H, $R_3$ is H, and A is phenyl substituted with one to two $R_4$. In another embodiment, $R_2$ is H, $R_3$ is H, and A is phenyl substituted with one to two $R_4$, and $R_1$ is $(C_3-C_7)$ cycloalkyl (e.g., cyclopropyl, cyclobutyl, cyclopentyl, cyclohexyl, or cycloheptyl) or 4- to 6-membered heterocyclyl comprising 1 to 3 heteroatoms selected from N, O, and S, wherein the cycloalkyl and heterocyclyl are optionally substituted with one to three $R_5$.

In some embodiments of the formulae above, $R_2$ is H. In another embodiment, $R_2$ is H and $R_3$ is H. In another embodiment, $R_2$ is H, $R_3$ is H, and A is 5- or 6-membered heteroaryl comprising 1 to 3 heteroatoms selected from N, O, and S and optionally substituted with one to two $R_4$. In another embodiment, $R_2$ is H, $R_3$ is H, and A is 5- or 6-membered heteroaryl comprising 1 to 3 heteroatoms selected from N, O, and S and optionally substituted with one to two $R_4$, and $R_1$ is $(C_3-C_7)$ cycloalkyl (e.g., cyclopropyl, cyclobutyl, cyclopentyl, cyclohexyl, or cycloheptyl) or 4- to 6-membered heterocyclyl comprising 1 to 3 heteroatoms selected from N, O, and S, wherein the cycloalkyl and heterocyclyl are optionally substituted with one to three $R_5$.

In some embodiments of the formulae above, $R_2$ is H. In another embodiment, $R_2$ is H and $R_3$ is H. In another embodiment, $R_2$ is H, $R_3$ is H, and A is 5- or 6-membered heteroaryl comprising 1 to 3 heteroatoms selected from N, O, and S and substituted with one to two $R_4$. In another embodiment, $R_2$ is H, $R_3$ is H, and A is 5- or 6-membered heteroaryl comprising 1 to 3 heteroatoms selected from N, O, and S and substituted with one to two R$_4$, and R$_1$ is (C$_3$-C$_7$) cycloalkyl (e.g., cyclopropyl, cyclobutyl, cyclopentyl, cyclohexyl, or cycloheptyl) or 4- to 6-membered heterocyclyl comprising 1 to 3 heteroatoms selected from N, O, and S, wherein the cycloalkyl and heterocyclyl are optionally substituted with one to three R$_5$.

In some embodiments of the formulae above, R$_2$ is H. In another embodiment, R$_2$ is H and R$_3$ is H. In another embodiment, R$_2$ is H, R$_3$ is H, and A is 5-membered heteroaryl comprising 1 to 3 heteroatoms selected from N, O, and S and optionally substituted with one to two R$_4$. In another embodiment, R$_2$ is H, R$_3$ is H, and A is 5-membered heteroaryl comprising 1 to 3 heteroatoms selected from N, O, and S and optionally substituted with one to two R$_4$, and R$_1$ is (C$_3$-C$_7$) cycloalkyl (e.g., cyclopropyl, cyclobutyl, cyclopentyl, cyclohexyl, or cycloheptyl) or 4- to 6-membered heterocyclyl comprising 1 to 3 heteroatoms selected from N, O, and S, wherein the cycloalkyl and heterocyclyl are optionally substituted with one to three R$_5$.

In some embodiments of the formulae above, R$_2$ is H. In another embodiment, R$_2$ is H and R$_3$ is H. In another embodiment, R$_2$ is H, R$_3$ is H, and A is 5-membered heteroaryl comprising 1 to 3 heteroatoms selected from N, O, and S and substituted with one to two R$_4$. In another embodiment, R$_2$ is H, R$_3$ is H, and A is 5-membered heteroaryl comprising 1 to 3 heteroatoms selected from N, O, and S and substituted with one to two R$_4$, and R$_1$ is (C$_3$-C$_7$) cycloalkyl (e.g., cyclopropyl, cyclobutyl, cyclopentyl, cyclohexyl, or cycloheptyl) or 4- to 6-membered heterocyclyl comprising 1 to 3 heteroatoms selected from N, O, and S, wherein the cycloalkyl and heterocyclyl are optionally substituted with one to three R$_5$.

In some embodiments of the formulae above, R$_2$ is H. In another embodiment, R$_2$ is H and R$_3$ is H. In another embodiment, R$_2$ is H, R$_3$ is H, and A is 6-membered heteroaryl comprising 1 to 3 heteroatoms selected from N, O, and S and optionally substituted with one to two R$_4$. In another embodiment, R$_2$ is H, R$_3$ is H, and A is 6-membered heteroaryl comprising 1 to 3 heteroatoms selected from N, O, and S and optionally substituted with one to two R$_4$, and R$_1$ is (C$_3$-C$_7$) cycloalkyl (e.g., cyclopropyl, cyclobutyl, cyclopentyl, cyclohexyl, or cycloheptyl) or 4- to 6-membered heterocyclyl comprising 1 to 3 heteroatoms selected from N, O, and S, wherein the cycloalkyl and heterocyclyl are optionally substituted with one to three R$_5$.

In some embodiments of the formulae above, R$_2$ is H. In another embodiment, R$_2$ is H and R$_3$ is H. In another embodiment, R$_2$ is H, R$_3$ is H, and A is 6-membered heteroaryl comprising 1 to 3 heteroatoms selected from N, O, and S and substituted with one to two R$_4$. In another embodiment, R$_2$ is H, R$_3$ is H, and A is 5- or 6-membered heteroaryl comprising 1 to 3 heteroatoms selected from N, O, and S and substituted with one to two R$_4$, and R$_1$ is (C$_3$-C$_7$) cycloalkyl (e.g., cyclopropyl, cyclobutyl, cyclopentyl, cyclohexyl, or cycloheptyl) or 4- to 6-membered heterocyclyl comprising 1 to 3 heteroatoms selected from N, O, and S, wherein the cycloalkyl and heterocyclyl are optionally substituted with one to three R$_5$.

In some embodiments of the formulae above, R$_2$ is H. In another embodiment, R$_2$ is H and R$_3$ is H. In another embodiment, R$_2$ is H, R$_3$ is H, and A is pyridinyl optionally substituted with one to two R$_4$. In another embodiment, R$_2$ is H, R$_3$ is H, and A is pyridinyl optionally substituted with one to two R$_4$, and R$_1$ is (C$_3$-C$_7$) cycloalkyl (e.g., cyclopropyl, cyclobutyl, cyclopentyl, cyclohexyl, or cycloheptyl) or 4- to 6-membered heterocyclyl comprising 1 to 3 heteroatoms selected from N, O, and S, wherein the cycloalkyl and heterocyclyl are optionally substituted with one to three R$_5$.

In some embodiments of the formulae above, R$_2$ is H. In another embodiment, R$_2$ is H and R$_3$ is H. In another embodiment, R$_2$ is H, R$_3$ is H, and A is pyridinyl substituted with one to two R$_4$. In another embodiment, R$_2$ is H, R$_3$ is H, and A is pyridinyl substituted with one to two R$_4$, and R$_1$ is (C$_3$-C$_7$) cycloalkyl (e.g., cyclopropyl, cyclobutyl, cyclopentyl, cyclohexyl, or cycloheptyl) or 4- to 6-membered heterocyclyl comprising 1 to 3 heteroatoms selected from N, O, and S, wherein the cycloalkyl and heterocyclyl are optionally substituted with one to three R$_5$.

In some embodiments of the formulae above, R$_2$ is H. In another embodiment, R$_2$ is H and R$_3$ is H. In another embodiment, R$_2$ is H, R$_3$ is H, and A is thiophenyl optionally substituted with one to two R$_4$. In another embodiment, R$_2$ is H, R$_3$ is H, and A is thiophenyl optionally substituted with one to two R$_4$, and R$_1$ is (C$_3$-C$_7$) cycloalkyl (e.g., cyclopropyl, cyclobutyl, cyclopentyl, cyclohexyl, or cycloheptyl) or 4- to 6-membered heterocyclyl comprising 1 to 3 heteroatoms selected from N, O, and S, wherein the cycloalkyl and heterocyclyl are optionally substituted with one to three R$_5$.

In some embodiments of the formulae above, R$_2$ is H. In another embodiment, R$_2$ is H and R$_3$ is H. In another embodiment, R$_2$ is H, R$_3$ is H, and A is thiophenyl substituted with one to two R$_4$. In another embodiment, R$_2$ is H, R$_3$ is H, and A is thiophenyl substituted with one to two R$_4$, and R$_1$ is (C$_3$-C$_7$) cycloalkyl (e.g., cyclopropyl, cyclobutyl, cyclopentyl, cyclohexyl, or cycloheptyl) or 4- to 6-membered heterocyclyl comprising 1 to 3 heteroatoms selected from N, O, and S, wherein the cycloalkyl and heterocyclyl are optionally substituted with one to three R$_5$.

In some embodiments of the formulae above, R$_1$ is a heterocycloalkyl selected from:

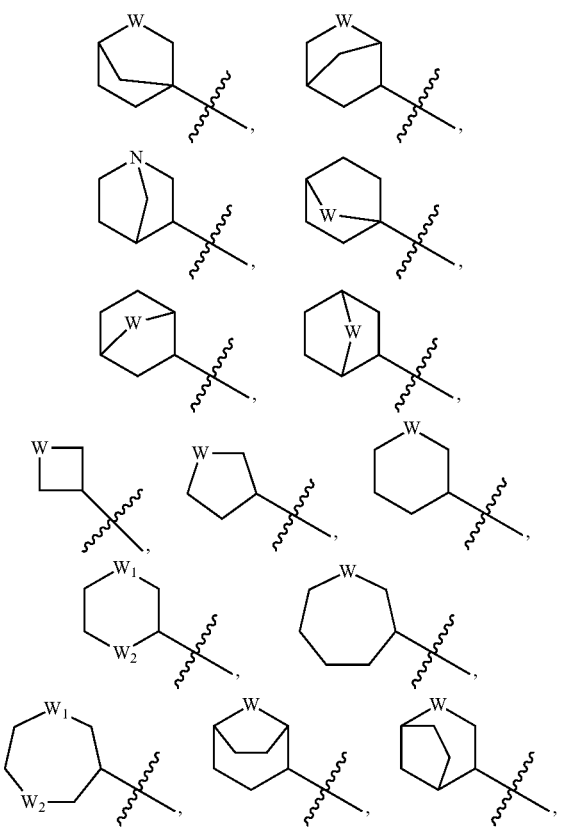

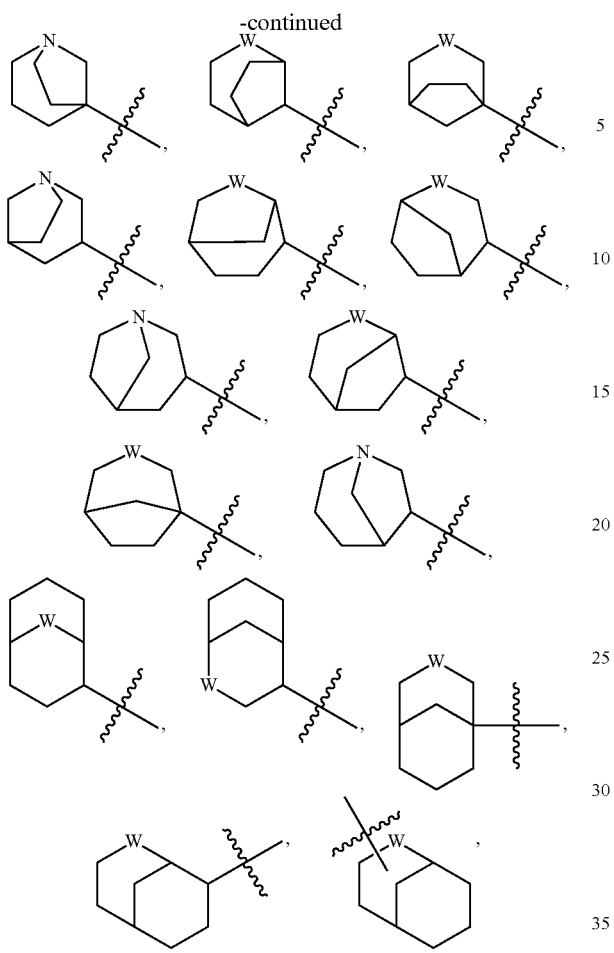
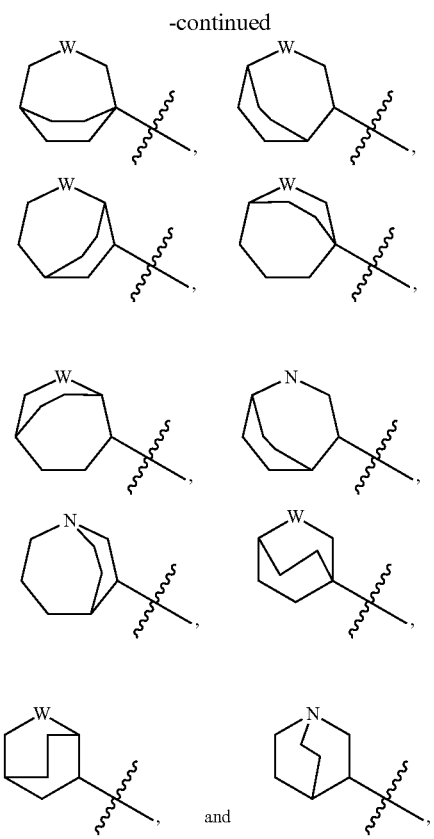
wherein W is O, S, NH, or N(C$_1$-C$_6$)alkyl.
Non-limiting illustrative compounds of the application include:
| Cmpd No. | Structure | Chemical name |
|---|---|---|
| I-1 | 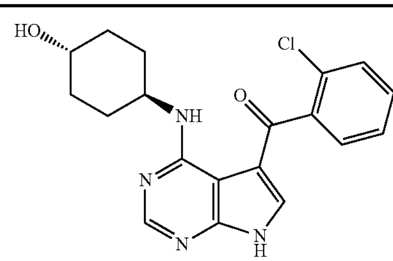 | (2-chlorophenyl)(4-((trans-4-hydroxycyclohexyl)amino)-7H-pyrrolo[2,3-d]pyrimidin-5-yl)methanone |
| I-2 | 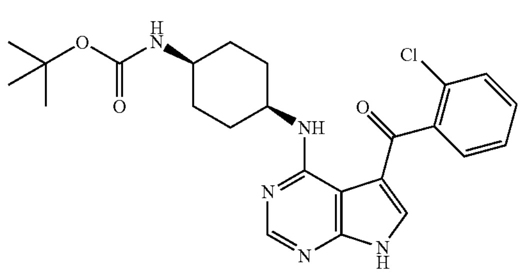 [SMILES: CC(C)(C)OC(=O)N[C@H]1CC[C@@H](Nc2ncnc3[nH]cc(C(=O)c4ccccc4Cl)c23)CC1] | tert-butyl (cis-4-((5-(2-chlorobenzoyl)-7H-pyrrolo[2,3-d]pyrimidin-4-yl)amino)cyclohexyl)carbamate |

-continued

| Cmpd No. | Structure | Chemical name |
|---|---|---|
| I-3 | 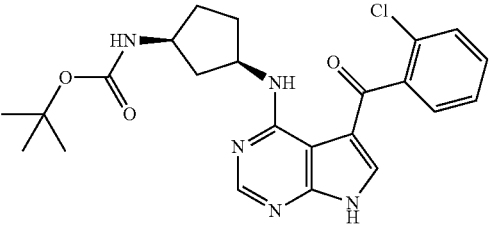 [SMILES: CC(C)(C)OC(=O)N[C@H]1CC[C@@H](Nc2ncnc3[nH]cc(C(=O)c4ccccc4Cl)c23)C1] | tert-butyl ((1S,3R)-3-((5-(2-chlorobenzoyl)-7H-pyrrolo[2,3-d]pyrimidin-4-yl)amino)cyclopentyl)carbamate |
| I-4 | 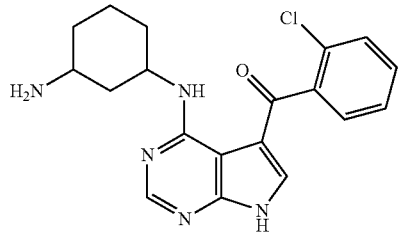 [SMILES: NC1CCCC(Nc2ncnc3[nH]cc(C(=O)c4ccccc4Cl)c23)C1] | (4-((3-aminocyclohexyl)amino)-7H-pyrrolo[2,3-d]pyrimidin-5-yl)(2-chlorophenyl)methanone |
| I-5 | 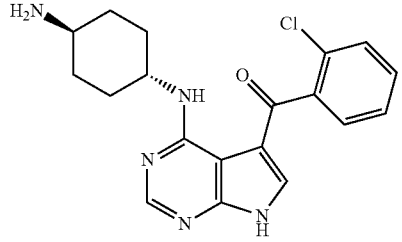 [SMILES: N[C@H]1CC[C@H](Nc2ncnc3[nH]cc(C(=O)c4ccccc4Cl)c23)CC1] | (4-((trans-4-aminocyclohexyl)amino)-7H-pyrrolo[2,3-d]pyrimidin-5-yl)(2-chlorophenyl)methanone |
| I-6 | 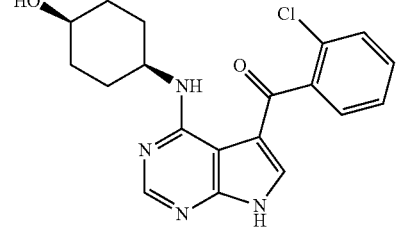 | (4-((cis-4-aminocyclohexyl)amino)-7H-pyrrolo[2,3-d]pyrimidin-5-yl)(2-chlorophenyl)methanone |
| I-7 | 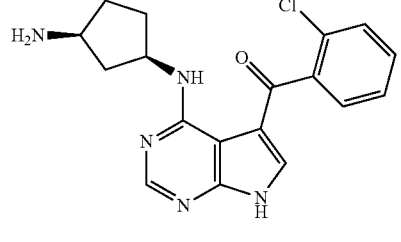 [SMILES: N[C@H]1CC[C@@H](Nc2ncnc3[nH]cc(C(=O)c4ccccc4Cl)c23)C1] | (4-(((1R,3S)-3-aminocyclopentyl)amino)-7H-pyrrolo[2,3-d]pyrimidin-5-yl)(2-chlorophenyl)methanone |
| I-8 | 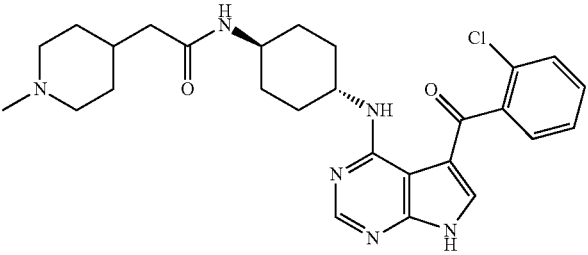 [SMILES: CN1CCC(CC(=O)N[C@H]2CC[C@H](Nc3ncnc4[nH]cc(C(=O)c5ccccc5Cl)c34)CC2)CC1] | N-(trans-4-((5-(2-chlorobenzoyl)-7H-pyrrolo[2,3-d]pyrimidin-4-yl)amino)cyclohexyl)-2-(1-methylpiperidin-4-yl)acetamide |

-continued

| Cmpd No. | Structure | Chemical name |
|---|---|---|
| I-9 | 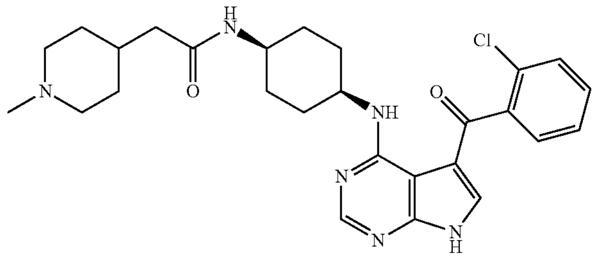 [SMILES: CN1CCC(CC(=O)N[C@H]2CC[C@@H](Nc3ncnc4[nH]cc(C(=O)c5ccccc5Cl)c34)CC2)CC1] | N-(cis-4-((5-(2-chlorobenzoyl)-7H-pyrrolo[2,3-d]pyrimidin-4-yl)amino)cyclohexyl)-2-(1-methylpiperidin-4-yl)acetamide |
| I-10 | 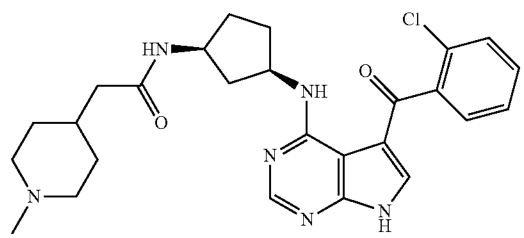 [SMILES: CN1CCC(CC(=O)N[C@H]2CC[C@@H](Nc3ncnc4[nH]cc(C(=O)c5ccccc5Cl)c34)C2)CC1] | N-((1S,3R)-3-((5-(2-chlorobenzoyl)-7H-pyrrolo[2,3-d]pyrimidin-4-yl)amino)cyclopentyl)-2-(1-methylpiperidin-4-yl)acetamide |
| I-11 | 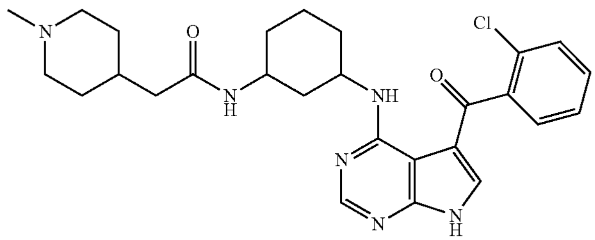 [SMILES: CN1CCC(CC(=O)NC2CCCC(Nc3ncnc4[nH]cc(C(=O)c5ccccc5Cl)c34)C2)CC1] | N-(3-((5-(2-chlorobenzoyl)-7H-pyrrolo[2,3-d]pyrimidin-4-yl)amino)cyclohexyl)-2-(1-methylpiperidin-4-yl)acetamide |
| I-12 | 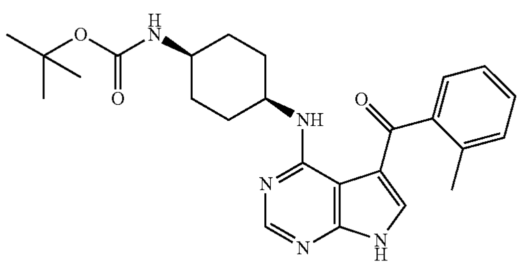 [SMILES: Cc1ccccc1C(=O)c1c[nH]c2ncnc(N[C@H]3CC[C@@H](NC(=O)OC(C)(C)C)CC3)c12] | tert-butyl (cis-4-((5-(2-methylbenzoyl)-7H-pyrrolo[2,3-d]pyrimidin-4-yl)amino)cyclohexyl)carbamate |
| I-13 | 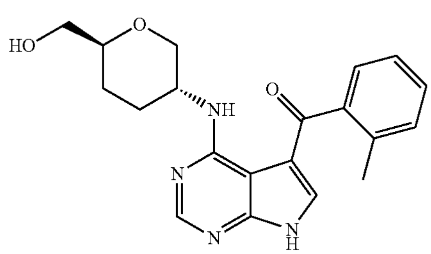 [SMILES: Cc1ccccc1C(=O)c1c[nH]c2ncnc(N[C@@H]3CC[C@@H](CO)OC3)c12] | (4-(((3R,6S)-6-(hydroxymethyl)tetrahydro-2H-pyran-3-yl)amino)-7H-pyrrolo[2,3-d]pyrimidin-5-yl)(o-tolyl)methanone |
| I-14 | 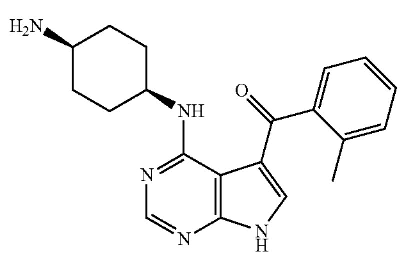 [SMILES: Cc1ccccc1C(=O)c1c[nH]c2ncnc(N[C@H]3CC[C@@H](N)CC3)c12] | (4-((cis-4-aminocyclohexyl)amino)-7H-pyrrolo[2,3-d]pyrimidin-5-yl)(o-tolyl)methanone |

-continued

| Cmpd No. | Structure | Chemical name |
| --- | --- | --- |
| I-15 | 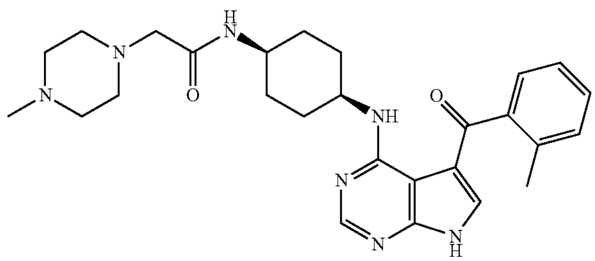 [SMILES: Cc1ccccc1C(=O)c1c[nH]c2ncnc(N[C@H]3CC[C@@H](NC(=O)CN4CCN(C)CC4)CC3)c12] | N-(cis-4-((5-(2-methylbenzoyl)-7H-pyrrolo[2,3-d]pyrimidin-4-yl)amino)cyclohexyl)-2-(4-methylpiperazin-1-yl)acetamide |
| I-16 | 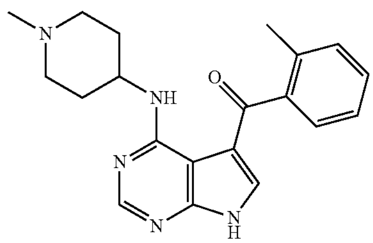 [SMILES: Cc1ccccc1C(=O)c1c[nH]c2ncnc(NC3CCN(C)CC3)c12] | (4-((1-methylpiperidin-4-yl)amino)-7H-pyrrolo[2,3-d]pyrimidin-5-yl)(o-tolyl)methanone |
| I-17 | 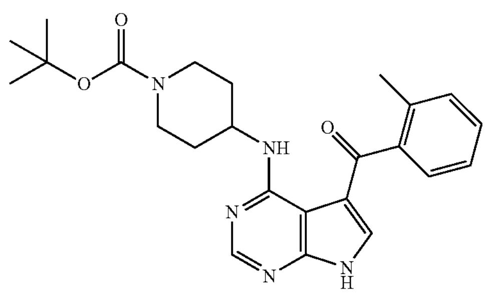 [SMILES: Cc1ccccc1C(=O)c1c[nH]c2ncnc(NC3CCN(C(=O)OC(C)(C)C)CC3)c12] | tert-butyl 4-((5-(2-methylbenzoyl)-7H-pyrrolo[2,3-d]pyrimidin-4-yl)amino)piperidine-1-carboxylate |
| I-18 | 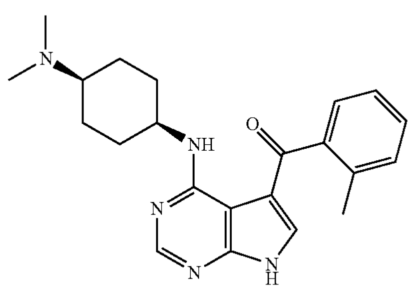 [SMILES: Cc1ccccc1C(=O)c1c[nH]c2ncnc(N[C@H]3CC[C@@H](N(C)C)CC3)c12] | (4-((cis-4-(dimethylamino)cyclohexyl)amino)-7H-pyrrolo[2,3-d]pyrimidin-5-yl)(o-tolyl)methanone |
| I-19 | 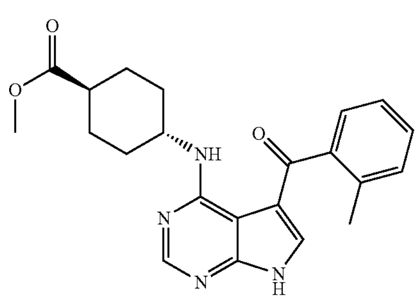 [SMILES: COC(=O)[C@H]1CC[C@H](Nc2ncnc3[nH]cc(C(=O)c4ccccc4C)c23)CC1] | methyl trans-4-((5-(2-methylbenzoyl)-7H-pyrrolo[2,3-d]pyrimidin-4-yl)amino)cyclohexane-1-carboxylate |

| Cmpd No. | Structure | Chemical name |
|---|---|---|
| I-20 | 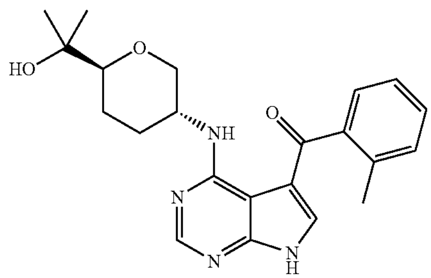 [SMILES: Cc1ccccc1C(=O)c1c[nH]c2ncnc(N[C@@H]3CC[C@@H](C(C)(C)O)OC3)c12] | (4-(((3R,6S)-6-(2-hydroxypropan-2-yl)tetrahydro-2H-pyran-3-yl)amino)-7H-pyrrolo[2,3-d]pyrimidin-5-yl)(o-tolyl)methanone |
| I-21 | 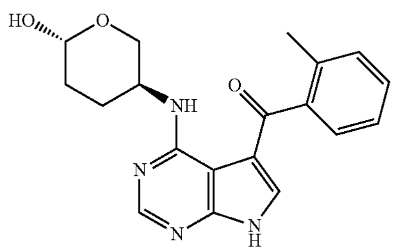 [SMILES: Cc1ccccc1C(=O)c1c[nH]c2ncnc(N[C@H]3CC[C@H](O)OC3)c12] | (4-((trans-4-hydroxycyclohexyl)amino)-7H-pyrrolo[2,3-d]pyrimidin-5-yl)(o-tolyl)methanone |
| I-22 | Chiral | (4-((cis-4-hydroxycyclohexyl)amino)-7H-pyrrolo[2,3-d]pyrimidin-5-yl)(o-tolyl)methanone |
| I-23 | 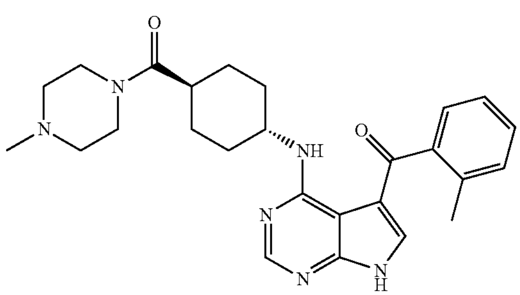 [SMILES: Cc1ccccc1C(=O)c1c[nH]c2ncnc(N[C@H]3CC[C@H](C(=O)N4CCN(C)CC4)CC3)c12] | ((2S,5R)-5-((5-(2-methylbenzoyl)-7H-pyrrolo[2,3-d]pyrimidin-4-yl)amino)tetrahydro-2H-pyran-2-yl)(4-methylpiperazin-1-yl)methanone |
| I-24 | 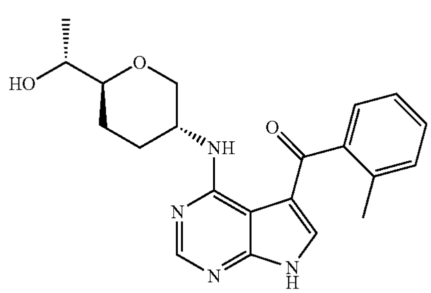 [SMILES: Cc1ccccc1C(=O)c1c[nH]c2ncnc(N[C@@H]3CC[C@@H]([C@@H](C)O)OC3)c12] | (4-(((3R,6S)-6-((R)-1-hydroxyethyl)tetrahydro-2H-pyran-3-yl)amino)-7H-pyrrolo[2,3-d]pyrimidin-5-yl)(o-tolyl)methanone |

-continued

| Cmpd No. | Structure | Chemical name |
|---|---|---|
| I-25 | 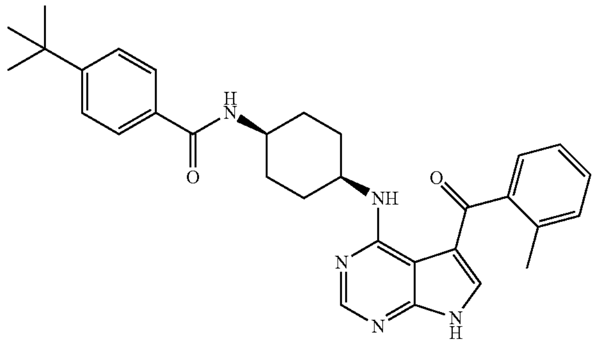 [SMILES: Cc1ccccc1C(=O)c1c[nH]c2ncnc(N[C@H]3CC[C@@H](NC(=O)c4ccc(C(C)(C)C)cc4)CC3)c12] | 4-(tert-butyl)-N-(cis-4((5-(2-methylbenzoyl)-7H-pyrrolo[2,3-d]pyrimidin-4-yl)amino)cyclohexyl)benzamide |
| I-26 | 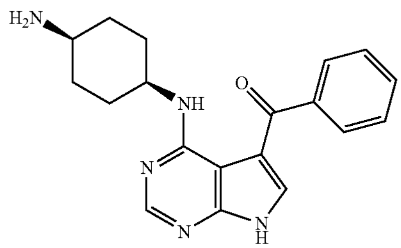 [SMILES: N[C@H]1CC[C@@H](Nc2ncnc3[nH]cc(C(=O)c4ccccc4)c23)CC1] | (4-((cis-4-aminocyclohexyl)amino)-7H-pyrrolo[2,3-d]pyrimidin-5-yl)(phenyl)methanone |
| I-27 | 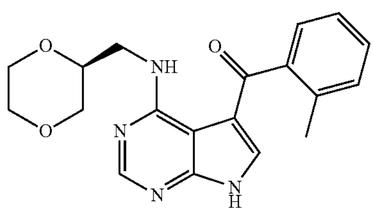 [SMILES: Cc1ccccc1C(=O)c1c[nH]c2ncnc(NC[C@H]3COCCO3)c12] | (S)-(4-(((1,4-dioxan-2-yl)methyl)amino)-7H-pyrrolo[2,3-d]pyrimidin-5-yl)(o-tolyl)methanone |
| I-28 | 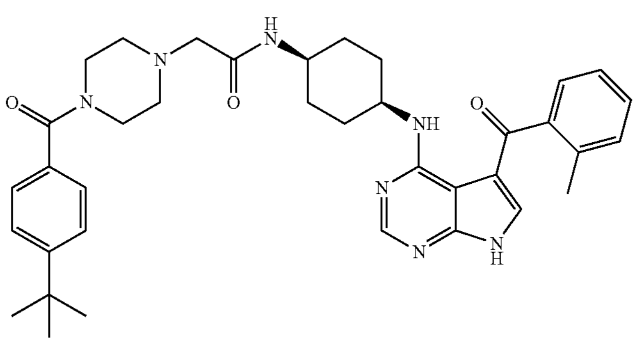 [SMILES: Cc1ccccc1C(=O)c1c[nH]c2ncnc(N[C@H]3CC[C@@H](NC(=O)CN4CCN(C(=O)c5ccc(C(C)(C)C)cc5)CC4)CC3)c12] | 2-(4-(4-(tert-butyl)benzoyl)piperazin-1-yl)-N-(cis-4-((5-(2-methylbenzoyl)-7H-pyrrolo[2,3-d]pyrimidin-4-yl)amino)cyclohexyl)acetamide |
| I-29 | 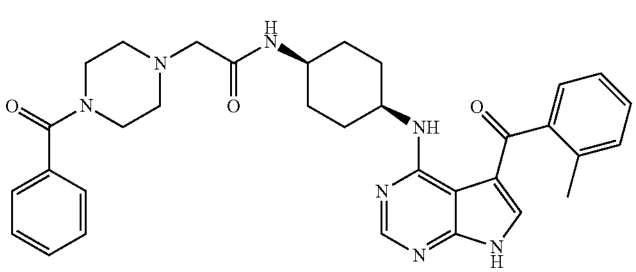 [SMILES: Cc1ccccc1C(=O)c1c[nH]c2ncnc(N[C@H]3CC[C@@H](NC(=O)CN4CCN(C(=O)c5ccccc5)CC4)CC3)c12] | 2-(4-benzoylpiperazin-1-yl)-N-(cis-4-((5-(2-methylbenzoyl)-7H-pyrrolo[2,3-d]pyrimidin-4-yl)amino)cyclohexyl)acetamide |

| Cmpd No. | Structure | Chemical name |
| --- | --- | --- |
| I-30 | 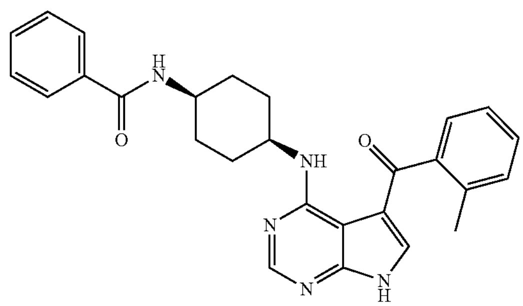 [SMILES: Cc1ccccc1C(=O)c1c[nH]c2ncnc(N[C@H]3CC[C@@H](NC(=O)c4ccccc4)CC3)c12] | N-(cis-4-((5-(2-methylbenzoyl)-7H-pyrrolo[2,3-d]pyrimidin-4-yl)amino)cyclohexyl)benzamide |
| I-31 | 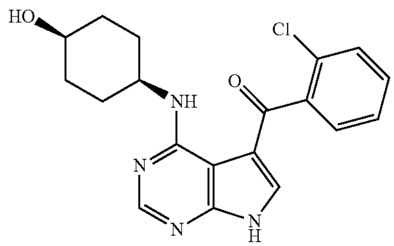 [SMILES: O=C(c1ccccc1Cl)c1c[nH]c2ncnc(N[C@H]3CC[C@@H](O)CC3)c12] | (2-chlorophenyl)(4-((cis-4-hydroxycyclohexyl)amino)-7H-pyrrolo[2,3-d]pyrimidin-5-yl)methanone |
| I-32 | 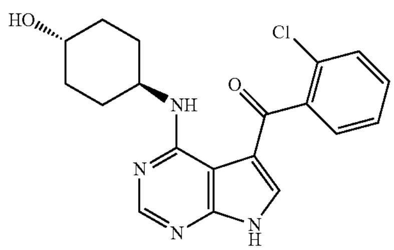 [SMILES: O=C(c1ccccc1Cl)c1c[nH]c2ncnc(N[C@H]3CC[C@H](O)CC3)c12] | (2-chlorophenyl)(4-((trans-4-hydroxycyclohexyl)amino)-7H-pyrrolo[2,3-d]pyrimidin-5-yl)methanone |
| I-33 | 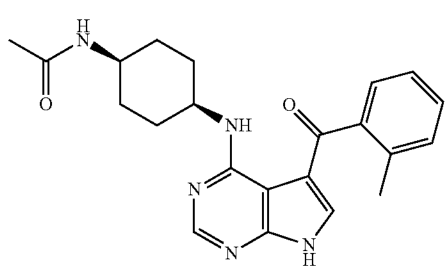 | N-(cis-4-((5-(2-methylbenzoyl)-7H-pyrrolo[2,3-d]pyrimidin-4-yl)amino)cyclohexyl)acetamide |
| I-34 | 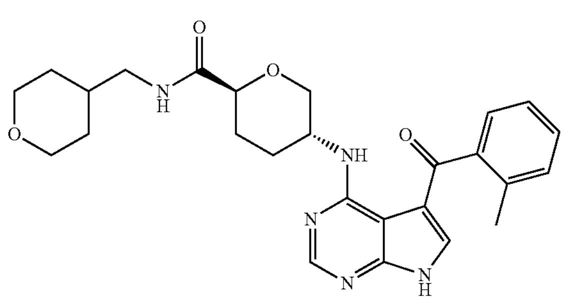 [SMILES: Cc1ccccc1C(=O)c1c[nH]c2ncnc(N[C@@H]3CC[C@@H](C(=O)NCC4CCOCC4)OC3)c12] | (2S,5R)-5-((5-(2-methylbenzoyl)-7H-pyrrolo[2,3-d]pyrimidin-4-yl)amino)-N-((tetrahydro-2H-pyran-4-yl)methyl)tetrahydro-2H-pyran-2-carboxamide |

-continued

| Cmpd No. | Structure | Chemical name |
| --- | --- | --- |
| I-35 | 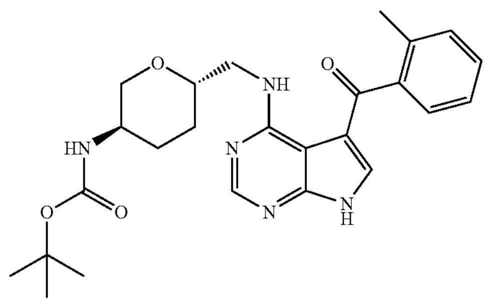 [SMILES: Cc1ccccc1C(=O)c1c[nH]c2ncnc(NC[C@@H]3CC[C@@H](NC(=O)OC(C)(C)C)CO3)c12] | tert-butyl ((3R,6S)-6-(((5-(2-methylbenzoyl)-7H-pyrrolo[2,3-d]pyrimidin-4-yl)amino)methyl)tetrahydro-2H-pyran-3-yl)carbamate |
| I-36 | 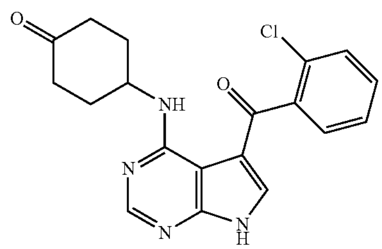 [SMILES: O=C1CCC(Nc2ncnc3[nH]cc(C(=O)c4ccccc4Cl)c23)CC1] | 4-((5-(2-chlorobenzoyl)-7H-pyrrolo[2,3-d]pyrimidin-4-yl)amino)cyclohexan-1-one |
| I-37 | 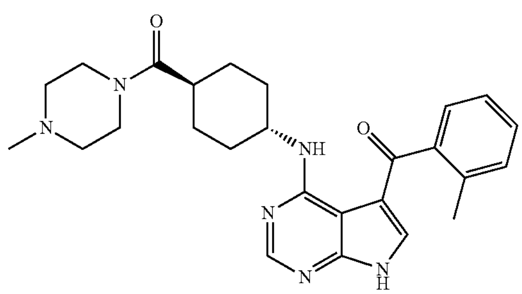 [SMILES: Cc1ccccc1C(=O)c1c[nH]c2ncnc(N[C@H]3CC[C@H](C(=O)N4CCN(C)CC4)CC3)c12] | (trans-4-((5-(2-methylbenzoyl)-7H-pyrrolo[2,3-d]pyrimidin-4-yl)amino)cyclohexyl)(4-methylpiperazin-1-yl)methanone |
| I-38 | 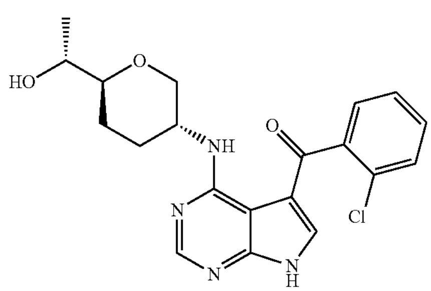 [SMILES: C[C@@H](O)[C@@H]1CC[C@@H](Nc2ncnc3[nH]cc(C(=O)c4ccccc4Cl)c23)CO1] | (2-chlorophenyl)(4-(((3R,6S)-6-((R)-1-hydroxyethyl)tetrahydro-2H-pyran-3-yl)amino)-7H-pyrrolo[2,3-d]pyrimidin-5-yl)methanone |
| I-39 | 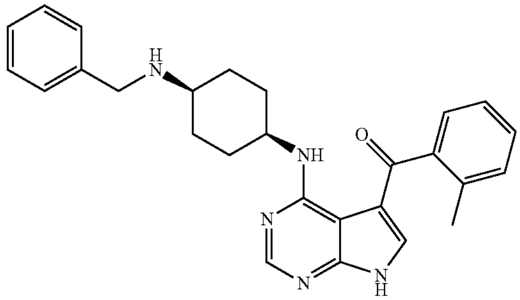 [SMILES: Cc1ccccc1C(=O)c1c[nH]c2ncnc(N[C@H]3CC[C@@H](NCc4ccccc4)CC3)c12] | (4-((cis-4-(benzylamino)cyclohexyl)amino)-7H-pyrrolo[2,3-d]pyrimidin-5-yl)(o-tolyl)methanone |

| Cmpd No. | Structure | Chemical name |
|---|---|---|
| I-40 | 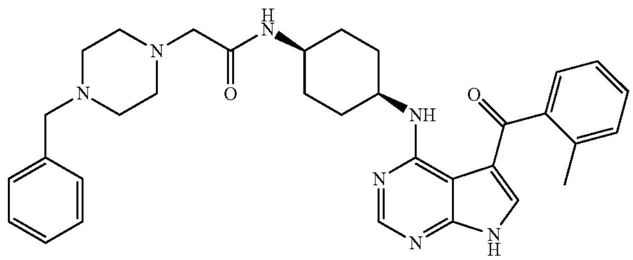 [SMILES: Cc1ccccc1C(=O)c1c[nH]c2ncnc(N[C@H]3CC[C@@H](NC(=O)CN4CCN(Cc5ccccc5)CC4)CC3)c12] | 2-(4-benzylpiperazin-1-yl)-N-(cis-4-((5-(2-methylbenzoyl)-7H-pyrrolo[2,3-d]pyrimidin-4-yl)amino)cyclohexyl)acetamide |
| I-41 | 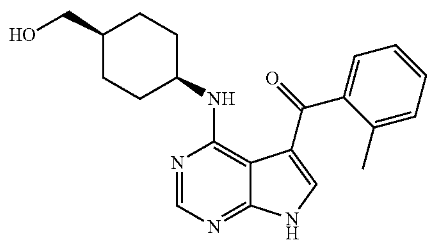 [SMILES: Cc1ccccc1C(=O)c1c[nH]c2ncnc(N[C@H]3CC[C@@H](CO)CC3)c12] | (4-((cis-4-(hydroxymethyl)cyclohexyl)amino)-7H-pyrrolo[2,3-d]pyrimidin-5-yl)(o-tolyl)methanone |
| I-42 | 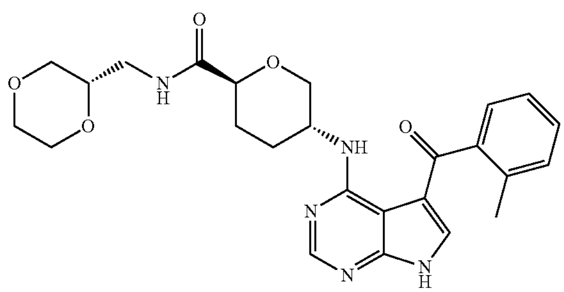 [SMILES: Cc1ccccc1C(=O)c1c[nH]c2ncnc(N[C@@H]3CC[C@@H](C(=O)NC[C@H]4COCCO4)OC3)c12] | (2S,5R)-N-(((S)-1,4-dioxan-2-yl)methyl)-5-((5-(2-methylbenzoyl)-7H-pyrrolo[2,3-d]pyrimidin-4-yl)amino)tetrahydro-2H-pyran-2-carboxamide |
| I-43 | 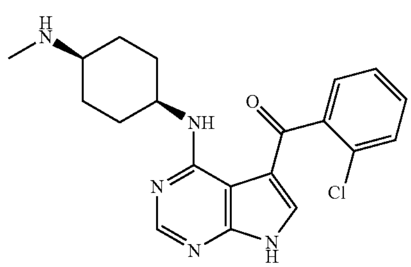 [SMILES: CN[C@H]1CC[C@@H](Nc2ncnc3[nH]cc(C(=O)c4ccccc4Cl)c23)CC1] | (2-chlorophenyl)(4-((cis-4-(methylamino)cyclohexyl)amino)-7H-pyrrolo[2,3-d]pyrimidin-5-yl)methanone |
| I-44 | 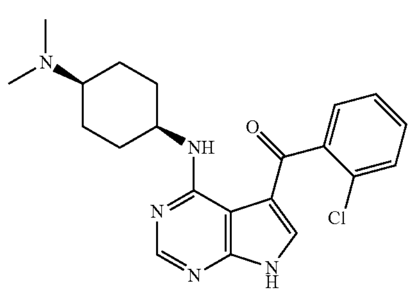 [SMILES: CN(C)[C@H]1CC[C@@H](Nc2ncnc3[nH]cc(C(=O)c4ccccc4Cl)c23)CC1] | (2-chlorophenyl)(4-((cis-4-(dimethylamino)cyclohexyl)amino)-7H-pyrrolo[2,3-d]pyrimidin-5-yl)methanone |

-continued

| Cmpd No. | Structure | Chemical name |
|---|---|---|
| I-45 | 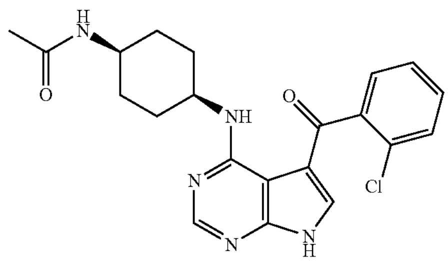 [SMILES: CC(=O)N[C@H]1CC[C@@H](Nc2ncnc3[nH]cc(C(=O)c4ccccc4Cl)c23)CC1] | N-(trans-4-((5-(2-chlorobenzoyl)-7H-pyrrolo[2,3-d]pyrimidin-4-yl)amino)cyclohexyl)acetamide |
| I-46 | 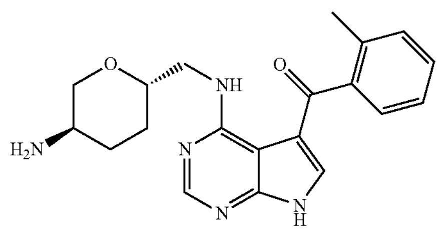 [SMILES: Cc1ccccc1C(=O)c1c[nH]c2ncnc(NC[C@@H]3CC[C@@H](N)CO3)c12] | (4-((((2S,5R)-5-aminotetrahydro-2H-pyran-2-yl)methyl)amino)-7H-pyrrolo[2,3-d]pyrimidin-5-yl)(o-tolyl)methanone |
| I-47 | 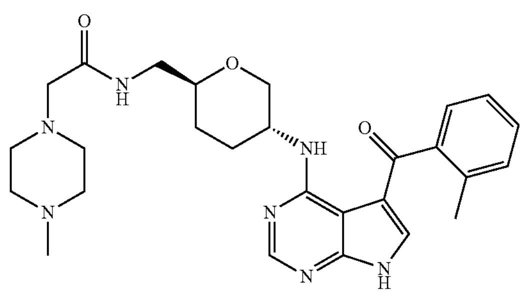 [SMILES: Cc1ccccc1C(=O)c1c[nH]c2ncnc(N[C@@H]3CC[C@@H](CNC(=O)CN4CCN(C)CC4)OC3)c12] | N-(((2S,5R)-5-((5-(2-methylbenzoyl)-7H-pyrrolo[2,3-d]pyrimidin-4-yl)amino)tetrahydro-2H-pyran-2-yl)methyl)-2-(4-methylpiperazin-1-yl)acetamide |
| I-48 | 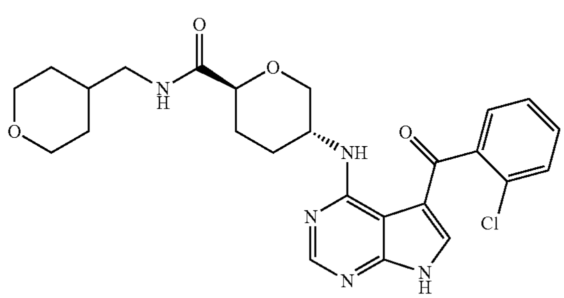 [SMILES: O=C(c1ccccc1Cl)c1c[nH]c2ncnc(N[C@@H]3CC[C@@H](C(=O)NCC4CCOCC4)OC3)c12] | (2S,5R)-5-((5-(2-chlorobenzoyl)-7H-pyrrolo[2,3-d]pyrimidin-4-yl)amino)-N-((tetrahydro-2H-pyran-4-yl)methyl)tetrahydro-2H-pyran-2-carboxamide |
| I-49 | 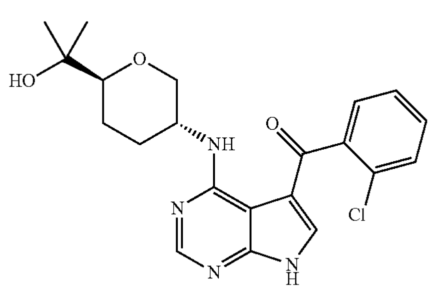 [SMILES: CC(C)(O)[C@@H]1CC[C@@H](Nc2ncnc3[nH]cc(C(=O)c4ccccc4Cl)c23)CO1] | (2-chlorophenyl)(4-(((3R,6S)-6-(2-hydroxypropan-2-yl)tetrahydro-2H-pyran-3-yl)amino)-7H-pyrrolo[2,3-d]pyrimidin-5-yl)methanone |

-continued

| Cmpd No. | Structure | Chemical name |
|---|---|---|
| I-50 | 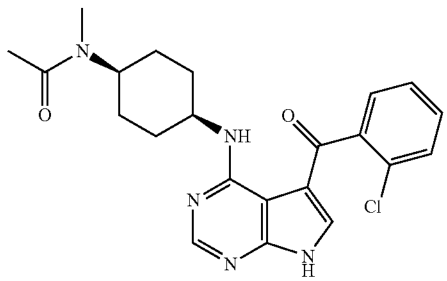 [SMILES: CC(=O)N(C)[C@H]1CC[C@@H](Nc2ncnc3[nH]cc(C(=O)c4ccccc4Cl)c23)CC1] | N-(cis-4-((5-(2-chlorobenzoyl)-7H-pyrrolo[2,3-d]pyrimidin-4-yl)amino)cyclohexyl)-N-methylacetamide |
| I-51 | 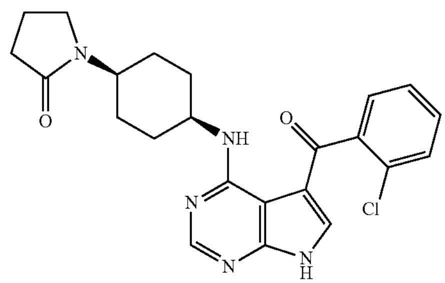 [SMILES: O=C(c1ccccc1Cl)c1c[nH]c2ncnc(N[C@H]3CC[C@@H](N4CCCC4=O)CC3)c12] | 1-(cis-4-((5-(2-chlorobenzoyl)-7H-pyrrolo[2,3-d]pyrimidin-4-yl)amino)cyclohexyl)pyrrolidin-2-one |
| I-52 | 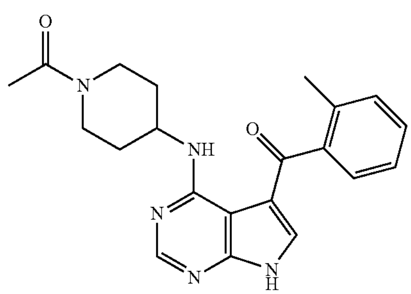 [SMILES: CC(=O)N1CCC(Nc2ncnc3[nH]cc(C(=O)c4ccccc4C)c23)CC1] | 1-(4-((5-(2-methylbenzoyl)-7H-pyrrolo[2,3-d]pyrimidin-4-yl)amino)piperidin-1-yl)ethan-1-one |
| I-53 | 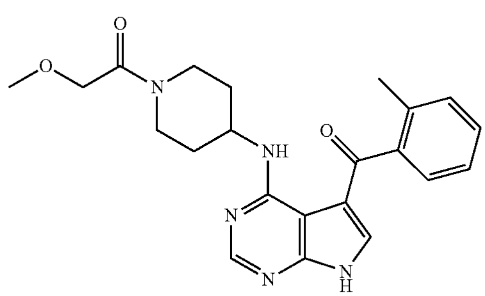 [SMILES: COCC(=O)N1CCC(Nc2ncnc3[nH]cc(C(=O)c4ccccc4C)c23)CC1] | 2-methoxy-1-(4-((5-(2-methylbenzoyl)-7H-pyrrolo[2,3-d]pyrimidin-4-yl)amino)piperidin-1-yl)ethan-1-one |
| I-54 | 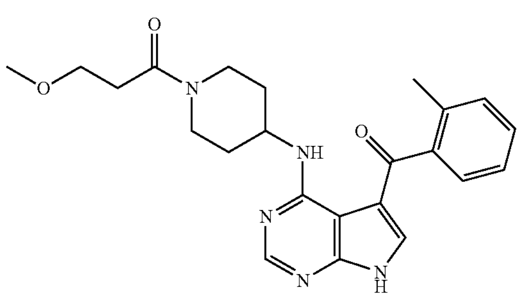 [SMILES: COCCC(=O)N1CCC(Nc2ncnc3[nH]cc(C(=O)c4ccccc4C)c23)CC1] | 3-methoxy-1-(4-((5-(2-methylbenzoyl)-7H-pyrrolo[2,3-d]pyrimidin-4-yl)amino)piperidin-1-yl)propan-1-one |

-continued

| Cmpd No. | Structure | Chemical name |
|---|---|---|
| I-55 | 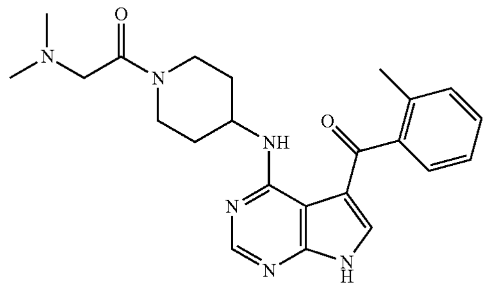 [SMILES: Cc1ccccc1C(=O)c1c[nH]c2ncnc(NC3CCN(C(=O)CN(C)C)CC3)c12] | 2-(dimethylamino)-1-(4-((5-(2-methylbenzoyl)-7H-pyrrolo[2,3-d]pyrimidin-4-yl)amino)piperidin-1-yl)ethan-1-one |
| I-56 | 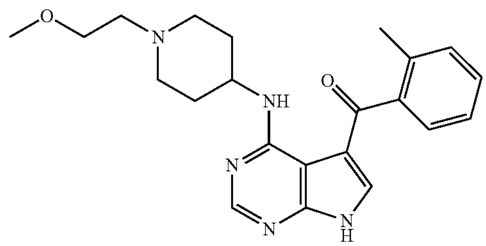 [SMILES: COCCN1CCC(Nc2ncnc3[nH]cc(C(=O)c4ccccc4C)c23)CC1] | (4-((1-(2-methoxyethyl)piperidin-4-yl)amino)-7H-pyrrolo[2,3-d]pyrimidin-5-yl)(o-tolyl)methanone |
| I-57 | 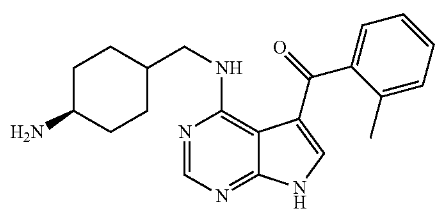 | (4-(((4-aminocyclohexyl)methyl)amino)-7H-pyrrolo[2,3-d]pyrimidin-5-yl)(o-tolyl)methanone |
| I-58 | 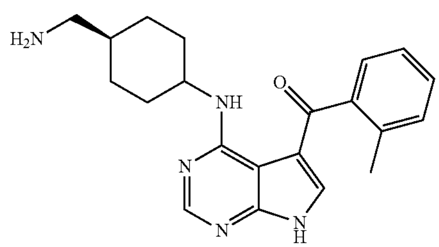 | (4-((4-(aminomethyl)cyclohexyl)amino)-7H-pyrrolo[2,3-d]pyrimidin-5-yl)(o-tolyl)methanone |
| I-59 | 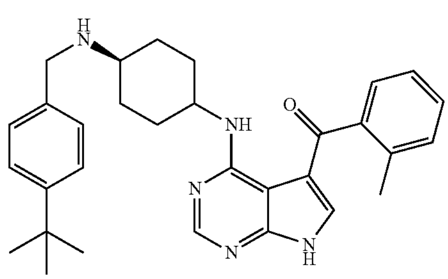 | (4-((4-((4-(tert-butyl)benzyl)amino)cyclohexyl)amino)-7H-pyrrolo[2,3-d]pyrimidin-5-yl)(o-tolyl)methanone |
| I-60 | 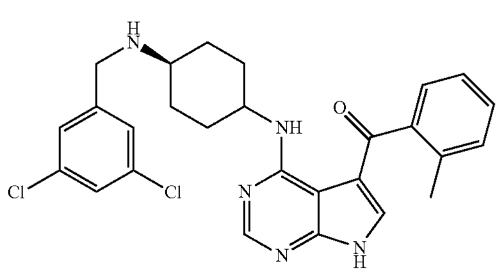 | (4-((4-((3,5-dichlorobenzyl)amino)cyclohexyl)amino)-7H-pyrrolo[2,3-d]pyrimidin-5-yl)(o-tolyl)methanone |

-continued

| Cmpd No. | Structure | Chemical name |
|---|---|---|
| I-61 | 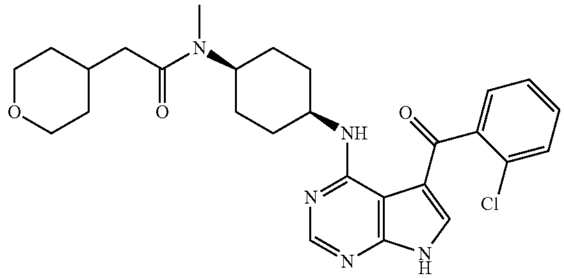 [SMILES: CN(C(=O)CC1CCOCC1)[C@H]1CC[C@@H](Nc2ncnc3[nH]cc(C(=O)c4ccccc4Cl)c23)CC1] | N-(cis-4-((5-(2-chlorobenzoyl)-7H-pyrrolo[2,3-d]pyrimidin-4-yl)amino)cyclohexyl)-N-methyl-2-(tetrahydro-2H-pyran-4-yl)acetamide |
| I-62 | 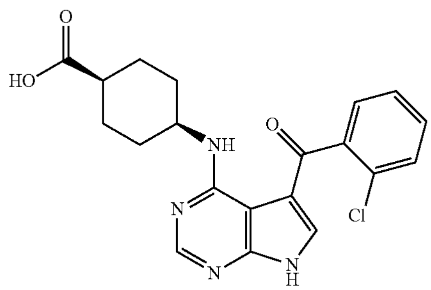 [SMILES: O=C(c1ccccc1Cl)c1c[nH]c2ncnc(N[C@H]3CC[C@@H](C(=O)O)CC3)c12] | cis-4-((5-(2-chlorobenzoyl)-7H-pyrrolo[2,3-d]pyrimidin-4-yl)amino)cyclohexane-1-carboxylic acid |
| I-63 | 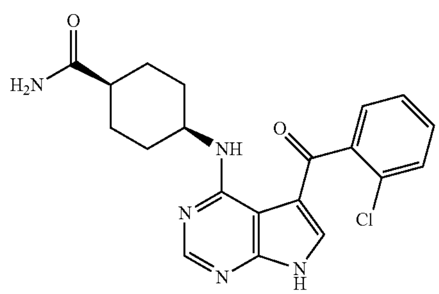 [SMILES: NC(=O)[C@H]1CC[C@@H](Nc2ncnc3[nH]cc(C(=O)c4ccccc4Cl)c23)CC1] | cis-4-((5-(2-chlorobenzoyl)-7H-pyrrolo[2,3-d]pyrimidin-4-yl)amino)cyclohexane-1-carboxamide |
| I-64 | 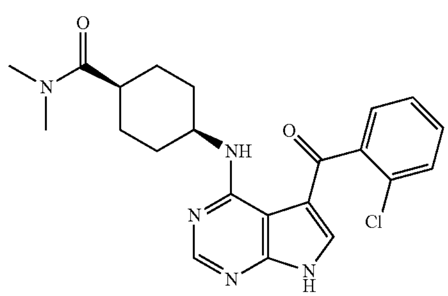 | cis-4-((5-(2-chlorobenzoyl)-7H-pyrrolo[2,3-d]pyrimidin-4-yl)amino)-N,N-dimethylcyclohexane-1-carboxamide |
| I-65 | 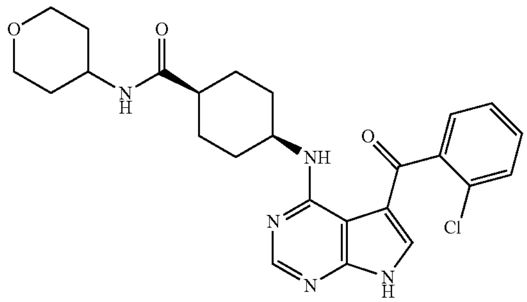 [SMILES: O=C(c1ccccc1Cl)c1c[nH]c2ncnc(N[C@H]3CC[C@@H](C(=O)NC4CCOCC4)CC3)c12] | cis-4-((5-(2-chlorobenzoyl)-7H-pyrrolo[2,3-d]pyrimidin-4-yl)amino)-N-(tetrahydro-2H-pyran-4-yl)cyclohexane-1-carboxamide |

| Cmpd No. | Structure | Chemical name |
|---|---|---|
| I-66 | 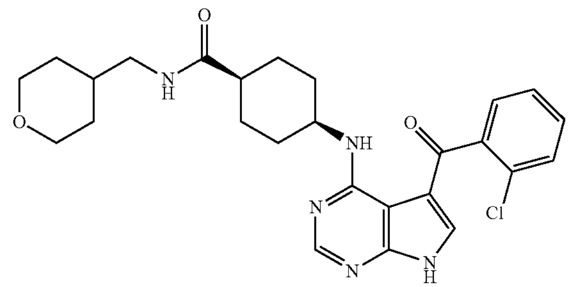 [SMILES: O=C(c1ccccc1Cl)c1c[nH]c2ncnc(N[C@H]3CC[C@@H](C(=O)NCC4CCOCC4)CC3)c12] | cis-4-((5-(2-chlorobenzoyl)-7H-pyrrolo[2,3-d]pyrimidin-4-yl)amino)-N-((tetrahydro-2H-pyran-4-yl)methyl)cyclohexane-1-carboxamide |
| I-67 | 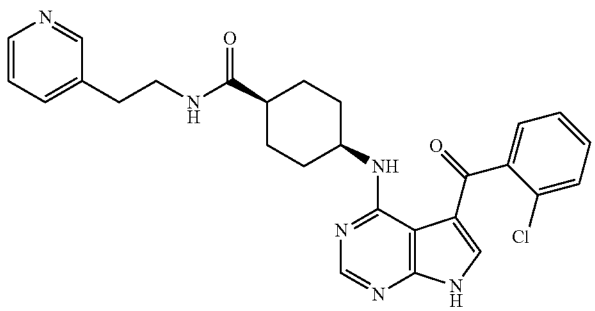 [SMILES: O=C(c1ccccc1Cl)c1c[nH]c2ncnc(N[C@H]3CC[C@@H](C(=O)NCCc4cccnc4)CC3)c12] | cis-4-((5-(2-chlorobenzoyl)-7H-pyrrolo[2,3-d]pyrimidin-4-yl)amino)-N-(2-(pyridin-3-yl)ethyl)cyclohexane-1-carboxamide |
| I-68 | 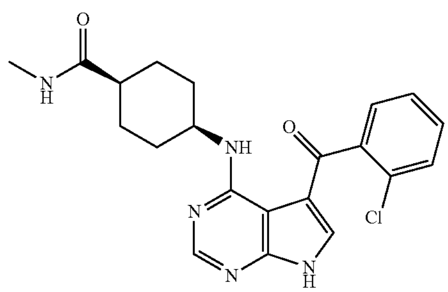 [SMILES: CNC(=O)[C@H]1CC[C@@H](Nc2ncnc3[nH]cc(C(=O)c4ccccc4Cl)c23)CC1] | cis-4-((5-(2-chlorobenzoyl)-7H-pyrrolo[2,3-d]pyrimidin-4-yl)amino)-N-methylcyclohexane-1-carboxamide |
| I-69 | 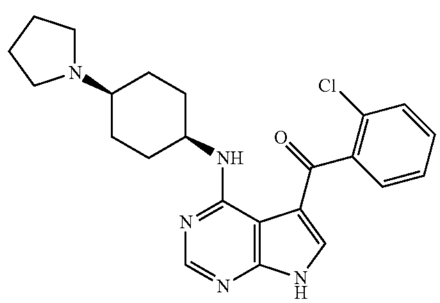 [SMILES: O=C(c1ccccc1Cl)c1c[nH]c2ncnc(N[C@H]3CC[C@@H](N4CCCC4)CC3)c12] | (2-chlorophenyl)(4-((cis-4-(pyrrolidin-1-yl)cyclohexyl)amino)-7H-pyrrolo[2,3-d]pyrimidin-5-yl)methanone |
| I-70 | 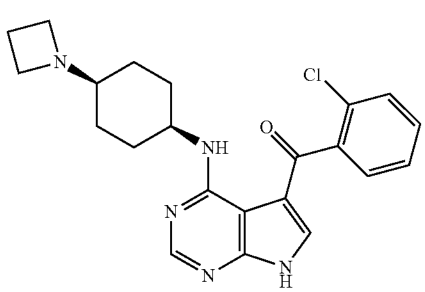 [SMILES: O=C(c1ccccc1Cl)c1c[nH]c2ncnc(N[C@H]3CC[C@@H](N4CCC4)CC3)c12] | (4-((cis-4-(azetidin-1-yl)cyclohexyl)amino)-7H-pyrrolo[2,3-d]pyrimidin-5-yl)(2-chlorophenyl)methanone |

-continued

| Cmpd No. | Structure | Chemical name |
| --- | --- | --- |
| I-71 | 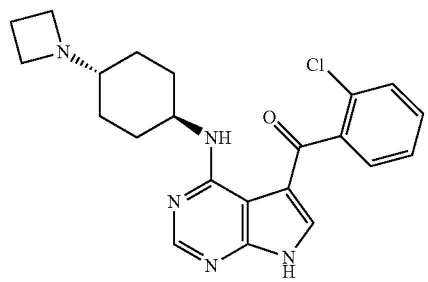 [SMILES: O=C(c1ccccc1Cl)c1c[nH]c2ncnc(N[C@H]3CC[C@H](N4CCC4)CC3)c12] | (4-((trans-4-(azetidin-1-yl)cyclohexyl)amino)-7H-pyrrolo[2,3-d]pyrimidin-5-yl)(2-chlorophenyl)methanone |
| I-72 | 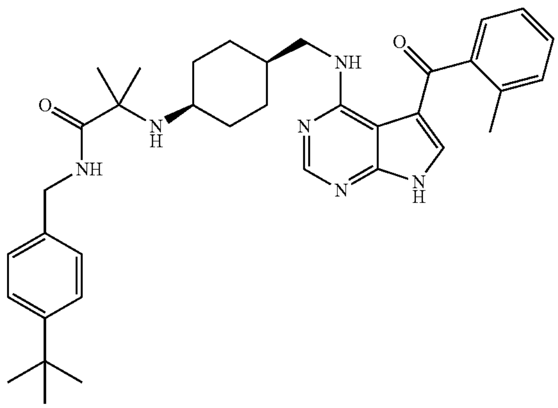 [SMILES: Cc1ccccc1C(=O)c1c[nH]c2ncnc(NC[C@H]3CC[C@@H](NC(C)(C)C(=O)NCc4ccc(C(C)(C)C)cc4)CC3)c12] | N-(4-(tert-butyl)benzyl)-2-methyl-2-((cis-4-(((5-(2-methylbenzoyl)-7H-pyrrolo[2,3-d]pyrimidin-4-yl)amino)methyl)cyclohexyl)amino)propanamide |
| I-73 | 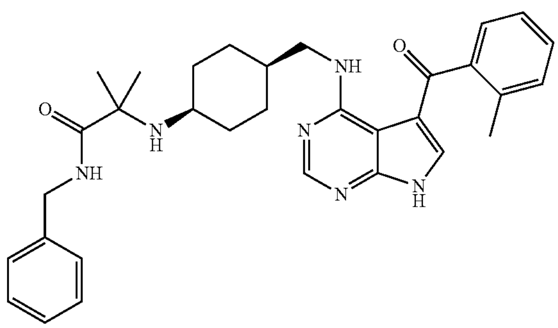 [SMILES: Cc1ccccc1C(=O)c1c[nH]c2ncnc(NC[C@H]3CC[C@@H](NC(C)(C)C(=O)NCc4ccccc4)CC3)c12] | N-benzyl-2-methyl-2-((cis-4-(((5-(2-methylbenzoyl)-7H-pyrrolo[2,3-d]pyrimidin-4-yl)amino)methyl)cyclohexyl)amino)propanamide |
| I-74 | 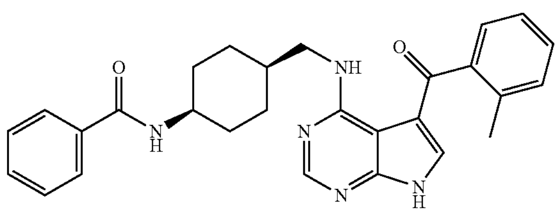 [SMILES: Cc1ccccc1C(=O)c1c[nH]c2ncnc(NC[C@H]3CC[C@@H](NC(=O)c4ccccc4)CC3)c12] | N-(cis-4-(((5-(2-methylbenzoyl)-7H-pyrrolo[2,3-d]pyrimidin-4-yl)amino)methyl)cyclohexyl)benzamide |
| I-75 | 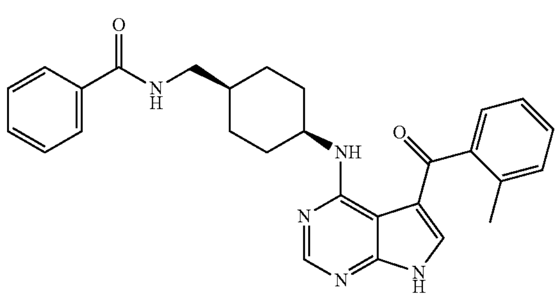 [SMILES: Cc1ccccc1C(=O)c1c[nH]c2ncnc(N[C@H]3CC[C@@H](CNC(=O)c4ccccc4)CC3)c12] | N-((cis-4-((5-(2-methylbenzoyl)-7H-pyrrolo[2,3-d]pyrimidin-4-yl)amino)cyclohexyl)methyl)benzamide |

-continued

| Cmpd No. | Structure | Chemical name |
|---|---|---|
| I-76 | 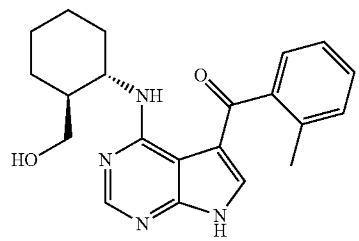 [SMILES: Cc1ccccc1C(=O)c1c[nH]c2ncnc(N[C@H]3CCCC[C@@H]3CO)c12] | (4-(((1S,2S)-2-(hydroxymethyl)cyclohexyl)amino)-7H-pyrrolo[2,3-d]pyrimidin-5-yl)(o-tolyl)methanone |
| I-77 | 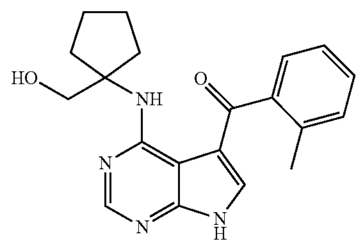 [SMILES: Cc1ccccc1C(=O)c1c[nH]c2ncnc(NC3(CO)CCCC3)c12] | (4-((1-(hydroxymethyl)cyclopentyl)amino)-7H-pyrrolo[2,3-d]pyrimidin-5-yl)(o-tolyl)methanone |
| I-78 | 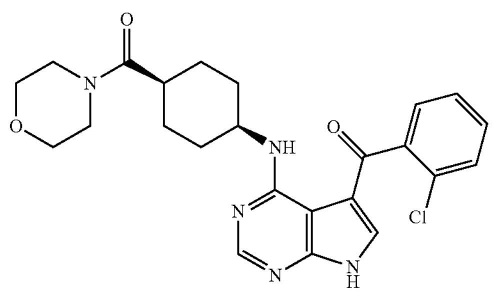 [SMILES: O=C(c1ccccc1Cl)c1c[nH]c2ncnc(N[C@H]3CC[C@@H](C(=O)N4CCOCC4)CC3)c12] | (cis-4-((5-(2-chlorobenzoyl)-7H-pyrrolo[2,3-d]pyrimidin-4-yl)amino)cyclohexyl)(morpholino)methanone |
| I-79 | 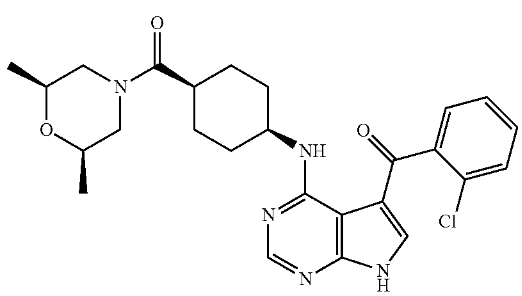 [SMILES: C[C@@H]1CN(C(=O)[C@H]2CC[C@@H](Nc3ncnc4[nH]cc(C(=O)c5ccccc5Cl)c34)CC2)C[C@H](C)O1] | (cis-4-((5-(2-chlorobenzoyl)-7H-pyrrolo[2,3-d]pyrimidin-4-yl)amino)cyclohexyl)((2S,6R)-2,6-dimethylmorpholino)methanone |
| I-80 | 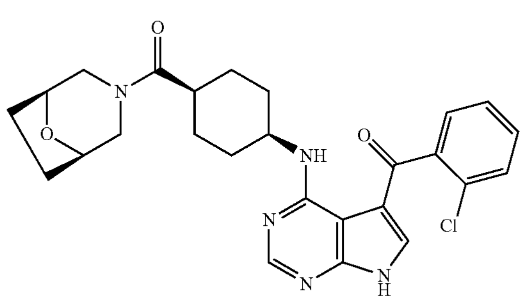 [SMILES: O=C(c1ccccc1Cl)c1c[nH]c2ncnc(N[C@H]3CC[C@@H](C(=O)N4C[C@H]5CC[C@@H](C4)O5)CC3)c12] | (4-((cis-4-((1R,5S)-8-oxa-3-azabicyclo[3.2.1]octane-3-carbonyl)cyclohexyl)amino)-7H-pyrrolo[2,3-d]pyrimidin-5-yl)(2-chlorophenyl)methanone |

-continued

| Cmpd No. | Structure | Chemical name |
|---|---|---|
| I-81 | 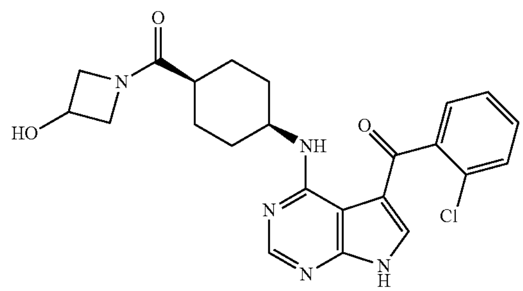 [SMILES: O=C(c1ccccc1Cl)c1c[nH]c2ncnc(N[C@H]3CC[C@@H](C(=O)N4CC(O)C4)CC3)c12] | (cis-4-((5-(2-chlorobenzoyl)-7H-pyrrolo[2,3-d]pyrimidin-4-yl)amino)cyclohexyl)(3-hydroxyazetidin-1-yl)methanone |
| I-82 | 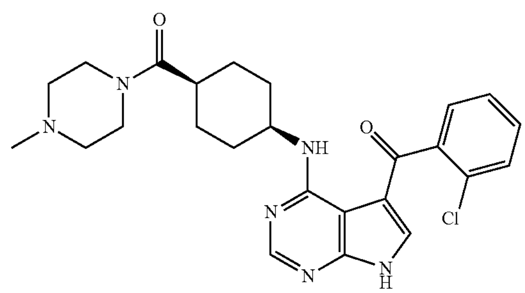 [SMILES: CN1CCN(C(=O)[C@H]2CC[C@@H](Nc3ncnc4[nH]cc(C(=O)c5ccccc5Cl)c34)CC2)CC1] | (cis-4-((5-(2-chlorobenzoyl)-7H-pyrrolo[2,3-d]pyrimidin-4-yl)amino)cyclohexyl)(4-methylpiperazin-1-yl)methanone |
| I-83 | 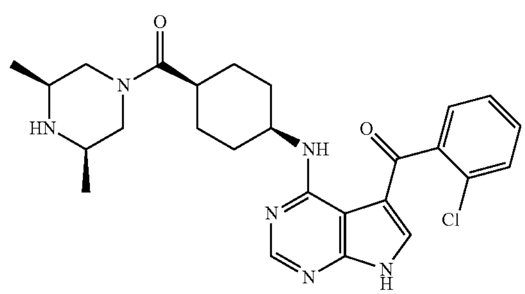 [SMILES: C[C@@H]1CN(C(=O)[C@H]2CC[C@@H](Nc3ncnc4[nH]cc(C(=O)c5ccccc5Cl)c34)CC2)C[C@H](C)N1] | (cis-4-((5-(2-chlorobenzoyl)-7H-pyrrolo[2,3-d]pyrimidin-4-yl)amino)cyclohexyl)((3S,5R)-3,5-dimethylpiperazin-1-yl)methanone |
| I-84 | 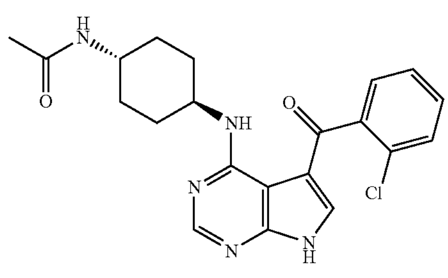 [SMILES: CC(=O)N[C@H]1CC[C@H](Nc2ncnc3[nH]cc(C(=O)c4ccccc4Cl)c23)CC1] | N-(trans-4-((5-(2-chlorobenzoyl)-7H-pyrrolo[2,3-d]pyrimidin-4-yl)amino)cyclohexyl)acetamide |
| I-85 | 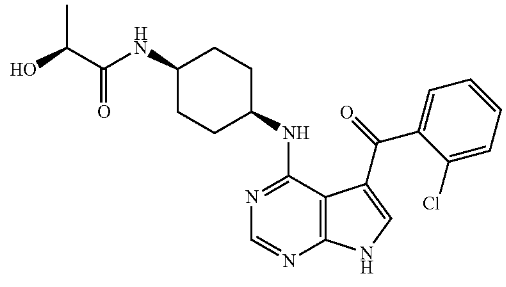 [SMILES: C[C@H](O)C(=O)N[C@H]1CC[C@@H](Nc2ncnc3[nH]cc(C(=O)c4ccccc4Cl)c23)CC1] | (S)-N-(cis-4-((5-(2-chlorobenzoyl)-7H-pyrrolo[2,3-d]pyrimidin-4-yl)amino)cyclohexyl)-2-hydroxypropanamide |

| Cmpd No. | Structure | Chemical name |
|---|---|---|
| I-86 | 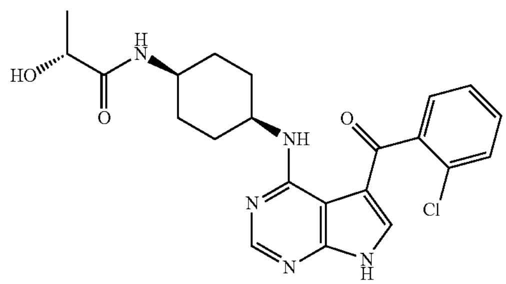 [SMILES: C[C@@H](O)C(=O)N[C@H]1CC[C@@H](Nc2ncnc3[nH]cc(C(=O)c4ccccc4Cl)c23)CC1] | (R)-N-(cis-4-((5-(2-chlorobenzoyl)-7H-pyrrolo[2,3-d]pyrimidin-4-yl)amino)cyclohexyl)-2-hydroxypropanamide |
| I-87 | 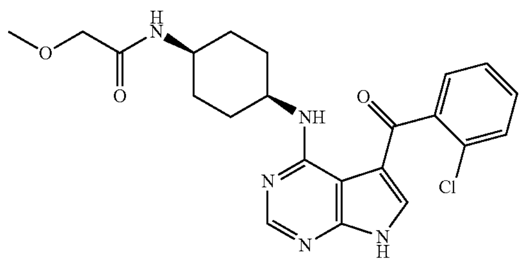 [SMILES: COCC(=O)N[C@H]1CC[C@@H](Nc2ncnc3[nH]cc(C(=O)c4ccccc4Cl)c23)CC1] | N-(cis-4-((5-(2-chlorobenzoyl)-7H-pyrrolo[2,3-d]pyrimidin-4-yl)amino)cyclohexyl)-2-methoxyacetamide |
| I-88 | 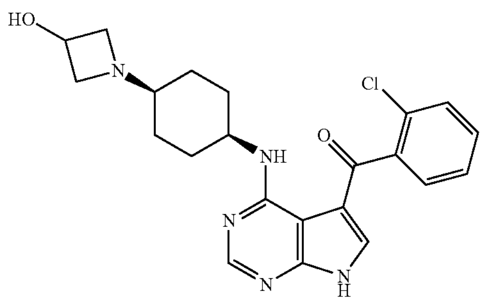 [SMILES: O=C(c1ccccc1Cl)c1c[nH]c2ncnc(N[C@H]3CC[C@@H](N4CC(O)C4)CC3)c12] | (2-chlorophenyl)(4-((cis-4-(3-hydroxyazetidin-1-yl)cyclohexyl)amino)-7H-pyrrolo[2,3-d]pyrimidin-5-yl)methanone |
| I-89 | 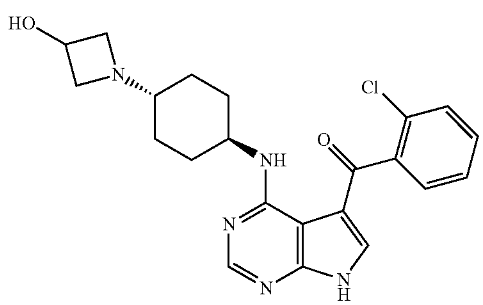 [SMILES: O=C(c1ccccc1Cl)c1c[nH]c2ncnc(N[C@H]3CC[C@H](N4CC(O)C4)CC3)c12] | (2-chlorophenyl)(4-((trans-4-(3-hydroxyazetidin-1-yl)cyclohexyl)amino)-7H-pyrrolo[2,3-d]pyrimidin-5-yl)methanone |
| I-90 | 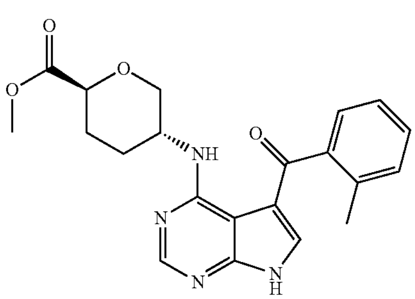 | methyl (2S,5R)-5-((5-(2-methylbenzoyl)-7H-pyrrolo[2,3-d]pyrimidin-4-yl)amino)tetrahydro-2H-pyran-2-carboxylate |

| Cmpd No. | Structure | Chemical name |
|---|---|---|
| I-91 | 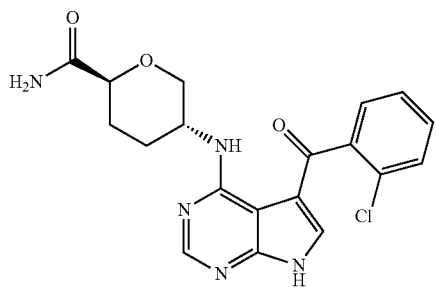 [SMILES: NC(=O)[C@@H]1CC[C@@H](Nc2ncnc3[nH]cc(C(=O)c4ccccc4Cl)c23)CO1] | (2S,5R)-5-((5-(2-chlorobenzoyl)-7H-pyrrolo[2,3-d]pyrimidin-4-yl)amino)tetrahydro-2H-pyran-2-carboxamide |
| I-92 | 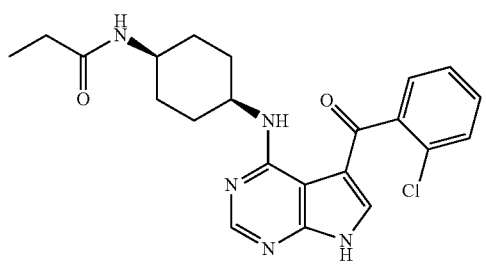 [SMILES: CCC(=O)N[C@H]1CC[C@@H](Nc2ncnc3[nH]cc(C(=O)c4ccccc4Cl)c23)CC1] | N-(cis-4-((5-(2-chlorobenzoyl)-7H-pyrrolo[2,3-d]pyrimidin-4-yl)amino)cyclohexyl)propionamide |
| I-93 | 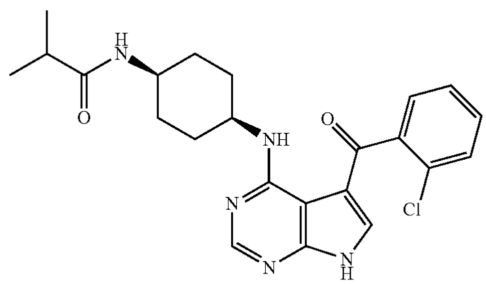 [SMILES: CC(C)C(=O)N[C@H]1CC[C@@H](Nc2ncnc3[nH]cc(C(=O)c4ccccc4Cl)c23)CC1] | N-(cis-4-((5-(2-chlorobenzoyl)-7H-pyrrolo[2,3-d]pyrimidin-4-yl)amino)cyclohexyl)isobutyramide |
| I-94 | 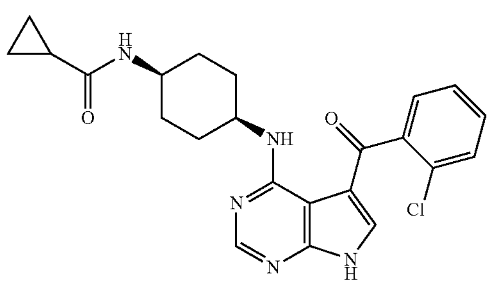 [SMILES: O=C(c1ccccc1Cl)c1c[nH]c2ncnc(N[C@H]3CC[C@@H](NC(=O)C4CC4)CC3)c12] | N-(cis-4-((5-(2-chlorobenzoyl)-7H-pyrrolo[2,3-d]pyrimidin-4-yl)amino)cyclohexyl)cyclopropane-carboxamide |
| I-95 | 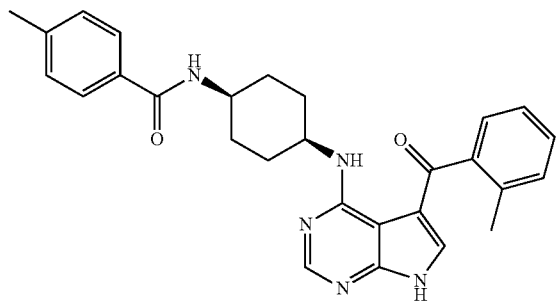 [SMILES: Cc1ccc(C(=O)N[C@H]2CC[C@@H](Nc3ncnc4[nH]cc(C(=O)c5ccccc5C)c34)CC2)cc1] | 4-methyl-N-(cis-4-((5-(2-methylbenzoyl)-7H-pyrrolo[2,3-d]pyrimidin-4-yl)amino)cyclohexyl)benzamide |

| Cmpd No. | Structure | Chemical name |
|---|---|---|
| I-96 | 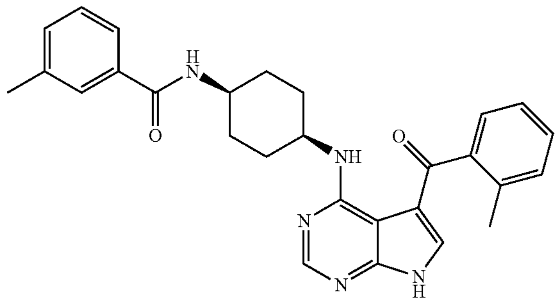 [SMILES: Cc1cccc(C(=O)N[C@H]2CC[C@@H](Nc3ncnc4[nH]cc(C(=O)c5ccccc5C)c34)CC2)c1] | 3-methyl-N-(cis-4-((5-(2-methylbenzoyl)-7H-pyrrolo[2,3-d]pyrimidin-4-yl)amino)cyclohexyl)benzamide |
| I-97 | 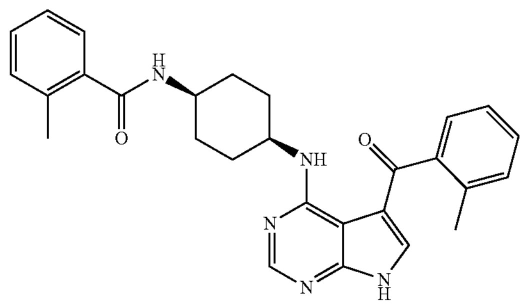 [SMILES: Cc1ccccc1C(=O)N[C@H]1CC[C@@H](Nc2ncnc3[nH]cc(C(=O)c4ccccc4C)c23)CC1] | 2-methyl-N-(cis-4-((5-(2-methylbenzoyl)-7H-pyrrolo[2,3-d]pyrimidin-4-yl)amino)cyclohexyl)benzamide |
| I-98 | 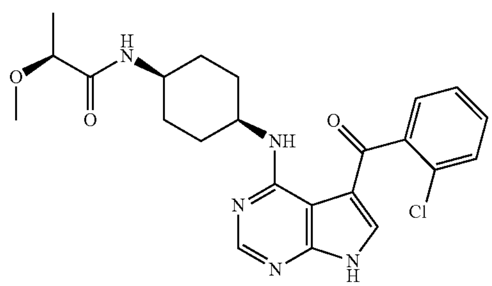 [SMILES: CO[C@@H](C)C(=O)N[C@H]1CC[C@@H](Nc2ncnc3[nH]cc(C(=O)c4ccccc4Cl)c23)CC1] | (S)-N-(cis-4-((5-(2-chlorobenzoyl)-7H-pyrrolo[2,3-d]pyrimidin-4-yl)amino)cyclohexyl)-2-methoxypropanamide |
| I-99 | 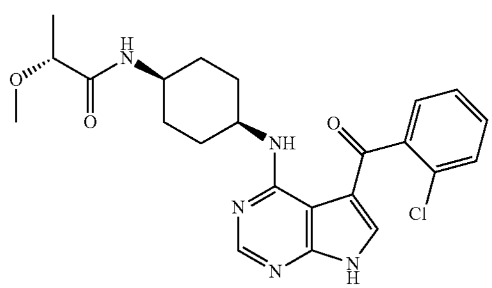 [SMILES: CO[C@H](C)C(=O)N[C@H]1CC[C@@H](Nc2ncnc3[nH]cc(C(=O)c4ccccc4Cl)c23)CC1] | (R)-N-(cis-4-((5-(2-chlorobenzoyl)-7H-pyrrolo[2,3-d]pyrimidin-4-yl)amino)cyclohexyl)-2-methoxypropanamide |
| I-100 | 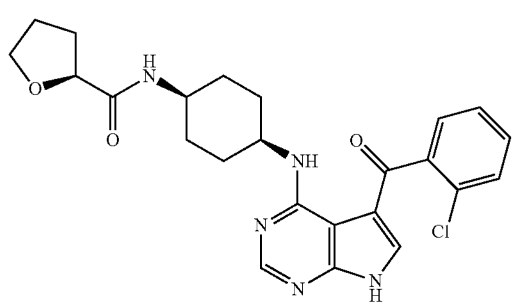 [SMILES: O=C(c1ccccc1Cl)c1c[nH]c2ncnc(N[C@H]3CC[C@@H](NC(=O)[C@@H]4CCCO4)CC3)c12] | (S)-N-(cis-4-((5-(2-chlorobenzoyl)-7H-pyrrolo[2,3-d]pyrimidin-4-yl)amino)cyclohexyl)tetrahydrofuran-2-carboxamide |

-continued

| Cmpd No. | Structure | Chemical name |
|---|---|---|
| I-101 | 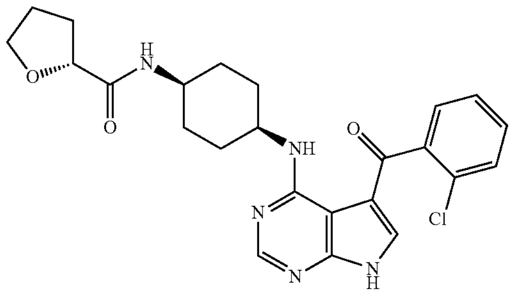 [SMILES: O=C(c1ccccc1Cl)c1c[nH]c2ncnc(N[C@H]3CC[C@@H](NC(=O)[C@H]4CCCO4)CC3)c12] | (R)-N-(cis-4-((5-(2-chlorobenzoyl)-7H-pyrrolo[2,3-d]pyrimidin-4-yl)amino)cyclohexyl)tetrahydrofuran-2-carboxamide |
| I-102 | 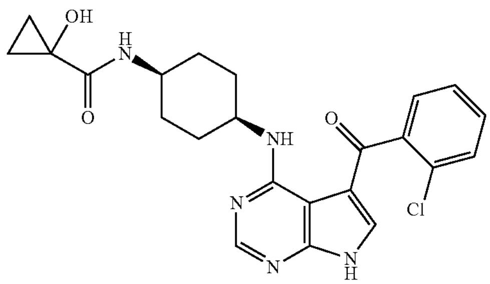 [SMILES: O=C(c1ccccc1Cl)c1c[nH]c2ncnc(N[C@H]3CC[C@@H](NC(=O)C4(O)CC4)CC3)c12] | N-(cis-4-((5-(2-chlorobenzoyl)-7H-pyrrolo[2,3-d]pyrimidin-4-yl)amino)cyclohexyl)-1-hydroxycyclopropane-1-carboxamide |
| I-103 | 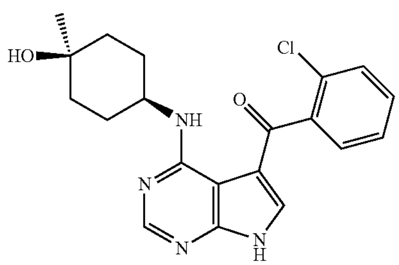 [SMILES: C[C@]1(O)CC[C@@H](Nc2ncnc3[nH]cc(C(=O)c4ccccc4Cl)c23)CC1] | (2-chlorophenyl)(4-((cis-4-hydroxy-4-methylcyclohexyl)amino)-7H-pyrrolo[2,3-d]pyrimidin-5-yl)methanone |
| I-104 | 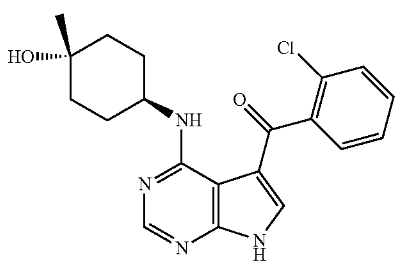 [SMILES: C[C@]1(O)CC[C@H](Nc2ncnc3[nH]cc(C(=O)c4ccccc4Cl)c23)CC1] | (2-chlorophenyl)(4-((trans-4-hydroxy-4-methylcyclohexyl)amino)-7H-pyrrolo[2,3-d]pyrimidin-5-yl)methanone |
| I-105 | 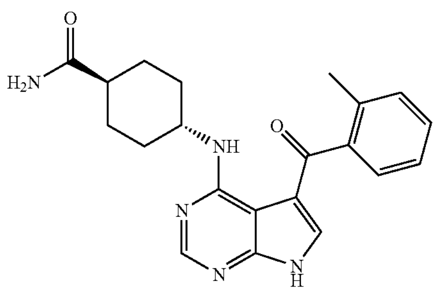 [SMILES: Cc1ccccc1C(=O)c1c[nH]c2ncnc(N[C@H]3CC[C@H](C(N)=O)CC3)c12] | trans-4-((5-(2-methylbenzoyl)-7H-pyrrolo[2,3-d]pyrimidin-4-yl)amino)cyclohexane-1-carboxamide |

-continued

| Cmpd No. | Structure | Chemical name |
|---|---|---|
| I-106 | 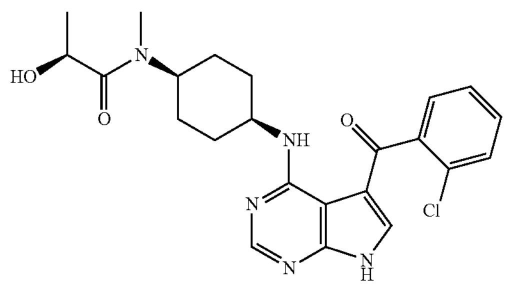 [SMILES: C[C@H](O)C(=O)N(C)[C@H]1CC[C@@H](Nc2ncnc3[nH]cc(C(=O)c4ccccc4Cl)c23)CC1] | (S)-N-(cis-4-((5-(2-chlorobenzoyl)-7H-pyrrolo[2,3-d]pyrimidin-4-yl)amino)cyclohexyl)-2-hydroxy-N-methylpropanamide |
| I-107 | 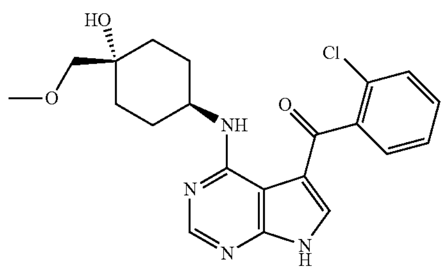 [SMILES: COC[C@]1(O)CC[C@H](Nc2ncnc3[nH]cc(C(=O)c4ccccc4Cl)c23)CC1] | (2-chlorophenyl)(4-((trans-4-hydroxy-4-(methoxymethyl)cyclohexyl)amino)-7H-pyrrolo[2,3-d]pyrimidin-5-yl)methanone |
| I-108 | 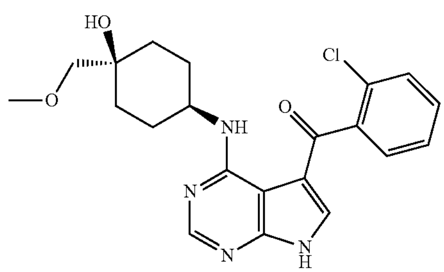 [SMILES: COC[C@]1(O)CC[C@@H](Nc2ncnc3[nH]cc(C(=O)c4ccccc4Cl)c23)CC1] | (2-chlorophenyl)(4-((cis-4-hydroxy-4-(methoxymethyl)cyclohexyl)amino)-7H-pyrrolo[2,3-d]pyrimidin-5-yl)methanone |
| I-109 | 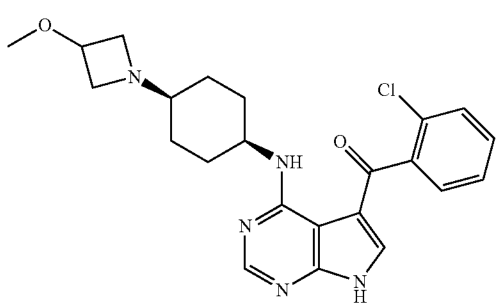 [SMILES: COC1CN([C@H]2CC[C@@H](Nc3ncnc4[nH]cc(C(=O)c5ccccc5Cl)c34)CC2)C1] | (2-chlorophenyl)(4-((cis-4-(3-methoxyazetidin-1-yl)cyclohexyl)amino)-7H-pyrrolo[2,3-d]pyrimidin-5-yl)methanone |
| I-110 | 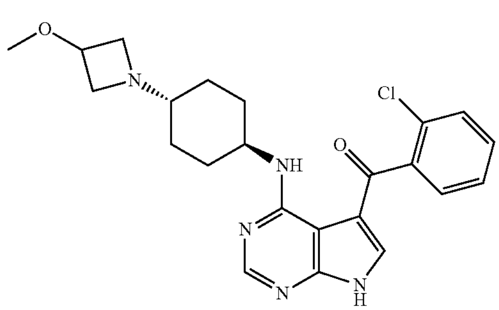 [SMILES: COC1CN([C@H]2CC[C@H](Nc3ncnc4[nH]cc(C(=O)c5ccccc5Cl)c34)CC2)C1] | (2-chlorophenyl)(4-((trans-4-(3-methoxyazetidin-1-yl)cyclohexyl)amino)-7H-pyrrolo[2,3-d]pyrimidin-5-yl)methanone |

-continued

| Cmpd No. | Structure | Chemical name |
| --- | --- | --- |
| I-111 | 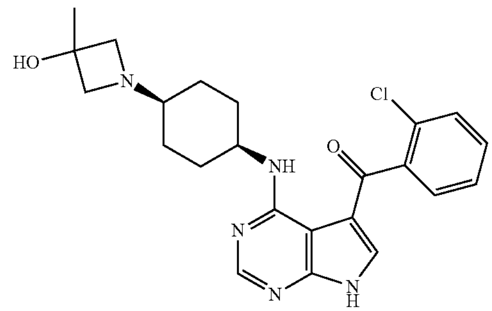 [SMILES: CC1(O)CN([C@H]2CC[C@@H](Nc3ncnc4[nH]cc(C(=O)c5ccccc5Cl)c34)CC2)C1] | (2-chlorophenyl)(4-((cis-4-(3-hydroxy-3-methylazetidin-1-yl)cyclohexyl)amino)-7H-pyrrolo[2,3-d]pyrimidin-5-yl)methanone |
| I-112 | 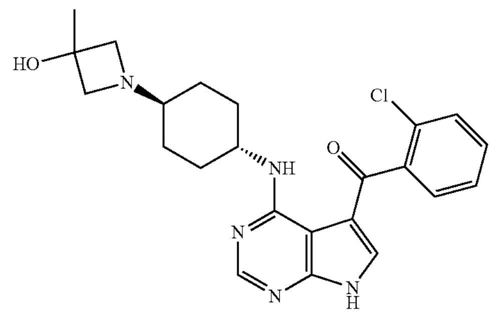 [SMILES: CC1(O)CN([C@H]2CC[C@H](Nc3ncnc4[nH]cc(C(=O)c5ccccc5Cl)c34)CC2)C1] | (2-chlorophenyl)(4-((trans-4-(3-hydroxy-3-methylazetidin-1-yl)cyclohexyl)amino)-7H-pyrrolo[2,3-d]pyrimidin-5-yl)methanone |
| I-113 | 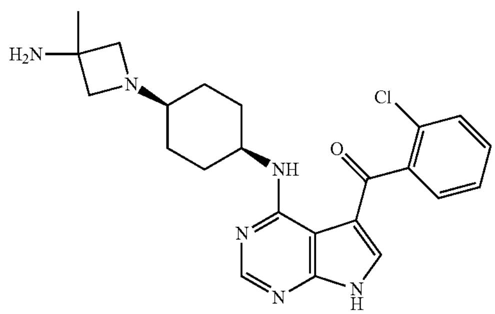 [SMILES: CC1(N)CN([C@H]2CC[C@@H](Nc3ncnc4[nH]cc(C(=O)c5ccccc5Cl)c34)CC2)C1] | (4-((cis-4-(3-amino-3-methylazetidin-1-yl)cyclohexyl)amino)-7H-pyrrolo[2,3-d]pyrimidin-5-yl)(2-chlorophenyl)methanone |
| I-114 | 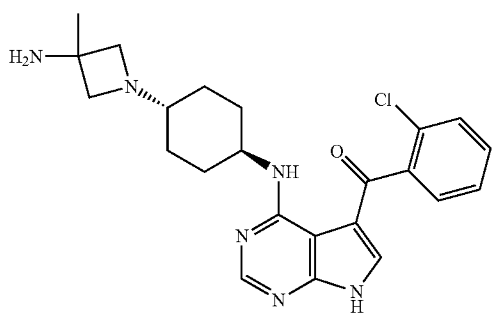 [SMILES: CC1(N)CN([C@H]2CC[C@H](Nc3ncnc4[nH]cc(C(=O)c5ccccc5Cl)c34)CC2)C1] | (4-((trans-4-(3-amino-3-methylazetidin-1-yl)cyclohexyl)amino)-7H-pyrrolo[2,3-d]pyrimidin-5-yl)(2-chlorophenyl)methanone |
| I-115 | 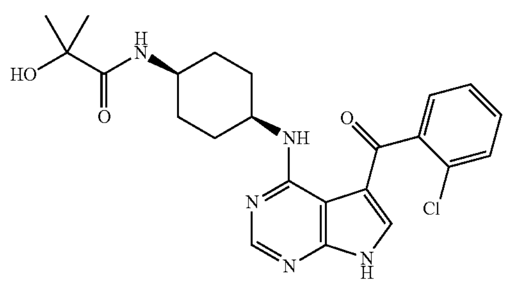 [SMILES: CC(C)(O)C(=O)N[C@H]1CC[C@@H](Nc2ncnc3[nH]cc(C(=O)c4ccccc4Cl)c23)CC1] | N-(cis-4-((5-(2-chlorobenzoyl)-7H-pyrrolo[2,3-d]pyrimidin-4-yl)amino)cyclohexyl)-2-hydroxy-2-methylpropanamide |

-continued

| Cmpd No. | Structure | Chemical name |
|---|---|---|
| I-116 | 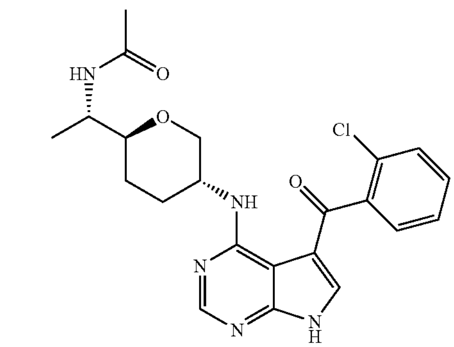 [SMILES: CC(=O)N[C@@H](C)[C@@H]1CC[C@@H](Nc2ncnc3[nH]cc(C(=O)c4ccccc4Cl)c23)CO1] | N-((S)-1-((2S,5R)-5-((5-(2-chlorobenzoyl)-7H-pyrrolo[2,3-d]pyrimidin-4-yl)amino)tetrahydro-2H-pyran-2-yl)ethyl)acetamide |
| I-117 | 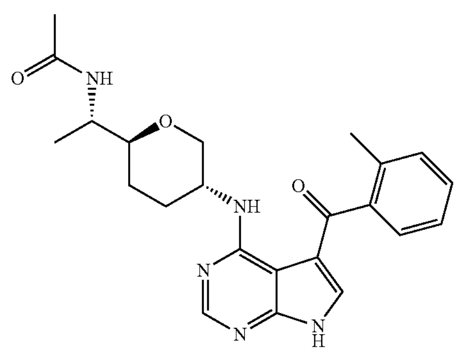 [SMILES: CC(=O)N[C@@H](C)[C@@H]1CC[C@@H](Nc2ncnc3[nH]cc(C(=O)c4ccccc4C)c23)CO1] | N-((S)-1-((2S,5R)-5-((5-(2-methylbenzoyl)-7H-pyrrolo[2,3-d]pyrimidin-4-yl)amino)tetrahydro-2H-pyran-2-yl)ethyl)acetamide |
| I-118 | 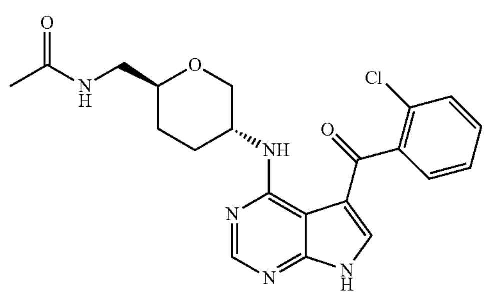 [SMILES: CC(=O)NC[C@@H]1CC[C@@H](Nc2ncnc3[nH]cc(C(=O)c4ccccc4Cl)c23)CO1] | N-(((2S,5R)-5-((5-(2-chlorobenzoyl)-7H-pyrrolo[2,3-d]pyrimidin-4-yl)amino)tetrahydro-2H-pyran-2-yl)methyl)acetamide |
| I-119 | 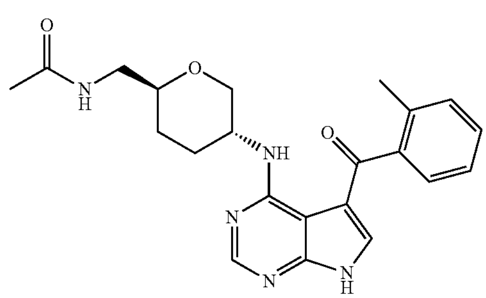 [SMILES: CC(=O)NC[C@@H]1CC[C@@H](Nc2ncnc3[nH]cc(C(=O)c4ccccc4C)c23)CO1] | N-(((2S,5R)-5-((5-(2-methylbenzoyl)-7H-pyrrolo[2,3-d]pyrimidin-4-yl)amino)tetrahydro-2H-pyran-2-yl)methyl)acetamide |
| I-120 | 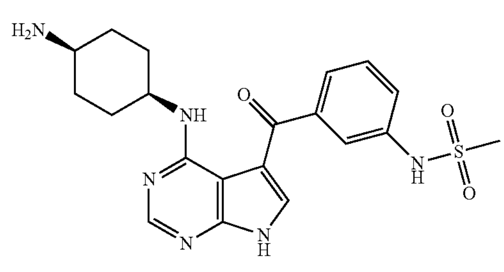 [SMILES: CS(=O)(=O)Nc1cccc(C(=O)c2c[nH]c3ncnc(N[C@H]4CC[C@@H](N)CC4)c23)c1] | N-(3-(4-((cis-4-aminocyclohexyl)amino)-7H-pyrrolo[2,3-d]pyrimidine-5-carbonyl)phenyl)methanesulfonamide |

-continued

| Cmpd No. | Structure | Chemical name |
| --- | --- | --- |
| I-121 | 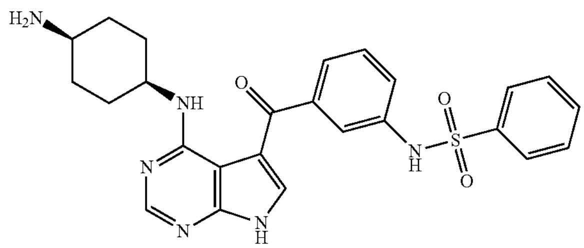 [SMILES: N[C@H]1CC[C@@H](Nc2ncnc3[nH]cc(C(=O)c4cccc(NS(=O)(=O)c5ccccc5)c4)c23)CC1] | N-(3-(4-((cis-4-aminocyclohexyl)amino)-7H-pyrrolo[2,3-d]pyrimidine-5-carbonyl)phenyl)benzenesulfonamide |
| I-122 | 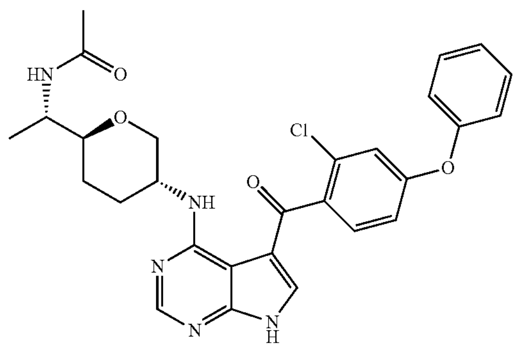 [SMILES: CC(=O)N[C@@H](C)[C@@H]1CC[C@@H](Nc2ncnc3[nH]cc(C(=O)c4ccc(Oc5ccccc5)cc4Cl)c23)CO1] | N-((S)-1-((2S,5R)-5-((5-(2-chloro-4-phenoxybenzoyl)-7H-pyrrolo[2,3-d]pyrimidin-4-yl)amino)tetrahydro-2H-pyran-2-yl)ethyl)acetamide |
| I-124 | 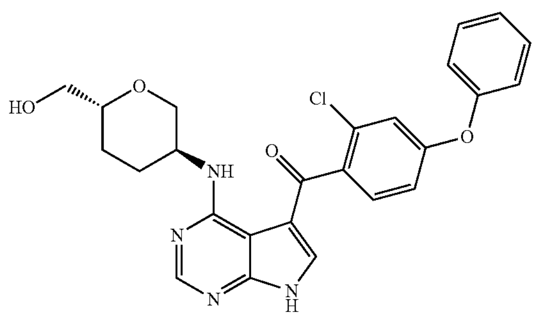 [SMILES: O=C(c1ccc(Oc2ccccc2)cc1Cl)c1c[nH]c2ncnc(N[C@H]3CC[C@H](CO)OC3)c12] | (2-chloro-4-phenoxyphenyl)(4-(((3S,6R)-6-(hydroxymethyl)tetrahydro-2H-pyran-3-yl)amino)-7H-pyrrolo[2,3-d]pyrimidin-5-yl)methanone |
| I-125 | 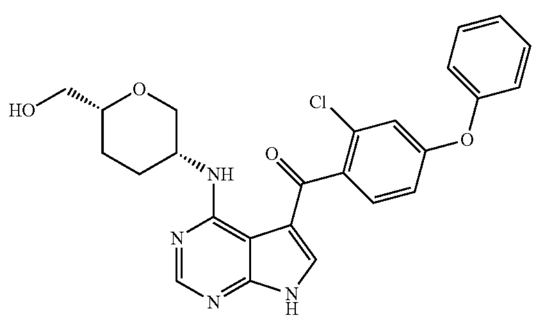 [SMILES: O=C(c1ccc(Oc2ccccc2)cc1Cl)c1c[nH]c2ncnc(N[C@@H]3CC[C@H](CO)OC3)c12] | (2-chloro-4-phenoxyphenyl)(4-(((3R,6R)-6-(hydroxymethyl)tetrahydro-2H-pyran-3-yl)amino)-7H-pyrrolo[2,3-d]pyrimidin-5-yl)methanone |
| I-126 | 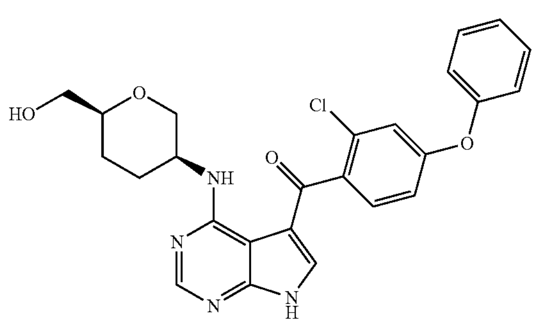 [SMILES: O=C(c1ccc(Oc2ccccc2)cc1Cl)c1c[nH]c2ncnc(N[C@H]3CC[C@@H](CO)OC3)c12] | (2-chloro-4-phenoxyphenyl)(4-(((3S,6S)-6-(hydroxymethyl)tetrahydro-2H-pyran-3-yl)amino)-7H-pyrrolo[2,3-d]pyrimidin-5-yl)methanone |

-continued

| Cmpd No. | Structure | Chemical name |
| --- | --- | --- |
| I-127 | 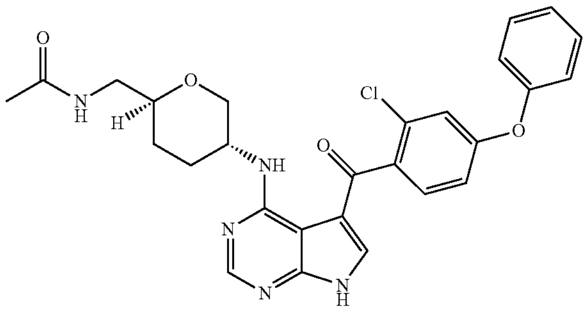 [SMILES: CC(=O)NC[C@@H]1CC[C@@H](Nc2ncnc3[nH]cc(C(=O)c4ccc(Oc5ccccc5)cc4Cl)c23)CO1] | N-(((2S,5R)-5-((5-(2-chloro-4-phenoxybenzoyl)-7H-pyrrolo[2,3-d]pyrimidin-4-yl)amino)tetrahydro-2H-pyran-2-yl)methyl)acetamide |
| I-128 | 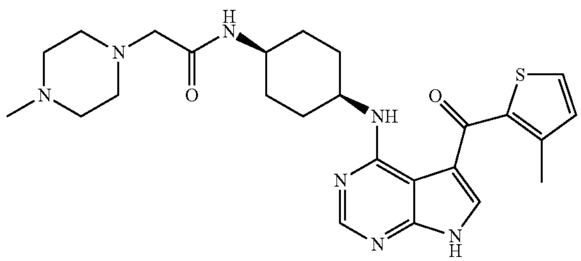 [SMILES: Cc1ccsc1C(=O)c1c[nH]c2ncnc(N[C@H]3CC[C@@H](NC(=O)CN4CCN(C)CC4)CC3)c12] | 2-(4-methylpiperazin-1-yl)-N-(cis-4-((5-(3-methylthiophene-2-carbonyl)-7H-pyrrolo[2,3-d]pyrimidin-4-yl)amino)cyclohexyl)acetamide |
| I-129 | 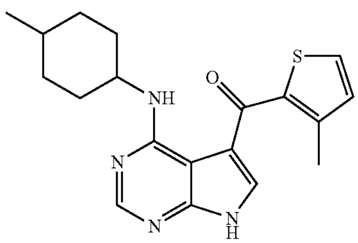 [SMILES: Cc1ccsc1C(=O)c1c[nH]c2ncnc(NC3CCC(C)CC3)c12] | (4-((4-methylcyclohexyl)amino)-7H-pyrrolo[2,3-d]pyrimidin-5-yl)(3-methylthiophen-2-yl)methanone |
| I-130 | 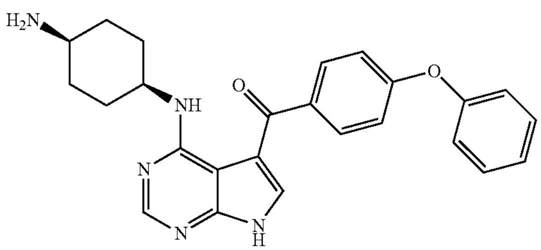 [SMILES: N[C@H]1CC[C@@H](Nc2ncnc3[nH]cc(C(=O)c4ccc(Oc5ccccc5)cc4)c23)CC1] | (4-((cis-4-aminocyclohexyl)amino)-7H-pyrrolo[2,3-d]pyrimidin-5-yl)(4-phenoxyphenyl)methanone |
| I-131 | 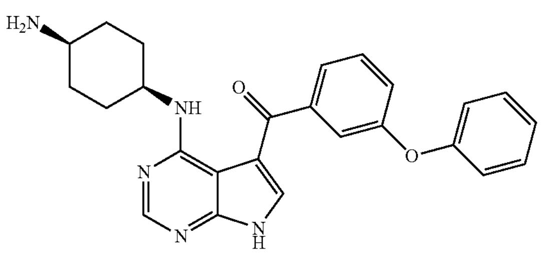 [SMILES: N[C@H]1CC[C@@H](Nc2ncnc3[nH]cc(C(=O)c4cccc(Oc5ccccc5)c4)c23)CC1] | (4-((cis-4-aminocyclohexyl)amino)-7H-pyrrolo[2,3-d]pyrimidin-5-yl)(3-phenoxyphenyl)methanone |
| I-132 | 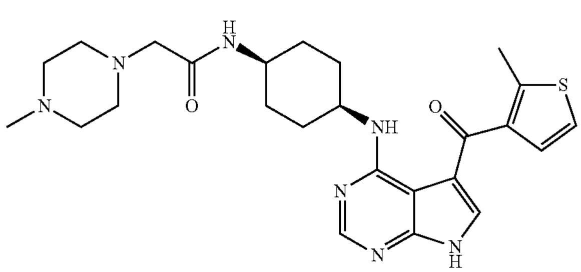 [SMILES: Cc1sccc1C(=O)c1c[nH]c2ncnc(N[C@H]3CC[C@@H](NC(=O)CN4CCN(C)CC4)CC3)c12] | 2-(4-methylpiperazin-1-yl)-N-(cis-4-((5-(2-methylthiophene-3-carbonyl)-7H-pyrrolo[2,3-d]pyrimidin-4-yl)amino)cyclohexyl)acetamide |

-continued

| Cmpd No. | Structure | Chemical name |
| --- | --- | --- |
| I-133 | 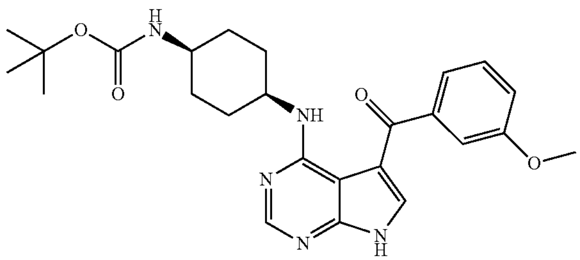 [SMILES: COc1cccc(C(=O)c2c[nH]c3ncnc(N[C@H]4CC[C@@H](NC(=O)OC(C)(C)C)CC4)c23)c1] | tert-butyl (cis-4-((5-(3-methoxybenzoyl)-7H-pyrrolo[2,3-d]pyrimidin-4-yl)amino)cyclohexyl)carbamate |
| I-134 | 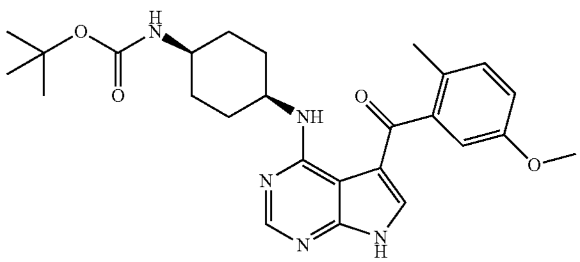 [SMILES: COc1ccc(C)c(C(=O)c2c[nH]c3ncnc(N[C@H]4CC[C@@H](NC(=O)OC(C)(C)C)CC4)c23)c1] | tert-butyl (cis-4-((5-(5-methoxy-2-methylbenzoyl)-7H-pyrrolo[2,3-d]pyrimidin-4-yl)amino)cyclohexyl)carbamate |
| I-135 | 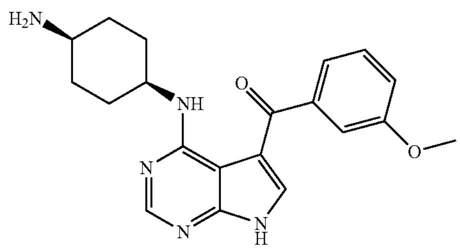 [SMILES: COc1cccc(C(=O)c2c[nH]c3ncnc(N[C@H]4CC[C@@H](N)CC4)c23)c1] | (4-((cis-4-aminocyclohexyl)amino)-7H-pyrrolo[2,3-d]pyrimidin-5-yl)(3-methoxyphenyl)methanone |
| I-136 | 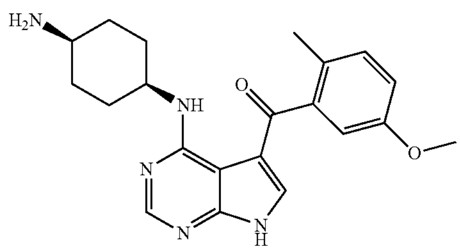 [SMILES: COc1ccc(C)c(C(=O)c2c[nH]c3ncnc(N[C@H]4CC[C@@H](N)CC4)c23)c1] | (4-((cis-4-aminocyclohexyl)amino)-7H-pyrrolo[2,3-d]pyrimidin-5-yl)(5-methoxy-2-methylphenyl)methanone |
| I-137 | 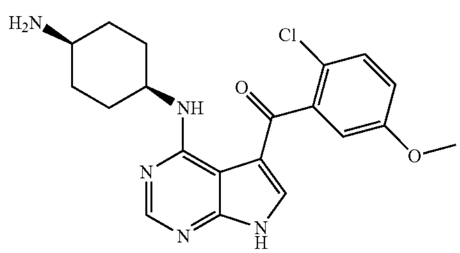 [SMILES: COc1ccc(Cl)c(C(=O)c2c[nH]c3ncnc(N[C@H]4CC[C@@H](N)CC4)c23)c1] | (4-((cis-4-aminocyclohexyl)amino)-7H-pyrrolo[2,3-d]pyrimidin-5-yl)(2-chloro-5-methoxyphenyl)methanone |
| I-138 | 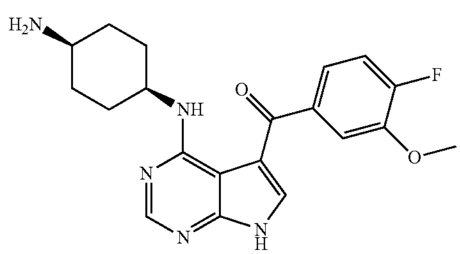 [SMILES: COc1cc(C(=O)c2c[nH]c3ncnc(N[C@H]4CC[C@@H](N)CC4)c23)ccc1F] | (4-((cis-4-aminocyclohexyl)amino)-7H-pyrrolo[2,3-d]pyrimidin-5-yl)(4-fluoro-3-methoxyphenyl)methanone |

-continued

| Cmpd No. | Structure | Chemical name |
|---|---|---|
| I-139 | 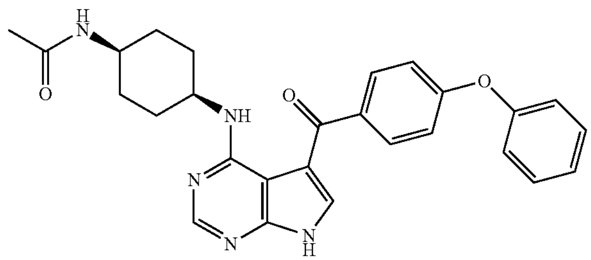 [SMILES: CC(=O)N[C@H]1CC[C@@H](Nc2ncnc3[nH]cc(C(=O)c4ccc(Oc5ccccc5)cc4)c23)CC1] | N-(cis-4-((5-(4-phenoxybenzoyl)-7H-pyrrolo[2,3-d]pyrimidin-4-yl)amino)cyclohexyl)acetamide |
| I-140 | 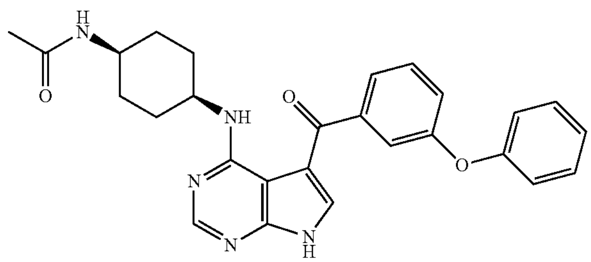 [SMILES: CC(=O)N[C@H]1CC[C@@H](Nc2ncnc3[nH]cc(C(=O)c4cccc(Oc5ccccc5)c4)c23)CC1] | N-(cis-4-((5-(3-phenoxybenzoyl)-7H-pyrrolo[2,3-d]pyrimidin-4-yl)amino)cyclohexyl)acetamide |
| I-141 | 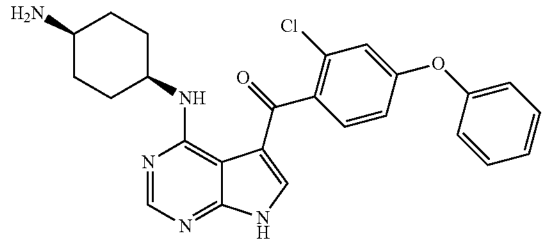 [SMILES: N[C@H]1CC[C@@H](Nc2ncnc3[nH]cc(C(=O)c4ccc(Oc5ccccc5)cc4Cl)c23)CC1] | (4-((cis-4-aminocyclohexyl)amino)-7H-pyrrolo[2,3-d]pyrimidin-5-yl)(2-chloro-4-phenoxyphenyl)methanone |
| I-142 | 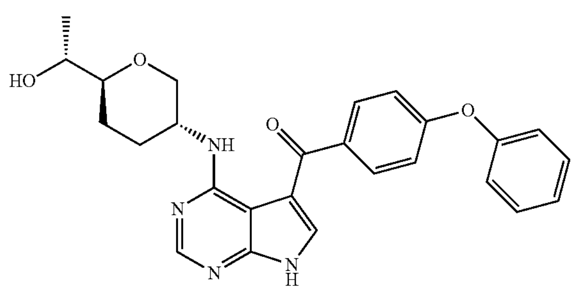 | (4-(((3R,6S)-6-((R)-1-hydroxyethyl)tetrahydro-2H-pyran-3-yl)amino)-7H-pyrrolo[2,3-d]pyrimidin-5-yl)(4-phenoxyphenyl)methanone |
| I-143 | 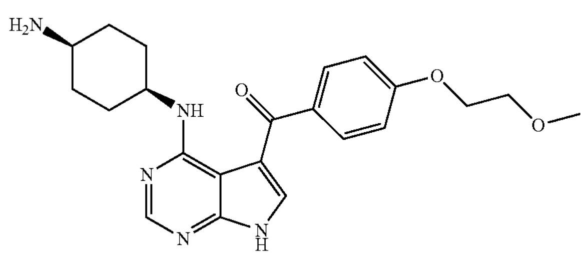 [SMILES: COCCOc1ccc(C(=O)c2c[nH]c3ncnc(N[C@H]4CC[C@@H](N)CC4)c23)cc1] | (4-((cis-4-aminocyclohexyl)amino)-7H-pyrrolo[2,3-d]pyrimidin-5-yl)(4-(2-methoxyethoxy)phenyl)methanone |

| Cmpd No. | Structure | Chemical name |
|---|---|---|
| I-144 | 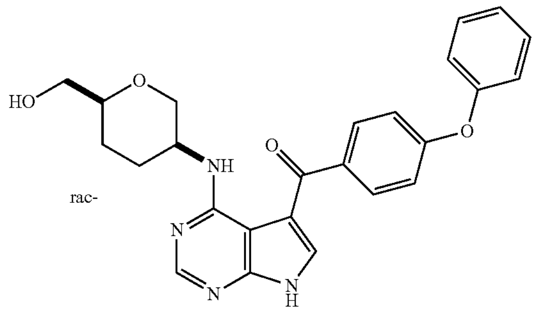 [SMILES: O=C(c1ccc(Oc2ccccc2)cc1)c1c[nH]c2ncnc(N[C@H]3CC[C@@H](CO)OC3)c12] | rac-(4-((cis-6-(hydroxymethyl)tetrahydro-2H-pyran-3-yl)amino)-7H-pyrrolo[2,3-d]pyrimidin-5-yl)(4-phenoxyphenyl)methanone |
| I-145 | 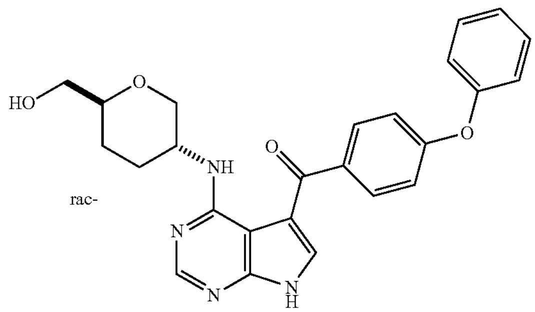 [SMILES: O=C(c1ccc(Oc2ccccc2)cc1)c1c[nH]c2ncnc(N[C@@H]3CC[C@@H](CO)OC3)c12] | rac-(4-((trans-6-(hydroxymethyl)tetrahydro-2H-pyran-3-yl)amino)-7H-pyrrolo[2,3-d]pyrimidin-5-yl)(4-phenoxyphenyl)methanone |
| I-146 | 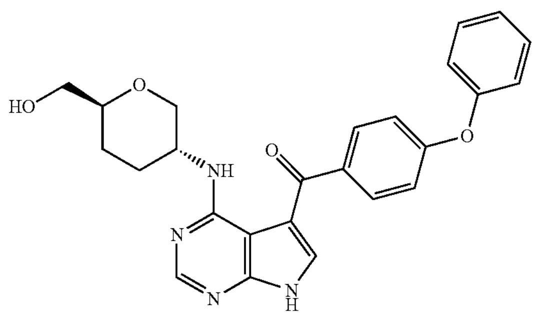 [SMILES: O=C(c1ccc(Oc2ccccc2)cc1)c1c[nH]c2ncnc(N[C@@H]3CC[C@@H](CO)OC3)c12] | (4-(((3R,6S)-6-(hydroxymethyl)tetrahydro-2H-pyran-3-yl)amino)-7H-pyrrolo[2,3-d]pyrimidin-5-yl)(4-phenoxyphenyl)methanone |
| I-147 | 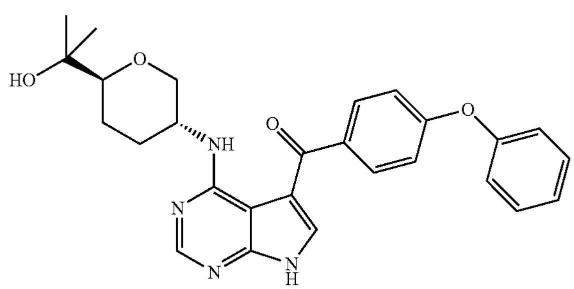 [SMILES: CC(C)(O)[C@@H]1CC[C@@H](Nc2ncnc3[nH]cc(C(=O)c4ccc(Oc5ccccc5)cc4)c23)CO1] | (4-(((3R,6S)-6-(2-hydroxypropan-2-yl)tetrahydro-2H-pyran-3-yl)amino)-7H-pyrrolo[2,3-d]pyrimidin-5-yl)(4-phenoxyphenyl)methanone |
| I-148 | 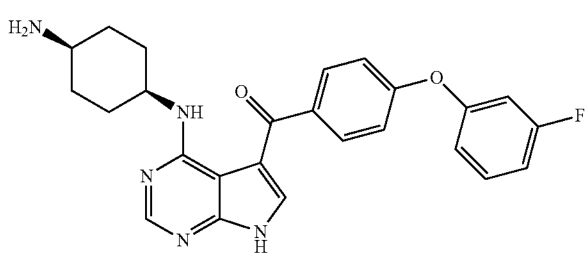 [SMILES: N[C@H]1CC[C@@H](Nc2ncnc3[nH]cc(C(=O)c4ccc(Oc5cccc(F)c5)cc4)c23)CC1] | (4-((cis-4-aminocyclohexyl)amino)-7H-pyrrolo[2,3-d]pyrimidin-5-yl)(4-(3-fluorophenoxy)phenyl)methanone |

| Cmpd No. | Structure | Chemical name |
|---|---|---|
| I-149 | 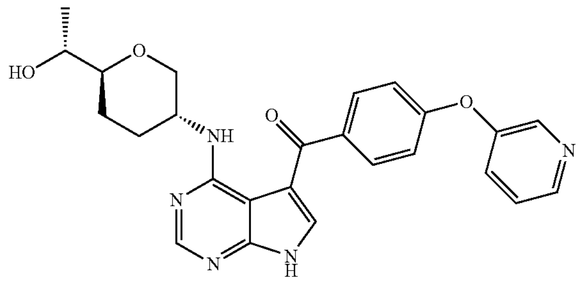 [SMILES: C[C@@H](O)[C@@H]1CC[C@@H](Nc2ncnc3[nH]cc(C(=O)c4ccc(Oc5cccnc5)cc4)c23)CO1] | (4-(((3R,6S)-6-((R)-1-hydroxyethyl)tetrahydro-2H-pyran-3-yl)amino)-7H-pyrrolo[2,3-d]pyrimidin-5-yl)(4-(pyridin-3-yloxy)phenyl)methanone |
| I-150 | 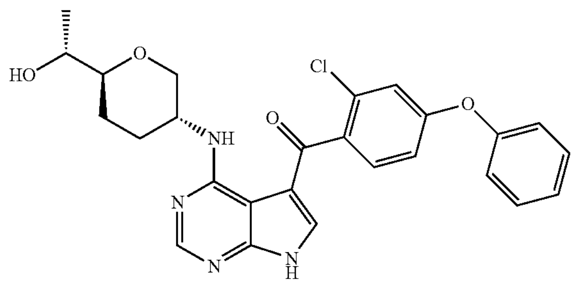 [SMILES: C[C@@H](O)[C@@H]1CC[C@@H](Nc2ncnc3[nH]cc(C(=O)c4ccc(Oc5ccccc5)cc4Cl)c23)CO1] | (2-chloro-4-phenoxyphenyl)(4-(((3R,6S)-6-((R)-1-hydroxyethyl)tetrahydro-2H-pyran-3-yl)amino)-7H-pyrrolo[2,3-d]pyrimidin-5-yl)methanone |
| I-151 | 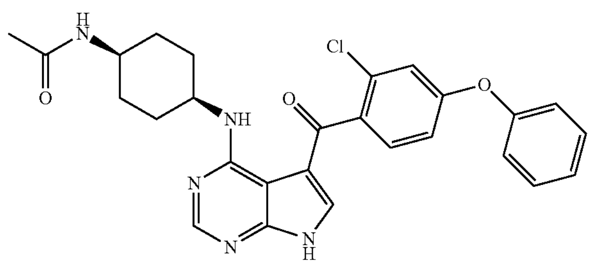 [SMILES: CC(=O)N[C@H]1CC[C@@H](Nc2ncnc3[nH]cc(C(=O)c4ccc(Oc5ccccc5)cc4Cl)c23)CC1] | N-(cis-4-((5-(2-chloro-4-phenoxybenzoyl)-7H-pyrrolo[2,3-d]pyrimidin-4-yl)amino)cyclohexyl)acetamide |
| I-152 | 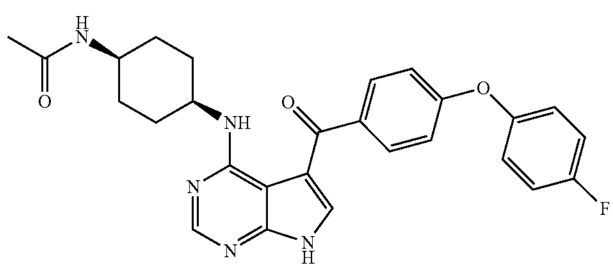 [SMILES: CC(=O)N[C@H]1CC[C@@H](Nc2ncnc3[nH]cc(C(=O)c4ccc(Oc5ccc(F)cc5)cc4)c23)CC1] | N-(cis-4-((5-(4-(4-fluorophenoxy)benzoyl)-7H-pyrrolo[2,3-d]pyrimidin-4-yl)amino)cyclohexyl)acetamide |
| I-153 | 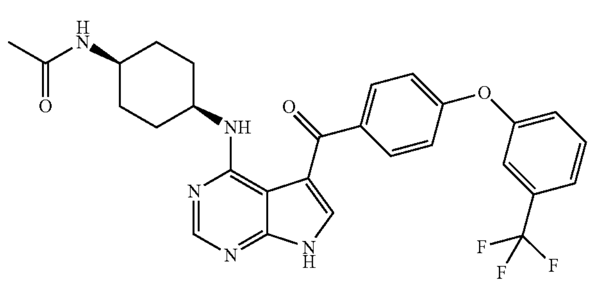 [SMILES: CC(=O)N[C@H]1CC[C@@H](Nc2ncnc3[nH]cc(C(=O)c4ccc(Oc5cccc(C(F)(F)F)c5)cc4)c23)CC1] | N-(cis-4-((5-(4-(3-(trifluoromethyl)phenoxy)benzoyl)-7H-pyrrolo[2,3-d]pyrimidin-4-yl)amino)cyclohexyl)acetamide |

-continued

| Cmpd No. | Structure | Chemical name |
| --- | --- | --- |
| I-154 | 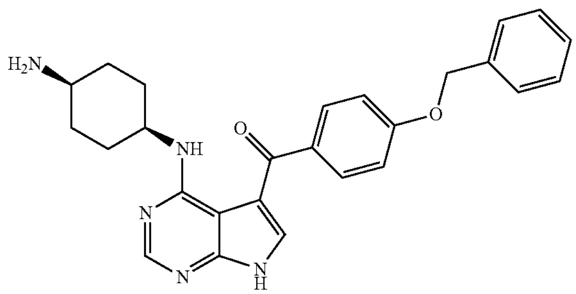 [SMILES: N[C@H]1CC[C@@H](Nc2ncnc3[nH]cc(C(=O)c4ccc(OCc5ccccc5)cc4)c23)CC1] | (4-((cis-4-aminocyclohexyl)amino)-7H-pyrrolo[2,3-d]pyrimidin-5-yl)(4-(benzyloxy)phenyl)methanone |
| I-155 | 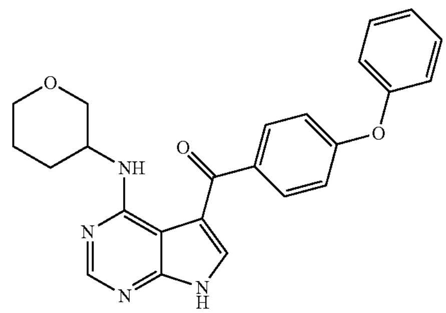 [SMILES: O=C(c1ccc(Oc2ccccc2)cc1)c1c[nH]c2ncnc(NC3CCCOC3)c12] | rac-(4-phenoxyphenyl)(4-((tetrahydro-2H-pyran-3-yl)amino)-7H-pyrrolo[2,3-d]pyrimidin-5-yl)methanone |
| I-156 | 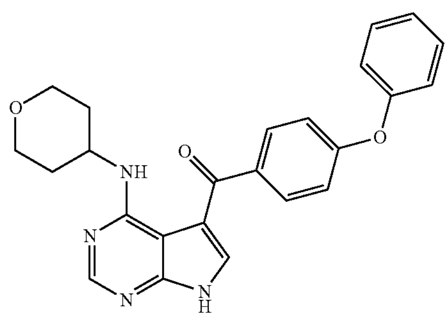 [SMILES: O=C(c1ccc(Oc2ccccc2)cc1)c1c[nH]c2ncnc(NC3CCOCC3)c12] | (4-phenoxyphenyl)(4-((tetrahydro-2H-pyran-4-yl)amino)-7H-pyrrolo[2,3-d]pyrimidin-5-yl)methanone |
| I-157 | 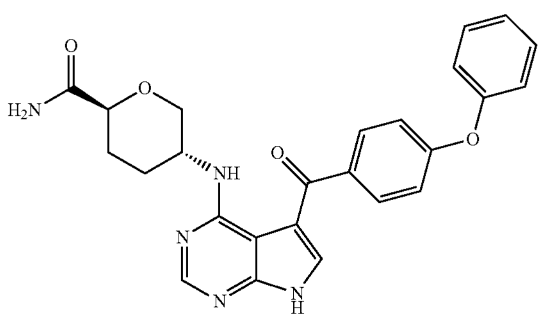 [SMILES: NC(=O)[C@@H]1CC[C@@H](Nc2ncnc3[nH]cc(C(=O)c4ccc(Oc5ccccc5)cc4)c23)CO1] | (2S,5R)-5-((5-(4-phenoxybenzoyl)-7H-pyrrolo[2,3-d]pyrimidin-4-yl)amino)tetrahydro-2H-pyran-2-carboxamide |
| I-158 | 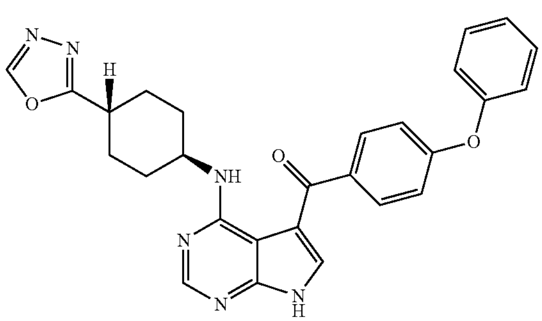 [SMILES: O=C(c1ccc(Oc2ccccc2)cc1)c1c[nH]c2ncnc(N[C@H]3CC[C@H](c4nnco4)CC3)c12] | (4-((trans-4-(1,3,4-oxadiazol-2-yl)cyclohexyl)amino)-7H-pyrrolo[2,3-d]pyrimidin-5-yl)(4-phenoxyphenyl)methanone |

-continued

| Cmpd No. | Structure | Chemical name |
| --- | --- | --- |
| I-159 | 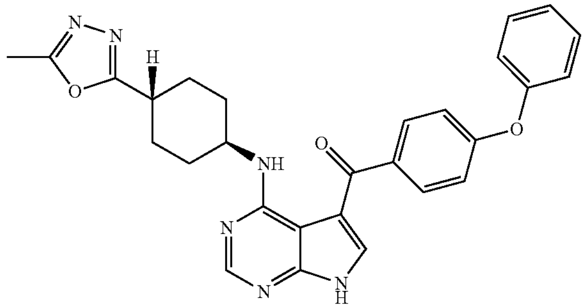 [SMILES: Cc1nnc([C@H]2CC[C@H](Nc3ncnc4[nH]cc(C(=O)c5ccc(Oc6ccccc6)cc5)c34)CC2)o1] | (4-((trans-4-(5-methyl-1,3,4-oxadiazol-2-yl)cyclohexyl)amino)-7H-pyrrolo[2,3-d]pyrimidin-5-yl)(4-phenoxyphenyl)methanone |
| I-160 | 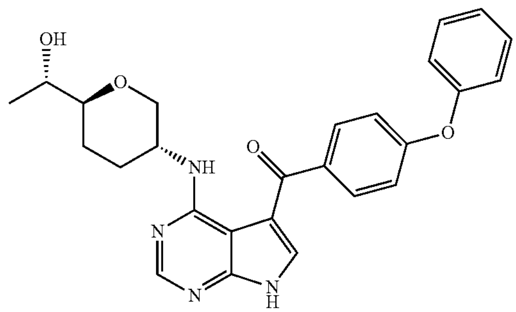 [SMILES: C[C@H](O)[C@@H]1CC[C@@H](Nc2ncnc3[nH]cc(C(=O)c4ccc(Oc5ccccc5)cc4)c23)CO1] | (4-(((3R,6S)-6-((S)-1-hydroxyethyl)tetrahydro-2H-pyran-3-yl)amino)-7H-pyrrolo[2,3-d]pyrimidin-5-yl)(4-phenoxyphenyl)methanone |
| I-161 | 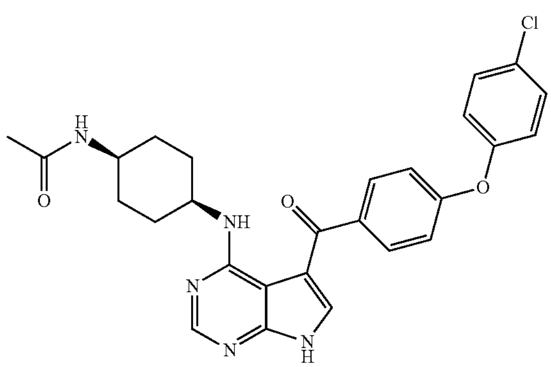 [SMILES: CC(=O)N[C@H]1CC[C@@H](Nc2ncnc3[nH]cc(C(=O)c4ccc(Oc5ccc(Cl)cc5)cc4)c23)CC1] | N-(cis-4-((5-(4-(4-chlorophenoxy)benzoyl)-7H-pyrrolo[2,3-d]pyrimidin-4-yl)amino)cyclohexyl)acetamide |
| I-162 | 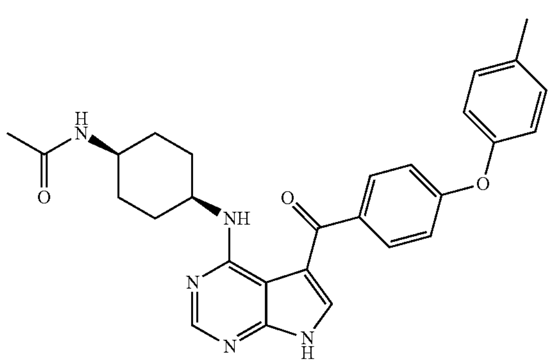 [SMILES: CC(=O)N[C@H]1CC[C@@H](Nc2ncnc3[nH]cc(C(=O)c4ccc(Oc5ccc(C)cc5)cc4)c23)CC1] | N-(cis-4-((5-(4-(p-tolyloxy)benzoyl)-7H-pyrrolo[2,3-d]pyrimidin-4-yl)amino)cyclohexyl)acetamide |

| Cmpd No. | Structure | Chemical name |
|---|---|---|
| I-163 | 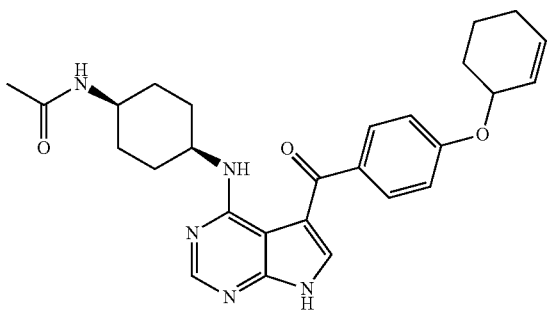 [SMILES: CC(=O)N[C@H]1CC[C@@H](Nc2ncnc3[nH]cc(C(=O)c4ccc(OC5C=CCCC5)cc4)c23)CC1] | N-(cis-4-((5-(4-(cyclohex-2-en-1-yloxy)benzoyl)-7H-pyrrolo[2,3-d]pyrimidin-4-yl)amino)cyclohexyl)acetamide |
| I-164 | 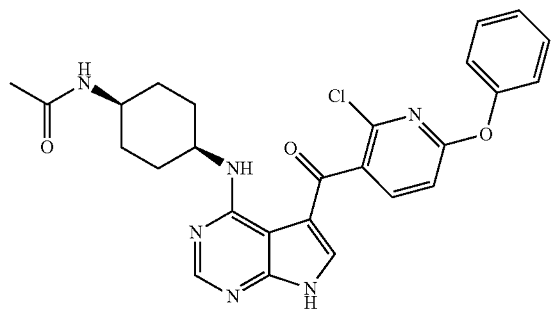 [SMILES: CC(=O)N[C@H]1CC[C@@H](Nc2ncnc3[nH]cc(C(=O)c4ccc(Oc5ccccc5)nc4Cl)c23)CC1] | N-(cis-4-((5-(2-chloro-6-phenoxynicotinoyl)-7H-pyrrolo[2,3-d]pyrimidin-4-yl)amino)cyclohexyl)acetamide |
| I-165 | 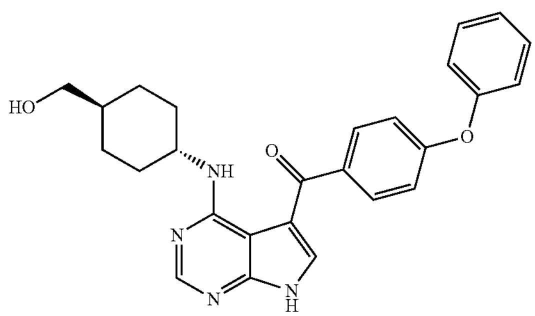 [SMILES: O=C(c1ccc(Oc2ccccc2)cc1)c1c[nH]c2ncnc(N[C@H]3CC[C@H](CO)CC3)c12] | (4-((trans-4-(hydroxymethyl)cyclohexyl)amino)-7H-pyrrolo[2,3-d]pyrimidin-5-yl)(4-phenoxyphenyl)methanone |
| I-166 | 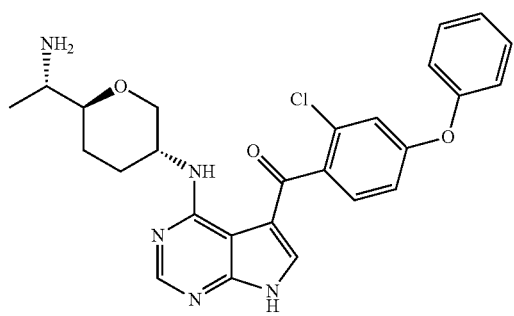 [SMILES: C[C@H](N)[C@@H]1CC[C@@H](Nc2ncnc3[nH]cc(C(=O)c4ccc(Oc5ccccc5)cc4Cl)c23)CO1] | (4-(((3R,6S)-6-((S)-1-aminoethyl)tetrahydro-2H-pyran-3-yl)amino)-7H-pyrrolo[2,3-d]pyrimidin-5-yl)(2-chloro-4-phenoxyphenyl)methanone |
| I-167 | 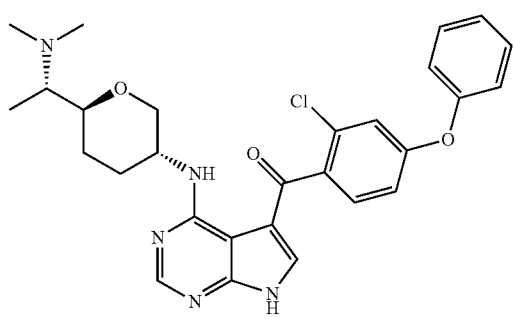 [SMILES: C[C@@H]([C@@H]1CC[C@@H](Nc2ncnc3[nH]cc(C(=O)c4ccc(Oc5ccccc5)cc4Cl)c23)CO1)N(C)C] | (2-chloro-4-phenoxyphenyl)(4-(((3R,6S)-6-((S)-1-(dimethylamino)ethyl)tetrahydro-2H-pyran-3-yl)amino)-7H-pyrrolo[2,3-d]pyrimidin-5-yl)methanone |

-continued

| Cmpd No. | Structure | Chemical name |
| --- | --- | --- |
| I-168 | 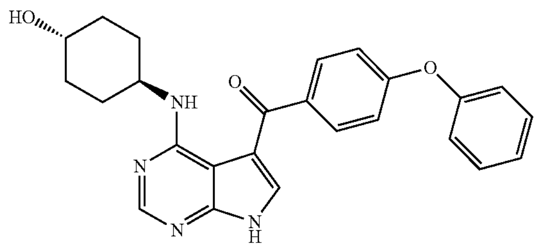 [SMILES: O=C(c1ccc(Oc2ccccc2)cc1)c1c[nH]c2ncnc(N[C@H]3CC[C@H](O)CC3)c12] | (4-((trans-4-hydroxycyclohexyl)amino)-7H-pyrrolo[2,3-d]pyrimidin-5-yl)(4-phenoxyphenyl)methanone |
| I-169 | 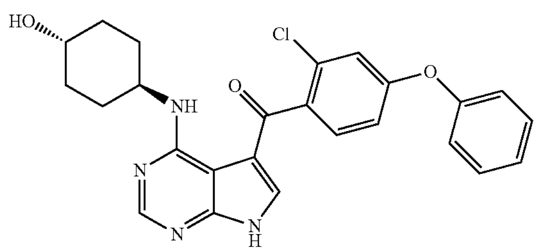 [SMILES: O=C(c1ccc(Oc2ccccc2)cc1Cl)c1c[nH]c2ncnc(N[C@H]3CC[C@H](O)CC3)c12] | (2-chloro-4-phenoxyphenyl)(4-((trans-4-hydroxycyclohexyl)amino)-7H-pyrrolo[2,3-d]pyrimidin-5-yl)methanone |
| I-170 | 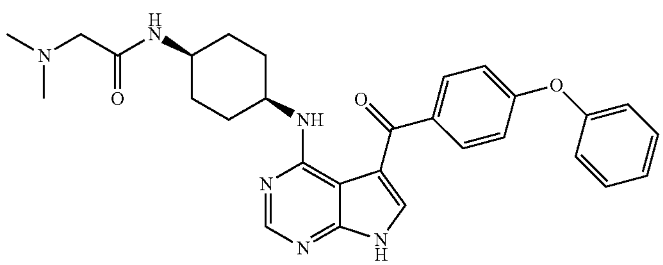 [SMILES: CN(C)CC(=O)N[C@H]1CC[C@@H](Nc2ncnc3[nH]cc(C(=O)c4ccc(Oc5ccccc5)cc4)c23)CC1] | 2-(dimethylamino)-N-(cis-4-((5-(4-phenoxybenzoyl)-7H-pyrrolo[2,3-d]pyrimidin-4-yl)amino)cyclohexyl)acetamide |
| I-171 | 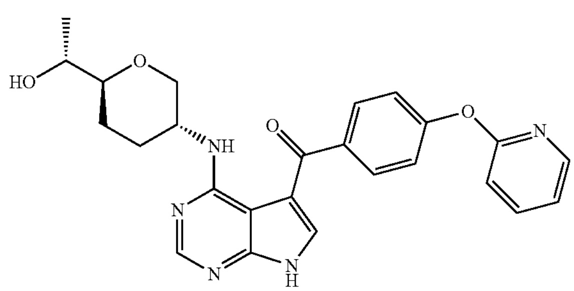 [SMILES: C[C@@H](O)[C@@H]1CC[C@@H](Nc2ncnc3[nH]cc(C(=O)c4ccc(Oc5ccccn5)cc4)c23)CO1] | (4-(((3R,6S)-6-((R)-1-hydroxyethyl)tetrahydro-2H-pyran-3-yl)amino)-7H-pyrrolo[2,3-d]pyrimidin-5-yl)(4-(pyridin-2-yloxy)phenyl)methanone |
| I-172 | 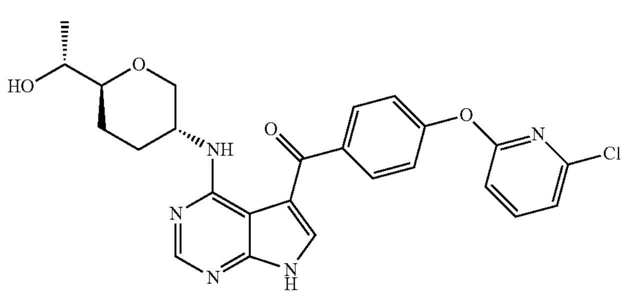 [SMILES: C[C@@H](O)[C@@H]1CC[C@@H](Nc2ncnc3[nH]cc(C(=O)c4ccc(Oc5cccc(Cl)n5)cc4)c23)CO1] | (4((6-chloropyridin-2-yl)oxy)phenyl)(4-(((3R,6S)-6-((R)-1-hydroxyethyl)tetrahydro-2H-pyran-3-yl)amino)-7H-pyrrolo[2,3-d]pyrimidin-5-yl)methanone |

-continued

| Cmpd No. | Structure | Chemical name |
| --- | --- | --- |
| I-173 | 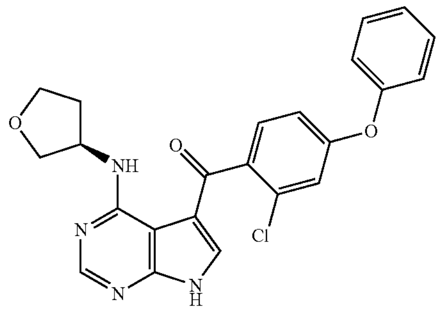 [SMILES: O=C(c1ccc(Oc2ccccc2)cc1Cl)c1c[nH]c2ncnc(N[C@@H]3CCOC3)c12] | (R)-(2-chloro-4-phenoxyphenyl)(4-((tetrahydrofuran-3-yl)amino)-7H-pyrrolo[2,3-d]pyrimidin-5-yl)methanone |
| I-174 | 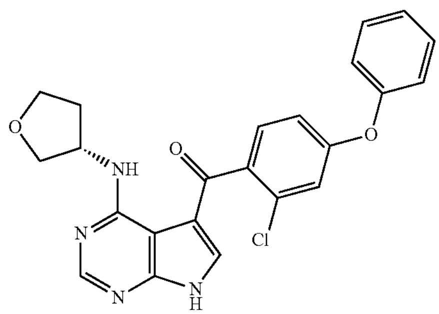 [SMILES: O=C(c1ccc(Oc2ccccc2)cc1Cl)c1c[nH]c2ncnc(N[C@H]3CCOC3)c12] | (S)-(2-chloro-4-phenoxyphenyl)(4-((tetrahydrofuran-3-yl)amino)-7H-pyrrolo[2,3-d]pyrimidin-5-yl)methanone |
| I-175 | 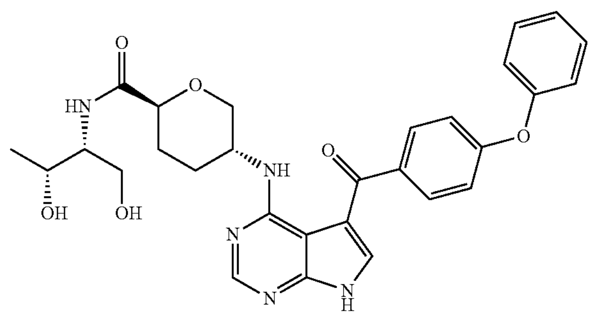 [SMILES: C[C@@H](O)[C@@H](CO)NC(=O)[C@@H]1CC[C@@H](Nc2ncnc3[nH]cc(C(=O)c4ccc(Oc5ccccc5)cc4)c23)CO1] | (2S,5R)-N-((2R,3R)-1,3-dihydroxybutan-2-yl)-5-((5-(4-phenoxybenzoyl)-7H-pyrrolo[2,3-d]pyrimidin-4-yl)amino)tetrahydro-2H-pyran-2-carboxamide |
| I-176 | 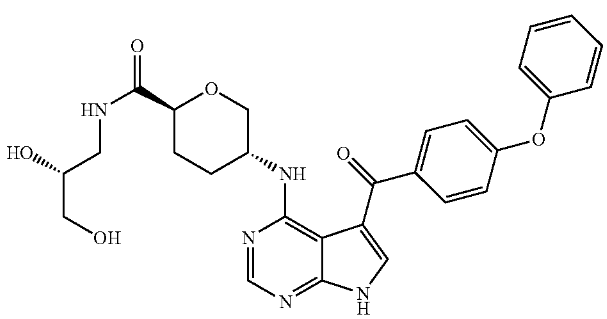 [SMILES: O=C(c1ccc(Oc2ccccc2)cc1)c1c[nH]c2ncnc(N[C@@H]3CC[C@@H](C(=O)NC[C@@H](O)CO)OC3)c12] | (2S,5R)-N-((R)-2,3-dihydroxypropyl)-5-((5-(4-phenoxybenzoyl)-7H-pyrrolo[2,3-d]pyrimidin-4-yl)amino)tetrahydro-2H-pyran-2-carboxamide |
| I-177 | 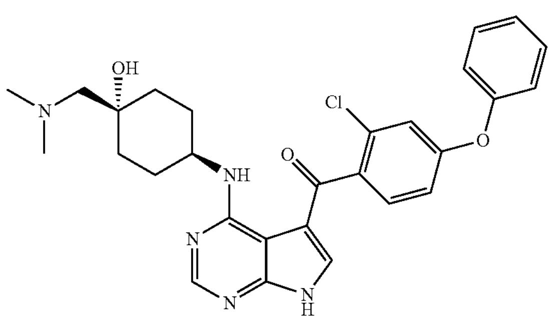 [SMILES: CN(C)C[C@]1(O)CC[C@H](Nc2ncnc3[nH]cc(C(=O)c4ccc(Oc5ccccc5)cc4Cl)c23)CC1] | (2-chloro-4-phenoxyphenyl)(4-((trans-4-((dimethylamino)methyl)-4-hydroxycyclohexyl)amino)-7H-pyrrolo[2,3-d]pyrimidin-5-yl)methanone |

| Cmpd No. | Structure | Chemical name |
|---|---|---|
| I-178 | 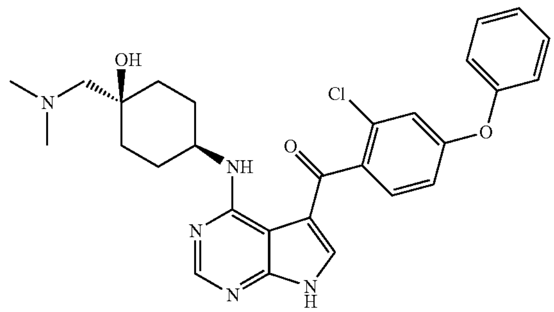 [SMILES: CN(C)C[C@]1(O)CC[C@@H](Nc2ncnc3[nH]cc(C(=O)c4ccc(Oc5ccccc5)cc4Cl)c23)CC1] | (2-chloro-4-phenoxyphenyl)(4-((cis-4-((dimethylamino)methyl)-4-hydroxycyclohexyl)amino)-7H-pyrrolo[2,3-d]pyrimidin-5-yl)methanone |
| I-179 | 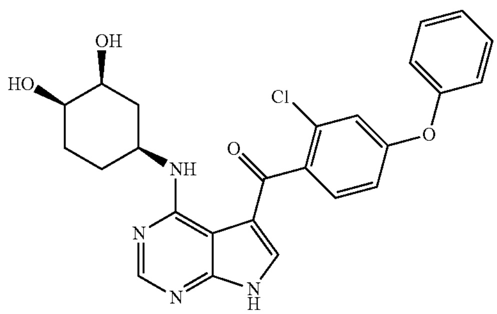 [SMILES: O=C(c1ccc(Oc2ccccc2)cc1Cl)c1c[nH]c2ncnc(N[C@H]3CC[C@@H](O)[C@@H](O)C3)c12] | rac-(2-chloro-4-phenoxyphenyl)(4-((((1S,3S,4R)-3,4-dihydroxycyclohexyl)amino)-7H-pyrrolo[2,3-d]pyrimidin-5-yl)methanone |
| I-180 | 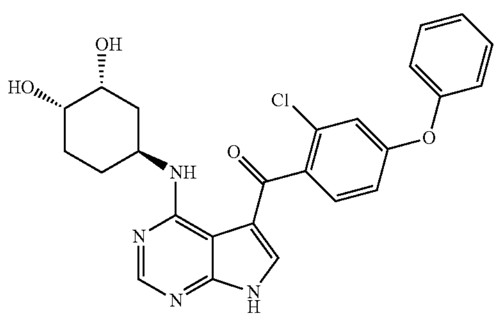 [SMILES: O=C(c1ccc(Oc2ccccc2)cc1Cl)c1c[nH]c2ncnc(N[C@H]3CC[C@H](O)[C@H](O)C3)c12] | rac-(2-chloro-4-phenoxyphenyl)(4-((((1S,3R,4S)-3,4-dihydroxycyclohexyl)amino)-7H-pyrrolo[2,3-d]pyrimidin-5-yl)methanone |
| I-181 | 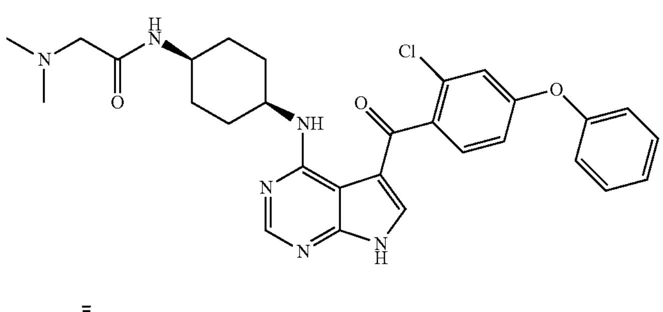 | N-(cis-4-((5-(2-chloro-4-phenoxybenzoyl)-7H-pyrrolo[2,3-d]pyrimidin-4-yl)amino)cyclohexyl)-2-(dimethylamino)acetamide |
| I-182 | 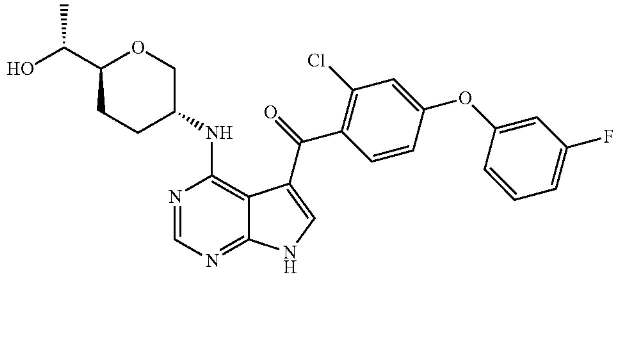 [SMILES: C[C@@H](O)[C@@H]1CC[C@@H](Nc2ncnc3[nH]cc(C(=O)c4ccc(Oc5cccc(F)c5)cc4Cl)c23)CO1] | (2-chloro-4-(3-fluorophenoxy)phenyl)(4-(((3R,6S)-6-((R)-1-hydroxyethyl)tetrahydro-2H-pyran-3-yl)amino)-7H-pyrrolo[2,3-d]pyrimidin-5-yl)methanone |

-continued

| Cmpd No. | Structure | Chemical name |
|---|---|---|
| I-183 | 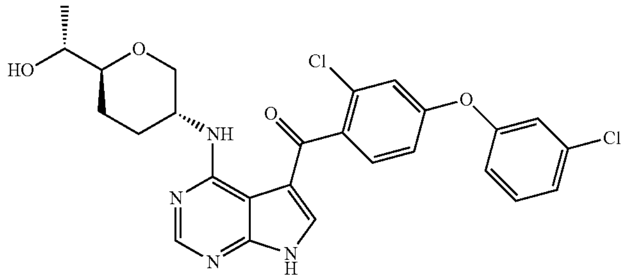 [SMILES: C[C@@H](O)[C@@H]1CC[C@@H](Nc2ncnc3[nH]cc(C(=O)c4ccc(Oc5cccc(Cl)c5)cc4Cl)c23)CO1] | (2-chloro-4-(3-chlorophenoxy)phenyl)(4-(((3R,6S)-6-((R)-1-hydroxyethyl)tetrahydro-2H-pyran-3-yl)amino)-7H-pyrrolo[2,3-d]pyrimidin-5-yl)methanone |
| I-184 | 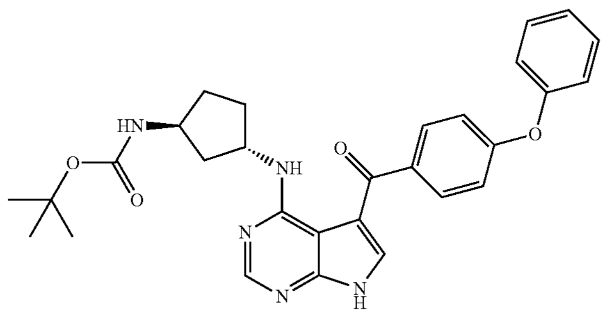 [SMILES: CC(C)(C)OC(=O)N[C@H]1CC[C@H](Nc2ncnc3[nH]cc(C(=O)c4ccc(Oc5ccccc5)cc4)c23)C1] | tert-butyl ((1S,3S)-3-((5-(4-phenoxybenzoyl)-7H-pyrrolo[2,3-d]pyrimidin-4-yl)amino)cyclopentyl)carbamate |
| I-185 | 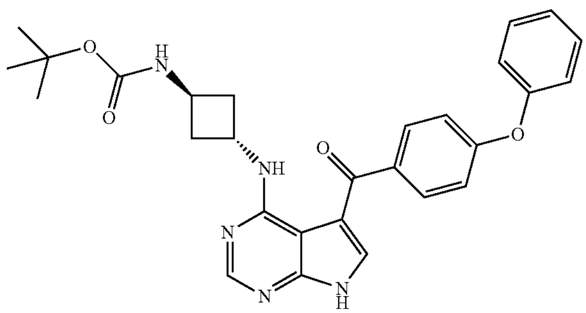 [SMILES: CC(C)(C)OC(=O)N[C@H]1C[C@H](Nc2ncnc3[nH]cc(C(=O)c4ccc(Oc5ccccc5)cc4)c23)C1] | tert-butyl (trans-3-((5-(4-phenoxybenzoyl)-7H-pyrrolo[2,3-d]pyrimidin-4-yl)amino)cyclobutyl)carbamate |
| I-186 | 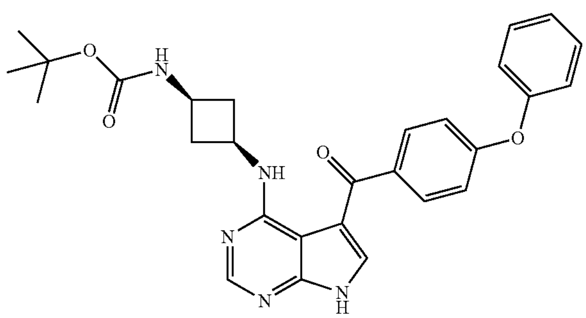 [SMILES: CC(C)(C)OC(=O)N[C@H]1C[C@@H](Nc2ncnc3[nH]cc(C(=O)c4ccc(Oc5ccccc5)cc4)c23)C1] | tert-butyl (cis-3-((5-(4-phenoxybenzoyl)-7H-pyrrolo[2,3-d]pyrimidin-4-yl)amino)cyclobutyl)carbamate |
| I-187 | 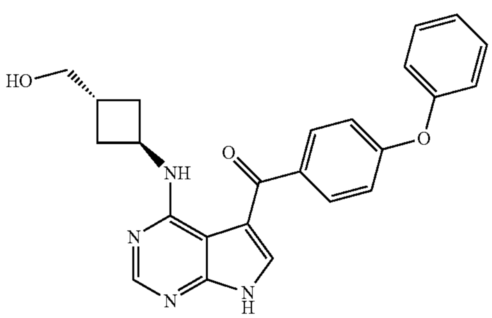 [SMILES: O=C(c1ccc(Oc2ccccc2)cc1)c1c[nH]c2ncnc(N[C@H]3C[C@H](CO)C3)c12] | (4-((trans-3-(hydroxymethyl)cyclobutyl)amino)-7H-pyrrolo[2,3-d]pyrimidin-5-yl)(4-phenoxyphenyl)methanone |

| Cmpd No. | Structure | Chemical name |
|---|---|---|
| I-188 | 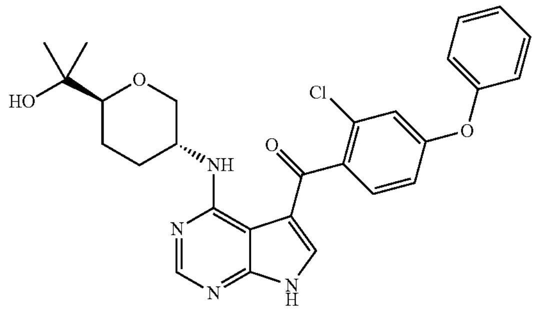 [SMILES: CC(C)(O)[C@@H]1CC[C@@H](Nc2ncnc3[nH]cc(C(=O)c4ccc(Oc5ccccc5)cc4Cl)c23)CO1] | (2-chloro-4-phenoxyphenyl)(4-(((3R,6S)-6-(2-hydroxypropan-2-yl)tetrahydro-2H-pyran-3-yl)amino)-7H-pyrrolo[2,3-d]pyrimidin-5-yl)methanone |
| I-189 | 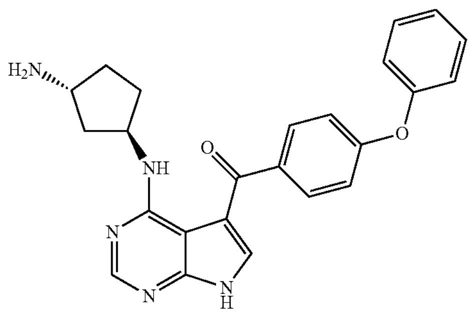 [SMILES: N[C@@H]1CC[C@@H](Nc2ncnc3[nH]cc(C(=O)c4ccc(Oc5ccccc5)cc4)c23)C1] | (4-(((1R,3R)-3-aminocyclopentyl)amino)-7H-pyrrolo[2,3-d]pyrimidin-5-yl)(4-phenoxyphenyl)methanone |
| I-190 | 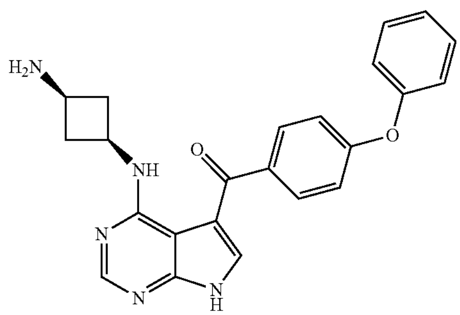 [SMILES: N[C@H]1C[C@@H](Nc2ncnc3[nH]cc(C(=O)c4ccc(Oc5ccccc5)cc4)c23)C1] | (4-((cis-3-aminocyclobutyl)amino)-7H-pyrrolo[2,3-d]pyrimidin-5-yl)(4-phenoxyphenyl)methanone |
| I-191 | 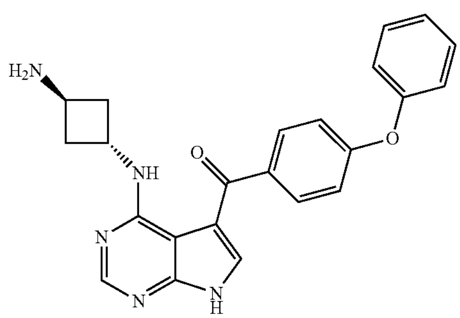 [SMILES: N[C@H]1C[C@H](Nc2ncnc3[nH]cc(C(=O)c4ccc(Oc5ccccc5)cc4)c23)C1] | (4-((trans-3-aminocyclobutyl)amino)-7H-pyrrolo[2,3-d]pyrimidin-5-yl)(4-phenoxyphenyl)methanone |
| I-192 | 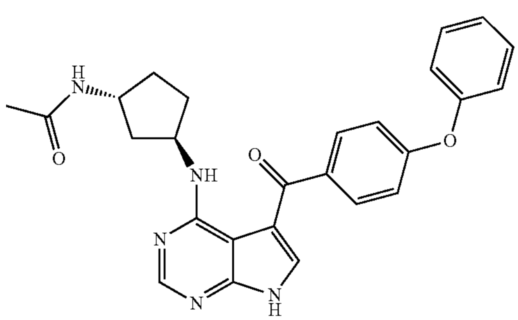 [SMILES: CC(=O)N[C@@H]1CC[C@@H](Nc2ncnc3[nH]cc(C(=O)c4ccc(Oc5ccccc5)cc4)c23)C1] | N-((1R,3R)-3-((5-(4-phenoxybenzoyl)-7H-pyrrolo[2,3-d]pyrimidin-4-yl)amino)cyclopentyl)acetamide |

-continued

| Cmpd No. | Structure | Chemical name |
|---|---|---|
| I-193 | 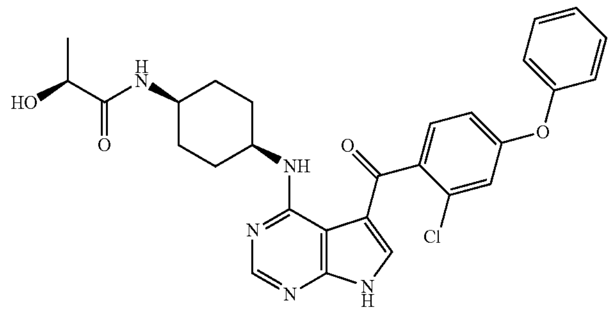 [SMILES: C[C@H](O)C(=O)N[C@H]1CC[C@@H](Nc2ncnc3[nH]cc(C(=O)c4ccc(Oc5ccccc5)cc4Cl)c23)CC1] | (S)-N-(cis-4-((5-(2-chloro-4-phenoxybenzoyl)-7H-pyrrolo[2,3-d]pyrimidin-4-yl)amino)cyclohexyl)-2-hydroxypropanamide |
| I-194 | 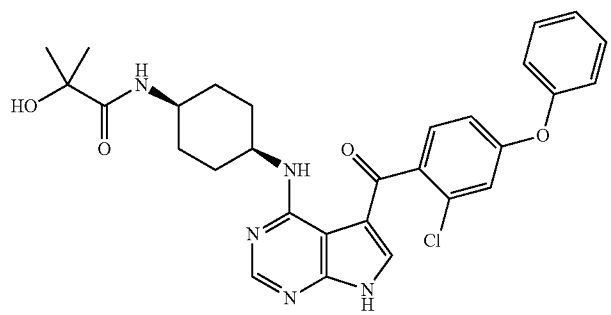 [SMILES: CC(C)(O)C(=O)N[C@H]1CC[C@@H](Nc2ncnc3[nH]cc(C(=O)c4ccc(Oc5ccccc5)cc4Cl)c23)CC1] | N-(cis-4-((5-(2-chloro-4-phenoxybenzoyl)-7H-pyrrolo[2,3-d]pyrimidin-4-yl)amino)cyclohexyl)-2-hydroxy-2-methylpropanamide |
| I-195 | 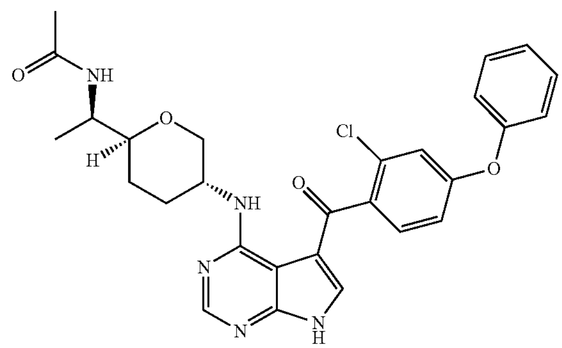 [SMILES: CC(=O)N[C@H](C)[C@@H]1CC[C@@H](Nc2ncnc3[nH]cc(C(=O)c4ccc(Oc5ccccc5)cc4Cl)c23)CO1] | N-((R)-1-((2S,5R)-5-((5-(2-chloro-4-phenoxybenzoyl)-7H-pyrrolo[2,3-d]pyrimidin-4-yl)amino)tetrahydro-2H-pyran-2-yl)ethyl)acetamide |
| I-196 | 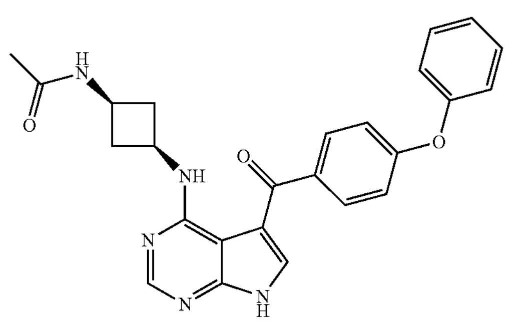 [SMILES: CC(=O)N[C@H]1C[C@@H](Nc2ncnc3[nH]cc(C(=O)c4ccc(Oc5ccccc5)cc4)c23)C1] | N-(cis-3-((5-(4-phenoxybenzoyl)-7H-pyrrolo[2,3-d]pyrimidin-4-yl)amino)cyclobutyl)acetamide |
| I-197 | 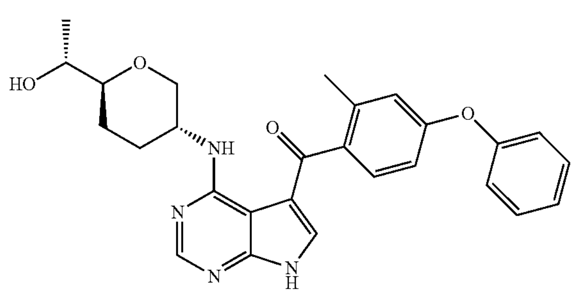 [SMILES: Cc1cc(Oc2ccccc2)ccc1C(=O)c1c[nH]c2ncnc(N[C@@H]3CC[C@@H]([C@@H](C)O)OC3)c12] | (4-(((3R,6S)-6-((R)-1-hydroxyethyl)tetrahydro-2H-pyran-3-yl)amino)-7H-pyrrolo[2,3-d]pyrimidin-5-yl)(2-methyl-4-phenoxyphenyl)methanone |

-continued

| Cmpd No. | Structure | Chemical name |
|---|---|---|
| I-198 | 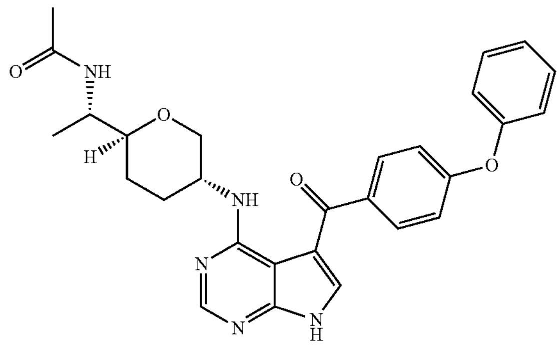 [SMILES: CC(=O)N[C@@H](C)[C@@H]1CC[C@@H](Nc2ncnc3[nH]cc(C(=O)c4ccc(Oc5ccccc5)cc4)c23)CO1] | N-((S)-1-((2S,5R)-5-((5-(4-phenoxybenzoyl)-7H-pyrrolo[2,3-d]pyrimidin-4-yl)amino)tetrahydro-2H-pyran-2-yl)ethyl)acetamide |
| I-199 | 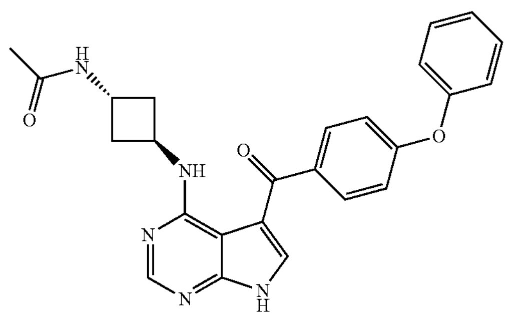 [SMILES: CC(=O)N[C@H]1C[C@H](Nc2ncnc3[nH]cc(C(=O)c4ccc(Oc5ccccc5)cc4)c23)C1] | N-(trans-3-((5-(4-phenoxybenzoyl)-7H-pyrrolo[2,3-d]pyrimidin-4-yl)amino)cyclobutyl)acetamide |
| I-200 | 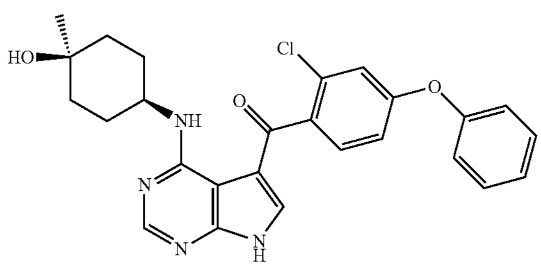 [SMILES: C[C@]1(O)CC[C@@H](Nc2ncnc3[nH]cc(C(=O)c4ccc(Oc5ccccc5)cc4Cl)c23)CC1] | (2-chloro-4-phenoxyphenyl)(4-((cis-4-hydroxy-4-methylcyclohexyl)amino)-7H-pyrrolo[2,3-d]pyrimidin-5-yl)methanone |
| I-201 | 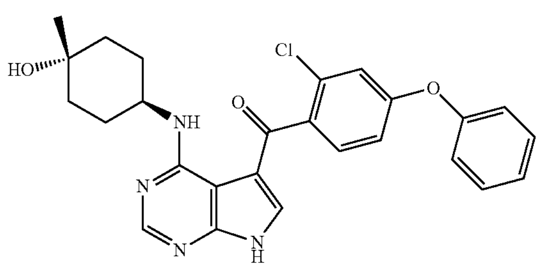 [SMILES: C[C@]1(O)CC[C@H](Nc2ncnc3[nH]cc(C(=O)c4ccc(Oc5ccccc5)cc4Cl)c23)CC1] | (2-chloro-4-phenoxyphenyl)(4-((trans-4-hydroxy-4-methylcyclohexyl)amino)-7H-pyrrolo[2,3-d]pyrimidin-5-yl)methanone |
| I-202 | 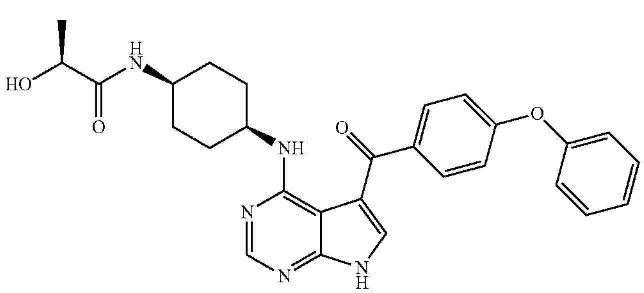 [SMILES: C[C@H](O)C(=O)N[C@H]1CC[C@@H](Nc2ncnc3[nH]cc(C(=O)c4ccc(Oc5ccccc5)cc4)c23)CC1] | (S)-2-hydroxy-N-(cis-4-((5-(4-phenoxybenzoyl)-7H-pyrrolo[2,3-d]pyrimidin-4-yl)amino)cyclohexyl)propanamide |

-continued

| Cmpd No. | Structure | Chemical name |
|---|---|---|
| I-203 | 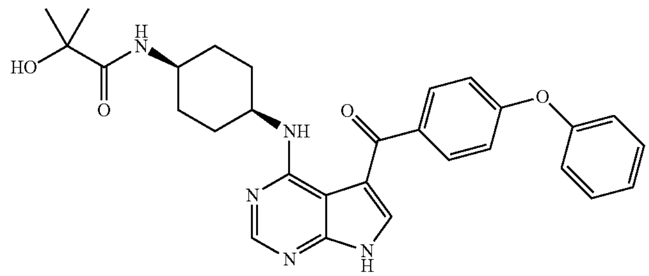 [SMILES: CC(C)(O)C(=O)N[C@H]1CC[C@@H](Nc2ncnc3[nH]cc(C(=O)c4ccc(Oc5ccccc5)cc4)c23)CC1] | 2-hydroxy-2-methyl-N-(cis-4-((5-(4-phenoxybenzoyl)-7H-pyrrolo[2,3-d]pyrimidin-4-yl)amino)cyclohexyl)propanamide |
| I-204 | 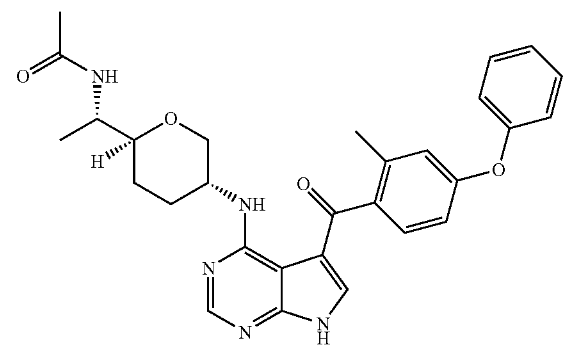 [SMILES: CC(=O)N[C@@H](C)[C@@H]1CC[C@@H](Nc2ncnc3[nH]cc(C(=O)c4ccc(Oc5ccccc5)cc4C)c23)CO1] | N-((S)-1-((2S,5R)-5-((5-(2-methyl-4-phenoxybenzoyl)-7H-pyrrolo[2,3-d]pyrimidin-4-yl)amino)tetrahydro-2H-pyran-2-yl)ethyl)acetamide |
| I-205 | 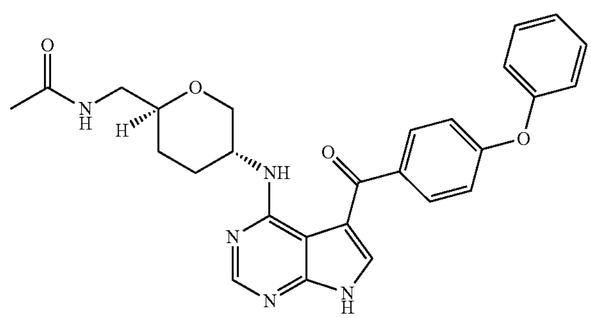 [SMILES: CC(=O)NC[C@@H]1CC[C@@H](Nc2ncnc3[nH]cc(C(=O)c4ccc(Oc5ccccc5)cc4)c23)CO1] | N-(((2S,5R)-5-((5-(4-phenoxybenzoyl)-7H-pyrrolo[2,3-d]pyrimidin-4-yl)amino)tetrahydro-2H-pyran-2-yl)methyl)acetamide |
| I-206 | 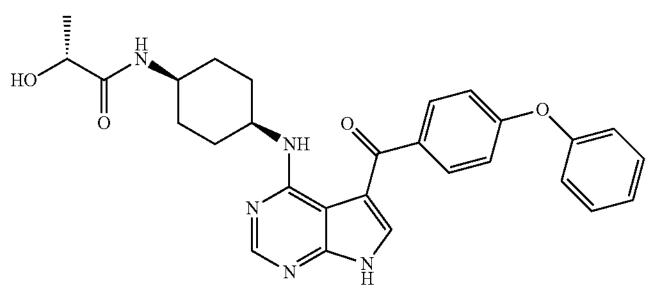 [SMILES: C[C@@H](O)C(=O)N[C@H]1CC[C@@H](Nc2ncnc3[nH]cc(C(=O)c4ccc(Oc5ccccc5)cc4)c23)CC1] | (R)-2-hydroxy-N-(cis-4-((5-(4-phenoxybenzoyl)-7H-pyrrolo[2,3-d]pyrimidin-4-yl)amino)cyclohexyl)propanamide |
| I-207 | 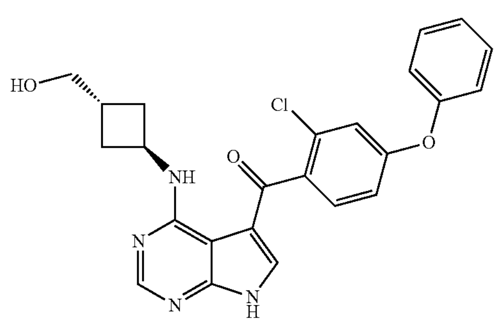 [SMILES: O=C(c1ccc(Oc2ccccc2)cc1Cl)c1c[nH]c2ncnc(N[C@H]3C[C@H](CO)C3)c12] | (2-chloro-4-phenoxyphenyl)(4-((trans-3-(hydroxymethyl)cyclobutyl)amino)-7H-pyrrolo[2,3-d]pyrimidin-5-yl)methanone |

-continued

| Cmpd No. | Structure | Chemical name |
|---|---|---|
| I-208 | 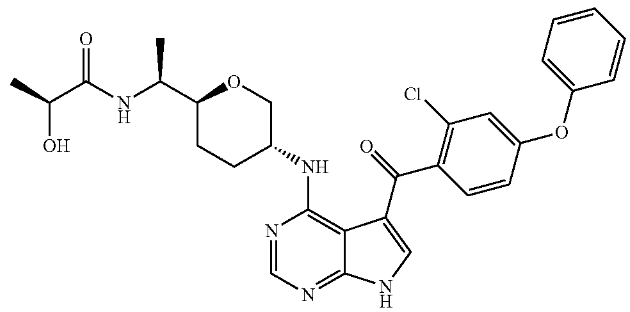 [SMILES: C[C@H](O)C(=O)N[C@@H](C)[C@@H]1CC[C@@H](Nc2ncnc3[nH]cc(C(=O)c4ccc(Oc5ccccc5)cc4Cl)c23)CO1] | (S)-N-((S)-1-((2S,5R)-5-((5-(2-chloro-4-phenoxybenzoyl)-7H-pyrrolo[2,3-d]pyrimidin-4-yl)amino)tetrahydro-2H-pyran-2-yl)ethyl)-2-hydroxypropanamide |
| I-209 | 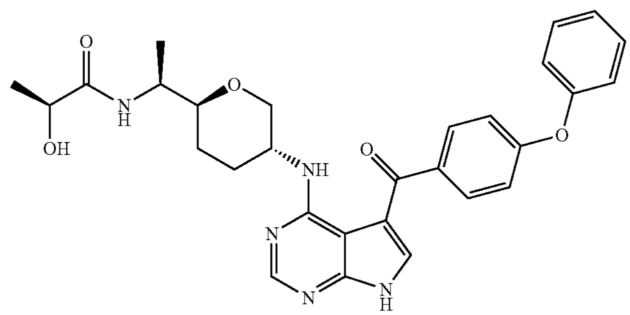 [SMILES: C[C@H](O)C(=O)N[C@@H](C)[C@@H]1CC[C@@H](Nc2ncnc3[nH]cc(C(=O)c4ccc(Oc5ccccc5)cc4)c23)CO1] | (S)-2-hydroxy-N-((S)-1-((2S,5R)-5-((5-(4-phenoxybenzoyl)-7H-pyrrolo[2,3-d]pyrimidin-4-yl)amino)tetrahydro-2H-pyran-2-yl)ethyl)propanamide |
| I-210 | 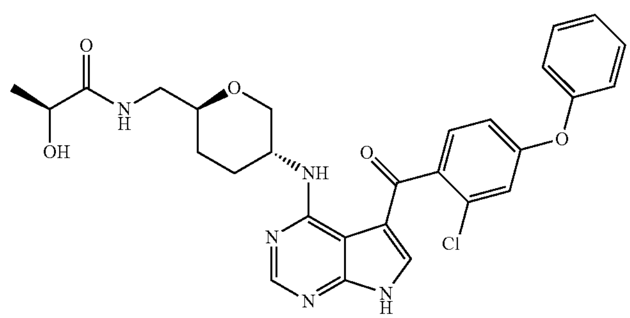 [SMILES: C[C@H](O)C(=O)NC[C@@H]1CC[C@@H](Nc2ncnc3[nH]cc(C(=O)c4ccc(Oc5ccccc5)cc4Cl)c23)CO1] | (S)-N-(((2S,5R)-5-((5-(2-chloro-4-phenoxybenzoyl)-7H-pyrrolo[2,3-d]pyrimidin-4-yl)amino)tetrahydro-2H-pyran-2-yl)methyl)-2-hydroxypropanamide |
| I-211 | 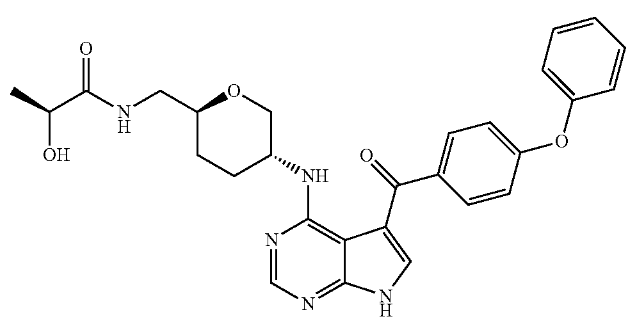 [SMILES: C[C@H](O)C(=O)NC[C@@H]1CC[C@@H](Nc2ncnc3[nH]cc(C(=O)c4ccc(Oc5ccccc5)cc4)c23)CO1] | (S)-2-hydroxy-N-(((2S,5R)-5-((5-(4-phenoxybenzoyl)-7H-pyrrolo[2,3-d]pyrimidin-4-yl)amino)tetrahydro-2H-pyran-2-yl)methyl)propanamide |
| I-212 | 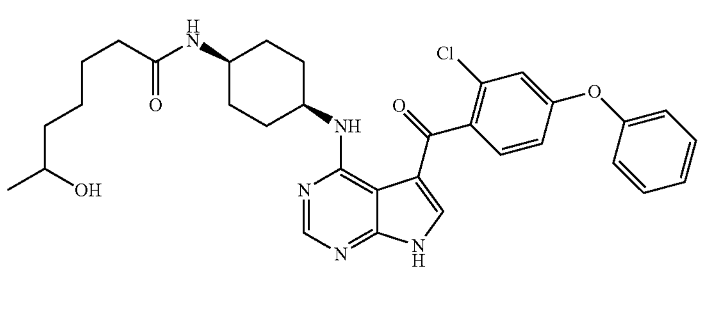 [SMILES: CC(O)CCCCC(=O)N[C@H]1CC[C@@H](Nc2ncnc3[nH]cc(C(=O)c4ccc(Oc5ccccc5)cc4Cl)c23)CC1] | rac-N-(cis-4-((5-(2-chloro-4-phenoxybenzoyl)-7H-pyrrolo[2,3-d]pyrimidin-4-yl)amino)cyclohexyl)-6-hydroxyheptanamide |

-continued

| Cmpd No. | Structure | Chemical name |
| --- | --- | --- |
| I-213 | 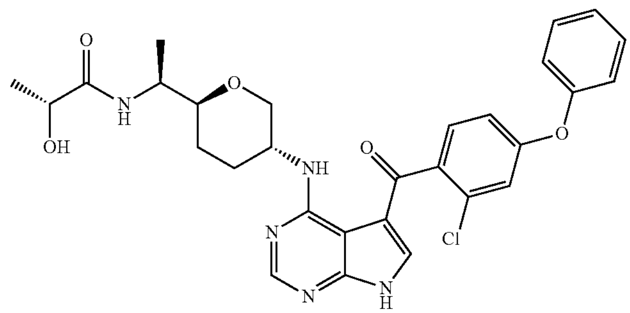 [SMILES: C[C@H](NC(=O)[C@@H](C)O)[C@@H]1CC[C@@H](Nc2ncnc3[nH]cc(C(=O)c4ccc(Oc5ccccc5)cc4Cl)c23)CO1] | (R)-N-((S)-1-((2S,5R)-5-((5-(2-chloro-4-phenoxybenzoyl)-7H-pyrrolo[2,3-d]pyrimidin-4-yl)amino)tetrahydro-2H-pyran-2-yl)ethyl)-2-hydroxypropanamide |
| I-214 | 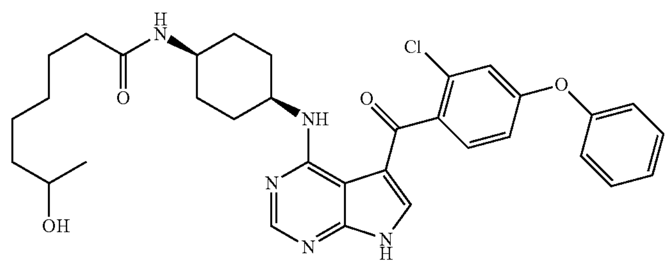 [SMILES: CC(O)CCCCCC(=O)N[C@H]1CC[C@@H](Nc2ncnc3[nH]cc(C(=O)c4ccc(Oc5ccccc5)cc4Cl)c23)CC1] | rac-N-(cis-4-((5-(2-chloro-4-phenoxybenzoyl)-7H-pyrrolo[2,3-d]pyrimidin-4-yl)amino)cyclohexyl)-7-hydroxyoctanamide |
| I-215 | 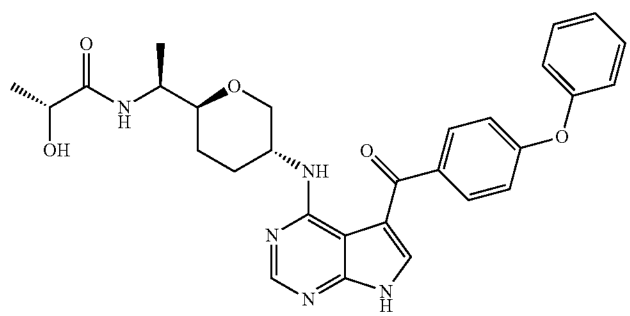 [SMILES: C[C@H](NC(=O)[C@@H](C)O)[C@@H]1CC[C@@H](Nc2ncnc3[nH]cc(C(=O)c4ccc(Oc5ccccc5)cc4)c23)CO1] | (R)-2-hydroxy-N-((S)-1-((2S,5R)-5-((5-(4-phenoxybenzoyl)-7H-pyrrolo[2,3-d]pyrimidin-4-yl)amino)tetrahydro-2H-pyran-2-yl)ethyl)propanamide |
| I-216 | 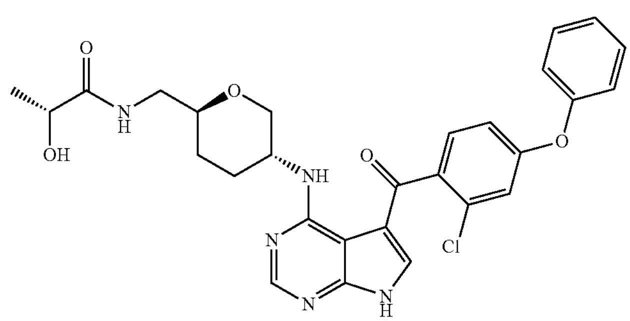 [SMILES: C[C@@H](O)C(=O)NC[C@@H]1CC[C@@H](Nc2ncnc3[nH]cc(C(=O)c4ccc(Oc5ccccc5)cc4Cl)c23)CO1] | (R)-N-(((2S,5R)-5-((5-(2-chloro-4-phenoxybenzoyl)-7H-pyrrolo[2,3-d]pyrimidin-4-yl)amino)tetrahydro-2H-pyran-2-yl)methyl)-2-hydroxypropanamide |
| I-217 | 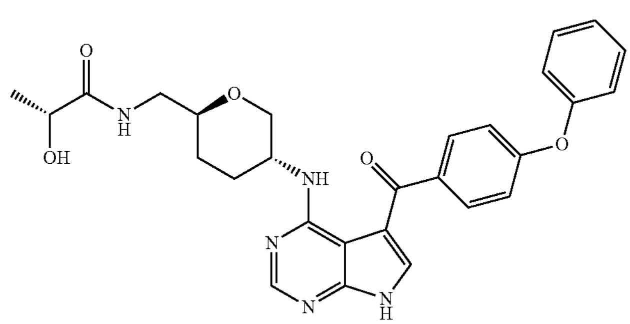 [SMILES: C[C@@H](O)C(=O)NC[C@@H]1CC[C@@H](Nc2ncnc3[nH]cc(C(=O)c4ccc(Oc5ccccc5)cc4)c23)CO1] | (R)-2-hydroxy-N-(((2S,5R)-5-((5-(4-phenoxybenzoyl)-7H-pyrrolo[2,3-d]pyrimidin-4-yl)amino)tetrahydro-2H-pyran-2-yl)methyl)propanamide |

-continued

| Cmpd No. | Structure | Chemical name |
|---|---|---|
| I-218 | 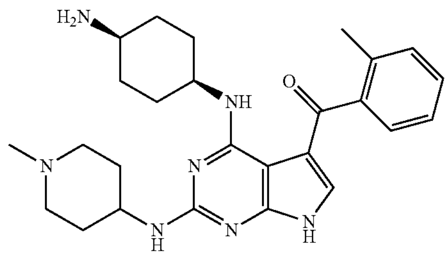 [SMILES: Cc1ccccc1C(=O)c1c[nH]c2nc(NC3CCN(C)CC3)nc(N[C@H]3CC[C@@H](N)CC3)c12] | (4-((cis-4-aminocyclohexyl)amino)-2-((1-methylpiperidin-4-yl)amino)-7H-pyrrolo[2,3-d]pyrimidin-5-yl)(o-tolyl)methanone |
| I-219 | 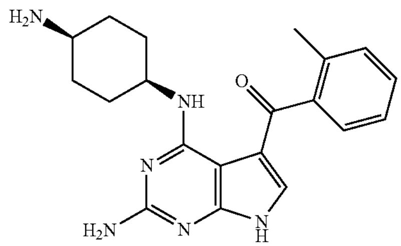 [SMILES: Cc1ccccc1C(=O)c1c[nH]c2nc(N)nc(N[C@H]3CC[C@@H](N)CC3)c12] | (2-amino-4-(cis-4-aminocyclohexyl)amino)-7H-pyrrolo[2,3-d]pyrimidin-5-yl)(o-tolyl)methanone |
| I-220 | 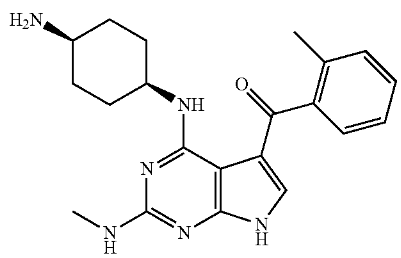 [SMILES: CNc1nc(N[C@H]2CC[C@@H](N)CC2)c2c(C(=O)c3ccccc3C)c[nH]c2n1] | (4-((cis-4-aminocyclohexyl)amino)-2-(methylamino)-7H-pyrrolo[2,3-d]pyrimidin-5-yl)(o-tolyl)methanone |
| I-221 | 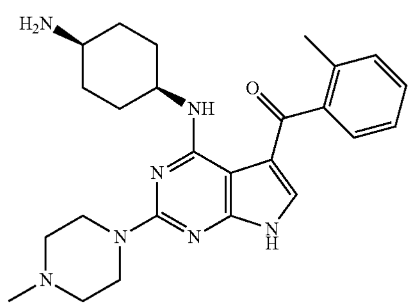 [SMILES: Cc1ccccc1C(=O)c1c[nH]c2nc(N3CCN(C)CC3)nc(N[C@H]3CC[C@@H](N)CC3)c12] | (4-((cis-4-aminocyclohexyl)amino)-2-(4-methylpiperazin-1-yl)-7H-pyrrolo[2,3-d]pyrimidin-5-yl)(o-tolyl)methanone |
| I-222 | 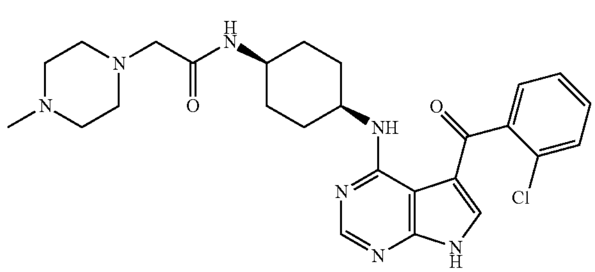 [SMILES: CN1CCN(CC(=O)N[C@H]2CC[C@@H](Nc3ncnc4[nH]cc(C(=O)c5ccccc5Cl)c34)CC2)CC1] | N-(cis-4-((5-(2-chlorobenzoyl)-7H-pyrrolo[2,3-d]pyrimidin-4-yl)amino)cyclohexyl)-2-(4-methylpiperazin-1-yl)acetamide |

-continued

| Cmpd No. | Structure | Chemical name |
| --- | --- | --- |
| I-223 | 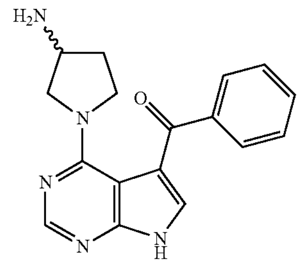 [SMILES: NC1CCN(c2ncnc3[nH]cc(C(=O)c4ccccc4)c23)C1] | rac-(4-(3-aminopyrrolidin-1-yl)-7H-pyrrolo[2,3-d]pyrimidin-5-yl)(phenyl)methanone |
| I-224 | 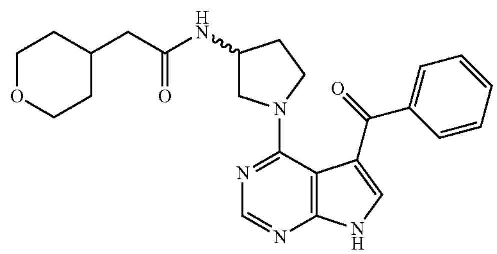 [SMILES: O=C(CC1CCOCC1)NC1CCN(c2ncnc3[nH]cc(C(=O)c4ccccc4)c23)C1] | rac-N-(1-(5-benzoyl-7H-pyrrolo[2,3-d]pyrimidin-4-yl)pyrrolidin-3-yl)-2-(tetrahydro-2H-pyran-4-yl)acetamide |
| I-225 | 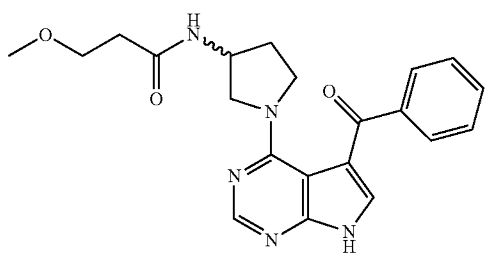 [SMILES: COCCC(=O)NC1CCN(c2ncnc3[nH]cc(C(=O)c4ccccc4)c23)C1] | rac-N-(1-(5-benzoyl-7H-pyrrolo[2,3-d]pyrimidin-4-yl)pyrrolidin-3-yl)-3-methoxypropanamide |
| I-226 | 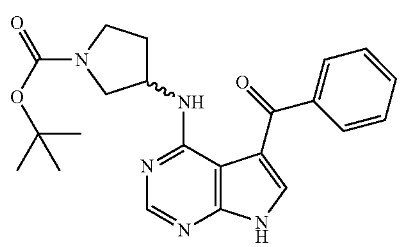 [SMILES: CC(C)(C)OC(=O)N1CCC(Nc2ncnc3[nH]cc(C(=O)c4ccccc4)c23)C1] | rac-tert-butyl 3-((5-benzoyl-7H-pyrrolo[2,3-d]pyrimidin-4-yl)amino)pyrrolidine-1-carboxylate |
| I-227 | 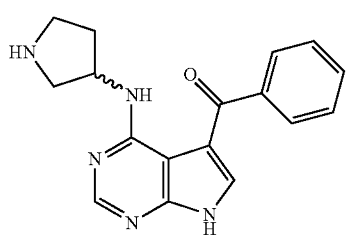 [SMILES: O=C(c1ccccc1)c1c[nH]c2ncnc(NC3CCNC3)c12] | rac-phenyl(4-(pyrrolidin-3-ylamino)-7H-pyrrolo[2,3-d]pyrimidin-5-yl)methanone |
| I-228 | 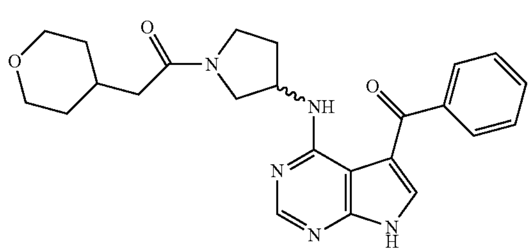 [SMILES: O=C(c1ccccc1)c1c[nH]c2ncnc(NC3CCN(C(=O)CC4CCOCC4)C3)c12] | rac-1-(3-((5-benzoyl-7H-pyrrolo[2,3-d]pyrimidin-4-yl)amino)pyrrolidin-1-yl)-2-(tetrahydro-2H-pyran-4-yl)ethan-1-one |

| Cmpd No. | Structure | Chemical name |
|---|---|---|
| I-229 | 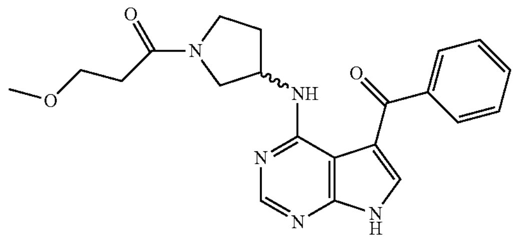 [SMILES: COCCC(=O)N1CCC(Nc2ncnc3[nH]cc(C(=O)c4ccccc4)c23)C1] | rac-1-(3-((5-benzoyl-7H-pyrrolo[2,3-d]pyrimidin-4-yl)amino)pyrrolidin-1-yl)-3-methoxypropan-1-one |
| I-230 | 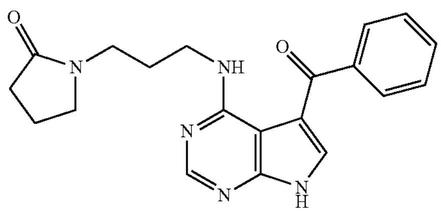 [SMILES: O=C(c1ccccc1)c1c[nH]c2ncnc(NCCCN3CCCC3=O)c12] | 1-(3-((5-benzoyl-7H-pyrrolo[2,3-d]pyrimidin-4-yl)amino)propyl)pyrrolidin-2-one |

In another embodiment, non-limiting examples of compounds of the invention include:

| Cmpd No. | Structure | Chemical name |
|---|---|---|
| I-231 | 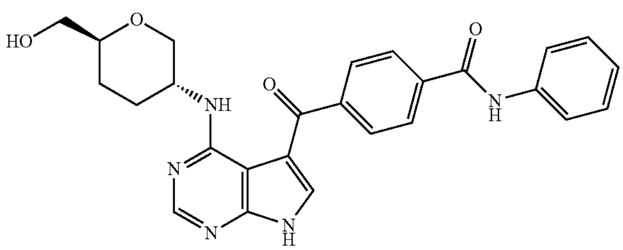 [SMILES: O=C(Nc1ccccc1)c1ccc(C(=O)c2c[nH]c3ncnc(N[C@@H]4CC[C@@H](CO)OC4)c23)cc1] | 4-(4-(((3R,6S)-6-(hydroxymethyl)tetrahydro-2H-pyran-3-yl)amino)-7H-pyrrolo[2,3-d]pyrimidine-5-carbonyl)-N-phenylbenzamide |
| I-232 | 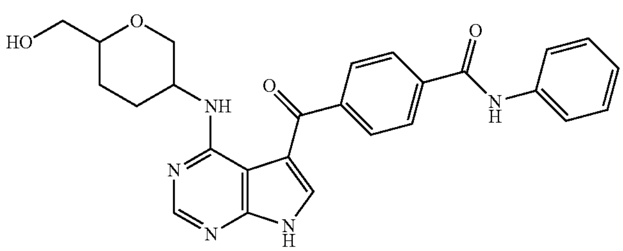 | 4-(4-((6-(hydroxymethyl)tetrahydro-2H-pyran-3-yl)amino)-7H-pyrrolo[2,3-d]pyrimidine-5-carbonyl)-N-phenylbenzamide |
| I-233 | 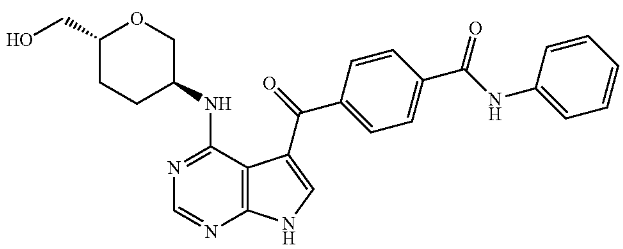 [SMILES: O=C(Nc1ccccc1)c1ccc(C(=O)c2c[nH]c3ncnc(N[C@H]4CC[C@H](CO)OC4)c23)cc1] | 4-(4-(((3S,6R)-6-(hydroxymethyl)tetrahydro-2H-pyran-3-yl)amino)-7H-pyrrolo[2,3-d]pyrimidine-5-carbonyl)-N-phenylbenzamide |

| Cmpd No. | Structure | Chemical name |
|---|---|---|
| I-234 | 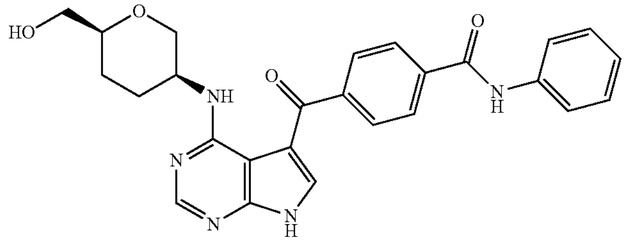 | 4-(4-(((3S,6S)-6-(hydroxymethyl)tetrahydro-2H-pyran-3-yl)amino)-7H-pyrrolo[2,3-d]pyrimidine-5-carbonyl)-N-phenylbenzamide |
| I-235 | 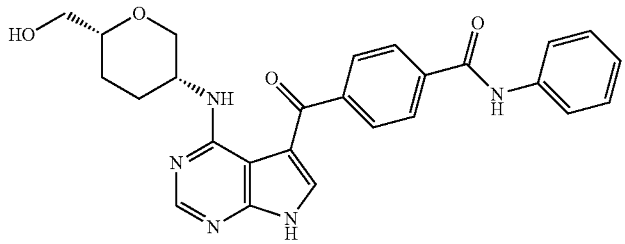 | 4-(4-(((3R,6R)-6-(hydroxymethyl)tetrahydro-2H-pyran-3-yl)amino)-7H-pyrrolo[2,3-d]pyrimidine-5-carbonyl)-N-phenylbenzamide |
| I-236 | 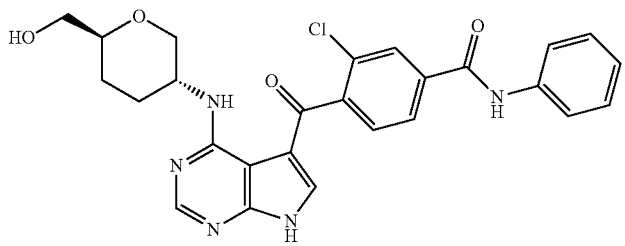 [SMILES: O=C(Nc1ccccc1)c1ccc(C(=O)c2c[nH]c3ncnc(N[C@@H]4CC[C@@H](CO)OC4)c23)c(Cl)c1] | 3-chloro-4-(4-(((3R,6S)-6-(hydroxymethyl)tetrahydro-2H-pyran-3-yl)amino)-7H-pyrrolo[2,3-d]pyrimidine-5-carbonyl)-N-phenylbenzamide |
| I-237 | 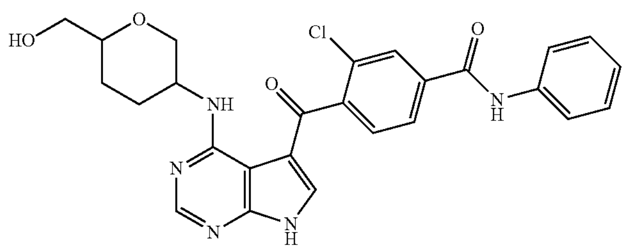 | 3-chloro-4-(4-((6-(hydroxymethyl)tetrahydro-2H-pyran-3-yl)amino)-7H-pyrrolo[2,3-d]pyrimidine-5-carbonyl)-N-phenylbenzamide |
| I-238 | 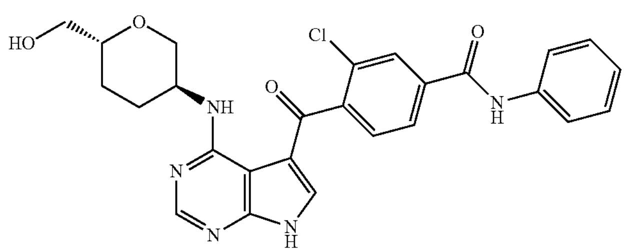 | 3-chloro-4-(4-(((3S,6R)-6-(hydroxymethyl)tetrahydro-2H-pyran-3-yl)amino)-7H-pyrrolo[2,3-d]pyrimidine-5-carbonyl)-N-phenylbenzamide |
| I-239 | 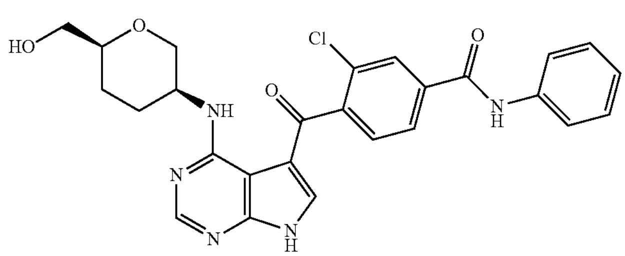 [SMILES: O=C(Nc1ccccc1)c1ccc(C(=O)c2c[nH]c3ncnc(N[C@H]4CC[C@@H](CO)OC4)c23)c(Cl)c1] | 3-chloro-4-(4-(((3S,6S)-6-(hydroxymethyl)tetrahydro-2H-pyran-3-yl)amino)-7H-pyrrolo[2,3-d]pyrimidine-5-carbonyl)-N-phenylbenzamide |

| Cmpd No. | Structure | Chemical name |
|---|---|---|
| I-240 | 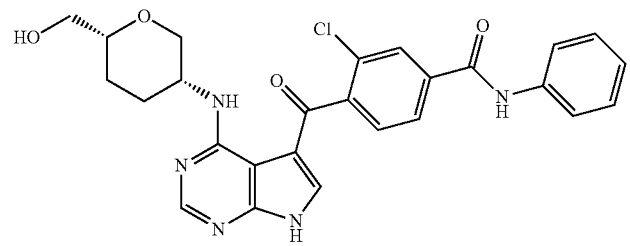 | 3-chloro-4-(4-(((3R,6R)-6-(hydroxymethyl)tetrahydro-2H-pyran-3-yl)amino)-7H-pyrrolo[2,3-d]pyrimidine-5-carbonyl)-N-phenylbenzamide |
| I-241 | 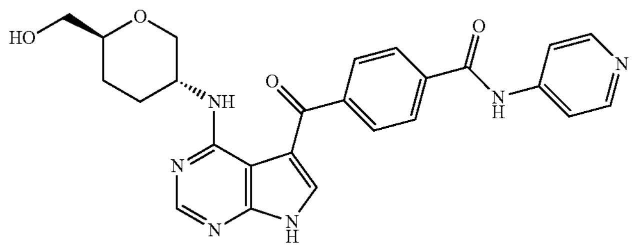 [SMILES: O=C(Nc1ccncc1)c1ccc(C(=O)c2c[nH]c3ncnc(N[C@@H]4CC[C@@H](CO)OC4)c23)cc1] | 4-(4-(((3R,6S)-6-(hydroxymethyl)tetrahydro-2H-pyran-3-yl)amino)-7H-pyrrolo[2,3-d]pyrimidine-5-carbonyl)-N-(pyridin-4-yl)benzamide |
| I-242 | 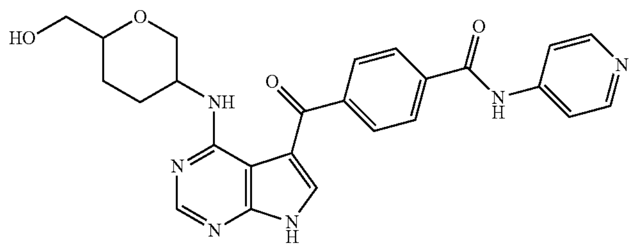 [SMILES: O=C(Nc1ccncc1)c1ccc(C(=O)c2c[nH]c3ncnc(NC4CCC(CO)OC4)c23)cc1] | 4-(4-((6-(hydroxymethyl)tetrahydro-2H-pyran-3-yl)amino)-7H-pyrrolo[2,3-d]pyrimidine-5-carbonyl)-N-(pyridin-4-yl)benzamide |
| I-243 | 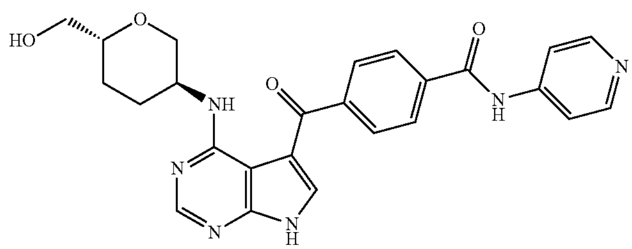 [SMILES: O=C(Nc1ccncc1)c1ccc(C(=O)c2c[nH]c3ncnc(N[C@H]4CC[C@H](CO)OC4)c23)cc1] | 4-(4-(((3S,6R)-6-(hydroxymethyl)tetrahydro-2H-pyran-3-yl)amino)-7H-pyrrolo[2,3-d]pyrimidine-5-carbonyl)-N-(pyridin-4-yl)benzamide |
| I-244 | 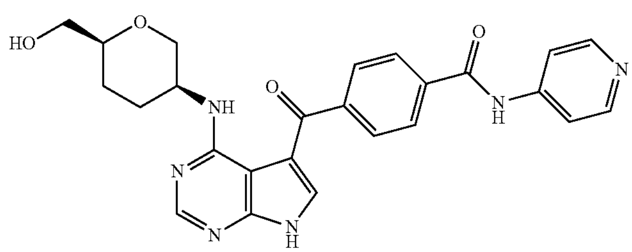 [SMILES: O=C(Nc1ccncc1)c1ccc(C(=O)c2c[nH]c3ncnc(N[C@H]4CC[C@@H](CO)OC4)c23)cc1] | 4-(4-(((3S,6S)-6-(hydroxymethyl)tetrahydro-2H-pyran-3-yl)amino)-7H-pyrrolo[2,3-d]pyrimidine-5-carbonyl)-N-(pyridin-4-yl)benzamide |
| I-245 | 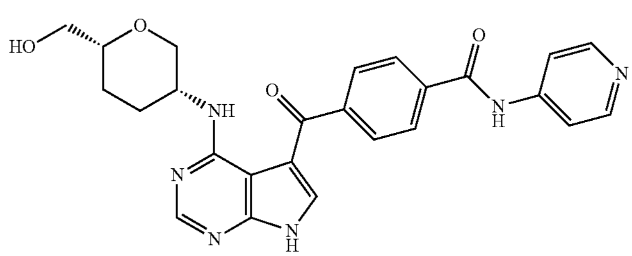 [SMILES: O=C(Nc1ccncc1)c1ccc(C(=O)c2c[nH]c3ncnc(N[C@@H]4CC[C@H](CO)OC4)c23)cc1] | 4-(4-(((3R,6R)-6-(hydroxymethyl)tetrahydro-2H-pyran-3-yl)amino)-7H-pyrrolo[2,3-d]pyrimidine-5-carbonyl)-N-(pyridin-4-yl)benzamide |

-continued

| Cmpd No. | Structure | Chemical name |
|---|---|---|
| I-246 | 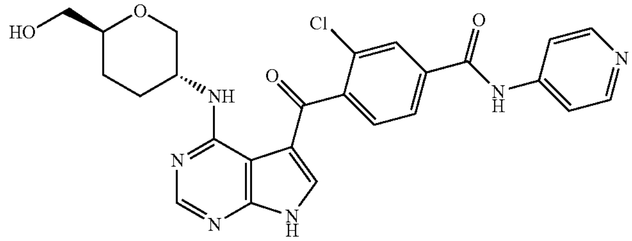 [SMILES: O=C(Nc1ccncc1)c1ccc(C(=O)c2c[nH]c3ncnc(N[C@@H]4CC[C@@H](CO)OC4)c23)c(Cl)c1] | 3-chloro-4-(4-(((3R,6S)-6-(hydroxymethyl)tetrahydro-2H-pyran-3-yl)amino)-7H-pyrrolo[2,3-d]pyrimidine-5-carbonyl)-N-(pyridin-4-yl)benzamide |
| I-247 | 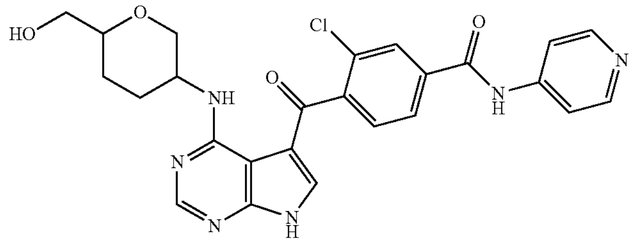 [SMILES: O=C(Nc1ccncc1)c1ccc(C(=O)c2c[nH]c3ncnc(NC4CCC(CO)OC4)c23)c(Cl)c1] | 3-chloro-4-(4-((6-(hydroxymethyl)tetrahydro-2H-pyran-3-yl)amino)-7H-pyrrolo[2,3-d]pyrimidine-5-carbonyl)-N-(pyridin-4-yl)benzamide |
| I-248 | 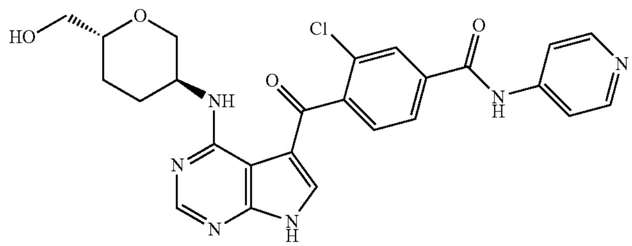 [SMILES: O=C(Nc1ccncc1)c1ccc(C(=O)c2c[nH]c3ncnc(N[C@H]4CC[C@H](CO)OC4)c23)c(Cl)c1] | 3-chloro-4-(4-(((3S,6R)-6-(hydroxymethyl)tetrahydro-2H-pyran-3-yl)amino)-7H-pyrrolo[2,3-d]pyrimidine-5-carbonyl)-N-(pyridin-4-yl)benzamide |
| I-249 | 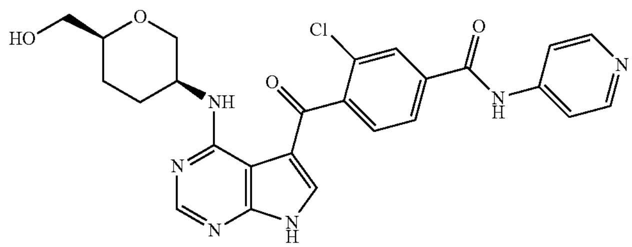 [SMILES: O=C(Nc1ccncc1)c1ccc(C(=O)c2c[nH]c3ncnc(N[C@H]4CC[C@@H](CO)OC4)c23)c(Cl)c1] | 3-chloro-4-(4-(((3S,6S)-6-(hydroxymethyl)tetrahydro-2H-pyran-3-yl)amino)-7H-pyrrolo[2,3-d]pyrimidine-5-carbonyl)-N-(pyridin-4-yl)benzamide |
| I-250 | 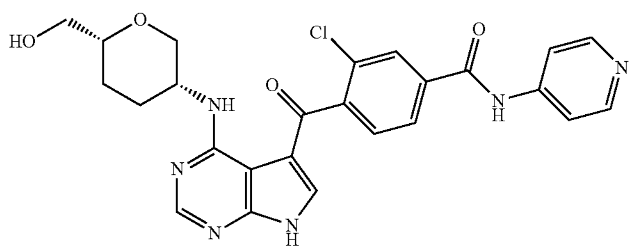 [SMILES: O=C(Nc1ccncc1)c1ccc(C(=O)c2c[nH]c3ncnc(N[C@@H]4CC[C@H](CO)OC4)c23)c(Cl)c1] | 3-chloro-4-(4-(((3R,6R)-6-(hydroxymethyl)tetrahydro-2H-pyran-3-yl)amino)-7H-pyrrolo[2,3-d]pyrimidine-5-carbonyl)-N-(pyridin-4-yl)benzamide |
| I-251 | 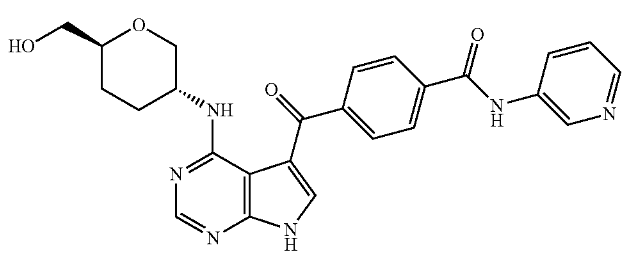 [SMILES: O=C(Nc1cccnc1)c1ccc(C(=O)c2c[nH]c3ncnc(N[C@@H]4CC[C@@H](CO)OC4)c23)cc1] | 4-(4-(((3R,6S)-6-(hydroxymethyl)tetrahydro-2H-pyran-3-yl)amino)-7H-pyrrolo[2,3-d]pyrimidine-5-carbonyl)-N-(pyridin-3-yl)benzamide |

-continued

| Cmpd No. | Structure | Chemical name |
|---|---|---|
| I-252 | 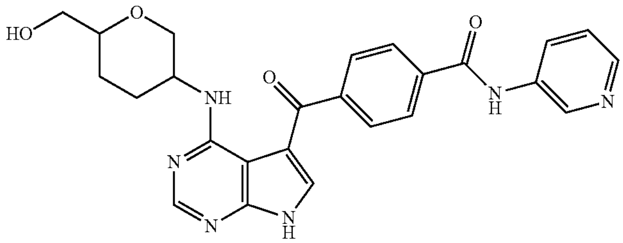 [SMILES: O=C(Nc1cccnc1)c1ccc(C(=O)c2c[nH]c3ncnc(NC4CCC(CO)OC4)c23)cc1] | 4-(4-((6-(hydroxymethyl)tetrahydro-2H-pyran-3-yl)amino)-7H-pyrrolo[2,3-d]pyrimidine-5-carbonyl)-N-(pyridin-3-yl)benzamide |
| I-253 | 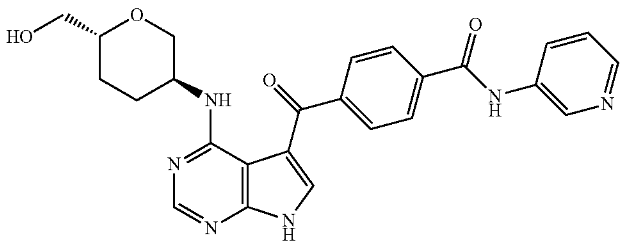 [SMILES: O=C(Nc1cccnc1)c1ccc(C(=O)c2c[nH]c3ncnc(N[C@H]4CC[C@H](CO)OC4)c23)cc1] | 4-(4-(((3S,6R)-6-(hydroxymethyl)tetrahydro-2H-pyran-3-yl)amino)-7H-pyrrolo[2,3-d]pyrimidine-5-carbonyl)-N-(pyridin-3-yl)benzamide |
| I-254 | 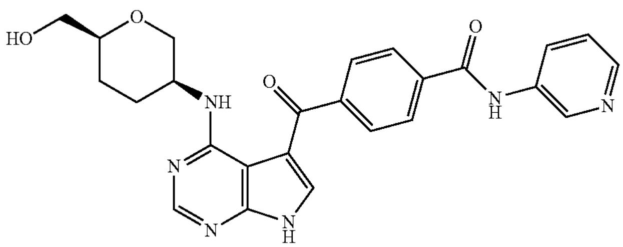 [SMILES: O=C(Nc1cccnc1)c1ccc(C(=O)c2c[nH]c3ncnc(N[C@H]4CC[C@@H](CO)OC4)c23)cc1] | 4-(4-(((3S,6S)-6-(hydroxymethyl)tetrahydro-2H-pyran-3-yl)amino)-7H-pyrrolo[2,3-d]pyrimidine-5-carbonyl)-N-(pyridin-3-yl)benzamide |
| I-255 | 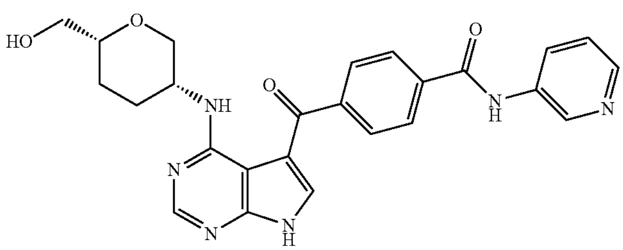 [SMILES: O=C(Nc1cccnc1)c1ccc(C(=O)c2c[nH]c3ncnc(N[C@@H]4CC[C@H](CO)OC4)c23)cc1] | 4-(4-(((3R,6R)-6-(hydroxymethyl)tetrahydro-2H-pyran-3-yl)amino)-7H-pyrrolo[2,3-d]pyrimidine-5-carbonyl)-N-(pyridin-3-yl)benzamide |
| I-256 | 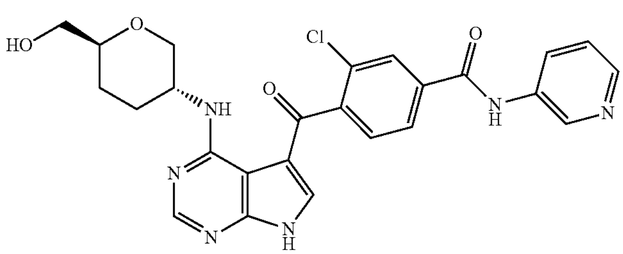 [SMILES: O=C(Nc1cccnc1)c1ccc(C(=O)c2c[nH]c3ncnc(N[C@@H]4CC[C@@H](CO)OC4)c23)c(Cl)c1] | 3-chloro-4-(4-(((3R,6S)-6-(hydroxymethyl)tetrahydro-2H-pyran-3-yl)amino)-7H-pyrrolo[2,3-d]pyrimidine-5-carbonyl)-N-(pyridin-3-yl)benzamide |
| I-257 | 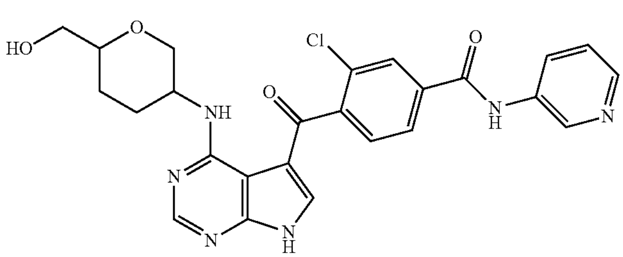 [SMILES: O=C(Nc1cccnc1)c1ccc(C(=O)c2c[nH]c3ncnc(NC4CCC(CO)OC4)c23)c(Cl)c1] | 3-chloro-4-(4-((6-(hydroxymethyl)tetrahydro-2H-pyran-3-yl)amino)-7H-pyrrolo[2,3-d]pyrimidine-5-carbonyl)-N-(pyridin-3-yl)benzamide |

| Cmpd No. | Structure | Chemical name |
|---|---|---|
| I-258 | 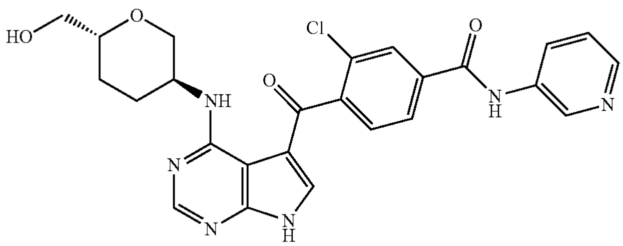 [SMILES: O=C(Nc1cccnc1)c1ccc(C(=O)c2c[nH]c3ncnc(N[C@H]4CC[C@H](CO)OC4)c23)c(Cl)c1] | 3-chloro-4-(4-(((3S,6R)-6-(hydroxymethyl)tetrahydro-2H-pyran-3-yl)amino)-7H-pyrrolo[2,3-d]pyrimidine-5-carbonyl)-N-(pyridin-3-yl)benzamide |
| I-259 | 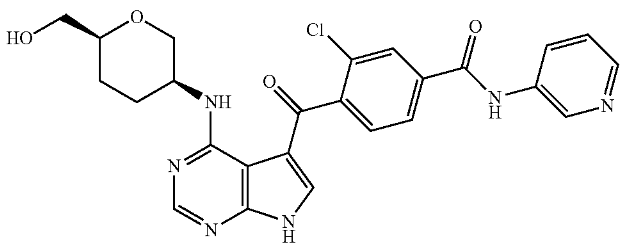 [SMILES: O=C(Nc1cccnc1)c1ccc(C(=O)c2c[nH]c3ncnc(N[C@H]4CC[C@@H](CO)OC4)c23)c(Cl)c1] | 3-chloro-4-(4-(((3S,6S)-6-(hydroxymethyl)tetrahydro-2H-pyran-3-yl)amino)-7H-pyrrolo[2,3-d]pyrimidine-5-carbonyl)-N-(pyridin-3-yl)benzamide |
| I-260 | 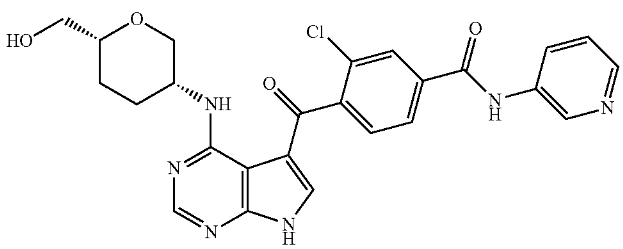 | 3-chloro-4-(4-(((3R,6R)-6-(hydroxymethyl)tetrahydro-2H-pyran-3-yl)amino)-7H-pyrrolo[2,3-d]pyrimidine-5-carbonyl)-N-(pyridin-3-yl)benzamide |
| I-261 | 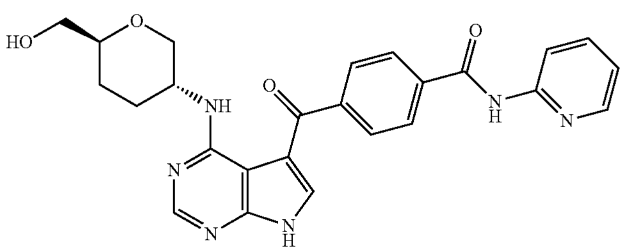 [SMILES: O=C(Nc1ccccn1)c1ccc(C(=O)c2c[nH]c3ncnc(N[C@@H]4CC[C@@H](CO)OC4)c23)cc1] | 4-(4-(((3R,6S)-6-(hydroxymethyl)tetrahydro-2H-pyran-3-yl)amino)-7H-pyrrolo[2,3-d]pyrimidine-5-carbonyl)-N-(pyridin-2-yl)benzamide |
| I-262 | 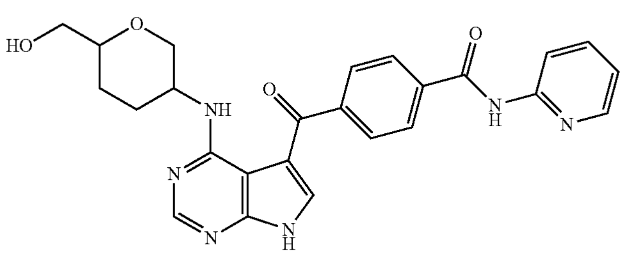 | 4-(4-((6-(hydroxymethyl)tetrahydro-2H-pyran-3-yl)amino)-7H-pyrrolo[2,3-d]pyrimidine-5-carbonyl)-N-(pyridin-2-yl)benzamide |
| I-263 | 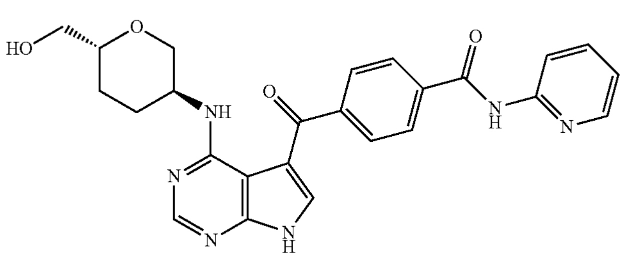 [SMILES: O=C(Nc1ccccn1)c1ccc(C(=O)c2c[nH]c3ncnc(N[C@H]4CC[C@H](CO)OC4)c23)cc1] | 4-(4-(((3S,6R)-6-(hydroxymethyl)tetrahydro-2H-pyran-3-yl)amino)-7H-pyrrolo[2,3-d]pyrimidine-5-carbonyl)-N-(pyridin-2-yl)benzamide |

| Cmpd No. | Structure | Chemical name |
|---|---|---|
| I-264 | 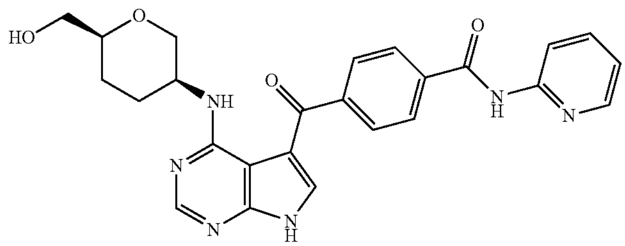 [SMILES: O=C(Nc1ccccn1)c1ccc(C(=O)c2c[nH]c3ncnc(N[C@H]4CC[C@@H](CO)OC4)c23)cc1] | 4-(4-(((3S,6S)-6-(hydroxymethyl)tetrahydro-2H-pyran-3-yl)amino)-7H-pyrrolo[2,3-d]pyrimidine-5-carbonyl)-N-(pyridin-2-yl)benzamide |
| I-265 | 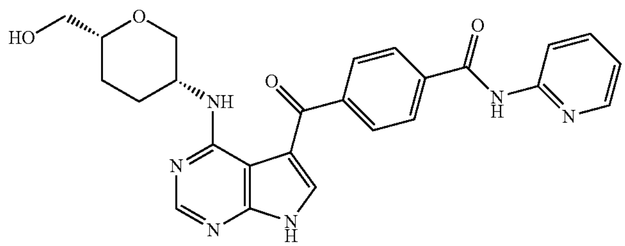 [SMILES: O=C(Nc1ccccn1)c1ccc(C(=O)c2c[nH]c3ncnc(N[C@@H]4CC[C@H](CO)OC4)c23)cc1] | 4-(4-(((3R,6R)-6-(hydroxymethyl)tetrahydro-2H-pyran-3-yl)amino)-7H-pyrrolo[2,3-d]pyrimidine-5-carbonyl)-N-(pyridin-2-yl)benzamide |
| I-266 | 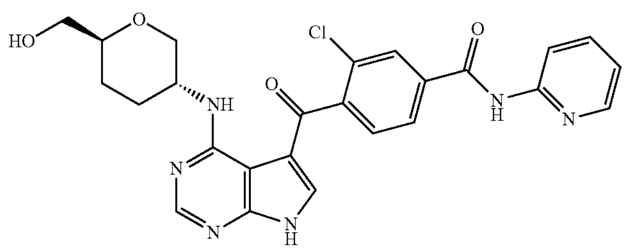 | 3-chloro-4-(4-(((3R,6S)-6-(hydroxymethyl)tetrahydro-2H-pyran-3-yl)amino)-7H-pyrrolo[2,3-d]pyrimidine-5-carbonyl)-N-(pyridin-2-yl)benzamide |
| I-267 | 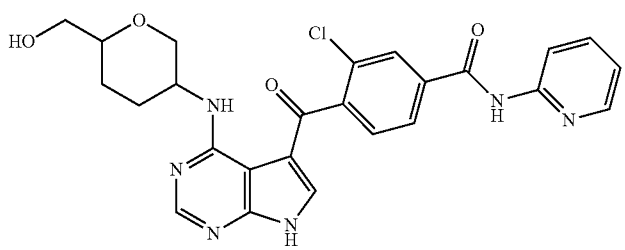 [SMILES: O=C(Nc1ccccn1)c1ccc(C(=O)c2c[nH]c3ncnc(NC4CCC(CO)OC4)c23)c(Cl)c1] | 3-chloro-4-(4-((6-(hydroxymethyl)tetrahydro-2H-pyran-3-yl)amino)-7H-pyrrolo[2,3-d]pyrimidine-5-carbonyl)-N-(pyridin-2-yl)benzamide |
| I-268 | 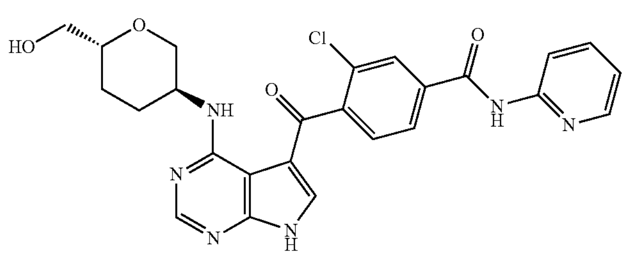 | 3-chloro-4-(4-(((3S,6R)-6-(hydroxymethyl)tetrahydro-2H-pyran-3-yl)amino)-7H-pyrrolo[2,3-d]pyrimidine-5-carbonyl)-N-(pyridin-2-yl)benzamide |
| I-269 | 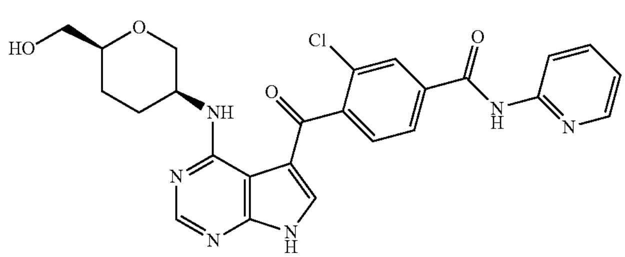 [SMILES: O=C(Nc1ccccn1)c1ccc(C(=O)c2c[nH]c3ncnc(N[C@H]4CC[C@@H](CO)OC4)c23)c(Cl)c1] | 3-chloro-4-(4-(((3S,6S)-6-(hydroxymethyl)tetrahydro-2H-pyran-3-yl)amino)-7H-pyrrolo[2,3-d]pyrimidine-5-carbonyl)-N-(pyridin-2-yl)benzamide |

| Cmpd No. | Structure | Chemical name |
|---|---|---|
| I-270 | 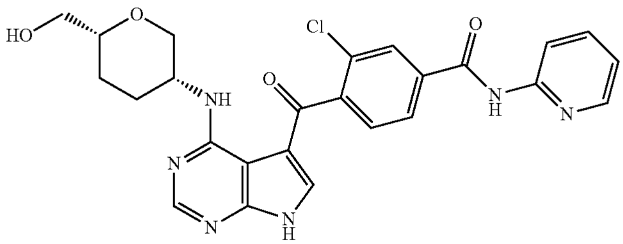 [SMILES: O=C(Nc1ccccn1)c1ccc(C(=O)c2c[nH]c3ncnc(N[C@@H]4CC[C@H](CO)OC4)c23)c(Cl)c1] | 3-chloro-4-(4-(((3R,6R)-6-(hydroxymethyl)tetrahydro-2H-pyran-3-yl)amino)-7H-pyrrolo[2,3-d]pyrimidine-5-carbonyl)-N-(pyridin-2-yl)benzamide |
| I-271 | 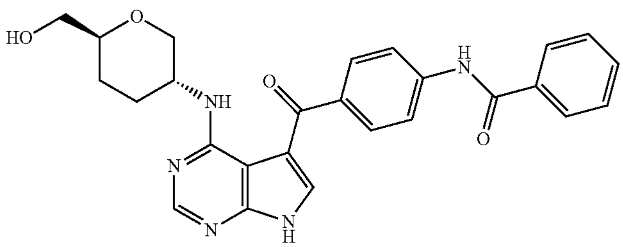 [SMILES: O=C(Nc1ccc(C(=O)c2c[nH]c3ncnc(N[C@@H]4CC[C@@H](CO)OC4)c23)cc1)c1ccccc1] | N-(4-(4-(((3R,6S)-6-hydroxymethyl)tetrahydro-2H-pyran-3-yl)amino)-7H-pyrrolo[2,3-d]pyrimidine-5-carbonyl)phenyl)benzamide |
| I-272 | 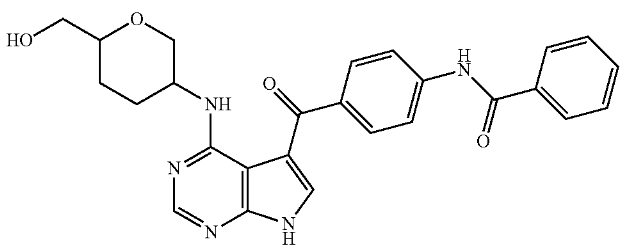 [SMILES: O=C(Nc1ccc(C(=O)c2c[nH]c3ncnc(NC4CCC(CO)OC4)c23)cc1)c1ccccc1] | N-(4-(4-((6-(hydroxymethyl)tetrahydro-2H-pyran-3-yl)amino)-7H-pyrrolo[2,3-d]pyrimidine-5-carbonyl)phenyl)benzamide |
| I-273 | 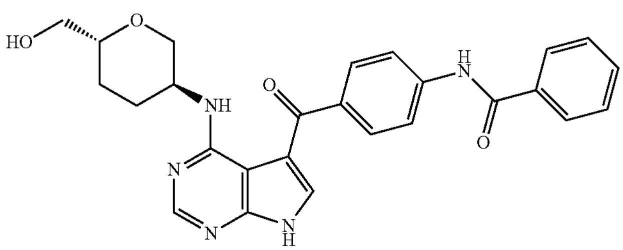 [SMILES: O=C(Nc1ccc(C(=O)c2c[nH]c3ncnc(N[C@H]4CC[C@H](CO)OC4)c23)cc1)c1ccccc1] | N-(4-(4-(((3S,6R)-6-(hydroxymethyl)tetrahydro-2H-pyran-3-yl)amino)-7H-pyrrolo[2,3-d]pyrimidine-5-carbonyl)phenyl)benzamide |
| I-274 | 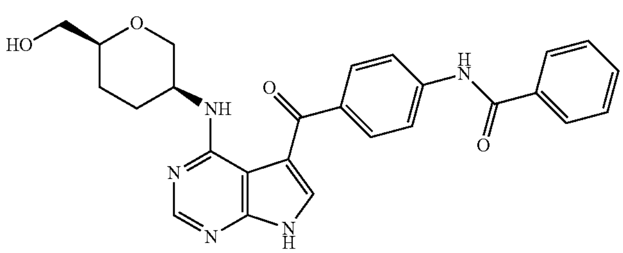 | N-(4-(4-(((3S,6S)-6-(hydroxymethyl)tetrahydro-2H-pyran-3-yl)amino)-7H-pyrrolo[2,3-d]pyrimidine-5-carbonyl)phenyl)benzamide |
| I-275 | 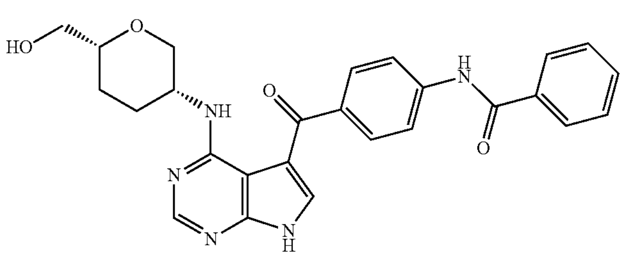 [SMILES: O=C(Nc1ccc(C(=O)c2c[nH]c3ncnc(N[C@@H]4CC[C@H](CO)OC4)c23)cc1)c1ccccc1] | N-(4-(4-(((3R,6R)-6-(hydroxymethyl)tetrahydro-2H-pyran-3-yl)amino)-7H-pyrrolo[2,3-d]pyrimidine-5-carbonyl)phenyl)benzamide |

| Cmpd No. | Structure | Chemical name |
|---|---|---|
| I-276 | 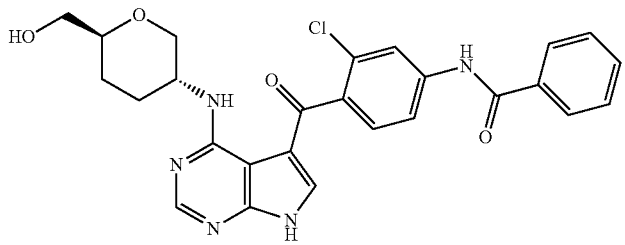 [SMILES: O=C(Nc1ccc(C(=O)c2c[nH]c3ncnc(N[C@@H]4CC[C@@H](CO)OC4)c23)c(Cl)c1)c1ccccc1] | N-(3-chloro-4-(4-(((3R,6S)-6-(hydroxymethyl)tetrahydro-2H-pyran-3-yl)amino)-7H-pyrrolo[2,3-d]pyrimidine-5-carbonyl)phenyl)benzamide |
| I-277 | 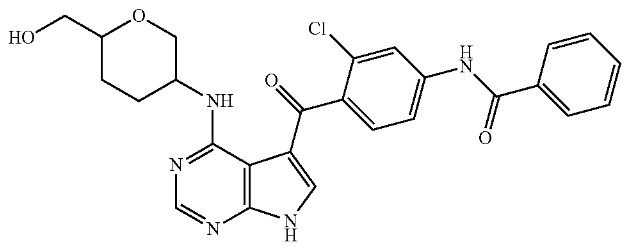 | N-(3-chloro-4-(4-((6-(hydroxymethyl)tetrahydro-2H-pyran-3-yl)amino)-7H-pyrrolo[2,3-d]pyrimidine-5-carbonyl)phenyl)benzamide |
| I-278 | 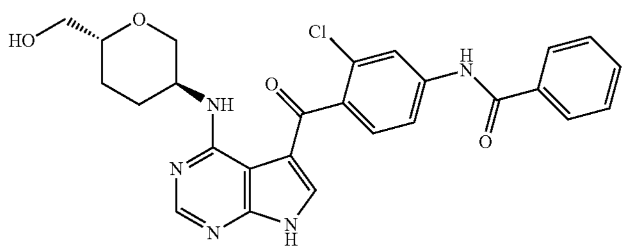 [SMILES: O=C(Nc1ccc(C(=O)c2c[nH]c3ncnc(N[C@H]4CC[C@H](CO)OC4)c23)c(Cl)c1)c1ccccc1] | N-(3-chloro-4-(4-(((3S,6R)-6-(hydroxymethyl)tetrahydro-2H-pyran-3-yl)amino)-7H-pyrrolo[2,3-d]pyrimidine-5-carbonyl)phenyl)benzamide |
| I-279 | 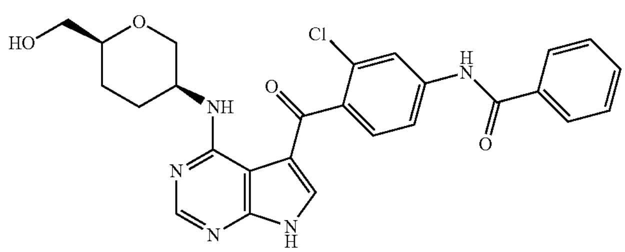 | N-(3-chloro-4-(4-(((3S,6S)-6-(hydroxymethyl)tetrahydro-2H-pyran-3-yl)amino)-7H-pyrrolo[2,3-d]pyrimidine-5-carbonyl)phenyl)benzamide |
| I-280 | 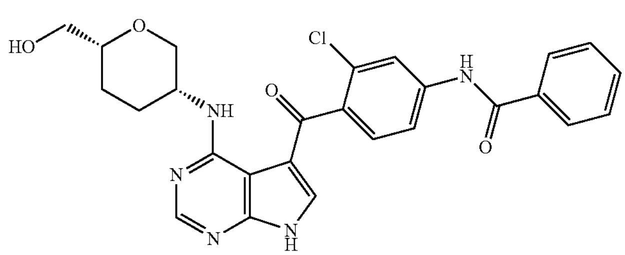 [SMILES: O=C(Nc1ccc(C(=O)c2c[nH]c3ncnc(N[C@@H]4CC[C@H](CO)OC4)c23)c(Cl)c1)c1ccccc1] | N-(3-chloro-4-(4-(((3R,6R)-6-(hydroxymethyl)tetrahydro-2H-pyran-3-yl)amino)-7H-pyrrolo[2,3-d]pyrimidine-5-carbonyl)phenyl)benzamide |
| I-281 | 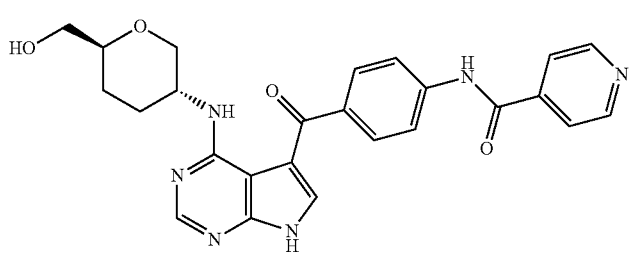 [SMILES: O=C(Nc1ccc(C(=O)c2c[nH]c3ncnc(N[C@@H]4CC[C@@H](CO)OC4)c23)cc1)c1ccncc1] | N-(4-(4-(((3R,6S)-6-(hydroxymethyl)tetrahydro-2H-pyran-3-yl)amino)-7H-pyrrolo[2,3-d]pyrimidine-5-carbonyl)phenyl)isonicotinamide |

-continued

| Cmpd No. | Structure | Chemical name |
| --- | --- | --- |
| I-282 | 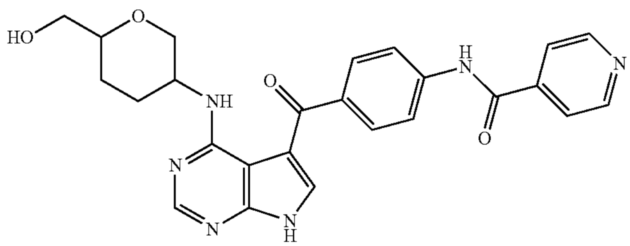 | N-(4-(4-((6-(hydroxymethyl)tetrahydro-2H-pyran-3-yl)amino)-7H-pyrrolo[2,3-d]pyrimidine-5-carbonyl)phenyl)isonicotinamide |
| I-283 | 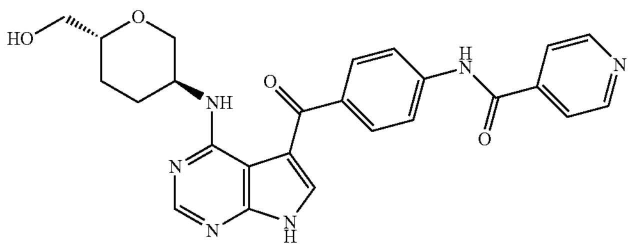 [SMILES: O=C(Nc1ccc(C(=O)c2c[nH]c3ncnc(N[C@H]4CC[C@H](CO)OC4)c23)cc1)c1ccncc1] | N-(4-(4-(((3S,6R)-6-(hydroxymethyl)tetrahydro-2H-pyran-3-yl)amino)-7H-pyrrolo[2,3-d]pyrimidine-5-carbonyl)phenyl)isonicotinamide |
| I-284 | 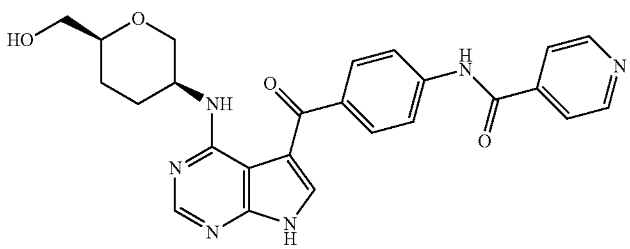 [SMILES: O=C(Nc1ccc(C(=O)c2c[nH]c3ncnc(N[C@H]4CC[C@@H](CO)OC4)c23)cc1)c1ccncc1] | N-(4-(4-(((3S,6S)-6-(hydroxymethyl)tetrahydro-2H-pyran-3-yl)amino)-7H-pyrrolo[2,3-d]pyrimidine-5-carbonyl)phenyl)isonicotinamide |
| I-285 | 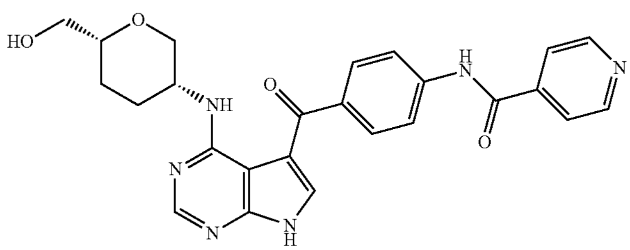 [SMILES: O=C(Nc1ccc(C(=O)c2c[nH]c3ncnc(N[C@@H]4CC[C@H](CO)OC4)c23)cc1)c1ccncc1] | N-(4-(4-(((3R,6R)-6-(hydroxymethyl)tetrahydro-2H-pyran-3-yl)amino)-7H-pyrrolo[2,3-d]pyrimidine-5-carbonyl)phenyl)isonicotinamide |
| I-286 | 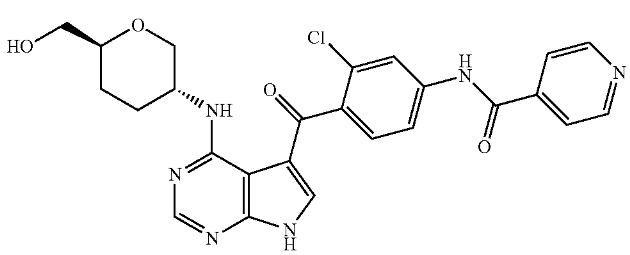 [SMILES: O=C(Nc1ccc(C(=O)c2c[nH]c3ncnc(N[C@@H]4CC[C@@H](CO)OC4)c23)c(Cl)c1)c1ccncc1] | N-(3-chloro-4-(4-(((3R,6S)-6-(hydroxymethyl)tetrahydro-2H-pyran-3-yl)amino)-7H-pyrrolo[2,3-d]pyrimidine-5-carbonyl)phenyl)isonicotinamide |
| I-287 | 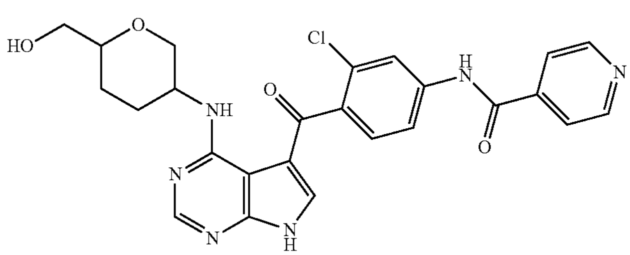 [SMILES: O=C(Nc1ccc(C(=O)c2c[nH]c3ncnc(NC4CCC(CO)OC4)c23)c(Cl)c1)c1ccncc1] | N-(3-chloro-4-(4-((6-(hydroxymethyl)tetrahydro-2H-pyran-3-yl)amino)-7H-pyrrolo[2,3-d]pyrimidine-5-carbonyl)phenyl)isonicotinamide |

-continued

| Cmpd No. | Structure | Chemical name |
|---|---|---|
| I-288 | 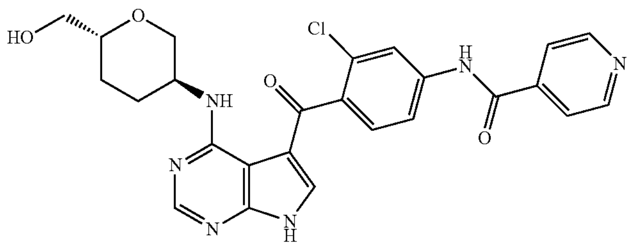 [SMILES: O=C(Nc1ccc(C(=O)c2c[nH]c3ncnc(N[C@H]4CC[C@H](CO)OC4)c23)c(Cl)c1)c1ccncc1] | N-(3-chloro-4-(4-(((3S,6R)-6-(hydroxymethyl)tetrahydro-2H-pyran-3-yl)amino)-7H-pyrrolo[2,3-d]pyrimidine-5-carbonyl)phenyl)isonicotinamide |
| I-289 | 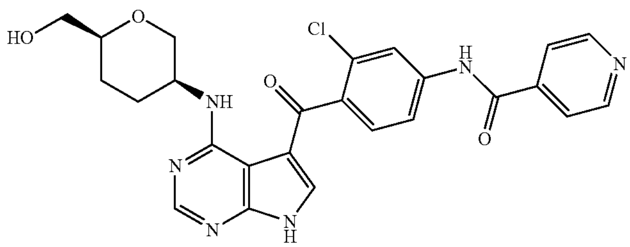 [SMILES: O=C(Nc1ccc(C(=O)c2c[nH]c3ncnc(N[C@H]4CC[C@@H](CO)OC4)c23)c(Cl)c1)c1ccncc1] | N-(3-chloro-4-(4-(((3S,6S)-6-(hydroxymethyl)tetrahydro-2H-pyran-3-yl)amino)-7H-pyrrolo[2,3-d]pyrimidine-5-carbonyl)phenyl)isonicotinamide |
| I-290 | 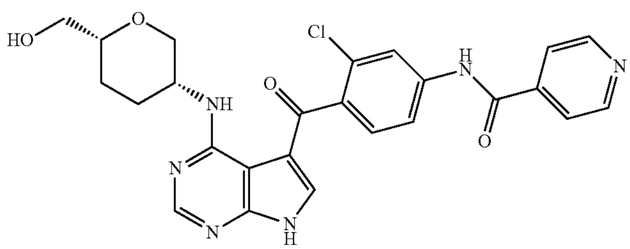 [SMILES: O=C(Nc1ccc(C(=O)c2c[nH]c3ncnc(N[C@@H]4CC[C@H](CO)OC4)c23)c(Cl)c1)c1ccncc1] | N-(3-chloro-4-(4-(((3R,6R)-6-(hydroxymethyl)tetrahydro-2H-pyran-3-yl)amino)-7H-pyrrolo[2,3-d]pyrimidine-5-carbonyl)phenyl)isonicotinamide |
| I-291 | 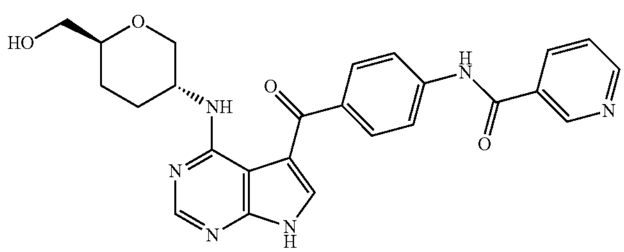 [SMILES: O=C(Nc1ccc(C(=O)c2c[nH]c3ncnc(N[C@@H]4CC[C@@H](CO)OC4)c23)cc1)c1cccnc1] | N-(4-(4-(((3R,6S)-6-(hydroxymethyl)tetrahydro-2H-pyran-3-yl)amino)-7H-pyrrolo[2,3-d]pyrimidine-5-carbonyl)phenyl)nicotinamide |
| I-292 | 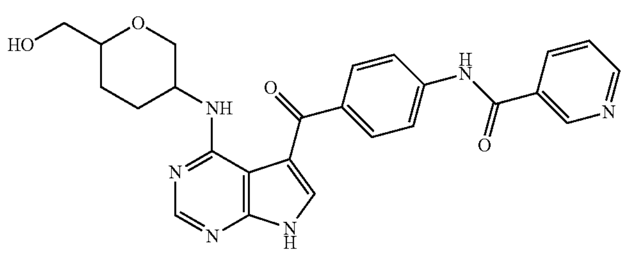 [SMILES: O=C(Nc1ccc(C(=O)c2c[nH]c3ncnc(NC4CCC(CO)OC4)c23)cc1)c1cccnc1] | N-(4-(4-((6-(hydroxymethyl)tetrahydro-2H-pyran-3-yl)amino)-7H-pyrrolo[2,3-d]pyrimidine-5-carbonyl)phenyl)nicotinamide |
| I-293 | 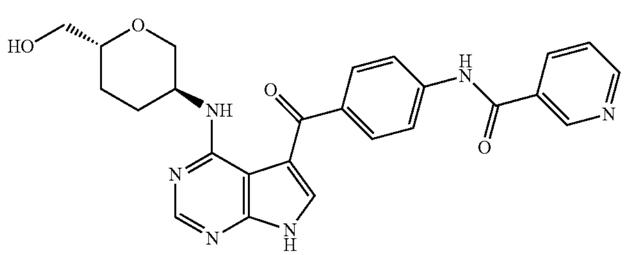 [SMILES: O=C(Nc1ccc(C(=O)c2c[nH]c3ncnc(N[C@H]4CC[C@H](CO)OC4)c23)cc1)c1cccnc1] | N-(4-(4-(((3S,6R)-6-(hydroxymethyl)tetrahydro-2H-pyran-3-yl)amino)-7H-pyrrolo[2,3-d]pyrimidine-5-carbonyl)phenyl)nicotinamide |

| Cmpd No. | Structure | Chemical name |
|---|---|---|
| I-294 | 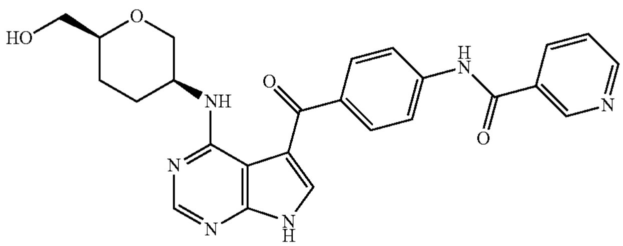 [SMILES: O=C(Nc1ccc(C(=O)c2c[nH]c3ncnc(N[C@H]4CC[C@@H](CO)OC4)c23)cc1)c1cccnc1] | N-(4-(4-(((3S,6S)-6-(hydroxymethyl)tetrahydro-2H-pyran-3-yl)amino)-7H-pyrrolo[2,3-d]pyrimidine-5-carbonyl)phenyl)nicotinamide |
| I-295 | 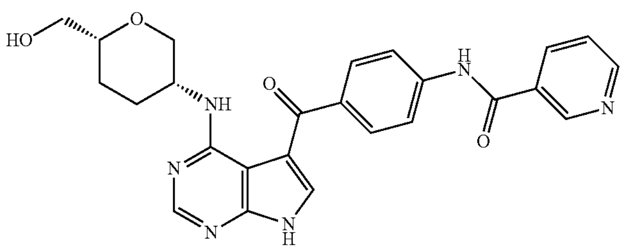 | N-(4-(4-(((3R,6R)-6-(hydroxymethyl)tetrahydro-2H-pyran-3-yl)amino)-7H-pyrrolo[2,3-d]pyrimidine-5-carbonyl)phenyl)nicotinamide |
| I-296 | 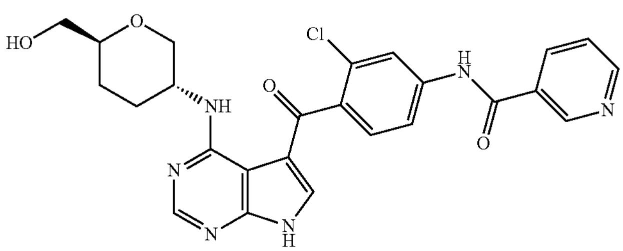 [SMILES: O=C(Nc1ccc(C(=O)c2c[nH]c3ncnc(N[C@@H]4CC[C@@H](CO)OC4)c23)c(Cl)c1)c1cccnc1] | N-(3-chloro-4-(4-(((3R,6S)-6-(hydroxymethyl)tetrahydro-2H-pyran-3-yl)amino)-7H-pyrrolo[2,3-d]pyrimidine-5-carbonyl)phenyl)nicotinamide |
| I-297 | 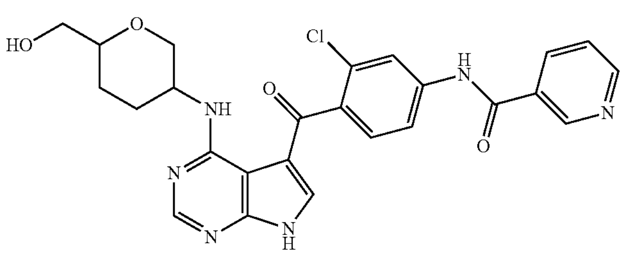 [SMILES: O=C(Nc1ccc(C(=O)c2c[nH]c3ncnc(NC4CCC(CO)OC4)c23)c(Cl)c1)c1cccnc1] | N-(3-chloro-4-(4-((6-(hydroxymethyl)tetrahydro-2H-pyran-3-yl)amino)-7H-pyrrolo[2,3-d]pyrimidine-5-carbonyl)phenyl)nicotinamide |
| I-298 | 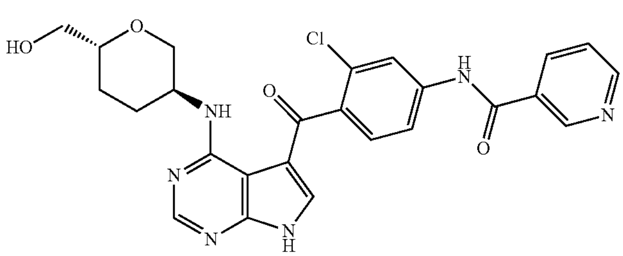 [SMILES: O=C(Nc1ccc(C(=O)c2c[nH]c3ncnc(N[C@H]4CC[C@H](CO)OC4)c23)c(Cl)c1)c1cccnc1] | N-(3-chloro-4-(4-(((3S,6R)-6-(hydroxymethyl)tetrahydro-2H-pyran-3-yl)amino)-7H-pyrrolo[2,3-d]pyrimidine-5-carbonyl)phenyl)nicotinamide |
| I-299 | 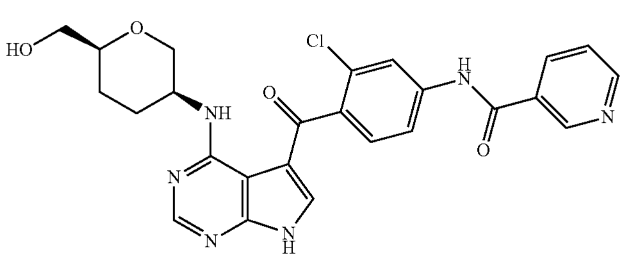 [SMILES: O=C(Nc1ccc(C(=O)c2c[nH]c3ncnc(N[C@H]4CC[C@@H](CO)OC4)c23)c(Cl)c1)c1cccnc1] | N-(3-chloro-4-(4-(((3S,6S)-6-(hydroxymethyl)tetrahydro-2H-pyran-3-yl)amino)-7H-pyrrolo[2,3-d]pyrimidine-5-carbonyl)phenyl)nicotinamide |

-continued

| Cmpd No. | Structure | Chemical name |
|---|---|---|
| I-300 | 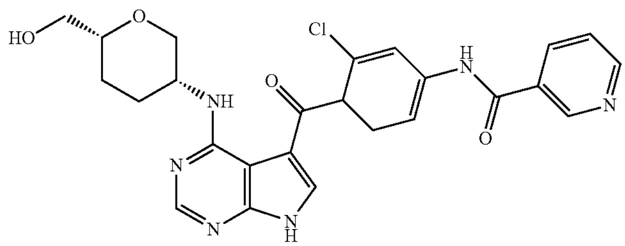 [SMILES: O=C(NC1=CCC(C(=O)c2c[nH]c3ncnc(N[C@@H]4CC[C@H](CO)OC4)c23)C(Cl)=C1)c1cccnc1] | N-(3-chloro-4-(4-(((3R,6R)-6-(hydroxymethyl)tetrahydro-2H-pyran-3-yl)amino)-7H-pyrrolo[2,3-d]pyrimidine-5-carbonyl)phenyl)nicotinamide |
| I-301 | 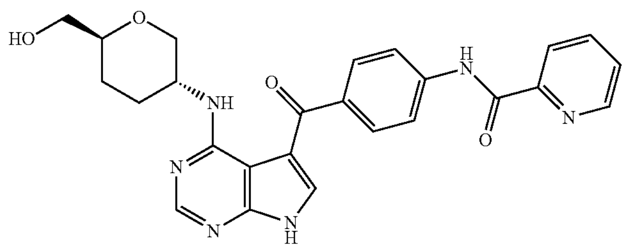 [SMILES: O=C(Nc1ccc(C(=O)c2c[nH]c3ncnc(N[C@@H]4CC[C@@H](CO)OC4)c23)cc1)c1ccccn1] | N-(4-(4-(((3R,6S)-6-(hydroxymethyl)tetrahydro-2H-pyran-3-yl)amino)-7H-pyrrolo[2,3-d]pyrimidine-5-carbonyl)phenyl)picolinamide |
| I-302 | 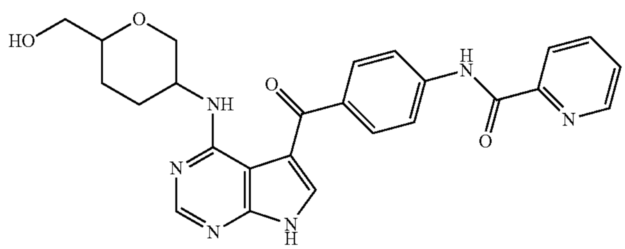 [SMILES: O=C(Nc1ccc(C(=O)c2c[nH]c3ncnc(NC4CCC(CO)OC4)c23)cc1)c1ccccn1] | N-(4-(4-((6-(hydroxymethyl)tetrahydro-2H-pyran-3-yl)amino)-7H-pyrrolo[2,3-d]pyrimidine-5-carbonyl)phenyl)picolinamide |
| I-303 | 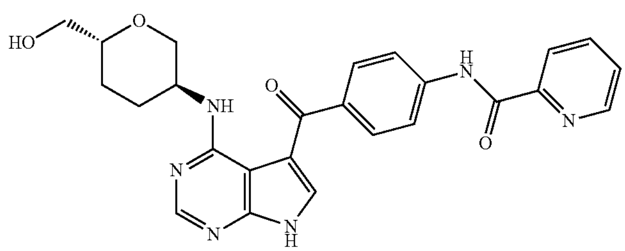 [SMILES: O=C(Nc1ccc(C(=O)c2c[nH]c3ncnc(N[C@H]4CC[C@H](CO)OC4)c23)cc1)c1ccccn1] | N-(4-(4-(((3S,6R)-6-(hydroxymethyl)tetrahydro-2H-pyran-3-yl)amino)-7H-pyrrolo[2,3-d]pyrimidine-5-carbonyl)phenyl)picolinamide |
| I-304 | 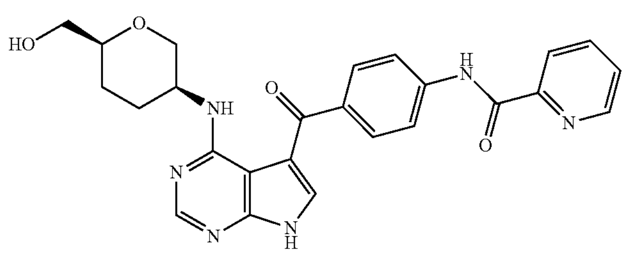 [SMILES: O=C(Nc1ccc(C(=O)c2c[nH]c3ncnc(N[C@H]4CC[C@@H](CO)OC4)c23)cc1)c1ccccn1] | N-(4-(4-(((3S,6S)-6-(hydroxymethyl)tetrahydro-2H-pyran-3-yl)amino)-7H-pyrrolo[2,3-d]pyrimidine-5-carbonyl)phenyl)picolinamide |
| I-305 | 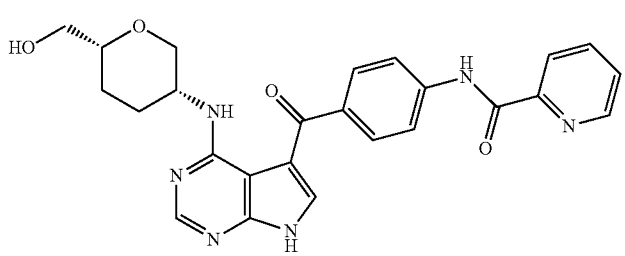 [SMILES: O=C(Nc1ccc(C(=O)c2c[nH]c3ncnc(N[C@@H]4CC[C@H](CO)OC4)c23)cc1)c1ccccn1] | N-(4-(4-(((3R,6R)-6-(hydroxymethyl)tetrahydro-2H-pyran-3-yl)amino)-7H-pyrrolo[2,3-d]pyrimidine-5-carbonyl)phenyl)picolinamide |

| Cmpd No. | Structure | Chemical name |
| --- | --- | --- |
| I-306 | 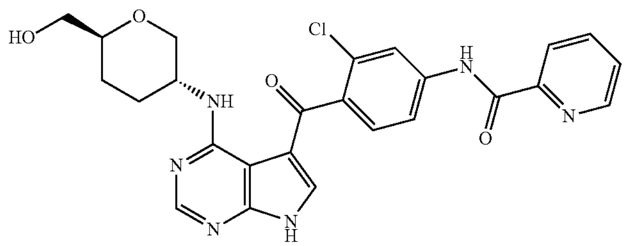 [SMILES: O=C(Nc1ccc(C(=O)c2c[nH]c3ncnc(N[C@@H]4CC[C@@H](CO)OC4)c23)c(Cl)c1)c1ccccn1] | N-(3-chloro-4-(4-(((3R,6S)-6-(hydroxymethyl)tetrahydro-2H-pyran-3-yl)amino)-7H-pyrrolo[2,3-d]pyrimidine-5-carbonyl)phenyl)picolinamide |
| I-307 | 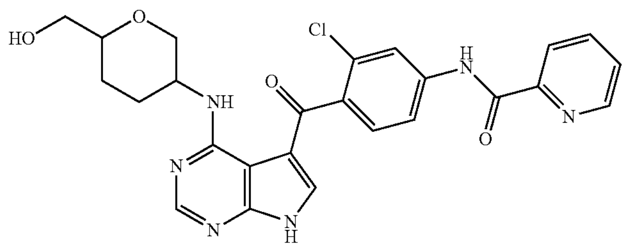 [SMILES: O=C(Nc1ccc(C(=O)c2c[nH]c3ncnc(NC4CCC(CO)OC4)c23)c(Cl)c1)c1ccccn1] | N-(3-chloro-4-(4-((6-(hydroxymethyl)tetrahydro-2H-pyran-3-yl)amino)-7H-pyrrolo[2,3-d]pyrimidine-5-carbonyl)phenyl)picolinamide |
| I-308 | 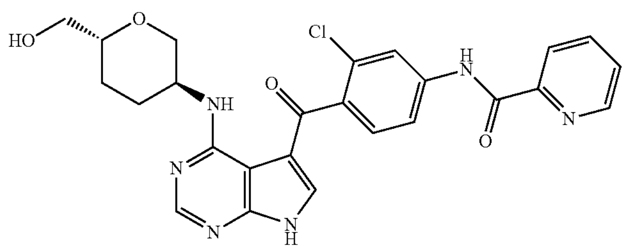 | N-(3-chloro-4-(4-(((3S,6R)-6-(hydroxymethyl)tetrahydro-2H-pyran-3-yl)amino)-7H-pyrrolo[2,3-d]pyrimidine-5-carbonyl)phenyl)picolinamide |
| I-309 | 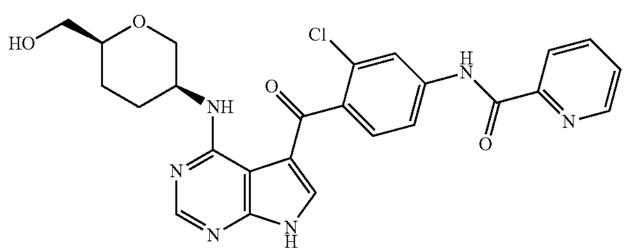 [SMILES: O=C(Nc1ccc(C(=O)c2c[nH]c3ncnc(N[C@H]4CC[C@@H](CO)OC4)c23)c(Cl)c1)c1ccccn1] | N-(3-chloro-4-(4-(((3S,6S)-6-(hydroxymethyl)tetrahydro-2H-pyran-3-yl)amino)-7H-pyrrolo[2,3-d]pyrimidine-5-carbonyl)phenyl)picolinamide |
| I-310 | 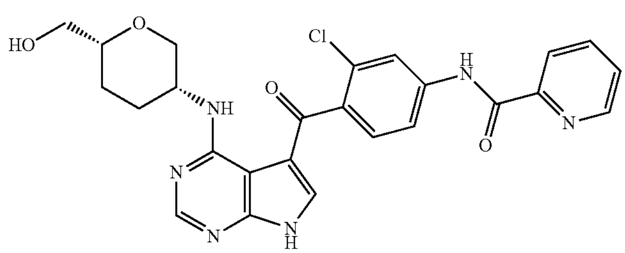 [SMILES: O=C(Nc1ccc(C(=O)c2c[nH]c3ncnc(N[C@@H]4CC[C@H](CO)OC4)c23)c(Cl)c1)c1ccccn1] | N-(3-chloro-4-(4-(((3R,6R)-6-(hydroxymethyl)tetrahydro-2H-pyran-3-yl)amino)-7H-pyrrolo[2,3-d]pyrimidine-5-carbonyl)phenyl)picolinamide |
| I-311 | 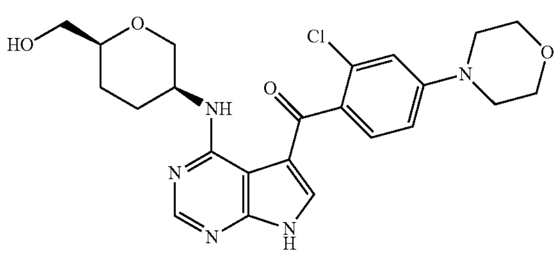 [SMILES: O=C(c1ccc(N2CCOCC2)cc1Cl)c1c[nH]c2ncnc(N[C@H]3CC[C@@H](CO)OC3)c12] | (2-chloro-4-morpholinophenyl)(4-(((3S,6S)-6-(hydroxymethyl)tetrahydro-2H-pyran-3-yl)amino)-7H-pyrrolo[2,3-d]pyrimidin-5-yl)methanone |

| Cmpd No. | Structure | Chemical name |
|---|---|---|
| I-311i | 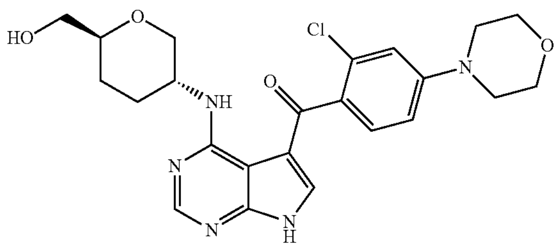 [SMILES: O=C(c1ccc(N2CCOCC2)cc1Cl)c1c[nH]c2ncnc(N[C@@H]3CC[C@@H](CO)OC3)c12] | (2-chloro-4-morpholinophenyl)(4-(((3R,6S)-6-(hydroxymethyl)tetrahydro-2H-pyran-3-yl)amino)-7H-pyrrolo[2,3-d]pyrimidin-5-yl)methanone |
| I-312 | 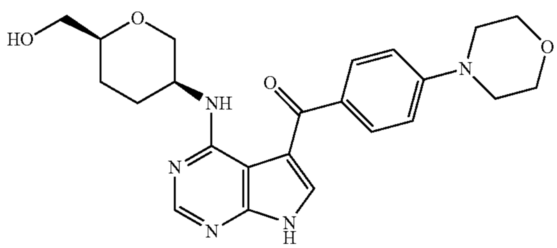 [SMILES: O=C(c1ccc(N2CCOCC2)cc1)c1c[nH]c2ncnc(N[C@H]3CC[C@@H](CO)OC3)c12] | (4-(((3S,6S)-6-(hydroxymethyl)tetrahydro-2H-pyran-3-yl)amino)-7H-pyrrolo[2,3-d]pyrimidin-5-yl)(4-morpholinophenyl)methanone |
| I-313 | 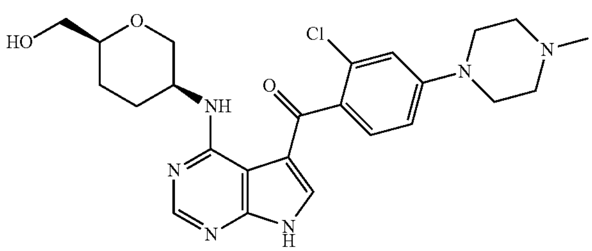 [SMILES: CN1CCN(c2ccc(C(=O)c3c[nH]c4ncnc(N[C@H]5CC[C@@H](CO)OC5)c34)c(Cl)c2)CC1] | (2-chloro-4-(4-methylpiperazin-1-yl)phenyl)(4-(((3S,6S)-6-(hydroxymethyl)tetrahydro-2H-pyran-3-yl)amino)-7H-pyrrolo[2,3-d]pyrimidin-5-yl)methanone |
| I-314 | 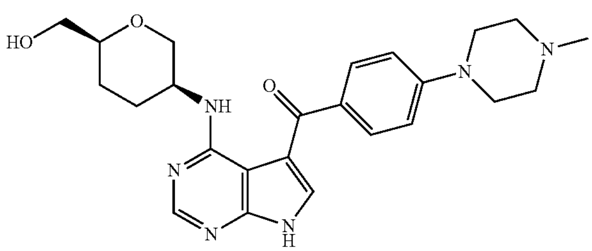 [SMILES: CN1CCN(c2ccc(C(=O)c3c[nH]c4ncnc(N[C@H]5CC[C@@H](CO)OC5)c34)cc2)CC1] | (4-(((3S,6S)-6-(hydroxymethyl)tetrahydro-2H-pyran-3-yl)amino)-7H-pyrrolo[2,3-d]pyrimidin-5-yl)(4-(4-methylpiperazin-1-yl)phenyl)methanone |
| I-315 | 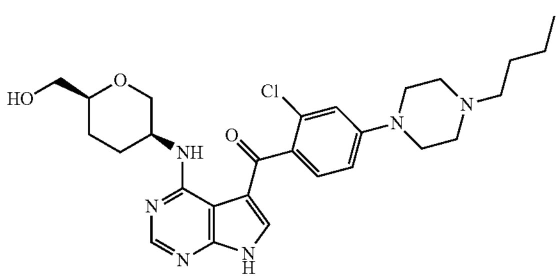 [SMILES: CCCCN1CCN(c2ccc(C(=O)c3c[nH]c4ncnc(N[C@H]5CC[C@@H](CO)OC5)c34)c(Cl)c2)CC1] | (4-(4-butylpiperazin-1-yl)-2-chlorophenyl)(4-(((3S,6S)-6-(hydroxymethyl)tetrahydro-2H-pyran-3-yl)amino)-7H-pyrrolo[2,3-d]pyrimidin-5-yl)methanone |
| I-316 | 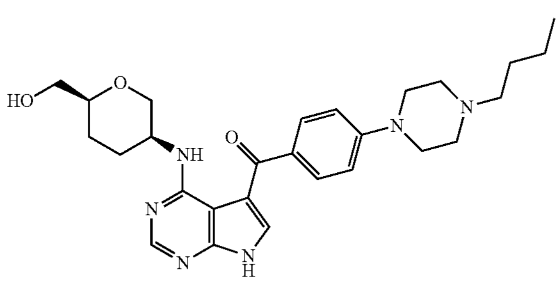 [SMILES: CCCCN1CCN(c2ccc(C(=O)c3c[nH]c4ncnc(N[C@H]5CC[C@@H](CO)OC5)c34)cc2)CC1] | (4-(4-butylpiperazin-1-yl)phenyl)(4-(((3S,6S)-6-(hydroxymethyl)tetrahydro-2H-pyran-3-yl)amino)-7H-pyrrolo]2,3-d]pyrimidin-5-yl)methanone |

-continued

| Cmpd No. | Structure | Chemical name |
|---|---|---|
| I-317 | 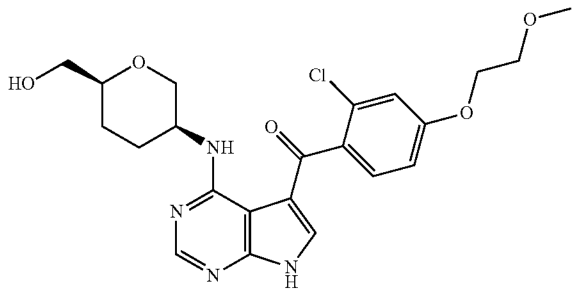 [SMILES: COCCOc1ccc(C(=O)c2c[nH]c3ncnc(N[C@H]4CC[C@@H](CO)OC4)c23)c(Cl)c1] | (2-chloro-4-(2-methoxyethoxy)phenyl)(4-(((3S,6S)-6-(hydroxymethyl)tetrahydro-2H-pyran-3-yl)amino)-7H-pyrrolo[2,3-d]pyrimidin-5-yl)methanone |
| I-317i | 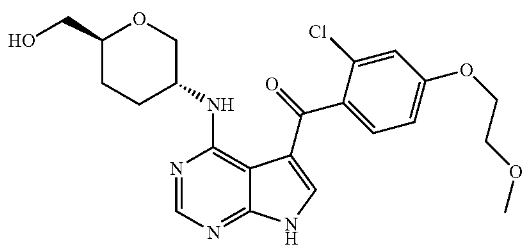 [SMILES: COCCOc1ccc(C(=O)c2c[nH]c3ncnc(N[C@@H]4CC[C@@H](CO)OC4)c23)c(Cl)c1] | 2-chloro-4-(2-methoxyethoxy)phenyl)(4-(((3R,6S)-6-(hydroxymethyl)tetrahydro-2H-pyran-3-yl)amino)-7H-pyrrolo[2,3-d]pyrimidin-5-yl)methanone |
| I-318 | 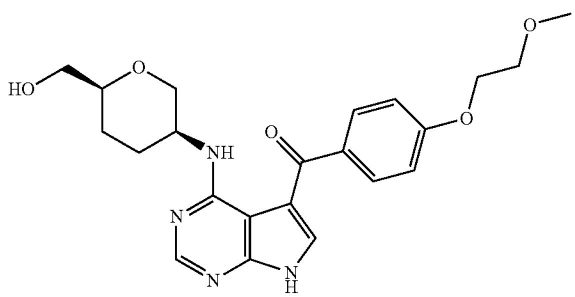 [SMILES: COCCOc1ccc(C(=O)c2c[nH]c3ncnc(N[C@H]4CC[C@@H](CO)OC4)c23)cc1] | (4-(((3S,6S)-6-(hydroxymethyl)tetrahydro-2H-pyran-3-yl)amino)-7H-pyrrolo[2,3-d]pyrimidin-5-yl)(4-(2-methoxyethoxy)phenyl)methanone |
| I-318i | 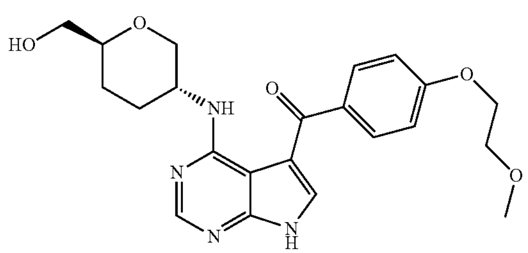 [SMILES: COCCOc1ccc(C(=O)c2c[nH]c3ncnc(N[C@@H]4CC[C@@H](CO)OC4)c23)cc1] | (4-(((3R,6S)-6-(hydroxymethyl)tetrahydro-2H-pyran-3-yl)amino)-7H-pyrrolo[2,3-d]pyrimidin-5-yl)(4-(2-methoxyethoxy)phenyl)methanone |
| I-319 | 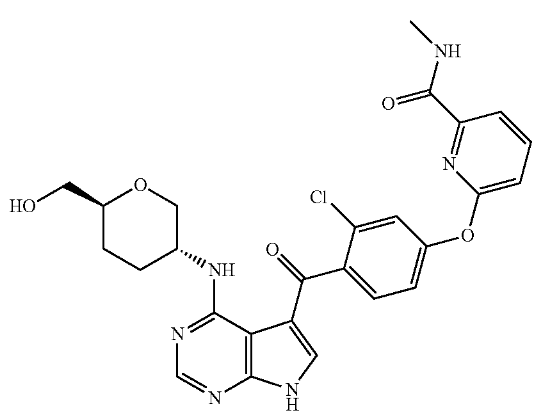 [SMILES: CNC(=O)c1cccc(Oc2ccc(C(=O)c3c[nH]c4ncnc(N[C@@H]5CC[C@@H](CO)OC5)c34)c(Cl)c2)n1] | 6-(3-chloro-4-(4-(((3R,6S)-6-(hydroxymethyl)tetrahydro-2H-pyran-3-yl)amino)-7H-pyrrolo[2,3-d]pyrimidine-5-carbonyl)phenoxy)-N-methylpicolinamide |

-continued

| Cmpd No. | Structure | Chemical name |
|---|---|---|
| I-320 | 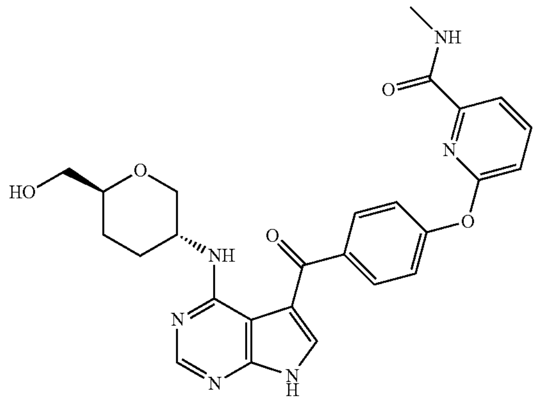 [SMILES: CNC(=O)c1cccc(Oc2ccc(C(=O)c3c[nH]c4ncnc(N[C@@H]5CC[C@@H](CO)OC5)c34)cc2)n1] | 6-(4-(4-(((3R,6S)-6-(hydroxymethyl)tetrahydro-2H-pyran-3-yl)amino)-7H-pyrrolo[2,3-d]pyrimidine-5-carbonyl)phenoxy)-N-methylpicolinamide |
| I-321 | 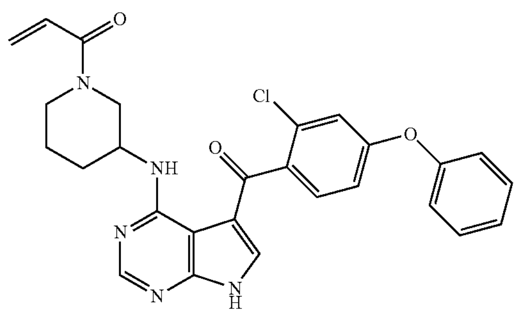 [SMILES: C=CC(=O)N1CCCC(Nc2ncnc3[nH]cc(C(=O)c4ccc(Oc5ccccc5)cc4Cl)c23)C1] | 1-(3-((5-(2-chloro-4-phenoxybenzoyl)-7H-pyrrolo[2,3-d]pyrimidin-4-yl)amino)piperidin-1-yl)but-2-en-1-one |
| I-321r | 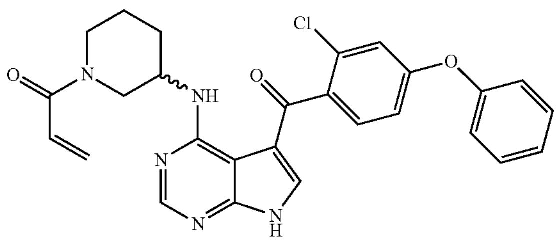 [SMILES: C=CC(=O)N1CCCC(Nc2ncnc3[nH]cc(C(=O)c4ccc(Oc5ccccc5)cc4Cl)c23)C1] | (racemic)-1-(3-((5-(2-chloro-4-phenoxybenzoyl)-7H-pyrrolo[2,3-d]pyrimidin-4-yl)amino)piperidin-1-yl)but-2-en-1-one |
| I-322 | 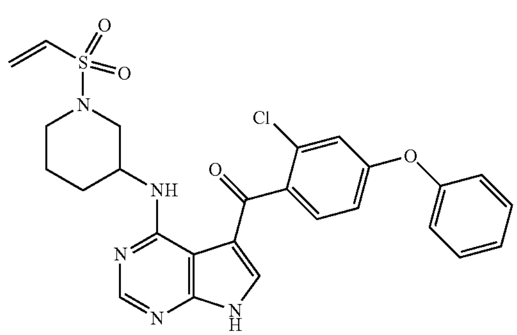 | (2-chloro-4-phenoxybenzoyl)-(4-((1-(vinylsulfonyl)piperidin-3-yl)amino-7H-pyrrolo[2,3-d]pyrimidin-5-yl)methanone |
| I-322r | 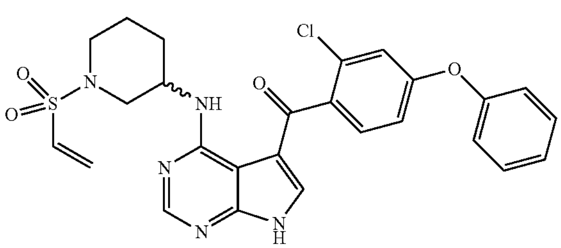 [SMILES: C=CS(=O)(=O)N1CCCC(Nc2ncnc3[nH]cc(C(=O)c4ccc(Oc5ccccc5)cc4Cl)c23)C1] | (racemic)-(2-chloro-4-phenoxyphenyl)(4-((1-(vinylsulfonyl)piperidin-3-yl)amino)-7H-pyrrolo[2,3-d]pyrimidin-5-yl)methanone |

| Cmpd No. | Structure | Chemical name |
|---|---|---|
| I-323 | 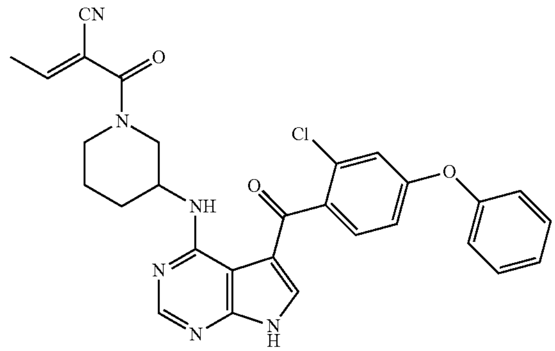 [SMILES: C/C=C(\C#N)C(=O)N1CCCC(Nc2ncnc3[nH]cc(C(=O)c4ccc(Oc5ccccc5)cc4Cl)c23)C1] | (E)-2-(3-((5-2-chloro-4-phenoxybenzoyl)-7H-pyrrolo[2,3-d]pyrimidin-4-yl)amino)piperidine-1-carbonyl)but-2-enenitrile |
| I-324 | 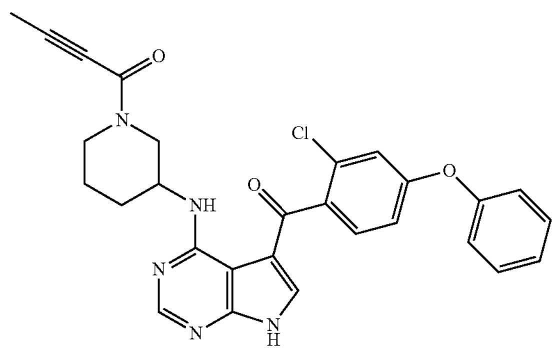 [SMILES: CC#CC(=O)N1CCCC(Nc2ncnc3[nH]cc(C(=O)c4ccc(Oc5ccccc5)cc4Cl)c23)C1] | 1-(3-((5-(2-chloro-4-phenoxybenzoyl)-7H-pyrrollo[2,3-d]pyrimidin-4-yl)amino)piperidin-1-yl)but-2-yn-1-one |
| I-324r | 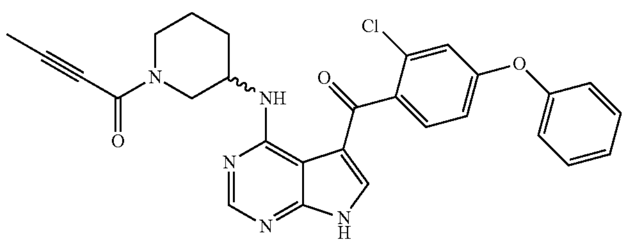 [SMILES: CC#CC(=O)N1CCCC(Nc2ncnc3[nH]cc(C(=O)c4ccc(Oc5ccccc5)cc4Cl)c23)C1] | (racemic)-1-(3-((5-(2-chloro-4-phenoxybenzoyl)-7H-pyrrolo[2,3-d]pyrimidin-4-yl)amino)piperidin-1-yl)but-2-yn-1-one |
| I-325 | 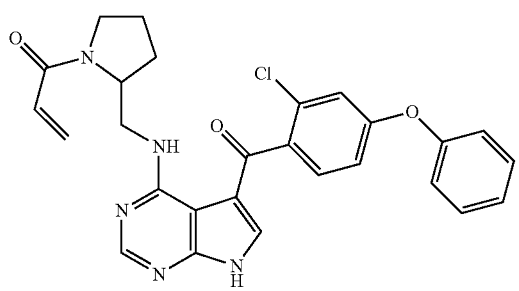 [SMILES: C=CC(=O)N1CCCC1CNc1ncnc2[nH]cc(C(=O)c3ccc(Oc4ccccc4)cc3Cl)c12] | 1-(2-(((5-(2-chloro-4-phenoxybenzoyl)-7H-pyrrolo[2,3-d]pyrimidin-4-yl)amino)methyl)pyrrolidin-1-yl)prop-2-en-1-one |
| I-325r | 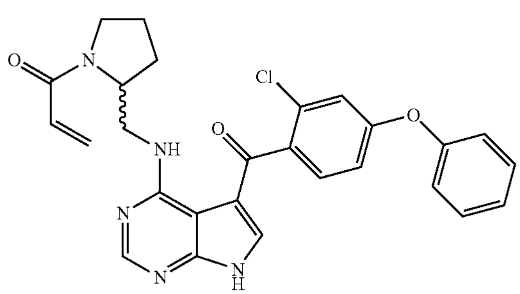 [SMILES: C=CC(=O)N1CCCC1CNc1ncnc2[nH]cc(C(=O)c3ccc(Oc4ccccc4)cc3Cl)c12] | (racemic)-1-(2-(((5-(2-chloro-4-phenoxybenzoyl)-7H-pyrrolo[2,3-d]pyrimidin-4-yl)amino)methyl)pyrrolidin-1-yl)prop-2-en-1-one |

| Cmpd No. | Structure | Chemical name |
|---|---|---|
| I-326 | 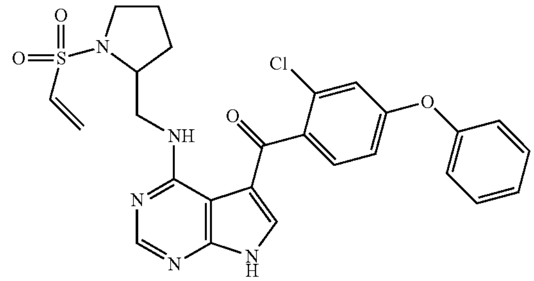 [SMILES: C=CS(=O)(=O)N1CCCC1CNc1ncnc2[nH]cc(C(=O)c3ccc(Oc4ccccc4)cc3Cl)c12] | (2-chloro-4-phenoxyphenyl)(4-(((1-(vinylsulfonyl)pyrrolidin-2-yl)methyl)amino)-7H-pyrrolo[2,3-d]pyrimidin-5-yl)methanone |
| I-326r | 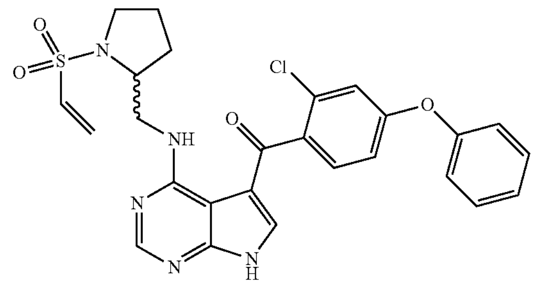 [SMILES: C=CS(=O)(=O)N1CCCC1CNc1ncnc2[nH]cc(C(=O)c3ccc(Oc4ccccc4)cc3Cl)c12] | (racemic)-(2-chloro-4-phenoxyphenyl)(4-(((1-(vinylsulfonyl)pyrrolidin-2-yl)methyl)amino)-7H-pyrrolo[2,3-d]pyrimidin-5-yl)methanone |
| I-327 | 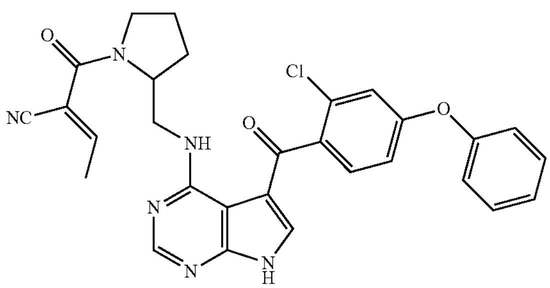 [SMILES: C/C=C(\C#N)C(=O)N1CCCC1CNc1ncnc2[nH]cc(C(=O)c3ccc(Oc4ccccc4)cc3Cl)c12] | (E)-2-(2-(((5-(2-chloro-4-phenoxybenzoyl)-7H-pyrrolo[2,3-d]pyrimidin-4-yl)amino)methyl)pyrrolidine-1-carbonyl)but-2-enenitrile |
| I-328 | 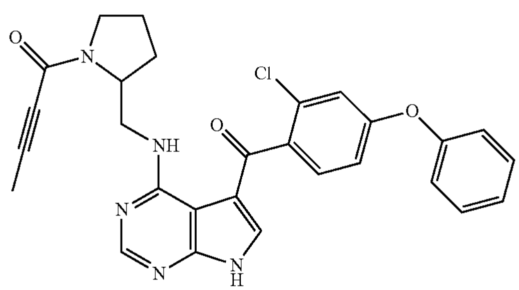 [SMILES: CC#CC(=O)N1CCCC1CNc1ncnc2[nH]cc(C(=O)c3ccc(Oc4ccccc4)cc3Cl)c12] | 1-(2-(((5-(2-chloro-4-phenoxybenzoyl)-7H-pyrrolo[2,3-d]pyrimidin-4-yl)amino)methyl)pyrrolidin-1-yl)but-2-yn-1-one |
| I-328r | 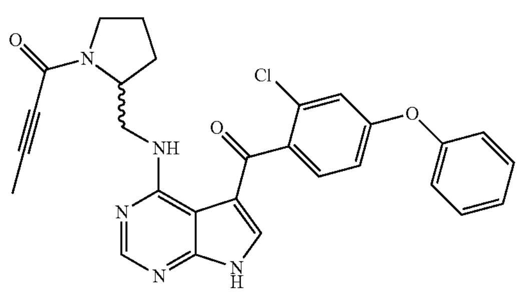 [SMILES: CC#CC(=O)N1CCCC1CNc1ncnc2[nH]cc(C(=O)c3ccc(Oc4ccccc4)cc3Cl)c12] | (racemic)-1-(2-(((5-(2-chloro-4-phenoxybenzoyl)-7H-pyrrolo[2,3-d]pyrimidin-4-yl)amino)methyl)pyrrolidin-1-yl)but-2-yn-1-one |

| Cmpd No. | Structure | Chemical name |
|---|---|---|
| I-329 | 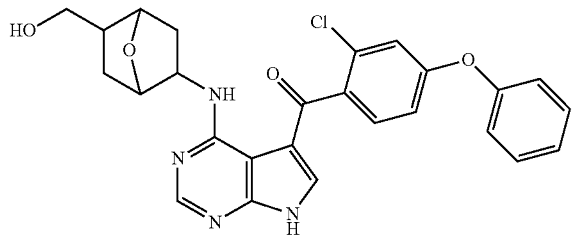 [SMILES: O=C(c1ccc(Oc2ccccc2)cc1Cl)c1c[nH]c2ncnc(NC3CC4OC3CC4CO)c12] | (2-chloro-4-phenoxyphenyl)(4-((5-(hydroxymethyl)-7-oxabicyclo[2.2.1]heptan-2-yl)amino)-7H-pyrrolo[2,3-d]pyrimidin-5-yl)methanone |
| I-330 | 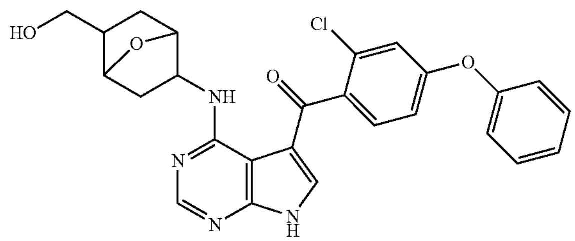 [SMILES: O=C(c1ccc(Oc2ccccc2)cc1Cl)c1c[nH]c2ncnc(NC3CC4OC3CC4CO)c12] | (2-chloro-4-phenoxyphenyl)(4-((5-(hydroxymethyl)-7-oxabicyclo[2.2.1]heptan-2-yl)amino)-7H-pyrrolo[2,3-d]pyrimidin-5-yl)methanone |
| I-331 | 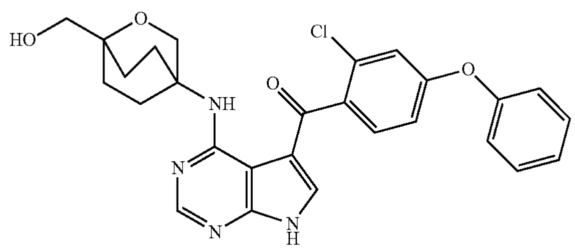 [SMILES: O=C(c1ccc(Oc2ccccc2)cc1Cl)c1c[nH]c2ncnc(NC34CCC(CO)(CC3)OC4)c12] | (2-chloro-4-phenoxyphenyl)(4-((1-(hydroxymethyl)-2-oxabicyclo[2.2.2]octan-4-yl)amino)-7H-pyrrolo[2,3-d]pyrimidin-5-yl)methanone |
| I-332 | 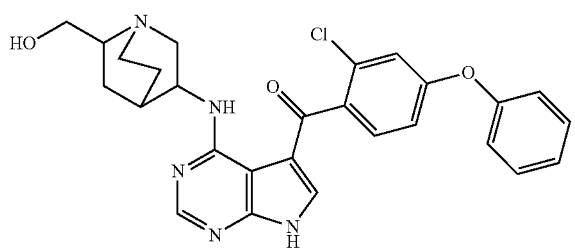 [SMILES: O=C(c1ccc(Oc2ccccc2)cc1Cl)c1c[nH]c2ncnc(NC3CN4CCC3CC4CO)c12] | (2-chloro-4-phenoxyphenyl)(4-((6-(hydroxymethyl)quinuclidin-3-yl)amino)-7H-pyrrolo[2,3-d]pyrimidin-5-yl)methanone |
| I-333 | 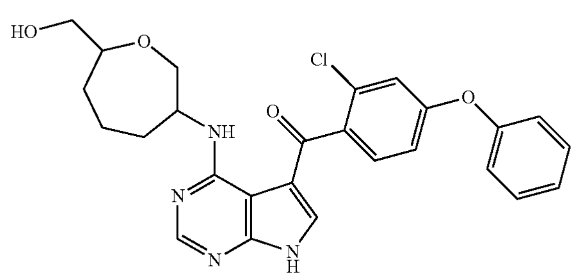 [SMILES: O=C(c1ccc(Oc2ccccc2)cc1Cl)c1c[nH]c2ncnc(NC3CCCC(CO)OC3)c12] | (2-chloro-4-phenoxyphenyl)(4-((7-(hydroxymethyl)oxepan-3-yl)amino)-7H-pyrrolo[2,3-d]pyrimidin-5-yl)methanone |
| I-334 | 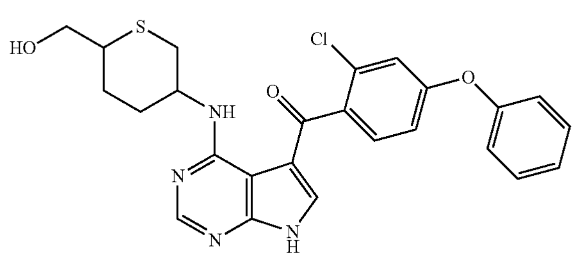 [SMILES: O=C(c1ccc(Oc2ccccc2)cc1Cl)c1c[nH]c2ncnc(NC3CCC(CO)SC3)c12] | (2-chloro-4-phenoxyphenyl)(4-((6-(hydroxymethyl)tetrahydro-2H-thiopyran-3-yl)amino)-7H-pyrrolo[2,3-d]pyrimidin-5-yl)methanone |

-continued

| Cmpd No. | Structure | Chemical name |
|---|---|---|
| I-335 | 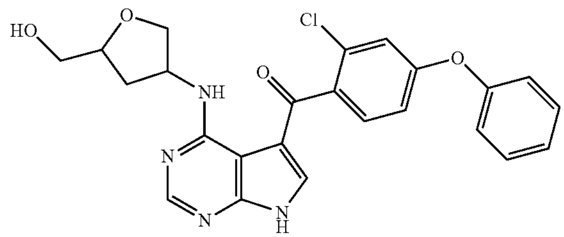 | (2-chloro-4-phenoxyphenyl)(4-((5-(hydroxymethyl)tetrahydrofuran-3-yl)amino)-7H-pyrrolo[2,3-d]pyrimidin-5-yl)methanone |
| I-336 | 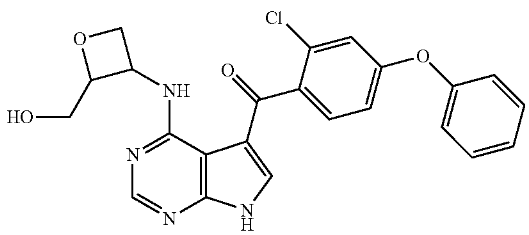 [SMILES: O=C(c1ccc(Oc2ccccc2)cc1Cl)c1c[nH]c2ncnc(NC3COC3CO)c12] | (2-chloro-4-phenoxyphenyl)(4-((2-(hydroxymethyl)oxetan-3-yl)amino)-7H-pyrrolo[2,3-d]pyrimidin-5-yl)methanone |
| I-337 | 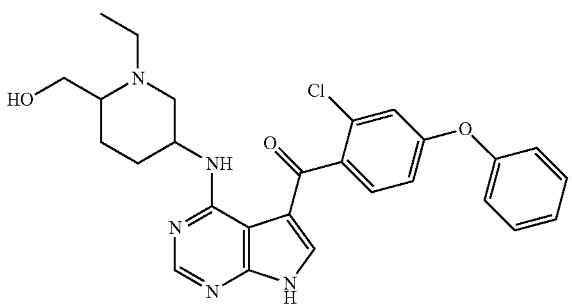 [SMILES: CCN1CC(Nc2ncnc3[nH]cc(C(=O)c4ccc(Oc5ccccc5)cc4Cl)c23)CCC1CO] | (2-chloro-4-phenoxyphenyl)(4-((1-ethyl-6-(hydroxymethyl)piperidin-3-yl)amino)-7H-pyrrolo[2,3-d]pyrimidin-5-yl)methanone |
| I-338 | 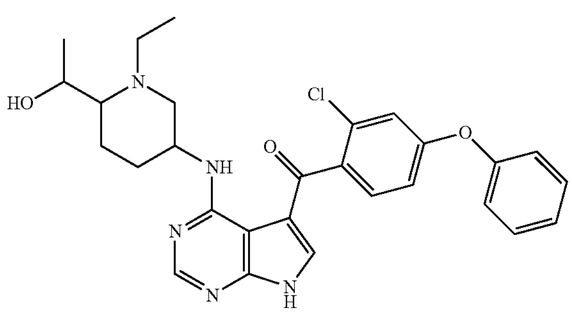 [SMILES: CCN1CC(Nc2ncnc3[nH]cc(C(=O)c4ccc(Oc5ccccc5)cc4Cl)c23)CCC1C(C)O] | (2-chloro-4-phenoxyphenyl)(4((1-ethyl-6-(1-hydroxyethyl)piperidin-3-yl)amino)-7H-pyrrolo[2,3-d]pyrimidin-5-yl)methanone |
| I-339 | 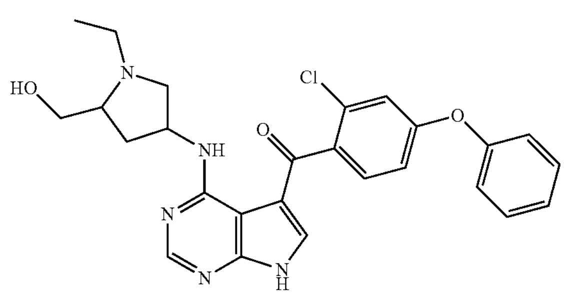 [SMILES: CCN1CC(Nc2ncnc3[nH]cc(C(=O)c4ccc(Oc5ccccc5)cc4Cl)c23)CC1CO] | (2-chloro-4-phenoxyphenyl)(4-((1-ethyl-5-(hydroxymethyl)pyrrolidin-3-yl)amino)-7H-pyrrolo[2,3-d]pyrimidin-5-yl)methanone |

-continued

| Cmpd No. | Structure | Chemical name |
|---|---|---|
| I-340 | 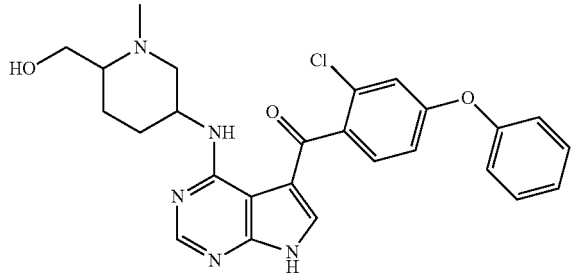 [SMILES: CN1CC(Nc2ncnc3[nH]cc(C(=O)c4ccc(Oc5ccccc5)cc4Cl)c23)CCC1CO] | (2-chloro-4-phenoxyphenyl)(4-((6-(hydroxymethyl)-1-methylpiperidin-3-yl)amino)-7H-pyrrolo[2,3-d]pyrimidin-5-yl)methanone |
| I-341 | 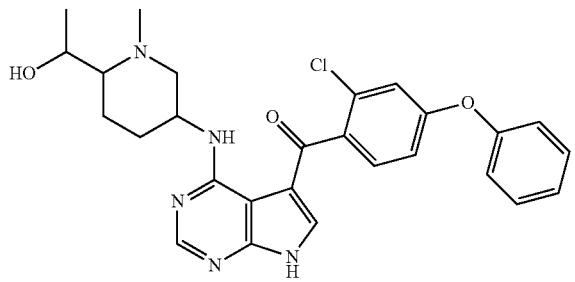 [SMILES: CC(O)C1CCC(Nc2ncnc3[nH]cc(C(=O)c4ccc(Oc5ccccc5)cc4Cl)c23)CN1C] | (2-chloro-4-phenoxyphenyl)(4-((6-(1-hydroxyethyl)-1-methylpiperidin-3-yl)amino)-7H-pyrrolo[2,3-d]pyrimidin-5-yl)methanone |
| I-342 | 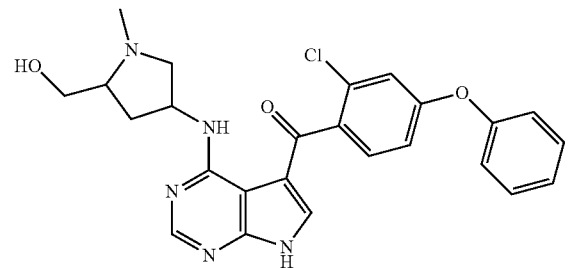 [SMILES: CN1CC(Nc2ncnc3[nH]cc(C(=O)c4ccc(Oc5ccccc5)cc4Cl)c23)CC1CO] | (2-chloro-4-phenoxyphenyl)(4-((5-(hydroxymethyl)-1-methylpyrrolidin-3-yl)amino)-7H-pyrrolo[2,3-d]pyrimidin-5-yl)methanone |
| I-342e | 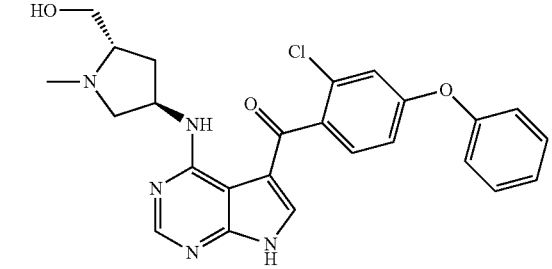 [SMILES: CN1C[C@H](Nc2ncnc3[nH]cc(C(=O)c4ccc(Oc5ccccc5)cc4Cl)c23)C[C@H]1CO] | (2-chloro-4-phenoxyphenyl)(4-(((3R,5S)-5-(hydroxymethyl)-1-methylpyrrolidin-3-yl)amino)-7H-pyrrolo[2,3-d]pyrimidin-5-yl)methanone |
| I-343 | 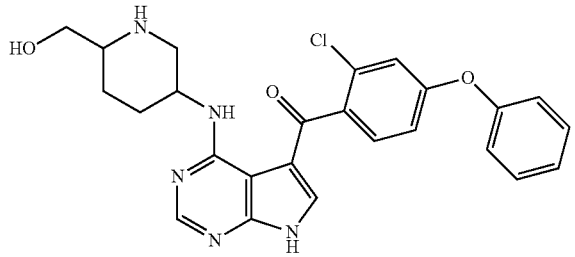 [SMILES: O=C(c1ccc(Oc2ccccc2)cc1Cl)c1c[nH]c2ncnc(NC3CCC(CO)NC3)c12] | (2-chloro-4-phenoxyphenyl)(4-((6-(hydroxymethyl)piperidin-3-yl)amino)-7H-pyrrolo[2,3-d]pyrimidin-5-yl)methanone |

-continued

| Cmpd No. | Structure | Chemical name |
|---|---|---|
| I-343r | 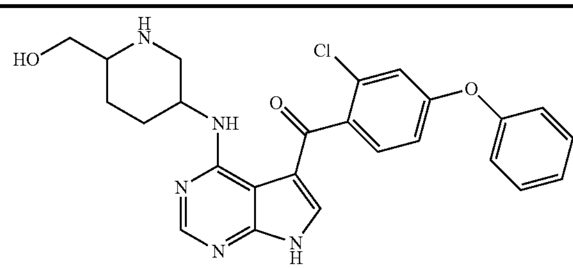 | (racemic)-(2-chloro-4-phenoxyphenyl)(4-((6-(hydroxymethyl)piperidin-3-yl)amino)-7H-pyrrolo[2,3-d]pyrimidin-5-yl)methanone |
| I-344 | 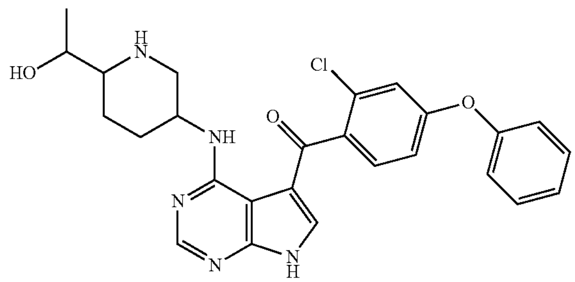 [SMILES: CC(O)C1CCC(Nc2ncnc3[nH]cc(C(=O)c4ccc(Oc5ccccc5)cc4Cl)c23)CN1] | (2-chloro-4-phenoxyphenyl)(4-((6-(1-hydroxyethyl)piperidin-3-yl)amino)-7H-pyrrolo[2,3-d]pyrimidin-5-yl)methanone |
| I-345 | 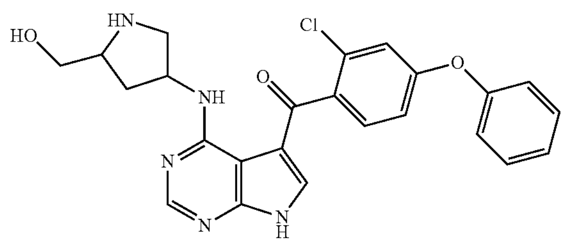 [SMILES: O=C(c1ccc(Oc2ccccc2)cc1Cl)c1c[nH]c2ncnc(NC3CNC(CO)C3)c12] | (2-chloro-4-phenoxyphenyl)(4-((5-(hydroxymethyl)pyrrolidin-3-yl)amino)-7H-pyrrolo[2,3-d]pyrimidin-5-yl)methanone |
| I-345e | 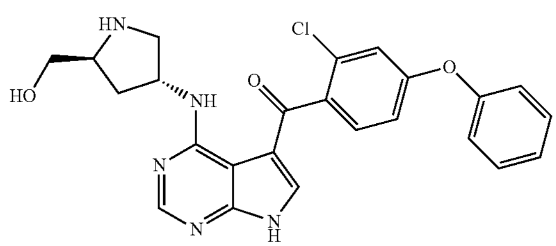 [SMILES: O=C(c1ccc(Oc2ccccc2)cc1Cl)c1c[nH]c2ncnc(N[C@H]3CN[C@H](CO)C3)c12] | (2-chloro-4-phenoxyphenyl)(4-(((3R,5S)-5-(hydroxymethyl)pyrrolidin-3-yl)amino)-7H-pyrrolo[2,3-d]pyrimidin-5-yl)methanone |
| I-346 | 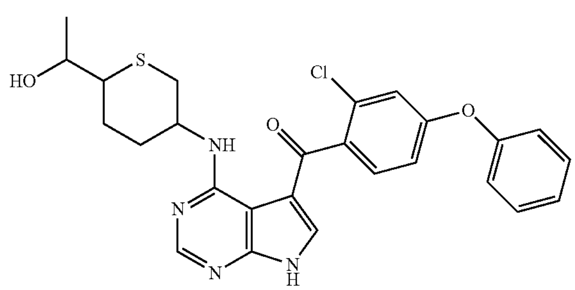 | (2-chloro-4-phenoxyphenyl)(4-((6-(1-hydroxyethyl)tetrahydro-2H-thiopyran-3-yl)amino)-7H-pyrrolo[2,3-d]pyrimidin-5-yl)methanone |
| I-347 | 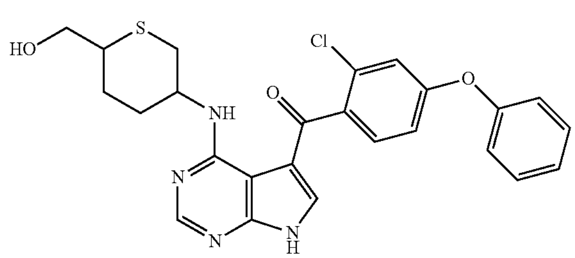 [SMILES: O=C(c1ccc(Oc2ccccc2)cc1Cl)c1c[nH]c2ncnc(NC3CCC(CO)SC3)c12] | (2-chloro-4-phenoxyphenyl)(4-((6-(hydroxymethyl)tetrahydro-2H-thiopyran-3-yl)amino)-7H-pyrrolo[2,3-d]pyrimidin-5-yl)methanone |

| Cmpd No. | Structure | Chemical name |
|---|---|---|
| I-348 | 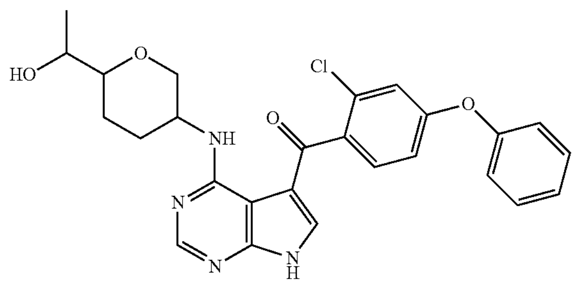 [SMILES: CC(O)C1CCC(Nc2ncnc3[nH]cc(C(=O)c4ccc(Oc5ccccc5)cc4Cl)c23)CO1] | (2-chloro-4-phenoxyphenyl)(4-((6-(1-hydroxyethyl)tetrahydro-2H-pyran-3-yl)amino)-7H-pyrrolo[2,3-d]pyrimidin-5-yl)methanone |
| I-349 | 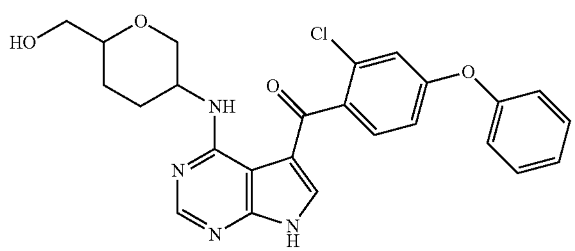 | (2-chloro-4-phenoxyphenyl)(4-((6-(hydroxymethyl)tetrahydro-2H-pyran-3-yl)amino)-7H-pyrrolo[2,3-d]pyrimidin-5-yl)methanone |
| I-350 | 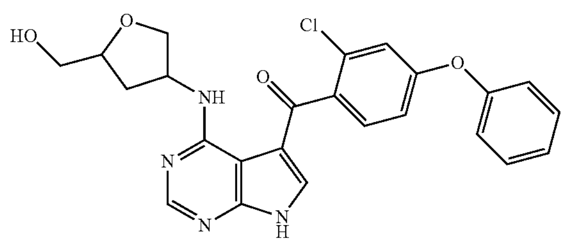 | (2-chloro-4-phenoxyphenyl)(4-((5-(hydroxymethyl)tetrahydrofuran-3-yl)amino)-7H-pyrrolo[2,3-d]pyrimidin-5-yl)methanone |
| I-351 | 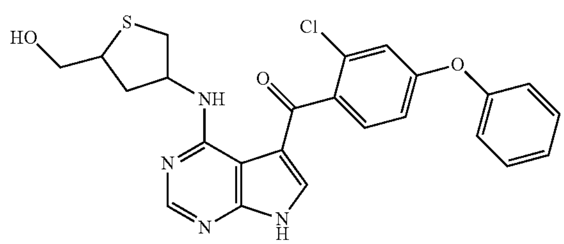 [SMILES: O=C(c1ccc(Oc2ccccc2)cc1Cl)c1c[nH]c2ncnc(NC3COC(CO)C3)c12] | (2-chloro-4-phenoxyphenyl)(4-((5-(hydroxymethyl)tetrahydrothiophen-3-yl)amino)-7H-pyrrolo[2,3-d]pyrimidin-5-yl)methanone |
| I-352 | 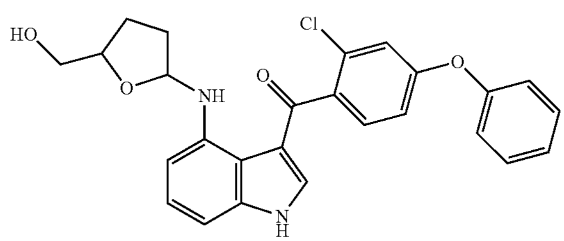 [SMILES: O=C(c1ccc(Oc2ccccc2)cc1Cl)c1c[nH]c2cccc(NC3CCC(CO)O3)c12] | (2-chloro-4-phenoxyphenyl)(4-((5-(hydroxymethyl)tetrahydrofuran-2-yl)amino)-7H-pyrrolo[2,3-d]pyrimidin-5-yl)methanone |
| I-353 | 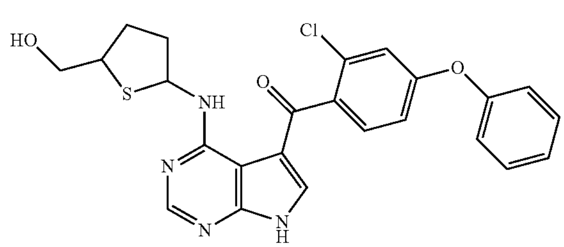 [SMILES: O=C(c1ccc(Oc2ccccc2)cc1Cl)c1c[nH]c2ncnc(NC3CCC(CO)S3)c12] | (2-chloro-4-phenoxyphenyl)(4-((5-(hydroxymethyl)tetrahydrothiophen-2-yl)amino)-7H-pyrrolo[2,3-d]pyrimidin-5-yl)methanone |

-continued

| Cmpd No. | Structure | Chemical name |
|---|---|---|
| I-354 | 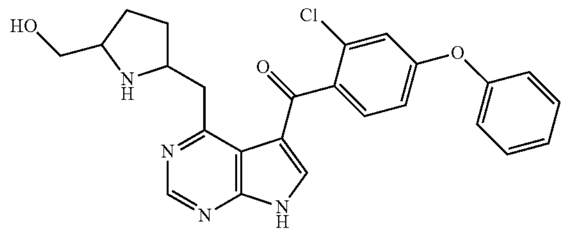 [SMILES: O=C(c1ccc(Oc2ccccc2)cc1Cl)c1c[nH]c2ncnc(CC3CCC(CO)N3)c12] | (2-chloro-4-phenoxyphenyl)(4-((5-(hydroxymethyl)pyrrolidin-2-yl)amino)-7H-pyrrolo[2,3-d]pyrimidin-5-yl)methanone |
| I-355 | 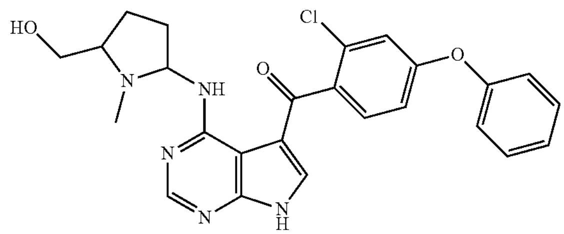 [SMILES: CN1C(CO)CCC1Nc1ncnc2[nH]cc(C(=O)c3ccc(Oc4ccccc4)cc3Cl)c12] | (2-chloro-4-phenoxyphenyl)(4-((5-(hydroxymethyl)-1-methylpyrrolidin-2-yl)amino)-7H-pyrrolo[2,3-d]pyrimidin-5-yl)methanone |
| I-356 | 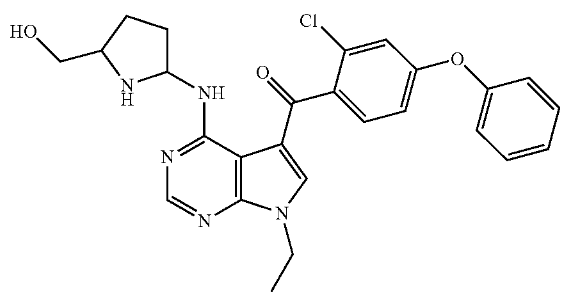 [SMILES: CCn1cc(C(=O)c2ccc(Oc3ccccc3)cc2Cl)c2c(NC3CCC(CO)N3)ncnc21] | (2-chloro-4-phenoxyphenyl)(7-ethyl-4-((5-(hydroxymethyl)pyrrolidin-2-yl)amino)-7H-pyrrolo[2,3-d]pyrimidin-5-yl)methanone |
| I-357 | 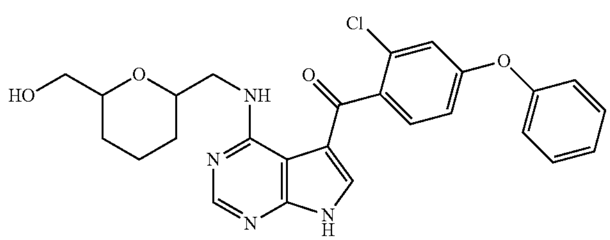 [SMILES: O=C(c1ccc(Oc2ccccc2)cc1Cl)c1c[nH]c2ncnc(NCC3CCCC(CO)S3)c12] | (2-chloro-4-phenoxyphenyl)(4-(((6-(hydroxymethyl)tetrahydro-2H-pyran-2-yl)methyl)amino)-7H-pyrrolo[2,3-d]pyrimidin-5-yl)methanone |
| I-358 | 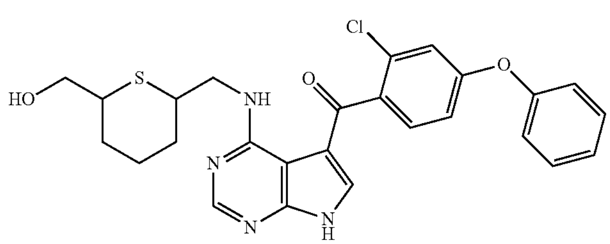 | (2-chloro-4-phenoxyphenyl)(4-(((6-(hydroxymethyl)tetrahydro-2H-thiopyran-2-yl)methyl)amino)-7H-pyrrolo[2,3-d]pyrimidin-5-yl)methanone |
| I-359 | 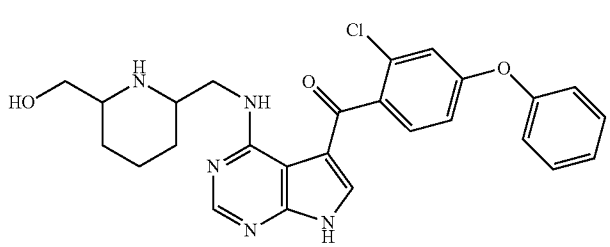 [SMILES: O=C(c1ccc(Oc2ccccc2)cc1Cl)c1c[nH]c2ncnc(NCC3CCCC(CO)N3)c12] | (2-chloro-4-phenoxyphenyl)(4-(((6-(hydroxymethyl)piperidin-2-yl)methyl)amino)-7H-pyrrolo[2,3-d]pyrimidin-5-yl)methanone |

| Cmpd No. | Structure | Chemical name |
| --- | --- | --- |
| I-359e | 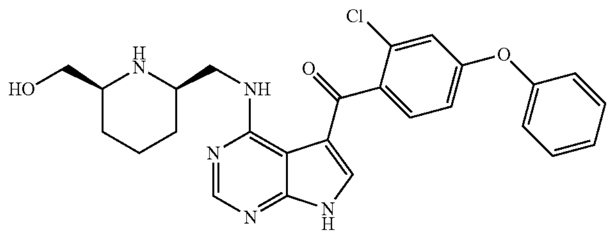 [SMILES: O=C(c1ccc(Oc2ccccc2)cc1Cl)c1c[nH]c2ncnc(NC[C@H]3CCC[C@@H](CO)N3)c12] | racemic-cis-(2-chloro-4-phenoxyphenyl)(4-(((6-(hydroxymethyl)piperidin-2-yl)methyl)amino)-7H-pyrrolo[2,3-d]pyrimidin-5-yl)methanone |
| I-360 | 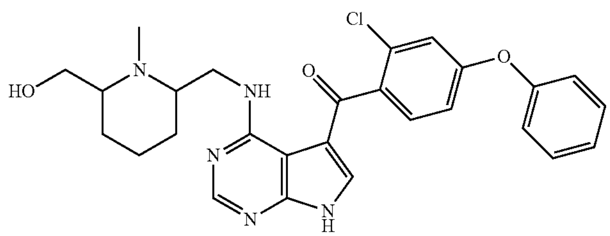 | (2-chloro-4-phenoxyphenyl)(4-(((6-(hydroxymethyl)-1-methylpiperidin-2-yl)methyl)amino)-7H-pyrrolo[2,3-d]pyrimidin-5-yl)methanone |
| I-360e | 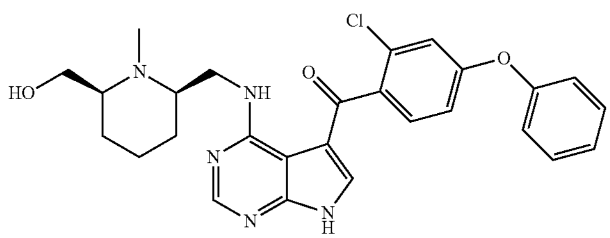 [SMILES: CN1[C@H](CO)CCC[C@@H]1CNc1ncnc2[nH]cc(C(=O)c3ccc(Oc4ccccc4)cc3Cl)c12] | racemic-cis-(2-chloro-4-phenoxyphenyl)(4-(((6-(hydroxymethyl)-1-methylpiperidin-2-yl)methyl)amino)-7H-pyrrolo[2,3-d]pyrimidin-5-yl)methanone |
| I-361 | 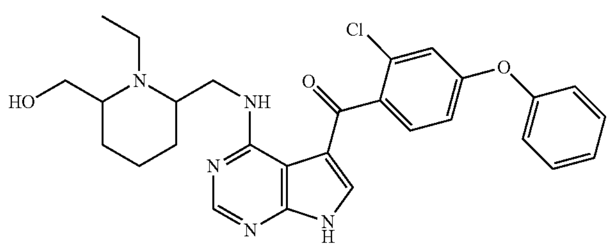 [SMILES: CCN1C(CO)CCCC1CNc1ncnc2[nH]cc(C(=O)c3ccc(Oc4ccccc4)cc3Cl)c12] | (2-chloro-4-phenoxyphenyl)(4-(((1-ethyl-6-(hydroxymethyl)piperidin-2-yl)methyl)amino)-7H-pyrrolo[2,3-d]pyrimidin-5-yl)methanone |
| I-362 | 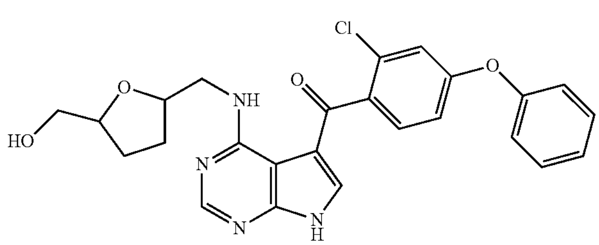 | (2-chloro-4-phenoxyphenyl)(4-(((5-(hydroxymethyl)tetrahydrofuran-2-yl)methyl)amino)-7H-pyrrolo[2,3-d]pyrimidin-5-yl)methanone |
| I-362e | 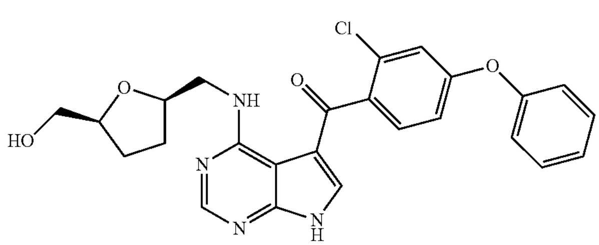 [SMILES: O=C(c1ccc(Oc2ccccc2)cc1Cl)c1c[nH]c2ncnc(NC[C@H]3CC[C@@H](CO)O3)c12] | (2-chloro-4-phenoxyphenyl)(4-((((2R,5S)-5-(hydroxymethyl)tetrahydrofuran-2-yl)methyl)amino)-7H-pyrrolo[2,3-d]pyrimidin-5-yl)methanone |

-continued

| Cmpd No. | Structure | Chemical name |
|---|---|---|
| I-363 | 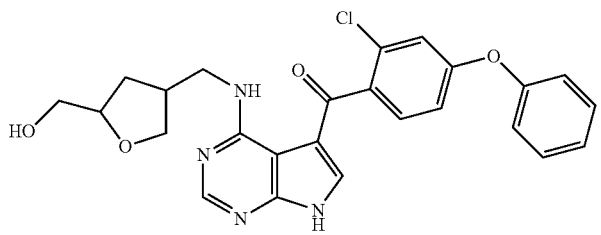 | (2-chloro-4-phenoxyphenyl)(4-(((5-(hydroxymethyl)tetrahydrofuran-3-yl)methyl)amino)-7H-pyrrolo[2,3-d]pyrimidin-5-yl)methanone |
| I-364 | 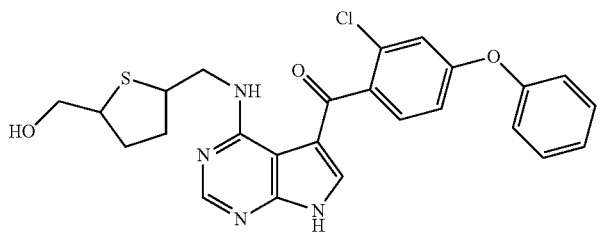 [SMILES: O=C(c1ccc(Oc2ccccc2)cc1Cl)c1c[nH]c2ncnc(NCC3CCC(CO)S3)c12] | (2-chloro-4-phenoxyphenyl)(4-(((5-(hydroxymethyl)tetrahydrothiophen-2-yl)methyl)amino)-7H-pyrrolo[2,3-d]pyrimidin-5-yl)methanone |
| I-365 | 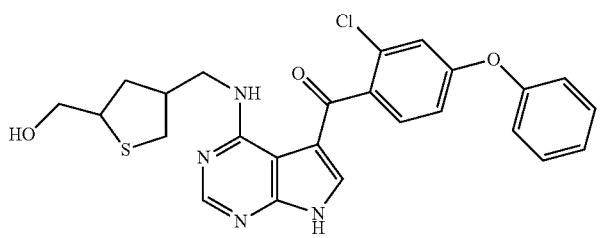 [SMILES: O=C(c1ccc(Oc2ccccc2)cc1Cl)c1c[nH]c2ncnc(NCC3CSC(CO)C3)c12] | (2-chloro-4-phenoxyphenyl)(4-(((5-(hydroxymethyl)tetrahydrothiophen-3-yl)methyl)amino)-7H-pyrrolo[2,3-d]pyrimidin-5-yl)methanone |
| I-366 | 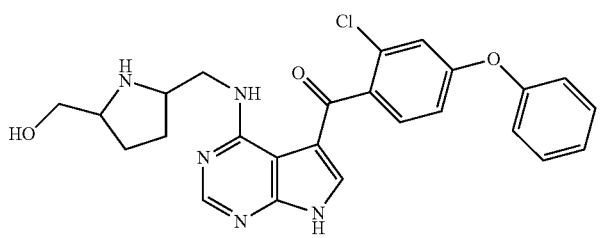 [SMILES: O=C(c1ccc(Oc2ccccc2)cc1Cl)c1c[nH]c2ncnc(NCC3CCC(CO)N3)c12] | (2-chloro-4-phenoxyphenyl)(4-(((5-(hydroxymethyl)pyrrolidin-2-yl)methyl)amino)-7H-pyrrolo[2,3-d]pyrimidin-5-yl)methanone |
| I-367 | 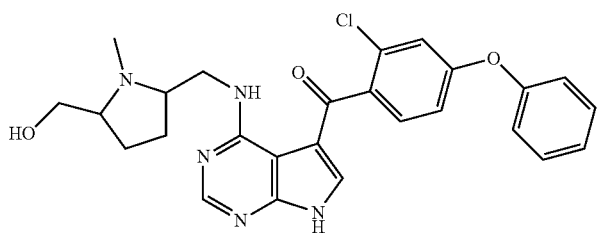 [SMILES: CN1C(CO)CCC1CNc1ncnc2[nH]cc(C(=O)c3ccc(Oc4ccccc4)cc3Cl)c12] | (2-chloro-4-phenoxyphenyl)(4-(((5-(hydroxymethyl)-1-methylpyrrolidin-2-yl)methyl)amino)-7H-pyrrolo[2,3-d]pyrimidin-5-yl)methanone |
| I-368 | 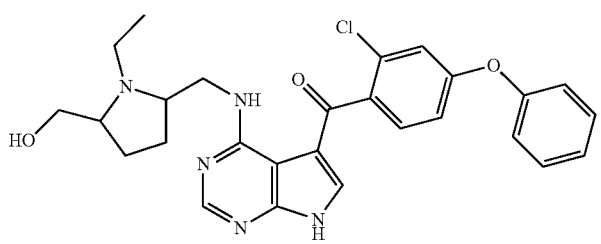 [SMILES: CCN1C(CO)CCC1CNc1ncnc2[nH]cc(C(=O)c3ccc(Oc4ccccc4)cc3Cl)c12] | (2-chloro-4-phenoxyphenyl)(4-(((1-ethyl-5-(hydroxymethyl)pyrrolidin-2-yl)methyl)amino)-7H-pyrrolo[2,3-d]pyrimidin-5-yl)methanone |

-continued

| Cmpd No. | Structure | Chemical name |
|---|---|---|
| I-369 | 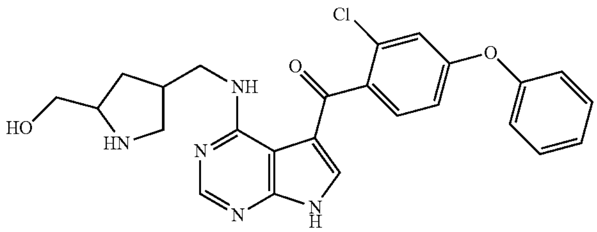 [SMILES: O=C(c1ccc(Oc2ccccc2)cc1Cl)c1c[nH]c2ncnc(NCC3CNC(CO)C3)c12] | (2-chloro-4-phenoxyphenyl)(4-(((5-(hydroxymethyl)pyrrolidin-3-yl)methyl)amino)-7H-pyrrolo[2,3-d]pyrimidin-5-yl)methanone |
| I-369e | 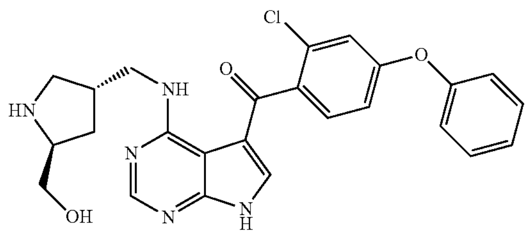 [SMILES: O=C(c1ccc(Oc2ccccc2)cc1Cl)c1c[nH]c2ncnc(NC[C@H]3CN[C@H](CO)C3)c12] | (2-chloro-4-phenoxyphenyl)(4-(((((3R,5S)-5-(hydroxymethyl)pyrrolidin-3-yl)methyl)amino)-7H-pyrrolo[2,3-d]pyrimidin-5-yl)methanone |
| I-370 | 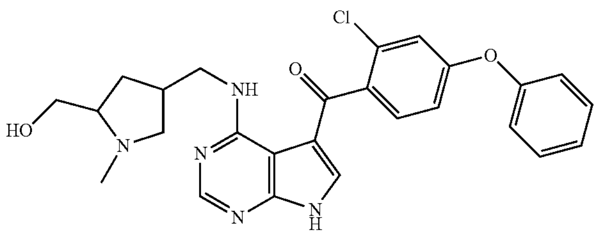 [SMILES: CN1CC(CNc2ncnc3[nH]cc(C(=O)c4ccc(Oc5ccccc5)cc4Cl)c23)CC1CO] | (2-chloro-4-phenoxyphenyl)(4-(((5-(hydroxymethyl)-1-methylpyrrolidin-3-yl)methyl)amino)-7H-pyrrolo[2,3-d]pyrimidin-5-yl)methanone |
| I-370e | 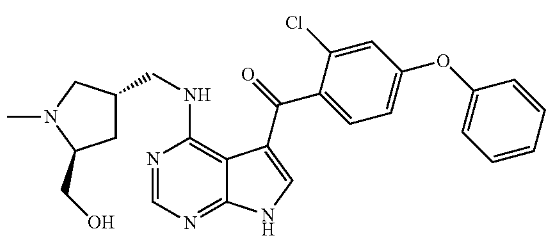 [SMILES: CN1C[C@H](CNc2ncnc3[nH]cc(C(=O)c4ccc(Oc5ccccc5)cc4Cl)c23)C[C@H]1CO] | (2-chloro-4-phenoxyphenyl)(4-(((((3S,5S)-5-(hydroxymethyl)-1-methylpyrrolidin-3-yl)methyl)amino)-7H-pyrrolo[2,3-d]pyrimidin-5-yl)methanone |
| I-371 | 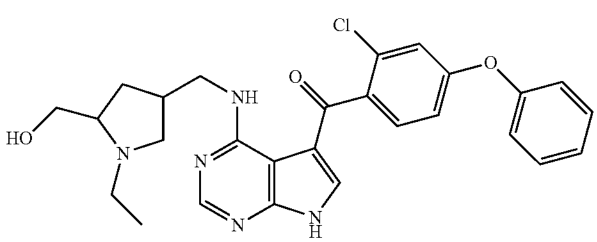 [SMILES: CCN1CC(CNc2ncnc3[nH]cc(C(=O)c4ccc(Oc5ccccc5)cc4Cl)c23)CC1CO] | (2-chloro-4-phenoxyphenyl)(4-(((1-ethyl-5-(hydroxymethyl)pyrrolidin-3-yl)methyl)amino)-7H-pyrrolo[2,3-d]pyrimidin-5-yl)methanone |
| I-372 | 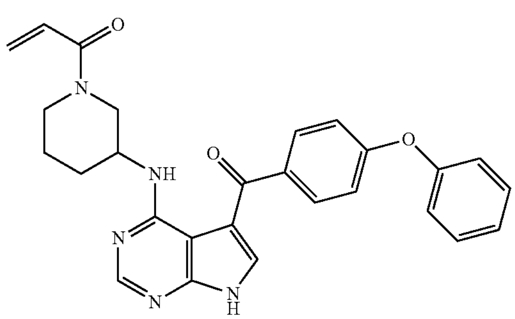 [SMILES: C=CC(=O)N1CCCC(Nc2ncnc3[nH]cc(C(=O)c4ccc(Oc5ccccc5)cc4)c23)C1] | 1-(3-((5-(4-phenoxybenzoyl)-7H-pyrrolo[2,3-d]pyrimidin-4-yl)amino)piperidin-1-yl)prop-2-en-1-one |

| Cmpd No. | Structure | Chemical name |
|---|---|---|
| I-373 | 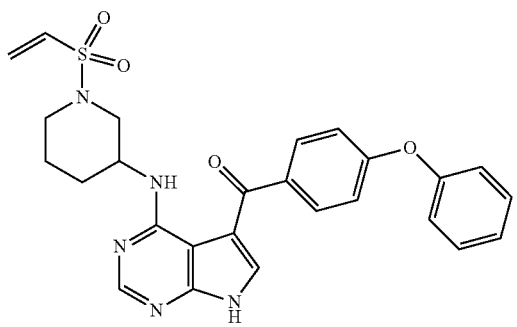 [SMILES: C=CS(=O)(=O)N1CCCC(Nc2ncnc3[nH]cc(C(=O)c4ccc(Oc5ccccc5)cc4)c23)C1] | (4-phenoxyphenyl)(4-((1-(vinylsulfonyl)piperidin-3-yl)amino)-7H-pyrrolo[2,3-d]pyrimidin-5-yl)methanone |
| I-374 | 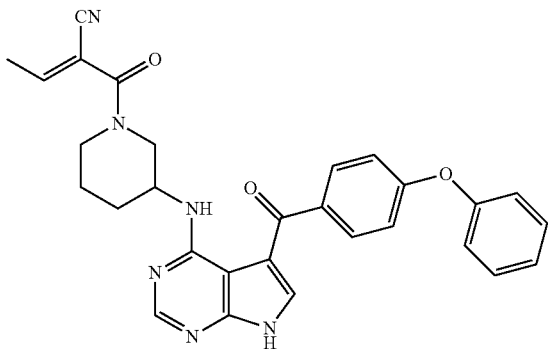 [SMILES: C/C=C(\C#N)C(=O)N1CCCC(Nc2ncnc3[nH]cc(C(=O)c4ccc(Oc5ccccc5)cc4)c23)C1] | (E)-2-(3-((5-(4-phenoxybenzoyl)-7H-pyrrolo[2,3-d]pyrimidin-4-yl)amino)piperidine-1-carbonyl)but-2-enenitrile |
| I-375 | 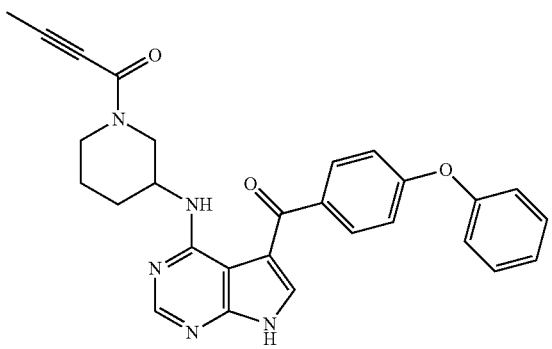 [SMILES: CC#CC(=O)N1CCCC(Nc2ncnc3[nH]cc(C(=O)c4ccc(Oc5ccccc5)cc4)c23)C1] | 1-(3-((5-(4-phenoxybenzoyl)-7H-pyrrolo[2,3-d]pyrimidin-4-yl)amino)piperidin-1-yl)but-2-yn-1-one |
| I-376 | 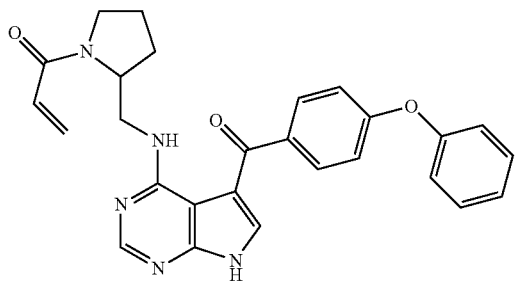 [SMILES: C=CC(=O)N1CCCC1CNc1ncnc2[nH]cc(C(=O)c3ccc(Oc4ccccc4)cc3)c12] | 1-(2-(((5-(4-phenoxybenzoyl)-7H-pyrrolo[2,3-d]pyrimidin-4-yl)amino)methyl)pyrrolidin-1-yl)prop-2-en-1-one |

-continued

| Cmpd No. | Structure | Chemical name |
|---|---|---|
| I-377 | 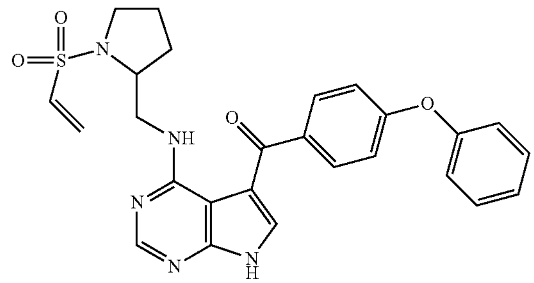 [SMILES: C=CS(=O)(=O)N1CCCC1CNc1ncnc2[nH]cc(C(=O)c3ccc(Oc4ccccc4)cc3)c12] | (4-phenoxyphenyl)(4-(((1-(vinylsulfonyl)pyrrolidin-2-yl)methyl)amino)-7H-pyrrolo[2,3-d]pyrimidin-5-yl)methanone |
| I-378 | 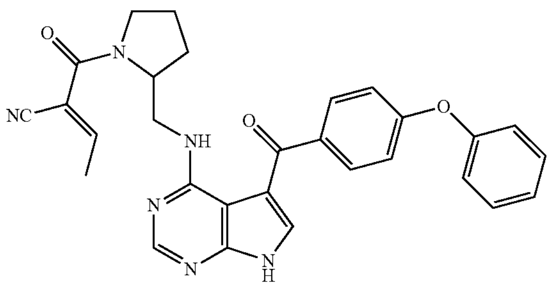 [SMILES: C/C=C(\C#N)C(=O)N1CCCC1CNc1ncnc2[nH]cc(C(=O)c3ccc(Oc4ccccc4)cc3)c12] | (E)-2-(2-(((5-(4-phenoxybenzoyl)-7H-pyrrolo[2,3-d]pyrimidin-4-yl)amino)methyl)pyrrolidine-1-carbonyl)but-2-enenitrile |
| I-379 | 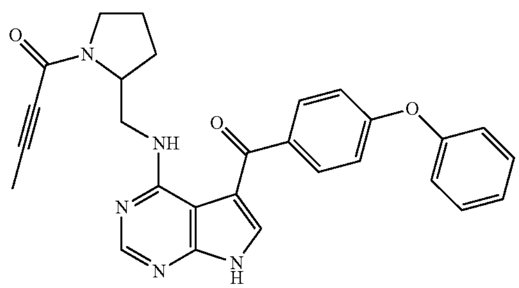 [SMILES: CC#CC(=O)N1CCCC1CNc1ncnc2[nH]cc(C(=O)c3ccc(Oc4ccccc4)cc3)c12] | 1-(2-(((5-(4-phenoxybenzoyl)-7H-pyrrolo[2,3-d]pyrimidin-4-yl)amino)methyl)pyrrolidin-1-yl)but-2-yn-1-one |
| I-380 | 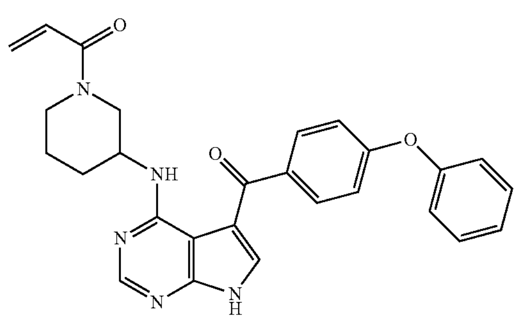 [SMILES: C=CC(=O)N1CCCC(Nc2ncnc3[nH]cc(C(=O)c4ccc(Oc5ccccc5)cc4)c23)C1] | 1-(3-((5-(4-phenoxybenzoyl)-7H-pyrrolo[2,3-d]pyrimidin-4-yl)amino)piperidin-1-yl)prop-2-en-1-one |
| I-381 | 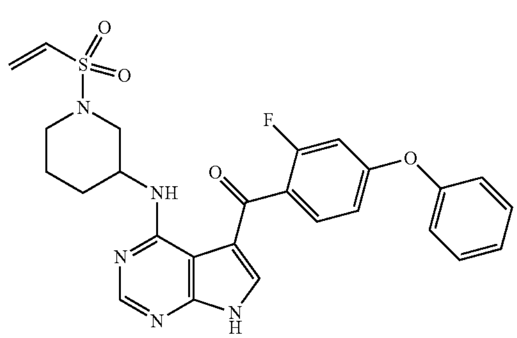 [SMILES: C=CS(=O)(=O)N1CCCC(Nc2ncnc3[nH]cc(C(=O)c4ccc(Oc5ccccc5)cc4F)c23)C1] | (2-fluoro-4-phenoxyphenyl)(4-((1-(vinylsulfonyl)piperidin-3-yl)amino)-7H-pyrrolo[2,3-d]pyrimidin-5-yl)methanone |

-continued

| Cmpd No. | Structure | Chemical name |
|---|---|---|
| I-382 | 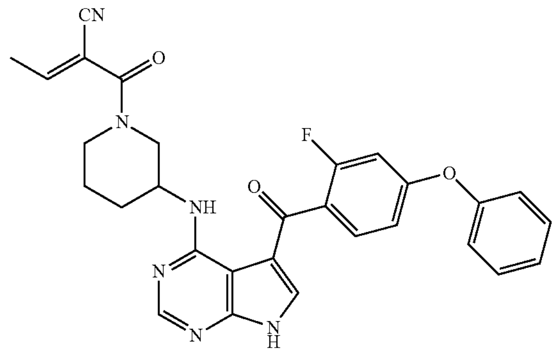 [SMILES: C/C=C(\C#N)C(=O)N1CCCC(Nc2ncnc3[nH]cc(C(=O)c4ccc(Oc5ccccc5)cc4F)c23)C1] | (E)-2-(3-((5-(2-fluoro-4-phenoxybenzoyl)-7H-pyrrolo[2,3-d]pyrimidin-4-yl)amino)piperidine-1-carbonyl)but-2-enenitrile |
| I-383 | 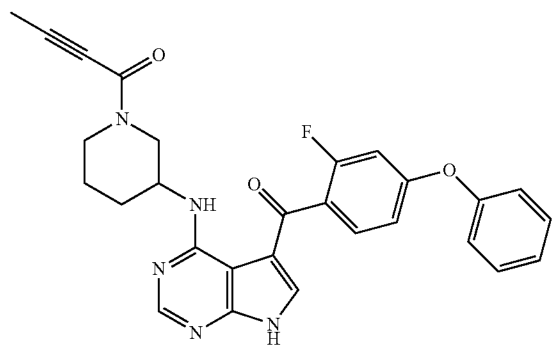 [SMILES: CC#CC(=O)N1CCCC(Nc2ncnc3[nH]cc(C(=O)c4ccc(Oc5ccccc5)cc4F)c23)C1] | 1-(3-((5-(2-fluoro-4-phenoxybenzoyl)-7H-pyrrolo[2,3-d]pyrimidin-4-yl)amino)piperidin-1-yl)but-2-yn-1-one |
| I-384 | 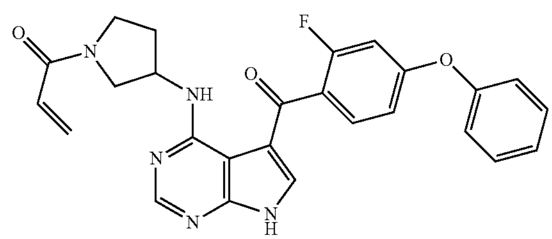 [SMILES: C=CC(=O)N1CCC(Nc2ncnc3[nH]cc(C(=O)c4ccc(Oc5ccccc5)cc4F)c23)C1] | 1-(2-(((5-(2-fluoro-4-phenoxybenzoyl)-7H-pyrrolo[2,3-d]pyrimidin-4-yl)amino)methyl)pyrrolidin-1-yl)prop-2-en-1-one |
| I-385 | 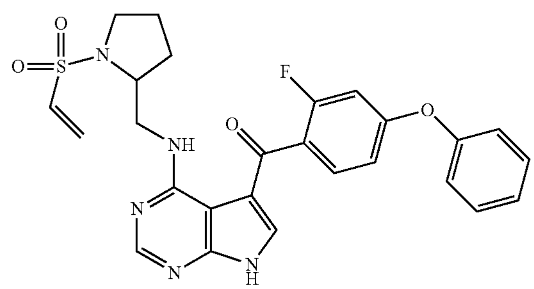 | (2-fluoro-4-phenoxyphenyl)(4-(((1-(vinylsulfonyl)pyrrolidin-2-yl)methyl)amino)-7H-pyrrolo[2,3-d]pyrimidin-5-yl)methanone |
| I-386 | 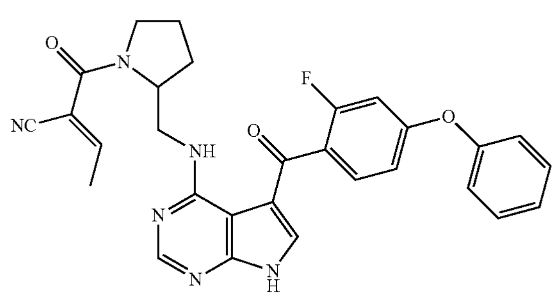 | (E)-2-(2-(((5-(2-fluoro-4-phenoxybenzoyl)-7H-pyrrolo[2,3-d]pyrimidin-4-yl)amino)methyl)pyrrolidine-1-carbonyl)but-2-enenitrile |

-continued

| Cmpd No. | Structure | Chemical name |
|---|---|---|
| I-387 | 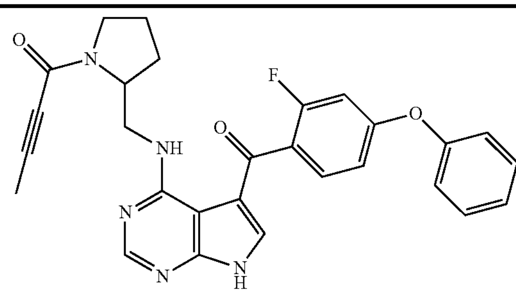 | 1-(2-(((5-(2-fluoro-4-phenoxybenzoyl)-7H-pyrrolo[2,3-d]pyrimidin-4-yl)amino)methyl)pyrrolidin-1-yl)but-2-yn-1-one |
| I-388 | 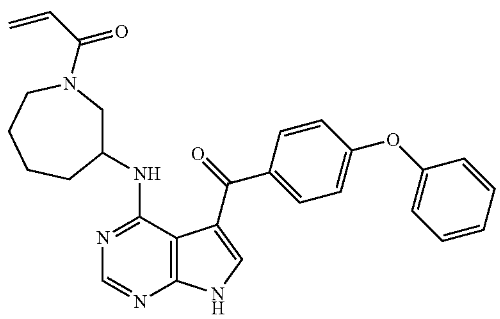 [SMILES: C=CC(=O)N1CCCCC(Nc2ncnc3[nH]cc(C(=O)c4ccc(Oc5ccccc5)cc4)c23)C1] | 1-(3-((5-(4-phenoxybenzoyl)-7H-pyrrolo[2,3-d]pyrimidin-4-yl)amino)azepan-1-yl)prop-2-en-1-one |
| I-389 | 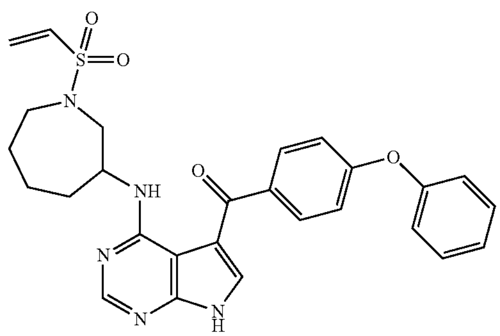 [SMILES: C=CS(=O)(=O)N1CCCCC(Nc2ncnc3[nH]cc(C(=O)c4ccc(Oc5ccccc5)cc4)c23)C1] | (4-phenoxyphenyl)(4-((1-(vinylsulfonyl)azepan-3-yl)amino)-7H-pyrrolo[2,3-d]pyrimidin-5-yl)methanone |
| I-390 | 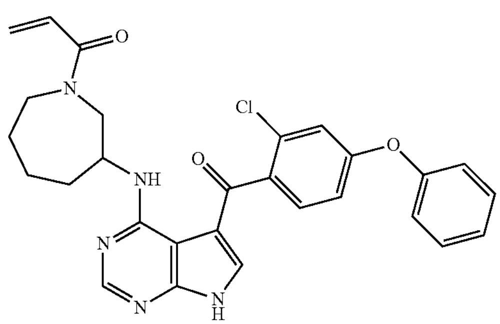 [SMILES: C=CC(=O)N1CCCCC(Nc2ncnc3[nH]cc(C(=O)c4ccc(Oc5ccccc5)cc4Cl)c23)C1] | 1-(3-((5-(2-chloro-4-phenoxybenzoyl)-7H-pyrrolo[2,3-d]pyrimidin-4-yl)amino)azepan-1-yl)prop-2-en-1-one |
| I-391 | 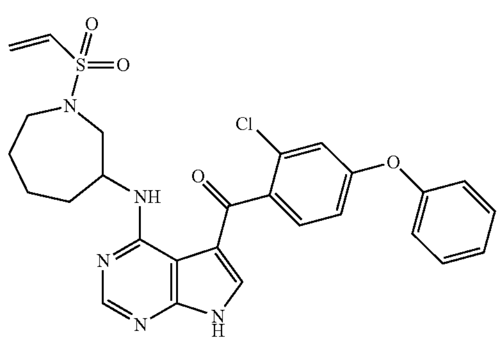 [SMILES: C=CS(=O)(=O)N1CCCCC(Nc2ncnc3[nH]cc(C(=O)c4ccc(Oc5ccccc5)cc4Cl)c23)C1] | (2-chloro-4-phenoxyphenyl)(4-((1-(vinylsulfonyl)azepan-3-yl)amino)-7H-pyrrolo[2,3-d]pyrimidin-5-yl)methanone |

| Cmpd No. | Structure | Chemical name |
|---|---|---|
| I-392 | 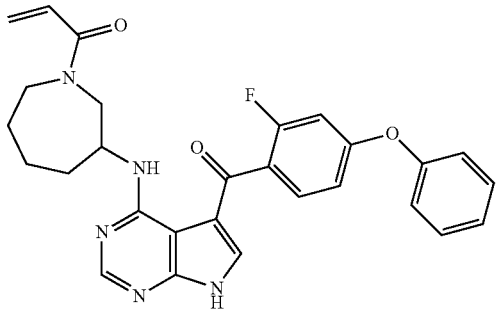 [SMILES: C=CC(=O)N1CCCCC(Nc2ncnc3[nH]cc(C(=O)c4ccc(Oc5ccccc5)cc4F)c23)C1] | 1-(3-((5-(2-fluoro-4-phenoxybenzoyl)-7H-pyrrolo[2,3-d]pyrimidin-4-yl)amino)azepan-1-yl)prop-2-en-1-one |
| I-393 | 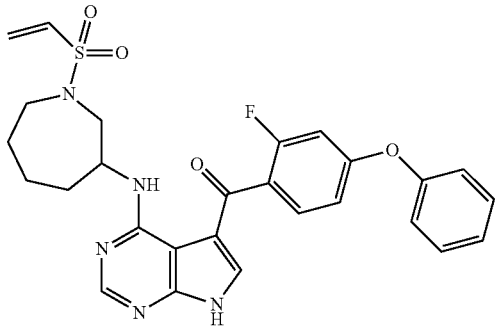 [SMILES: C=CS(=O)(=O)N1CCCCC(Nc2ncnc3[nH]cc(C(=O)c4ccc(Oc5ccccc5)cc4F)c23)C1] | (2-fluoro-4-phenoxyphenyl)(4-((1-(vinylsulfonyl)azepan-3-yl)amino)-7H-pyrrolo[2,3-d]pyrimidin-5-yl)methanone |
| I-394 | 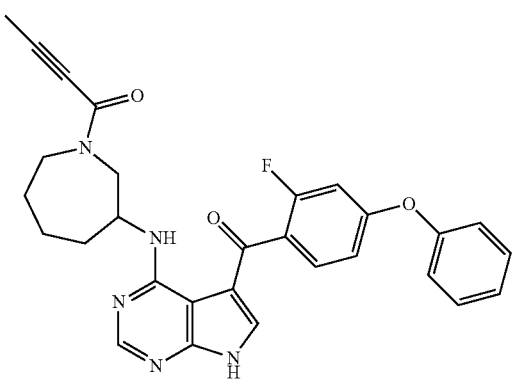 [SMILES: CC#CC(=O)N1CCCCC(Nc2ncnc3[nH]cc(C(=O)c4ccc(Oc5ccccc5)cc4F)c23)C1] | 1-(3-((5-(2-fluoro-4-phenoxybenzoyl)-7H-pyrrolo[2,3-d]pyrimidin-4-yl)amino)azepan-1-yl)but-2-yn-1-one |
| I-395 | 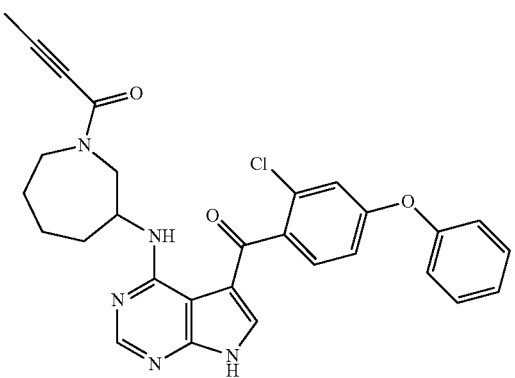 [SMILES: CC#CC(=O)N1CCCCC(Nc2ncnc3[nH]cc(C(=O)c4ccc(Oc5ccccc5)cc4Cl)c23)C1] | 1-(3-((5-(2-chloro-4-phenoxybenzoyl)-7H-pyrrolo[2,3-d]pyrimidin-4-yl)amino)azepan-1-yl)but-2-yn-1-one |

| Cmpd No. | Structure | Chemical name |
| --- | --- | --- |
| I-396 | 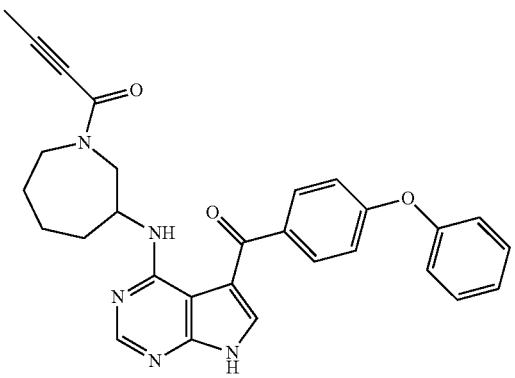 [SMILES: CC#CC(=O)N1CCCCC(Nc2ncnc3[nH]cc(C(=O)c4ccc(Oc5ccccc5)cc4)c23)C1] | 1-(3-((5-(4-phenoxybenzoyl)-7H-pyrrolo[2,3-d]pyrimidin-4-yl)amino)azepan-1-yl)but-2-yn-1-one |
| I-397 | 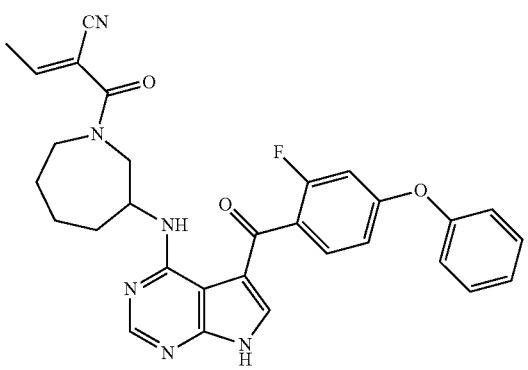 [SMILES: C/C=C(\C#N)C(=O)N1CCCCC(Nc2ncnc3[nH]cc(C(=O)c4ccc(Oc5ccccc5)cc4F)c23)C1] | (E)-2-(3-((5-(2-fluoro-4-phenoxybenzoyl)-7H-pyrrolo[2,3-d]pyrimidin-4-yl)amino)azepane-1-carbonyl)but-2-enenitrile |
| I-398 | 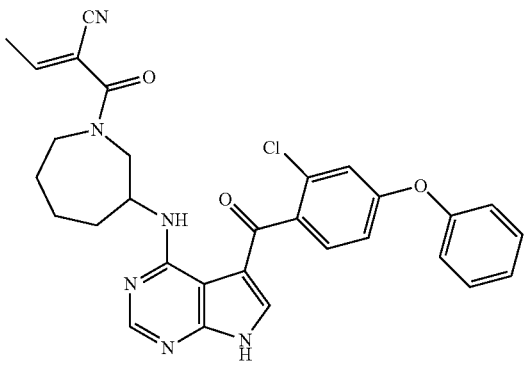 | (E)-2-(3-((5-(2-chloro-4-phenoxybenzoyl)-7H-pyrrolo[2,3-d]pyrimidin-4-yl)amino)azepane-1-carbonyl)but-2-enenitrile |
| I-399 | 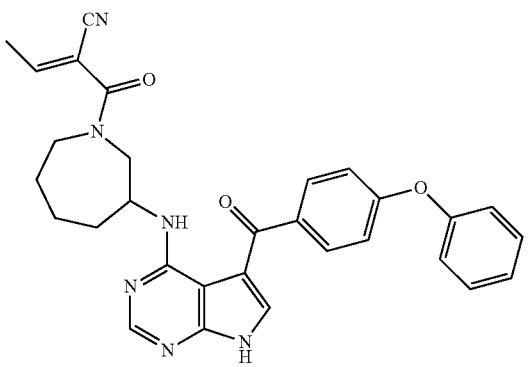 [SMILES: C/C=C(\C#N)C(=O)N1CCCCC(Nc2ncnc3[nH]cc(C(=O)c4ccc(Oc5ccccc5)cc4)c23)C1] | (E)-2-(3-((5-(4-phenoxybenzoyl)-7H-pyrrolo[2,3-d]pyrimidin-4-yl)amino)azepane-1-carbonyl)but-2-enenitrile |

-continued

| Cmpd No. | Structure | Chemical name |
|---|---|---|
| I-400 | 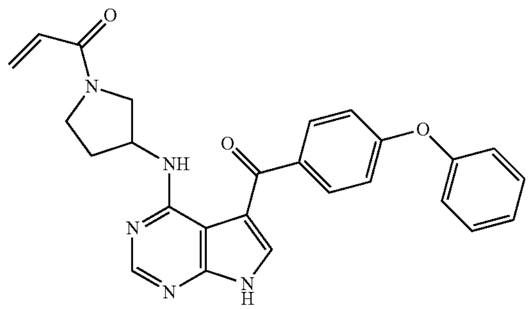 [SMILES: C=CC(=O)N1CCC(Nc2ncnc3[nH]cc(C(=O)c4ccc(Oc5ccccc5)cc4)c23)C1] | 1-(3-((5-(4-phenoxybenzoyl)-7H-pyrrolo[2,3-d]pyrimidin-4-yl)amino)pyrrolidin-1-yl)prop-2-en-1-one |
| I-401 | 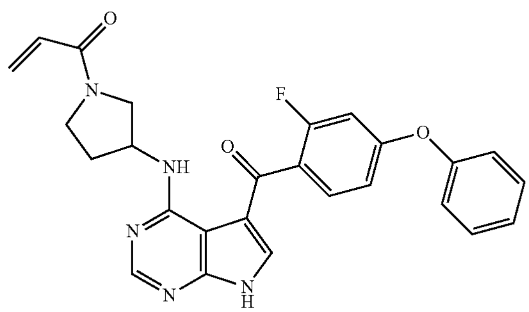 [SMILES: C=CC(=O)N1CCC(Nc2ncnc3[nH]cc(C(=O)c4ccc(Oc5ccccc5)cc4F)c23)C1] | 1-(3-((5-(2-fluoro-4-phenoxybenzoyl)-7H-pyrrolo[2,3-d]pyrimidin-4-yl)amino)pyrrolidin-1-yl)prop-2-en-1-one |
| I-402 | 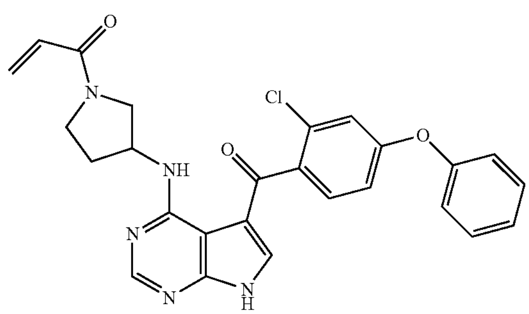 [SMILES: C=CC(=O)N1CCC(Nc2ncnc3[nH]cc(C(=O)c4ccc(Oc5ccccc5)cc4Cl)c23)C1] | 1-(3-((5-(2-chloro-4-phenoxybenzoyl)-7H-pyrrolo[2,3-d]pyrimidin-4-yl)amino)pyrrolidin-1-yl)prop-2-en-1-one |
| I-403 | 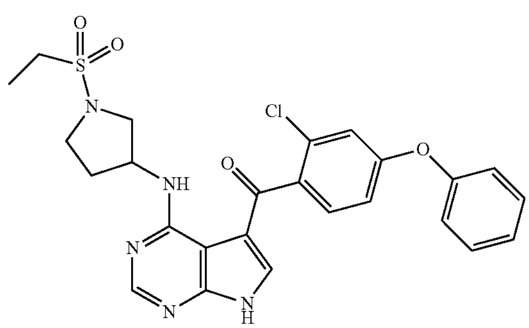 [SMILES: CCS(=O)(=O)N1CCC(Nc2ncnc3[nH]cc(C(=O)c4ccc(Oc5ccccc5)cc4Cl)c23)C1] | (2-chloro-4-phenoxyphenyl)(4-((1-(vinylsulfonyl)pyrrolidin-3-yl)amino)-7H-pyrrolo[2,3-d]pyrimidin-5-yl)methanone |
| I-404 | 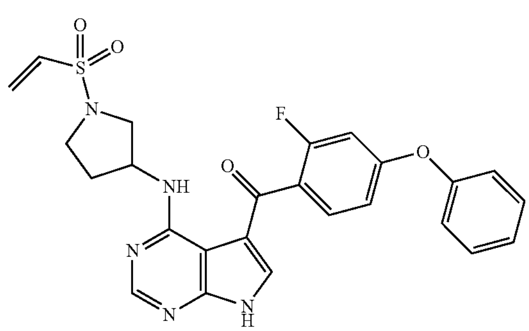 [SMILES: C=CS(=O)(=O)N1CCC(Nc2ncnc3[nH]cc(C(=O)c4ccc(Oc5ccccc5)cc4F)c23)C1] | (2-fluoro-4-phenoxyphenyl)(4-((1-(vinylsulfonyl)pyrrolidin-3-yl)amino)-7H-pyrrolo[2,3-d]pyrimidin-5-yl)methanone |

-continued

| Cmpd No. | Structure | Chemical name |
|---|---|---|
| I-405 | 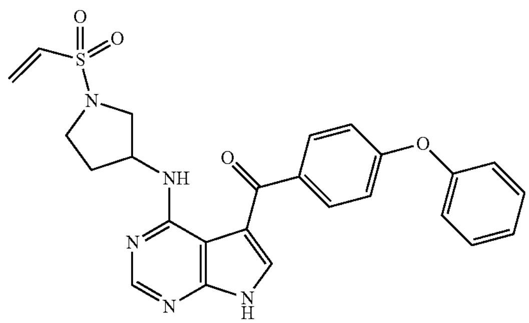 [SMILES: C=CS(=O)(=O)N1CCC(Nc2ncnc3[nH]cc(C(=O)c4ccc(Oc5ccccc5)cc4)c23)C1] | (4-phenoxyphenyl)(4-((1-(vinylsulfonyl)pyrrolidin-3-yl)amino)-7H-pyrrolo[2,3-d]pyrimidin-5-yl)methanone |
| I-406 | 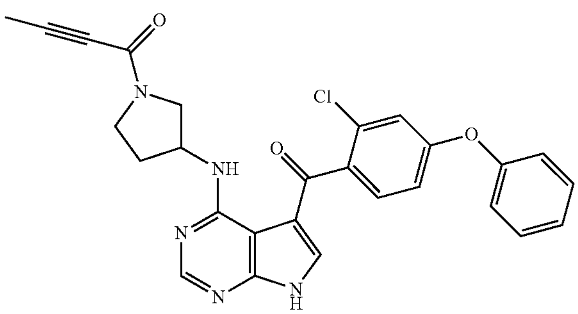 [SMILES: CC#CC(=O)N1CCC(Nc2ncnc3[nH]cc(C(=O)c4ccc(Oc5ccccc5)cc4Cl)c23)C1] | 1-(3-((5-(2-chloro-4-phenoxybenzoyl)-7H-pyrrolo[2,3-d]pyrimidin-4-yl)amino)pyrrolidin-1-yl)but-2-yn-1-one |
| I-407 | 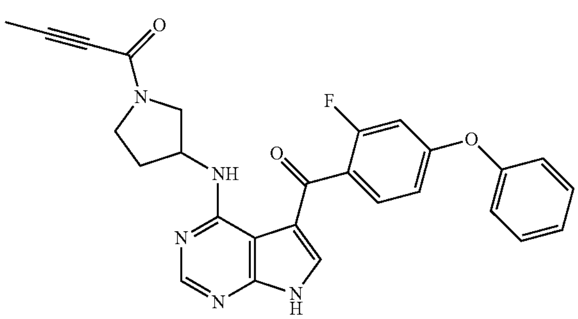 [SMILES: CC#CC(=O)N1CCC(Nc2ncnc3[nH]cc(C(=O)c4ccc(Oc5ccccc5)cc4F)c23)C1] | 1-(3-((5-(2-fluoro-4-phenoxybenzoyl)-7H-pyrrolo[2,3-d]pyrimidin-4-yl)amino)pyrrolidin-1-yl)but-2-yn-1-one |
| I-408 | 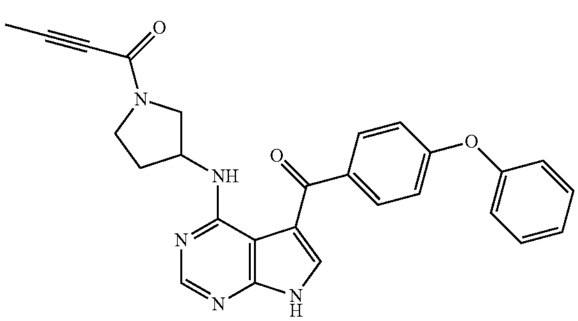 [SMILES: CC#CC(=O)N1CCC(Nc2ncnc3[nH]cc(C(=O)c4ccc(Oc5ccccc5)cc4)c23)C1] | 1-(3-((5-(4-phenoxybenzoyl)-7H-pyrrolo[2,3-d]pyrimidin-4-yl)amino)pyrrolidin-1-yl)but-2-yn-1-one |

| Cmpd No. | Structure | Chemical name |
|---|---|---|
| I-409 | 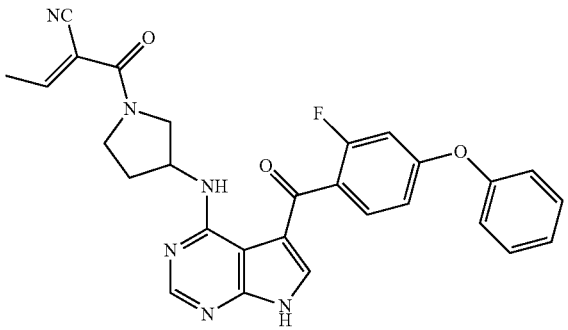 [SMILES: C/C=C(\C#N)C(=O)N1CCC(Nc2ncnc3[nH]cc(C(=O)c4ccc(Oc5ccccc5)cc4F)c23)C1] | (E)-2-(3-((5-(2-fluoro-4-phenoxybenzoyl)-7H-pyrrolo[2,3-d]pyrimidin-4-yl)amino)pyrrolidine-1-carbonyl)but-2-enenitrile |
| I-410 | 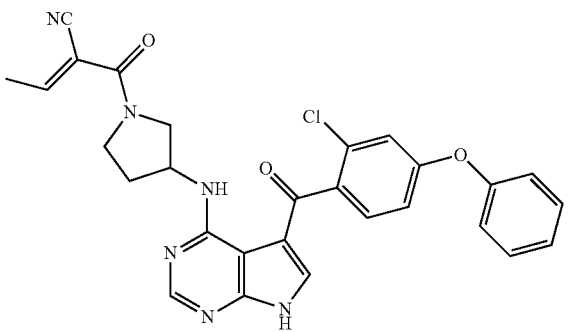 [SMILES: C/C=C(\C#N)C(=O)N1CCC(Nc2ncnc3[nH]cc(C(=O)c4ccc(Oc5ccccc5)cc4Cl)c23)C1] | (E)-2-(3-((5-(2-chloro-4-phenoxybenzoyl)-7H-pyrrolo[2,3-d]pyrimidin-4-yl)amino)pyrrolidine-1-carbonyl)but-2-enenitrile |
| I-411 | 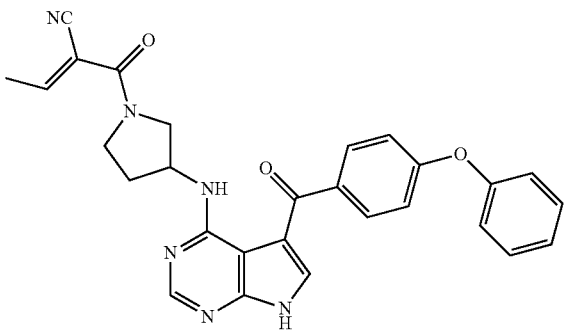 [SMILES: C/C=C(\C#N)C(=O)N1CCC(Nc2ncnc3[nH]cc(C(=O)c4ccc(Oc5ccccc5)cc4)c23)C1] | (E)-2-(34(5-(4-phenoxybenzoyl)-7H-pyrrolo[2,3-d]pyrimidin-4-yl)amino)pyrrolidine-1-carbonyl)but-2-enenitrile |
| I-412 | 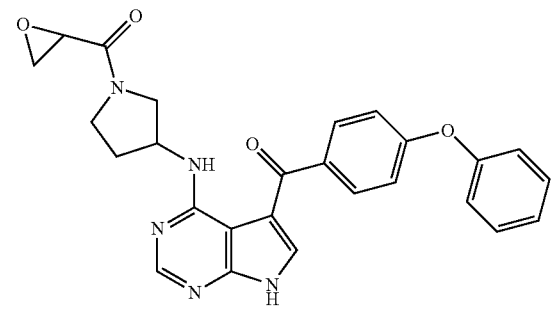 [SMILES: O=C(c1ccc(Oc2ccccc2)cc1)c1c[nH]c2ncnc(NC3CCN(C(=O)C4CO4)C3)c12] | oxiran-2-yl(3-((5-(4-phenoxybenzoyl)-7H-pyrrolo[2,3-d]pyrimidin-4-yl)amino)pyrrolidin-1-yl)methanone |

| Cmpd No. | Structure | Chemical name |
|---|---|---|
| I-413 | 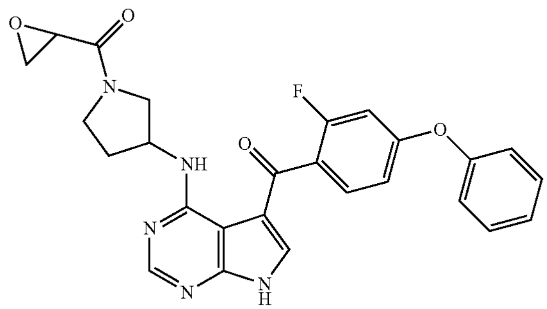 [SMILES: O=C(c1ccc(Oc2ccccc2)cc1F)c1c[nH]c2ncnc(NC3CCN(C(=O)C4CO4)C3)c12] | (3-((5-(2-fluoro-4-phenoxybenzoyl)-7H-pyrrolo[2,3-d]pyrimidin-4-yl)amino)pyrrolidin-1-yl)(oxiran-2-yl)methanone |
| I-414 | 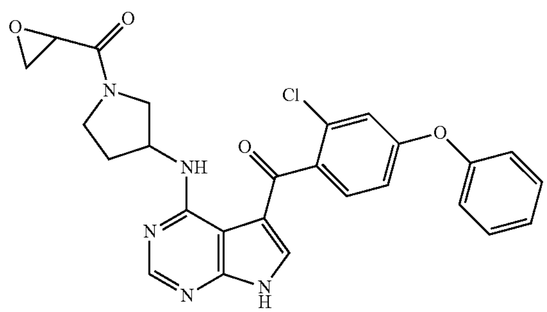 [SMILES: O=C(c1ccc(Oc2ccccc2)cc1Cl)c1c[nH]c2ncnc(NC3CCN(C(=O)C4CO4)C3)c12] | (3-((5-(2-chloro-4-phenoxybenzoyl)-7H-pyrrolo[2,3-d]pyrimidin-4-yl)amino)pyrrolidin-1-yl)(oxiran-2-yl)methanone |
| I-415 | 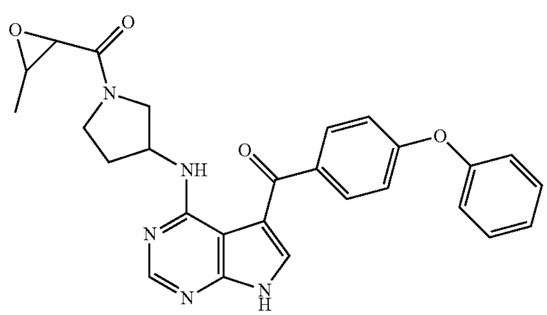 [SMILES: CC1OC1C(=O)N1CCC(Nc2ncnc3[nH]cc(C(=O)c4ccc(Oc5ccccc5)cc4)c23)C1] | (3-methyloxiran-2-yl)(3-((5-(4-phenoxybenzoyl)-7H-pyrrolo[2,3-d]pyrimidin-4-yl)amino)pyrrolidin-1-yl)methanone |
| I-416 | 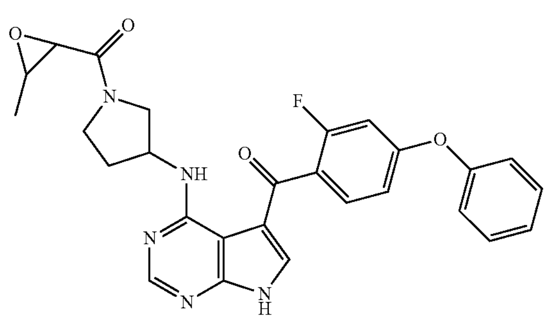 [SMILES: CC1OC1C(=O)N1CCC(Nc2ncnc3[nH]cc(C(=O)c4ccc(Oc5ccccc5)cc4F)c23)C1] | (3-((5-(2-fluoro-4-phenoxybenzoyl)-7H-pyrrolo[2,3-d]pyrimidin-4-yl)amino)pyrrolidin-1-yl)(3-methyloxiran-2-yl)methanone |
| I-417 | 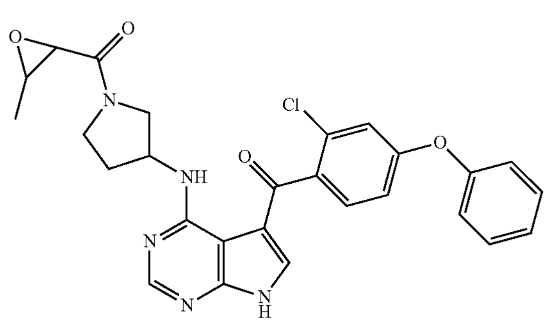 [SMILES: CC1OC1C(=O)N1CCC(Nc2ncnc3[nH]cc(C(=O)c4ccc(Oc5ccccc5)cc4Cl)c23)C1] | (3-((5-(2-chloro-4-phenoxybenzoyl)-7H-pyrrolo[2,3-d]pyrimidin-4-yl)amino)pyrrolidin-1-yl)(3-methyloxiran-2-yl)methanone |

| Cmpd No. | Structure | Chemical name |
|---|---|---|
| I-418 | 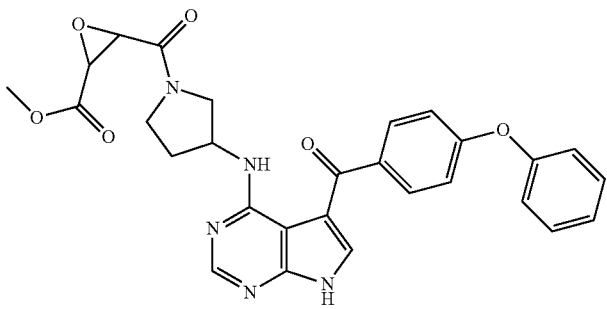 [SMILES: COC(=O)C1OC1C(=O)N1CCC(Nc2ncnc3[nH]cc(C(=O)c4ccc(Oc5ccccc5)cc4)c23)C1] | methyl 3-(3-((5-(4-phenoxybenzoyl)-7H-pyrrolo[2,3-d]pyrimidin-4-yl)amino)pyrrolidine-1-carbonyl)oxirane-2-carboxylate |
| I-419 | 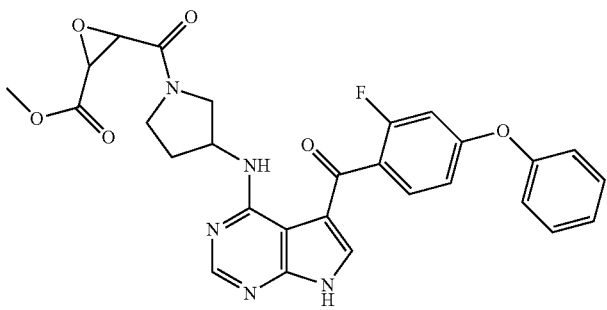 | methyl 3-(3-((5-(2-fluoro-4-phenoxybenzoyl)-7H-pyrrolo[2,3-d]pyrimidin-4-yl)amino)pyrrolidine-1-carbonyl)oxirane-2-carboxylate |
| I-420 | 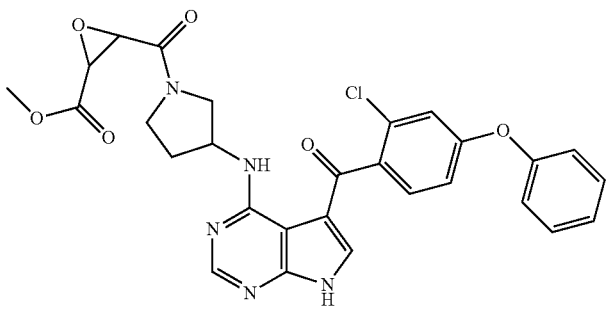 [SMILES: COC(=O)C1OC1C(=O)N1CCC(Nc2ncnc3[nH]cc(C(=O)c4ccc(Oc5ccccc5)cc4F)c23)C1] | methyl 3-(3-((5-(2-chloro-4-phenoxybenzoyl)-7H-pyrrolo[2,3-d]pyrimidin-4-yl)amino)pyrrolidine-1-carbonyl)oxirane-2-carboxylate |
| I-421 | 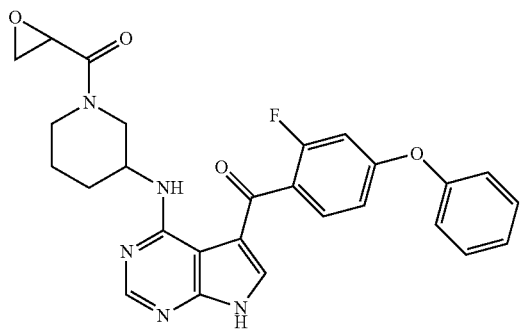 [SMILES: O=C(c1ccc(Oc2ccccc2)cc1F)c1c[nH]c2ncnc(NC3CCCN(C(=O)C4CO4)C3)c12] | (3-((5-(2-fluoro-4-phenoxybenzoyl)-7H-pyrrolo[2,3-d]pyrimidin-4-yl)amino)piperidin-1-yl)(oxiran-2-yl)methanone |

| Cmpd No. | Structure | Chemical name |
|---|---|---|
| I-422 | 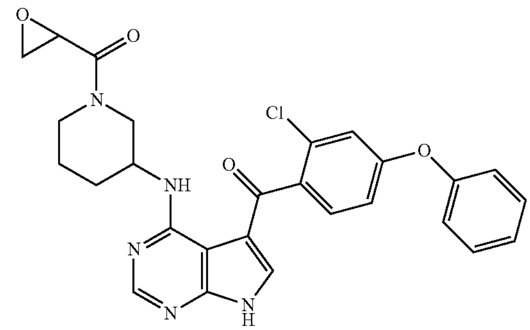 [SMILES: O=C(c1ccc(Oc2ccccc2)cc1Cl)c1c[nH]c2ncnc(NC3CCCN(C(=O)C4CO4)C3)c12] | (3-((5-(2-chloro-4-phenoxybenzoyl)-7H-pyrrolo[2,3-d]pyrimidin-4-yl)amino)piperidin-1-yl)(oxiran-2-yl)methanone |
| I-423 | 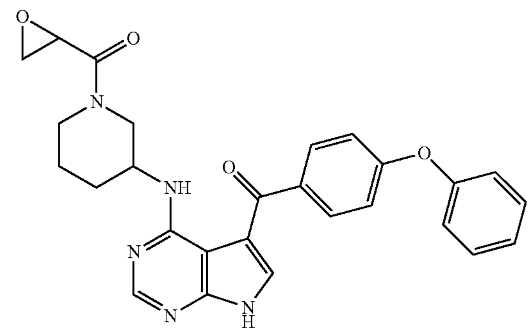 [SMILES: O=C(c1ccc(Oc2ccccc2)cc1)c1c[nH]c2ncnc(NC3CCCN(C(=O)C4CO4)C3)c12] | oxiran-2-yl(3-((5-(4-phenoxybenzoyl)-7H-pyrrolo[2,3-d]pyrimidin-4-yl)amino)piperidin-1-yl)methanone |
| I-424 | 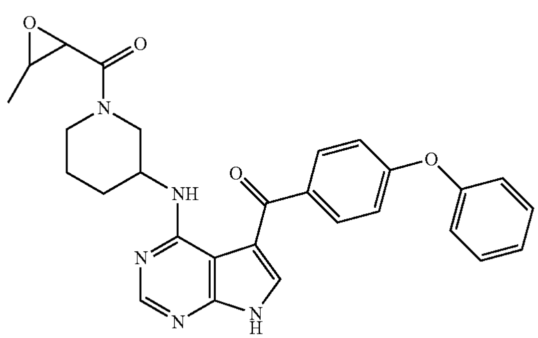 [SMILES: CC1OC1C(=O)N1CCCC(Nc2ncnc3[nH]cc(C(=O)c4ccc(Oc5ccccc5)cc4)c23)C1] | (3-methyloxiran-2-yl)(3-((5-(4-phenoxybenzoyl)-7H-pyrrolo[2,3-d]pyrimidin-4-yl)amino)piperidin-1-yl)methanone |
| I-425 | 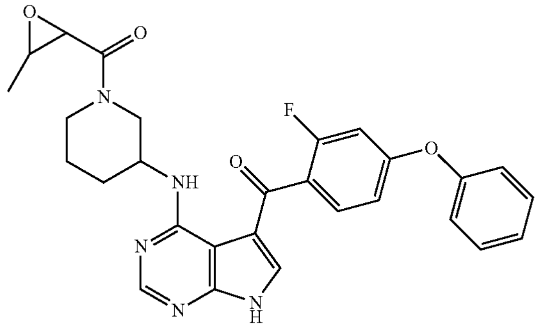 [SMILES: CC1OC1C(=O)N1CCCC(Nc2ncnc3[nH]cc(C(=O)c4ccc(Oc5ccccc5)cc4F)c23)C1] | (3-((5-(2-fluoro-4-phenoxybenzoyl)-7H-pyrrolo[2,3-d]pyrimidin-4-yl)amino)piperidin-1-yl)(3-methyloxiran-2-yl)methanone |

| Cmpd No. | Structure | Chemical name |
| --- | --- | --- |
| I-426 | 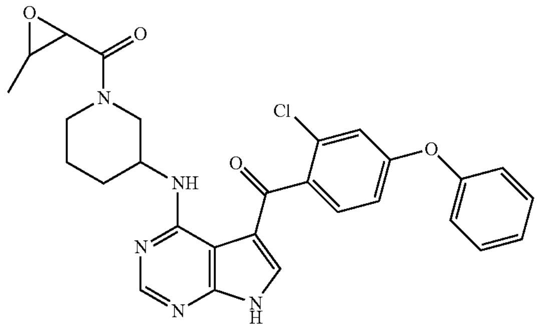 [SMILES: CC1OC1C(=O)N1CCCC(Nc2ncnc3[nH]cc(C(=O)c4ccc(Oc5ccccc5)cc4Cl)c23)C1] | (3-((5-(2-chloro-4-phenoxybenzoyl)-7H-pyrrolo[2,3-d]pyrimidin-4-yl)amino)piperidin-1-yl)(3-methyloxiran-2-yl)methanone |
| I-427 | 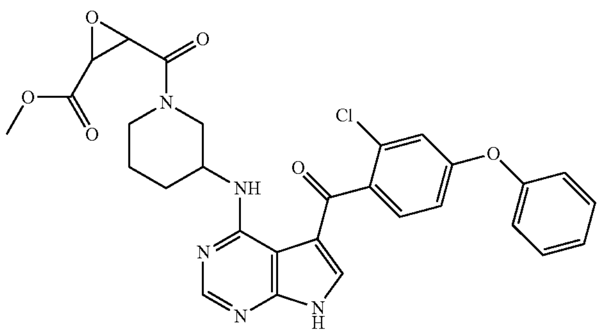 [SMILES: COC(=O)C1OC1C(=O)N1CCCC(Nc2ncnc3[nH]cc(C(=O)c4ccc(Oc5ccccc5)cc4Cl)c23)C1] | methyl 3-(3-((5-(2-chloro-4-phenoxybenzoyl)-7H-pyrrolo[2,3-d]pyrimidin-4-yl)amino)piperidine-1-carbonyl)oxirane-2-carboxylate |
| I-428 | 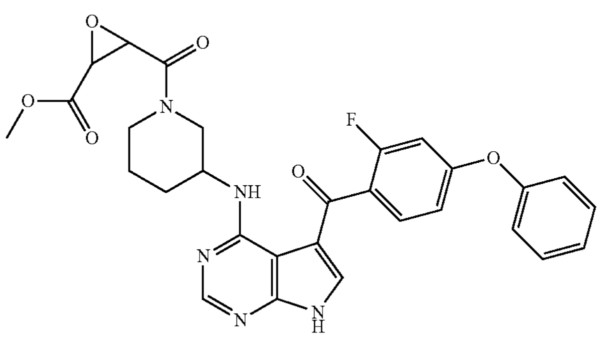 [SMILES: COC(=O)C1OC1C(=O)N1CCCC(Nc2ncnc3[nH]cc(C(=O)c4ccc(Oc5ccccc5)cc4F)c23)C1] | methyl 3-(3-((5-(2-fluoro-4-phenoxybenzoyl)-7H-pyrrolo[2,3-d]pyrimidin-4-yl)amino)piperidine-1-carbonyl)oxirane-2-carboxylate |
| I-429 | 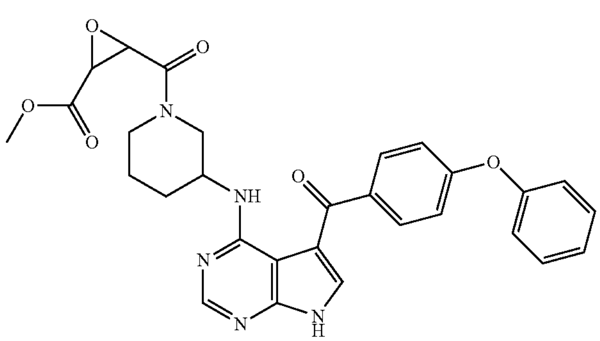 [SMILES: COC(=O)C1OC1C(=O)N1CCCC(Nc2ncnc3[nH]cc(C(=O)c4ccc(Oc5ccccc5)cc4)c23)C1] | methyl 3-(3-((5-(4-phenoxybenzoyl)-7H-pyrrolo[2,3-d]pyrimidin-4-yl)amino)piperidine-1-carbonyl)oxirane-2-carboxylate |

-continued

| Cmpd No. | Structure | Chemical name |
|---|---|---|
| I-430 | 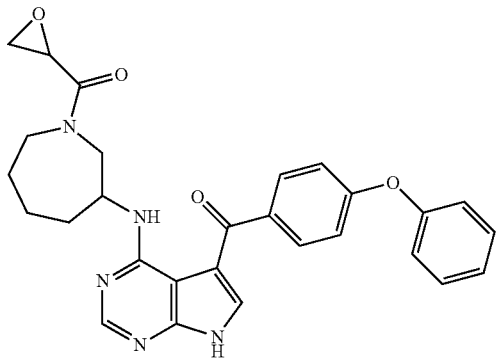 [SMILES: O=C(c1ccc(Oc2ccccc2)cc1)c1c[nH]c2ncnc(NC3CCCCN(C(=O)C4CO4)C3)c12] | oxiran-2-yl(3-((5-(4-phenoxybenzoyl)-7H-pyrrolo[2,3-d]pyrimidin-4-yl)amino)azepan-1-yl)methanone |
| I-431 | 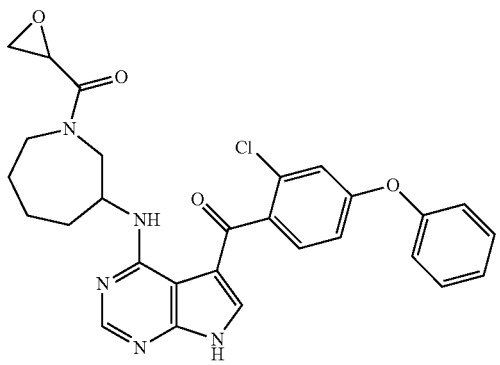 [SMILES: O=C(c1ccc(Oc2ccccc2)cc1Cl)c1c[nH]c2ncnc(NC3CCCCN(C(=O)C4CO4)C3)c12] | (3-((5-(2-chloro-4-phenoxybenzoyl)-7H-pyrrolo[2,3-d]pyrimidin-4-yl)amino)azepan-1-yl)(oxiran-2-yl)methanone |
| I-432 | 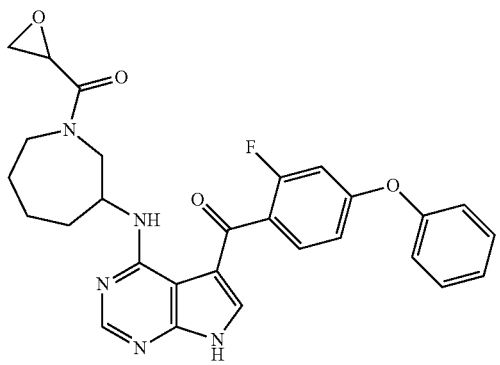 [SMILES: O=C(c1ccc(Oc2ccccc2)cc1F)c1c[nH]c2ncnc(NC3CCCCN(C(=O)C4CO4)C3)c12] | (3-((5-(2-fluoro-4-phenoxybenzoyl)-7H-pyrrolo[2,3-d]pyrimidin-4-yl)amino)azepan-1-yl)(oxiran-2-yl)methanone |
| I-433 | 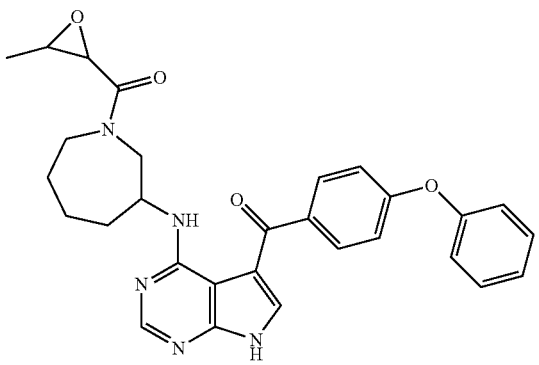 [SMILES: CC1OC1C(=O)N1CCCCC(Nc2ncnc3[nH]cc(C(=O)c4ccc(Oc5ccccc5)cc4)c23)C1] | (3-methyloxiran-2-yl)(3-((5-(4-phenoxybenzoyl)-7H-pyrrolo[2,3-d]pyrimidin-4-yl)amino)azepan-1-yl)methanone |

-continued

| Cmpd No. | Structure | Chemical name |
|---|---|---|
| I-434 | 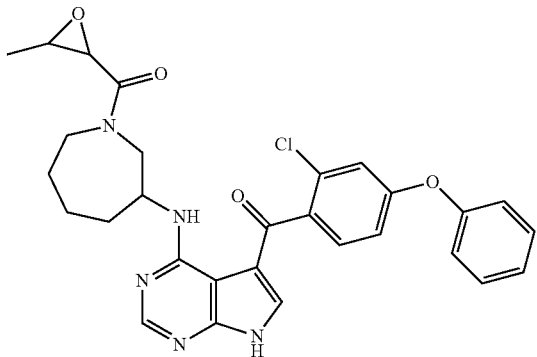 [SMILES: CC1OC1C(=O)N1CCCCC(Nc2ncnc3[nH]cc(C(=O)c4ccc(Oc5ccccc5)cc4F)c23)C1] | (3-((5-(2-chloro-4-phenoxybenzoyl)-7H-pyrrolo[2,3-d]pyrimidin-4-yl)amino)azepan-1-yl)(3-methyloxiran-2-yl)methanone |
| I-435 | 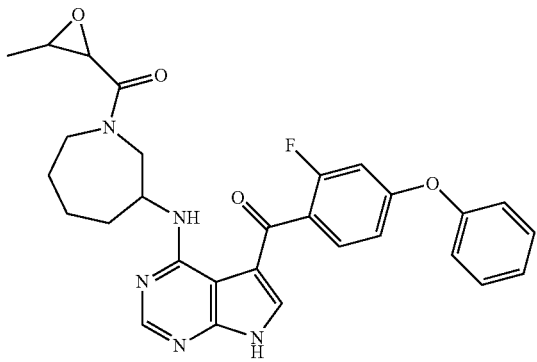 | (3-((5-(2-fluoro-4-phenoxybenzoyl)-7H-pyrrolo[2,3-d]pyrimidin-4-yl)amino)azepan-1-yl)(3-methyloxiran-2-yl)methanone |
| I-436 | 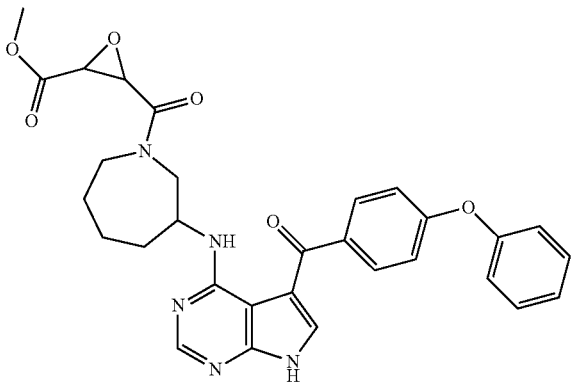 [SMILES: COC(=O)C1OC1C(=O)N1CCCCC(Nc2ncnc3[nH]cc(C(=O)c4ccc(Oc5ccccc5)cc4)c23)C1] | methyl 3-(3-((5-(4-phenoxybenzoyl)-7H-pyrrolo[2,3-d]pyrimidin-4-yl)amino)azepane-1-carbonyl)oxirane-2-carboxylate |
| I-437 | 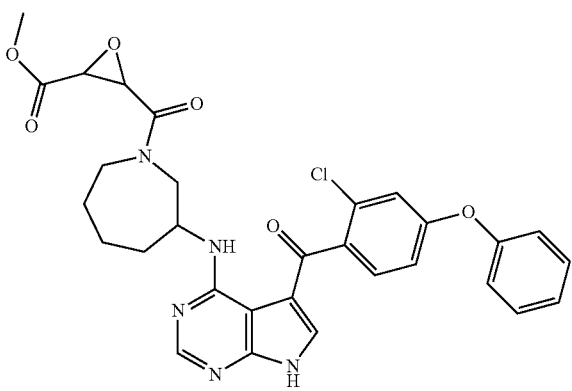 | methyl 3-(3-((5-(2-chloro-4-phenoxybenzoyl)-7H-pyrrolo[2,3-d]pyrimidin-4-yl)amino)azepane-1-carbonyl)oxirane-2-carboxylate |

| Cmpd No. | Structure | Chemical name |
|---|---|---|
| I-438 | 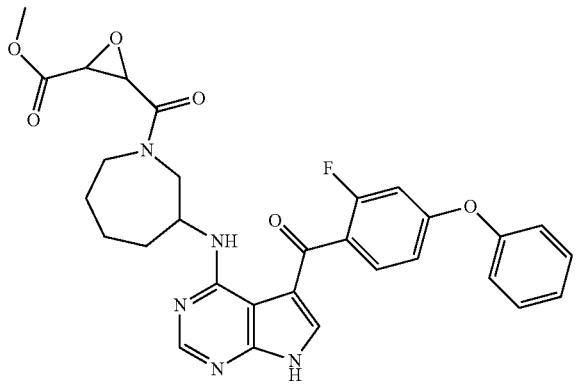 [SMILES: COC(=O)C1OC1C(=O)N1CCCCC(Nc2ncnc3[nH]cc(C(=O)c4ccc(Oc5ccccc5)cc4F)c23)C1] | methyl 3-(3-((5-(2-fluoro-4-phenoxybenzoyl)-7H-pyrrolo[2,3-d]pyrimidin-4-yl)amino)azepane-1-carbonyl)oxirane-2-carboxylate |
| I-439 | 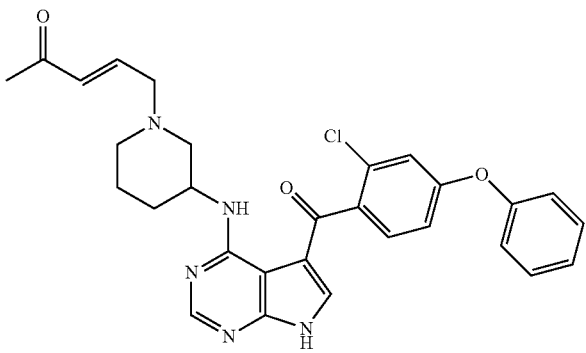 [SMILES: CC(=O)/C=C/CN1CCCC(Nc2ncnc3[nH]cc(C(=O)c4ccc(Oc5ccccc5)cc4Cl)c23)C1] | (E)-5-(3-((5-(2-chloro-4-phenoxybenzoyl)-7H-pyrrolo[2,3-d]pyrimidin-4-yl)amino)piperidin-1-yl)pent-3-en-2-one |
| I-440 | 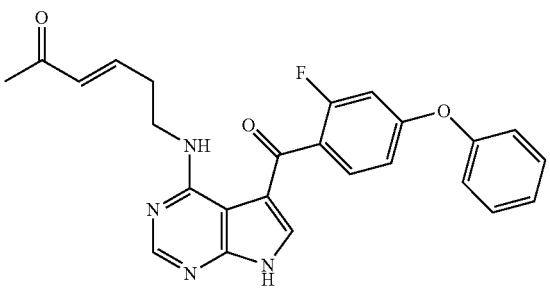 [SMILES: CC(=O)/C=C/CCNc1ncnc2[nH]cc(C(=O)c3ccc(Oc4ccccc4)cc3F)c12] | (E)-5-(3-((5-(2-fluoro-4-phenoxybenzoyl)-7H-pyrrolo[2,3-d]pyrimidin-4-yl)amino)piperidin-1-yl)pent-3-en-2-one |
| I-441 | 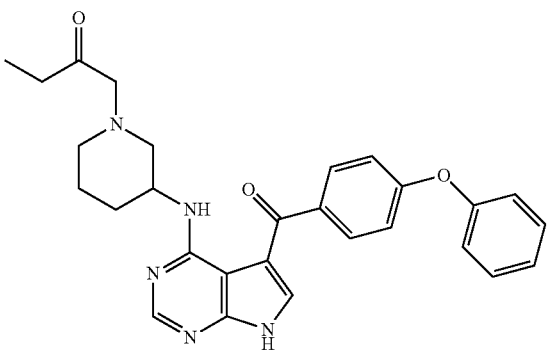 [SMILES: CCC(=O)CN1CCCC(Nc2ncnc3[nH]cc(C(=O)c4ccc(Oc5ccccc5)cc4)c23)C1] | (E)-5-(3-((5-(4-phenoxybenzoyl)-7H-pyrrolo[2,3-d]pyrimidin-4-yl)amino)piperidin-1-yl)pent-3-en-2-one |

| Cmpd No. | Structure | Chemical name |
|---|---|---|
| I-442 | 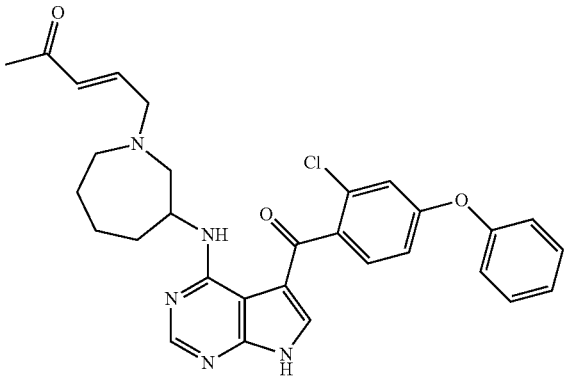 [SMILES: CC(=O)/C=C/CN1CCCCC(Nc2ncnc3[nH]cc(C(=O)c4ccc(Oc5ccccc5)cc4Cl)c23)C1] | (E)-5-(3-((5-(2-chloro-4-phenoxybenzoyl)-7H-pyrrolo[2,3-d]pyrimidin-4-yl)amino)azepan-1-yl)pent-3-en-2-one |
| I-443 | 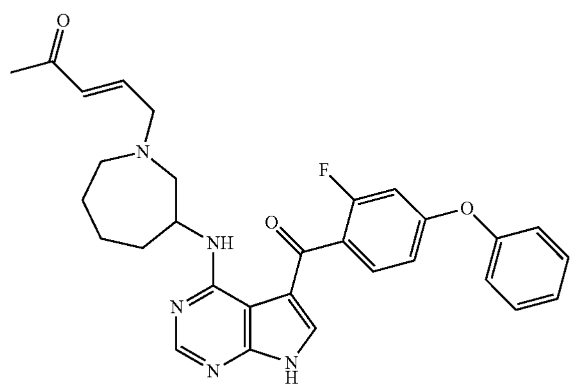 [SMILES: CC(=O)/C=C/CN1CCCCC(Nc2ncnc3[nH]cc(C(=O)c4ccc(Oc5ccccc5)cc4F)c23)C1] | (E)-5-(3-((5-(2-fluoro-4-phenoxybenzoyl)-7H-pyrrolo[2,3-d]pyrimidin-4-yl)amino)azepan-1-yl)pent-3-en-2-one |
| I-444 | 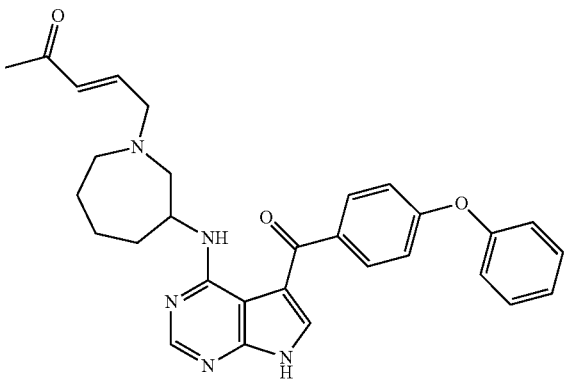 [SMILES: CC(=O)/C=C/CN1CCCCC(Nc2ncnc3[nH]cc(C(=O)c4ccc(Oc5ccccc5)cc4)c23)C1] | (E)-5-(3-((5-(4-phenoxybenzoyl)-7H-pyrrolo[2,3-d]pyrimidin-4-yl)amino)azepan-1-yl)pent-3-en-2-one |
| I-445 | 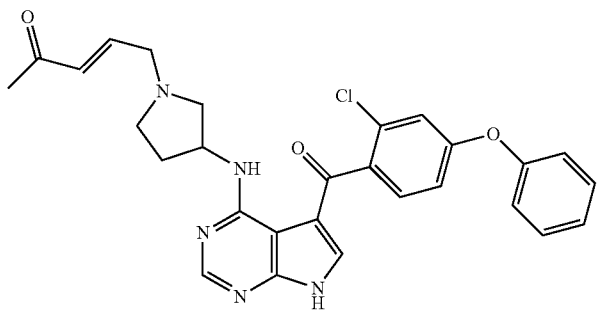 [SMILES: CC(=O)/C=C/CN1CCC(Nc2ncnc3[nH]cc(C(=O)c4ccc(Oc5ccccc5)cc4Cl)c23)C1] | (E)-5-(3-((5-(2-chloro-4-phenoxybenzoyl)-7H-pyrrolo[2,3-d]pyrimidin-4-yl)amino)pyrrolidin-1-yl)pent-3-en-2-one |

| Cmpd No. | Structure | Chemical name |
|---|---|---|
| I-446 | 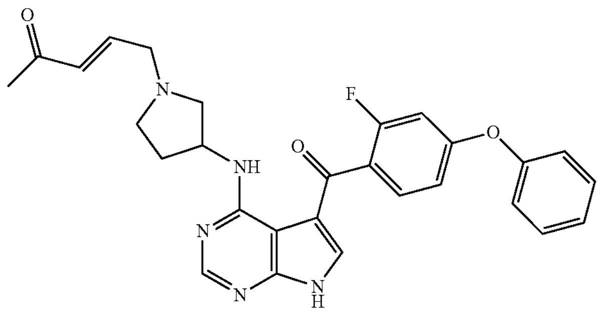 [SMILES: CC(=O)/C=C/CN1CCC(Nc2ncnc3[nH]cc(C(=O)c4ccc(Oc5ccccc5)cc4F)c23)C1] | (E)-5-(3-((5-(2-fluoro-4-phenoxybenzoyl)-7H-pyrrolo[2,3-d]pyrimidin-4-yl)amino)pyrrolidin-1-yl)pent-3-en-2-one |
| I-447 | 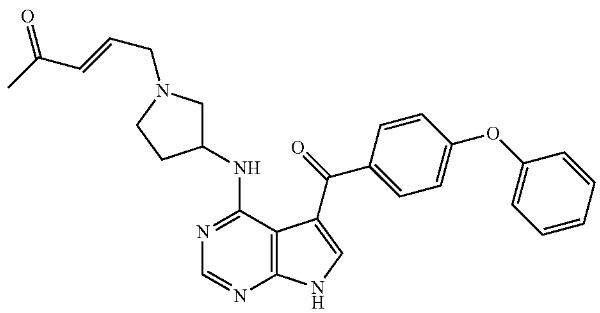 [SMILES: CC(=O)/C=C/CN1CCC(Nc2ncnc3[nH]cc(C(=O)c4ccc(Oc5ccccc5)cc4)c23)C1] | (E)-5-(3-((5-(4-phenoxybenzoyl)-7H-pyrrolo[2,3-d]pyrimidin-4-yl)amino)pyrrolidin-1-yl)pent-3-en-2-one |
| I-448 | 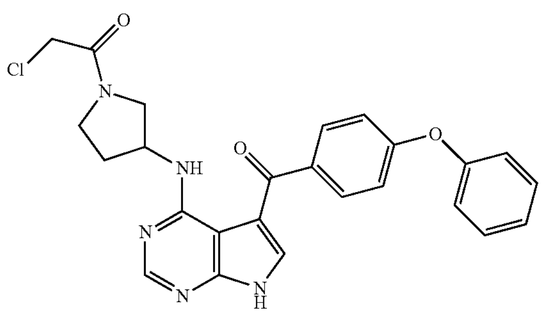 [SMILES: O=C(c1ccc(Oc2ccccc2)cc1)c1c[nH]c2ncnc(NC3CCN(C(=O)CCl)C3)c12] | 2-chloro-1-(3-((5-(4-phenoxybenzoyl)-7H-pyrrolo[2,3-d]pyrimidin-4-yl)amino)pyrrolidin-1-yl)ethan-1-one |
| I-449 | 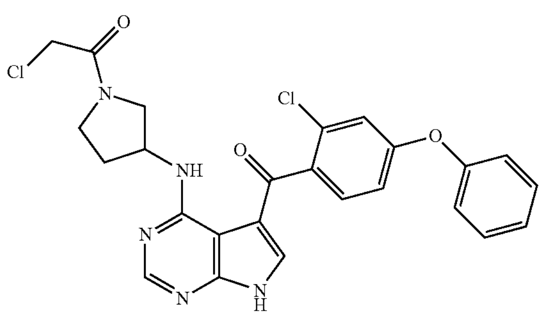 | 2-chloro-1-(3-((5-(2-chloro-4-phenoxybenzoyl)-7H-pyrrolo[2,3-d]pyrimidin-4-yl)amino)pyrrolidin-1-yl)ethan-1-one |
| I-450 | 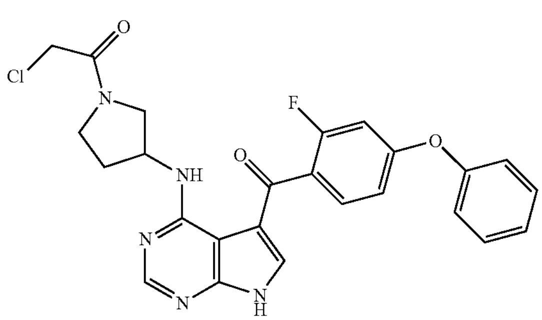 | 2-chloro-1-(3-((5-(2-fluoro-4-phenoxybenzoyl)-7H-pyrrolo[2,3-d]pyrimidin-4-yl)amino)pyrrolidin-1-yl)ethan-1-one |

-continued

| Cmpd No. | Structure | Chemical name |
|---|---|---|
| I-451 | 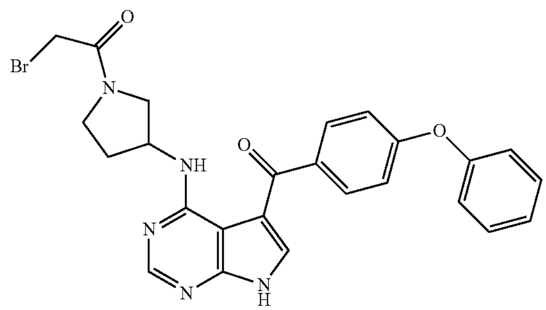 | 2-bromo-1-(3-((5-(4-phenoxybenzoyl)-7H-pyrrolo[2,3-d]pyrimidin-4-yl)amino)pyrrolidin-1-yl)ethan-1-one |
| I-452 | 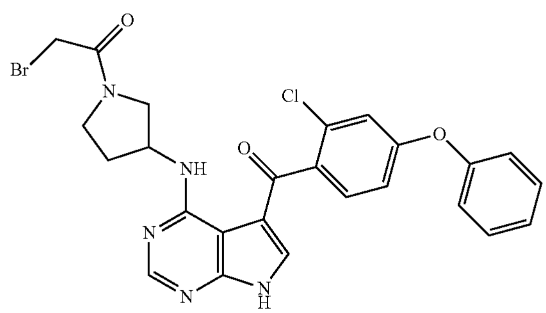 [SMILES: O=C(c1ccc(Oc2ccccc2)cc1Cl)c1c[nH]c2ncnc(NC3CCN(C(=O)CCl)C3)c12] | 2-bromo-1-(3-((5-(2-chloro-4-phenoxybenzoyl)-7H-pyrrolo[2,3-d]pyrimidin-4-yl)amino)pyrrolidin-1-yl)ethan-1-one |
| I-453 | 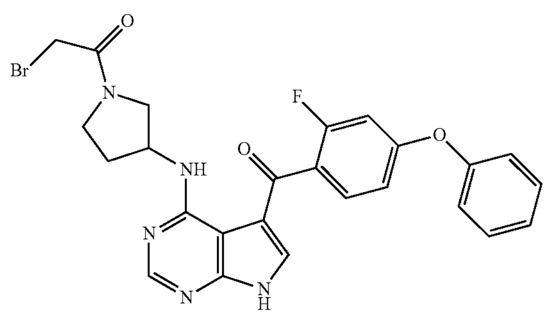 [SMILES: O=C(c1ccc(Oc2ccccc2)cc1F)c1c[nH]c2ncnc(NC3CCN(C(=O)CCl)C3)c12] | 2-bromo-1-(3-((5-(2-fluoro-4-phenoxybenzoyl)-7H-pyrrolo[2,3-d]pyrimidin-4-yl)amino)pyrrolidin-1-yl)ethan-1-one |
| I-454 | 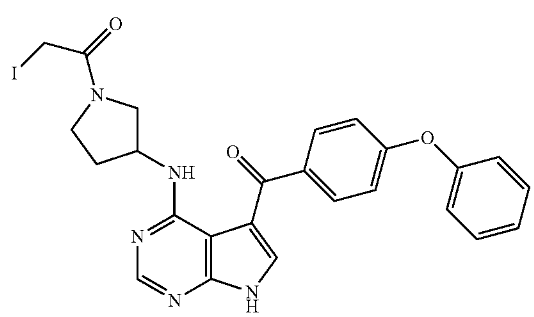 [SMILES: O=C(c1ccc(Oc2ccccc2)cc1)c1c[nH]c2ncnc(NC3CCN(C(=O)CI)C3)c12] | 2-iodo-1-(3-((5-(4-phenoxybenzoyl)-7H-pyrrolo[2,3-d]pyrimidin-4-yl)amino)pyrrolidin-1-yl)ethan-1-one |
| I-455 | 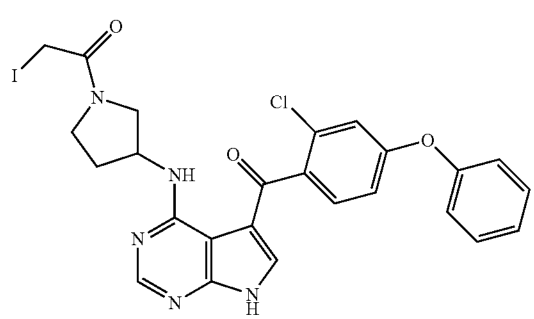 [SMILES: O=C(c1ccc(Oc2ccccc2)cc1Cl)c1c[nH]c2ncnc(NC3CCN(C(=O)CI)C3)c12] | 1-(3-((5-(2-chloro-4-phenoxybenzoyl)-7H-pyrrolo[2,3-d]pyrimidin-4-yl)amino)pyrrolidin-1-yl)-2-iodoethan-1-one |

-continued

| Cmpd No. | Structure | Chemical name |
|---|---|---|
| I-456 | 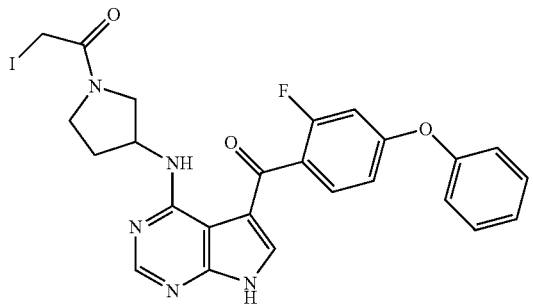 | 1-(3-((5-(2-fluoro-4-phenoxybenzoyl)-7H-pyrrolo[2,3-d]pyrimidin-4-yl)amino)pyrrolidin-1-yl)-2-iodoethan-1-one |
| I-457 | 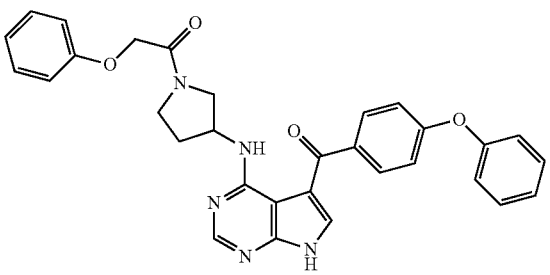 [SMILES: O=C(c1ccc(Oc2ccccc2)cc1)c1c[nH]c2ncnc(NC3CCN(C(=O)COc4ccccc4)C3)c12] | 2-phenoxy-1-(3-((5-(4-phenoxybenzoyl)-7H-pyrrolo[2,3-d]pyrimidin-4-yl)amino)pyrrolidin-1-yl)ethan-1-one |
| I-458 | 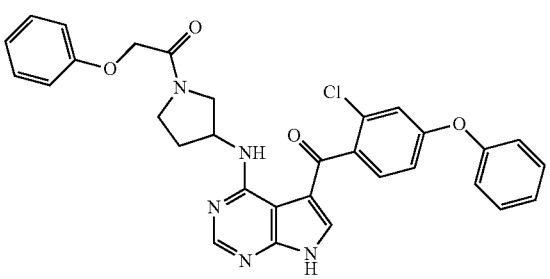 | 1-(3-((5-(2-chloro-4-phenoxybenzoyl)-7H-pyrrolo[2,3-d]pyrimidin-4-yl)amino)pyrrolidin-1-yl)-2-phenoxyethan-1-one |
| I-459 | 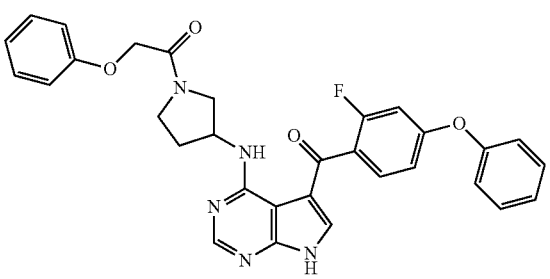 [SMILES: O=C(c1ccc(Oc2ccccc2)cc1Cl)c1c[nH]c2ncnc(NC3CCN(C(=O)COc4ccccc4)C3)c12] | 1-(3-((5-(2-fluoro-4-phenoxybenzoyl)-7H-pyrrolo[2,3-d]pyrimidin-4-yl)amino)pyrrolidin-1-yl)-2-phenoxyethan-1-one |
| I-460 | 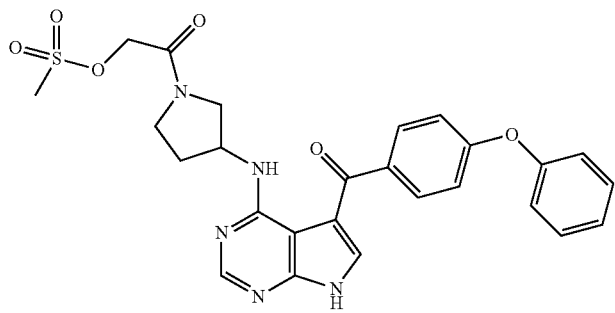 [SMILES: CS(=O)(=O)OCC(=O)N1CCC(Nc2ncnc3[nH]cc(C(=O)c4ccc(Oc5ccccc5)cc4)c23)C1] | 2-oxo-2-(3-((5-(4-phenoxybenzoyl)-7H-pyrrolo[2,3-d]pyrimidin-4-yl)amino)pyrrolidin-1-yl)ethyl methanesulfonate |

-continued

| Cmpd No. | Structure | Chemical name |
| --- | --- | --- |
| I-461 | 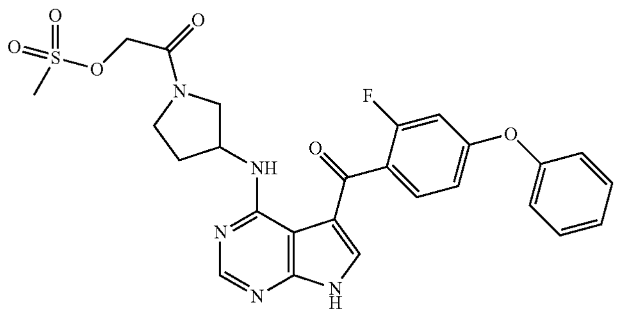 | 2-(3-((5-(2-fluoro-4-phenoxybenzoyl)-7H-pyrrol[2,3-d]pyrimidin-4-yl)amino)pyrrolidin-1-yl)-2-oxoethyl methanesulfonate |
| I-462 | 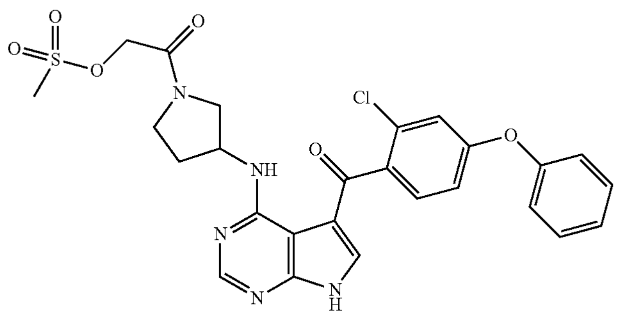 [SMILES: CS(=O)(=O)OCC(=O)N1CCC(Nc2ncnc3[nH]cc(C(=O)c4ccc(Oc5ccccc5)cc4Cl)c23)C1] | 2-(3-((5-(2-chloro-4-phenoxybenzoyl)-7H-pyrrolo[2,3-d]pyrimidin-4-yl)amino)pyrrolidin-1-yl)-2-oxoethyl methanesulfonate |
| I-463 | 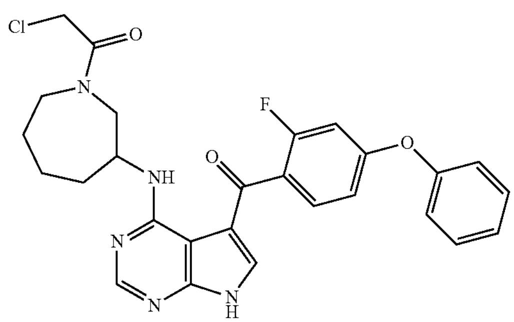 [SMILES: O=C(c1ccc(Oc2ccccc2)cc1F)c1c[nH]c2ncnc(NC3CCCCN(C(=O)CCl)C3)c12] | 2-chloro-1-(3-((5-(2-fluoro-4-phenoxybenzoyl)-7H-pyrrolo[2,3-d]pyrimidin-4-yl)amino)azepan-1-yl)ethan-1-one |
| I-464 | 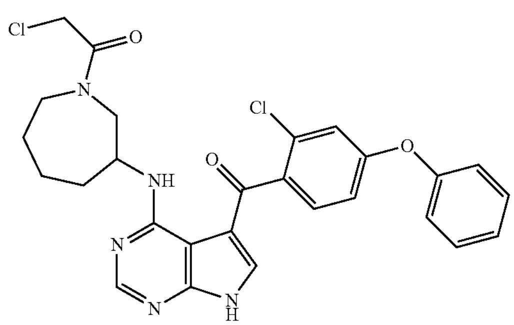 [SMILES: O=C(c1ccc(Oc2ccccc2)cc1Cl)c1c[nH]c2ncnc(NC3CCCCN(C(=O)CCl)C3)c12] | 2-chloro-1-(3-((5-(2-chloro-4-phenoxybenzoyl)-7H-pyrrolo[2,3-d]pyrimidin-4-yl)amino)azepan-1-yl)ethan-1-one |
| I-465 | 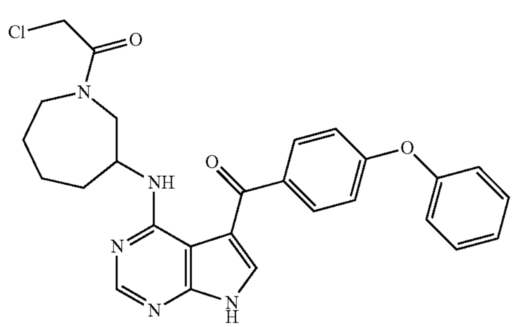 [SMILES: O=C(c1ccc(Oc2ccccc2)cc1)c1c[nH]c2ncnc(NC3CCCCN(C(=O)CCl)C3)c12] | 2-chloro-1-(3-((5-(4-phenoxybenzoyl)-7H-pyrrolo[2,3-d]pyrimidin-4-yl)amino)azepan-1-yl)ethan-1-one |

-continued

| Cmpd No. | Structure | Chemical name |
|---|---|---|
| I-466 | 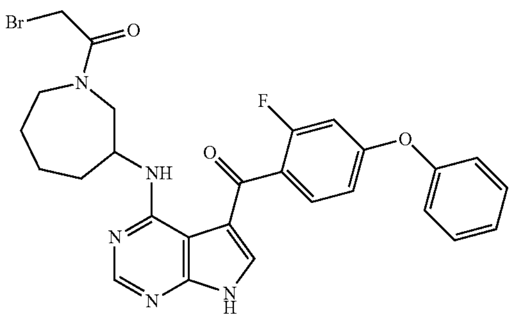 [SMILES: O=C(c1ccc(Oc2ccccc2)cc1Cl)c1c[nH]c2ncnc(NC3CCCCN(C(=O)CBr)C3)c12] | 2-bromo-1-(3-((5-(2-fluoro-4-phenoxybenzoyl)-7H-pyrrolo[2,3-d]pyrimidin-4-yl)amino)azepan-1-yl)ethan-1-one |
| I-467 | 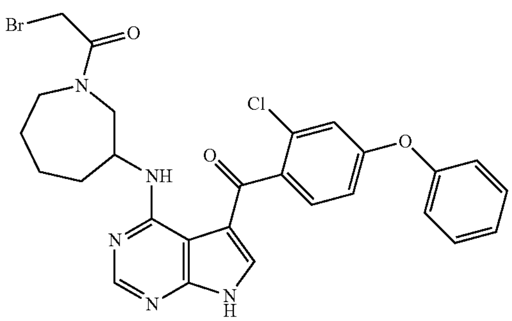 | 2-bromo-1-(3-((5-(2-chloro-4-phenoxybenzoyl)-7H-pyrrolo[2,3-d]pyrimidin-4-yl)amino)azepan-1-yl)ethan-1-one |
| I-468 | 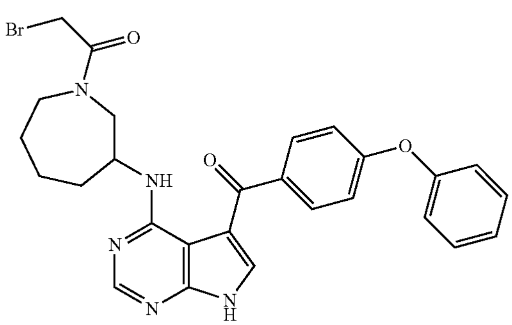 [SMILES: O=C(c1ccc(Oc2ccccc2)cc1)c1c[nH]c2ncnc(NC3CCCCN(C(=O)CBr)C3)c12] | 2-bromo-1-(3-((5-(4-phenoxybenzoyl)-7H-pyrrolo[2,3-d]pyrimidin-4-yl)amino)azepan-1-yl)ethan-1-one |
| I-469 | 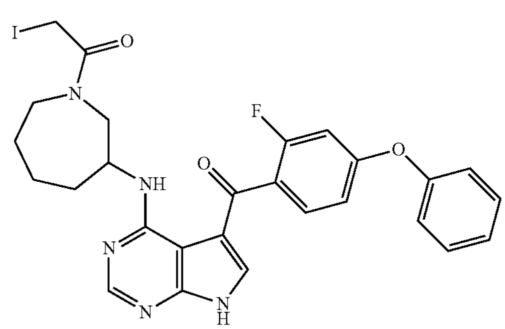 | 1-(3-((5-(2-fluoro-4-phenoxybenzoyl)-7H-pyrrolo[2,3-d]pyrimidin-4-yl)amino)azepan-1-yl)-2-iodoethan-1-one |

| Cmpd No. | Structure | Chemical name |
|---|---|---|
| I-470 | 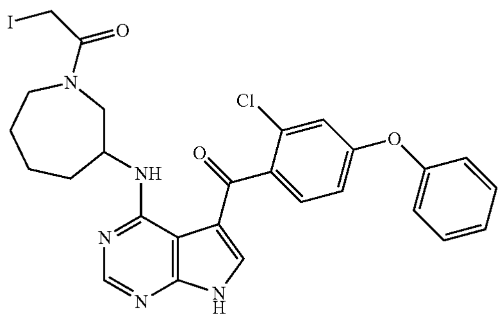 [SMILES: O=C(c1ccc(Oc2ccccc2)cc1Cl)c1c[nH]c2ncnc(NC3CCCCN(C(=O)CI)C3)c12] | 1-(3-((5-(2-chloro-4-phenoxybenzoyl)-7H-pyrrolo[2,3-d]pyrimidin-4-yl)amino)azepan-1-yl)-2-iodoethan-1-one |
| I-471 | 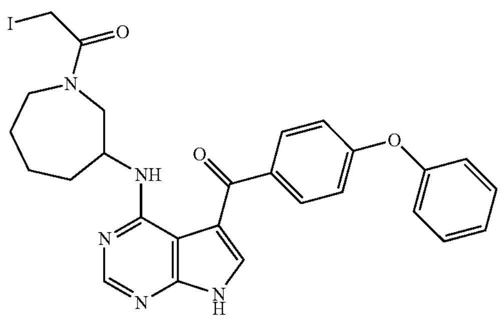 [SMILES: O=C(c1ccc(Oc2ccccc2)cc1)c1c[nH]c2ncnc(NC3CCCCN(C(=O)CI)C3)c12] | 2-iodo-1-(3-((5-(4-phenoxybenzoyl)-7H-pyrrolo[2,3-d]pyrimidin-4-yl)amino)azepan-1-yl)ethan-1-one |
| I-472 | 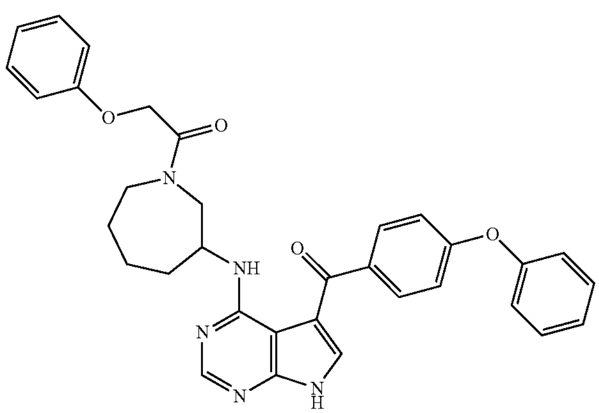 [SMILES: O=C(c1ccc(Oc2ccccc2)cc1)c1c[nH]c2ncnc(NC3CCCCN(C(=O)COc4ccccc4)C3)c12] | 2-phenoxy-1-(3-((5-(4-phenoxybenzoyl)-7H-pyrrolo[2,3-d]pyrimidin-4-yl)amino)azepan-1-yl)ethan-1-one |
| I-473 | 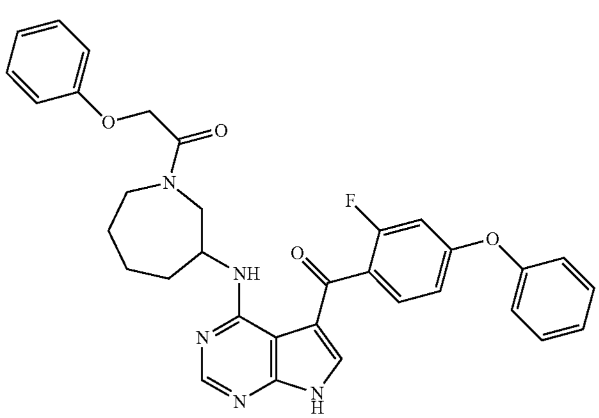 [SMILES: O=C(c1ccc(Oc2ccccc2)cc1F)c1c[nH]c2ncnc(NC3CCCCN(C(=O)COc4ccccc4)C3)c12] | 1-(3-((5-(2-fluoro-4-phenoxybenzoyl)-7H-pyrrolo[2,3-d]pyrimidin-4-yl)amino)azepan-1-yl)-2-phenoxyethan-1-one |

-continued

| Cmpd No. | Structure | Chemical name |
|---|---|---|
| I-474 | 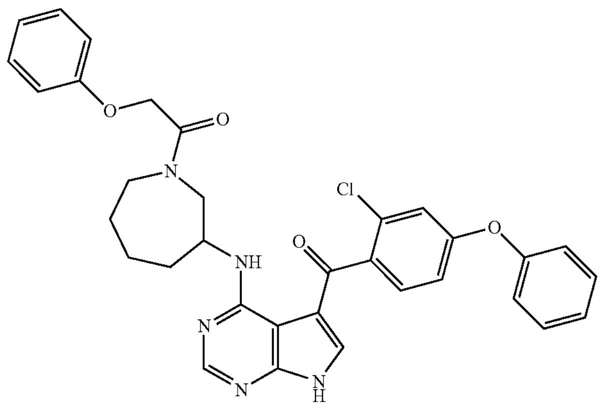 [SMILES: O=C(c1ccc(Oc2ccccc2)cc1Cl)c1c[nH]c2ncnc(NC3CCCCN(C(=O)COc4ccccc4)C3)c12] | 1-(3-((5-(2-chloro-4-phenoxybenzoyl)-7H-pyrrolo[2,3-d]pyrimidin-4-yl)amino)azepan-1-yl)-2-phenoxyethan-1-one |
| I-475 | 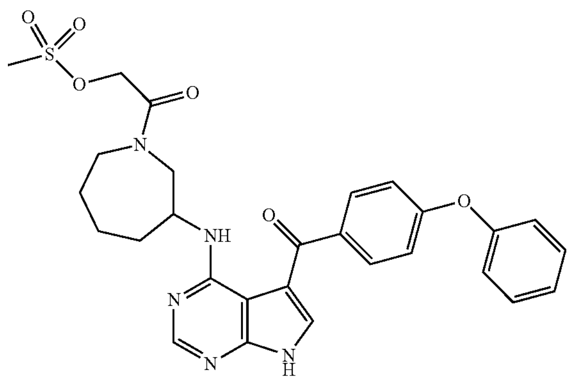 [SMILES: CS(=O)(=O)OCC(=O)N1CCCCC(Nc2ncnc3[nH]cc(C(=O)c4ccc(Oc5ccccc5)cc4)c23)C1] | 2-oxo-2-(3-((5-(4-phenoxybenzoyl)-7H-pyrrolo[2,3-d]pyrimidin-4-yl)amino)azepan-1-yl)ethyl methanesulfonate |
| I-476 | 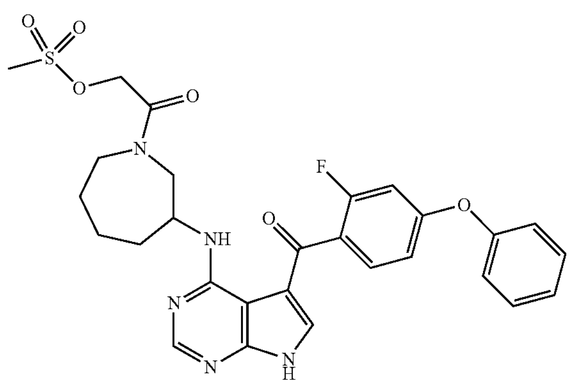 [SMILES: CS(=O)(=O)OCC(=O)N1CCCCC(Nc2ncnc3[nH]cc(C(=O)c4ccc(Oc5ccccc5)cc4F)c23)C1] | 2-(3-((5-(2-fluoro-4-phenoxybenzoyl)-7H-pyrrolo[2,3-d]pyrimidin-4-yl)amino)azepan-1-yl)-2-oxoethyl methanesulfonate |
| I-477 | 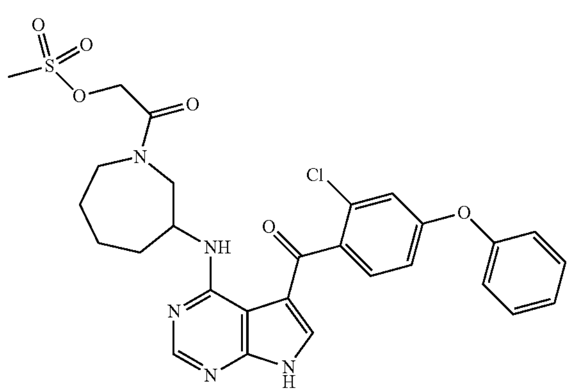 [SMILES: CS(=O)(=O)OCC(=O)N1CCCCC(Nc2ncnc3[nH]cc(C(=O)c4ccc(Oc5ccccc5)cc4Cl)c23)C1] | 2-(3-((5-(2-chloro-4-phenoxybenzoyl)-7H-pyrrolo[2,3-d]pyrimidin-4-yl)amino)azepan-1-yl)-2-oxoethyl methanesulfonate |

| Cmpd No. | Structure | Chemical name |
|---|---|---|
| I-478 | 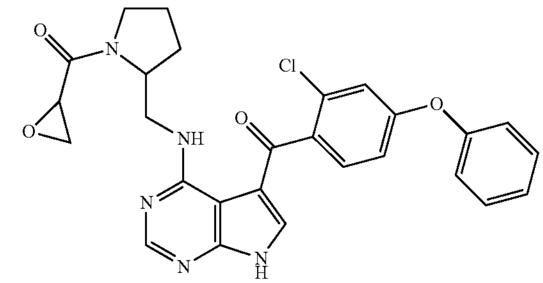 [SMILES: O=C(c1ccc(Oc2ccccc2)cc1Cl)c1c[nH]c2ncnc(NCC3CCCN3C(=O)C3CO3)c12] | (2-(((5-(2-chloro-4-phenoxybenzoyl)-7H-pyrrolo[2,3-d]pyrimidin-4-yl)amino)methyl)pyrrolidin-1-yl)(oxiran-2-yl)methanone |
| I-479 | 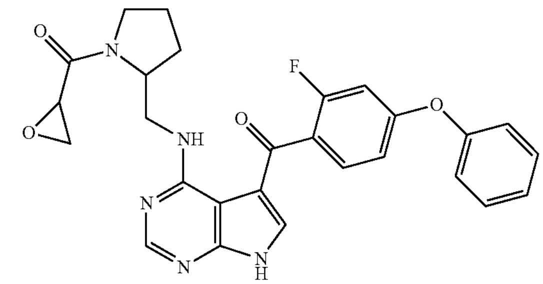 [SMILES: O=C(c1ccc(Oc2ccccc2)cc1F)c1c[nH]c2ncnc(NCC3CCCN3C(=O)C3CO3)c12] | (2-(((5-(2-fluoro-4-phenoxybenzoyl)-7H-pyrrolo[2,3-d]pyrimidin-4-yl)amino)methyl)pyrrolidin-1-yl)(oxiran-2-yl)methanone |
| I-480 | 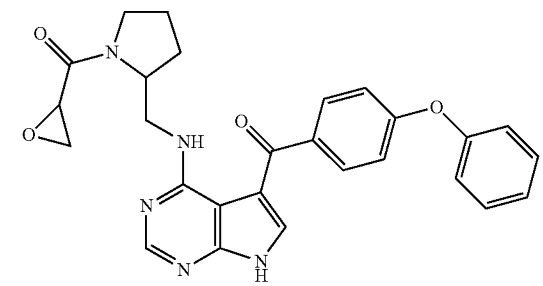 [SMILES: O=C(c1ccc(Oc2ccccc2)cc1)c1c[nH]c2ncnc(NCC3CCCN3C(=O)C3CO3)c12] | oxiran-2-yl(2-(((5-(4-phenoxybenzoyl)-7H-pyrrolo[2,3-d]pyrimidin-4-yl)amino)methyl)pyrrolidin-1-yl)methanone |
| I-481 | 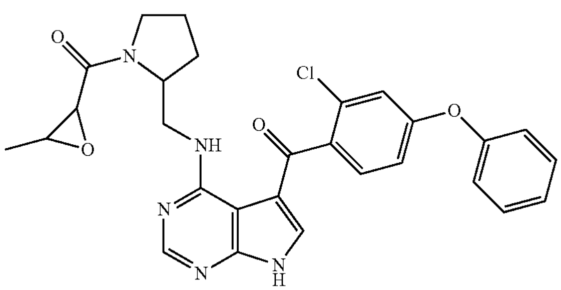 [SMILES: CC1OC1C(=O)N1CCCC1CNc1ncnc2[nH]cc(C(=O)c3ccc(Oc4ccccc4)cc3Cl)c12] | (2-(((5-(2-chloro-4-phenoxybenzoyl)-7H-pyrrolo[2,3-d]pyrimidin-4-yl)amino)methyl)pyrrolidin-1-yl)(3-methyloxiran-2-yl)methanone |
| I-482 | 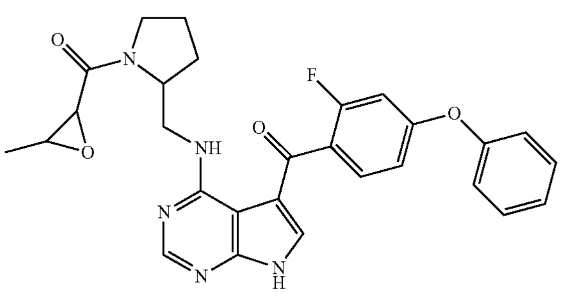 [SMILES: CC1OC1C(=O)N1CCCC1CNc1ncnc2[nH]cc(C(=O)c3ccc(Oc4ccccc4)cc3F)c12] | (2-(((5-(2-fluoro-4-phenoxybenzoyl)-7H-pyrrolo[2,3-d]pyrimidin-4-yl)amino)methyl)pyrrolidin-1-yl)(3-methyloxiran-2-yl)methanone |

| Cmpd No. | Structure | Chemical name |
|---|---|---|
| I-483 | 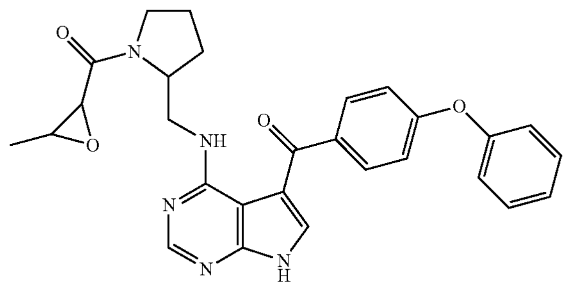 [SMILES: CC1OC1C(=O)N1CCCC1CNc1ncnc2[nH]cc(C(=O)c3ccc(Oc4ccccc4)cc3)c12] | (3-methyloxiran-2-yl)(2-(((5-(4-phenoxybenzoyl)-7H-pyrrolo[2,3-d]pyrimidin-4-yl)amino)methyl)pyrrolidin-1-yl)methanone |
| I-484 | 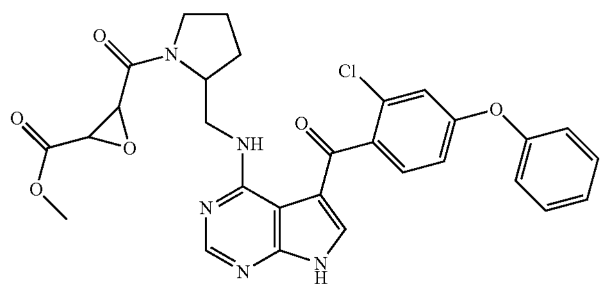 [SMILES: COC(=O)C1OC1C(=O)N1CCCC1CNc1ncnc2[nH]cc(C(=O)c3ccc(Oc4ccccc4)cc3Cl)c12] | methyl 3-(2-(((5-(2-chloro-4-phenoxybenzoyl)-7H-pyrrolo[2,3-d]pyrimidin-4-yl)amino)methyl)pyrrolidine-1-carbonyl)oxirane-2-carboxylate |
| I-485 | 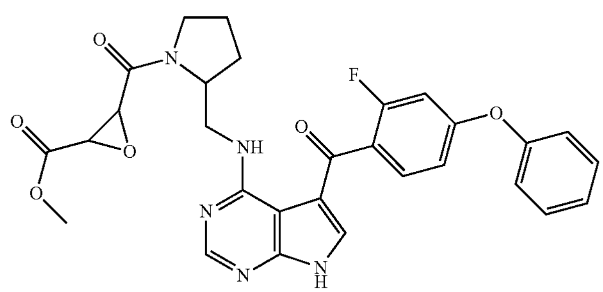 [SMILES: COC(=O)C1OC1C(=O)N1CCCC1CNc1ncnc2[nH]cc(C(=O)c3ccc(Oc4ccccc4)cc3F)c12] | methyl 3-(2-(((5-(2-fluoro-4-phenoxybenzoyl)-7H-pyrrolo[2,3-d]pyrimidin-4-yl)amino)methyl)pyrrolidine-1-carbonyl)oxirane-2-carboxylate |
| I-486 | 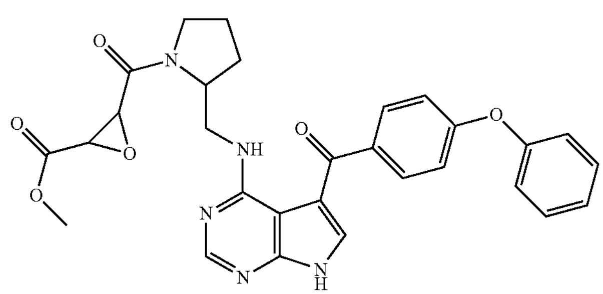 [SMILES: COC(=O)C1OC1C(=O)N1CCCC1CNc1ncnc2[nH]cc(C(=O)c3ccc(Oc4ccccc4)cc3)c12] | methyl 3-(2-(((5-(4-phenoxybenzoyl)-7H-pyrrolo[2,3-d]pyrimidin-4-yl)amino)methyl)pyrrolidine-1-carbonyl)oxirane-2-carboxylate |
| I-487 | 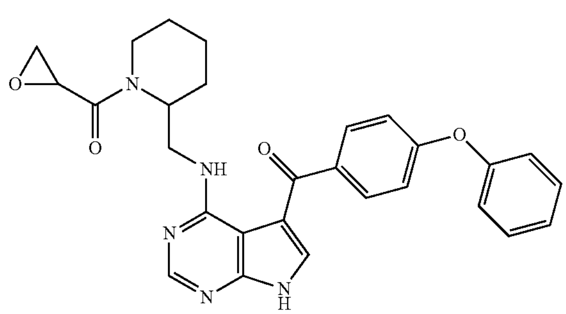 [SMILES: O=C(c1ccc(Oc2ccccc2)cc1)c1c[nH]c2ncnc(NCC3CCCCN3C(=O)C3CO3)c12] | oxiran-2-yl(2-(((5-(4-phenoxybenzoyl)-7H-pyrrolo[2,3-d]pyrimidin-4-yl)amino)methyl)piperidin-1-yl)methanone |

| Cmpd No. | Structure | Chemical name |
|---|---|---|
| I-488 | 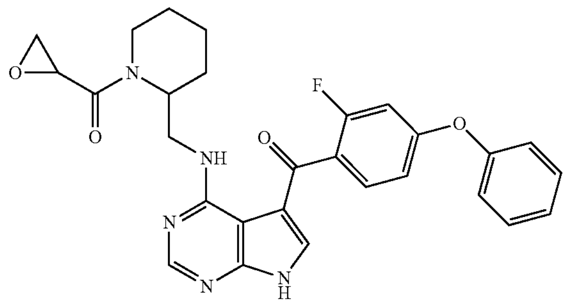 [SMILES: O=C(c1ccc(Oc2ccccc2)cc1F)c1c[nH]c2ncnc(NCC3CCCCN3C(=O)C3CO3)c12] | (2-(((5-(2-fluoro-4-phenoxybenzoyl)-7H-pyrrolo[2,3-d]pyrimidin-4-yl)amino)methyl)piperidin-1-yl)(oxiran-2-yl)methanone |
| I-489 | 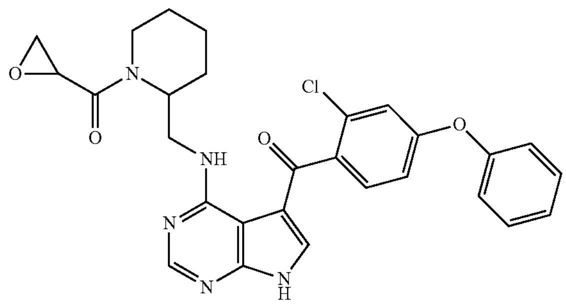 [SMILES: O=C(c1ccc(Oc2ccccc2)cc1Cl)c1c[nH]c2ncnc(NCC3CCCCN3C(=O)C3CO3)c12] | (2-(((5-(2-chloro-4-phenoxybenzoyl)-7H-pyrrolo[2,3-d]pyrimidin-4-yl)amino)methyl)piperidin-1-yl)(oxiran-2-yl)methanone |
| I-490 | 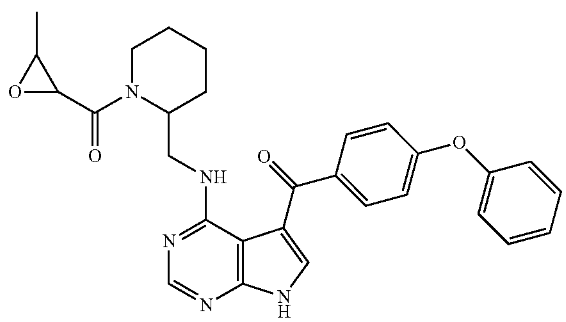 [SMILES: CC1OC1C(=O)N1CCCCC1CNc1ncnc2[nH]cc(C(=O)c3ccc(Oc4ccccc4)cc3)c12] | (3-methyloxiran-2-yl)(2-(((5-(4-phenoxybenzoyl)-7H-pyrrolo[2,3-d]pyrimidin-4-yl)amino)methyl)piperidin-1-yl)methanone |
| I-491 | 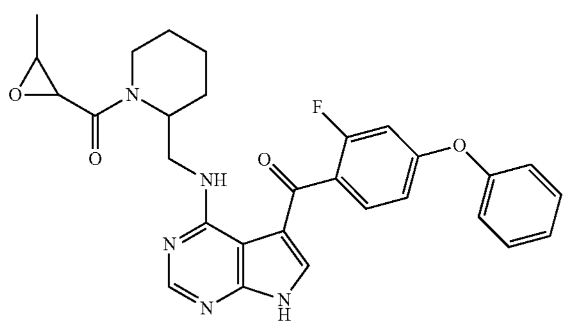 [SMILES: CC1OC1C(=O)N1CCCCC1CNc1ncnc2[nH]cc(C(=O)c3ccc(Oc4ccccc4)cc3F)c12] | (2-(((5-(2-fluoro-4-phenoxybenzoyl)-7H-pyrrolo[2,3-d]pyrimidin-4-yl)amino)methyl)piperidin-1-yl)(3-methyloxiran-2-yl)methanone |
| I-492 | 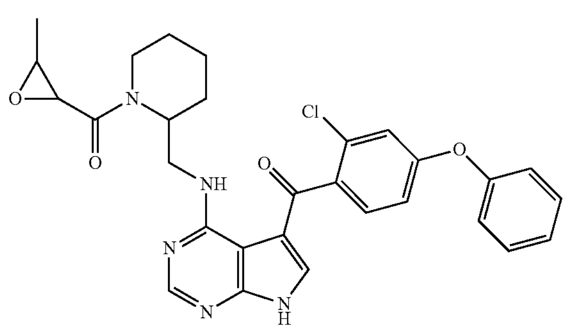 [SMILES: CC1OC1C(=O)N1CCCCC1CNc1ncnc2[nH]cc(C(=O)c3ccc(Oc4ccccc4)cc3Cl)c12] | (2-(((5-(2-chloro-4-phenoxybenzoyl)-7H-pyrrolo[2,3-d]pyrimidin-4-yl)amino)methyl)piperidin-1-yl)(3-methyloxiran-2-yl)methanone |

-continued

| Cmpd No. | Structure | Chemical name |
|---|---|---|
| I-493 | 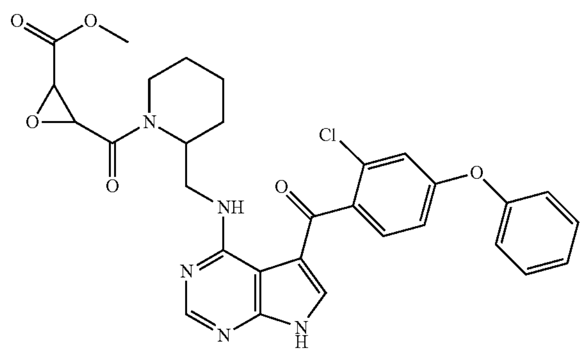 [SMILES: COC(=O)C1OC1C(=O)N1CCCCC1CNc1ncnc2[nH]cc(C(=O)c3ccc(Oc4ccccc4)cc3Cl)c12] | methyl 3-(2-(((5-(2-chloro-4-phenoxybenzoyl)-7H-pyrrolo[2,3-d]pyrimidin-4-yl)amino)methyl)piperidine-1-carbonyl)oxirane-2-carboxylate |
| I-494 | 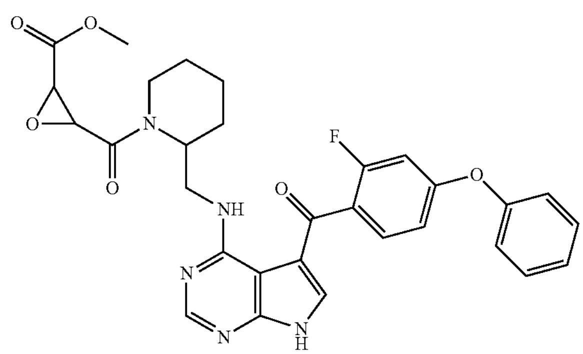 [SMILES: COC(=O)C1OC1C(=O)N1CCCCC1CNc1ncnc2[nH]cc(C(=O)c3ccc(Oc4ccccc4)cc3F)c12] | methyl 3-(2-(((5-(2-fluoro-4-phenoxybenzoyl)-7H-pyrrolo[2,3-d]pyrimidin-4-yl)amino)methyl)piperidine-1-carbonyl)oxirane-2-carboxylate |
| I-495 | 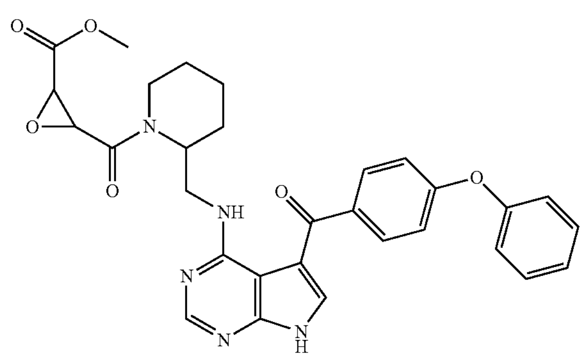 [SMILES: COC(=O)C1OC1C(=O)N1CCCCC1CNc1ncnc2[nH]cc(C(=O)c3ccc(Oc4ccccc4)cc3)c12] | methyl 3-(2-(((5-(4-phenoxybenzoyl)-7H-pyrrolo[2,3-d]pyrimidin-4-yl)amino)methyl)piperidine-1-carbonyl)oxirane-2-carboxylate |
| I-496 | 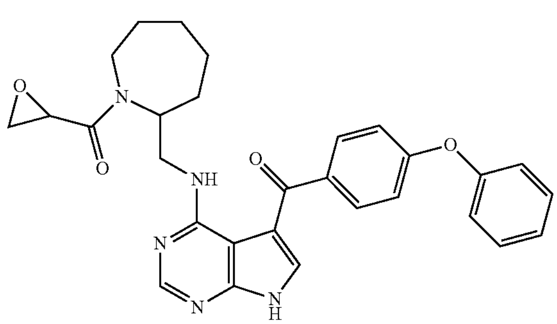 [SMILES: O=C(c1ccc(Oc2ccccc2)cc1)c1c[nH]c2ncnc(NCC3CCCCCN3C(=O)C3CO3)c12] | oxiran-2-yl(2-(((5-(4-phenoxybenzoyl)-7H-pyrrolo[2,3-d]pyrimidin-4-yl)amino)methyl)azepan-1-yl)methanone |

-continued

| Cmpd No. | Structure | Chemical name |
|---|---|---|
| I-497 | 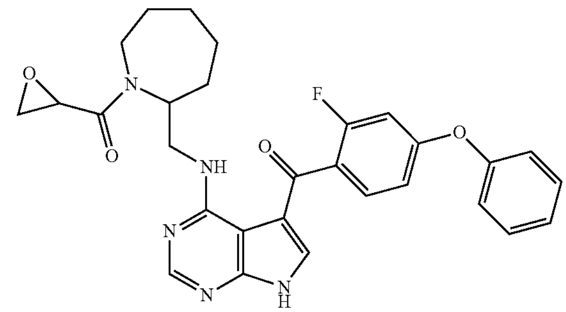 [SMILES: O=C(c1ccc(Oc2ccccc2)cc1F)c1c[nH]c2ncnc(NCC3CCCCCN3C(=O)C3CO3)c12] | (2-(((5-(2-fluoro-4-phenoxybenzoyl)-7H-pyrrolo[2,3-d]pyrimidin-4-yl)amino)methyl)azepan-1-yl)(oxiran-2-yl)methanone |
| I-498 | 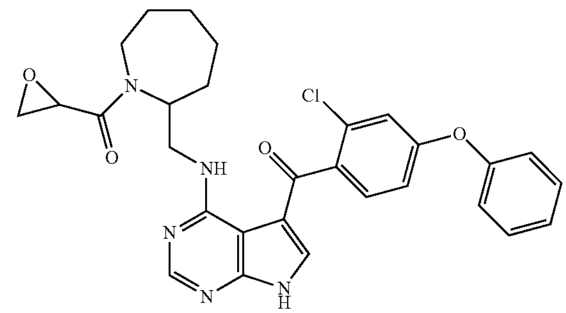 [SMILES: O=C(c1ccc(Oc2ccccc2)cc1Cl)c1c[nH]c2ncnc(NCC3CCCCCN3C(=O)C3CO3)c12] | (2-(((5-(2-chloro-4-phenoxybenzoyl)-7H-pyrrolo[2,3-d]pyrimidin-4-yl)amino)methyl)azepan-1-yl)(oxiran-2-yl)methanone |
| I-499 | 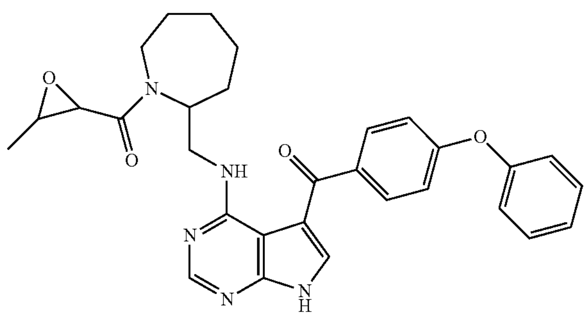 [SMILES: CC1OC1C(=O)N1CCCCCC1CNc1ncnc2[nH]cc(C(=O)c3ccc(Oc4ccccc4)cc3)c12] | (3-methyloxiran-2-yl)(2-(((5-(4-phenoxybenzoyl)-7H-pyrrolo[2,3-d]pyrimidin-4-yl)amino)methyl)azepan-1-yl)methanone |
| I-500 | 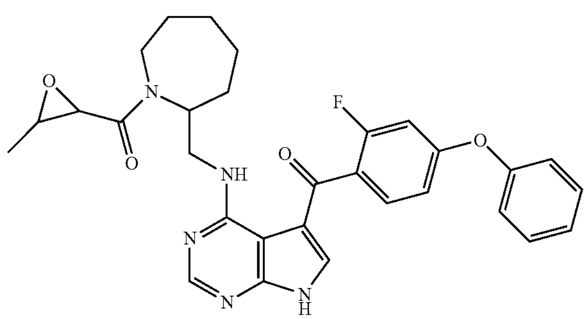 [SMILES: CC1OC1C(=O)N1CCCCCC1CNc1ncnc2[nH]cc(C(=O)c3ccc(Oc4ccccc4)cc3F)c12] | (2-(((5-(2-fluoro-4-phenoxybenzoyl)-7H-pyrrolo[2,3-d]pyrimidin-4-yl)amino)methyl)azepan-1-yl)(3-methyloxiran-2-yl)methanone |
| I-501 | 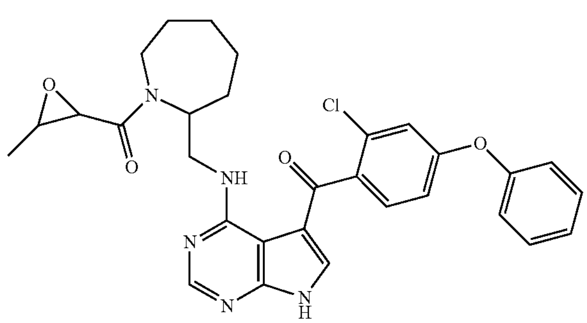 [SMILES: CC1OC1C(=O)N1CCCCCC1CNc1ncnc2[nH]cc(C(=O)c3ccc(Oc4ccccc4)cc3Cl)c12] | (2-(((5-(2-chloro-4-phenoxybenzoyl)-7H-pyrrolo[2,3-d]pyrimidin-4-yl)amino)methyl)azepan-1-yl)(3-methyloxiran-2-yl)methanone |

-continued

| Cmpd No. | Structure | Chemical name |
| --- | --- | --- |
| I-502 | 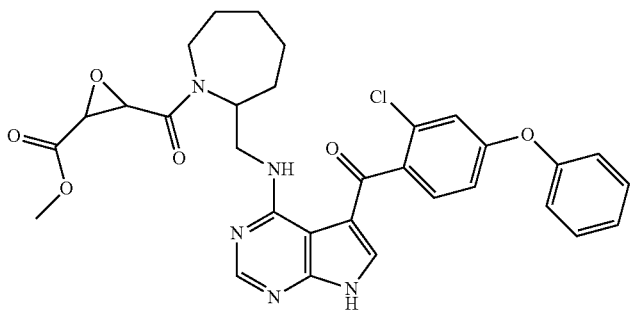 [SMILES: COC(=O)C1OC1C(=O)N1CCCCCC1CNc1ncnc2[nH]cc(C(=O)c3ccc(Oc4ccccc4)cc3Cl)c12] | methyl 3-(2-(((5-(2-chloro-4-phenoxybenzoyl)-7H-pyrrolo[2,3-d]pyrimidin-4-yl)amino)methyl)azepane-1-carbonyl)oxirane-2-carboxylate |
| I-503 | 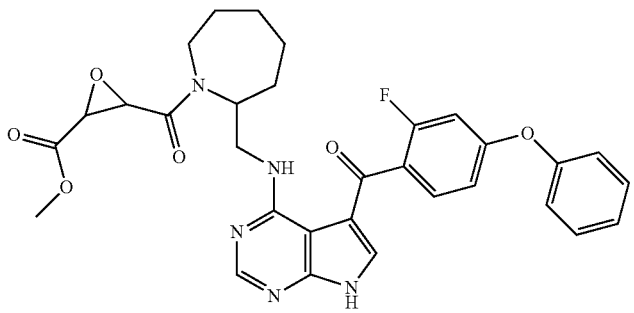 [SMILES: COC(=O)C1OC1C(=O)N1CCCCCC1CNc1ncnc2[nH]cc(C(=O)c3ccc(Oc4ccccc4)cc3F)c12] | methyl 3-(2-(((5-(2-fluoro-4-phenoxybenzoyl)-7H-pyrrolo[2,3-d]pyrimidin-4-yl)amino)methyl)azepane-1-carbonyl)oxirane-2-carboxylate |
| I-504 | 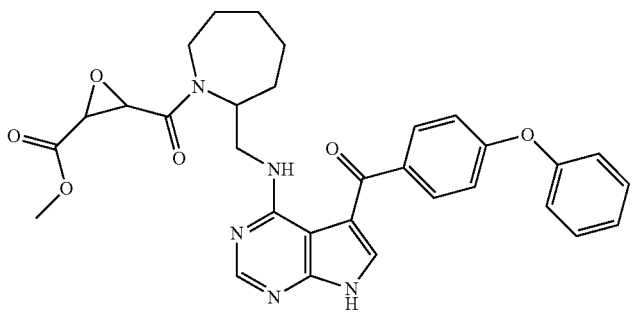 [SMILES: COC(=O)C1OC1C(=O)N1CCCCCC1CNc1ncnc2[nH]cc(C(=O)c3ccc(Oc4ccccc4)cc3)c12] | methyl 3-(2-(((5-(4-phenoxybenzoyl)-7H-pyrrolo[2,3-d]pyrimidin-4-yl)amino)methyl)azepane-1-carbonyl)oxirane-2-carboxylate |
| I-505 | 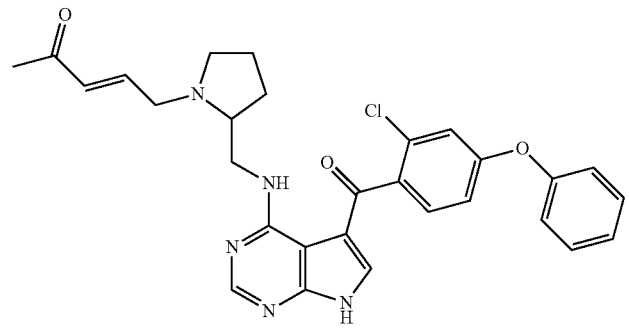 [SMILES: CC(=O)/C=C/CN1CCCC1CNc1ncnc2[nH]cc(C(=O)c3ccc(Oc4ccccc4)cc3Cl)c12] | (E)-5-(2-(((5-(2-chloro-4-phenoxybenzoyl)-7H-pyrrolo[2,3-d]pyrimidin-4-yl)amino)methyl)pyrrolidin-1-yl)pent-3-en-2-one |

-continued

| Cmpd No. | Structure | Chemical name |
|---|---|---|
| I-506 | 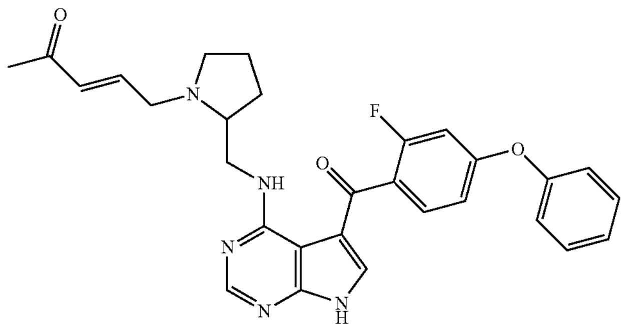 [SMILES: CC(=O)/C=C/CN1CCCC1CNc1ncnc2[nH]cc(C(=O)c3ccc(Oc4ccccc4)cc3F)c12] | (E)-5-(2-(((5-(2-fluoro-4-phenoxybenzoyl)-7H-pyrrolo[2,3-d]pyrimidin-4-yl)amino)methyl)pyrrolidin-1-yl)pent-3-en-2-one |
| I-507 | 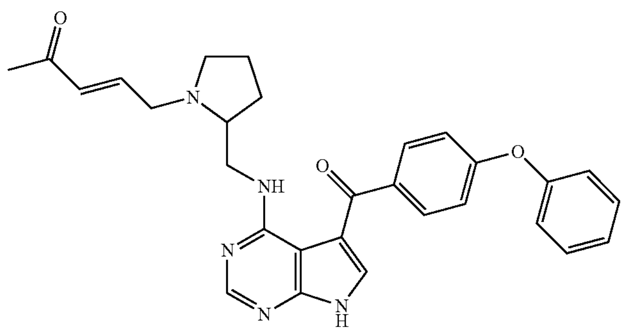 [SMILES: CC(=O)/C=C/CN1CCCC1CNc1ncnc2[nH]cc(C(=O)c3ccc(Oc4ccccc4)cc3)c12] | (E)-5-(2-(((5-(4-phenoxybenzoyl)-7H-pyrrolo[2,3-d]pyrimidin-4-yl)amino)methyl)pyrrolidin-1-yl)pent-3-en-2-one |
| I-508 | 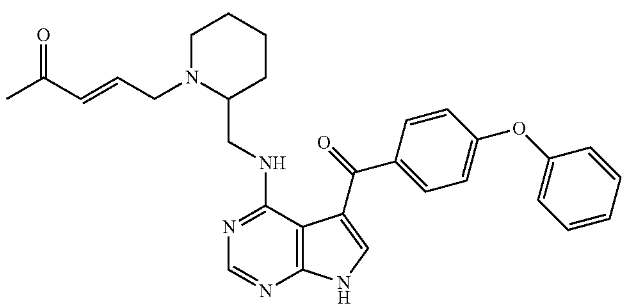 [SMILES: CC(=O)/C=C/CN1CCCCC1CNc1ncnc2[nH]cc(C(=O)c3ccc(Oc4ccccc4)cc3)c12] | (E)-5-(2-(((5-(4-phenoxybenzoyl)-7H-pyrrolo[2,3-d]pyrimidin-4-yl)amino)methyl)piperidin-1-yl)pent-3-en-2-one |
| I-509 | 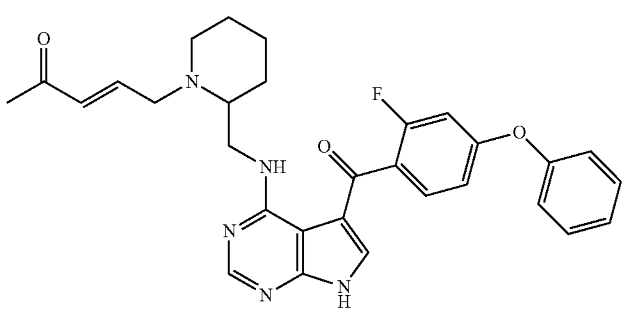 [SMILES: CC(=O)/C=C/CN1CCCCC1CNc1ncnc2[nH]cc(C(=O)c3ccc(Oc4ccccc4)cc3F)c12] | (E)-5-(2-(((5-(2-fluoro-4-phenoxybenzoyl)-7H-pyrrolo[2,3-d]pyrimidin-4-yl)amino)methyl)piperidin-1-yl)pent-3-en-2-one |
| I-510 | 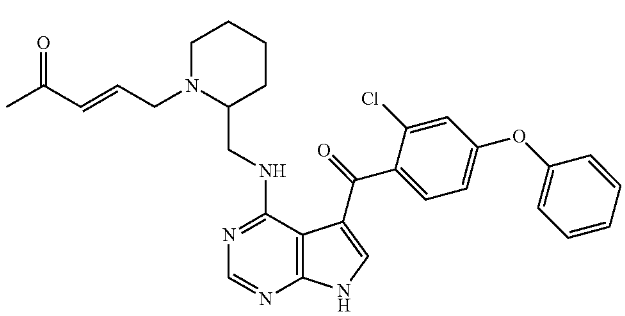 [SMILES: CC(=O)/C=C/CN1CCCCC1CNc1ncnc2[nH]cc(C(=O)c3ccc(Oc4ccccc4)cc3Cl)c12] | (E)-5-(2-(((5-(2-chloro-4-phenoxybenzoyl)-7H-pyrrolo[2,3-d]pyrimidin-4-yl)amino)methyl)piperidin-1-yl)pent-3-en-2-one |

-continued

| Cmpd No. | Structure | Chemical name |
|---|---|---|
| I-511 | 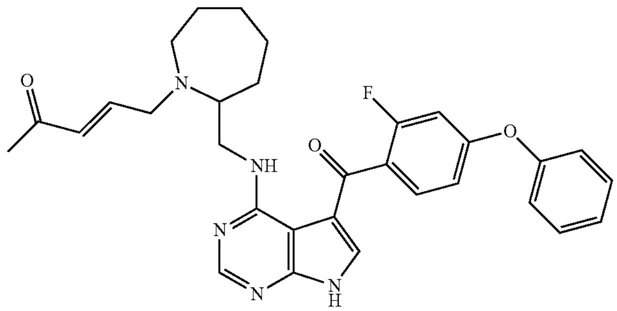 [SMILES: CC(=O)/C=C/CN1CCCCCC1CNc1ncnc2[nH]cc(C(=O)c3ccc(Oc4ccccc4)cc3F)c12] | (E)-5-(2-(((5-(2-fluoro-4-phenoxybenzoyl)-7H-pyrrolo[2,3-d]pyrimidin-4-yl)amino)methyl)azepan-1-yl)pent-3-en-2-one |
| I-512 | 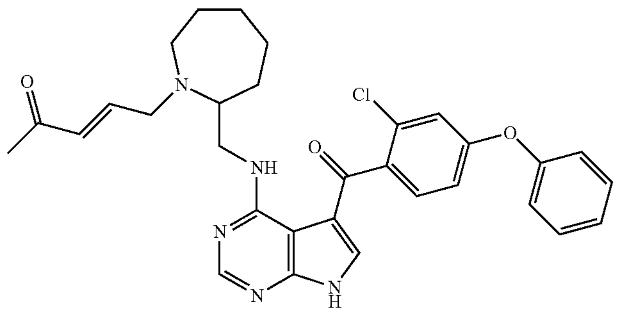 [SMILES: CC(=O)/C=C/CN1CCCCCC1CNc1ncnc2[nH]cc(C(=O)c3ccc(Oc4ccccc4)cc3Cl)c12] | (E)-5-(2-(((5-(2-chloro-4-phenoxybenzoyl)-7H-pyrrolo[2,3-d]pyrimidin-4-yl)amino)methyl)azepan-1-yl)pent-3-en-2-one |
| I-513 | 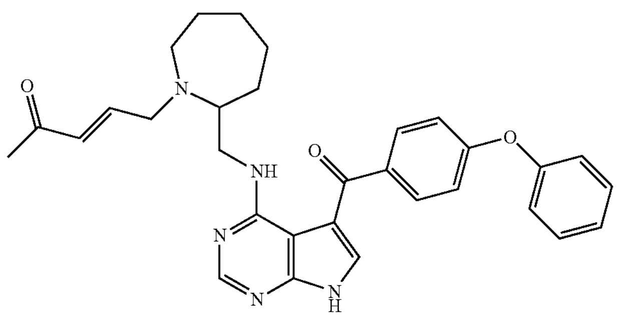 [SMILES: CC(=O)/C=C/CN1CCCCCC1CNc1ncnc2[nH]cc(C(=O)c3ccc(Oc4ccccc4)cc3)c12] | (E)-5-(2-(((5-(4-phenoxybenzoyl)-7H-pyrrolo[2,3-d]pyrimidin-4-yl)amino)methyl)azepan-1-yl)pent-3-en-2-one |
| I-514 | 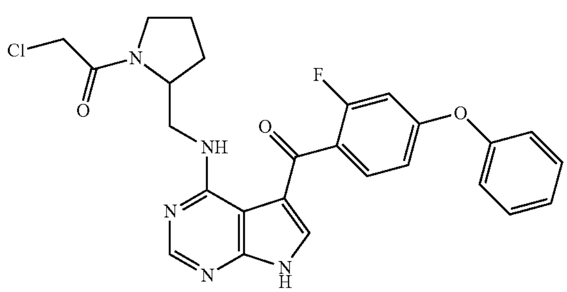 [SMILES: O=C(c1ccc(Oc2ccccc2)cc1F)c1c[nH]c2ncnc(NCC3CCCN3C(=O)CCl)c12] | 2-chloro-1-(2-(((5-(2-fluoro-4-phenoxybenzoyl)-7H-pyrrolo[2,3-d]pyrimidin-4-yl)amino)methyl)pyrrolidin-1-yl)ethan-1-one |
| I-515 | 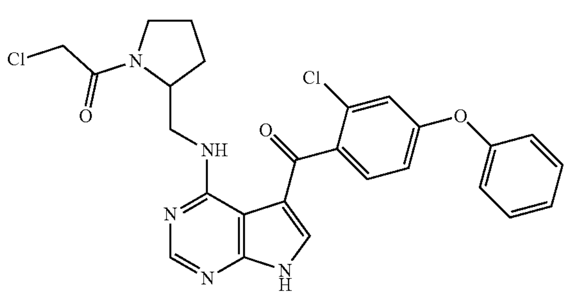 [SMILES: O=C(c1ccc(Oc2ccccc2)cc1Cl)c1c[nH]c2ncnc(NCC3CCCN3C(=O)CCl)c12] | 2-chloro-1-(2-(((5-(2-chloro-4-phenoxybenzoyl)-7H-pyrrolo[2,3-d]pyrimidin-4-yl)amino)methyl)pyrrolidin-1-yl)ethan-1-one |

-continued

| Cmpd No. | Structure | Chemical name |
|---|---|---|
| I-516 | 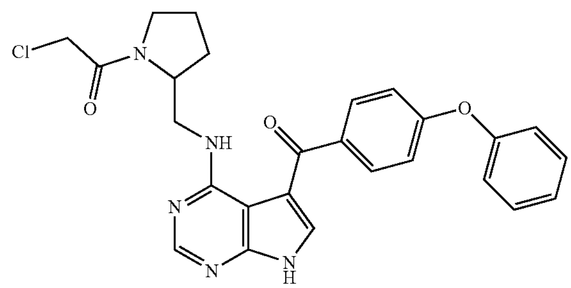 [SMILES: O=C(c1ccc(Oc2ccccc2)cc1)c1c[nH]c2ncnc(NCC3CCCN3C(=O)CCl)c12] | 2-chloro-1-(2-(((5-(4-phenoxybenzoyl)-7H-pyrrolo[2,3-d]pyrimidin-4-yl)amino)methyl)pyrrolidin-1-yl)ethan-1-one |
| I-517 | 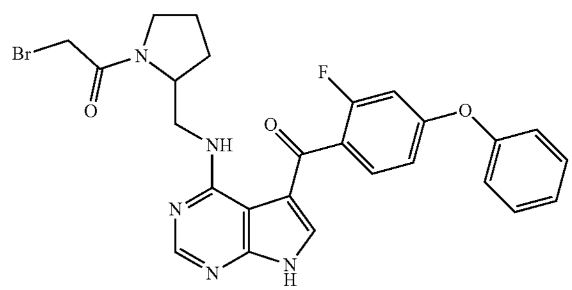 [SMILES: O=C(c1ccc(Oc2ccccc2)cc1F)c1c[nH]c2ncnc(NCC3CCCN3C(=O)CBr)c12] | 2-bromo-1-(2-(((5-(2-fluoro-4-phenoxybenzoyl)-7H-pyrrolo[2,3-d]pyrimidin-4-yl)amino)methyl)pyrrolidin-1-yl)ethan-1-one |
| I-518 | 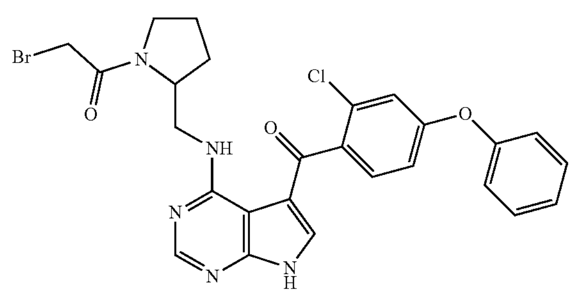 [SMILES: O=C(c1ccc(Oc2ccccc2)cc1Cl)c1c[nH]c2ncnc(NCC3CCCN3C(=O)CBr)c12] | 2-bromo-1-(2-(((5-(2-chloro-4-phenoxybenzoyl)-7H-pyrrolo[2,3-d]pyrimidin-4-yl)amino)methyl)pyrrolidin-1-yl)ethan-1-one |
| I-519 | 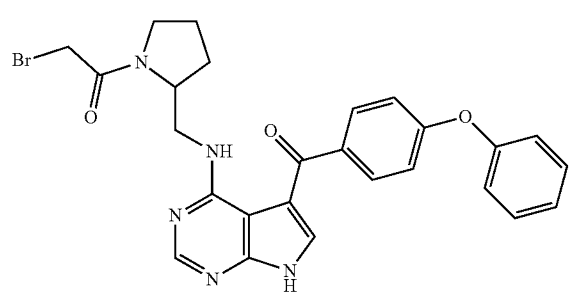 [SMILES: O=C(c1ccc(Oc2ccccc2)cc1)c1c[nH]c2ncnc(NCC3CCCN3C(=O)CBr)c12] | 2-bromo-1-(2-(((5-(4-phenoxybenzoyl)-7H-pyrrolo[2,3-d]pyrimidin-4-yl)amino)methyl)pyrrolidin-1-yl)ethan-1-one |
| I-520 | 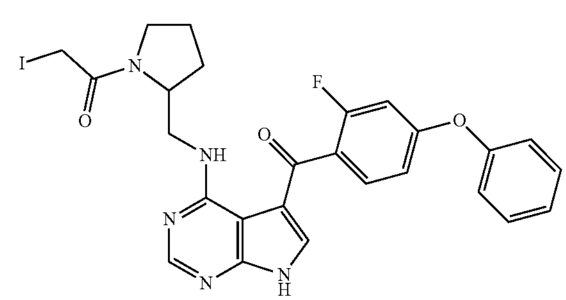 [SMILES: O=C(c1ccc(Oc2ccccc2)cc1F)c1c[nH]c2ncnc(NCC3CCCN3C(=O)CI)c12] | 1-(2-(((5-(2-fluoro-4-phenoxybenzoyl)-7H-pyrrolo[2,3-d]pyrimidin-4-yl)amino)methyl)pyrrolidin-1-yl)-2-iodoethan-1-one |

| Cmpd No. | Structure | Chemical name |
|---|---|---|
| I-521 | 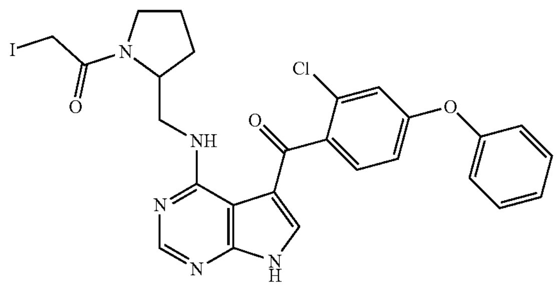 [SMILES: O=C(c1ccc(Oc2ccccc2)cc1Cl)c1c[nH]c2ncnc(NCC3CCCN3C(=O)CI)c12] | 1-(2-(((5-(2-chloro-4-phenoxybenzoyl)-7H-pyrrolo[2,3-d]pyrimidin-4-yl)amino)methyl)pyrrolidin-1-yl)-2-iodoethan-1-one |
| I-522 | 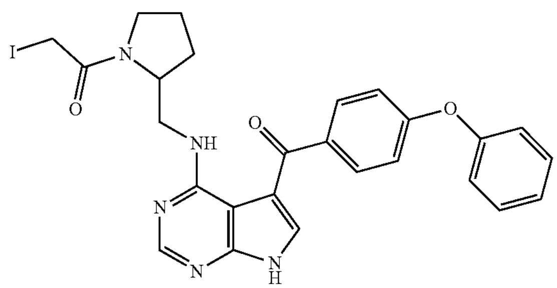 [SMILES: O=C(c1ccc(Oc2ccccc2)cc1)c1c[nH]c2ncnc(NCC3CCCN3C(=O)CI)c12] | 2-iodo-1-(2-(((5-(4-phenoxybenzoyl)-7H-pyrrolo[2,3-d]pyrimidin-4-yl)amino)methyl)pyrrolidin-1-yl)ethan-1-one |
| I-523 | 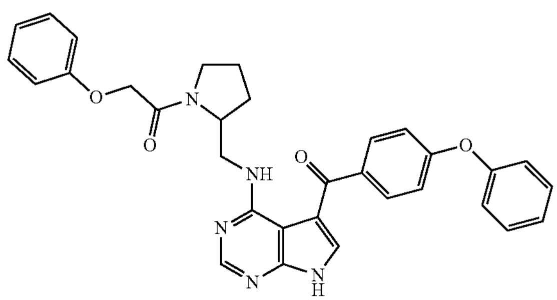 [SMILES: O=C(c1ccc(Oc2ccccc2)cc1)c1c[nH]c2ncnc(NCC3CCCN3C(=O)COc3ccccc3)c12] | 2-phenoxy-1-(2-(((5-(4-phenoxybenzoyl)-7H-pyrrolo[2,3-d]pyrimidin-4-yl)amino)methyl)pyrrolidin-1-yl)ethan-1-one |
| I-524 | 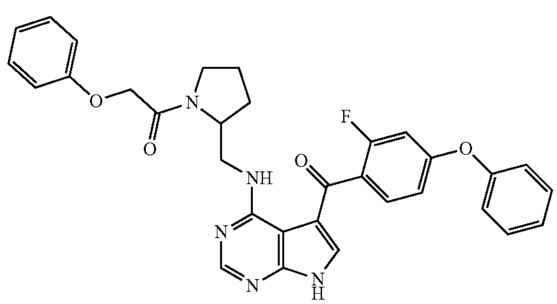 [SMILES: O=C(c1ccc(Oc2ccccc2)cc1F)c1c[nH]c2ncnc(NCC3CCCN3C(=O)COc3ccccc3)c12] | 1-(2-(((5-(2-fluoro-4-phenoxybenzoyl)-7H-pyrrolo[2,3-d]pyrimidin-4-yl)amino)methyl)pyrrolidin-1-yl)-2-phenoxyethan-1-one |
| I-525 | 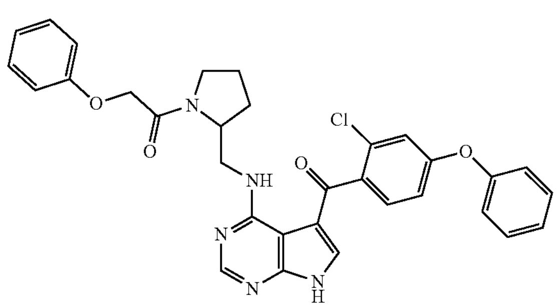 [SMILES: O=C(c1ccc(Oc2ccccc2)cc1Cl)c1c[nH]c2ncnc(NCC3CCCN3C(=O)COc3ccccc3)c12] | 1-(2-(((5-(2-chloro-4-phenoxybenzoyl)-7H-pyrrolo[2,3-d]pyrimidin-4-yl)amino)methyl)pyrrolidin-1-yl)-2-phenoxyethan-1-one |

-continued

| Cmpd No. | Structure | Chemical name |
|---|---|---|
| I-526 | 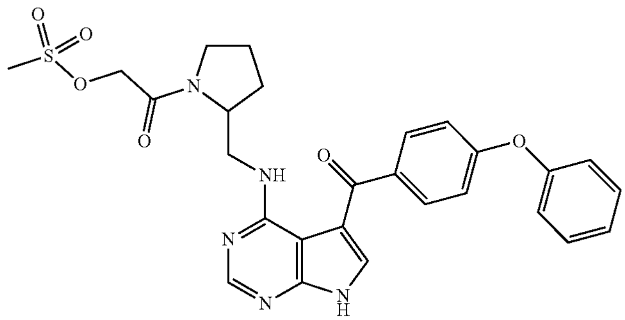 [SMILES: CS(=O)(=O)OCC(=O)N1CCCC1CNc1ncnc2[nH]cc(C(=O)c3ccc(Oc4ccccc4)cc3)c12] | 2-oxo-2-(2-(((5-(4-phenoxybenzoyl)-7H-pyrrolo[2,3-d]pyrimidin-4-yl)amino)methyl)pyrrolidin-1-yl)ethyl methanesulfonate |
| I-527 | 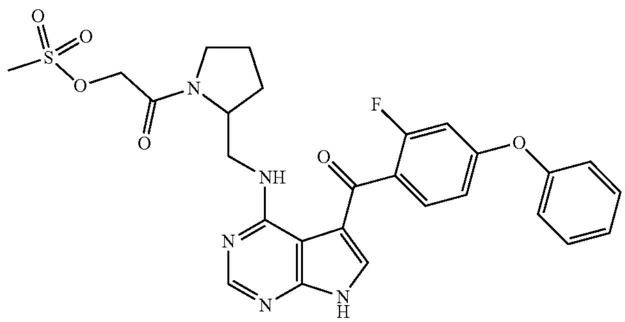 [SMILES: CS(=O)(=O)OCC(=O)N1CCCC1CNc1ncnc2[nH]cc(C(=O)c3ccc(Oc4ccccc4)cc3F)c12] | 2-(2-(((5-(2-fluoro-4-phenoxybenzoyl)-7H-pyrrolo[2,3-d]pyrimidin-4-yl)amino)methyl)pyrrolidin-1-yl)-2-oxoethyl methanesulfonate |
| I-528 | 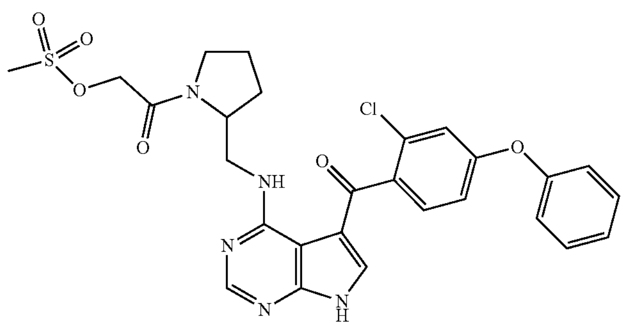 [SMILES: CS(=O)(=O)OCC(=O)N1CCCC1CNc1ncnc2[nH]cc(C(=O)c3ccc(Oc4ccccc4)cc3Cl)c12] | 2-(2-(((5-(2-chloro-4-phenoxybenzoyl)-7H-pyrrolo[2,3-d]pyrimidin-4-yl)amino)methyl)pyrrolidin-1-yl)-2-oxoethyl methanesulfonate |
| I-529 | 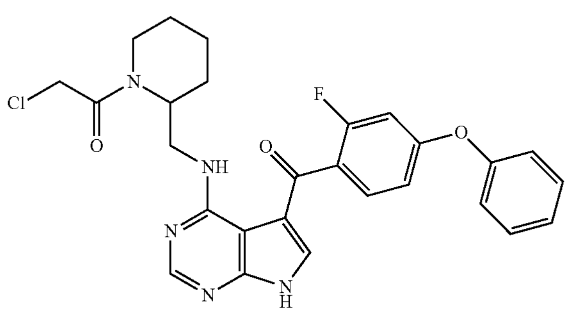 | 2-chloro-1-(2-(((5-(2-fluoro-4-phenoxybenzoyl)-7H-pyrrolo[2,3-d]pyrimidin-4-yl)amino)methyl)piperidin-1-yl)ethan-1-one |
| I-530 | 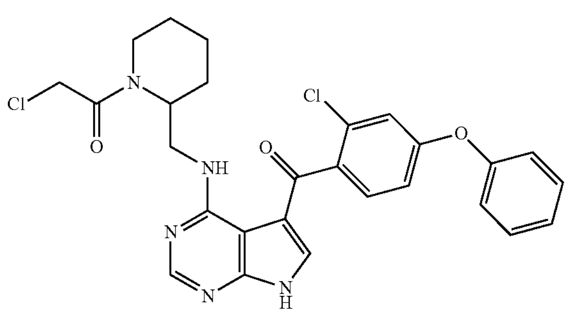 | 2-chloro-1-(2-(((5-(2-chloro-4-phenoxybenzoyl)-7H-pyrrolo[2,3-d]pyrimidin-4-yl)amino)methyl)piperidin-1-yl)ethan-1-one |

| Cmpd No. | Structure | Chemical name |
| --- | --- | --- |
| I-531 | 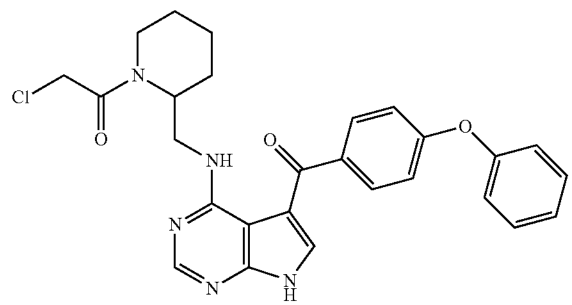 | 2-chloro-1-(2-(((5-(4-phenoxybenzoyl)-7H-pyrrolo[2,3-d]pyrimidin-4-yl)amino)methyl)piperidin-1-yl)ethan-1-one |
| I-532 | 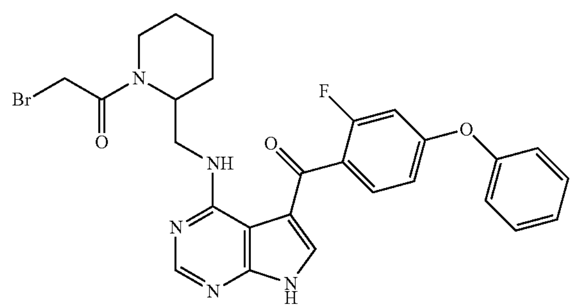 [SMILES: O=C(c1ccc(Oc2ccccc2)cc1F)c1c[nH]c2ncnc(NCC3CCCCN3C(=O)CCl)c12] | 2-bromo-1-(2-(((5-(2-fluoro-4-phenoxybenzoyl)-7H-pyrrolo[2,3-d]pyrimidin-4-yl)amino)methyl)piperidin-1-yl)ethan-1-one |
| I-533 | 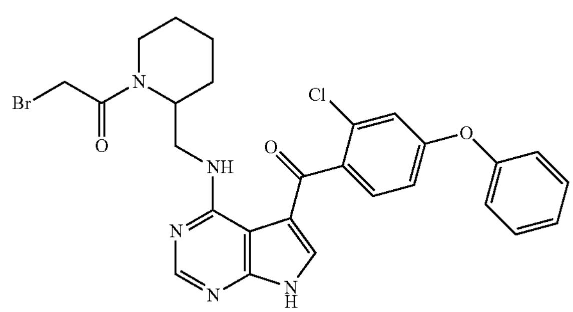 [SMILES: O=C(c1ccc(Oc2ccccc2)cc1Cl)c1c[nH]c2ncnc(NCC3CCCCN3C(=O)CCl)c12] | 2-bromo-1-(2-(((5-(2-chloro-4-phenoxybenzoyl)-7H-pyrrolo[2,3-d]pyrimidin-4-yl)amino)methyl)piperidin-1-yl)ethan-1-one |
| I-534 | 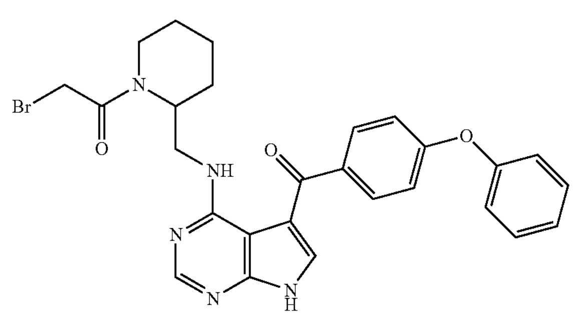 [SMILES: O=C(c1ccc(Oc2ccccc2)cc1)c1c[nH]c2ncnc(NCC3CCCCN3C(=O)CCl)c12] | 2-bromo-1-(2-(((5-(4-phenoxybenzoyl)-7H-pyrrolo[2,3-d]pyrimidin-4-yl)amino)methyl)piperidin-1-yl)ethan-1-one |
| I-535 | 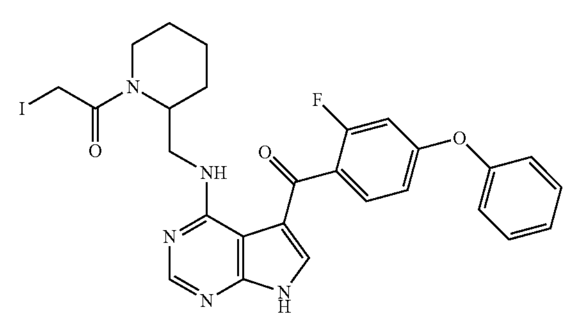 [SMILES: O=C(c1ccc(Oc2ccccc2)cc1F)c1c[nH]c2ncnc(NCC3CCCCN3C(=O)CI)c12] | 1-(2-(((5-(2-fluoro-4-phenoxybenzoyl)-7H-pyrrolo[2,3-d]pyrimidin-4-yl)amino)methyl)piperidin-1-yl)-2-iodoethan-1-one |

| Cmpd No. | Structure | Chemical name |
|---|---|---|
| I-536 | 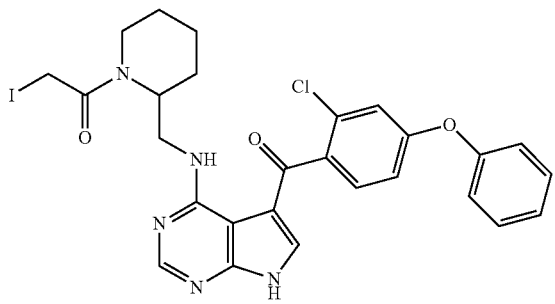 [SMILES: O=C(c1ccc(Oc2ccccc2)cc1Cl)c1c[nH]c2ncnc(NCC3CCCCN3C(=O)CI)c12] | 1-(2-(((5-(2-chloro-4-phenoxybenzoyl)-7H-pyrrolo[2,3-d]pyrimidin-4-yl)amino)methyl)piperidin-1-yl)-2-iodoethan-1-one |
| I-537 | 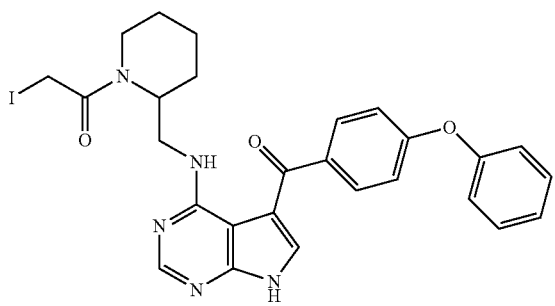 [SMILES: O=C(c1ccc(Oc2ccccc2)cc1)c1c[nH]c2ncnc(NCC3CCCCN3C(=O)CI)c12] | 2-iodo-1-(2-(((5-(4-phenoxybenzoyl)-7H-pyrrolo[2,3-d]pyrimidin-4-yl)amino)methyl)piperidin-1-yl)ethan-1-one |
| I-538 | 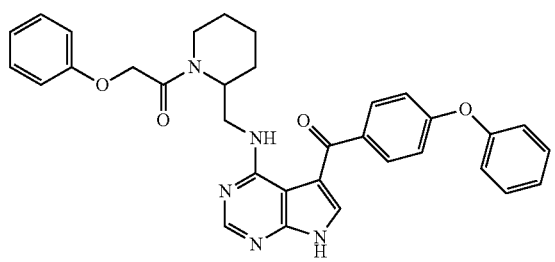 [SMILES: O=C(c1ccc(Oc2ccccc2)cc1)c1c[nH]c2ncnc(NCC3CCCCN3C(=O)COc3ccccc3)c12] | 2-phenoxy-1-(2-(((5-(4-phenoxybenzoyl)-7H-pyrrolo[2,3-d]pyrimidin-4-yl)amino)methyl)piperidin-1-yl)ethan-1-one |
| I-539 | 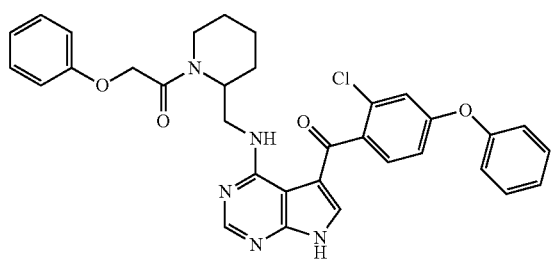 [SMILES: O=C(c1ccc(Oc2ccccc2)cc1Cl)c1c[nH]c2ncnc(NCC3CCCCN3C(=O)COc3ccccc3)c12] | 1-(2-(((5-(2-chloro-4-phenoxybenzoyl)-7H-pyrrolo[2,3-d]pyrimidin-4-yl)amino)methyl)piperidin-1-yl)-2-phenoxyethan-1-one |
| I-540 | 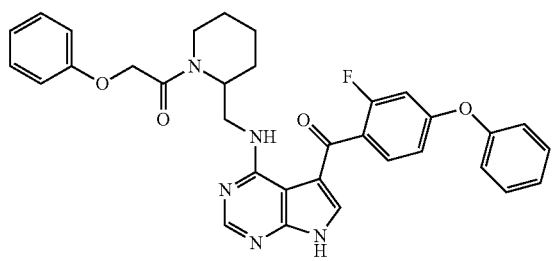 [SMILES: O=C(c1ccc(Oc2ccccc2)cc1F)c1c[nH]c2ncnc(NCC3CCCCN3C(=O)COc3ccccc3)c12] | 1-(2-(((5-(2-fluoro-4-phenoxybenzoyl)-7H-pyrrolo[2,3-d]pyrimidin-4-yl)amino)methyl)piperidin-1-yl)-2-phenoxyethan-1-one |

| Cmpd No. | Structure | Chemical name |
|---|---|---|
| I-541 | 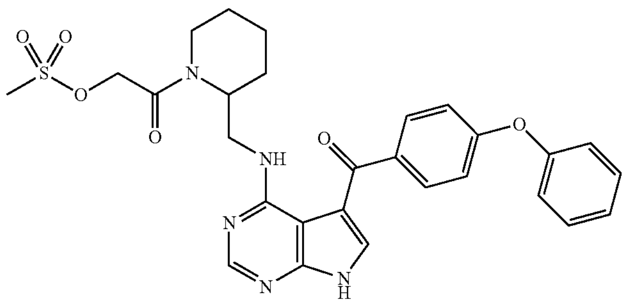 [SMILES: CS(=O)(=O)OCC(=O)N1CCCCC1CNc1ncnc2[nH]cc(C(=O)c3ccc(Oc4ccccc4)cc3)c12] | 2-oxo-2-(2-(((5-(4-phenoxybenzoyl)-7H-pyrrolo[2,3-d]pyrimidin-4-yl)amino)methyl)piperidin-1-yl)ethyl methanesulfonate |
| I-542 | 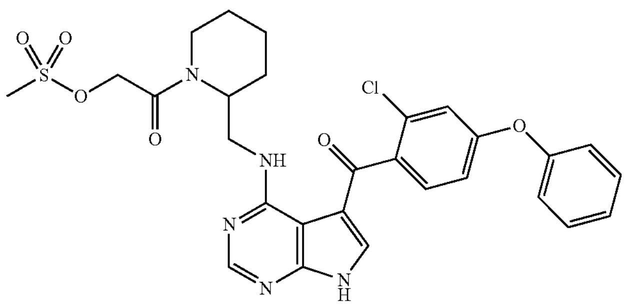 [SMILES: CS(=O)(=O)OCC(=O)N1CCCCC1CNc1ncnc2[nH]cc(C(=O)c3ccc(Oc4ccccc4)cc3Cl)c12] | 2-(2-(((5-(2-chloro-4-phenoxybenzoyl)-7H-pyrrolo[2,3-d]pyrimidin-4-yl)amino)methyl)piperidin-oxoethyl methanesulfonate |
| I-543 | 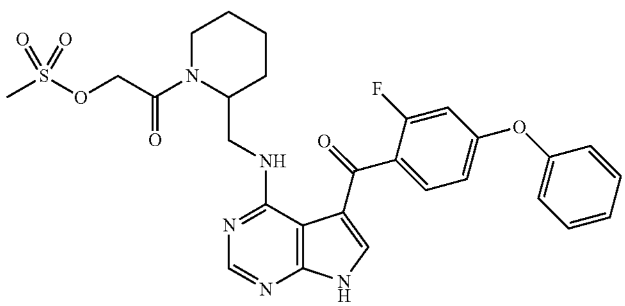 [SMILES: CS(=O)(=O)OCC(=O)N1CCCCC1CNc1ncnc2[nH]cc(C(=O)c3ccc(Oc4ccccc4)cc3F)c12] | 2-(2-(((5-(2-fluoro-4-phenoxybenzoyl)-7H-pyrrolo[2,3-d]pyrimidin-4-yl)amino)methyl)piperidin-1-yl)-2-oxoethyl methanesulfonate |
| I-544 | 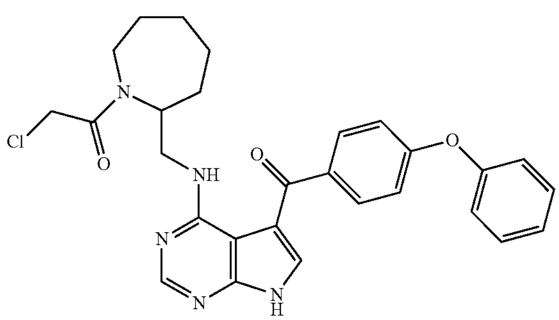 [SMILES: O=C(c1ccc(Oc2ccccc2)cc1)c1c[nH]c2ncnc(NCC3CCCCCN3C(=O)CCl)c12] | 2-chloro-1-(2-(((5-(4-phenoxybenzoyl)-7H-pyrrolo[2,3-d]pyrimidin-4-yl)amino)methyl)azepan-1-yl)ethan-1-one |
| I-545 | 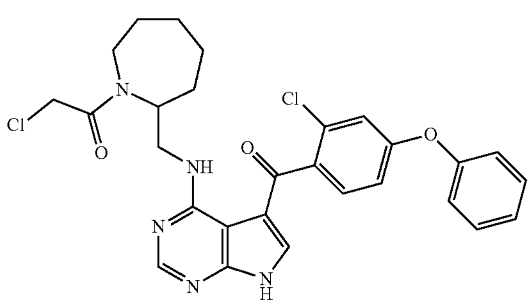 [SMILES: O=C(c1ccc(Oc2ccccc2)cc1Cl)c1c[nH]c2ncnc(NCC3CCCCCN3C(=O)CCl)c12] | 2-chloro-1-(2-(((5-(2-chloro-4-phenoxybenzoyl)-7H-pyrrolo[2,3-d]pyrimidin-4-yl)amino)methyl)azepan-1-yl)ethan-1-one |

-continued

| Cmpd No. | Structure | Chemical name |
|---|---|---|
| I-546 | 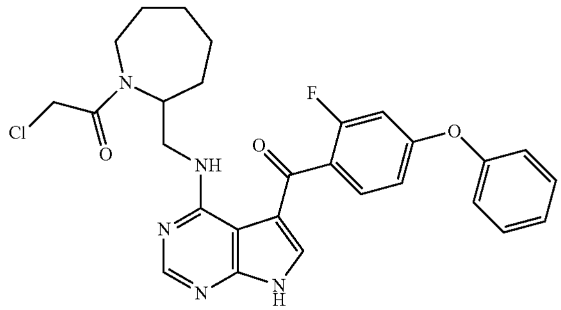 | 2-chloro-1-(2-(((5-(2-fluoro-4-phenoxybenzoyl)-7H-pyrrolo[2,3-d]pyrimidin-4-yl)amino)methyl)azepan-1-yl)ethan-1-one |
| I-547 | 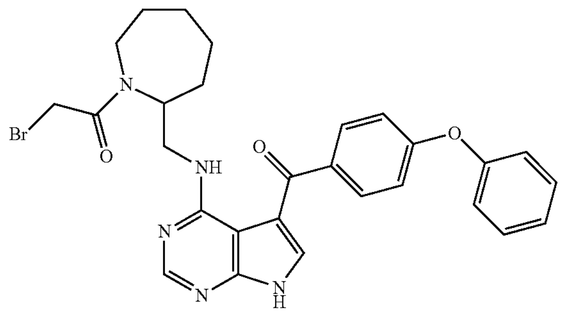 | 2-bromo-1-(2-(((5-(4-phenoxybenzoyl)-7H-pyrrolo[2,3-d]pyrimidin-4-yl)amino)methyl)azepan-1-yl)ethan-1-one |
| I-548 | 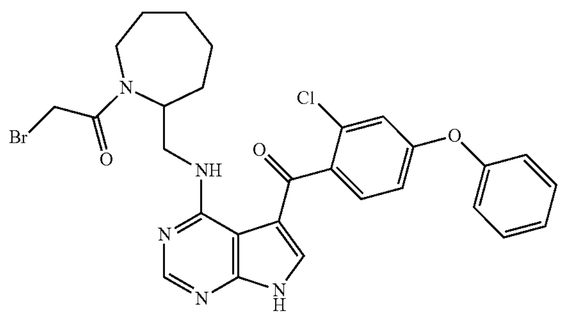 | 2-bromo-1-(2-(((5-(2-chloro-4-phenoxybenzoyl)-7H-pyrrolo[2,3-d]pyrimidin-4-yl)amino)methyl)azepan-1-yl)ethan-1-one |
| I-549 | 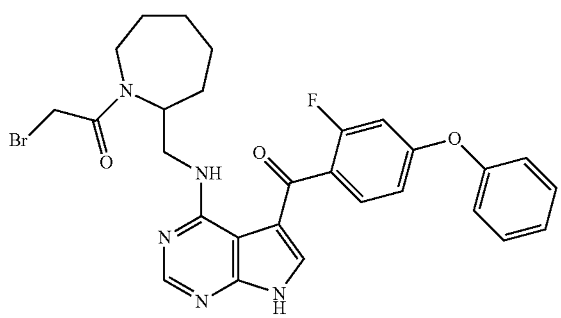 [SMILES: O=C(c1ccc(Oc2ccccc2)cc1F)c1c[nH]c2ncnc(NCC3CCCCCN3C(=O)CCl)c12] | 2-bromo-1-(2-(((5-(2-fluoro-4-phenoxybenzoyl)-7H-pyrrolo[2,3-d]pyrimidin-4-yl)amino)methyl)azepan-1-yl)ethan-1-one |
| I-550 | 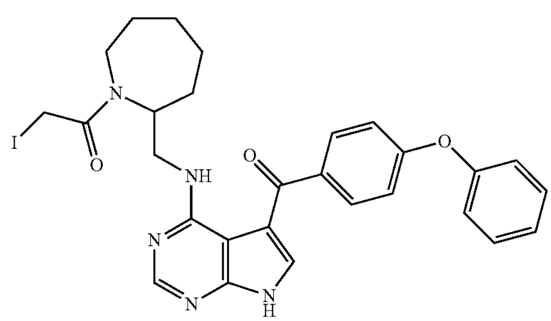 [SMILES: O=C(c1ccc(Oc2ccccc2)cc1)c1c[nH]c2ncnc(NCC3CCCCCN3C(=O)CI)c12] | 2-iodo-1-(2-(((5-(4-phenoxybenzoyl)-7H-pyrrolo[2,3-d]pyrimidin-4-yl)amino)methyl)azepan-1-yl)ethan-1-one |

-continued

| Cmpd No. | Structure | Chemical name |
|---|---|---|
| I-551 | 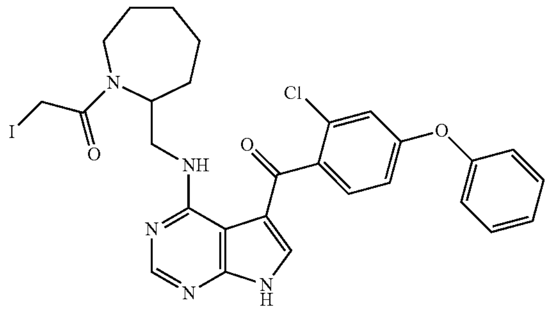 [SMILES: O=C(c1ccc(Oc2ccccc2)cc1Cl)c1c[nH]c2ncnc(NCC3CCCCCN3C(=O)CI)c12] | 1-(2-(((5-(2-chloro-4-phenoxybenzoyl)-7H-pyrrolo[2,3-d]pyrimidin-4-yl)amino)methyl)azepan-iodoethan-1-one |
| I-552 | 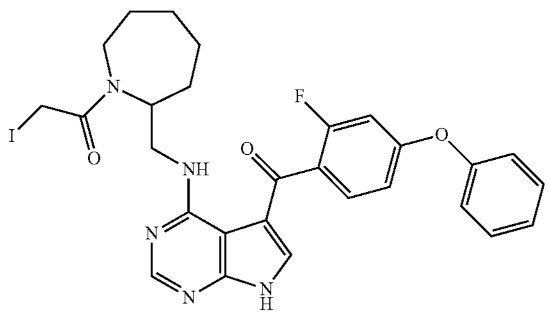 [SMILES: O=C(c1ccc(Oc2ccccc2)cc1F)c1c[nH]c2ncnc(NCC3CCCCCN3C(=O)CI)c12] | 1-(2-(((5-(2-fluoro-4-phenoxybenzoyl)-7H-pyrrolo[2,3-d]pyrimidin-4-yl)amino)methyl)azepan-1-yl)-2-iodoethan-1-one |
| I-553 | 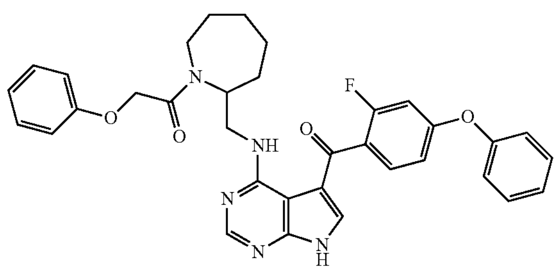 [SMILES: O=C(c1ccc(Oc2ccccc2)cc1F)c1c[nH]c2ncnc(NCC3CCCCCN3C(=O)COc3ccccc3)c12] | 1-(2-(((5-(2-fluoro-4-phenoxybenzoyl)-7H-pyrrolo[2,3-d]pyrimidin-4-yl)amino)methyl)azepan-1-yl)-2-phenoxyethan-1-one |
| I-554 | 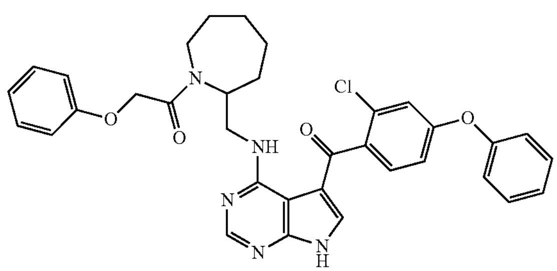 [SMILES: O=C(c1ccc(Oc2ccccc2)cc1Cl)c1c[nH]c2ncnc(NCC3CCCCCN3C(=O)COc3ccccc3)c12] | 1-(2-(((5-(2-chloro-4-phenoxybenzoyl)-7H-pyrrolo[2,3-d]pyrimidin-4-yl)amino)methyl)azepan-1-yl)-2-phenoxyethan-1-one |
| I-555 | 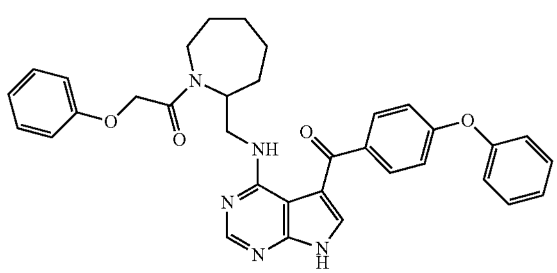 [SMILES: O=C(c1ccc(Oc2ccccc2)cc1)c1c[nH]c2ncnc(NCC3CCCCCN3C(=O)COc3ccccc3)c12] | 2-phenoxy-1-(2-(((5-(4-phenoxybenzoyl)-7H-pyrrolo[2,3-d]pyrimidin-4-yl)amino)methyl)azepan-1-yl)ethan-1-one |

| Cmpd No. | Structure | Chemical name |
| --- | --- | --- |
| I-556 | 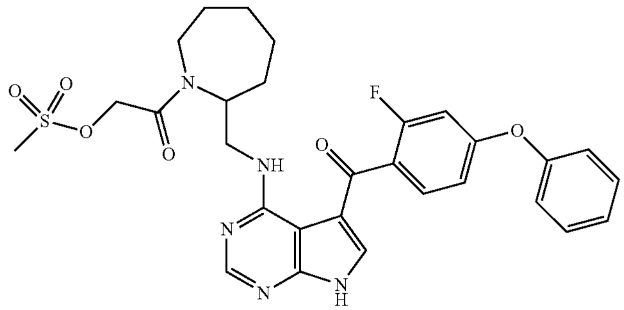 [SMILES: CS(=O)(=O)OCC(=O)N1CCCCCC1CNc1ncnc2[nH]cc(C(=O)c3ccc(Oc4ccccc4)cc3F)c12] | 2-(2-(((5-(2-fluoro-4-phenoxybenzoyl)-7H-pyrrolo[2,3-d]pyrimidin-4-yl)amino)methyl)azepan-1-yl)-2-oxoethyl methanesulfonate |
| I-557 | 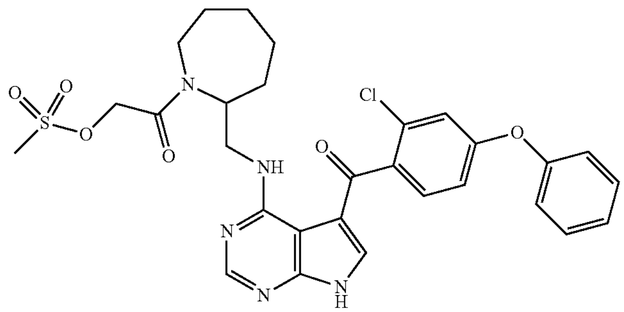 [SMILES: CS(=O)(=O)OCC(=O)N1CCCCCC1CNc1ncnc2[nH]cc(C(=O)c3ccc(Oc4ccccc4)cc3Cl)c12] | 2-(2-(((5-(2-chloro-4-phenoxybenzoyl)-7H-pyrrolo[2,3-d]pyrimidin-4-yl)amino)methyl)azepan-1-yl)-2-oxoethyl methanesulfonate |
| I-558 | 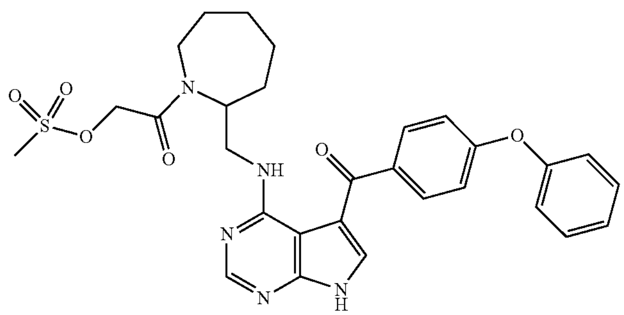 [SMILES: CS(=O)(=O)OCC(=O)N1CCCCCC1CNc1ncnc2[nH]cc(C(=O)c3ccc(Oc4ccccc4)cc3)c12] | 2-oxo-2-(2-(((5-(4-phenoxybenzoyl)-7H-pyrrolo[2,3-d]pyrimidin-4-yl)amino)methyl)azepan-1-yl)ethyl methanesulfonate |
| I-559 | 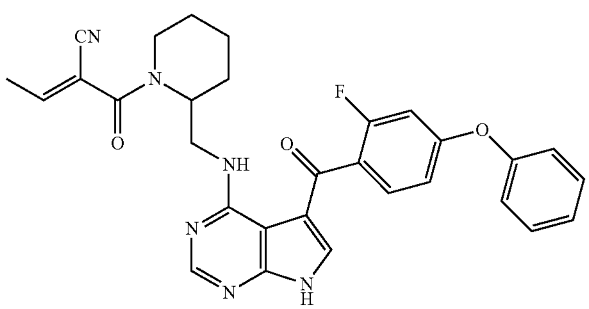 [SMILES: C/C=C(\C#N)C(=O)N1CCCCC1CNc1ncnc2[nH]cc(C(=O)c3ccc(Oc4ccccc4)cc3F)c12] | (E)-2-(2-(((5-(2-fluoro-4-phenoxybenzoyl)-7H-pyrrolo[2,3-d]pyrimidin-4-yl)amino)methyl)piperidine-1-carbonyl)but-2-enenitrile |
| I-560 | 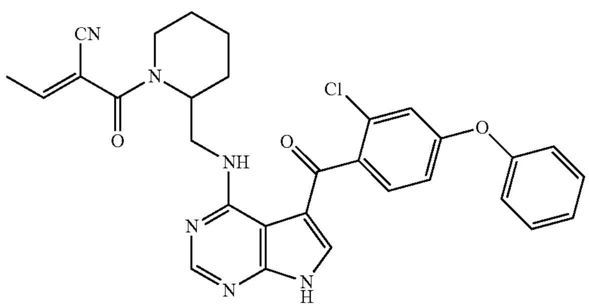 [SMILES: C/C=C(\C#N)C(=O)N1CCCCC1CNc1ncnc2[nH]cc(C(=O)c3ccc(Oc4ccccc4)cc3Cl)c12] | (E)-2-(2-(((5-(2-chloro-4-phenoxybenzoyl)-7H-pyrrolo[2,3-d]pyrimidin-4-yl)amino)methyl)piperidine-1-carbonyl)but-2-enenitrile |

-continued

| Cmpd No. | Structure | Chemical name |
|---|---|---|
| I-561 | 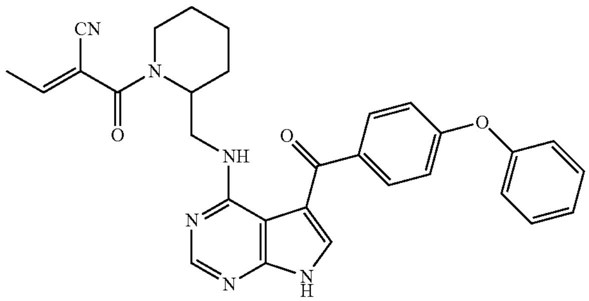 [SMILES: C/C=C(\C#N)C(=O)N1CCCCC1CNc1ncnc2[nH]cc(C(=O)c3ccc(Oc4ccccc4)cc3)c12] | (E)-2-(2-(((5-(4-phenoxybenzoyl)-7H-pyrrolo[2,3-d]pyrimidin-4-yl)amino)methyl)piperidine-1-carbonyl)but-2-enenitrile |
| I-562 | 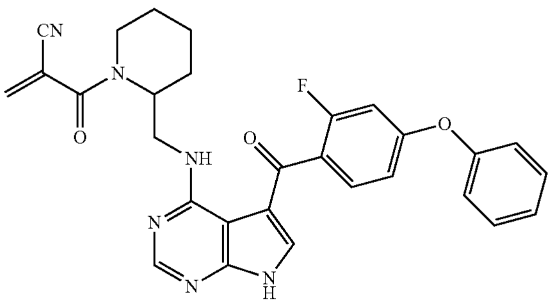 [SMILES: C=C(C#N)C(=O)N1CCCCC1CNc1ncnc2[nH]cc(C(=O)c3ccc(Oc4ccccc4)cc3F)c12] | 2-(2-(((5-(2-fluoro-4-phenoxybenzoyl)-7H-pyrrolo[2,3-d]pyrimidin-4-yl)amino)methyl)piperidine-1-carbonyl)acrylonitrile |
| I-563 | 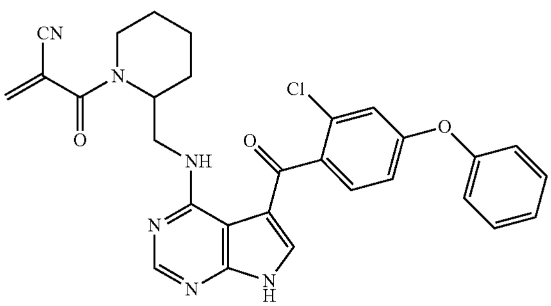 | 2-(2-(((5-(2-chloro-4-phenoxybenzoyl)-7H-pyrrolo[2,3-d]pyrimidin-4-yl)amino)methyl)piperidine-1-carbonyl)acrylonitrile |
| I-564 | 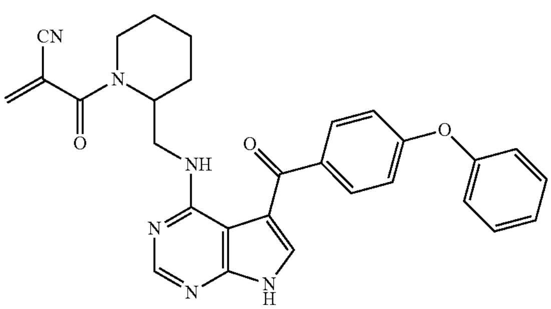 [SMILES: C=C(C#N)C(=O)N1CCCCC1CNc1ncnc2[nH]cc(C(=O)c3ccc(Oc4ccccc4)cc3)c12] | 2-(2-(((5-(4-phenoxybenzoyl)-7H-pyrrolo[2,3-d]pyrimidin-4-yl)amino)methyl)piperidine-1-carbonyl)acrylonitrile |
| I-565 | 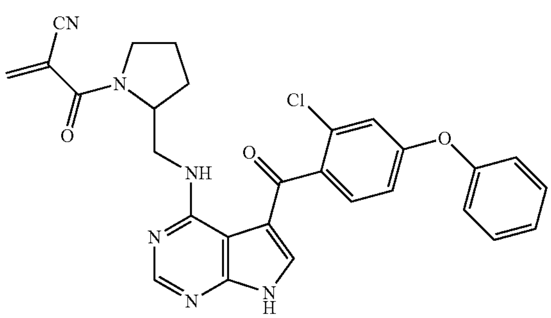 | 2-(2-(((5-(2-chloro-4-phenoxybenzoyl)-7H-pyrrolo[2,3-d]pyrimidin-4-yl)amino)methyl)pyrrolidine-1-carbonyl)acrylonitrile |

-continued

| Cmpd No. | Structure | Chemical name |
|---|---|---|
| I-566 | 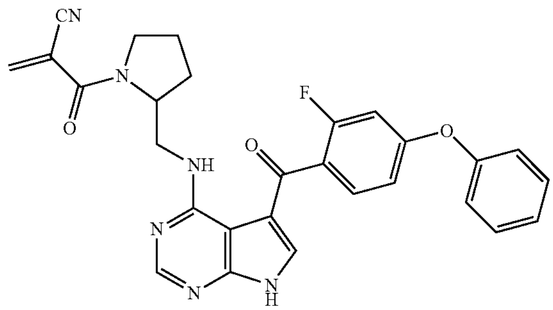 [SMILES: C=C(C#N)C(=O)N1CCCC1CNc1ncnc2[nH]cc(C(=O)c3ccc(Oc4ccccc4)cc3F)c12] | 2-(2-(((5-(2-fluoro-4-phenoxybenzoyl)-7H-pyrrolo[2,3-d]pyrimidin-4-yl)amino)methyl)pyrrolidine-1-carbonyl)acrylonitrile |
| I-567 | 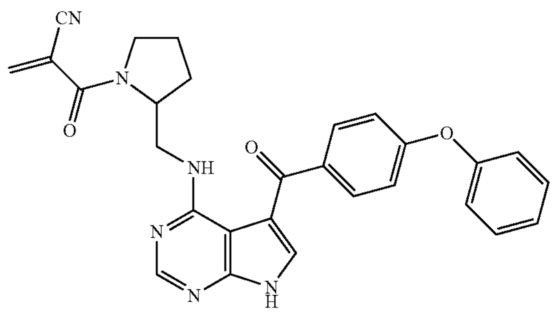 [SMILES: C=C(C#N)C(=O)N1CCCC1CNc1ncnc2[nH]cc(C(=O)c3ccc(Oc4ccccc4)cc3)c12] | 2-(2-(((5-(4-phenoxybenzoyl)-7H-pyrrolo[2,3-d]pyrimidin-4-yl)amino)methyl)pyrrolidine-1-carbonyl)acrylonitrile |
| I-568 | 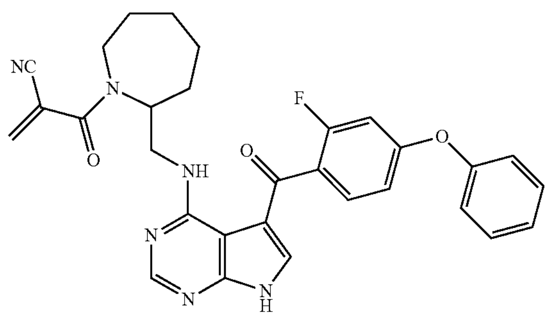 [SMILES: C=C(C#N)C(=O)N1CCCCCC1CNc1ncnc2[nH]cc(C(=O)c3ccc(Oc4ccccc4)cc3F)c12] | 2-(2-(((5-(2-fluoro-4-phenoxybenzoyl)-7H-pyrrolo[2,3-d]pyrimidin-4-yl)amino)methyl)azepane-1-carbonyl)acrylonitrile |
| I-569 | 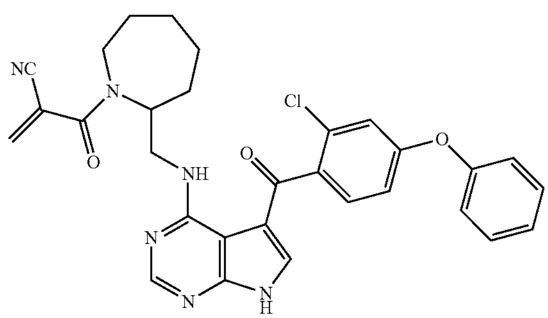 [SMILES: C=C(C#N)C(=O)N1CCCCCC1CNc1ncnc2[nH]cc(C(=O)c3ccc(Oc4ccccc4)cc3Cl)c12] | 2-(2-(((5-(2-chloro-4-phenoxybenzoyl)-7H-pyrrolo[2,3-d]pyrimidin-4-yl)amino)methyl)azepane-1-carbonyl)acrylonitrile |
| I-570 | 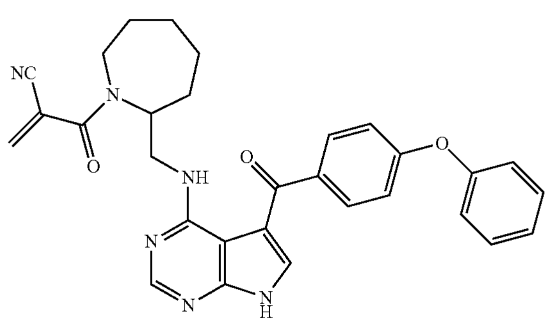 [SMILES: C=C(C#N)C(=O)N1CCCCCC1CNc1ncnc2[nH]cc(C(=O)c3ccc(Oc4ccccc4)cc3)c12] | 2-(2-(((5-(4-phenoxybenzoyl)-7H-pyrrolo[2,3-d]pyrimidin-4-yl)amino)methyl)azepane-1-carbonyl)acrylonitrile |

-continued

| Cmpd No. | Structure | Chemical name |
| --- | --- | --- |
| I-571 | 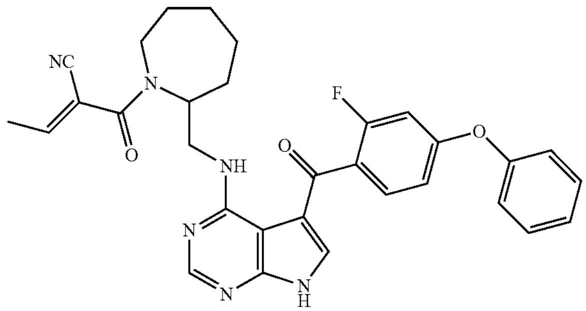 [SMILES: C/C=C(\C#N)C(=O)N1CCCCCC1CNc1ncnc2[nH]cc(C(=O)c3ccc(Oc4ccccc4)cc3F)c12] | (E)-2-(2-(((5-(2-fluoro-4-phenoxybenzoyl)-7H-pyrrolo[2,3-d]pyrimidin-4-yl)amino)methyl)azepane-1-carbonyl)but-2-enenitrile |
| I-572 | 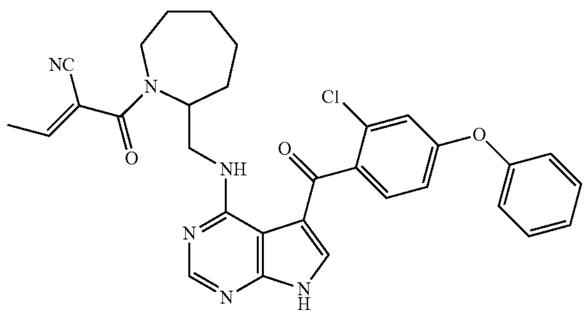 [SMILES: C/C=C(\C#N)C(=O)N1CCCCCC1CNc1ncnc2[nH]cc(C(=O)c3ccc(Oc4ccccc4)cc3Cl)c12] | (E)-2-(2-(((5-(2-chloro-4-phenoxybenzoyl)-7H-pyrrolo[2,3-d]pyrimidin-4-yl)amino)methyl)azepane-1-carbonyl)but-2-enenitrile |
| I-573 | 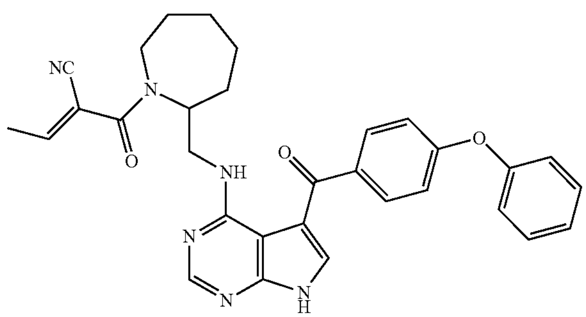 [SMILES: C/C=C(\C#N)C(=O)N1CCCCCC1CNc1ncnc2[nH]cc(C(=O)c3ccc(Oc4ccccc4)cc3)c12] | (E)-2-(2-(((5-(4-phenoxybenzoyl)-7H-pyrrolo[2,3-d]pyrimidin-4-yl)amino)methyl)azepane-1-carbonyl)but-2-enenitrile |
| I-574 | 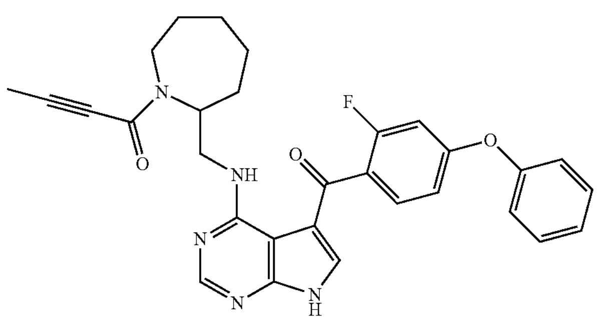 [SMILES: CC#CC(=O)N1CCCCCC1CNc1ncnc2[nH]cc(C(=O)c3ccc(Oc4ccccc4)cc3F)c12] | 1-(2-(((5-(2-fluoro-4-phenoxybenzoyl)-7H-pyrrolo[2,3-d]pyrimidin-4-yl)amino)methyl)azepan-1-yl)but-2-yn-1-one |
| I-575 | 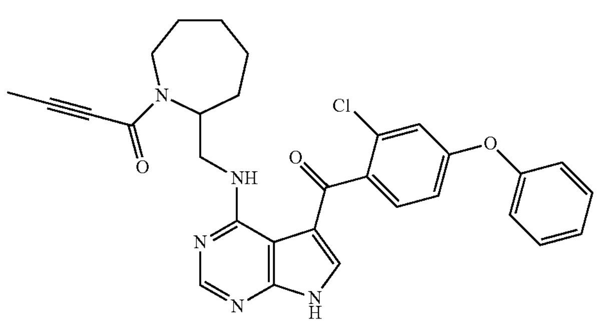 [SMILES: CC#CC(=O)N1CCCCCC1CNc1ncnc2[nH]cc(C(=O)c3ccc(Oc4ccccc4)cc3Cl)c12] | 1-(2-(((5-(2-chloro-4-phenoxybenzoyl)-7H-pyrrolo[2,3-d]pyrimidin-4-yl)amino)methyl)azepan-1-yl)but-2-yn-1-one |

-continued

| Cmpd No. | Structure | Chemical name |
|---|---|---|
| I-576 | 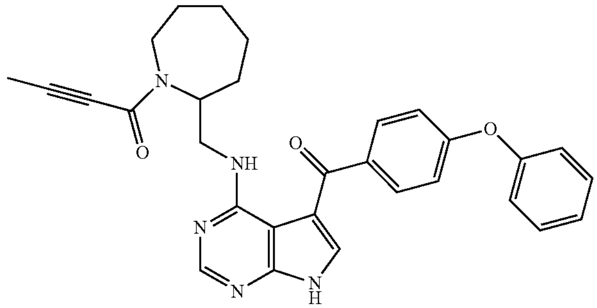 [SMILES: CC#CC(=O)N1CCCCCC1CNc1ncnc2[nH]cc(C(=O)c3ccc(Oc4ccccc4)cc3)c12] | 1-(2-(((5-(4-phenoxybenzoyl)-7H-pyrrolo[2,3-d]pyrimidin-4-yl)amino)methyl)azepan-1-yl)but-2-yn-1-one |
| I-577 | 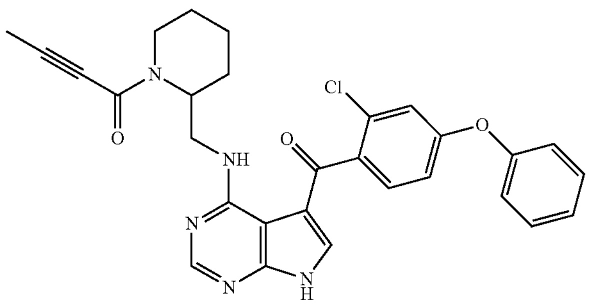 [SMILES: CC#CC(=O)N1CCCCC1CNc1ncnc2[nH]cc(C(=O)c3ccc(Oc4ccccc4)cc3Cl)c12] | 1-(2-(((5-(2-chloro-4-phenoxybenzoyl)-7H-pyrrolo[2,3-d]pyrimidin-4-yl)amino)methyl)piperidin-1-yl)but-2-yn-1-one |
| I-578 | 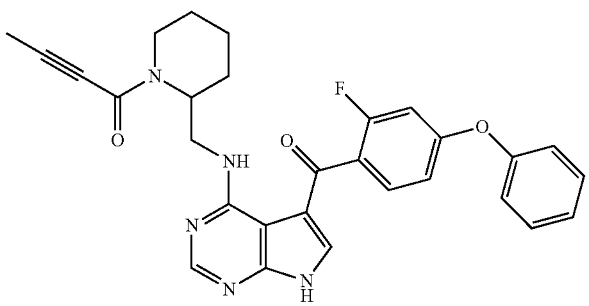 [SMILES: CC#CC(=O)N1CCCCC1CNc1ncnc2[nH]cc(C(=O)c3ccc(Oc4ccccc4)cc3F)c12] | 1-(2-(((5-(2-fluoro-4-phenoxybenzoyl)-7H-pyrrolo[2,3-d]pyrimidin-4-yl)amino)methyl)piperidin-1-yl)but-2-yn-1-one |
| I-579 | 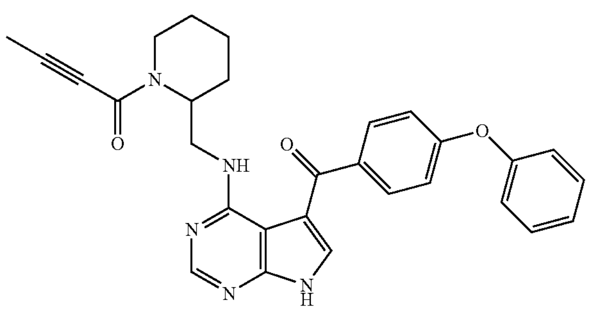 [SMILES: CC#CC(=O)N1CCCCC1CNc1ncnc2[nH]cc(C(=O)c3ccc(Oc4ccccc4)cc3)c12] | 1-(2-(((5-(4-phenoxybenzoyl)-7H-pyrrolo[2,3-d]pyrimidin-4-yl)amino)methyl)piperidin-1-yl)but-2-yn-1-one |
| I-580 | 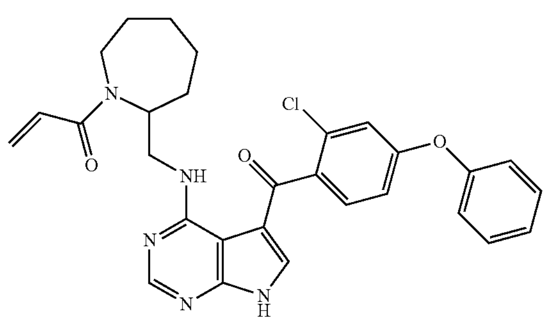 [SMILES: C=CC(=O)N1CCCCCC1CNc1ncnc2[nH]cc(C(=O)c3ccc(Oc4ccccc4)cc3Cl)c12] | 1-(2-(((5-(2-chloro-4-phenoxybenzoyl)-7H-pyrrolo[2,3-d]pyrimidin-4-yl)amino)methyl)azepan-1-yl)prop-2-en-1-one |

| Cmpd No. | Structure | Chemical name |
|---|---|---|
| I-581 | 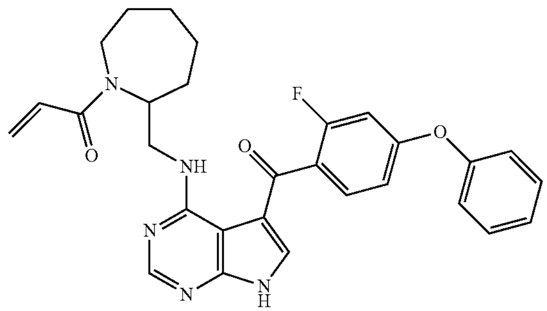 [SMILES: C=CC(=O)N1CCCCCC1CNc1ncnc2[nH]cc(C(=O)c3ccc(Oc4ccccc4)cc3F)c12] | 1-(2-(((5-(2-fluoro-4-phenoxybenzoyl)-7H-pyrrolo[2,3-d]pyrimidin-4-yl)amino)methyl)azepan-1-yl)prop-2-en-1-one |
| I-582 | 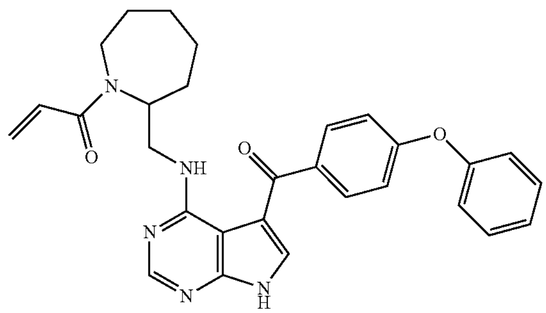 [SMILES: C=CC(=O)N1CCCCCC1CNc1ncnc2[nH]cc(C(=O)c3ccc(Oc4ccccc4)cc3)c12] | 1-(2-(((5-(4-phenoxybenzoyl)-7H-pyrrolo[2,3-d]pyrimidin-4-yl)amino)methyl)azepan-1-yl)prop-2-en-1-one |
| I-583 | 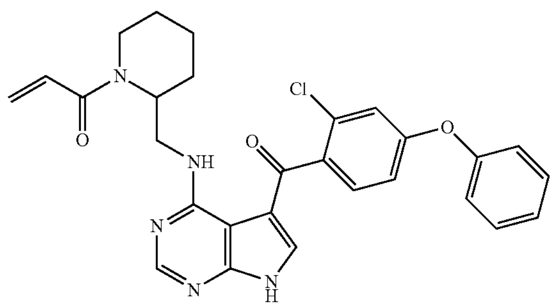 [SMILES: C=CC(=O)N1CCCCC1CNc1ncnc2[nH]cc(C(=O)c3ccc(Oc4ccccc4)cc3Cl)c12] | 1-(2-(((5-(2-chloro-4-phenoxybenzoyl)-7H-pyrrolo[2,3-d]pyrimidin-4-yl)amino)methyl)piperidin-1-yl)prop-2-en-1-one |
| I-584 | 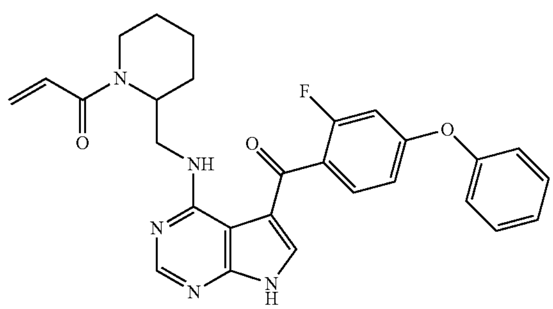 [SMILES: C=CC(=O)N1CCCCC1CNc1ncnc2[nH]cc(C(=O)c3ccc(Oc4ccccc4)cc3F)c12] | 1-(2-(((5-(2-fluoro-4-phenoxybenzoyl)-7H-pyrrolo[2,3-d]pyrimidin-4-yl)amino)methyl)piperidin-1-yl)prop-2-en-1-one |
| I-585 | 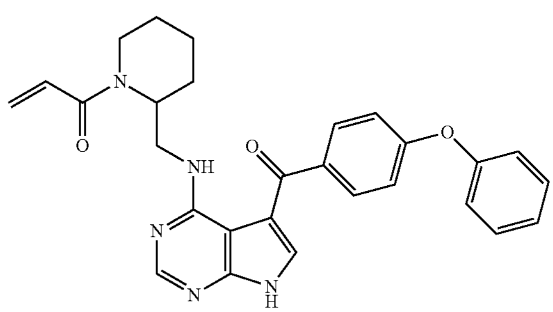 [SMILES: C=CC(=O)N1CCCCC1CNc1ncnc2[nH]cc(C(=O)c3ccc(Oc4ccccc4)cc3)c12] | 1-(2-(((5-(4-phenoxybenzoyl)-7H-pyrrolo[2,3-d]pyrimidin-4-yl)amino)methyl)piperidin-1-yl)prop-2-en-1-one |

-continued

| Cmpd No. | Structure | Chemical name |
|---|---|---|
| I-586 | 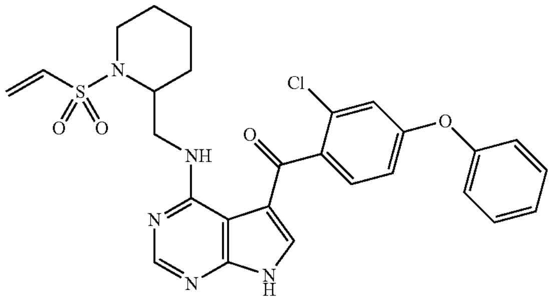 [SMILES: C=CS(=O)(=O)N1CCCCC1CNc1ncnc2[nH]cc(C(=O)c3ccc(Oc4ccccc4)cc3Cl)c12] | (2-chloro-4-phenoxyphenyl)(4-(((1-(vinylsulfonyl)piperidin-2-yl)methyl)amino)-7H-pyrrolo[2,3-d]pyrimidin-5-yl)methanone |
| I-587 | 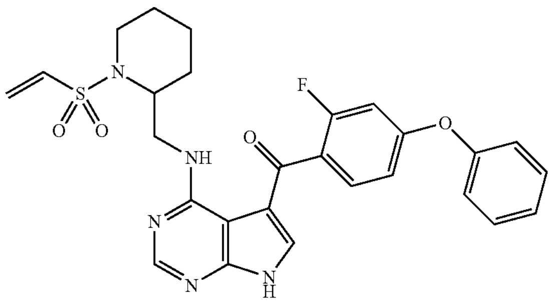 [SMILES: C=CS(=O)(=O)N1CCCCC1CNc1ncnc2[nH]cc(C(=O)c3ccc(Oc4ccccc4)cc3F)c12] | (2-fluoro-4-phenoxyphenyl)(4-(((1-(vinylsulfonyl)piperidin-2-yl)methyl)amino)-7H-pyrrolo[2,3-d]pyrimidin-5-yl)methanone |
| I-588 | 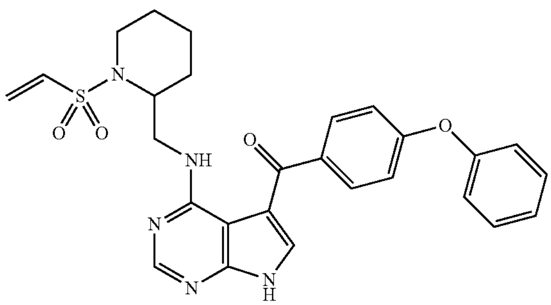 [SMILES: C=CS(=O)(=O)N1CCCCC1CNc1ncnc2[nH]cc(C(=O)c3ccc(Oc4ccccc4)cc3)c12] | (4-phenoxyphenyl)(4-(((1-(vinylsulfonyl)piperidin-2-yl)methyl)amino)-7H-pyrrolo[2,3-d]pyrimidin-5-yl)methanone |
| I-589 | 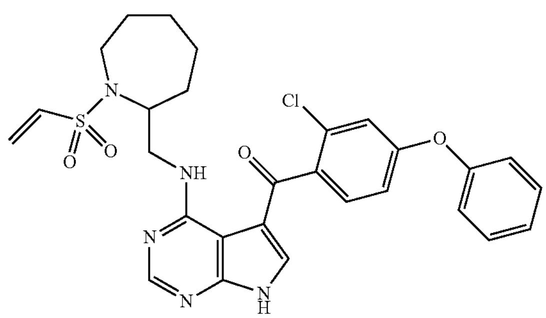 [SMILES: C=CS(=O)(=O)N1CCCCCC1CNc1ncnc2[nH]cc(C(=O)c3ccc(Oc4ccccc4)cc3Cl)c12] | (2-chloro-4-phenoxyphenyl)(4-(((1-(vinylsulfonyl)azepan-2-yl)methyl)amino)-7H-pyrrolo[2,3-d]pyrimidin-5-yl)methanone |
| I-590 | 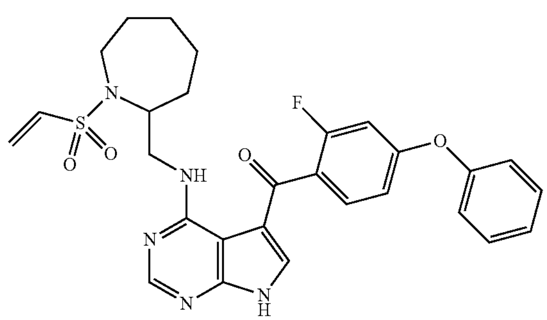 [SMILES: C=CS(=O)(=O)N1CCCCCC1CNc1ncnc2[nH]cc(C(=O)c3ccc(Oc4ccccc4)cc3F)c12] | (2-fluoro-4-phenoxyphenyl)(4-(((1-(vinylsulfonyl)azepan-2-yl)methyl)amino)-7H-pyrrolo[2,3-d]pyrimidin-5-yl)methanone |

-continued

| Cmpd No. | Structure | Chemical name |
|---|---|---|
| I-591 | 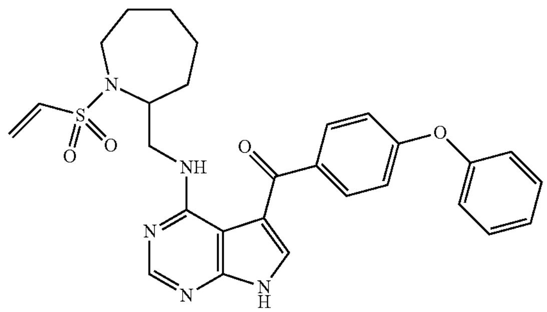 [SMILES: C=CS(=O)(=O)N1CCCCCC1CNc1ncnc2[nH]cc(C(=O)c3ccc(Oc4ccccc4)cc3)c12] | (4-phenoxyphenyl)(4-(((1-(vinylsulfonyl)azepan-2-yl)methyl)amino)-7H-pyrrolo[2,3-d]pyrimidin-5-yl)methanone |
| I-592 | 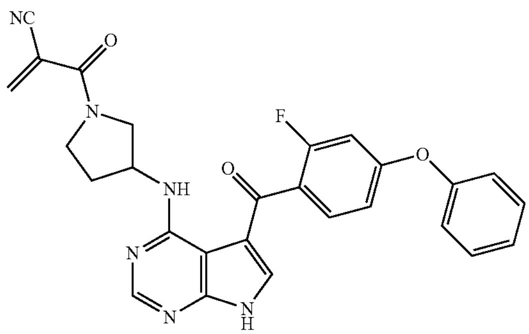 [SMILES: C=C(C#N)C(=O)N1CCC(Nc2ncnc3[nH]cc(C(=O)c4ccc(Oc5ccccc5)cc4F)c23)C1] | 2-(3-((5-(2-fluoro-4-phenoxybenzoyl)-7H-pyrrolo[2,3-d]pyrimidin-4-yl)amino)pyrrolidine-1-carbonyl)acrylonitrile |
| I-593 | 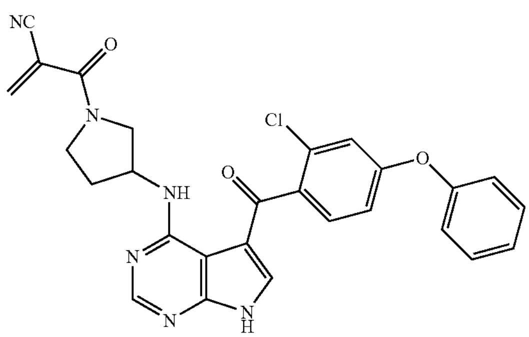 [SMILES: C=C(C#N)C(=O)N1CCC(Nc2ncnc3[nH]cc(C(=O)c4ccc(Oc5ccccc5)cc4Cl)c23)C1] | 2-(3-((5-(2-chloro-4-phenoxybenzoyl)-7H-pyrrolo[2,3-d]pyrimidin-4-yl)amino)pyrrolidine-1-carbonyl)acrylonitrile |
| I-594 | 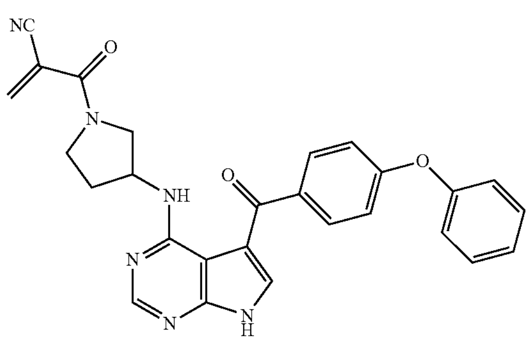 [SMILES: C=C(C#N)C(=O)N1CCC(Nc2ncnc3[nH]cc(C(=O)c4ccc(Oc5ccccc5)cc4)c23)C1] | 2-(3-((5-(4-phenoxybenzoyl)-7H-pyrrolo[2,3-d]pyrimidin-4-yl)amino)pyrrolidine-1-carbonyl)acrylonitrile |

-continued

| Cmpd No. | Structure | Chemical name |
| --- | --- | --- |
| I-595 | 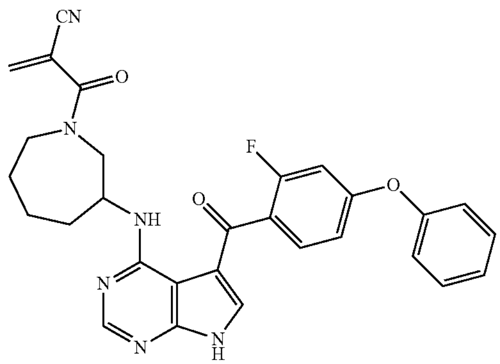 [SMILES: C=C(C#N)C(=O)N1CCCCC(Nc2ncnc3[nH]cc(C(=O)c4ccc(Oc5ccccc5)cc4F)c23)C1] | 2-(3-((5-(2-fluoro-4-phenoxybenzoyl)-7H-pyrrolo[2,3-d]pyrimidin-4-yl)amino)azepane-1-carbonyl)acrylonitrile |
| I-596 | 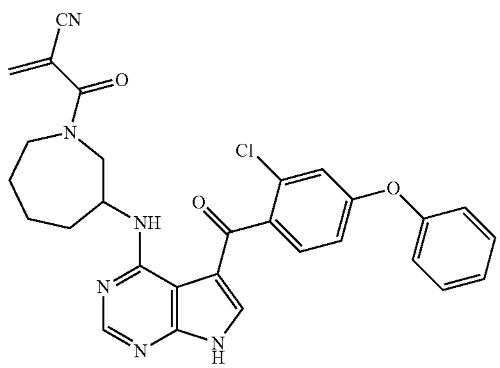 [SMILES: C=C(C#N)C(=O)N1CCCCC(Nc2ncnc3[nH]cc(C(=O)c4ccc(Oc5ccccc5)cc4Cl)c23)C1] | 2-(3-((5-(2-chloro-4-phenoxybenzoyl)-7H-pyrrolo[2,3-d]pyrimidin-4-yl)amino)azepane-1-carbonyl)acrylonitrile |
| I-597 | 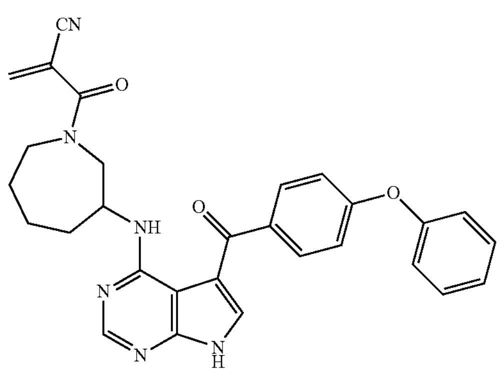 [SMILES: C=C(C#N)C(=O)N1CCCCC(Nc2ncnc3[nH]cc(C(=O)c4ccc(Oc5ccccc5)cc4)c23)C1] | 2-(3-((5-(4-phenoxybenzoyl)-7H-pyrrolo[2,3-d]pyrimidin-4-yl)amino)azepane-1-carbonyl)acrylonitrile |
| I-598 | 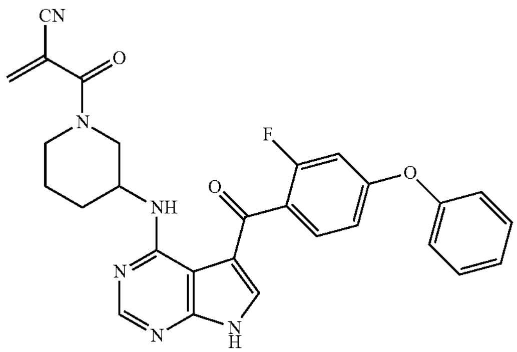 [SMILES: C=C(C#N)C(=O)N1CCCC(Nc2ncnc3[nH]cc(C(=O)c4ccc(Oc5ccccc5)cc4F)c23)C1] | 2-(3-((5-(2-fluoro-4-phenoxybenzoyl)-7H-pyrrolo[2,3-d]pyrimidin-4-yl)amino)piperidine-1-carbonyl)acrylonitrile |

| Cmpd No. | Structure | Chemical name |
|---|---|---|
| I-599 | 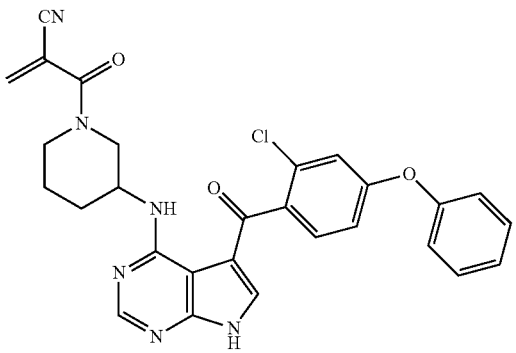 [SMILES: C=C(C#N)C(=O)N1CCCC(Nc2ncnc3[nH]cc(C(=O)c4ccc(Oc5ccccc5)cc4Cl)c23)C1] | 2-(3-((5-(2-chloro-4-phenoxybenzoyl)-7H-pyrrolo[2,3-d]pyrimidin-4-yl)amino)piperidine-1-carbonyl)acrylonitrile |
| I-600 | 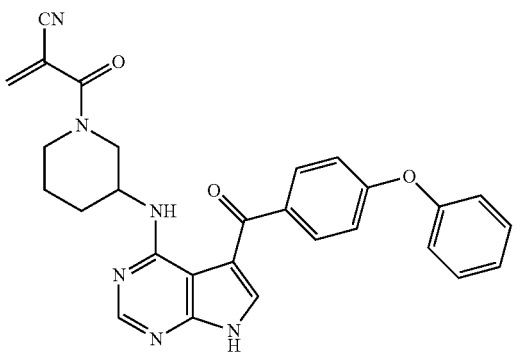 [SMILES: C=C(C#N)C(=O)N1CCCC(Nc2ncnc3[nH]cc(C(=O)c4ccc(Oc5ccccc5)cc4)c23)C1] | 2-(3-((5-(4-phenoxybenzoyl)-7H-pyrrolo[2,3-d]pyrimidin-4-yl)amino)piperidine-1-carbonyl)acrylonitrile |
| I-601 | 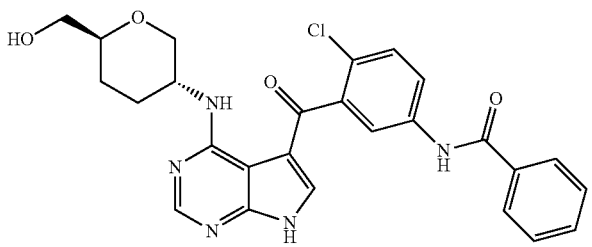 [SMILES: O=C(Nc1ccc(Cl)c(C(=O)c2c[nH]c3ncnc(N[C@@H]4CC[C@@H](CO)OC4)c23)c1)c1ccccc1] | N-(4-chloro-3-(4-(((3R,6S)-6-(hydroxymethyl)tetrahydro-2H-pyran-3-yl)amino)-7H-pyrrolo[2,3-d]pyrimidine-5-carbonyl)phenyl)benzamide |
| I-602 | 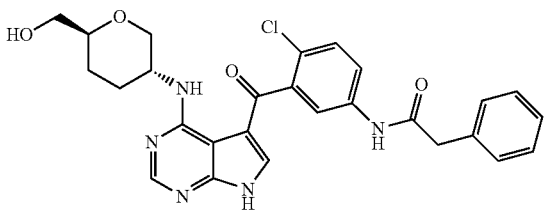 [SMILES: O=C(Cc1ccccc1)Nc1ccc(Cl)c(C(=O)c2c[nH]c3ncnc(N[C@@H]4CC[C@@H](CO)OC4)c23)c1] | N-(4-chloro-3-(4-(((3R,6S)-6-(hydroxymethyl)tetrahydro-2H-pyran-3-yl)amino)-7H-pyrrolo[2,3-d]pyrimidine-5-carbonyl)phenyl)-2-phenylacetamide |
| I-603 | 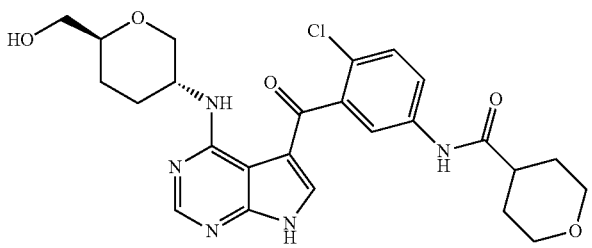 [SMILES: O=C(c1cc(NC(=O)C2CCOCC2)ccc1Cl)c1c[nH]c2ncnc(N[C@@H]3CC[C@@H](CO)OC3)c12] | N-(4-chloro-3-(4-(((3R,6S)-6-(hydroxymethyl)tetrahydro-2H-pyran-3-yl)amino)-7H-pyrrolo[2,3-d]pyrimidine-5-carbonyl)phenyl)tetrahydro-2H-pyran-4-carboxamide |

| Cmpd No. | Structure | Chemical name |
| --- | --- | --- |
| I-604 | 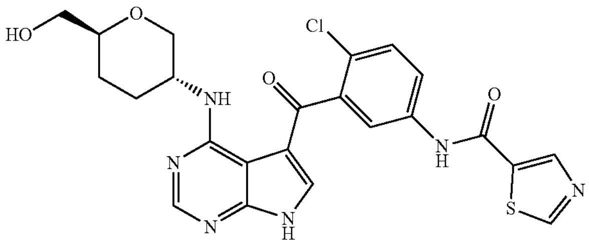 [SMILES: O=C(Nc1ccc(Cl)c(C(=O)c2c[nH]c3ncnc(N[C@@H]4CC[C@@H](CO)OC4)c23)c1)c1cncs1] | N-(4-chloro-3-(4-(((3R,6S)-6-(hydroxymethyl)tetrahydro-2H-pyran-3-yl)amino)-7H-pyrrolo[2,3-d]pyrimidine-5-carbonyl)phenyl)thiazole-5-carboxamide |
| I-605 | 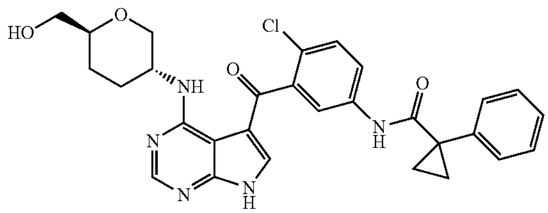 [SMILES: O=C(c1cc(NC(=O)C2(c3ccccc3)CC2)ccc1Cl)c1c[nH]c2ncnc(N[C@@H]3CC[C@@H](CO)OC3)c12] | N-(4-chloro-3-(4-(((3R,6S)-6-(hydroxymethyl)tetrahydro-2H-pyran-3-yl)amino)-7H-pyrrolo[2,3-d]pyrimidine-5-carbonyl)phenyl)-1-phenylcyclopropane-1-carboxamide |
| I-606 | 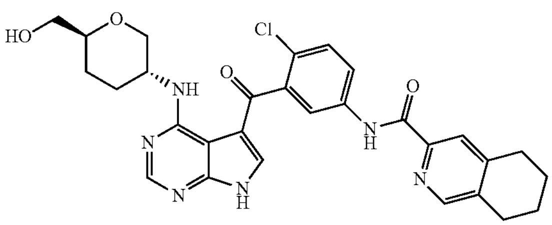 [SMILES: O=C(Nc1ccc(Cl)c(C(=O)c2c[nH]c3ncnc(N[C@@H]4CC[C@@H](CO)OC4)c23)c1)c1cc2c(cn1)CCCC2] | N-(4-chloro-3-(4-(((3R,6S)-6-(hydroxymethyl)tetrahydro-2H-pyran-3-yl)amino)-7H-pyrrolo[2,3-d]pyrimidine-5-carbonyl)phenyl)-5,6,7,8-tetrahydroisoquinoline-3-carboxamide |
| I-607 | 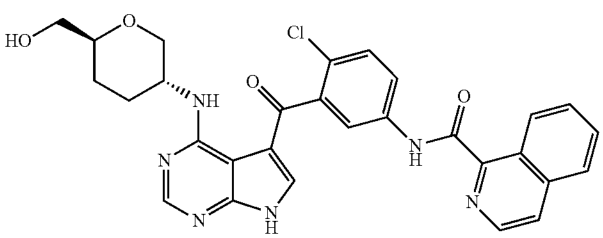 [SMILES: O=C(Nc1ccc(Cl)c(C(=O)c2c[nH]c3ncnc(N[C@@H]4CC[C@@H](CO)OC4)c23)c1)c1nccc2ccccc12] | N-(4-chloro-3-(4-(((3R,6S)-6-(hydroxymethyl)tetrahydro-2H-pyran-3-yl)amino)-7H-pyrrolo[2,3-d]pyrimidine-5-carbonyl)phenyl)isoquinoline-1-carboxamide |
| I-608 | 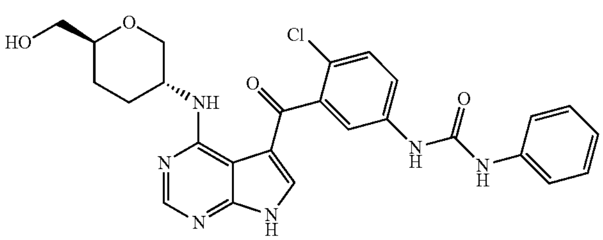 [SMILES: O=C(Nc1ccccc1)Nc1ccc(Cl)c(C(=O)c2c[nH]c3ncnc(N[C@@H]4CC[C@@H](CO)OC4)c23)c1] | 1-(4-chloro-3-(4-(((3R,6S)-6-(hydroxymethyl)tetrahydro-2H-pyran-3-yl)amino)-7H-pyrrolo[2,3-d]pyrimidine-5-carbonyl)phenyl)-3-phenylurea |
| I-609 | 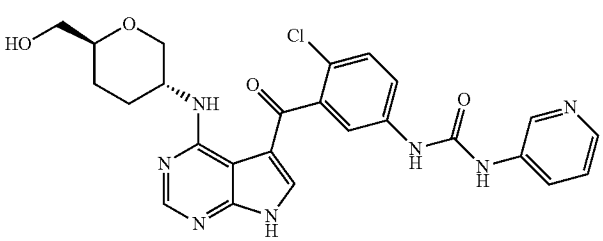 [SMILES: O=C(Nc1cccnc1)Nc1ccc(Cl)c(C(=O)c2c[nH]c3ncnc(N[C@@H]4CC[C@@H](CO)OC4)c23)c1] | 1-(4-chloro-3-(4-(((3R,6S)-6-(hydroxymethyl)tetrahydro-2H-pyran-3-yl)amino)-7H-pyrrolo[2,3-d]pyrimidine-5-carbonyl)phenyl)-3-(pyridin-3-yl)urea |

-continued

| Cmpd No. | Structure | Chemical name |
|---|---|---|
| I-610 | 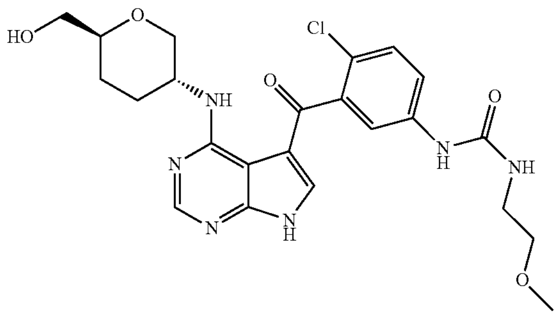 [SMILES: COCCNC(=O)Nc1ccc(Cl)c(C(=O)c2c[nH]c3ncnc(N[C@@H]4CC[C@@H](CO)OC4)c23)c1] | 3-chloro-4-(4-(((3R,6S)-6-(hydroxymethyl)tetrahydro-2H-pyran-3-yl)amino)-7H-pyrrolo[2,3-d]pyrimidine-5-carbonyl)-N-(2-methoxyethyl)benzamide |
| I-611 | 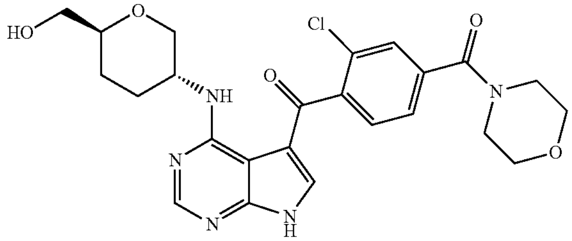 [SMILES: O=C(c1ccc(C(=O)N2CCOCC2)cc1Cl)c1c[nH]c2ncnc(N[C@@H]3CC[C@@H](CO)OC3)c12] | (3-chloro-4-(4-(((3R,6S)-6-(hydroxymethyl)tetrahydro-2H-pyran-3-yl)amino)-7H-pyrrolo[2,3-d]pyrimidine-5-carbonyl)phenyl)(morpholino)methanone |
| I-612 | 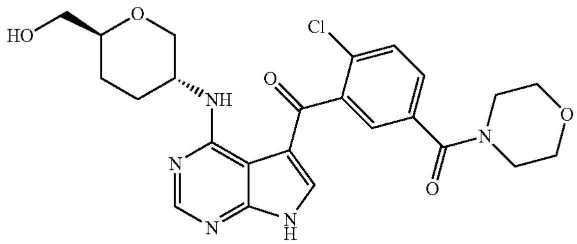 [SMILES: O=C(c1cc(C(=O)N2CCOCC2)ccc1Cl)c1c[nH]c2ncnc(N[C@@H]3CC[C@@H](CO)OC3)c12] | (4-chloro-3-(4-(((3R,6S)-6-(hydroxymethyl)tetrahydro-2H-pyran-3-yl)amino)-7H-pyrrolo[2,3-d]pyrimidine-5-carbonyl)phenyl)(morpholino)methanone |
| I-613 | 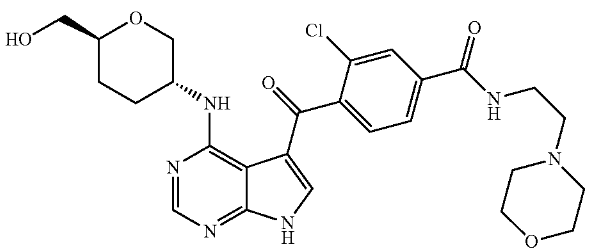 [SMILES: O=C(NCCN1CCOCC1)c1ccc(C(=O)c2c[nH]c3ncnc(N[C@@H]4CC[C@@H](CO)OC4)c23)c(Cl)c1] | 3-chloro-4-(4-(((3R,6S)-6-(hydroxymethyl)tetrahydro-2H-pyran-3-yl)amino)-7H-pyrrolo[2,3-d]pyrimidine-5-carbonyl)-N-(2-morpholinoethyl)benzamide |
| I-614 | 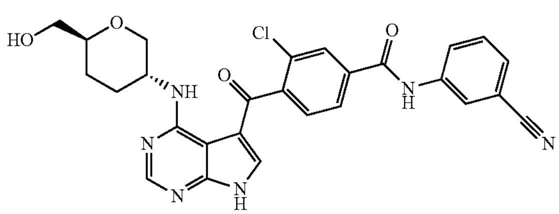 [SMILES: N#Cc1cccc(NC(=O)c2ccc(C(=O)c3c[nH]c4ncnc(N[C@@H]5CC[C@@H](CO)OC5)c34)c(Cl)c2)c1] | 3-chloro-N-(3-cyanophenyl)-4-(4-(((3R,6S)-6-(hydroxymethyl)tetrahydro-2H-pyran-3-yl)amino)-7H-pyrrolo[2,3-d]pyrimidine-5-carbonyl)benzamide |
| I-615 | 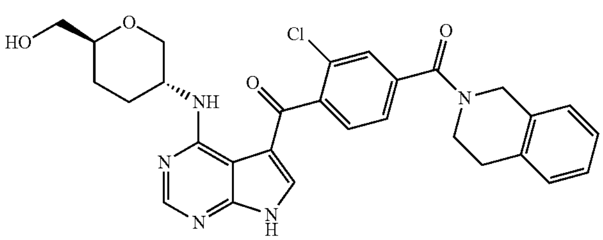 [SMILES: O=C(c1ccc(C(=O)N2CCc3ccccc3C2)cc1Cl)c1c[nH]c2ncnc(N[C@@H]3CC[C@@H](CO)OC3)c12] | (2-chloro-4-(1,2,3,4-tetrahydroisoquinoline-2-carbonyl)phenyl)(4-(((3R,6S)-6-(hydroxymethyl)tetrahydro-2H-pyran-3-yl)amino)-7H-pyrrolo[2,3-d]pyrimidin-5-yl)methanone |

-continued

| Cmpd No. | Structure | Chemical name |
|---|---|---|
| I-616 | 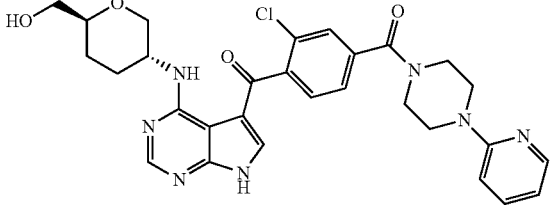 | (3-chloro-4-(4-(((3R,6S)-6-(hydroxymethyl)tetrahydro-2H-pyran-3-yl)amino)-7H-pyrrolo[2,3-d]pyrimidine-5-carbonyl)phenyl)(4-(pyridin-2-yl)piperazin-1-yl)methanone |
| I-617 | 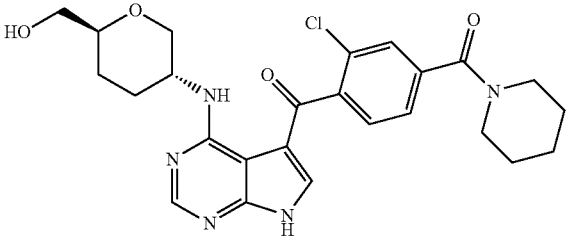 | (3-chloro-4-(4-(((3R,6S)-6-(hydroxymethyl)tetrahydro-2H-pyran-3-yl)amino)-7H-pyrrolo[2,3-d]pyrimidine-5-carbonyl)phenyl)(piperidin-1-yl)methanone |
| I-618 | 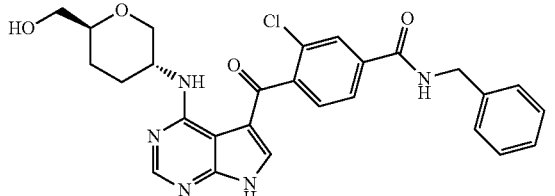 | N-benzyl-3-chloro-4-(4-(((3R,6S)-6-(hydroxymethyl)tetrahydro-2H-pyran-3-yl)amino)-7H-pyrrolo[2,3-d]pyrimidine-5-carbonyl)benzamide |
| I-619 | 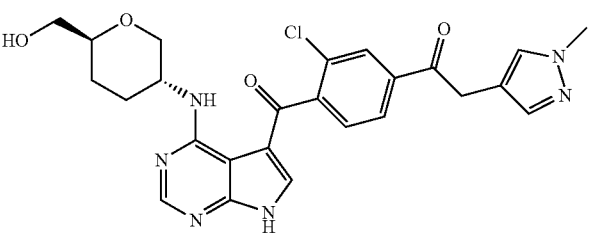 [SMILES: Cn1cc(CC(=O)c2ccc(C(=O)c3c[nH]c4ncnc(N[C@@H]5CC[C@@H](CO)OC5)c34)c(Cl)c2)cn1] | 3-chloro-4-(4-(((3R,6S)-6-(hydroxymethyl)tetrahydro-2H-pyran-3-yl)amino)-7H-pyrrolo[2,3-d]pyrimidine-5-carbonyl)-N-(1-methyl-1H-pyrazol-4-yl)benzamide |
| I-620 | 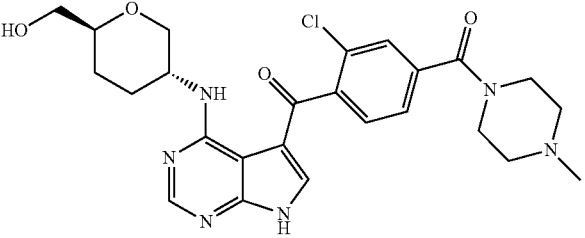 [SMILES: CN1CCN(C(=O)c2ccc(C(=O)c3c[nH]c4ncnc(N[C@@H]5CC[C@@H](CO)OC5)c34)c(Cl)c2)CC1] | (3-chloro-4-(4-(((3R,6S)-6-(hydroxymethyl)tetrahydro-2H-pyran-3-yl)amino)-7H-pyrrolo[2,3-d]pyrimidine-5-carbonyl)phenyl)(4-methylpiperazin-1-yl)methanone |
| I-621 | 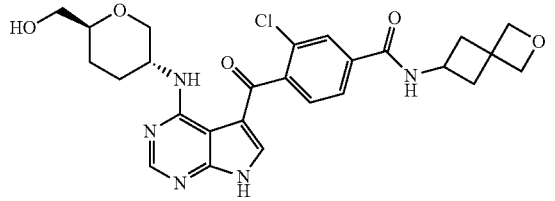 [SMILES: O=C(NC1CC2(COC2)C1)c1ccc(C(=O)c2c[nH]c3ncnc(N[C@@H]4CC[C@@H](CO)OC4)c23)c(Cl)c1] | 3-chloro-4-(4-(((3R,6S)-6-(hydroxymethyl)tetrahydro-2H-pyran-3-yl)amino)-7H-pyrrolo[2,3-d]pyrimidine-5-carbonyl)-N-(2-oxaspiro[3.3]heptan-6-yl)benzamide |

| Cmpd No. | Structure | Chemical name |
|---|---|---|
| I-622 | 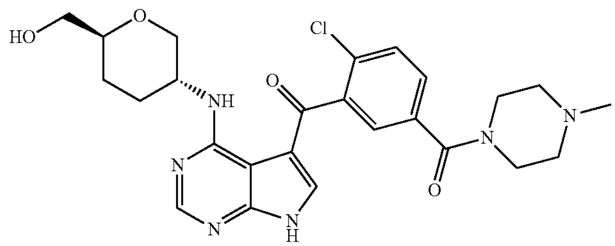 [SMILES: CN1CCN(C(=O)c2ccc(Cl)c(C(=O)c3c[nH]c4ncnc(N[C@@H]5CC[C@@H](CO)OC5)c34)c2)CC1] | (4-chloro-3-(4-(((3R,6S)-6-(hydroxymethyl)tetrahydro-2H-pyran-3-yl)amino)-7H-pyrrolo[2,3-d]pyrimidine-5-carbonyl)phenyl)(4-methylpiperazin-1-yl)methanone |
| I-623 | 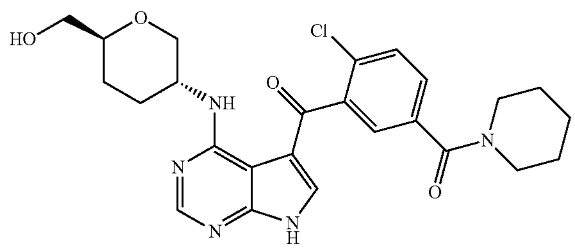 [SMILES: O=C(c1cc(C(=O)N2CCCCC2)ccc1Cl)c1c[nH]c2ncnc(N[C@@H]3CC[C@@H](CO)OC3)c12] | (4-chloro-3-(4-(((3R,6S)-6-(hydroxymethyl)tetrahydro-2H-pyran-3-yl)amino)-7H-pyrrolo[2,3-d]pyrimidine-5-carbonyl)phenyl)(piperidin-1-yl)methanone |
| I-624 | 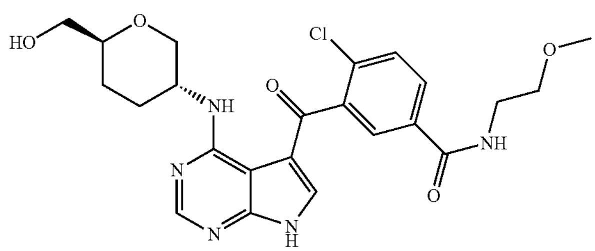 [SMILES: COCCNC(=O)c1ccc(Cl)c(C(=O)c2c[nH]c3ncnc(N[C@@H]4CC[C@@H](CO)OC4)c23)c1] | 4-chloro-3-(4-(((3R,6S)-6-(hydroxymethyl)tetrahydro-2H-pyran-3-yl)amino)-7H-pyrrolo[2,3-pyrimidine-5-carbonyl)-N-(2-methoxyethyl)benzamide |
| I-625 | 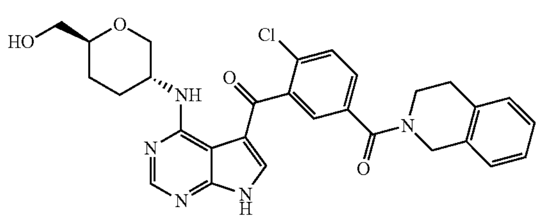 [SMILES: O=C(c1cc(C(=O)N2CCc3ccccc3C2)ccc1Cl)c1c[nH]c2ncnc(N[C@@H]3CC[C@@H](CO)OC3)c12] | (4-chloro-3-(4-(((3R,6S)-6-(hydroxymethyl)tetrahydro-2H-pyran-3-yl)amino)-7H-pyrrolo[2,3-d]pyrimidine-5-carbonyl)phenyl)(3,4-dihydroisoquinolin-2(1H)-yl)methanone |
| I-626 | 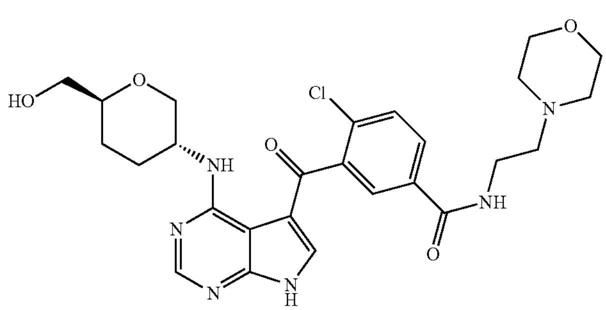 [SMILES: O=C(NCCN1CCOCC1)c1ccc(Cl)c(C(=O)c2c[nH]c3ncnc(N[C@@H]4CC[C@@H](CO)OC4)c23)c1] | 4-chloro-3-(4-(((3R,6S)-6-(hydroxymethyl)tetrahydro-2H-pyran-3-yl)amino)-7H-pyrrolo[2,3-d]pyrimidine-5-carbonyl)-N-(2-morpholinoethyl)benzamide |
| I-627 | 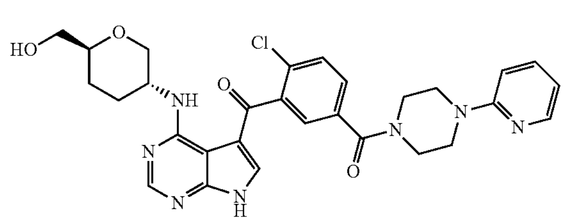 [SMILES: O=C(c1cc(C(=O)N2CCN(c3ccccn3)CC2)ccc1Cl)c1c[nH]c2ncnc(N[C@@H]3CC[C@@H](CO)OC3)c12] | (4-chloro-3-(4-(((3R,6S)-6-(hydroxymethyl)tetrahydro-2H-pyran-3-yl)amino)-7H-pyrrolo[2,3-d]pyrimidine-5-carbonyl)phenyl)(4-(pyridin-2-yl)piperazin-1-yl)methanone |

| Cmpd No. | Structure | Chemical name |
|---|---|---|
| I-628 | 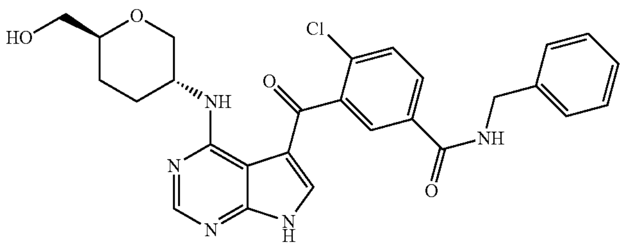 [SMILES: O=C(NCc1ccccc1)c1ccc(Cl)c(C(=O)c2c[nH]c3ncnc(N[C@@H]4CC[C@@H](CO)OC4)c23)c1] | N-benzyl-4-chloro-3-(4-(((3R,6S)-6-(hydroxymethyl)tetrahydro-2H-pyran-3-yl)amino)-7H-pyrrolo[2,3-d]pyrimidine-5-carbonyl)benzamide |
| I-629 | 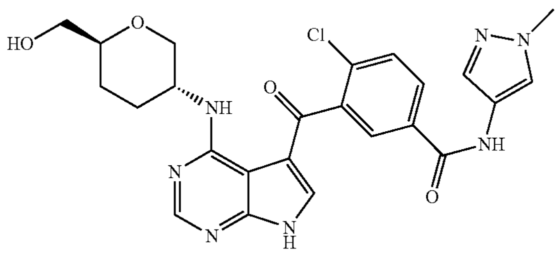 [SMILES: Cn1cc(NC(=O)c2ccc(Cl)c(C(=O)c3c[nH]c4ncnc(N[C@@H]5CC[C@@H](CO)OC5)c34)c2)cn1] | 4-chloro-3-(4-(((3R,6S)-6-(hydroxymethyl)tetrahydro-2H-pyran-3-yl)amino)-7H-pyrrolo[2,3-d]pyrimidine-5-carbonyl)-N-(1-methyl-1H-pyrazol-4-yl)benzamide |
| I-630 | 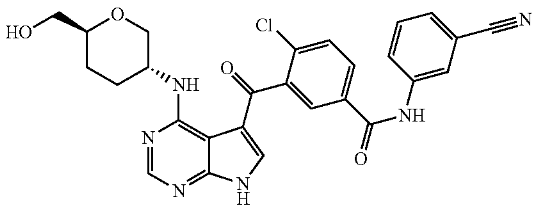 [SMILES: N#Cc1cccc(NC(=O)c2ccc(Cl)c(C(=O)c3c[nH]c4ncnc(N[C@@H]5CC[C@@H](CO)OC5)c34)c2)c1] | 4-chloro-N-(3-cyanophenyl)-3-(4-(((3R,6S)-6-(hydroxymethyl)tetrahydro-2H-pyran-3-yl)amino)-7H-pyrrolo[2,3-d]pyrimidine-5-carbonyl)benzamide |
| I-631 | 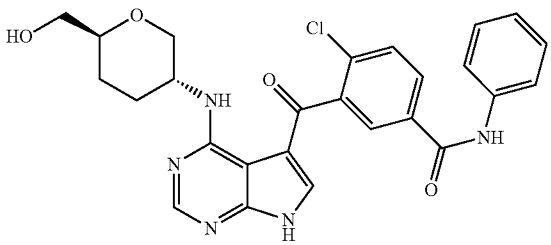 [SMILES: O=C(Nc1ccccc1)c1ccc(Cl)c(C(=O)c2c[nH]c3ncnc(N[C@@H]4CC[C@@H](CO)OC4)c23)c1] | 4-chloro-3-(4-(((3R,6S)-6-(hydroxymethyl)tetrahydro-2H-pyran-3-yl)amino)-7H-pyrrolo[2,3-d]pyrimidine-5-carbonyl)-N-phenylbenzamide |
| I-632 | 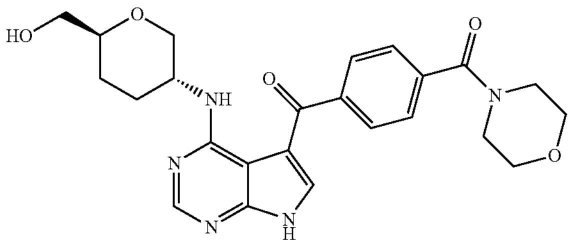 [SMILES: O=C(c1ccc(C(=O)N2CCOCC2)cc1)c1c[nH]c2ncnc(N[C@@H]3CC[C@@H](CO)OC3)c12] | (4-(((3R,6S)-6-(hydroxymethyl)tetrahydro-2H-pyran-3-yl)amino)-7H-pyrrolo[2,3-d]pyrimidin-5-yl)(4-(morpholine-4-carbonyl)phenyl)methanone |
| I-633 | 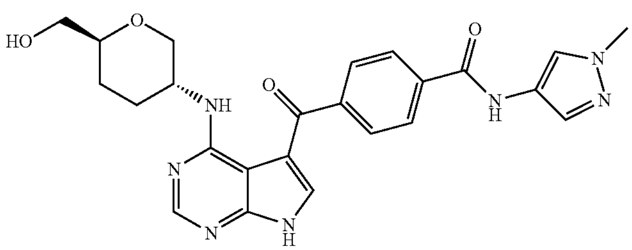 [SMILES: Cn1cc(NC(=O)c2ccc(C(=O)c3c[nH]c4ncnc(N[C@@H]5CC[C@@H](CO)OC5)c34)cc2)cn1] | 4-(4-(((3R,6S)-6-(hydroxymethyl)tetrahydro-2H-pyran-3-yl)amino)-7H-pyrrolo[2,3-d]pyrimidine-5-carbonyl)-N-(1-methyl-1H-pyrazol-4-yl)benzamide |

| Cmpd No. | Structure | Chemical name |
|---|---|---|
| I-634 | 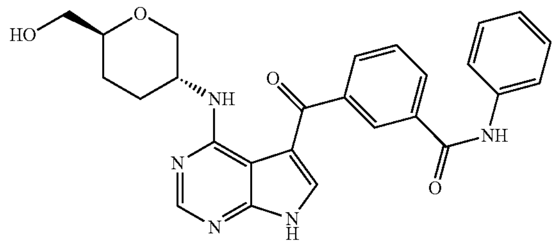 [SMILES: O=C(Nc1ccccc1)c1cccc(C(=O)c2c[nH]c3ncnc(N[C@@H]4CC[C@@H](CO)OC4)c23)c1] | 3-(4-(((3R,6S)-6-(hydroxymethyl)tetrahydro-2H-pyran-3-yl)amino)-7H-pyrrolo[2,3-d]pyrimidine-5-carbonyl)-N-phenylbenzamide |
| I-635 | 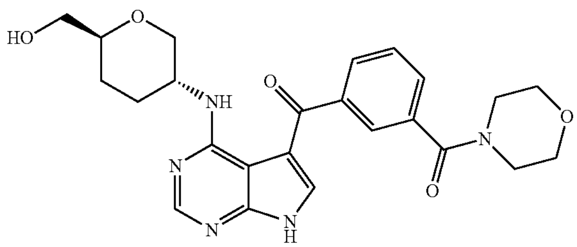 [SMILES: O=C(c1cccc(C(=O)N2CCOCC2)c1)c1c[nH]c2ncnc(N[C@@H]3CC[C@@H](CO)OC3)c12] | (4-(((3R,6S)-6-(hydroxymethyl)tetrahydro-2H-pyran-3-yl)amino)-7H-pyrrolo[2,3-d]pyrimidin-5-yl)(3-(morpholine-4-carbonyl)phenyl)methanone |
| I-636 | 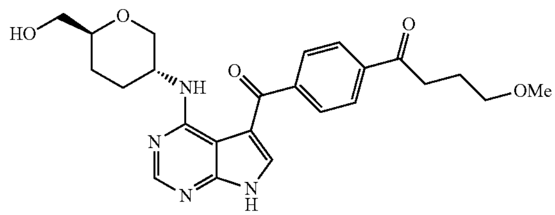 [SMILES: COCCCC(=O)c1ccc(C(=O)c2c[nH]c3ncnc(N[C@@H]4CC[C@@H](CO)OC4)c23)cc1] | 4-(4-(((3R,6S)-6-(hydroxymethyl)tetrahydro-2H-pyran-3-yl)amino)-7H-pyrrolo[2,3-d]pyrimidine-5-carbonyl)-N-(2-methoxyethyl)benzamide |
| I-637 | 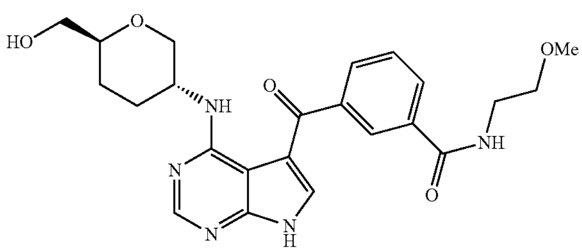 [SMILES: COCCNC(=O)c1cccc(C(=O)c2c[nH]c3ncnc(N[C@@H]4CC[C@@H](CO)OC4)c23)c1] | 3-(4-(((3R,6S)-6-(hydroxymethyl)tetrahydro-2H-pyran-3-yl)amino)-7H-pyrrolo[2,3-d]pyrimidine-5-carbonyl)-N-(2-methoxyethyl)benzamide |
| I-638 | 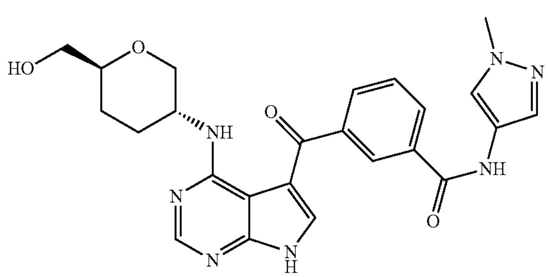 [SMILES: Cn1cc(NC(=O)c2cccc(C(=O)c3c[nH]c4ncnc(N[C@@H]5CC[C@@H](CO)OC5)c34)c2)cn1] | 3-(4-(((3R,6S)-6-(hydroxymethyl)tetrahydro-2H-pyran-3-yl)amino)-7H-pyrrolo[2,3-d]pyrimidine-5-carbonyl)-N-(1-methyl-1H-pyrazol-4-yl)benzamide |
| I-639 | 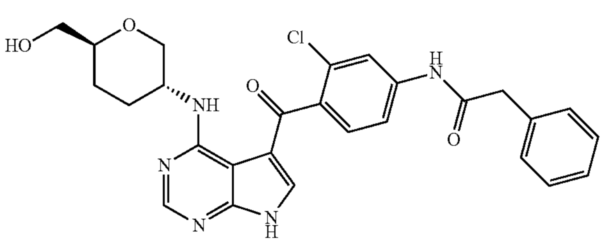 [SMILES: O=C(Cc1ccccc1)Nc1ccc(C(=O)c2c[nH]c3ncnc(N[C@@H]4CC[C@@H](CO)OC4)c23)c(Cl)c1] | N-(3-chloro-4-(4-(((3R,6S)-6-(hydroxymethyl)tetrahydro-2H-pyran-3-yl)amino)-7H-pyrrolo[2,3-d]pyrimidine-5-carbonyl)phenyl)-2-phenylacetamide |

-continued

| Cmpd No. | Structure | Chemical name |
|---|---|---|
| I-640 | 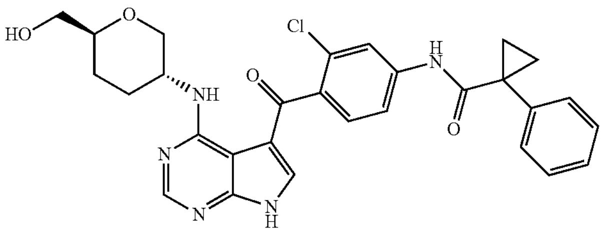 [SMILES: O=C(c1ccc(NC(=O)C2(c3ccccc3)CC2)cc1Cl)c1c[nH]c2ncnc(N[C@@H]3CC[C@@H](CO)OC3)c12] | N-(3-chloro-4-(4-(((3R,6S)-6-(hydroxymethyl)tetrahydro-2H-pyran-3-yl)amino)-7H-pyrrolo[2,3-d]pyrimidine-5-carbonyl)phenyl)-1-phenylcyclopropane-1-carboxamide |
| I-641 | 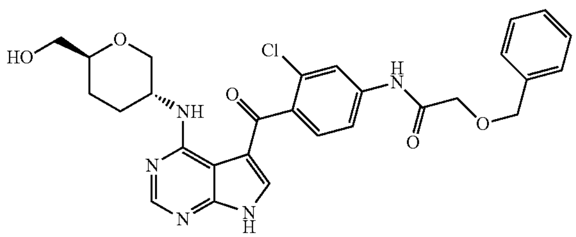 [SMILES: O=C(COCc1ccccc1)Nc1ccc(C(=O)c2c[nH]c3ncnc(N[C@@H]4CC[C@@H](CO)OC4)c23)c(Cl)c1] | 2-(benzyloxy)-N-(3-chloro-4-(4-(((3R,6S)-6-(hydroxymethyl)tetrahydro-2H-pyran-3-yl)amino)-7H-pyrrolo[2,3-d]pyrimidine-5-carbonyl)phenyl)acetamide |
| I-642 | 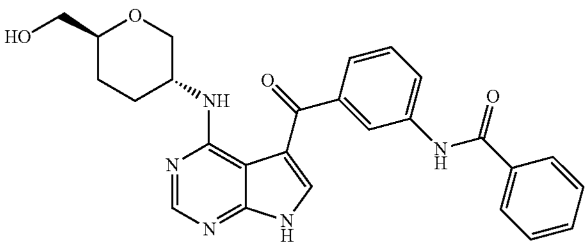 [SMILES: O=C(Nc1cccc(C(=O)c2c[nH]c3ncnc(N[C@@H]4CC[C@@H](CO)OC4)c23)c1)c1ccccc1] | N-(3-(4-(((3R,6S)-6-(hydroxymethyl)tetrahydro-2H-pyran-3-yl)amino)-7H-pyrrolo[2,3-d]pyrimidine-5-carbonyl)phenyl)benzamide |
| I-643 | 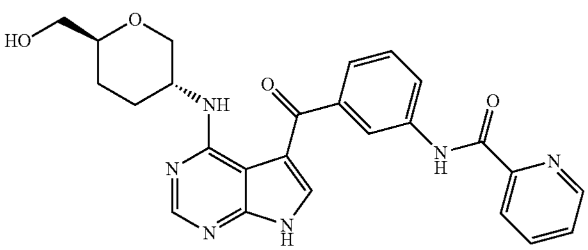 [SMILES: O=C(Nc1cccc(C(=O)c2c[nH]c3ncnc(N[C@@H]4CC[C@@H](CO)OC4)c23)c1)c1ccccn1] | N-(3-(4-(((3R,6S)-6-(hydroxymethyl)tetrahydro-2H-pyran-3-yl)amino)-7H-pyrrolo[2,3-d]pyrimidine-5-carbonyl)phenyl)picolinamide |
| I-644 | 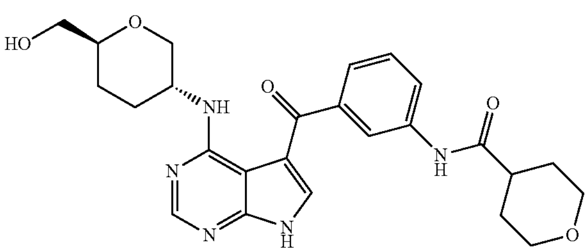 [SMILES: O=C(c1cccc(NC(=O)C2CCOCC2)c1)c1c[nH]c2ncnc(N[C@@H]3CC[C@@H](CO)OC3)c12] | N-(3-(4-(((3R,6S)-6-(hydroxymethyl)tetrahydro-2H-pyran-3-yl)amino)-7H-pyrrolo[2,3-d]pyrimidine-5-carbonyl)phenyl)tetrahydro-2H-pyran-4-carboxamide |
| I-645 | 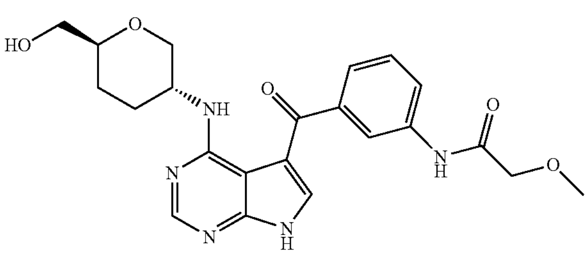 [SMILES: COCC(=O)Nc1cccc(C(=O)c2c[nH]c3ncnc(N[C@@H]4CC[C@@H](CO)OC4)c23)c1] | N-(3-(4-(((3R,6S)-6-(hydroxymethyl)tetrahydro-2H-pyran-3-yl)amino)-7H-pyrrolo[2,3-d]pyrimidine-5-carbonyl)phenyl)-2-methoxyacetamide |

| Cmpd No. | Structure | Chemical name |
|---|---|---|
| I-646 | 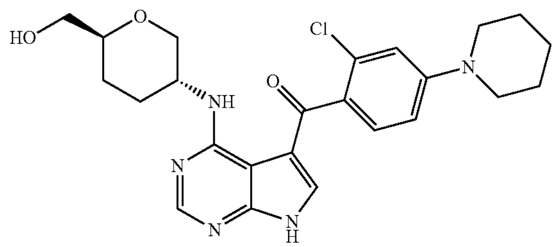 [SMILES: O=C(c1ccc(N2CCCCC2)cc1Cl)c1c[nH]c2ncnc(N[C@@H]3CC[C@@H](CO)OC3)c12] | (2-chloro-4-(piperidin-1-yl)phenyl)(4-(((3R,6S)-6-(hydroxymethyl)tetrahydro-2H-pyran-3-yl)amino)-7H-pyrrolo[2,3-d]pyrimidin-5-yl)methanone |
| I-647 | 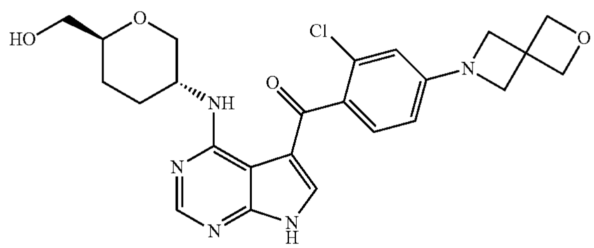 [SMILES: O=C(c1ccc(N2CC3(COC3)C2)cc1Cl)c1c[nH]c2ncnc(N[C@@H]3CC[C@@H](CO)OC3)c12] | (2-chloro-4-(2-oxa-6-azaspiro[3.3]heptan-6-yl)phenyl)(4-(((3R,6S)-6-(hydroxymethyl)tetrahydro-2H-pyran-3-yl)amino)-7H-pyrrolo[2,3-d]pyrimidin-5-yl)methanone |
| I-648 | 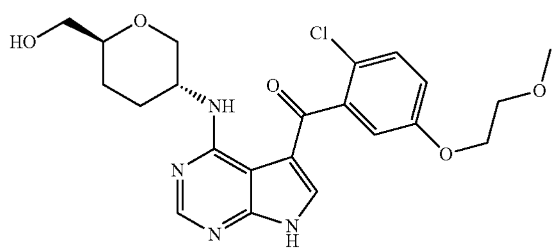 [SMILES: COCCOc1ccc(Cl)c(C(=O)c2c[nH]c3ncnc(N[C@@H]4CC[C@@H](CO)OC4)c23)c1] | (2-chloro-5-(2-methoxyethoxy)phenyl)(4-(((3R,6S)-6-(hydroxymethyl)tetrahydro-2H-pyran-3-yl)amino)-7H-pyrrolo[2,3-d]pyrimidin-5-yl)methanone |
| I-649 | 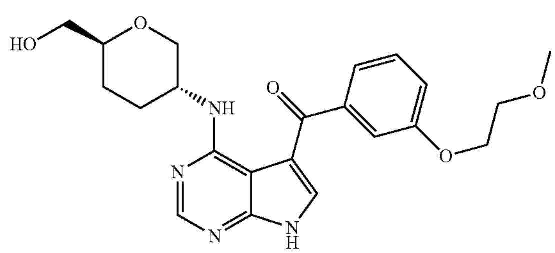 [SMILES: COCCOc1cccc(C(=O)c2c[nH]c3ncnc(N[C@@H]4CC[C@@H](CO)OC4)c23)c1] | (4-(((3R,6S)-6-(hydroxymethyl)tetrahydro-2H-pyran-3-yl)amino)-7H-pyrrolo[2,3-d]pyrimidin-5-yl)(3-(2-methoxyethoxy)phenyl)methanone |
| I-650 | 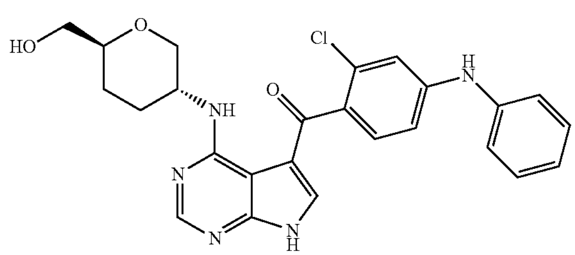 [SMILES: O=C(c1ccc(Nc2ccccc2)cc1Cl)c1c[nH]c2ncnc(N[C@@H]3CC[C@@H](CO)OC3)c12] | (2-chloro-4-(phenylamino)phenyl)(4-(((3R,6S)-6-(hydroxymethyl)tetrahydro-2H-pyran-3-yl)amino)-7H-pyrrolo[2,3-d]pyrimidin-5-yl)methanone |
| I-651 | 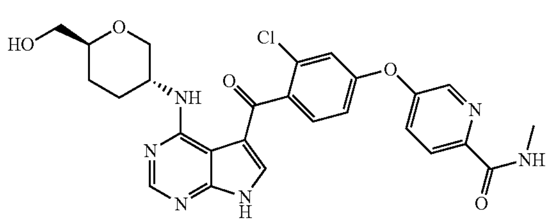 [SMILES: CNC(=O)c1ccc(Oc2ccc(C(=O)c3c[nH]c4ncnc(N[C@@H]5CC[C@@H](CO)OC5)c34)c(Cl)c2)cn1] | 5-(3-chloro-4-(4-(((3R,6S)-6-(hydroxymethyl)tetrahydro-2H-pyran-3-yl)amino)-7H-pyrrolo[2,3-d]pyrimidine-5-carbonyl)phenoxy)-N-methylpicolinamide |

| Cmpd No. | Structure | Chemical name |
|---|---|---|
| I-652 | 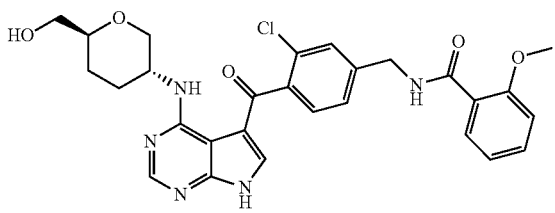 [SMILES: COc1ccccc1C(=O)NCc1ccc(C(=O)c2c[nH]c3ncnc(N[C@@H]4CC[C@@H](CO)OC4)c23)c(Cl)c1] | N-(4-(4-(((3R,6S)-6-(hydroxymethyl)tetrahydro-2H-pyran-3-yl)amino)-7H-pyrrolo[2,3-d]pyrimidine-5-carbonyl)benzyl)-2-methoxybenzamide |
| I-653 | 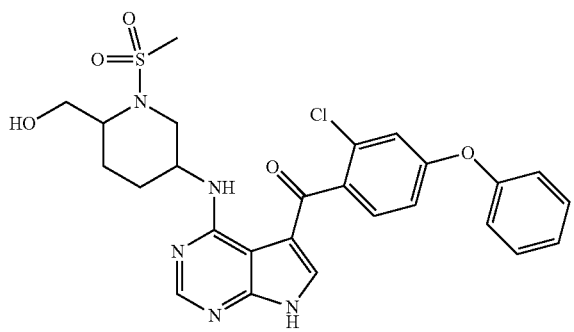 [SMILES: CS(=O)(=O)N1CC(Nc2ncnc3[nH]cc(C(=O)c4ccc(Oc5ccccc5)cc4Cl)c23)CCC1CO] | (racemic)-(2-chloro-4-phenoxyphenyl)(4-((6-(hydroxymethyl)-1-(methylsulfonyl)piperidin-3-yl)amino)-7H-pyrrolo[2,3-d]pyrimidin-5-yl)methanone |
| I-654 | 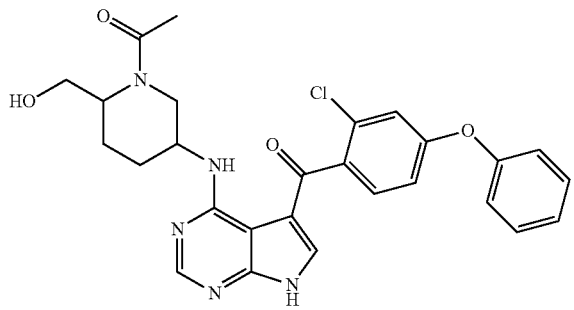 [SMILES: CC(=O)N1CC(Nc2ncnc3[nH]cc(C(=O)c4ccc(Oc5ccccc5)cc4Cl)c23)CCC1CO] | (racemic)-1-(5-((5-(2-chloro-4-phenoxybenzoyl)-7H-pyrrolo[2,3-d]pyrimidin-4-yl)amino)-2-(hydroxymethyl)-piperidin-1-yl)ethan-1-one |
| I-655 | 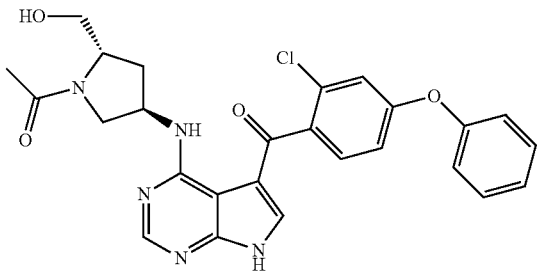 [SMILES: CC(=O)N1C[C@H](Nc2ncnc3[nH]cc(C(=O)c4ccc(Oc5ccccc5)cc4Cl)c23)C[C@H]1CO] | 1-((2S,4R)-4-((5-(2-chloro-4-phenoxybenzoyl)-7H-pyrrolo[2,3-d]pyrimidin-4-yl)amino)-2-(hydroxymethyl)pyrrolidin-1-yl)ethan-1-one |
| I-656 | 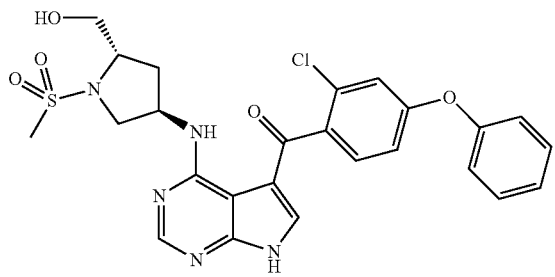 [SMILES: CS(=O)(=O)N1C[C@H](Nc2ncnc3[nH]cc(C(=O)c4ccc(Oc5ccccc5)cc4Cl)c23)C[C@H]1CO] | (2-chloro-4-phenoxyphenyl)(4-(((3R,5S)-5-(hydroxymethyl)-1-(methylsulfonyl)pyrrolidin-3-yl)amino)-7H-pyrrolo[2,3-d]pyrimidin-5-yl)methanone |

| Cmpd No. | Structure | Chemical name |
|---|---|---|
| I-657 | 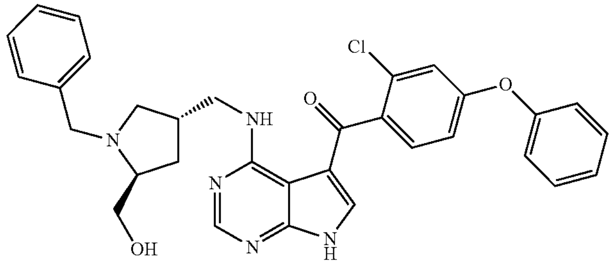 [SMILES: O=C(c1ccc(Oc2ccccc2)cc1Cl)c1c[nH]c2ncnc(NC[C@@H]3C[C@@H](CO)N(Cc4ccccc4)C3)c12] | (4-((((3S,5S)-1-benzyl-5-(hydroxymethyl)pyrrolidin-3-yl)methyl)amino)-7H-pyrrolo[2,3-d]pyrimidin-5-yl)(2-chloro-4-phenoxyphenyl)methanone |

In one embodiment, a compound of the present application (e.g., a compound of any of the formulae or any individual compounds disclosed herein) is a pharmaceutically acceptable salt. In another embodiment, a compound of the present application (e.g., a compound of any of the formulae or any individual compounds disclosed herein) is a solvate. In another embodiment, a compound of the present application (e.g., a compound of any of the formulae or any individual compounds disclosed herein) is a hydrate.

The details of the application are set forth in the accompanying description below. Although methods and materials similar or equivalent to those described herein can be used in the practice or testing of the present application, illustrative methods and materials are now described. Other features, objects, and advantages of the application will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this application belongs. All patents and publications cited in this specification are incorporated herein by reference in their entireties.

Definitions

The articles "a" and "an" are used in this application to refer to one or more than one (i.e., at least one) of the grammatical object of the article. By way of example, "an element" means one element or more than one element.

The term "and/or" is used in this application to mean either "and" or "or" unless indicated otherwise.

The application also includes pharmaceutical compositions comprising an effective amount of a compound of Formula (I) and a pharmaceutically acceptable carrier.

The term "alkyl," as used herein, refers to saturated, straight or branched-chain hydrocarbon radicals containing, in certain embodiments, between one and six carbon atoms. Examples of $C_1$-$C_8$ alkyl radicals include, but are not limited to, methyl, ethyl, propyl, isopropyl, n-butyl, tert-butyl, neopentyl, n-hexyl, n-heptyl, and n-octyl radicals. Examples of $C_1$-$C_6$ alkyl radicals include, but are not limited to, methyl, ethyl, propyl, isopropyl, n-butyl, tert-butyl, neopentyl, and n-hexyl radicals.

The term "alkenyl," as used herein, denotes a monovalent group derived from a hydrocarbon moiety containing, in certain embodiments, from two to six carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl and the like.

The term "alkoxy" refers to an —O-alkyl radical.

The terms "hal," "halo," and "halogen," as used herein, refer to an atom selected from fluorine, chlorine, bromine and iodine.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, indenyl and the like.

The term "aralkyl," as used herein, refers to an alkyl residue attached to an aryl ring. Examples include, but are not limited to, benzyl, phenethyl and the like.

The term "cycloalkyl," as used herein, denotes a monovalent group derived from a monocyclic or polycyclic saturated or partially unsaturated carbocyclic ring compound. Examples of $C_3$-$C_8$ cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1] heptyl, and bicyclo [2.2.2] octyl. Also contemplated is a monovalent group derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one ring atoms is selected from S, O, and N; zero, one, or two ring atoms are additional heteroatoms independently selected from S, O, and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroaralkyl" as used herein, refers to an alkyl residue attached to a heteroaryl ring. Examples include, but are not limited to, pyridinylmethyl, pyrimidinylethyl and the like.

The term "heterocyclyl," or "heterocycloalkyl," as used herein, refers to a saturated or unsaturated non-aromatic 3-, 4-, 5-, 6-, 7-, or 8-membered monocyclic, 7-, 8-, 9-, 10-, 11-, or 12-membered bicyclic (fused, bridged, or spiro rings), or 11-, 12, 13, or 14-membered tricyclic ring system (fused, bridged, or spiro rings), where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, and (iv) the nitrogen heteroatom may optionally be quaternized. Representative heterocycloalkyl groups include, but are not limited to, [1,3]dioxolanyl, pyrrolidinyl, pyrazolidinyl, pyrazolinyl, imidazolinyl, imidazolidinyl, piperidinyl, piperazinyl, oxazolidinyl, isoxazolidinyl, morpholinyl, tetrahydropyranyl, thiazolidinyl, isothiazolidinyl, tetrahydrofuryl, dioxanyl, oxetanyl, azetidinyl, thietanyl, oxiranyl, aziridinyl, thiiranyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 2-azaspiro[3.3]heptan-5-amine, 1-azaspiro[3.3]heptan-5-amine, 1-oxa-6-azaspiro[3.3]heptan-3-amine, 2-azaspiro[3.3]heptan-6-amine, 1-azaspiro[3.3]heptan-6-amine, 6-azaspiro[3.4]octan-2-amine, 5-azaspiro[3.4]octan-2-amine, 6-azaspiro[3.4]octan-1-amine, 5-azaspiro[3.4]octan-1-amine, 5-oxa-2-azaspiro[3.4]octan-7-amine, 7-amino-5-thia-2-azaspiro[3.4]octane 5,5-dioxide, 5-oxa-2-azaspiro[3.4]octan-8-amine, 8-amino-5-thia-2-azaspiro[3.4]octane 5,5-dioxide, and the like.

The term "alkylamino" refers to a group having the structure, e.g., $NH(C_1-C_6$ alkyl), where $C_1-C_6$ alkyl is as previously defined.

The term "dialkylamino" refers to a group having the structure, e.g., $N(C_1-C_6$ alkyl$)_2$, where $C_1-C_6$ alkyl is as previously defined.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

In accordance with the application, any of the aryls, substituted aryls, heteroaryls and substituted heteroaryls described herein, can be any aromatic group. Aromatic groups can be substituted or unsubstituted.

As described herein, compounds of the application may optionally be substituted with one or more substituents, such as are illustrated generally above, or as exemplified by particular classes, subclasses, and species of the application. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted alkenyl," "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocyclyl," and any other optionally substituted group as used herein, refer to groups that are substituted or unsubstituted by independent replacement of one, two, or three or more of the hydrogen atoms thereon with substituents including, but not limited to: —F, —Cl, —Br, —I, —OH, protected hydroxy, —NO$_2$, —CN, —NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_{12}$-alkenyl, —O—C$_2$-C$_{12}$-alkenyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkenyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkenyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_{12}$-alkenyl, —OCO$_2$—C$_2$-C$_{12}$-alkenyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkenyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—C$_2$-C$_{12}$-alkenyl, —NHC(O)—C$_2$-C$_{12}$-alkenyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkenyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, —NHC(O)NH—C$_1$-C$_{12}$-alkyl, —NHC(O)NH—C$_2$-C$_{12}$-alkenyl, —NHC(O)NH—C$_2$-C$_{12}$-alkenyl, —NHC(O)NH—C$_3$-C$_{12}$-cycloalkyl, —NHC(O)NH-aryl, —NHC(O)NH-heteroaryl, NHC(O)NH-heterocycloalkyl, —NHC(S)NH$_2$, —NHC(S)NH—C$_1$-C$_{12}$-alkyl, —NHC(S)NH—C$_2$-C$_{12}$-alkenyl, —NHC(S)NH—C$_2$-C$_{12}$-alkenyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_{12}$-alkenyl, —NHC(NH)NH—C$_2$-C$_{12}$-alkenyl, —NHC(NH)NH—C$_3$-C$_{12}$-cycloalkyl, —NHC(NH)NH-aryl, —NHC(NH)NH-heteroaryl, —NHC(NH)NHheterocycloalkyl, —NHC(NH)—C$_1$-C$_{12}$-alkyl, —NHC(NH)—C$_2$-C$_{12}$-alkenyl, —NHC(NH)—C$_2$-C$_{12}$-alkenyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkenyl, C(NH)NH—C$_3$-C$_{12}$-cycloalkyl, —C(NH)NH-aryl, —C(NH)NH-heteroaryl, —C(NH)NHheterocycloalkyl, —S(O)—C$_1$-C$_{12}$-alkyl, —S(O)—C$_2$-C$_{12}$-alkenyl, —S(O)—C$_2$-C$_{12}$-alkenyl, —S(O)—C$_3$-C$_{12}$-cycloalkyl, —S(O)-aryl, —S(O)-heteroaryl, —S(O)-heterocycloalkyl —SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkenyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkenyl, —NHS$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl.

The term "carrier", as used in this application, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The compounds of the present application may form salts which are also within the scope of this application. Reference to a compound of the Formula herein is understood to include reference to salts thereof, unless otherwise indicated.

Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The compounds of the present application, for example, including the pharmaceutically acceptable salts, tautomers, prodrugs, and polymorphs of the compounds, can exist in a solvated form with other solvent molecules or in an unsolvated form.

"Solvate" means solvent addition forms that contain either stoichiometric or non stoichiometric amounts of solvent. Some compounds or salts have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this application, as are positional isomers (such as, for example, 4-pyridyl and 3-pyridyl). For example, if a compound of Formula (I) incorporates a double bond or a fused ring, both the cis- and trans-forms, as well as mixtures, are embraced within the scope of the application. Individual stereoisomers of the compound of the application may, for example, be substantially free of other isomers, or may be admixed, for example, as racemates or with all other, or other selected, stereoisomers. The chiral centers of the present application can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures or as individual enantiomers or diastereomers.

In the present specification, the structural formula of the compound represents a certain isomer for convenience in some cases, but the present application includes all isomers, such as geometrical isomers, optical isomers based on an asymmetrical carbon, stereoisomers, tautomers, and the like.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

The compounds of the application may contain asymmetric or chiral centers, and, therefore, exist in different stereoisomeric forms. It is intended that all stereoisomeric forms of the compounds of the application as well as mixtures thereof, including racemic mixtures, form part of the present application. In addition, the present application embraces all geometric and positional isomers. For example, if a compound of the application incorporates a double bond or a fused ring, both the cis- and trans-forms, as well as mixtures, are embraced within the scope of the application. Each compound herein disclosed includes all the enantiomers that conform to the general structure of the compound. The compound may be in a racemic or enantiomerically pure form, or any other form in terms of stereochemistry. The assay results may reflect the data collected for the racemic form, the enantiomerically pure form, or any other form in terms of stereochemistry.

A carbon atom bonded to four non-identical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

In another embodiment of the application, the compound of Formula (I) is an enantiomer. In some embodiments the compound is the (S)-enantiomer. In other embodiments the compound is the (R)-enantiomer. In yet other embodiments, the compounds of Formula (I) may be (+) or (−) enantiomers. The compound may contain more than one stereocenter.

In another embodiment of the application, the compounds of Formula (I) are diastereomers. In some embodiments, the compounds are the syn diastereomer. In other embodiments, the compounds are the anti diastereomer.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by use of a chiral HPLC column.

It is also possible that the compounds of the application may exist in different tautomeric forms, and all such forms are embraced within the scope of the application. Also, for example, all keto-enol and imine-enamine forms of the compounds are included in the application.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-imine. For example, (Pyrrolopyrimidinyl)methanone-(Pyrrolopyrimidinyl) methanol tautomeric pairs are included in the present application:

The present application relates to a compound of Formula (I) or pharmaceutically acceptable salts thereof, tautomers, prodrugs, solvates, metabolites, polymorphs, analogs or derivatives thereof, capable of inhibiting BTK, which are useful for the treatment of diseases and disorders associated with modulation of a BTK kinase. The application further relates to compounds of Formula (I), or pharmaceutically acceptable salts thereof, tautomers, prodrugs, solvates, metabolites, polymorphs, analogs or derivatives thereof, which are useful for inhibiting BTK. In some embodiments, the BTK is wild-type BTK. In other embodiments, the BTK is a mutant BTK.

Another aspect of the application relates to a compound of Formula (I), wherein the compound inhibits kinase activity of a mutant BTK, such as a drug-resistant mutant BTK harboring a drug-resistance mutation (e.g., C481S mutation). In some embodiments, the patient or subject does not respond to a BTK inhibitor or relapses after the treatment with a BTK inhibitor, due to a mutation of BTK kinase (e.g., a C481S mutation) that prevents target inhibition. In one embodiment, the BTK mutation is a C481S mutation.

In some embodiments, the application provides a compound of Formula (I), wherein the compound is more potent than one or more known BTK inhibitors, including, but not limited to Ibrutinib, GDC-0834, $RN_{486}$, CGI-560, CGI-1746, HM-71224, CC-292, ONO-4059, CNX-774, and LFM-A13, at inhibiting the activity of BTK. For example, the compound can be at least about 2-fold, 3-fold, 5-fold, 10-fold, 25-fold, 50-fold or about 100-fold more potent (e.g., as measured by $IC_{50}$) than Ibrutinib, GDC-0834, $RN_{486}$, CGI-560, CGI-1746, HM-71224, CC-292, ONO-4059, CNX-774, and/or LFM-A13 at inhibiting the activity of the BTK.

In some embodiments, the application provides a compound of Formula (I), wherein the compound is more potent than one or more known BTK inhibitors, including, but not limited to Ibrutinib, GDC-0834, $RN_{486}$, CGI-560, CGI-1746, HM-71224, CC-292, ONO-4059, CNX-774, and LFM-A13, at inhibiting the activity of BTK containing one or more mutations as described herein, e.g., C481S. For example, the compound can be at least about 2-fold, 3-fold, 5-fold, 10-fold, 25-fold, 50-fold or about 100-fold more potent (e.g., as measured by $IC_{50}$) than Ibrutinib, GDC-0834, $RN_{486}$, CGI-560, CGI-1746, HM-71224, CC-292, ONO-4059, CNX-774, and/or LFM-A13 at inhibiting the activity of the BTK containing one or more mutations as described herein. A drug-resistant BTK mutant can have without limitation a drug resistance mutation comprising C481S mutation.

Potency of the inhibitor can be determined by $IC_{50}$ value. A compound with a lower $IC_{50}$ value, as determined under

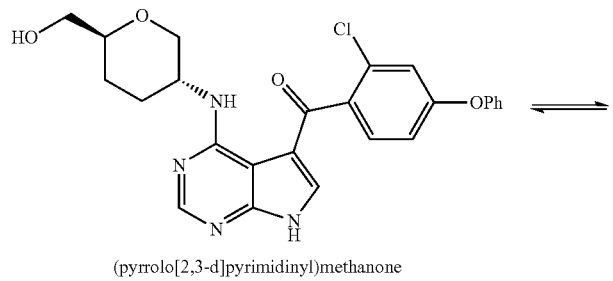

(pyrrolo[2,3-d]pyrimidinyl)methanone

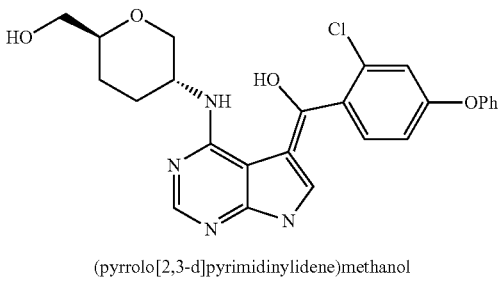

(pyrrolo[2,3-d]pyrimidinylidene)methanol substantially similar conditions, is a more potent inhibitor relative to a compound with a higher $IC_{50}$ value.

The compounds of the present application can be converted to N-oxides by treatment with an oxidizing agent (e.g., 3-chloroperoxybenzoic acid (m-CPBA) and/or hydrogen peroxides) to afford other compounds of the present application. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present application can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compounds as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

The term "prodrug," as used in this application, means a compound which is convertible in vivo by metabolic means (e.g., by hydrolysis) to a disclosed compound.

Since prodrugs are known to enhance numerous desirable qualities of pharmaceuticals (e.g., solubility, bioavailability, manufacturing, etc.) the compounds of Formula (I), or pharmaceutically acceptable salts, tautomers, solvates, metabolites, polymorphs, analogs or derivatives thereof can be delivered in prodrug form. Thus, the present application is intended to cover prodrugs of a compound of Formula (I), or a pharmaceutically acceptable salt, tautomer, solvate, metabolite, polymorph, analog or derivative thereof, methods of delivering the same and compositions containing the same. "Prodrugs" are intended to include any covalently bonded carriers that release an active parent drug of the present application in vivo when such prodrug is administered to a mammalian subject. Prodrugs are prepared by modifying functional groups present in the compound in such a way that the modifications are cleaved, either in routine manipulation or in vivo, to the parent compound. Prodrugs include compounds of the application wherein a hydroxyl or amino, group is bonded to any group that, when the prodrug of the present application is administered to a mammalian subject, it cleaves to form a free hydroxyl or free amino group, respectively. Examples of prodrugs include, but are not limited to, acetate, formate, and benzoate derivatives of alcohol and amine functional groups in the compounds of each of the formulae described herein or a pharmaceutically acceptable salt, solvate, prodrug, stereoisomer, or tautomer thereof.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

As used herein, the term "analog" refers to a compound that is structurally similar to another compound but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

The application also comprehends isotopically-labeled compounds, which are identical to those recited in the each of the formulae described herein, but for the fact that one or more atoms are replaced by an atom having an atomic mass or mass number different from the atomic mass or mass number most commonly found in nature. Examples of isotopes that can be incorporated into compounds of the application include isotopes of hydrogen, carbon, nitrogen, fluorine, such as $^3H$, $^{11}C$, $^{14}C$, $^2H$ and $^{18}F$.

Compounds of Formula (I), or pharmaceutically acceptable salts, tautomers, prodrugs, solvates, metabolites, polymorphs, analogs or derivatives thereof, that contain the aforementioned isotopes and/or other isotopes of other atoms are within the scope of the present application. Isotopically-labeled compounds of the present application, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are useful for their ease of preparation and detectability. $^{11}C$ and $^{18}F$ isotopes are useful in PET (positron emission tomography). PET is useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances, isotopically labeled compounds of Formula (I), or pharmaceutically acceptable salts, tautomers, prodrugs, solvates, metabolites, polymorphs, analogs or derivatives thereof, can generally be prepared by carrying out the procedures disclosed in the Schemes and/or in the Examples described herein, by substituting a readily available isotopically labeled reagent for a non-isotopically labeled reagent. In one embodiment, the compound of Formula (I) or pharmaceutically acceptable salts, tautomers, prodrugs, solvates, metabolites, polymorphs, analogs or derivatives thereof, is not isotopically labelled.

The present application relates to a compound which is a modulator of BTK (wild-type BTK or mutant BTK). In one embodiment, the compound of the present application is an inhibitor of BTK (wild-type BTK or mutant BTK).

The term "administer", "administering", or "administration" as used in this application refers to either directly administering a disclosed compound or pharmaceutically acceptable salt of the disclosed compound or a composition to a subject, or administering a prodrug, derivative or analog of the compound or pharmaceutically acceptable salt of the compound or a composition to the subject, which can form an equivalent amount of active compound within the subject's body.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" or "therapeutically effective amount" when used in connection with a compound or pharmaceutical composition is an amount effective for treating or preventing a disease in a subject as described herein.

The term "treating" with regard to a subject, refers to improving at least one symptom of the subject's disorder. Treating includes curing, improving, or at least partially ameliorating the disorder.

The compounds of the present application, or a pharmaceutically acceptable salt, solvate, prodrug, stereoisomer, or tautomer thereof, can also be used to prevent a disease, condition or disorder. As used herein, "preventing" or "prevent" describes reducing or eliminating the onset of the symptoms or complications of the disease, condition or disorder.

The term "disorder" is used in this application to mean, and is used interchangeably with, the terms disease, condition, or illness, unless otherwise indicated.

As used herein, the term "BTK-mediated" diseases or disorders means any disease or other deleterious condition in which BTK, or a mutant thereof, is known to play a role. Accordingly, another embodiment of the present application relates to treating or lessening the severity of one or more diseases in which BTK, or a mutant thereof, is known to play a role. Specifically, the present application relates to a method of treating or lessening the severity of a disease or condition selected from a proliferative disorder or an autoimmune disorder, wherein said method comprises administering to a subject in need thereof a compounds of Formula (I), or pharmaceutically acceptable salts, tautomers, prodrugs, solvates, metabolites, polymorphs, analogs or derivatives thereof, or a composition according to the present application.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the application encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. Preferably, the methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

Methods for Preparing the Compounds

The compounds of the present application may be made by a variety of methods, including standard chemistry. Suitable synthetic routes are depicted in the Schemes given below.

The compounds of Formula (I) may be prepared by methods known in the art of organic synthesis as set forth in part by the following synthetic schemes. In the scheme described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of the compounds of the present application.

Those skilled in the art will recognize if a stereocenter exists in the compounds of Formula (I). Accordingly, the present application includes both possible stereoisomers (unless specified in the synthesis) and includes not only racemic compound but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

The compounds of the present application can be prepared in a number of ways well known to those skilled in the art of organic synthesis. By way of example, the compounds of the present application can be synthesized using the methods described below, together with synthetic methods known in the art of synthetic organic chemistry, or variations thereon as appreciated by those skilled in the art. Preferred methods include but are not limited to those methods described below. The compounds of the present application (i.e., a compound of Formula (I)) can be synthesized by following the steps outlined in General Schemes 1-3 which comprises a sequence of assembling intermediates 7-a to 7-i. Starting materials are either commercially available or made by known procedures in the reported literature or as illustrated.

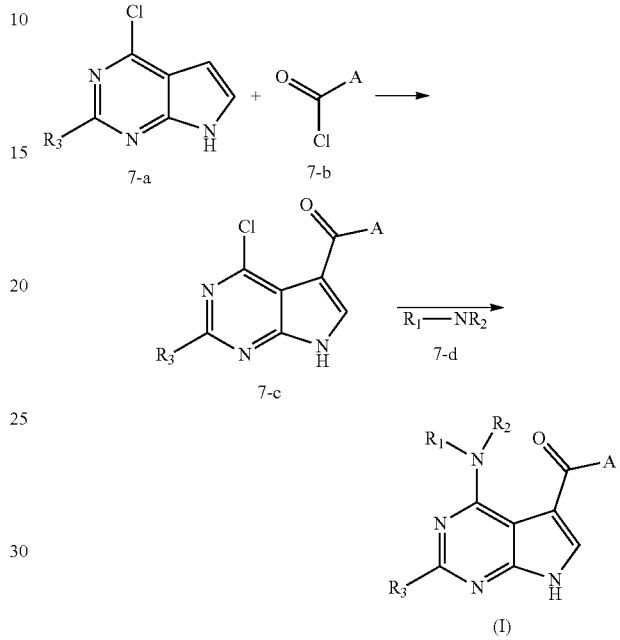

General Scheme 1

The general way of preparing compounds of Formula (I) by using intermediates 7-a, 7-b, 7-c, and 7-d is outlined in General Scheme 1 and further illustrated in Example 2. Acylation of 7-a with aroyl chloride or heteroaroyl chloride 7-b using a lewis acid catalyst (e.g., aluminum chloride (AlCl$_3$)) and a solvent (e.g., nitrobenzene, toluene, etc.) provides intermediate 7-c. Amination of 7-c with amine 7-d optionally using a base (e.g., triethylamine (TEA), pyridine, and/or potassium carbonate (K$_2$CO$_3$)), optionally in a solvent (e.g., N,N-dimethylformamide (DMF), isopropyl alcohol, etc.) and optionally at elevated temperature provides a compound of Formula (I).

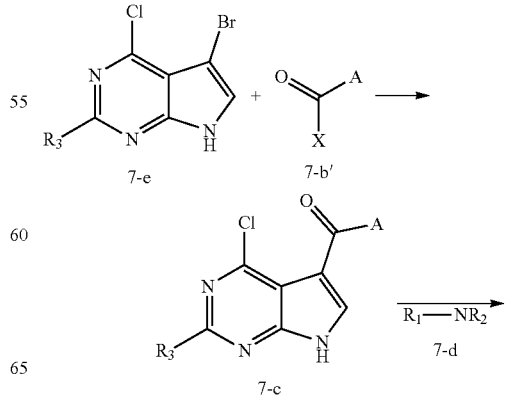

General Scheme 2

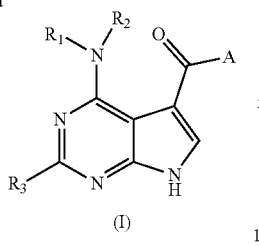
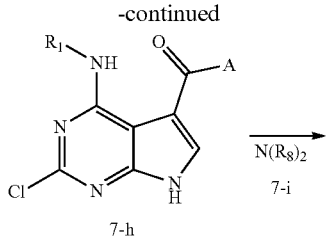

X is Cl or O-alkyl

Another general way of preparing compounds of Formula (I) by using intermediates 7-e, 7-b', 7-c, and 7-d is outlined in General Scheme 2 and further illustrated in Example 99. Acylation of 7-e with aroyl chloride or heteroaroyl chloride or alkyl ester 7-b' using a strong base (e.g., n-butyl lithium) and a solvent (e.g., hexanes, tetrahydrofuran, diethylether, etc.) provides intermediate 7-c. Amination of 7-c with amine 7-d optionally using a base (e.g., triethylamine (TEA), pyridine, and/or potassium carbonate ($K_2CO_3$)), optionally in a solvent (e.g., N,N-dimethylformamide (DMF), isopropyl alcohol, etc.) and optionally at elevated temperature provides a compound of Formula (I).

Another general way of preparing compounds of Formula (I) by using intermediates 7-b, 7-d, 7-f, 7-g, 7-h, and 7-i is outlined in General Scheme 3 and further illustrated in Example 141. Acylation of 7-f with aroyl chloride or heteroaroyl chloride 7-b using a lewis acid catalyst (e.g., aluminum chloride ($AlCl_3$)) and a solvent (e.g., nitrobenzene, toluene, etc.) provides intermediate 7-g. Amination of 7-g with amine 7-d optionally using a base (e.g., triethylamine (TEA), pyridine, and/or potassium carbonate ($K_2CO_3$)), optionally in a solvent (e.g., N,N-dimethylformamide (DMF), isopropyl alcohol, etc.) and optionally at elevated temperature provides intermediate 7-h. Amination of 7-h with amine 7-i optionally using a base (e.g., triethylamine (TEA), pyridine, and/or potassium carbonate ($K_2CO_3$)), optionally in a solvent (e.g., N,N-dimethylformamide (DMF), isopropyl alcohol, etc.) and optionally at elevated temperature provides a compound of Formula (I).

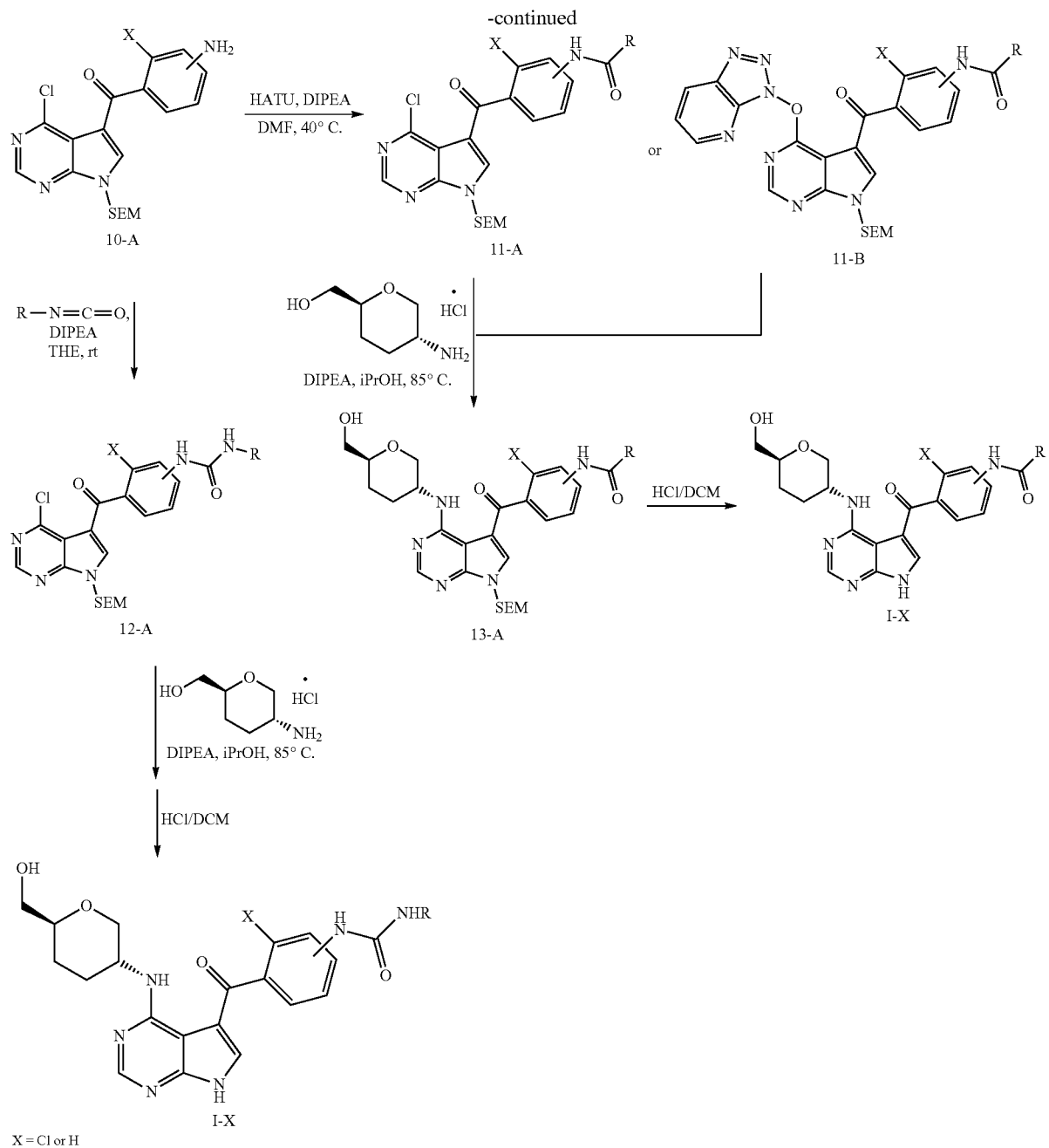
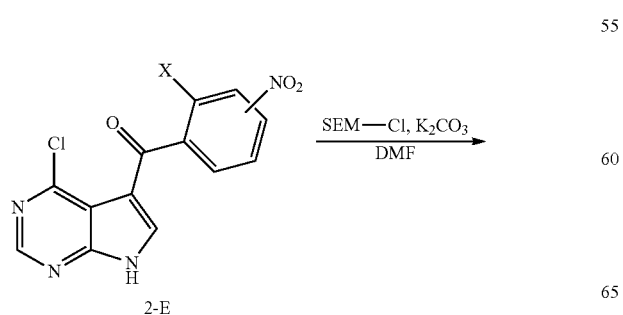
General Procedure D
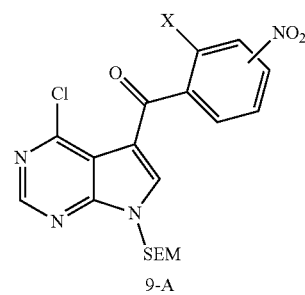

To a solution of pyrrolo[2,3-d]pyrimidine (8-A)(1 eq.) in DMF (1 mL/0.28 mmol) at room temperature was added potassium carbonate (2 eq.) and SEM-Cl (1.2 eq.). The reaction mixture was stirred at room temperature for 3 hours. The reaction mixture was then poured into 1:1 water/EtOAc and partitioned. The aqueous layer was extracted with EtOAc. The combined organic layers were washed with brine, dried over MgSO$_4$, filtered and concentrated to dryness. The residue was purified by flash chromatography on silica gel eluting with 30-100% EtOAc/hexanes to afford the product.

General Procedure E

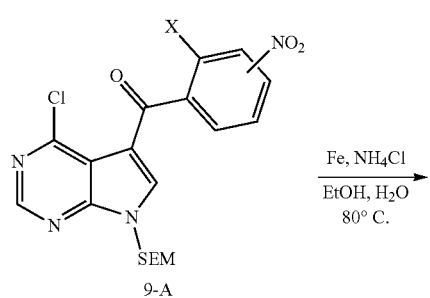

9-A

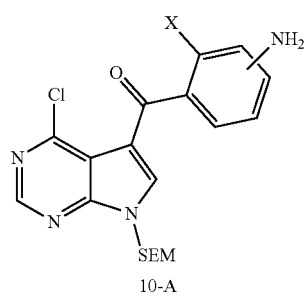

10-A

A suspension of the arylnitro compound (9-A) (1 eq.), ammonium chloride (10 eq. and iron (5 eq) in EtOH (1 mL/0.12 mmol) and water (1 mL/0.25 mmol) was heated to 80° C. for 2 hours. Upon cooling to room temperature, methanol was added, the reaction mixture was vigorously stirred for 30 min, filtered through Celite and washed with methanol and EtOAc. The filtrate was concentrated to dryness. The residue was triturated in water and the solids were collected by filtration, dried under high vacuum to afford the corresponding arylamine.

General Procedure F

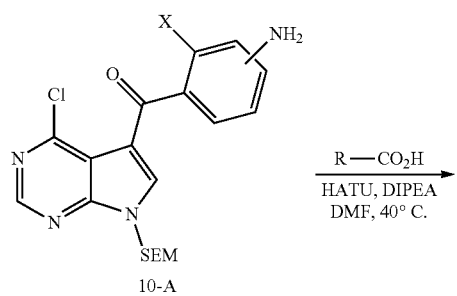

10-A

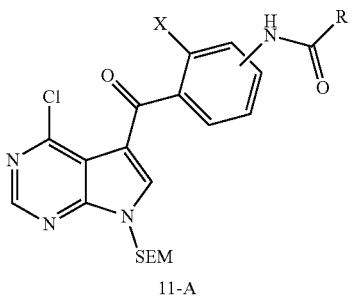

11-A

To a solution of the arylamine (10-A) (1 eq.) in DMF (2 mL/0.16 mmol) were added carboxylic acid (1.5 eq.), HATU (1.2 eq.) and DIPEA (2.5 eq.) and the reaction mixture was allowed to stir at room temperature for 18 hours or heated to 40-50° C. for 3-90 hours. Upon cooling to room temperature, the reaction mixture diluted with aqueous saturated NaHCO$_3$ and ethyl acetate. The layers were partitioned and the aqueous layer was extracted with ethyl acetate. The combined organic layer were washed with brine, dried over magnesium sulfate, filtered and concentrated to dryness under reduced pressure. The crude product was adsorbed onto silica gel for purification by ISCO CombiFlash (eluted with 0-10% MeOH/DCM or EtOAc/hexanes) or purified by reverse phase C$_{18}$ column chromatography (10-95% acetonitrile in water, 0.1% formic acid) to yield the amide product (11-A).

General Procedure G

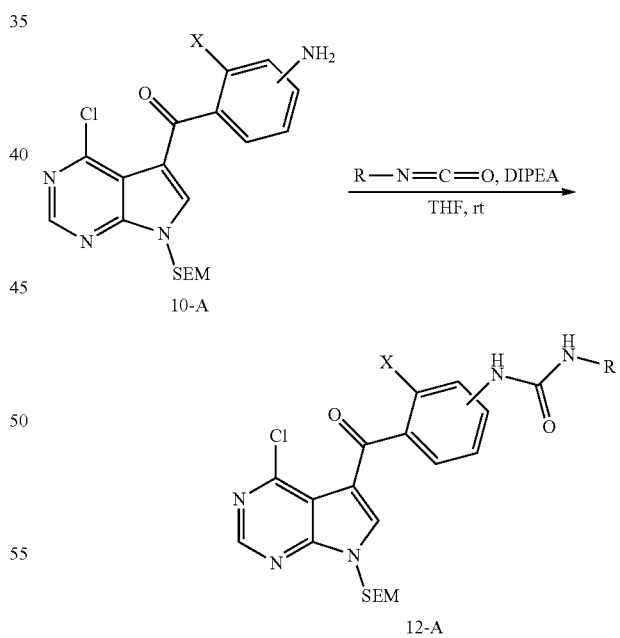

To a solution of the arylamine (1 eq.) in THF (2 mL/0.343 mmol) were added isocyanate (1.2 eq.) and DIPEA (2.5 eq.). The reaction mixture was allowed to stir at room temperature for 18 hours. The volatiles were removed under reduced pressure and the residue was adsorbed in silica gel purification by ISCO CombiFlash eluting with EtOAc/hexanes to yield the urea product.

General Procedure H

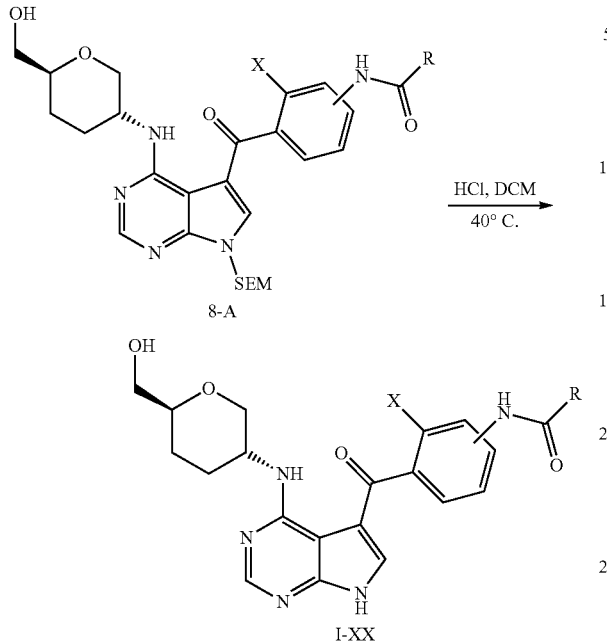

8-A

HCl, DCM
40° C.

I-XX

To a solution of SEM-protected substrate (8-A) (1 eq.) in DCM (1 mL/0.044 mmol) was added a solution of HCl (4N in dioxane, 60-81 eq.). The mixture was heated to 40° C. for 18 hours and concentrated to dryness under reduced pressure. The residue was diluted with 10 mL of DCM/MeOH/NH$_4$OH (90:9:1) and adsorbed onto silica gel for purification by flash chromatography on silica gel eluting with MeOH/DCM (9:1) and DCM/MeOH/NH$_{40}$H (90:9:1) to yield the deprotected product.

General Scheme 5

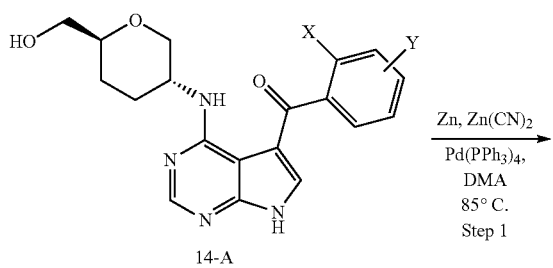

14-A

Zn, Zn(CN)$_2$
Pd(PPh$_3$)$_4$,
DMA
85° C.
Step 1

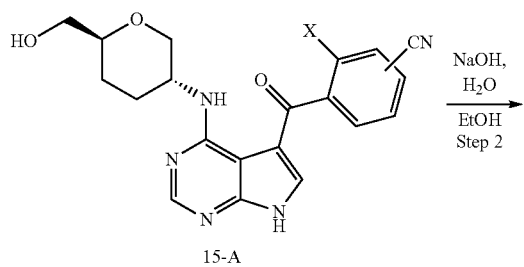

15-A

NaOH,
H$_2$O
EtOH
Step 2

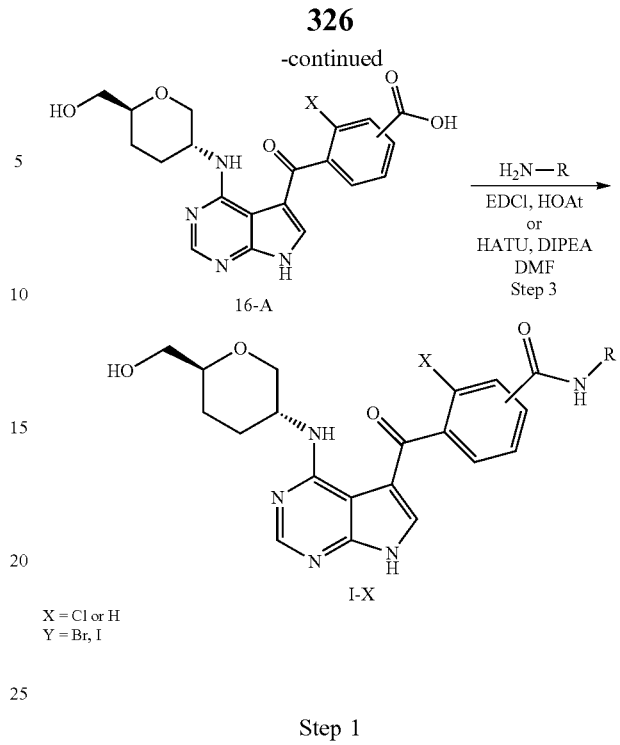

16-A

H$_2$N—R
EDCl, HOAt
or
HATU, DIPEA
DMF
Step 3

I-X

X = Cl or H
Y = Br, I

Step 1

To a solution of aryl halide (14-A) in DMA (1 mL/0.12 mmol) was added zinc dust (0.1 eq.) and zinc cyanide (0.5 eq.). The mixture was bubbled with nitrogen gas for 10 min, and Pd(PPh$_3$)$_4$ (0.05 eq.) was added. The mixture was bubbled again with nitrogen for 10 min and heated to 85° C. overnight. Upon cooling to room temperature, the reaction mixture was diluted with EtOAc and water. The layers were partitioned; the aqueous layer was extracted with EtOAc. The combined organic layers were washed with brine, dried over MgSO$_4$, and concentrated under reduced pressure. The residue was purified by flash chromatography on silica gel using MeOH/DCM to afford the desired material.

Step 2

The benzonitrile substrate (15-A) (1 eq.) was suspended in EtOH (1 mL/0.05 mmol) and 2N NaOH (10 eq.) was added. The suspension became a clear yellow solution. The reaction mixture was heated at 85° C. overnight. Upon cooling to room temperature, the pH was adjusted to 6 with 1N HCl and the mixture was concentrated to dryness under reduced pressure. The residue was dissolved in DMF to make a stock solution of 0.04M. The mixture was filtered through fritted funnel to remove NaCl residue. The stock solution of the benzoic acid product (0.04M) was used as such for subsequent amide coupling without further purification.

Step 3

To the benzoic acid substrate (16-A) (1 eq.) in DMF (0.04M) was added amine (1.1 eq.), EDCi (1.2 eq.) and HOAt (1.3 eq.) and the reaction mixture was allowed to stir at room temperature for 3-72 hours. Water (2-5 mL/mmol) was added and the mixture was concentrated to dryness under reduced pressure. The crude product was adsorbed onto silica gel for purification by ISCO CombiFlash eluting with 0-10% MeOH/DCM. Purification by reverse phase C$_{18}$ column chromatography (5-95% acetonitrile in water, 0.1%

Formic acid) was also used as an alternative method. The product fractions were combined and concentrated to dryness under reduced pressure to yield the amide product.

Step 3 (Alternative Method)

To the benzoic acid substrate (16-A) (1 eq.) in DMF (0.04M) was added amine (1.5-3 eq.), HATU (1.5-2 eq.) and DIPEA (2.5-5 eq.) and the reaction mixture was allowed to stir at room temperature for 18 hours or heated to 60° C. for 18 hours. Water (2-5 mL/mmol) was added and the mixture was concentrated to dryness under reduced pressure or the reaction mixture was diluted with aqueous saturated NaHCO$_3$ and ethyl acetate. The layers were partitioned and the aqueous layer was extracted with ethyl acetate. The combined organic layer were washed with brine, dried over magnesium sulfate, filtered and concentrated to dryness under reduced pressure. The crude product was adsorbed onto silica gel for purification by ISCO CombiFlash eluting with 0-10% MeOH/DCM or purified by high pressure HPLC system (column: Max-RP C-18, 21×50 mm, 10 μM), 10-80% acetonitrile in water, +0.1% formic acid) to yield the amide product.

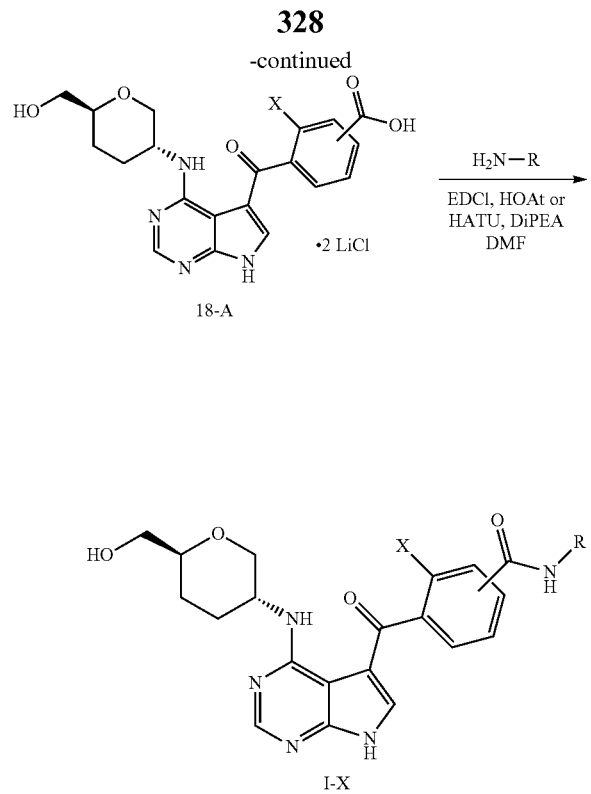

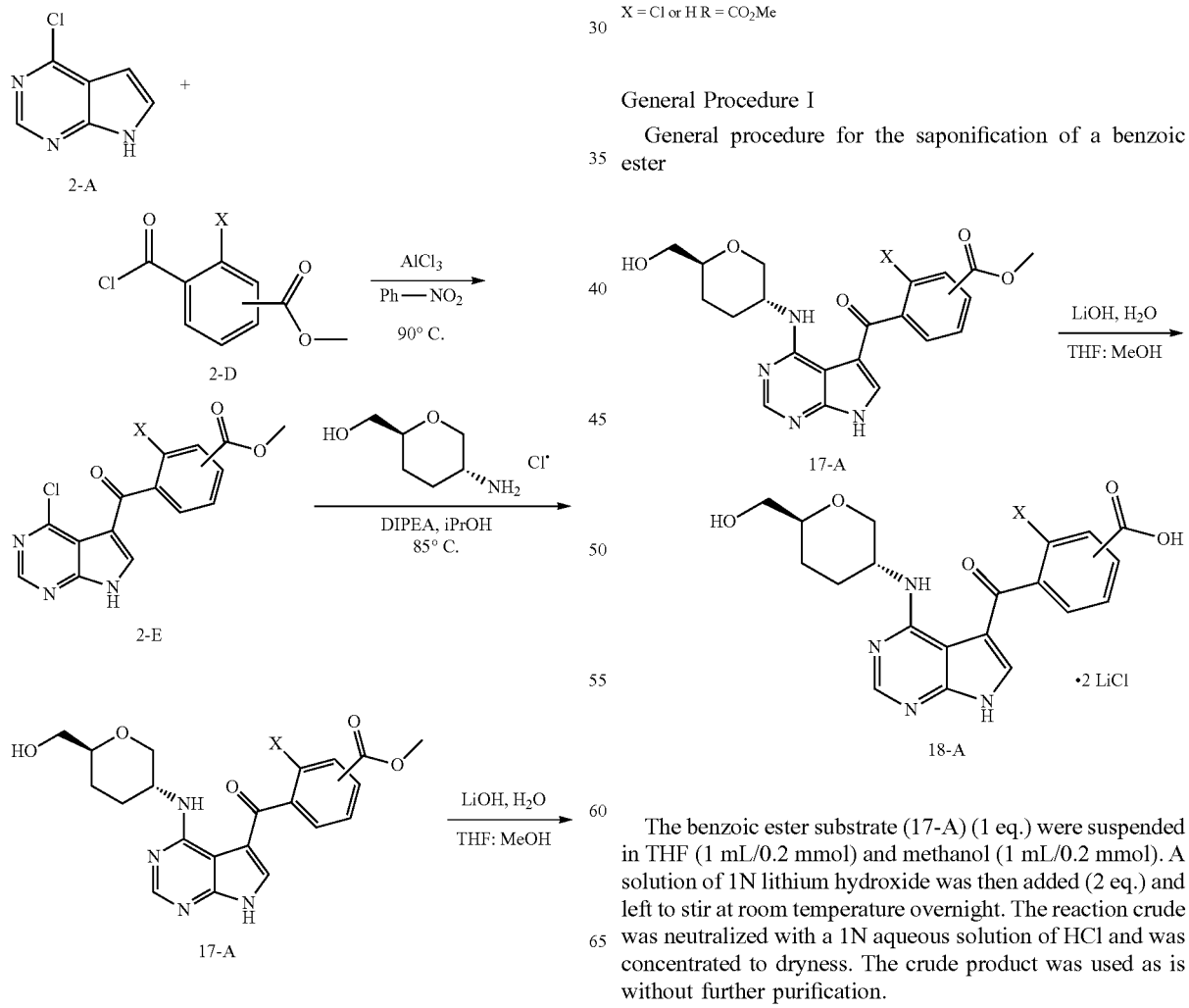

General Procedure I

General procedure for the saponification of a benzoic ester

The benzoic ester substrate (17-A) (1 eq.) were suspended in THF (1 mL/0.2 mmol) and methanol (1 mL/0.2 mmol). A solution of 1N lithium hydroxide was then added (2 eq.) and left to stir at room temperature overnight. The reaction crude was neutralized with a 1N aqueous solution of HCl and was concentrated to dryness. The crude product was used as is without further purification.

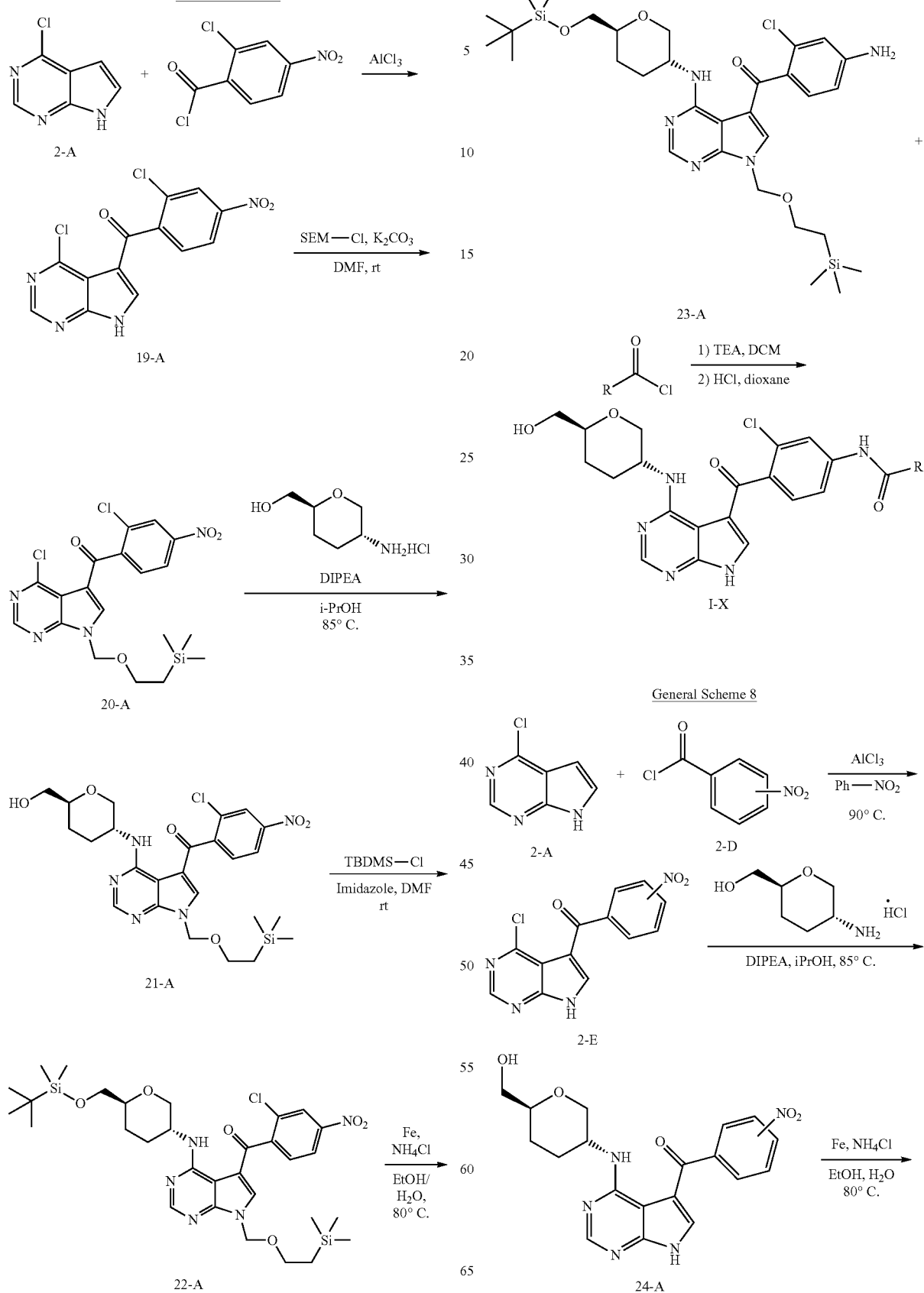

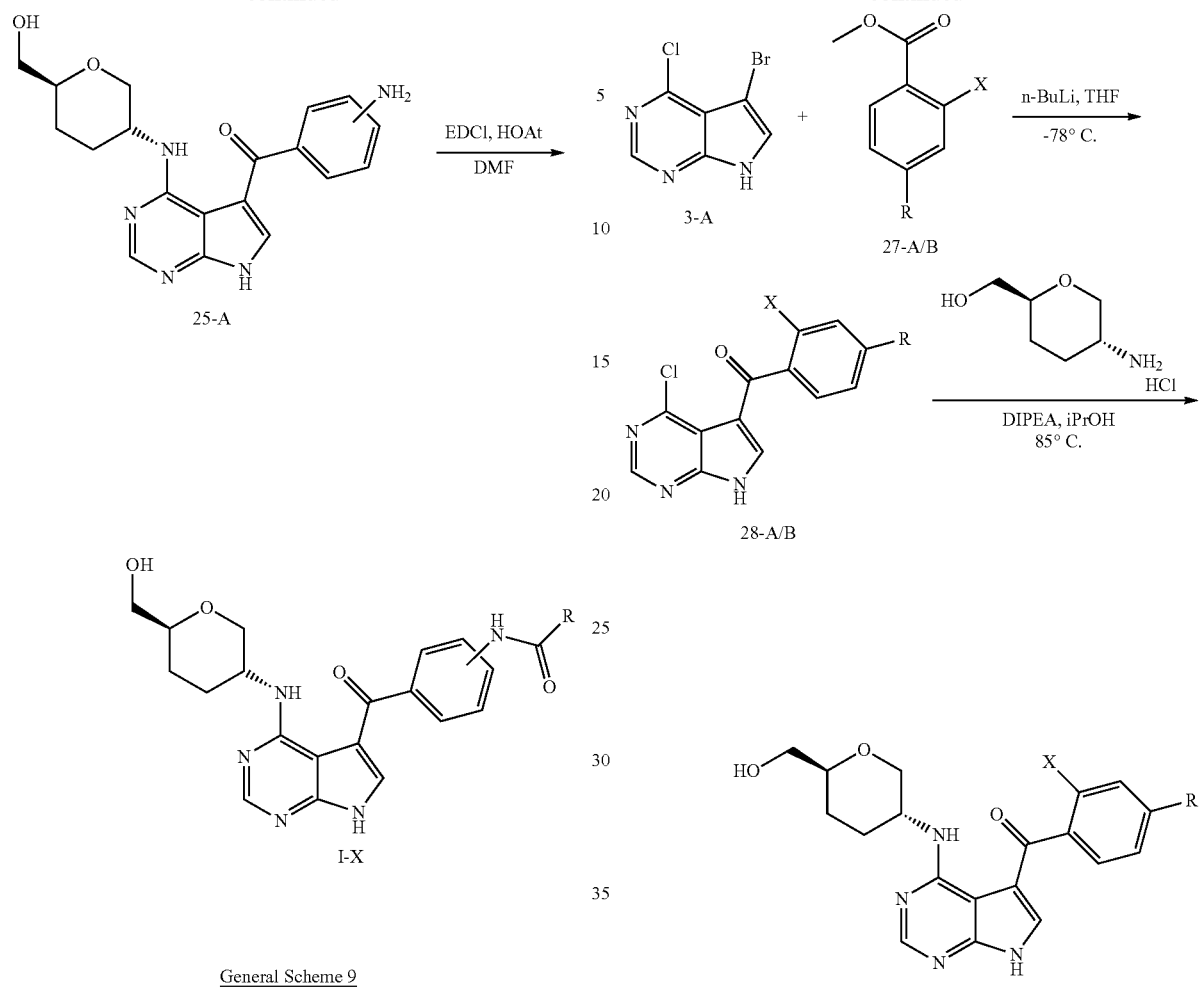
General Scheme 9
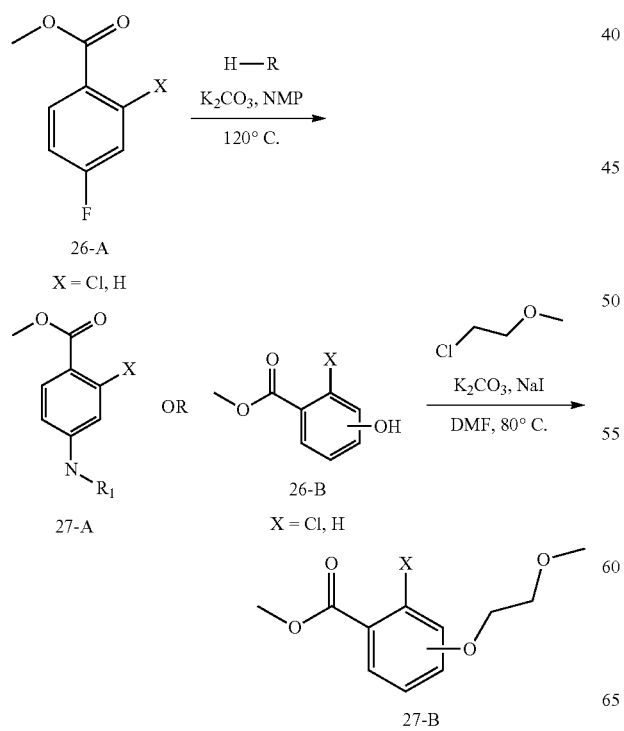
General Scheme 10
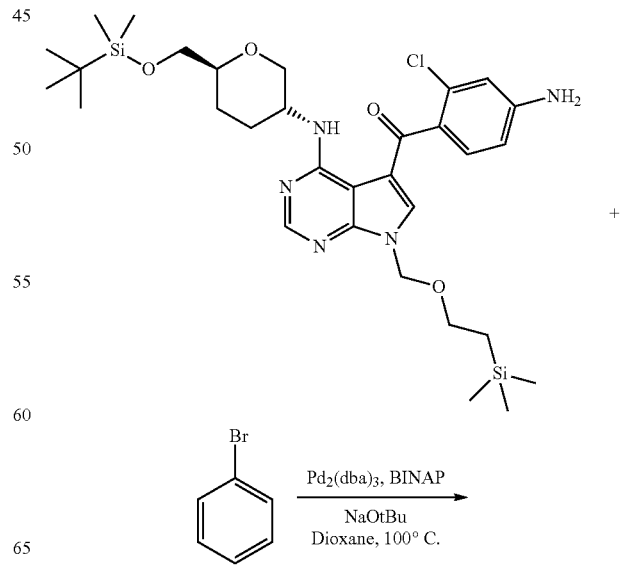

333
-continued
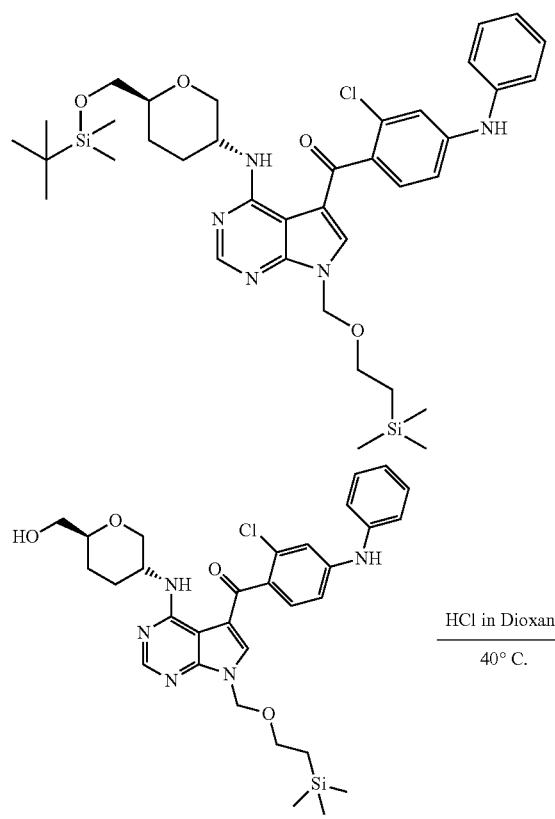
General Scheme 11
334
-continued
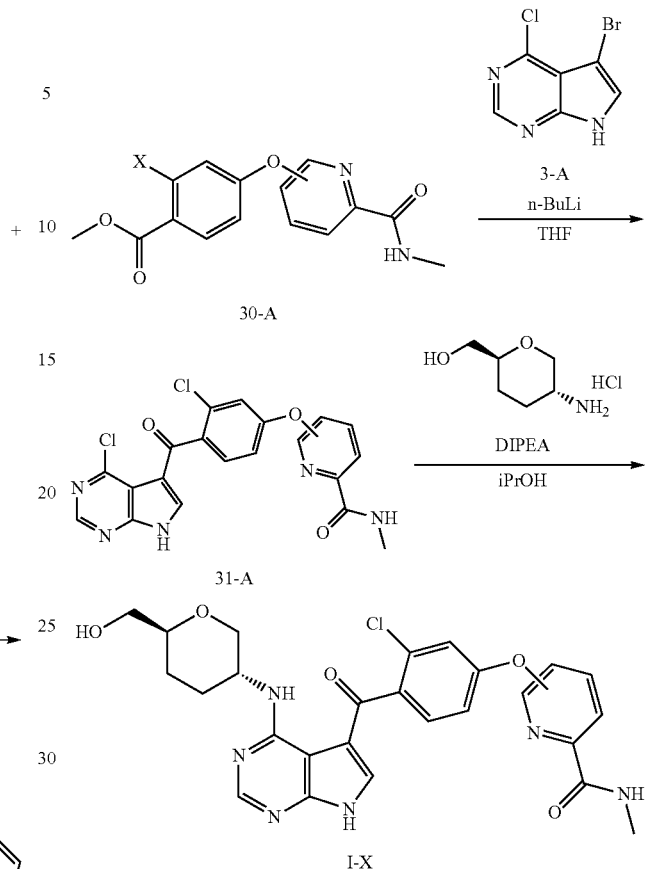
X = Cl, H
Scheme 12
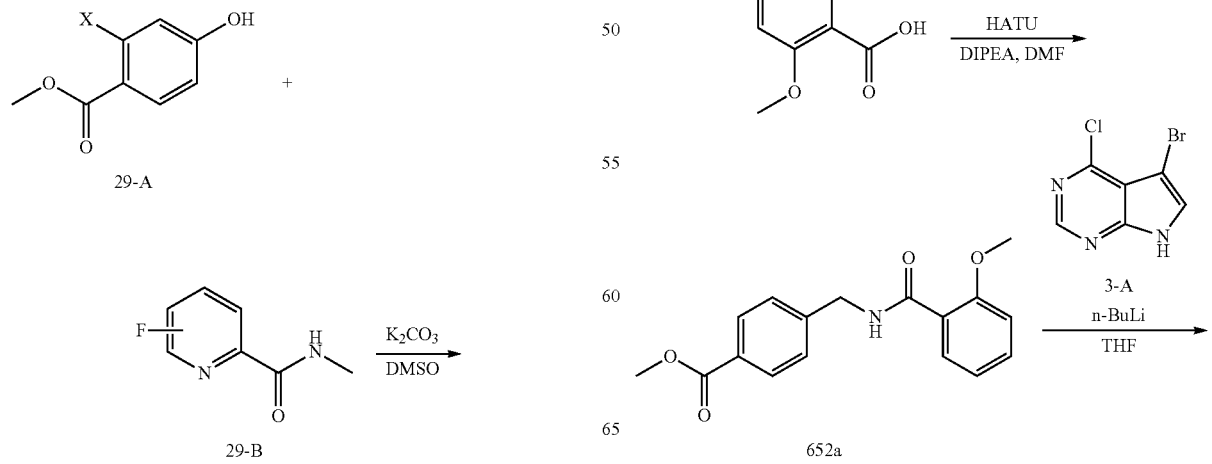

335
-continued
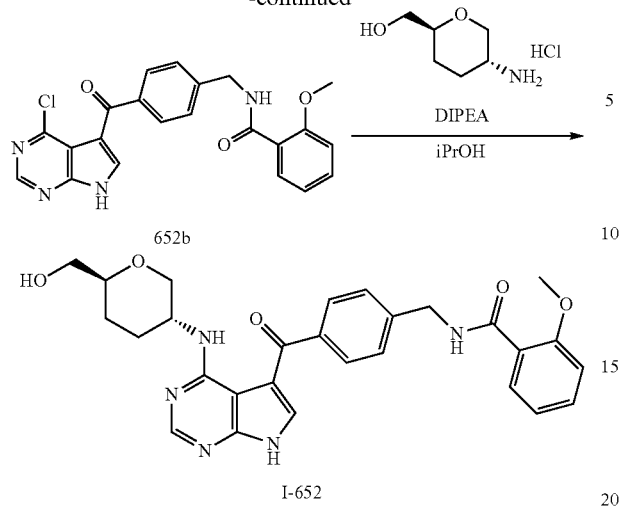
652b
I-652
General Scheme 13
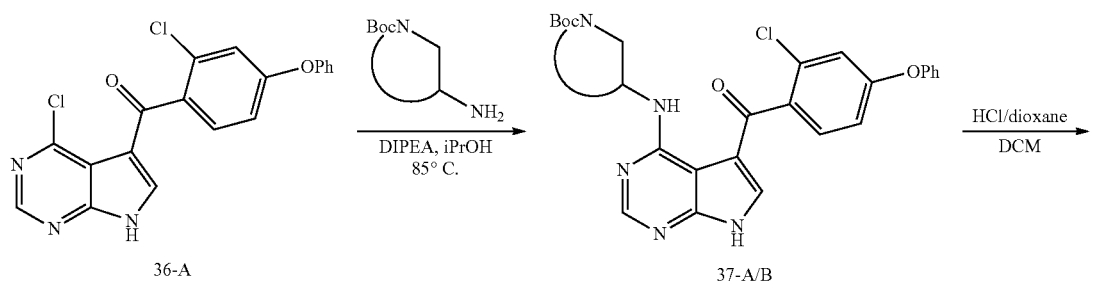
36-A      37-A/B
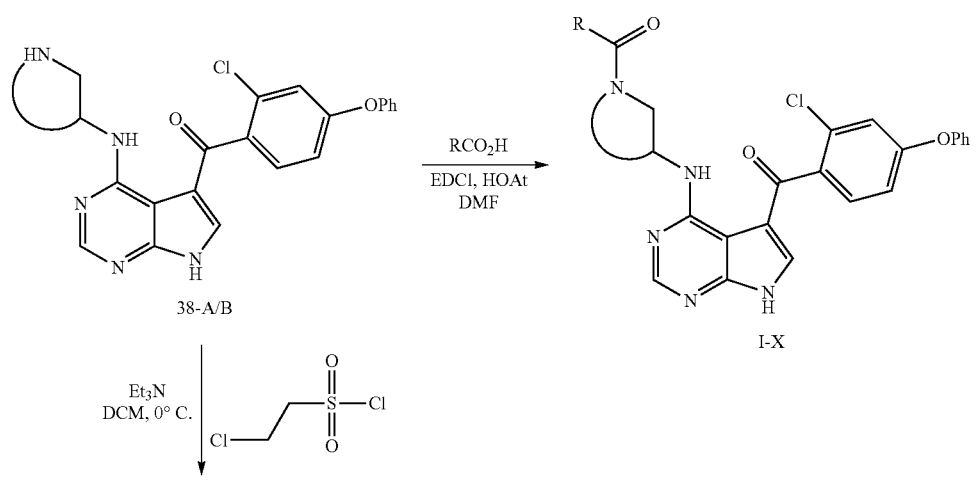
38-A/B      I-X -continued
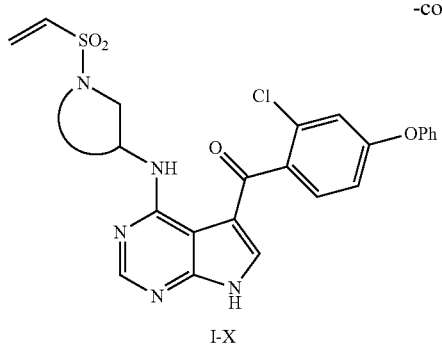
I-X General Scheme 14
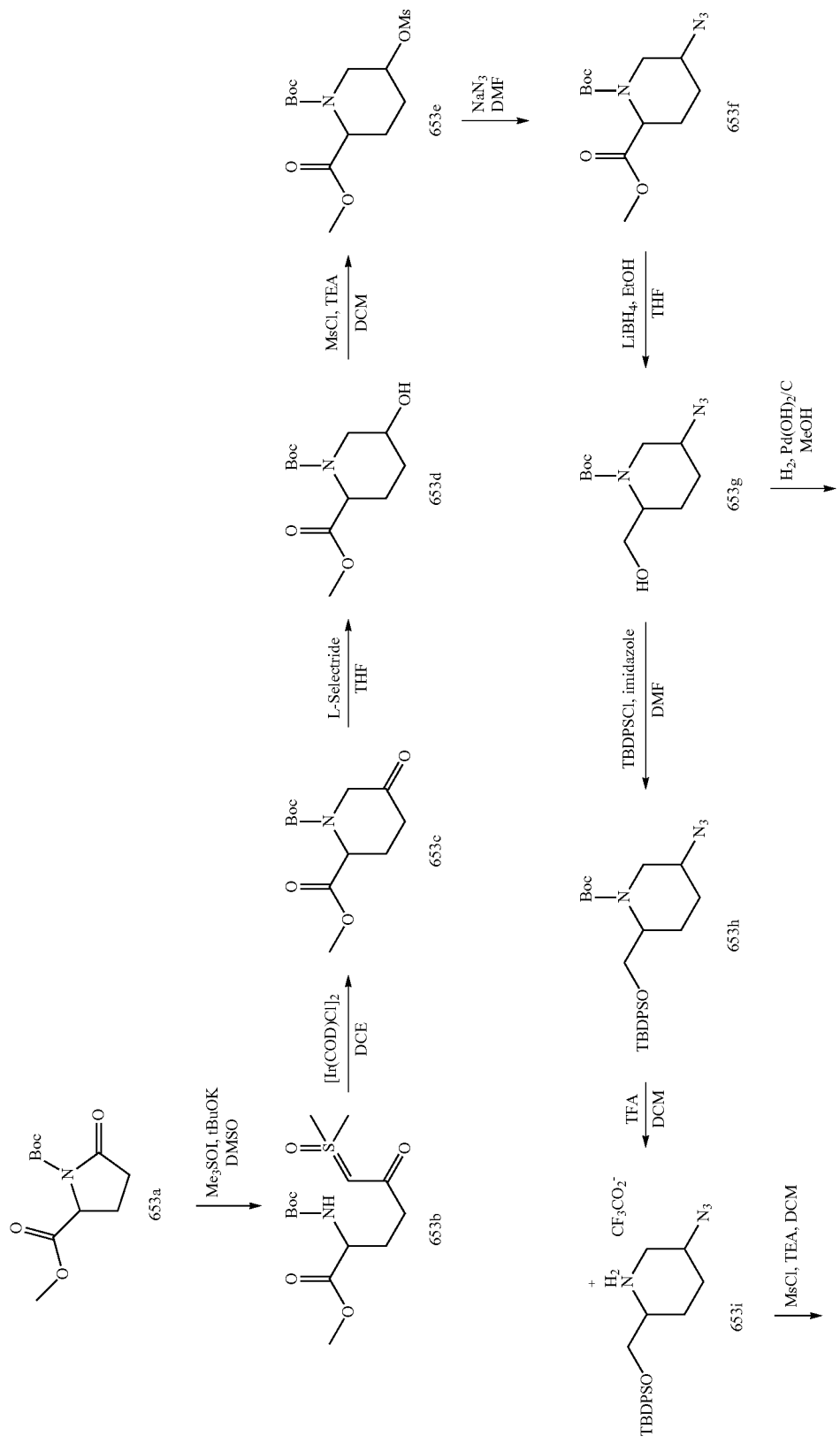

-continued
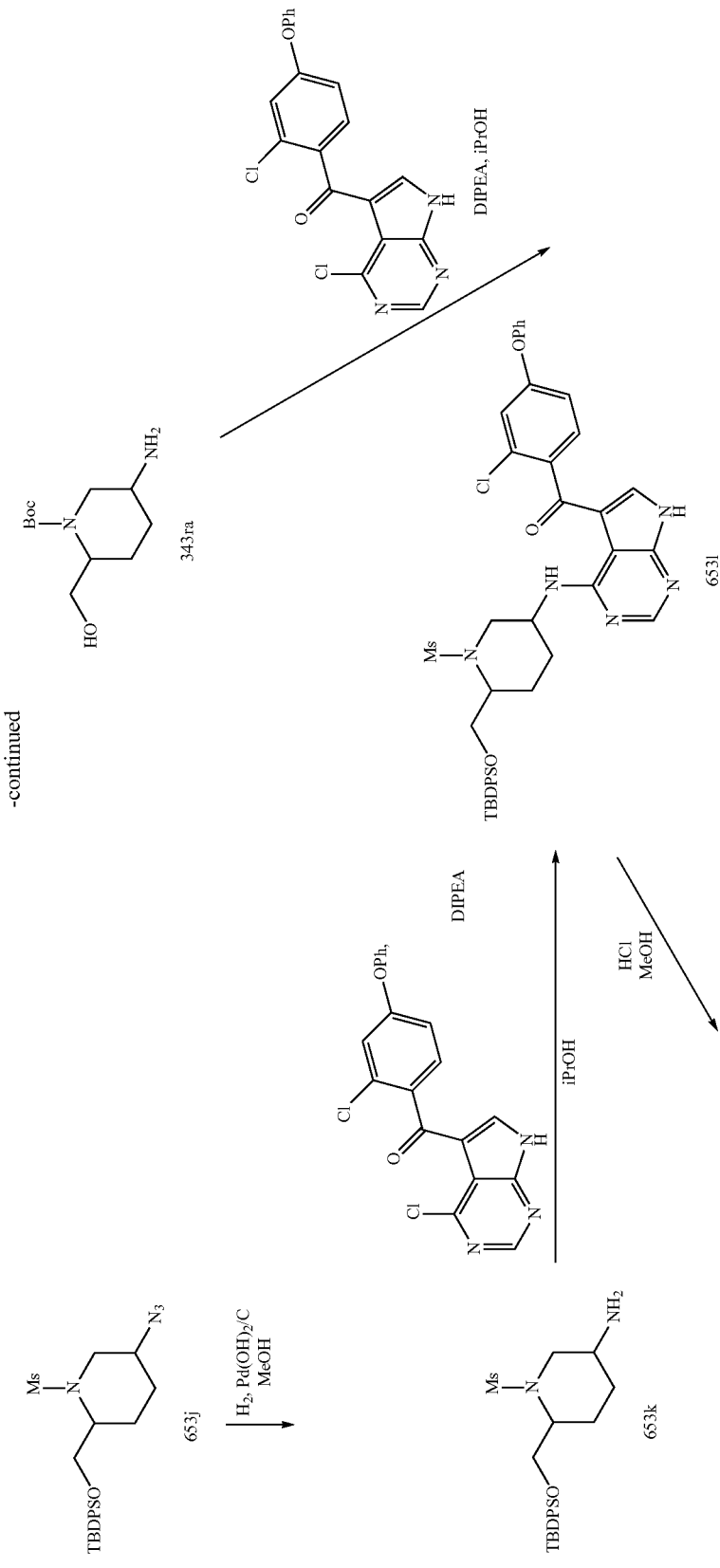

-continued
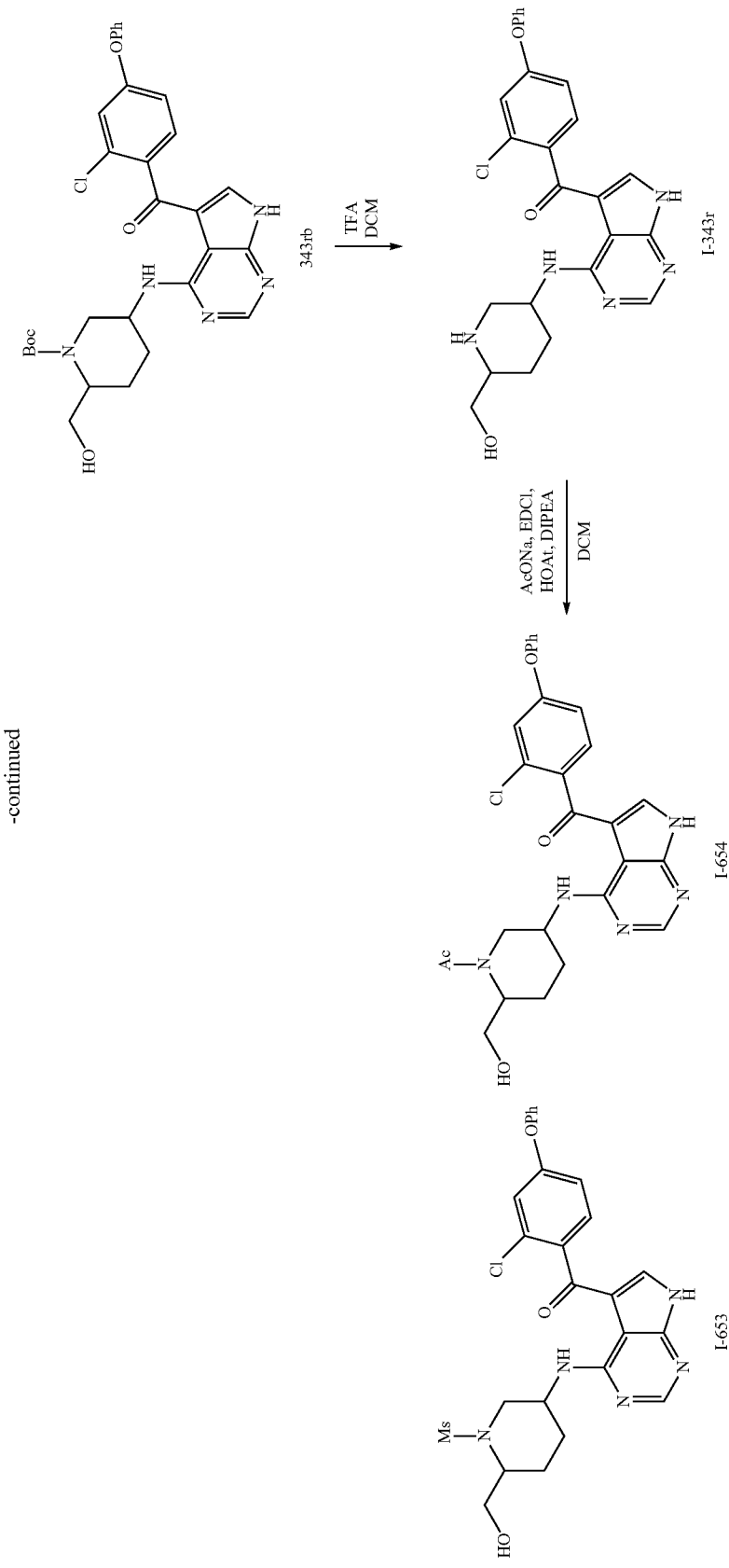

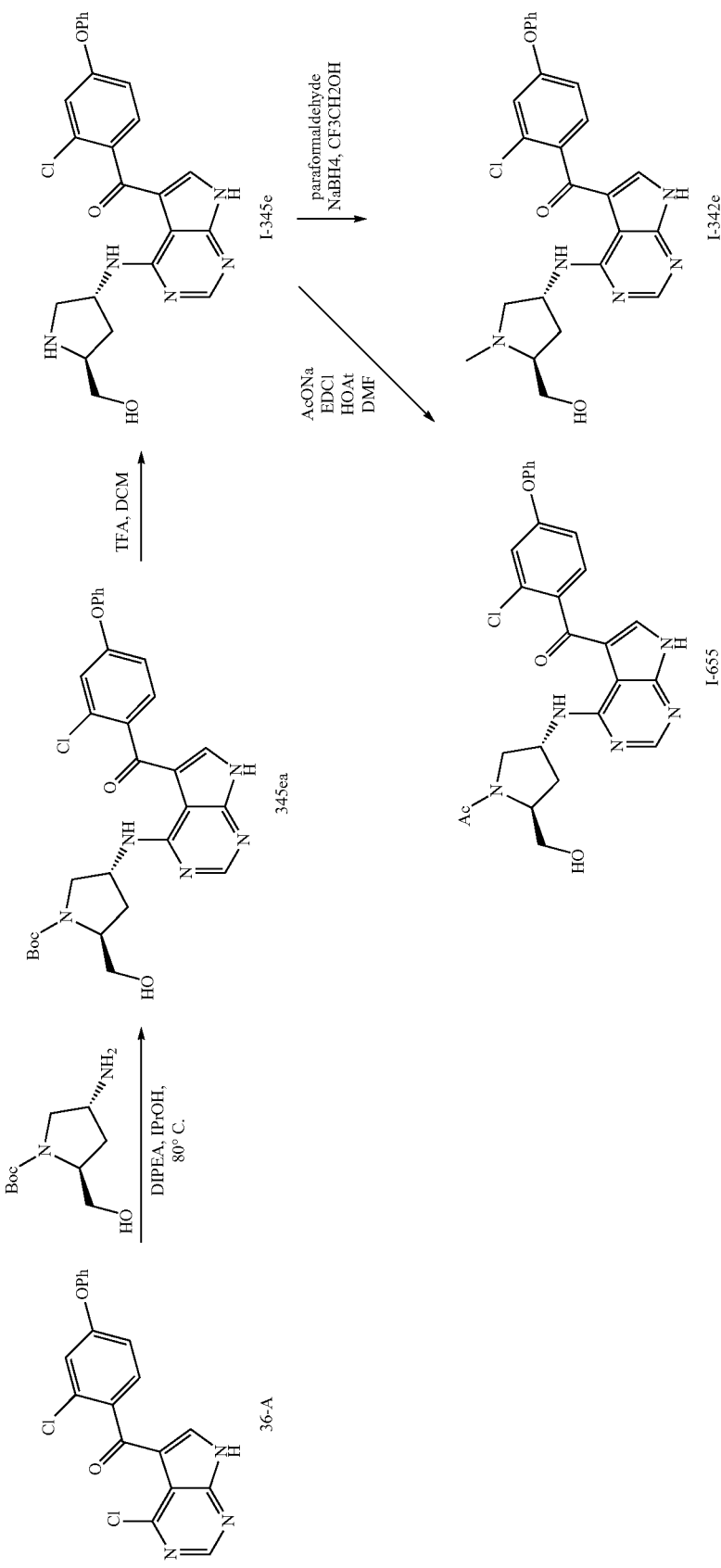

General Scheme 16
General Scheme 17
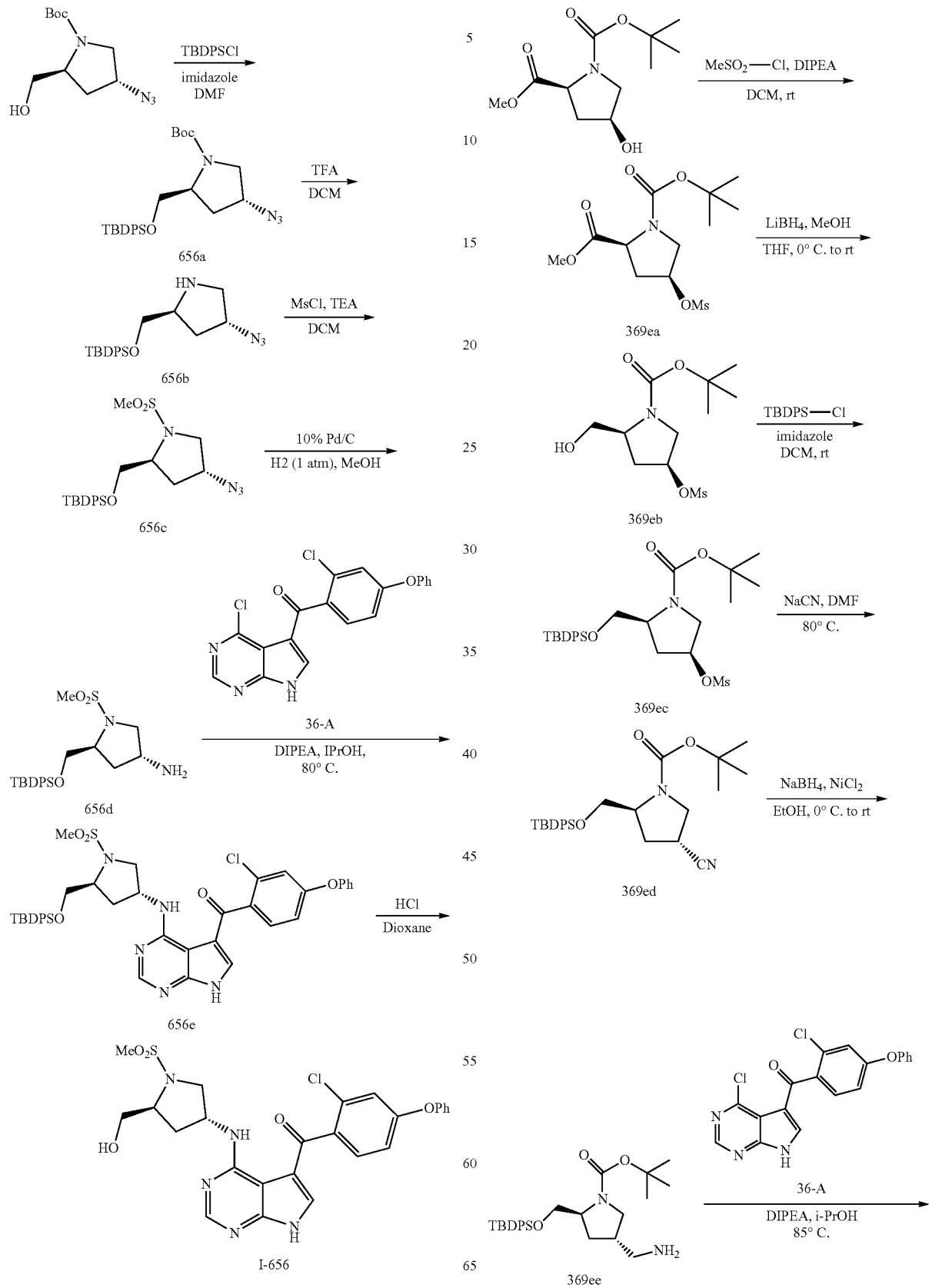

349
-continued
350
-continued
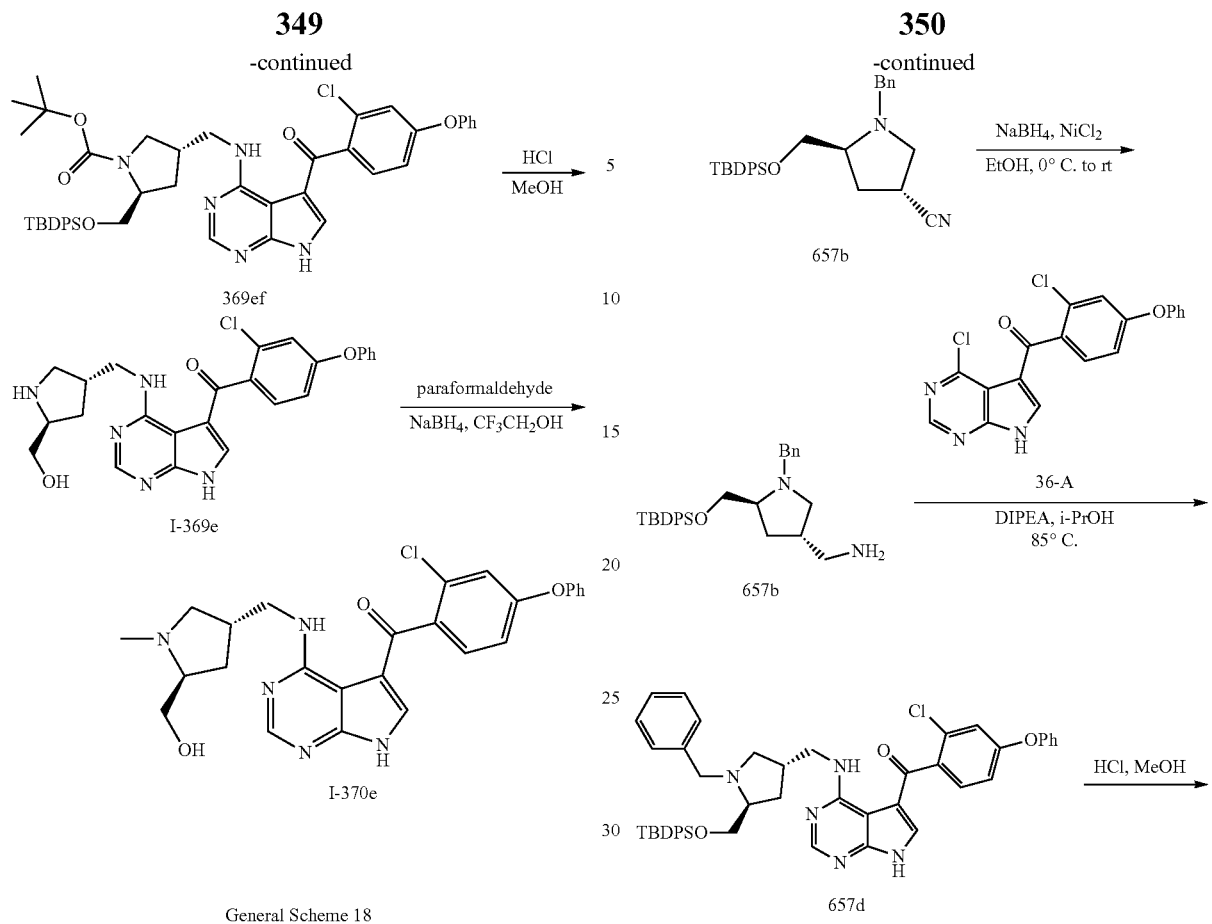
General Scheme 18
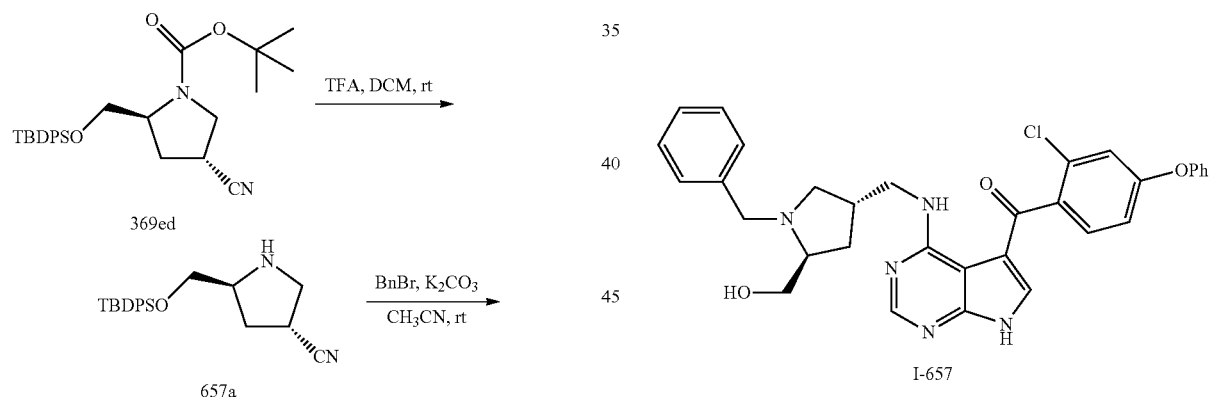
General Scheme 19
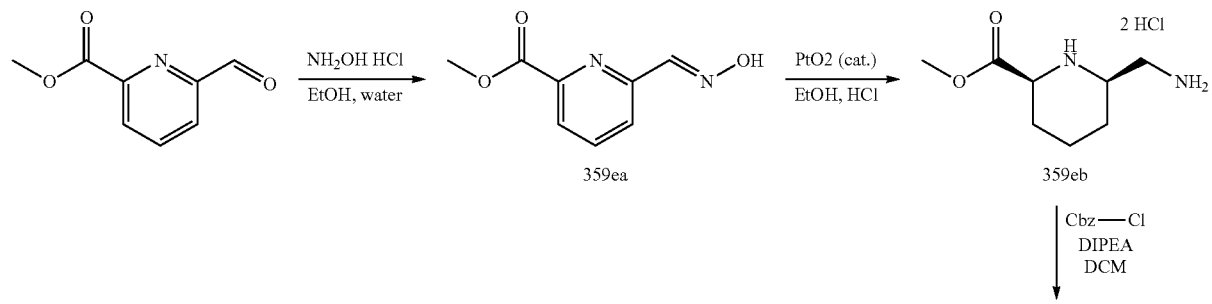

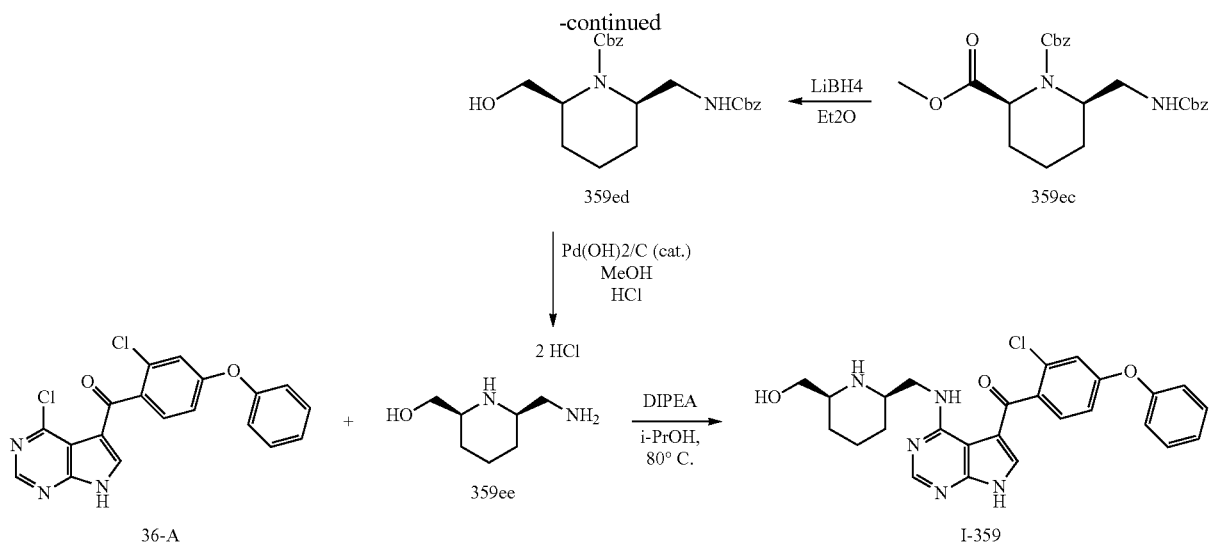

General Procedure J
A general method for amide formation using an acyl chloride with silyl-protected aniline substrate followed by desilylation

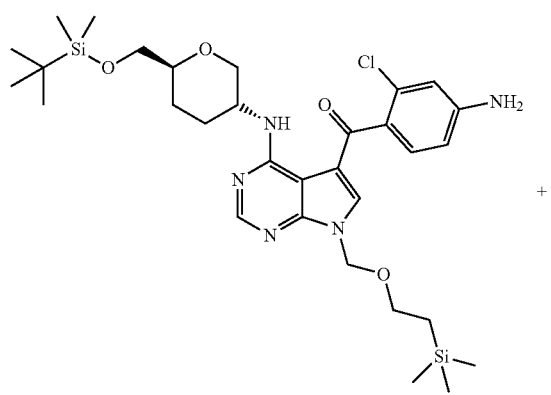

A solution of (4-amino-2-chlorophenyl)(4-(((3R,6S)-6-(((tert-butyldimethylsilyl) oxy)methyl)-tetrahydro-2H-pyran-3-yl)amino)-7-((2-(trimethylsilyl)ethoxy)methyl)-7H-pyrrolo[2,3-d]pyrimidin-5-yl)methanone (23-A) (1 eq) in DCM (1 mL/0.05 mmol) is treated with corresponding acyl chloride (1.5 eq) and triethylamine (3 eq) at room temperature for 3 h. The mixture is then concentrated and 4M HCl in dioxane (2 mL/0.05 mmol) is added. The mixture is stirred at 40° C. overnight then concentrated and the residue purified by preparative reverse phase HPLC (gradient from 30% to 95% of acetonitrile+0.1% formic acid).

Step 5: Synthesis of N-(3-chloro-4-(4-(((3R,6S)-6-(hydroxymethyl)tetrahydro-2H-pyran-3-yl)amino)-7H-pyrrolo[2,3-d]pyrimidine-5-carbonyl)phenyl) benzamide (I-276)

N-(3-Chloro-4-(4-(((3R,6S)-6-(hydroxymethyl)tetrahydro-2H-pyran-3-yl)amino)-7H-pyrrolo[2,3-d]pyrimidine-5-carbonyl)phenyl)benzamide was synthesized according to General Scheme 7, using benzoyl chloride. $^1$H NMR (DMSO-d$_6$, 400 MHz): δ 12.90 (bs, 1H), 10.62 (s, 1), 8.85 (bs, 1H), 8.29 (s, 1H), 8.13 (d, J=1.8 Hz, 1H), 7.99-7.97 (m, 2H), 7.87 (dd, J=8.4 Hz, J=1.8 Hz, 1H), 7.65-7.55 (m, 5H), 4.18-4.10 (m, 2H), 3.45-3.33 (m, 3H), 3.18-3.13 (m, 1H), 2.22-2.19 (m, 1H), 1.81-1.75 (m, 1H), 1.66-1.56 (m, 1H), 1.44-1.34 (m, 1H). LCMS [M+H]$^+$: 506.2.

General Procedure K
A general procedure for arylamine formation

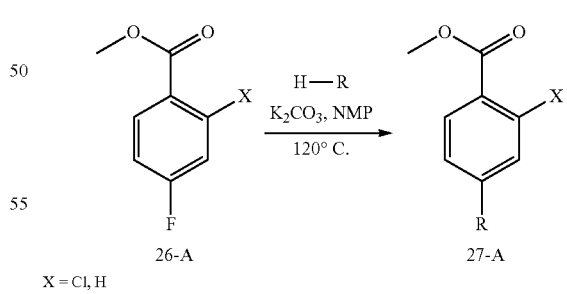

X = Cl, H

The arylfluoride substrate (26-A) (1 eq.) was diluted in NMP (1 mL/1.32 mmol). Cyclic amine (1.1 eq.) and potassium carbonate (2 eq.) were added and the mixture was stirred at 120° C. overnight. The reaction mixture was allowed to cool to room temperature and was diluted with water. The crude mixture was extracted with ethyl acetate (×3) and the combined organics were washed with water General Procedure L
A general procedure for phenol alkylation

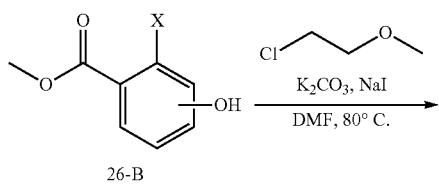

X = Cl, H

A mixture of phenol (26-B) (1 eq.), 1-chloro-2-methoxy-ethane (1.5 eq.), potassium carbonate (2 eq.) and sodium iodide (0.2 eq.) in DMF (1 mL/0.45 mmol) is heated overnight at 80° C. The reaction mixture is then cooled to room temperature and poured in water, stirred for 15 min and filtered then dried under high vacuum. The product was used as is without further purification.

General Procedure M
A general procedure for ketone formation through aryl-lithium attack on an ester

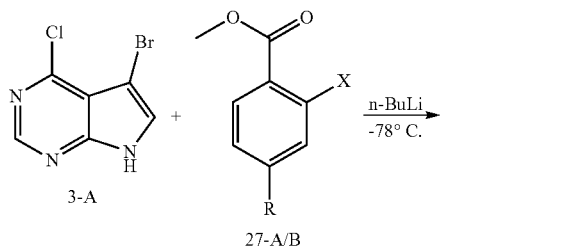

X = Cl, H 5-bromo-4-chloro-7H-pyrrolo[2,3-d]pyrimidine (3-A) (1 eq.) was diluted in dry THF (1 mL/0.21 mmol) and was cooled to −78° C. n-BuLi (2.1 eq.) was added dropwise and the temperature was monitored with an internal thermo-couple to ensure the reaction temperature never rose above −60° C. The reaction mixture was stirred for 1 hour before the substituted methyl benzoate (27-A/B) (1.05 eq.) in dry THF (1 mL/0.9 mmol) was added dropwise with the internal temperature never exceeding −60° C. The mixture was stirred at −78° C. for 1 hour then quenched with saturated aqueous Ammonium chloride solution and extracted with ethyl acetate (×3). The combined organic layers were washed with sodium bicarbonate and dried over magnesium sulfate, filtered and concentrated. The resulting residue was purified by silica gel column chromatography (10-100% ethyl acetate in hexanes).

General Procedure N
One general procedure for formation of a diaryl ether is described.

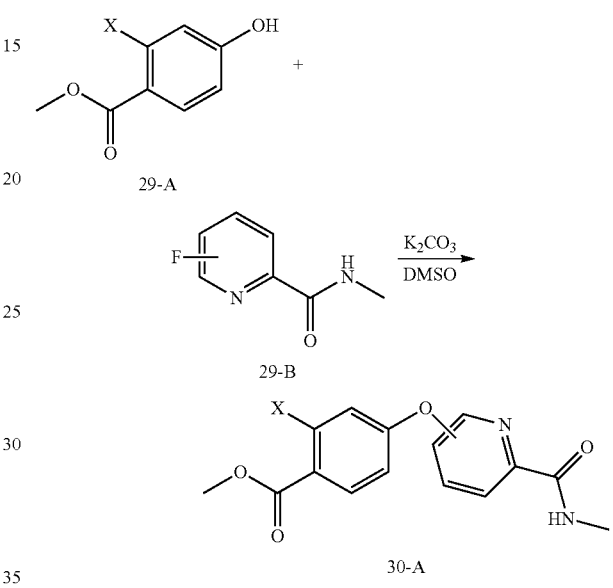

X = Cl, H

Fluoropyridine substrate (29-B) (1 eq.), methyl-hydroxy-benzoate (29-A) (1 eq.) and potassium carbonate (1 eq.) were dissolved in DMSO (1 mL/0.3 mmol). The mixture was stirred at 120° C. under argon atmosphere overnight. After cooled, the reaction mixture was diluted in water and extracted several times with ethyl acetate. Combined organics were washed with water and dried over magnesium sulfate and concentrated under reduced pressure. The product was purified by column chromatography (0-100% ethyl acetate in hexanes).

General Procedure O
One general procedure for Boc-deprotection is described.

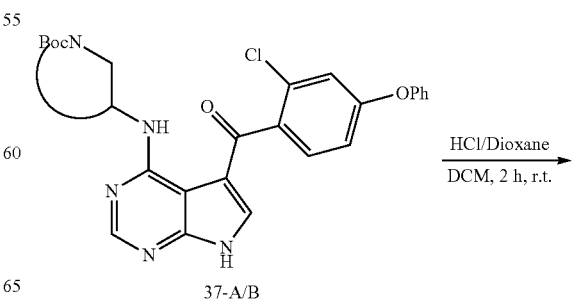

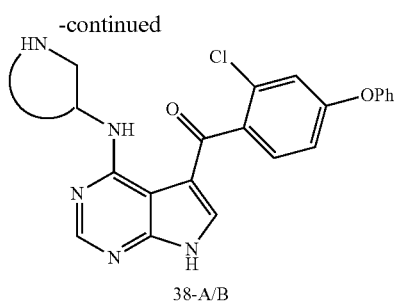

38-A/B

Boc-protected amine (37-A/B) (1.0 equiv) was dissolved in DCM (1.0 mL/mmol) and a 4.0M HCl/Dioxane solution (4.0 equiv) was added. Mixture was stirred at room temperature for 2.0 h, then concentrated under vacuum. A 1:10 solution of aqueous ammonia in EtOH was added until complete dissolution of the residue. The residue was absorbed onto silica and purified by normal phase column chromatography to give the purified amine product.

Step 2: Synthesis of (racemic)-(2-chloro-4-phenoxyphenyl)(4-(piperidin-3-ylamino)-7H-pyrrolo[2,3-d]pyrimidin-5-yl)methanone (38-A)

Step 2': Synthesis of (racemic)-(2-chloro-4-phenoxyphenyl)(4-((pyrrolidin-2-ylmethyl)amino)-7H-pyrrolo[2,3-d]pyrimidin-5-yl)methanone (38-B)

General Procedure P
One general procedure for vinysulfonamide formation.

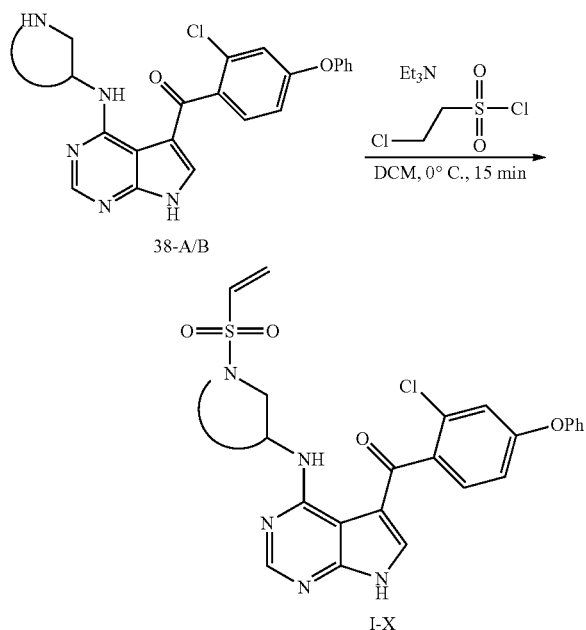

A solution of 2-chloroethanesulfonyl chloride (1.0 equiv) and Et$_3$N (1.0 equiv) in DCM (18 mL/mmol) cooled to 0° C. was added dropwise to a suspension of secondary amine (38-A/B) (1.0 equiv) and Et$_3$N (1.0 equiv) in DCM (18 mL/mmol), also cooled to 0° C. After 15 minutes, the reaction mixture was washed with saturated aqueous NaHCO$_3$ (twice), dried over MgSO$_4$ and concentrated under vacuum. The residue was purified by normal phase chromatography (75%-100% EtOAc/hexanes).

A mixture of enantiomers, diastereomers, cis/trans isomers resulting from the processes described above can be separated into their single components by chiral salt technique, chromatography using normal phase, reverse phase or chiral column, depending on the nature of the separation.

Analytical Methods, Materials, and Instrumentation

Unless otherwise noted, reagents and solvents were used as received from commercial suppliers. Proton nuclear magnetic resonance (NMR) spectra were obtained on either Bruker or Varian spectrometers at 400 MHz. Spectra are given in ppm (δ) and coupling constants, J, are reported in Hertz. Tetramethylsilane (TMS) was used as an internal standard. Mass spectra were collected using a Waters ZQ Single Quad Mass Spectrometer (ion trap ESI). Purity and low resolution mass spectral data were measured using Waters Acquity i-class ultra-performance liquid chromatography (UPLC) system with Acquity Photo Diode Array Detector, Acquity Evaporative Light Scattering Detector (ELSD) and Waters ZQ Mass Spectrometer. Data was acquired using Waters MassLynx 4.1 software and purity characterized by UV wavelength 220 nm, ELSD and ESI. Column: Acquity UPLC BEH C18 1.7 μm 2.1×50 mm; Flow rate 0.6 mL/min; Solvent A (95/5/0.1 10 mM ammonium formate/acetonitrile/formic acid), Solvent B (95/5/0.09 acetonitrile/water/formic acid); gradient: 5-100% B from 0 to 2 min, hold 100% B to 2.2 min, then 5% B at 2.21 min.

Abbreviations used in the following examples and elsewhere herein are:
DIPEA N,N-diisopropylethylamine
DMF N,N-dimethylformamide
DMSO dimethylsulfoxide
IPA iso-propyl alcohol
IPE di-isopropyl ether
LC/MS liquid chromatography-mass spectrometry
MeOH methanol
MS mass spectrometry
n-BuOH n-butyl alcohol
NMP N-methyl pyrrolidinone
NMR nuclear magnetic resonance
ppm parts per million
TEA triethylamine Biological Assays
Radiometric Assay Enzyme assay using full length recombinant active form of wild-type BTK and BTK-C481S is measured as described previously (Anastassiadis T, et al., Nat. Biotechnol. 29(11): 1039-45 (2011)). Compounds are tested in multi-point dose IC$_{50}$ mode with several folds serial dilution. BTK kinase activity is assayed in a buffer solution. Compounds are mixed with kinase (wild-type BTK or mutant BTK), and substrate is added into the kinase reaction mixture and incubated. The reaction is initiated by adding ATP containing $^{33}$P-ATP into the mixture and incubated. Kinase activity is detected by P81 filter-binding $^{33}$P radioisotope based radiometric method. The raw data is fit to a 4-parameter logistic model to derive the IC$_{50}$ value for kinase activity inhibition.

Mobility Shift Assay

Compounds are tested either in the inactive or active BTK assays on Caliper LabChip microfluidic mobility shift assay platform.

Full length unphosphorylated form of BTK expressed in Sf9 cells is employed to test inhibitory activity in the inactive BTK assay. The enzyme and increasing concentrations of inhibitor are incubated, and the kinase reaction is initiated by the addition an activation mixture containing ATP. The plates are incubated, and after the reaction is stopped, measured.

The active BTK assay consists of phosphorylated form of full length BTK. The assay is performed in a buffer solution utilized in the inactive BTK assay. The enzyme inhibitor complexes is incubated, before the kinase activation reaction is initiated. After incubation, the reaction is stopped and the mobility shift is measured as described above for the inactive BTK assay. The data of inactive and active BTK assays is fit to a 4 parameter logistic model to calculate the $IC_{50}$ value.

Methods of Using the Compounds

Another aspect of the application relates to a method of treating, preventing, inhibiting, or eliminating a disease or disorder associated with modulation of BTK (e.g., inhibition of BTK). The method comprises administering to a subject in need of a treatment for diseases or disorders associated with modulation of BTK an effective amount a compound of Formula (I) or a pharmaceutically acceptable salt, solvate, prodrug, stereoisomer, or tautomer thereof or a pharmaceutical composition of a compound of Formula (I). In one embodiment, the BTK-mediated disorder is selected from immune disorders, cancer, cardiovascular diseases, viral infections, inflammation, metabolism/endocrine function disorders and neurological disorders. In some embodiments, the method further comprises administering an additional therapeutic agent selected from an anti-inflammatory agent, an immunomodulatory agent, chemotherapeutic agent, a neurotropic factor, an agent for treating cardiovascular disease, an agent for treating liver disease, an anti-viral agent, an agent for treating blood disorders, an agent for treating diabetes, and an agent for treating immunodeficiency disorders. In some embodiments, the BTK is wild-type BTK. In other embodiments, the BTK is mutant BTK (e.g., BTK C481S mutant).

Another aspect of the application relates to a method of treating, preventing, inhibiting, or eliminating a cell proliferative disorder, the method comprising administering to a subject in need thereof a therapeutically effective amount of a compound of Formula (I), or a pharmaceutically acceptable salt, solvate, prodrug, stereoisomer, or tautomer thereof, or a pharmaceutical composition of a compound of Formula (I). In one embodiment, the cell proliferative disorder is a cancer. In some embodiments, the method further comprises administering an additional therapeutic agent selected from an anti-inflammatory agent, an immunomodulatory agent, chemotherapeutic agent, a neurotropic factor, an agent for treating cardiovascular disease, an agent for treating liver disease, an anti-viral agent, an agent for treating blood disorders, an agent for treating diabetes, and an agent for treating immunodeficiency disorders.

Another aspect of the application relates to a method of modulating BTK, the method comprising administering to a subject in need thereof a therapeutically effective amount of a compound of Formula (I), or a pharmaceutically acceptable salt, solvate, prodrug, stereoisomer, or tautomer thereof, or a pharmaceutical composition of a compound of Formula (I). In one embodiment, modulating BTK is inhibiting BTK. In some embodiments, the BTK is wild-type BTK. In other embodiments, the BTK is mutant BTK (e.g., BTK C481S mutant).

Another aspect of the application relates to a compound of Formula (I), or a pharmaceutically acceptable salt, solvate, prodrug, stereoisomer, or tautomer thereof, for use in a method of treating a BTK-mediated disorder. In one embodiment, the disease or disorder is selected from immune disorders, cancer, cardiovascular diseases, viral infections, inflammation, metabolism/endocrine function disorders and neurological disorders. In some embodiments, the method further comprises administering an additional therapeutic agent selected from an anti-inflammatory agent, an immunomodulatory agent, chemotherapeutic agent, a neurotropic factor, an agent for treating cardiovascular disease, an agent for treating liver disease, an anti-viral agent, an agent for treating blood disorders, an agent for treating diabetes, and an agent for treating immunodeficiency disorders. In some embodiments, the BTK is wild-type BTK. In other embodiments, the BTK is mutant BTK (e.g., BTK C481S mutant).

In another aspect, the present application relates to a pharmaceutical composition of a compound of Formula (I), or a pharmaceutically acceptable salt, solvate, prodrug, stereoisomer, or tautomer thereof, for use in a method of treating a BTK-mediated disorder. In one embodiment, the disease or disorder is selected from immune disorders, cancer, cardiovascular diseases, viral infections, inflammation, metabolism/endocrine function disorders and neurological disorders. In some embodiments, the method further comprises administering an additional therapeutic agent selected from an anti-inflammatory agent, an immunomodulatory agent, chemotherapeutic agent, a neurotropic factor, an agent for treating cardiovascular disease, an agent for treating liver disease, an anti-viral agent, an agent for treating blood disorders, an agent for treating diabetes, and an agent for treating immunodeficiency disorders. In some embodiments, the BTK is wild-type BTK. In other embodiments, the BTK is mutant BTK (e.g., BTK C481S mutant).

Another aspect of the application relates to a compound of Formula (I), or a pharmaceutically acceptable salt, solvate, prodrug, stereoisomer, or tautomer thereof, for use in a method of treating, preventing, inhibiting, or eliminating a cell proliferative disorder. In one embodiment, the cell proliferative disorder is a cancer.

In another aspect, the present application relates to a pharmaceutical composition of a compound of Formula (I), or a pharmaceutically acceptable salt, solvate, prodrug, stereoisomer, or tautomer thereof, for use in a method of treating, preventing, inhibiting, or eliminating a cell proliferative disorder. In one embodiment, the cell proliferative disorder is a cancer.

Another aspect of the application relates to a compound of Formula (I), or a pharmaceutically acceptable salt, solvate, prodrug, stereoisomer, or tautomer thereof, for use in modulating BTK. In one embodiment, modulating BTK is inhibiting BTK. In some embodiments, the BTK is wild-type BTK. In other embodiments, the BTK is mutant BTK (e.g., BTK C481S mutant).

In another aspect, the present application relates to a pharmaceutical composition of a compound of Formula (I), or a pharmaceutically acceptable salt, solvate, prodrug, stereoisomer, or tautomer thereof, for use in modulating BTK. In one embodiment, modulating BTK is inhibiting BTK. In some embodiments, the BTK is wild-type BTK. In other embodiments, the BTK is mutant BTK (e.g., BTK C481S mutant).

Another aspect of the application relates to the use of a compound of Formula (I), or a pharmaceutically acceptable salt, solvate, prodrug, stereoisomer, or tautomer thereof, in the manufacture of a medicament for treating a BTK-mediated disease or disorder. In one embodiment, the disease or disorder is selected from immune disorders, cancer, cardiovascular diseases, viral infections, inflammation, metabolism/endocrine function disorders and neurological disorders. In some embodiments, the treatment further comprises administering an additional therapeutic agent selected from an anti-inflammatory agent, an immunomodulatory agent, chemotherapeutic agent, a neurotropic factor, an agent for treating cardiovascular disease, an agent for treating liver disease, an anti-viral agent, an agent for treating blood disorders, an agent for treating diabetes, and an agent for treating immunodeficiency disorders. In some embodiments, the BTK is wild-type BTK. In other embodiments, the BTK is mutant BTK (e.g., BTK C481S mutant).

In another aspect, the present application relates to the use of a pharmaceutical composition of a compound of Formula (I), or a pharmaceutically acceptable salt, solvate, prodrug, stereoisomer, or tautomer thereof, in the manufacture of a medicament for treating a BTK-mediated disease or disorder. In one embodiment, the disease or disorder is selected from immune disorders, cancer, cardiovascular diseases, viral infections inflammation, metabolism/endocrine function disorders and neurological disorders. In some embodiments, the treatment further comprises administering an additional therapeutic agent selected from an anti-inflammatory agent, an immunomodulatory agent, chemotherapeutic agent, a neurotropic factor, an agent for treating cardiovascular disease, an agent for treating liver disease, an anti-viral agent, an agent for treating blood disorders, an agent for treating diabetes, and an agent for treating immunodeficiency disorders. In some embodiments, the BTK is wild-type BTK. In other embodiments, the BTK is mutant BTK (e.g., BTK C481S mutant).

Another aspect of the application relates to the use of a compound of Formula (I), or a pharmaceutically acceptable salt, solvate, prodrug, stereoisomer, or tautomer thereof, in the manufacture of a medicament for treating, preventing, inhibiting, or eliminating a cell proliferative disorder. In one embodiment, the cell proliferative disorder is a cancer.

In another aspect, the present application relates to the use of a pharmaceutical composition of a compound of Formula (I), or a pharmaceutically acceptable salt, solvate, prodrug, stereoisomer, or tautomer thereof, in the manufacture of a medicament for treating, preventing, inhibiting, or eliminating a cell proliferative disorder. In one embodiment, the cell proliferative disorder is a cancer.

Another aspect of the application relates to the use of a compound of Formula (I), or a pharmaceutically acceptable salt, solvate, prodrug, stereoisomer, or tautomer thereof, in the manufacture of a medicament for modulating BTK. In one embodiment, modulating BTK is inhibiting BTK. In some embodiments, the BTK is wild-type BTK. In other embodiments, the BTK is mutant BTK (e.g., BTK C481S mutant).

In another aspect, the present application relates to the use of a pharmaceutical composition of a compound of Formula (I), or a pharmaceutically acceptable salt, solvate, prodrug, stereoisomer, or tautomer thereof, in the manufacture of a medicament for modulating BTK. In one embodiment, modulating BTK is inhibiting BTK. In some embodiments, the BTK is wild-type BTK. In other embodiments, the BTK is mutant BTK (e.g., BTK C481S mutant).

In some embodiments of the methods and uses described herein, the cancer is selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic myelogenous leukemia, lymphocytic leukemia, chronic lymphoid leukemia (CLL), myeloid leukemia, oral cavity and pharynx, non-Hodgkin lymphoma, melanoma, and villous colon adenoma.

In any of the embodiments of the application, the cancer can be any cancer in any organ, for example, a cancer is selected from the group consisting of glioma, thyroid carcinoma, breast carcinoma, small-cell lung carcinoma, non-small-cell carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, anaplastic large-cell lymphoma, leukemia, multiple myeloma, mesothelioma, and melanoma, and combinations thereof.

In some embodiments of the methods and uses described herein, the disease or disorder is an immune disorder. In one embodiment, the immune disorder is rheumatoid arthritis.

In some embodiments of the methods and uses described herein, the disease or disorder is systemic and local inflammation, arthritis, inflammation related to immune suppression, organ transplant rejection, allergies, ulcerative colitis, Crohn's disease, dermatitis, asthma, systemic lupus erythematosus, Sjogren's Syndrome, multiple sclerosis, scleroderma/systemic sclerosis, idiopathic thrombocytopenic purpura (ITP), anti-neutrophil cytoplasmic antibodies (ANCA) vasculitis, chronic obstructive pulmonary disease (COPD), psoriasis.

In one embodiment, methods of treating a disease or disorder associated with modulation of BTK including, immune disorders, cancer, cardiovascular diseases, viral infections, inflammation, metabolism/endocrine function disorders and neurological disorders, comprise administering to a subject suffering from at least one of said diseases or disorder a compound of Formula (I).

The disclosed compound of the application can be administered in effective amounts to treat or prevent a disorder and/or prevent the development thereof in subjects.

The compound of the application can be administered in therapeutically effective amounts in a combinational therapy with one or more therapeutic agents (pharmaceutical combinations) or modalities, e.g., non-drug therapies. For example, synergistic effects can occur with other antiproliferative, anti-cancer, immunomodulatory or anti-inflammatory substances. In some embodiments, a compound of Formula (I) is administered in combination with an additional therapeutic agent selected from an anti-inflammatory agent, an immunomodulatory agent, chemotherapeutic agent, a neurotropic factor, an agent for treating cardiovascular disease, an agent for treating liver disease, an anti-viral agent, an agent for treating blood disorders, an agent for treating diabetes, and an agent for treating immunodeficiency disorders. Where the compound of the application is administered in conjunction with other therapies, dosages of the co-administered compounds will of course vary depending on the type of co-drug employed, on the specific drug employed, on the condition being treated and so forth.

Combination therapy includes the administration of the subject compound in further combination with other biologically active ingredients (such as, but not limited to, an anti-inflammatory agent, an immunomodulatory agent, chemotherapeutic agent, a neurotropic factor, an agent for treating cardiovascular disease, an agent for treating liver disease, an anti-viral agent, an agent for treating blood disorders, an agent for treating diabetes, and an agent for treating immunodeficiency disorders) and non-drug therapies (such as, but not limited to, surgery or radiation treatment). For instance, the compound of the application can be used in combination with other pharmaceutically active compounds, preferably compounds that are able to enhance the effect of the compound of the application. The compound of the application can be administered simultaneously (as a single preparation or separate preparation) or sequentially to the other drug therapy or treatment modality. In general, a combination therapy envisions administration of two or more drugs during a single cycle or course of therapy.

Pharmaceutical Compositions

The present application also provides pharmaceutical compositions comprising a compound of Formula (I), or a pharmaceutically acceptable salt, solvate, prodrug, stereoisomer, or tautomer thereof, in combination with at least one pharmaceutically acceptable excipient or carrier.

A "pharmaceutical composition" is a formulation containing the compound of the present application in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or a pharmaceutically acceptable salt, solvate, prodrug, stereoisomer, or tautomer thereof thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this application include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical compositions of the application are formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the application can be administered to a subject in many of the well-known methods currently used for chemotherapeutic treatment. For example, for treatment of cancers, a compound of the application may be injected directly into tumors, injected into the blood stream or body cavities or taken orally or applied through the skin with patches. The dose chosen should be sufficient to constitute effective treatment but not as high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In one embodiment, the disease or disorder is selected from immune disorders, cancer, cardiovascular diseases, viral infections, inflammation, metabolism/endocrine function disorders and neurological disorders. In another embodiment, the disease or condition to be treated is cancer. In another embodiment, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compound (i.e., a compound of Formula (I)) of the present application may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compound into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compound is delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compound is formulated into ointments, salves, gels, or creams as generally known in the art.

The active compound can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the application are dictated by and directly dependent on the unique characteristics of the active compound and the particular therapeutic effect to be achieved.

In therapeutic applications, the dosages of the pharmaceutical compositions used in accordance with the application vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. An effective amount of a pharmaceutical agent is that which provides an objectively identifiable improvement as noted by the clinician or other qualified observer. For example, regression of a tumor in a subject may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

As used herein, "pharmaceutically acceptable salts" refer to derivatives of the compound of the present application wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present application also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The compound of the present application can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., an acetate, propionate or other ester.

The compound of the present application can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compound of the present application can be delivered in prodrug form. Thus, the present application is intended to cover prodrugs of the presently claimed compound, methods of delivering the same and compositions containing the same. "Prodrugs" are intended to include any covalently bonded carriers that release an active parent drug of the present application in vivo when such prodrug is administered to a subject. Prodrugs in the present application are prepared by modifying functional groups present in the compound in such a way that the modifications are cleaved, either in routine manipulation or in vivo, to the parent compound. Prodrugs include the compound of the present application wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl)N-Mannich bases, Schiff bases and enaminones of amino functional groups, oximes, acetals, ketals and enol esters of ketone and aldehyde functional groups in the compound of the application, and the like, See Bundegaard, H., *Design of Prodrugs*, p 1-92, Elsevier, New York-Oxford (1985).

The compound, or pharmaceutically acceptable salts, tautomers, prodrugs, solvates, metabolites, polymorphs, analogs or derivatives thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound or a pharmaceutically acceptable salt, solvate, prodrug, stereoisomer, or tautomer thereof is administered orally. One skilled in the art will recognize the advantages of certain routes of administration.

The dosage regimen utilizing the compound is selected in accordance with a variety of factors including type, species, age, weight, sex and medical condition of the patient; the severity of the condition to be treated; the route of administration; the renal and hepatic function of the patient; and the particular compound or pharmaceutically acceptable salt, tautomer, prodrug, solvate, metabolite, polymorph, analog or derivative thereof employed. An ordinarily skilled physician or veterinarian can readily determine and prescribe the effective amount of the drug required to prevent, counter or arrest the progress of the condition.

Techniques for formulation and administration of the disclosed compound of the application can be found in *Remington: the Science and Practice of Pharmacy*, 19th edition, Mack Publishing Co., Easton, Pa. (1995). In an embodiment, the compound described herein, and the pharmaceutically acceptable salts, tautomers, prodrugs, solvates, metabolites, polymorphs, analogs or derivatives thereof, are used in pharmaceutical preparations in combination with a pharmaceutically acceptable carrier or diluent. Suitable pharmaceutically acceptable carriers include inert solid fillers or diluents and sterile aqueous or organic solutions. The compound or pharmaceutically acceptable salts, prodrugs, solvates, metabolites, polymorphs, analogs or derivatives thereof will be present in such pharmaceutical compositions in amounts sufficient to provide the desired dosage amount in the range described herein.

All percentages and ratios used herein, unless otherwise indicated, are by weight. Other features and advantages of the present application are apparent from the different examples. The provided examples illustrate different components and methodology useful in practicing the present application. The examples do not limit the claimed application. Based on the present application the skilled artisan can identify and employ other components and methodology useful for practicing the present application.

EXAMPLES

The application is further illustrated by the following examples and synthesis schemes, which are not to be construed as limiting this application in scope or spirit to the specific procedures herein described. It is to be understood that the examples are provided to illustrate certain embodiments and that no limitation to the scope of the application is intended thereby. It is to be further understood that resort may be had to various other embodiments, modifications, and equivalents thereof which may suggest themselves to those skilled in the art without departing from the spirit of the present application and/or scope of the appended claims.

Example 1: (2-chlorophenyl)-(4-((trans-4-hydroxycyclohexyl)amino)-7H-pyrrolo[2,3-d]pyrimidin-5-yl)methanone (I-1)

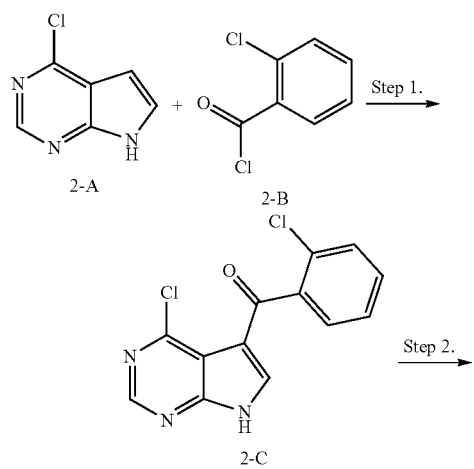

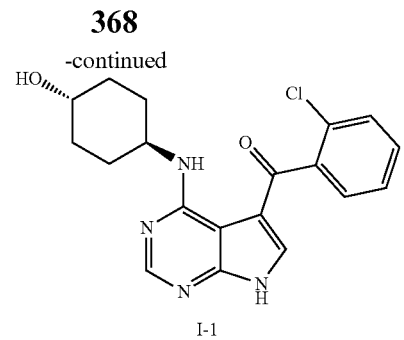

Step 1: Synthesis of (2-chlorophenyl)-(4-chloro-7H-pyrrolo[2,3-d]pyrimidin-5-yl)methanone (2-C)

A mixture of 4-chloro-7H-pyrrolo[2,3-d]pyrimidine (2-A, 4.61 g, 30 mmol), 2-chlorobenzoyl chloride (2-B, 5.21 mL, 39 mmol), AlCl$_3$ (12.0 g, 90 mmol) and nitrobenzene (30 mL) was heated at 80° C. for 9.5 hrs. The resultant mixture was poured into ice-water (300 mL) and extracted with EtOAc (×3). The combined extracts were washed with water (×2), saturated aqueous NaHCO$_3$, and brine, then dried over anhydrous Na$_2$SO$_4$, filtered through silica gel pad and concentrated in vacuo. Hexane was added to the residue. The resulting precipitated solid was collected by filtration, washed with hexane (×2) and IPE (×2), and then dried at 50° C. to provide (2-chlorophenyl)-(4-chloro-7H-pyrrolo[2,3-d]pyrimidin-5-yl)methanone (2-C, 6.07 g, 22.4 mmol, 75%) as pale brown powder. $^1$H-NMR (DMSO-d$_6$) δ: 13.44 (1H, br s), 8.76 (1H, s), 8.03 (1H, s), 7.62-7.55 (3H, m), 7.50-7.45 (1H, m). LC/MS: 292 [M+H].

Step 2: Synthesis of (2-chlorophenyl)-(4-((trans-4-hydroxycyclohexyl)amino)-7H-pyrrolo[2,3-d]pyrimidin-5-yl)methanone (I-1)

A mixture of (2-chlorophenyl)-(4-chloro-7H-pyrrolo[2,3-d]pyrimidin-5-yl) methanone (2-C, 406 mg, 1.39 mmol), trans-4-aminocyclohexanol (240 mg, 2.08 mmol), DIPEA (363 μL, 2.08 mmol) and IPA (12 mL) was stirred at 160° C. for 1 h under microwave irradiation followed by concentration under reduced pressure. Water was added to the resultant mixture and extracted with EtOAc, and then the extract was washed with brine, dried over anhydrous Na$_2$SO$_4$, filtered, and concentrated in vacuo. The residue was purified by column chromatography over SiO$_2$ with CHCl$_3$-MeOH, then the obtained crude product was suspended in diethyl ether and precipitate was collected by filtration to give (2-chlorophenyl)-(4-((trans-4-hydroxycyclohexyl)amino)-7H-pyrrolo[2,3-d]pyrimidin-5-yl)methanone (I-1, 510 mg, 1.38 mmol, 99%) as pale yellow solid. $^1$H-NMR (DMSO-d$_6$) δ: 12.71 (1H, s), 8.71 (1H, d, J=7.9 Hz), 8.24 (1H, s), 7.59-7.55 (3H, m), 7.49-7.44 (2H, m), 4.63-4.60 (1H, m), 4.03-4.01 (1H, m), 3.54-3.52 (1H, m), 2.09-2.06 (2H, m), 1.91-1.88 (2H, m), 1.38-1.24 (4H, m). LC/MS: 371 [M+H].

Example 2: General Procedure A

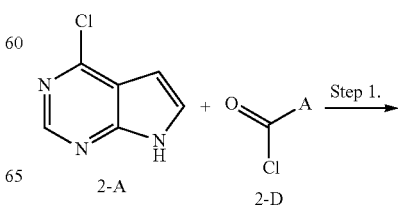

-continued

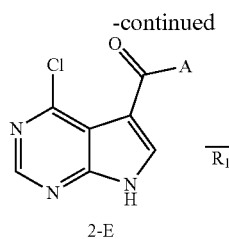

2-E

Step 2.
R₁—NH₂
2-F

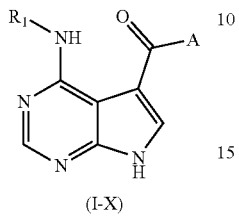

(I-X)

A is aryl or heteroaryl wherein $R_2$ and $R_3$ are H

Step 1. Intermediate 2-E

A mixture of 4-chloro-7H-pyrrolo[2,3-d]pyrimidine (2-A), an aroyl chloride or heteroaroyl chloride (2-D, 1.1-1.5 eq.), AlCl₃ (2-5 eq.) and nitrobenzene (0.3-1M) was heated at 80-100° C. for 1 to 10 hrs. Work-up and/or purification provided the corresponding aryl- or heteroaryl-(4-chloro-7H-pyrrolo[2,3-d]pyrimidin-5-yl)methanone (2-E).

Step 2. Compounds of Formula I-X

A mixture of 2-E, a primary amine (2-F, 1-4 eq.), and optionally a base (e.g., TEA, DIPEA, pyridine, and/or K₂CO₃ (1-5 eq.)) in a solvent (e.g., DMF, NMP, IPA, n-BuOH or neat) was heated (70-160° C.) for 5-50 hrs or heated (100-220° C.) under microwave radiation for 0.5-5 hrs. Work-up and/or purification provided a compound of Formula (I) (aryl- or heteroaryl-[4-(substituted-amino)]-7H-pyrrolo[2,3-d]pyrimidin-5-yl]methanone (I-X)).

The compounds of Formula (I) in Table 1 below were made according to General Procedure A.

TABLE 1

| Cmpd No. | ¹H NMR and/or LC/MS data |
|---|---|
| I-2 | ¹H-NMR (DMSO-d₆) δ: 12.69 (1H, s), 8.89 (1H, d, J = 7.3 Hz), 8.23 (1H, s), 7.61-7.54 (3H, m), 7.50-7.45 (2H, m), 7.00-6.96 (1H, m), 4.25-4.18 (1H, m), 3.46-3.40 (1H, m), 1.84-1.58 (8H, m), 1.38 (9H, s). LC/MS: 470 [M + H]. |
| I-3 | ¹H-NMR (DMSO-d₆) δ: 12.71 (1H, s), 8.83 (1H, d, J = 6.7 Hz), 8.24 (1H, s), 7.62-7.53 (3H, m), 7.49-7.45 (2H, m), 7.05 (1H, d, J = 7.3 Hz), 4.43-4.34 (1H, m), 3.87-3.78 (1H, m), 2.49-2.40 (1H, m), 2.13-2.03 (1H, m), 1.93-1.84 (1H, m), 1.54-1.67 (2H, m), 1.39-1.48 (1H, m), 1.37 (9H, s). LC/MS: 456 [M + H]. |
| I-4 | ¹H-NMR (DMSO-d₆) δ: 8.97 (0.4H, d, J = 7.9 Hz), 8.73 (0.6H, d, J = 7.9 Hz), 8.19 (0.4H, s), 8.18 (0.6H, s), 7.57-7.53 (3H, m), 7.48-7.43 (1H, m), 7.40 (0.4H, s), 7.39 (0.6H, s), 4.58-4.52 (0.4H, m), 4.09-3.98 (0.6H, m), 3.11-3.04 (0.4H, m), 2.73-2.81 (0.6H, m), 2.26-1.00 (8H, m). LC/MS: 370 [M + H]. (6:4 diastereomeric mixture of I-4). |
| I-13 | ¹H-NMR (CDCl₃) δ: 12.36 (1H, br s), 9.01 (1H, d, J = 7.3 Hz), 8.32 (1H, s), 7.43-7.37 (2H, m), 7.30 (2H, t, J = 8.5 Hz), 4.41-4.32 (2H, m), 3.71-3.65 (1H, m), 3.61-3.49 (2H, m), 3.31 (1H, t, J = 11.3 Hz), 2.40-2.31 (4H, m), 1.80-1.55 (4H, m). LC/MS: 367 [M + H]. |
| I-16 | ¹H-NMR (DMSO-d₆) δ: 12.43 (1H, br s), 8.95 (1H, d, J = 7.3 Hz), 8.23 (1H, s), 7.45-7.28 (5H, m), 4.09-4.04 (1H, m), 2.73-2.68 (2H, m), 2.28 (3H, s), 2.19 (3H, s), 2.17-2.11 (2H, m), 2.04-1.98 (2H, m), 1.61-1.53 (2H, m). LC/MS: 350 [M + H]. |
| I-17 | ¹H-NMR (DMSO-d₆) δ: 12.63 (1H, br s), 8.99 (1H, d, J = 7.3 Hz), 8.24 (1H, s), 7.45-7.28 (5H, m), 4.31-4.23 (1H, m), 3.87-3.81 (2H, m), 3.16-3.05 (2H, m), 2.28 (3H, s), 2.04-1.99 (2H, m), 1.47-1.40 (11H, m). LC/MS: 436 [M + H]. |
| I-19 | ¹H-NMR (CDCl₃) δ: 12.80 (1H, br s), 9.13 (1H, d, J = 7.3 Hz), 8.31 (1H, s), 7.44-7.37 (2H, m), 7.33-7.25 (2H, m), 4.63-4.62 (4H, m), 4.21-4.10 (1H, m), 3.69 (3H, s), 2.42-2.26 (5H, m), 2.14-2.07 (2H, m), 1.54-1.42 (2H, m). LC/MS: 393 [M + H]. |
| I-20 | ¹H-NMR (CDCl₃) δ: 12.60 (1H, br s), 9.02 (1H, d, J = 7.9 Hz), 8.33 (1H, s), 7.45-7.37 (2H, m), 7.33-7.26 (3H, m), 4.45-4.26 (2H, m), 3.29 (1H, t, J = 10.7 Hz), 3.22-3.16 (1H, m), 2.40-2.32 (4H, m), 1.84-1.18 (10H, m). LC/MS: 395 [M + H]. |
| I-21 | ¹H-NMR (DMSO-d₆) δ: 12.59 (1H, br s), 8.85 (1H, d, J = 7.3 Hz), 8.22 (1H, s), 7.45-7.40 (2H, m), 7.35-7.27 (3H, m), 4.61 (1H, d, J = 4.3 Hz), 4.02-4.00 (1H, m), 3.55-3.52 (1H, m), 2.27 (3H, s), 2.08-2.06 (2H, m), 1.91-1.88 (2H, m), 1.37-1.35 (4H, m). LC/MS: 351 [M + H]. |
| I-22 | ¹H-NMR (DMSO-d₆) δ: 12.58 (1H, s), 9.04 (1H, d, J = 7.3 Hz), 8.21 (1H, s), 7.44 (2H, t, J = 7.3 Hz), 7.35-7.30 (3H, m), 4.55 (1H, d, J = 3.7 Hz), 4.20-4.17 (1H, m), 3.68-3.66 (1H, m), 2.29 (3H, s), 1.81-1.63 (8H, m). LC/MS: 351 [M + H]. |
| I-24 | ¹H-NMR (CDCl₃) δ: 8.98 (1H, d, J = 7.3 Hz), 8.33 (1H, s), 7.43-7.36 (2H, m), 7.33-7.22 (3H, m), 4.42-4.28 (2H, m), 3.95-3.87 (1H, m), 3.36-3.27 (2H, m), 2.40-2.33 (4H, m), 1.79-1.24 (4H, m), 1.18 (3H, d, J = 6.0 Hz). LC/MS: 381 [M + H]. |
| I-26 | ¹H-NMR (DMSO-d₆) δ: 9.05 (1H, d, J = 7.3 Hz), 8.19 (1H, s), 7.78 (2H, d, J = 6.7 Hz), 7.69 (1H, s), 7.63 (1H, t, J = 7.3 Hz), 7.54 (2H, t, J = 7.6 Hz), 4.25-4.20 (1H, m), 2.84-2.77 (1H, m), 1.89-1.80 (2H, m), 1.70-1.60 (4H, m), 1.43-1.53 (2H, m). LC/MS: 336 [M + H]. |
| I-27 | ¹H-NMR (CDCl₃) δ: 12.62 (1H, br s), 9.31 (1H, t, J = 5.5 Hz), 8.34 (1H, s), 7.43-7.38 (2H, m), 7.33-7.25 (3H, m), 4.01-3.49 (9H, m), 2.39 (3H, s). LC/MS: 353 [M + H]. |
| I-31 | ¹H-NMR (DMSO-d₆) δ: 12.69 (1H, s), 8.88 (1H, d, J = 7.3 Hz), 8.22 (1H, s), 7.59-7.56 (3H, m), 7.49-7.45 (2H, m), 4.56 (1H, d, J = 3.1 Hz), 4.20-4.18 (1H, m), 3.69-3.66 (1H, m), 1.81-1.63 (8H, m). LC/MS: 371 [M + H]. |

TABLE 1-continued

| Cmpd No. | $^1$H NMR and/or LC/MS data |
| --- | --- |
| I-32 | $^1$H-NMR (DMSO-$d_6$) δ: 12.71 (1H, s), 8.71 (1H, d, J = 7.9 Hz), 8.24 (1H, s), 7.59-7.55 (3H, m), 7.49-7.44 (2H, m), 4.63-4.60 (1H, m), 4.03-4.01 (1H, m), 3.54-3.52 (1H, m), 2.09-2.06 (2H, m), 1.91-1.88 (2H, m), 1.38-1.24 (4H, m). LC/MS: 371 [M + H]. |
| I-35 | $^1$H-NMR (CDCl$_3$) δ: 11.92 (1H, br s), 9.31-9.25 (1H, m), 8.33 (1H, s), 7.42-7.22 (5H, m), 4.28-4.13 (2H, m), 3.86-3.78 (1H, m), 3.73-3.57 (3H, m), 3.09 (1H, t, J = 10.7 Hz), 2.38 (3H, s), 2.18-2.10 (1H, m), 1.91-1.84 (1H, m), 1.62-1.27 (11H, m). LC/MS: 466 [M + H]. |
| I-38 | $^1$H-NMR (CDCl$_3$) δ: 13.48 (1H, br s), 8.88 (1H, d, J = 7.9 Hz), 8.31 (1H, s), 7.53-7.36 (4H, m), 7.32 (1H, s), 4.41-4.28 (2H, m), 3.95-3.87 (1H, m), 3.37-3.27 (2H, m), 2.39-2.30 (1H, m), 1.80-1.66 (3H, m), 1.18 (3H, d, J = 6.1 Hz). LC/MS: 401 [M + H]. |
| I-41 | $^1$H-NMR (DMSO-$d_6$) δ: 12.57 (1H, s), 9.22 (1H, d, J = 7.3 Hz), 8.21 (1H, s), 7.44 (2H, t, J = 6.1 Hz), 7.28-7.36 (3H, m), 4.44-4.45 (2H, m), 3.27-3.28 (2H, m), 2.28 (3H, s), 1.50-1.89 (7H, m), 1.36-1.39 (2H, m). LC/MS: 365 [M + H]. |
| I-49 | $^1$H-NMR (CDCl$_3$) δ: 13.11 (1H, s), 8.86 (1H, d, J = 7.3 Hz), 8.34 (1H, s), 7.54-7.37 (4H, m), 7.31 (1H, s), 4.43-4.26 (2H, m), 3.29 (1H, t, J = 10.4 Hz), 3.22-3.16 (1H, m), 2.39-2.31 (1H, m), 1.85-1.55 (4H, m), 1.22 (3H, s), 1.19 (3H, s). LC/MS: 415 [M + H]. |
| I-62 | $^1$H-NMR (DMSO-$d_6$) δ: 12.69 (1H, br s), 12.15 (1H, br s), 8.92 (1H, d, J = 7.3 Hz), 8.23 (1H, s), 7.61-7.53 (3H, m), 7.50-7.41 (2H, m), 4.33-4.26 (1H, m), 2.40-2.46 (1H, m), 1.68-1.91 (8H, m). LC/MS: 399 [M + H]. |
| I-76 | $^1$H-NMR (CDCl$_3$) δ: 13.17 (1H, br s), 9.19 (1H, d, J = 8.0 Hz), 8.26 (1H, s), 7.44-7.38 (2H, m), 7.33-7.26 (3H, m), 4.09-3.98 (1H, m), 3.76 (1H, dd, J = 12.2, 2.2 Hz), 3.34 (1H, d, J = 12.2 Hz), 2.39 (3H, m), 2.18-2.11 (1H, m), 1.91-1.58 (6H, m), 1.48-1.28 (3H, m). LC/MS: 365 [M + H]. |
| I-77 | $^1$H-NMR (CDCl$_3$) δ: 13.23 (1H, s), 9.65 (1H, s), 8.24 (1H, s), 7.44-7.25 (5H, m), 3.82 (2H, s), 2.38 (3H, s), 2.15-2.00 (4H, m), 1.94-1.70 (4H, m). LC/MS: 351 [M + H]. |
| I-90 | $^1$H-NMR (CDCl$_3$) δ: 13.32 (1H, br s), 9.08 (1H, d, J = 7.3 Hz), 8.31 (1H, s), 7.44-7.37 (2H, m), 7.33-7.25 (3H, m), 4.51-4.40 (2H, m), 4.09 (1H, dd, J = 10.4, 2.4 Hz), 3.80 (3H, s), 3.44-3.35 (1H, m), 2.42-2.34 (4H, m), 2.25-2.18 (1H, m), 1.95-1.72 (2H, m). LC/MS: 395 [M + H]. |
| I-91 | $^1$H-NMR (CDCl$_3$) δ: 12.12 (1H, br s), 8.88 (1H, d, J = 7.3 Hz), 8.35 (1H, s), 7.53-7.37 (4H, m), 7.30 (1H, s), 6.58 (1H, d, J = 4.3 Hz), 5.55 (1H, d, J = 4.3 Hz), 4.46-4.30 (2H, m), 3.90 (1H, dd, J = 11.0, 2.4 Hz), 3.35 (1H, t, J = 10.4 Hz), 2.43-2.30 (2H, m), 1.84-1.69 (2H, m). LC/MS: 400 [M + H]. |
| I-103 | $^1$H-NMR (DMSO-$d_6$) δ: 12.67 (1H, s), 8.71 (1H, d, J = 7.3 Hz), 8.22 (1H, s), 7.61-7.53 (3H, m), 7.49-7.44 (2H, m), 4.18 (1H, s), 4.00-3.98 (1H, m), 1.83-1.81 (2H, m), 1.73-1.60 (4H, m), 1.46-1.40 (2H, m), 1.11 (3H, s). LC/MS: 385 [M + H]. |
| I-104 | $^1$H-NMR (DMSO-$d_6$) δ: 12.69 (1H, s), 8.92 (1H, d, J = 7.9 Hz), 8.23 (1H, s), 7.61-7.53 (3H, m), 7.49-7.45 (2H, m), 4.27-4.24 (2H, m), 2.00-1.98 (2H, m), 1.68-1.64 (2H, m), 1.57-1.46 (4H, m), 1.15 (3H, s). LC/MS: 385 [M + H]. |
| I-105 | $^1$H-NMR (CDCl$_3$) δ: 13.06 (1H, br s), 9.12 (1H, d, J = 7.3 Hz), 8.30 (1H, s), 7.43-7.37 (2H, m), 7.33-7.25 (3H, m), 5.84 (1H, br s), 5.55 (1H, br s), 4.22-4.10 (1H, m), 2.40-2.30 (5H, m), 2.28-2.03 (3H, m), 1.80-1.66 (2H, m), 1.54-1.42 (2H, m). LC/MS: 378 [M + H]. |
| I-107 | $^1$H-NMR (DMSO-$d_6$) δ: 12.68 (1H, s), 8.72 (1H, d, J = 7.3 Hz), 8.22 (1H, s), 7.61-7.54 (3H, m), 7.47-7.45 (2H, m), 4.31 (1H, s), 3.98-3.95 (1H, m), 3.28 (3H, s), 3.15 (2H, s), 1.87-1.84 (2H, m), 1.64-1.55 (6H, m). LC/MS: 415 [M + H]. |
| I-108 | $^1$H-NMR (DMSO-$d_6$) δ: 12.67 (1H, s), 8.95 (1H, d, J = 7.3 Hz), 8.23 (1H, s), 7.59-7.56 (3H, m), 7.47-7.44 (2H, m), 4.30 (2H, s), 3.29 (3H, s), 3.23 (2H, s), 2.00-1.95 (2H, m), 1.78-1.71 (2H, m), 1.60-1.57 (2H, m), 1.46-1.43 (2H, m). LC/MS: 415 [M + H]. |

Example 3: (4-((trans-4-aminocyclohexyl)amino)-7H-pyrrolo[2,3-d]pyrimidin-5-yl)(2-chlorophenyl) methanone (I-5)

Boc deprotection of tert-butyl N-(trans-4-((5-(2-chlorobenzoyl)-7H-pyrrolo[2,3-d]pyrimidin-4-yl]amino]cyclohexyl]carbamate provided Compound I-5. tert-Butyl N-(trans-4-((5-(2-chlorobenzoyl)-7H-pyrrolo[2,3-d]pyrimidin-4-yl] amino]cyclohexyl]carbamate was synthesized according to General Procedure A using tert-butyl N-(trans-4-amino-1-cyclohexyl)carbamate. $^1$H-NMR (DMSO-$d_6$) δ: 8.70 (1H, d, J=7.3 Hz), 8.19 (1H, s), 7.59-7.51 (3H, m), 7.47-7.43 (1H, m), 7.38 (1H, s), 4.01-3.91 (1H, m), 2.76-2.66 (1H, m), 2.12-2.06 (2H, m), 1.89-1.82 (2H, m), 1.21-1.39 (4H, m). LC/MS: 370 [M+H].

Example 4: (4-((cis-4-aminocyclohexyl)amino)-7H-pyrrolo[2,3-d]pyrimidin-5-yl)(2-chlorophenyl) methanone (I-6)

Boc deprotection of Compound I-2 provided Compound I-6. $^1$H-NMR (DMSO-$d_6$) δ: 8.95 (1H, d, J=7.9 Hz), 8.18 (1H, s), 7.60-7.51 (3H, m), 7.49-7.44 (1H, m), 7.40 (1H, s), 4.28-4.21 (1H, m), 2.89-2.82 (1H, m), 1.89-1.79 (2H, m), 1.72-1.63 (4H, m), 1.45-1.56 (2H, m). LC/MS: 370 [M+H].

Example 5: (4-(((1R,3S)-3-aminocyclopentyl)amino)-7H-pyrrolo[2,3-d]pyrimidin-5-yl)(2-chlorophenyl) methanone (I-7)

Boc deprotection of Compound I-3 provided Compound I-7. $^1$H-NMR (DMSO-$d_6$) δ: 8.89 (1H, d, J=6.7 Hz), 8.19

(1H, s), 7.59-7.51 (3H, m), 7.48-7.43 (1H, m), 7.39 (1H, s), 4.46-4.38 (1H, m), 3.37-3.29 (7H, m), 2.43-2.36 (1H, m), 2.12-2.03 (1H, m), 1.89-1.80 (1H, m), 1.74-1.64 (1H, m), 1.55-1.46 (1H, m), 1.27-1.35 (1H, m). LC/MS: 356 [M+H].

Example 6: N-(trans-4-((5-(2-chlorobenzoyl)-7H-pyrrolo[2,3-d]pyrimidin-4-yl)amino)cyclohexyl)-2-(1-methylpiperidin-4-yl)acetamide (I-8)

Acylation of Compound I-5 provided Compound I-8. $^1$H-NMR (DMSO-$d_6$) δ: 12.66 (1H, br s), 8.70 (1H, d, J=7.3 Hz), 8.24 (1H, s), 7.75 (1H, d, J=7.9 Hz), 7.61-7.53 (3H, m), 7.49-7.44 (2H, m), 4.02-3.93 (1H, m), 3.65-3.56 (1H, br m), 2.74-2.66 (2H, m), 2.16-2.10 (5H, m), 1.96 (2H, d, J=6.7 Hz), 1.88-1.76 (3H, m), 1.62-1.52 (3H, m), 1.43-1.27 (4H, m), 1.09-1.21 (2H, m). LC/MS: 509 [M+H].

Example 7: N-(cis-4-((5-(2-chlorobenzoyl)-7H-pyrrolo[2,3-d]pyrimidin-4-yl)amino)cyclohexyl)-2-(1-methylpiperidin-4-yl)acetamide (I-9)

Acylation of Compound I-6 provided Compound I-9. $^1$H-NMR (DMSO-$d_6$) δ: 8.92 (1H, d, J=7.3 Hz), 8.23 (1H, s), 7.86 (1H, d, J=7.9 Hz), 7.62-7.53 (3H, m), 7.49-7.45 (2H, m), 4.25-4.19 (1H, m), 3.78-3.71 (1H, m), 2.65-2.70 (2H, m), 2.09 (3H, s), 1.99 (2H, d, J=6.7 Hz), 1.80-1.52 (13H, m), 1.19-1.08 (2H, m). LC/MS: 509 [M+H].

Example 8: N-((1S,3R)-3-((5-(2-chlorobenzoyl)-7H-pyrrolo[2,3-d]pyrimidin-4-yl)amino)cyclopentyl)-2-(1-methylpiperidin-4-yl)acetamide (I-10)

Acylation of Compound I-7 provided Compound I-10. $^1$H-NMR (DMSO-$d_6$) δ: 8.85 (1H, d, J=7.3 Hz), 8.24 (1H, s), 7.95 (1H, d, J=7.3 Hz), 7.61-7.54 (3H, m), 7.49-7.45 (2H, m), 4.46-4.37 (1H, m), 4.11-4.04 (1H, m), 2.69-2.58 (2H, m), 2.49-2.41 (1H, m), 2.16-2.06 (4H, m), 1.96-1.87 (3H, m), 1.76-1.41 (8H, m), 1.05-1.17 (2H, m). LC/MS: 495 [M+H].

Example 9: N-3-((5-(2-chlorobenzoyl)-7H-pyrrolo[2,3-d]pyrimidin-4-yl)amino)cyclohexyl)-2-(1-methylpiperidin-4-yl)acetamide (6:4 diastereomeric mixture) (I-11)

Acylation of Compound I-4 provided Compound I-11. $^1$H-NMR (DMSO-$d_6$) δ: 12.68 (1H, br s), 8.92 (0.4H, d, J=7.9 Hz), 8.71 (0.6H, d, J=7.9 Hz), 8.24 (0.6H, s), 8.22 (0.4H, s), 7.81-7.76 (1H, m), 7.62-7.53 (3H, m), 7.49-7.45 (2H, m), 4.53-4.46 (0.4H, m), 4.14-4.02 (0.6H, m), 4.01-3.91 (0.4H, m), 3.75-3.64 (0.6H, m), 2.69-2.65 (2H, m), 2.05-2.23 (4H, m), 1.99-1.09 (16H, m). LC/MS: 509 [M+H].

Example 10: tert-butyl (cis-4-((5-(2-methylbenzoyl)-7H-pyrrolo[2,3-d]pyrimidin-4-yl)amino)cyclohexyl) carbamate (I-12)

Compound I-12 was synthesized according to General Procedure A described herein above using (4-chloro-7H-pyrrolo[2,3-d]pyrimidin-5-yl)-(o-tolyl)methanone.
NMR data for (4-chloro-7H-pyrrolo[2,3-d]pyrimidin-5-yl)-(o-tolyl)methanone intermediate: $^1$H-NMR (DMSO-$d_6$) δ: 13.30 (1H, br s), 8.74 (1H, s), 7.94 (1H, d, J=3.1 Hz), 7.48-7.44 (2H, m), 7.38-7.35 (1H, m), 7.31-7.26 (1H, m), 2.36 (3H, s).
NMR data for Compound I-12: $^1$H-NMR (DMSO-$d_6$) δ: 12.58 (1H, br s), 9.05 (1H, d, J=7.3 Hz), 8.21 (1H, s), 7.46-7.40 (2H, m), 7.37-7.27 (3H, m), 6.99-6.94 (1H, m), 4.25-4.19 (1H, m), 3.45-3.39 (1H, m), 2.29 (3H, s), 1.87-1.78 (2H, m), 1.58-1.76 (6H, m). LC/MS: 450 [M+H].

Example 11: (4-((cis-4-aminocyclohexyl)amino)-7H-pyrrolo[2,3-d]pyrimidin-5-yl)(o-tolyl)methanone (I-14)

Boc deprotection of Compound I-12 provided Compound I-14. $^1$H-NMR (DMSO-$d_6$) δ: 9.12 (1H, d, J=7.3 Hz), 8.19 (1H, s), 7.44-7.39 (2H, m), 7.35-7.27 (3H, m), 4.28-4.21 (1H, m), 2.85-2.78 (1H, m), 2.28 (3H, s), 1.89-1.79 (2H, m), 1.71-1.60 (4H, m), 1.54-1.43 (2H, m). LC/MS: 350 [M+H].

Example 12: N-(cis-4-((5-(2-methylbenzoyl)-7H-pyrrolo[2,3-d]pyrimidin-4-yl)amino) cyclohexyl)-2-(4-methylpiperazin-1-yl)acetamide (I-15)

Acylation of Compound I-14 provided Compound I-15. $^1$H-NMR (DMSO-$d_6$) δ: 12.61 (1H, s), 9.17 (1H, d, J=7.3 Hz), 8.22 (1H, s), 7.55 (1H, d, J=7.9 Hz), 7.46-7.41 (2H, m), 7.38-7.27 (3H, m), 4.33-4.25 (1H, m), 3.82-3.74 (1H, m), 2.89 (2H, s), 2.16-2.45 (12H, m), 2.02 (3H, s), 1.82-1.63 (8H, m). LC/MS: 490 [M+H].

Example 13: (4-((cis-4-(dimethylamino)cyclohexyl) amino)-7H-pyrrolo[2,3-d]pyrimidin-5-yl)(o-tolyl) methanone (I-18)

Reductive alkylation of Compound I-14 with formaline provided Compound I-18. $^1$H-NMR (DMSO-$d_6$) δ: 12.58 (1H, br s), 9.19 (1H, d, J=7.9 Hz), 8.21 (1H, s), 7.45-7.42 (2H, m), 7.37-7.28 (3H, m), 4.37-4.32 (1H, m), 2.27 (3H, s), 2.22-2.8 (1H, m) 2.20 (6H, s), 1.82-1.89 (2H, m), 1.60-1.77 (6H, m). LC/MS: 378 [M+H].

Example 14: ((2S,5R)-5-((5-(2-methylbenzoyl)-7H-pyrrolo[2,3-d]pyrimidin-4-yl)amino)tetrahydro-2H-pyran-2-yl)(4-methylpiperazin-1-yl)methanone (I-23)

Synthesis of (2S,5R)-5-((5-(2-methylbenzoyl)-7H-pyrrolo[2,3-d]pyrimidin-4-yl)amino)tetrahydro-2H-pyran-2-carboxylic acid using General Procedure A (LC/MS: 381 [M+H]) followed by a subsequent condensation reaction provided Compound I-23. $^1$H-NMR (CDCl$_3$) δ: 9.09 (1H, d, J=7.3 Hz), 8.33 (1H, s), 7.43-7.37 (2H, m), 7.33-7.25 (3H, m), 4.47-4.30 (2H, m), 4.22-4.17 (1H, m), 3.80-3.67 (2H, m), 3.64-3.53 (2H, m), 3.45-3.38 (1H, m), 2.49-2.37 (8H, m), 2.32 (3H, s), 2.10-1.99 (2H, m), 1.83-1.71 (1H, m). LC/MS: 463 [M+H].

Example 15: 4-(tert-butyl)-N-(cis-4-((5-(2-methylbenzoyl)-7H-pyrrolo[2,3-d]pyrimidin-4-yl)amino) cyclohexyl)benzamide (I-25)

Acylation of Compound I-14 provided Compound I-25. $^1$H-NMR (DMSO-$d_6$) δ: 12.60 (1H, br s), 9.14 (1H, d, J=7.3 Hz), 8.27 (1H, d, J=7.3 Hz), 8.24 (1H, s), 7.76-7.78 (2H, m), 7.44 (4H, t, J=5.8 Hz), 7.30-7.35 (3H, m), 4.29-4.31 (1H, m), 3.91-3.93 (1H, m), 2.30 (3H, s), 1.96-1.99 (2H, m), 1.78-1.79 (6H, m), 1.28 (9H, s). LC/MS: 510 [M+H].

Example 16: 2-(4-(4-(tert-butyl)benzoyl)piperazin-1-yl)-N-(cis-4-((5-(2-methylbenzoyl)-7H-pyrrolo[2,3-d]pyrimidin-4-yl)amino)cyclohexyl)acetamide (I-28)

Step 1. tert-butyl 4-(2-((4-((5-(2-methylbenzoyl)-7H-pyrrolo[2,3-d]pyrimidin-4-yl)amino)cyclohexyl)amino)-2-oxo-ethyl)piperazine-1-carboxylate (28a)

Acylation of Compound I-14 provided Compound 28a. $^1$H-NMR (CDCl$_3$) δ: 9.45 (1H, d, J=7.3 Hz), 8.33 (1H, s), 7.20-7.45 (6H, m), 4.46-4.48 (1H, m), 3.99-4.02 (1H, m), 3.39 (4H, s), 3.00 (2H, s), 2.45 (4H, s), 2.39 (3H, s), 1.65-1.99 (8H, m), 1.44 (9H, s). LC/MS: 576 [M+H].

Step 2. N-(4-((5-(2-methylbenzoyl)-7H-pyrrolo[2,3-d]pyrimidin-4-yl)amino)cyclohexyl)-2-piperazin-1-yl-acetamide (28b)

Boc deprotection of 28a provided Compound 28b. $^1$H-NMR (CDCl$_3$) δ: 9.39 (1H, d, J=7.9 Hz), 8.33 (1H, s), 7.41-7.42 (2H, m), 7.25-7.30 (5H, m), 4.43-4.46 (1H, m), 3.99-4.02 (1H, m), 2.96-2.98 (2H, m), 2.83-2.84 (4H, m), 2.47-2.49 (4H, m), 2.40 (3H, s), 1.71.91 (8H, m), 1.57-1.59 (5H, m). LC/MS: 476 [M+H].

Step 3. 2-(4-(4-(tert-butyl)benzoyl)piperazin-1-yl)-N-(cis-4-((5-(2-methylbenzoyl)-7H-pyrrolo[2,3-d]pyrimidin-4-yl)amino)cyclohexyl)acetamide (I-28)

Acylation of 28b provided Compound I-28. $^1$H-NMR (DMSO-d$_6$) δ: 12.61 (1H, s), 9.13 (1H, d, J=7.3 Hz), 8.23 (1H, s), 7.68 (1H, d, J=7.9 Hz), 7.28-7.40 (8H, m), 4.27 (1H, s), 3.78 (1H, s), 3.57 (1H, s), 3.29-3.35 (4H, m), 2.97 (2H, s), 2.41-2.51 (4H, m), 2.28 (3H, s), 1.63-1.78 (8H, m), 1.28 (9H, s). LC/MS: 636 [M+H].

Example 17: 2-(4-benzoylpiperazin-1-yl)-N-(cis-4-((5-(2-methylbenzoyl)-7H-pyrrolo[2,3-d]pyrimidin-4-yl)amino)cyclohexyl)acetamide (I-29)

Acylation of N-(4-((5-(2-methylbenzoyl)-7H-pyrrolo[2,3-d]pyrimidin-4-yl)amino)cyclohexyl)-2-piperazin-1-yl-acetamide provided Compound I-29. $^1$H-NMR (DMSO-d$_6$) δ: 12.61 (1H, s), 9.13 (1H, d, J=7.3 Hz), 8.22 (1H, s), 7.69 (1H, d, J=7.3 Hz), 7.28-7.45 (9H, m), 4.27-4.29 (1H, m), 3.76-3.79 (1H, m), 3.58-3.60 (1H, m), 3.30-3.32 (4H, m), 2.98 (2H, s), 2.48-2.49 (4H, m), 2.28 (3H, s). LC/MS: 580 [M+H].

Example 18: N-(cis-4-((5-(2-methylbenzoyl)-7H-pyrrolo[2,3-d]pyrimidin-4-yl)amino)cyclohexyl)benzamide (I-30)

Acylation of Compound I-14 provided Compound I-30. $^1$H-NMR (DMSO-d$_6$) δ: 12.60 (1H, s), 9.15 (1H, d, J=6.7 Hz), 8.37 (1H, d, J=7.3 Hz), 8.24 (1H, s), 7.84 (2H, d, J=7.3 Hz), 7.35-7.44 (8H, m), 4.29-4.31 (1H, m), 3.92-3.94 (1H, m), 2.30 (3H, s), 1.97-1.99 (2H, m), 1.79-1.80 (6H, m). LC/MS: 454 [M+H].

Example 19: N-(cis-4-((5-(2-methylbenzoyl)-7H-pyrrolo[2,3-d]pyrimidin-4-yl)amino)cyclohexyl)acetamide (I-33)

Acylation of Compound I-14 provided Compound I-33. $^1$H-NMR (DMSO-d$_6$) δ: 12.60 (1H, s), 9.09 (1H, d, J=7.3 Hz), 8.22 (1H, s), 7.89 (1H, d, J=7.3 Hz), 7.46-7.42 (2H, m), 7.36-7.28 (3H, m), 4.27-4.21 (1H, m), 3.68-3.75 (1H, m), 2.29 (3H, s), 1.83-1.59 (11H, m). LC/MS: 392 [M+H].

Example 20: (2S,5R)-5-((5-(2-methylbenzoyl)-7H-pyrrolo[2,3-d]pyrimidin-4-yl)amino)-N-((tetrahydro-2H-pyran-4-yl)methyl)tetrahydro-2H-pyran-2-carboxamide (I-34)

Condensation of (2S,5R)-5-((5-(2-methylbenzoyl)-7H-pyrrolo[2,3-d]pyrimidin-4-yl)amino)tetrahydro-2H-pyran-2-carboxylic acid with the applicable amine provided Compound I-34. $^1$H-NMR (CDCl$_3$) δ: 9.04 (1H, d, J=7.3 Hz), 8.35 (1H, s), 7.44-7.23 (5H, m), 6.72 (1H, t, J=6.4 Hz), 4.46-4.29 (2H, m), 3.99 (2H, dd, J=11.3, 4.0 Hz), 3.90-3.85 (1H, m), 3.43-3.29 (3H, m), 3.25-3.12 (2H, m), 2.41-2.32 (5H, m), 1.85-1.24 (7H, m). LC/MS: 478 [M+H].

Example 21: (4-((5-(2-chlorobenzoyl)-7H-pyrrolo[2,3-d]pyrimidin-4-yl)amino)cyclohexan-1-one (I-36)

Oxidation of Compound I-32 using Dess-Martin Periodinane provided Compound I-36. $^1$H-NMR (DMSO-d$_6$) δ: 12.76 (1H, s), 8.92 (1H, d, J=7.3 Hz), 8.29 (1H, s), 7.61-7.53 (3H, m), 7.50-7.45 (2H, m), 4.56-4.54 (1H, m), 2.61-2.53 (1H, m), 2.38-2.28 (5H, m), 1.92-1.89 (2H, m). LC/MS: 369 [M+H].

Example 22: (trans-4-((5-(2-methylbenzoyl)-7H-pyrrolo[2,3-d]pyrimidin-4-yl)amino)cyclohexyl)(4-methylpiperazin-1-yl)methanone (I-37)

Condensation of trans-4-((5-(2-methylbenzoyl)-7H-pyrrolo[2,3-d]pyrimidin-4-yl)amino]cyclohexanecarboxylic acid with the applicable amine provided Compound I-37. trans-4-((5-(2-methylbenzoyl)-7H-pyrrolo[2,3-d]pyrimidin-4-yl]amino]cyclohexanecarboxylic acid was synthesized according to General Procedure A. $^1$H-NMR (CDCl$_3$) δ: 9.13 (1H, d, J=7.9 Hz), 8.31 (1H, s), 7.43-7.37 (2H, m), 7.33-7.25 (3H, m), 4.25-4.14 (1H, m), 3.69-3.62 (2H, m), 3.57-3.51 (2H, m), 2.60-2.29 (13H, m), 1.92-1.41 (6H, m). LC/MS: 461 [M+H].

Example 23: (4-((cis-4-(benzylamino)cyclohexyl)amino)-7H-pyrrolo[2,3-d]pyrimidin-5-yl)(o-tolyl)methanone (I-39)

Reductive alkylation of Compound I-14 with benzaldehyde provided Compound I-39. $^1$H-NMR (CDCl$_3$) δ: 9.45 (1H, d, J=7.3 Hz), 8.30 (1H, s), 7.20-7.42 (10H, m), 4.40-4.43 (1H, m), 3.84 (2H, s), 2.71-2.73 (1H, m), 2.37 (3H, d, J=7.9 Hz), 2.00-2.03 (2H, m), 1.69-1.89 (6H, m). LC/MS: 440 [M+H].

Example 24: 2-(4-benzylpiperazin-1-yl)-N-(cis-4-((5-(2-methylbenzoyl)-7H-pyrrolo[2,3-d]pyrimidin-4-yl)amino)cyclohexyl)acetamide (I-40)

Reductive alkylation of N-(4-((5-(2-methylbenzoyl)-7H-pyrrolo[2,3-d]pyrimidin-4-yl)amino)cyclohexyl)-2-piperazin-1-yl-acetamide with benzaldehyde provided Compound I-40. $^1$H-NMR (DMSO-d$_6$) δ: 12.61 (1H, s), 9.17 (1H, d, J=7.9 Hz), 8.23 (1H, s), 7.56 (1H, d, J=7.9 Hz), 7.16-7.47 (10H, m), 4.29-4.31 (1H, m), 3.77-3.80 (1H, m), 3.30 (2H, s), 2.90 (2H, s), 2.23-2.51 (11H, m), 1.63-1.82 (8H, m). LC/MS: 566 [M+H].

Example 25: (2S,5R)—N—(((S)-1,4-dioxan-2-yl)methyl)-5-((5-(2-methylbenzoyl)-7H-pyrrolo[2,3-d]pyrimidin-4-yl)amino)tetrahydro-2H-pyran-2-carboxamide (I-42)

Condensation of (2S,5R)-5-((5-(2-methylbenzoyl)-7H-pyrrolo[2,3-d]pyrimidin-4-yl)amino)tetrahydro-2H-pyran-2-carboxylic acid with the applicable amine provided Compound I-42. $^1$H-NMR (CDCl$_3$) δ: 12.99 (1H, s), 9.09 (1H, d, J=7.3 Hz), 8.34 (1H, s), 7.45-7.26 (5H, m), 6.94 (1H, t, J=5.8 Hz), 4.47-4.29 (2H, m), 3.92-3.58 (7H, m), 3.50-3.42 (1H, m), 3.37-3.29 (2H, m), 3.25-3.17 (1H, m), 2.41-2.31 (5H, m), 1.85-1.60 (2H, m). LC/MS: 480 [M+H].

Example 26: (2-chlorophenyl)(4-((cis-4-(methylamino)cyclohexyl)amino)-7H-pyrrolo[2,3-d]pyrimidin-5-yl)methanone (I-43)

tert-Butyl N-(cis-4-amino-1-cyclohexyl)carbamate was derivatized to the corresponding 2-nitrobezenesulfonamide product. N-methylation of the sulfonamide followed by Boc deprotection provided N-(cis-4-amino-1-cyclohexyl)-N-methyl-2-nitrobenzenesulfonamide.

Compound I-43 was then synthesized according to General Procedure A from reaction of N-(cis-4-amino-1-cyclohexyl)-N-methyl-2-nitrobenzenesulfonamide with (2-chlorophenyl)-(4-chloro-7H-pyrrolo[2,3-d]pyrimidin-5-yl)methanone. $^1$H-NMR (DMSO-d$_6$) δ: 8.91 (1H, d, J=7.3 Hz), 8.20 (1H, s), 7.60-7.53 (3H, m), 7.49-7.42 (2H, m), 4.28-4.22 (1H, m), 2.48-2.48 (1H, m), 2.29 (3H, s), 1.84-1.76 (2H, m), 1.72-1.62 (4H, m), 1.51-1.61 (2H, m). LC/MS: 384 [M+H].

Example 27: (2-chlorophenyl)(4-((cis-4-(dimethylamino)cyclohexyl)amino)-7H-pyrrolo[2,3-d]pyrimidin-5-yl)methanone (I-44)

Reductive alkylation of Compound I-6 with formaline provided Compound I-44. $^1$H-NMR (DMSO-d$_6$) δ: 12.57 (1H, br s), 9.00 (1H, d, J=7.9 Hz), 8.22 (1H, s), 7.61-7.53 (3H, m), 7.50-7.44 (2H, m), 4.37-4.31 (1H, m), 2.21-2.17 (7H, m), 1.81-1.89 (2H, m), 1.75-1.62 (6H, m). LC/MS: 398 [M+H].

Example 28: N-(trans-4-((5-(2-chlorobenzoyl)-7H-pyrrolo[2,3-d]pyrimidin-4-yl)amino)cyclohexyl)acetamide (I-45)

Acylation of Compound I-6 provided Compound I-45. $^1$H-NMR (DMSO-d$_6$) δ: 12.70 (1H, br s), 8.93 (1H, d, J=7.3 Hz), 8.23 (1H, s), 7.90 (1H, d, J=7.9 Hz), 7.62-7.54 (3H, m), 7.50-7.45 (2H, m), 4.28-4.20 (1H, m), 3.69-3.77 (1H, m), 1.85-1.58 (11H, m). LC/MS: 412 [M+H].

Example 29: (4-((((2S,5R)-5-aminotetrahydro-2H-pyran-2-yl)methyl)amino)-7H-pyrrolo[2,3-d]pyrimidin-5-yl)(o-tolyl)methanone (I-46)

Boc deprotection of Compound I-35 provided Compound I-46. $^1$H-NMR (CDCl$_3$) δ: 9.32 (1H, t, J=5.5 Hz), 8.33 (1H, s), 7.43-7.25 (5H, m), 4.06-4.00 (1H, m), 3.86-3.79 (1H, m), 3.72-3.58 (2H, m), 3.08 (1H, t, J=10.6 Hz), 2.92-2.83 (1H, m), 2.38 (3H, s), 2.12-2.04 (1H, m), 1.89-1.22 (5H, m). LC/MS: 366 [M+H].

Example 30: N-(((2S,5R)-5-((5-(2-methylbenzoyl)-7H-pyrrolo[2,3-d]pyrimidin-4-yl)amino)tetrahydro-2H-pyran-2-yl)methyl)-2-(4-methylpiperazin-1-yl)acetamide (I-47)

tert-butyl N-((3R,6S)-6-(((2-(4-methylpiperazin-1-yl)acetyl)amino)methyl)tetrahydro-2H-pyran-3-yl]carbamate was synthesized using a typical condensation reaction. LC/MS: 371 [M+H]. Boc deprotection of tert-butyl N-((3R,6S)-6-(((2-(4-methylpiperazin-1-yl)acetyl)amino)methyl)tetrahydro-2H-pyran-3-yl]carbamate followed by halogen displacement using (4-chloro-7H-pyrrolo[2,3-d]pyrimidin-5-yl)-(o-tolyl)methanone provided Compound I-47. $^1$H-NMR (CDCl$_3$) δ: 12.38 (1H, br s), 9.00 (1H, d, J=6.7 Hz), 8.33 (1H, s), 7.57-7.50 (1H, m), 7.45-7.36 (2H, m), 7.33-7.24 (2H, m), 4.40-4.27 (2H, m), 3.68-3.60 (1H, m), 3.51-3.42 (1H, m), 3.32-3.24 (1H, m), 3.20-3.11 (1H, m), 3.06 (1H, d, J=16.1 Hz), 3.01 (1H, d, J=16.1 Hz), 2.65-2.26 (15H, m), 1.85-1.50 (4H, m). LC/MS: 506 [M+H].

Example 31: (2S,5R)-5-((5-(2-chlorobenzoyl)-7H-pyrrolo[2,3-d]pyrimidin-4-yl)amino)-N-((tetrahydro-2H-pyran-4-yl)methyl)tetrahydro-2H-pyran-2-carboxamide (I-48)

Condensation of (2S,5R)-5-((5-(2-chlorobenzoyl)-7H-pyrrolo[2,3-d]pyrimidin-4yl)amino)tetrahydro-2H-pyran-2-carboxylic acid with the applicable amine provided Compound I-48. $^1$H-NMR (CDCl$_3$) δ: 13.61 (1H, br s), 8.94 (1H, d, J=7.9 Hz), 8.34 (1H, s), 7.54-7.38 (4H, m), 7.34 (1H, s), 6.73 (1H, t, J=6.1 Hz), 4.45-4.30 (2H, m), 4.02-3.95 (1H, m), 3.88 (1H, dd, J=11.6, 1.8 Hz), 3.43-3.29 (3H, m), 3.26-3.13 (2H, m), 2.42-2.32 (2H, m), 2.06-1.57 (5H, m), 1.40-1.27 (2H, m). LCMS: 498 [M+H].

Example 32: N-(cis-4-((5-(2-chlorobenzoyl)-7H-pyrrolo[2,3-d]pyrimidin-4-yl)amino)cyclohexyl)-N-methylacetamide (I-50)

Acylation of Compound I-43 provided Compound I-50. $^1$H-NMR (DMSO-d$_6$) δ: 12.75 (1H, br s), 9.22 (1H, d, J=7.9 Hz), 8.25 (1H, s), 7.62-7.55 (3H, m), 7.51-7.47 (2H, m), 4.50-4.38 (1.6H, m), 3.69-3.78 (0.4H, m), 2.87 (1.8H, s), 2.73 (1.2H, s), 2.06-1.42 (11H, m). LC/MS: 426 [M+H].

Example 33: 1-(cis-4-((5-(2-chlorobenzoyl)-7H-pyrrolo[2,3-d]pyrimidin-4-yl)amino)cyclohexyl)pyrrolidin-2-one (I-51)

Step 1. 1-(cis-4-aminocyclohexyl)pyrrolidin-2-one (51a)

Acylation of tert-butyl N-(4-aminocyclohexyl)carbamate with 4-chlorobutanoyl chloride followed cyclization using sodium hydride Boc deprotection provided 51a. $^1$H-NMR (CD$_3$OD) δ: 3.94-3.85 (1H, m), 3.52-3.46 (3H, m), 2.38 (2H, t, J=8.2 Hz), 2.08-1.64 (11H, m). LC/MS: 183 [M+H].

Step 2. 1-(cis-4-((5-(2-chlorobenzoyl)-7H-pyrrolo[2,3-d]pyrimidin-4-yl)amino)cyclohexyl)pyrrolidin-2-one (I-51)

Compound I-51 was synthesized using General Procedure A from 51a and (2-chlorophenyl)-(4-chloro-7H-pyrrolo[2,3-d]pyrimidin-5-yl)methanone. $^1$H-NMR (DMSO-d$_6$) δ: 12.74 (1H, br s), 9.19 (1H, d, J=7.9 Hz), 8.25 (1H, s), 7.63-7.54 (3H, m), 7.51-7.46 (2H, m), 4.49-4.43 (1H, m), 3.95-3.86 (1H, m), 3.38-3.31 (2H, m), 2.20 (2H, t, J=7.9 Hz), 1.99-1.80 (6H, m), 1.77-1.67 (2H, m), 1.55-1.47 (2H, m). LC/MS: 438 [M+H].

Example 34: 1-(4-((5-(2-methylbenzoyl)-7H-pyrrolo[2,3-d]pyrimidin-4-yl)amino)piperidin-1-yl)ethan-1-one (I-52)

Boc deprotection of Compound I-17 followed by acylation provided Compound I-52. $^1$H-NMR (CDCl$_3$) δ: 12.62-11.97 (1H, m), 9.36-9.32 (1H, m), 8.33 (1H, s), 7.49-7.39 (2H, m), 7.33-7.26 (3H, m), 4.49-4.42 (1H, m), 4.38-4.28 (1H, m), 3.88-3.82 (1H, m), 3.46-3.34 (1H, m), 3.24-3.18 (1H, m), 2.38 (3H, s), 2.21-2.08 (5H, m), 1.79-1.67 (2H, m). LC/MS: 378 [M+H].

Example 35: 2-methoxy-1-(4-((5-(2-methylbenzoyl)-7H-pyrrolo[2,3-d]pyrimidin-4-yl)amino)piperidin-1-yl)ethan-1-one (I-53)

Boc deprotection of Compound I-17 followed by acylation provided Compound I-53. $^1$H-NMR (CDCl$_3$) δ: 12.46-11.92 (1H, m), 9.32 (1H, d, J=7.3 Hz), 8.33 (1H, s), 7.43-7.38 (2H, m), 7.32-7.26 (3H, m), 4.50-4.42 (1H, m), 4.35-4.29 (1H, m), 4.15 (2H, d, J=2.4 Hz), 3.93-3.87 (1H, m), 3.45 (3H, s), 3.41-3.33 (1H, m), 3.28-3.21 (1H, m), 2.38 (3H, s), 2.22-2.15 (2H, m), 1.79-1.69 (2H, m). LC/MS: 408 [M+H].

Example 36: 3-methoxy-1-(4-((5-(2-methylbenzoyl)-7H-pyrrolo[2,3-d]pyrimidin-4-yl)amino)piperidin-1-yl)propan-1-one (I-54)

Boc deprotection of Compound I-17 followed by acylation provided Compound I-54. $^1$H-NMR (CDCl$_3$) δ: 9.34 (1H, d, J=7.3 Hz), 8.32 (1H, s), 7.43-7.37 (2H, m), 7.32-7.25 (3H, m), 4.46-4.42 (1H, m), 4.37-4.31 (1H, m), 3.93-3.87 (1H, m), 3.74-3.68 (2H, m), 3.42-3.33 (4H, m), 3.26-3.19 (1H, m), 2.65 (2H, t, J=6.7 Hz), 2.38 (3H, s), 2.19-2.13 (2H, m), 1.81-1.66 (2H, m). LC/MS: 422 [M+H].

Example 37: 2-(dimethylamino)-1-(4-((5-(2-methylbenzoyl)-7H-pyrrolo[2,3-d]pyrimidin-4-yl)amino)piperidin-1-yl)ethan-1-one (I-55)

Boc deprotection of Compound I-17 followed by acylation provided Compound I-55. $^1$H-NMR (CDCl$_3$) δ: 12.96 (1H, br s), 9.32 (1H, d, J=7.9 Hz), 8.33 (1H, s), 7.42-7.38 (2H, m), 7.32-7.27 (3H, m), 4.47-4.41 (1H, m), 4.35-4.29 (1H, m), 4.11-4.05 (1H, m), 3.43-3.36 (1H, m), 3.22-3.10 (3H, m), 2.38 (3H, s), 2.30 (6H, s), 2.20-2.13 (2H, m), 1.78-1.62 (2H, m). LC/MS: 421 [M+H].

Example 38: (4-((1-(2-methoxyethyl)piperidin-4-yl)amino)-7H-pyrrolo[2,3-d]pyrimidin-5-yl)(o-tolyl)methanone (I-56)

Boc deprotection of Compound I-17 followed by acylation provided Compound I-56. $^1$H-NMR (D$_2$O) δ: 8.11 (1H, s), 7.51 (1H, s), 7.39-718 (4H, m), 4.00-3.92 (1H, m), 3.52 (2H, t, J=5.9 Hz), 3.32 (3H, s), 2.74-2.66 (2H, m), 2.53 (2H, t, J=5.9 Hz), 2.42-2.34 (2H, m), 2.23 (3H, s), 2.00-1.93 (2H, m), 1.69-1.60 (2H, m). LC/MS: 394 [M+H].

Example 39: (4-(((4-aminocyclohexyl)methyl)amino)-7H-pyrrolo[2,3-d]pyrimidin-5-yl)(o-tolyl)methanone (I-57)

Step 1. tert-butyl N-(4-(((5-(2-methylbenzoyl)-7H-pyrrolo[2,3-d]pyrimidin-4-yl)amino)methyl)-cyclohexyl)carbamate (57a)

tert-butyl N-(4-(((5-(2-methylbenzoyl)-7H-pyrrolo[2,3-d]pyrimidin-4-yl)amino)methyl)-cyclohexyl)carbamate (57a) was synthesized according to General Procedure A from (4-chloro-7H-pyrrolo[2,3-d]pyrimidin-5-yl)(o-tolyl)methanone. $^1$H-NMR (DMSO-d$_6$) δ: 12.59 (1H, s), 8.95 (1H, t, J=5.5 Hz), 8.22 (1H, s), 7.41-7.45 (2H, m), 7.28-7.35 (3H, m), 6.75 (1H, d, J=6.7 Hz), 3.46-3.48 (3H, m), 2.27 (3H, s), 1.73-1.76 (1H, m), 1.50-1.58 (8H, m), 1.38 (9H, s). LC/MS: 464 [M+H].

Step 2. (4-(((4-aminocyclohexyl)methyl)amino)-7H-pyrrolo[2,3-d]pyrimidin-5-yl)(o-tolyl)methanone (I-57)

Boc deprotection of 57a provided Compound I-57. $^1$H-NMR (DMSO-d$_6$) δ: 8.35 (1H, s), 7.95 (3H, s), 7.58 (1H, s), 7.44-7.49 (2H, m), 7.31-7.38 (2H, m), 3.58 (3H, t, J=6.4 Hz), 3.23 (1H, m), 2.29 (3H, s), 1.90 (1H, m), 1.60-1.73 (8H, m). LC/MS: 364 [M+H].

Example 40: (4-((4-(aminomethyl)cyclohexyl)amino)-7H-pyrrolo[2,3-d]pyrimidin-5-yl)(o-tolyl)methanone (I-58)

Step 1. 2-((4-((5-(2-methyl-benzoyl)-7H-pyrrolo[2,3-d]pyrimidin-4-yl)amino)cyclohexyl)methyl)isoindoline-1,3-dione (58a)

2-((4-((5-(2-methyl-benzoyl)-7H-pyrrolo[2,3-d]pyrimidin-4-yl)amino)cyclohexyl)methyl)isoindoline-1,3-dione (58a) was synthesized according to General Procedure A from cis-2-((4-aminocyclohexyl)methyl)benzo[c]azolidine-1,3-dione and (4-chloro-7H-pyrrolo[2,3-d]pyrimidin-5-yl)-(2-methylphenyl)methanone. $^1$H-NMR (DMSO-d$_6$) δ: 1.41-1.51 (2H, m), 1.62-1.65 (4H, m), 1.84-1.85 (3H, m), 2.27 (3H, s), 3.54 (2H, d, J=6.7 Hz), 4.38-4.41 (1H, m), 7.29-7.47 (5H, m), 7.77-7.80 (4H, m), 8.20 (1H, s), 9.24 (1H, d, J=7.9 Hz), 12.57 (1H, s). LC/MS: 494 [M+H].

Step 2. (4-((4-(aminomethyl)cyclohexyl)amino)-7H-pyrrolo[2,3-d]pyrimidin-5-yl)(o-tolyl)methanone (I-58)

Deprotection of the phthalimide group on 58a provided Compound I-58. $^1$H-NMR (DMSO-d$_6$) δ: 9.24 (1H, d, J=7.3 Hz), 8.19 (1H, s), 7.41-7.43 (2H, m), 7.28-7.34 (3H, m), 4.41-4.44 (1H, m), 2.47 (2H, d, J=4.9 Hz), 2.27 (3H, s), 1.78-1.82 (2H, m), 1.64-1.65 (4H, m), 1.36-1.38 (3H, m). LC/MS: 364 [M+H].

Example 41: (4-((4-((4-(tert-butyl)benzyl)amino)cyclohexyl)amino)-7H-pyrrolo[2,3-d]pyrimidin-5-yl)(o-tolyl)methanone (I-59)

Reductive alkylation of Compound I-14 provided Compound I-59. $^1$H-NMR (DMSO-d$_6$) δ: 9.08 (1H, d, J=7.9 Hz), 8.21 (1H, s), 7.43-7.44 (2H, m), 7.25-7.36 (7H, m), 4.23-

4.25 (1H, m), 3.69 (2H, s), 2.60-2.62 (1H, m), 2.29 (3H, s), 1.82-1.83 (2H, m), 1.64-1.66 (6H, m), 1.26 (9H, s). LC/MS: 496 [M+H].

Example 42: (4-((4-((3,5-dichlorobenzyl)amino) cyclohexyl)amino)-7H-pyrrolo[2,3-d]pyrimidin-5-yl)(o-tolyl)methanone (I-60)

Reductive alkylation of Compound I-14 provided Compound I-60. $^1$H-NMR (DMSO-$d_6$) δ: 12.57 (1H, brs), 9.09 (1H, d, J=7.3 Hz), 8.21 (1H, s), 7.44 (5H, dd, J=7.9, 4.9 Hz), 7.28-7.35 (3H, m), 4.23-4.26 (1H, m), 3.75 (2H, s), 2.54-2.56 (1H, m), 2.29 (3H, s), 1.81-1.84 (2H, m), 1.62-1.66 (6H, m). LC/MS: 508 [M+H].

Example 43: N-(cis-4-((5-(2-chlorobenzoyl)-7H-pyrrolo[2,3-d]pyrimidin-4-yl)amino) cyclohexyl)-N-methyl-2-(tetrahydro-2H-pyran-4-yl)acetamide (I-61)

Acylation of Compound I-43 provided compound I-61. $^1$H-NMR (DMSO-$d_6$) δ: 12.73 (1H, br s), 9.21 (1H, d, J=7.9 Hz), 8.24 (1H, s), 7.62-7.55 (3H, m), 7.51-7.46 (2H, m), 4.51-4.42 (1.8H, m), 3.84-3.76 (2.2H, m), 3.30-3.23 (2H, m), 2.88 (1.8H, s), 2.75 (1.2H, s), 2.33-2.30 (0.8H, m), 2.23-2.20 (1.2H, m), 1.99-1.16 (13H, m). LC/MS: 510 [M+H].

Example 44: cis-4-((5-(2-chlorobenzoyl)-7H-pyrrolo[2,3-d]pyrimidin-4-yl)amino) cyclohexane-1-carboxamide (I-63)

Amidation of Compound I-62 with the applicable amine provided Compound I-63. $^1$H-NMR (DMSO-$d_6$) δ: 12.68 (1H, br s), 8.95 (1H, d, J=7.3 Hz), 8.23 (1H, s), 7.61-7.52 (3H, m), 7.49-7.43 (2H, m), 7.19 (1H, s), 6.72 (1H, s), 4.32 (1H, s), 2.20-2.27 (1H, m), 1.63-1.89 (8H, m). LC/MS: 398 [M+H].

Example 45: cis-4-((5-(2-chlorobenzoyl)-7H-pyrrolo[2,3-d]pyrimidin-4-yl)amino)-N,N-dimethylcyclohexane-1-carboxamide (I-64)

Amidation of Compound I-62 with the applicable amine provided Compound I-64. $^1$H-NMR (DMSO-$d_6$) δ: 12.68 (1H, br s), 9.03 (1H, d, J=7.3 Hz), 8.23 (1H, s), 7.62-7.53 (3H, m), 7.50-7.44 (2H, m), 4.42-4.36 (1H, m), 3.02 (3H, s), 2.79 (3H, s), 2.74-2.66 (1H, m), 1.97-1.91 (2H, m), 1.81-1.71 (4H, m), 1.56-1.63 (2H, m). LC/MS: 426 [M+H].

Example 46: cis-4-((5-(2-chlorobenzoyl)-7H-pyrrolo[2,3-d]pyrimidin-4-yl)amino)-N-(tetrahydro-2H-pyran-4-yl)cyclohexane-1-carboxamide (I-65)

Amidation of Compound I-62 with the applicable amine provided Compound I-65. $^1$H-NMR (DMSO-$d_6$) δ: 12.68 (1H, br s), 8.97 (1H, d, J=7.9 Hz), 8.22 (1H, s), 7.67 (1H, d, J=7.9 Hz), 7.62-7.53 (3H, m), 7.49-7.45 (2H, m), 4.36-4.31 (1H, m), 3.82-3.66 (3H, m), 3.33-3.27 (2H, m), 2.26-2.19 (1H, m), 1.90-1.60 (10H, m), 1.31-1.41 (2H, m). LC/MS: 482 [M+H].

Example 47: cis-4-((5-(2-chlorobenzoyl)-7H-pyrrolo[2,3-d]pyrimidin-4-yl)amino)-N-((tetrahydro-2H-pyran-4-yl)methyl)cyclohexane-1-carboxamide (I-66)

Amidation of Compound I-62 with the applicable amine provided Compound I-66. $^1$H-NMR (DMSO-$d_6$) δ: 12.68 (1H, br s), 8.98 (1H, d, J=7.3 Hz), 8.22 (1H, s), 7.72 (1H, t, J=5.8 Hz), 7.61-7.54 (3H, m), 7.49-7.45 (2H, m), 4.37-4.32 (1H, m), 3.81-3.75 (2H, m), 3.23-3.16 (2H, m), 2.92 (2H, t, J=6.4 Hz), 2.28-2.23 (1H, m), 1.91-1.49 (10H, m), 1.13-1.07 (2H, m). LC/MS: 496 [M+H].

Example 48: cis-4-((5-(2-chlorobenzoyl)-7H-pyrrolo[2,3-d]pyrimidin-4-yl)amino)-N-(2-(pyridin-3-yl)ethyl)cyclohexane-1-carboxamide (I-67)

Amidation of Compound I-62 with the applicable amine provided Compound I-67. $^1$H-NMR (DMSO-$d_6$) δ: 12.68 (1H, br s), 8.96 (1H, d, J=7.3 Hz), 8.40-8.36 (2H, m), 8.22 (1H, s), 7.82 (1H, t, J=5.5 Hz), 7.62-7.53 (4H, m), 7.50-7.45 (2H, m), 7.28 (1H, dd, J=7.6, 4.6 Hz), 4.35-4.29 (1H, m), 3.32-3.26 (2H, m), 2.74-2.69 (2H, m), 2.16-2.24 (1H, m), 1.87-1.58 (8H, m). LC/MS: 503 [M+H].

Example 49: cis-4-((5-(2-chlorobenzoyl)-7H-pyrrolo[2,3-d]pyrimidin-4-yl)amino)-N-methylcyclohexane-1-carboxamide (I-68)

Amidation of Compound I-62 with the applicable amine provided Compound I-68. $^1$H-NMR (DMSO-$d_6$) δ: 12.68 (1H, br s), 8.96 (1H, d, J=7.3 Hz), 8.22 (1H, s), 7.68-7.64 (1H, m), 7.62-7.54 (3H, m), 7.50-7.45 (2H, m), 4.36-4.30 (1H, m), 2.55 (3H, d, J=4.9 Hz), 2.19-2.26 (1H, m), 1.89-1.62 (8H, m). LC/MS: 412 [M+H].

Example 50: (2-chlorophenyl)(4-((cis-4-(pyrrolidin-1-yl)cyclohexyl)amino)-7H-pyrrolo[2,3-d]pyrimidin-5-yl)methanone (I-69)

Reductive amination of Compound I-36 provided Compound I-69. $^1$H-NMR (DMSO-$d_6$) δ: 8.89 (1H, d, J=7.9 Hz), 8.22 (1H, s), 7.61-7.53 (3H, m), 7.49-7.45 (2H, m), 4.28-4.26 (1H, m), 3.46-3.33 (4H, m), 2.13-2.10 (1H, m), 1.81-1.69 (12H, m). LC/MS: 424 [M+H].

Example 51: (4-((cis-4-(azetidin-1-yl)cyclohexyl)amino)-7H-pyrrolo[2,3-d]pyrimidin-5-yl)(2-chlorophenyl)methanone (I-70)

Reductive amination of Compound I-36 and subsequent isomer separation provided Compound I-70. $^1$H-NMR (DMSO-$d_6$) δ: 12.65 (1H, br s), 8.85 (1H, d, J=7.3 Hz), 8.21 (1H, s), 7.62-7.54 (3H, m), 7.49-7.44 (2H, m), 4.21-4.20 (1H, m), 3.07-3.06 (4H, m), 2.14-2.12 (1H, m), 1.94-1.87 (2H, m), 1.72-1.68 (4H, m), 1.53-1.36 (4H, m). LC/MS: 410 [M+H].

Example 52: (4-((trans-4-(azetidin-1-yl)cyclohexyl)amino)-7H-pyrrolo[2,3-d]pyrimidin-5-yl)(2-chlorophenyl)methanone (I-71)

Reductive amination of Compound I-36 and subsequent isomer separation provided Compound I-71. $^1$H-NMR (DMSO-$d_6$) δ: 8.72 (1H, d, J=7.3 Hz), 8.23 (1H, s), 7.59-7.54 (3H, m), 7.48-7.45 (2H, m), 4.00-3.99 (1H, m), 3.08 (4H, t, J=7.0 Hz), 2.08-2.05 (3H, m), 1.93-1.87 (2H, m), 1.78-1.75 (2H, m), 1.33-1.27 (2H, m), 1.11-1.05 (2H, m). LC/MS: 410 [M+H].

Example 53: N-(4-(tert-butyl)benzyl)-2-methyl-2-((cis-4-(((5-(2-methylbenzoyl)-7H-pyrrolo[2,3-d]pyrimidin-4-yl)amino)methyl)cyclohexyl) amino) propanamide (I-72)

Step 1. 2-bromo-N-[(4-tert-butylphenyl)methyl]-2-methyl-propanamide (72a)

Acylation of 4-tert-butylbenzylamine with 2-bromo-2-methylpropanoic acid chloride provided 2-bromo-N-[(4- tert-butylphenyl)methyl]-2-methyl-propanamide (72a). $^1$H-NMR (CDCl$_3$) δ: 7.38 (2H, d, J=7.9 Hz), 7.23 (2H, d, J=7.9 Hz), 6.99 (1H, br s), 4.44 (2H, d, J=6.1 Hz), 2.00 (6H, s), 1.32 (9H, s). LC/MS: 312 [M+H].

Step 2. N-(4-(tert-butyl)benzyl)-2-methyl-2-((cis-4-(((5-(2-methylbenzoyl)-7H-pyrrolo[2,3-d]pyrimidin-4-yl)amino)methyl)cyclohexyl) amino)propanamide (I-72)

Alkylation of Compound I-57 with 2-bromo-N-[(4-tert-butylphenyl)methyl]-2-methyl-propanamide (72a) provided Compound I-72. $^1$H-NMR (CDCl$_3$) δ: 9.17 (1H, t, J=4.9 Hz), 8.32 (1H, s), 7.83 (1H, t, J=5.5 Hz), 7.23-7.36 (9H, m), 4.36 (2H, d, J=5.5 Hz), 3.55 (2H, t, J=6.1 Hz), 2.80 (1H, s), 3.35 (1H, m), 2.36 (3H, s), 1.24-1.88 (23H, m). LC/MS: 595 [M+H].

Example 54: N-benzyl-2-methyl-2-((cis-4-(((5-(2-methylbenzoyl)-7H-pyrrolo[2,3-d]pyrimidin-4-yl)amino)methyl)cyclohexyl) amino)propanamide (I-73)

Alkylation of Compound I-57 provided Compound I-73. $^1$H-NMR (CDCl$_3$) δ: 9.17 (1H, t, J=5.2 Hz), 8.32 (1H, s), 7.87 (1H, t, J=6.1 Hz), 7.19-7.42 (10H, m), 4.38 (2H, d, J=6.1 Hz), 3.54 (2H, t, J=6.1 Hz), 2.80 (1H, s), 2.37 (3H, s), 1.40-1.89 (9H, m), 1.34 (6H, s). LC/MS: 539 [M+H].

Example 55: N-(cis-4-(((5-(2-methylbenzoyl)-7H-pyrrolo[2,3-d]pyrimidin-4-yl)amino)methyl) cyclohexyl)benzamide (I-74)

Acylation of Compound I-57 provided Compound I-74. $^1$H-NMR (DMSO-d$_6$) δ: 12.60 (1H, s), 8.98 (1H, t, J=5.5 Hz), 8.23 (1H, s), 8.13 (1H, d, J=7.3 Hz), 7.84-7.83 (2H, m), 7.52-7.28 (8H, m), 3.97 (1H, m), 3.58 (2H, t, J=6.4 Hz), 2.27 (3H, s), 1.91-1.57 (9H, m). LC/MS: 468 [M+H].

Example 56: N-((cis-4-((5-(2-methylbenzoyl)-7H-pyrrolo[2,3-d]pyrimidin-4-yl)amino) cyclohexyl) methyl)benzamide (I-75)

Acylation of Compound I-58 provided Compound I-75. $^1$H-NMR (DMSO-d$_6$) δ: 12.58 (1H, s), 9.24 (1H, d, J=7.3 Hz), 8.50 (1H, t, J=5.8 Hz), 8.22 (1H, s), 7.83-7.82 (2H, m), 7.51-7.29 (8H, m), 4.43-4.40 (1H, m), 3.20 (2H, t, J=6.4 Hz), 2.29 (3H, s), 1.86-1.67 (7H, m), 1.47-1.44 (2H, m). LC/MS: 468 [M+H].

Example 57: (cis-4-((5-(2-chlorobenzoyl)-7H-pyrrolo[2,3-d]pyrimidin-4-yl)amino)cyclohexyl)(morpholino)methanone (I-78)

Amidation of Compound I-62 provided Compound I-78. $^1$H-NMR (DMSO-d$_6$) δ: 12.68 (1H, br s), 9.04 (1H, d, J=7.3 Hz), 8.23 (1H, s), 7.62-7.54 (3H, m), 7.49-7.45 (2H, m), 4.42-4.37 (1H, m), 3.59-3.40 (8H, m), 2.74-2.66 (1H, m), 1.95-1.90 (2H, m), 1.84-1.69 (4H, m), 1.57-1.63 (2H, m). LC/MS: 468 [M+H].

Example 58: (cis-4-((5-(2-chlorobenzoyl)-7H-pyrrolo[2,3-d]pyrimidin-4-yl)amino)cyclohexyl)((2S,6R)-2,6-dimethylmorpholino)methanone (I-79)

Amidation of Compound I-62 provided Compound I-79. $^1$H-NMR (DMSO-d$_6$) δ: 12.68 (1H, br s), 9.03 (1H, d, J=7.3 Hz), 8.23 (1H, s), 7.61-7.54 (3H, m), 7.49-7.45 (2H, m), 4.43-4.38 (1H, m), 4.25 (1H, d, J=12.8 Hz), 3.86 (1H, d, J=13.4 Hz), 3.51-3.35 (2H, m), 2.79-2.67 (2H, m), 2.17 (1H, t, J=11.9 Hz), 1.97-1.51 (8H, m), 1.04-1.13 (6H, m). LC/MS: 496 [M+H].

Example 59: (4-((cis-4-((1R,5S)-8-oxa-3-azabicyclo[3.2.1]octane-3-carbonyl)cyclohexyl)amino)-7H-pyrrolo[2,3-d]pyrimidin-5-yl)(2-chlorophenyl)methanone (I-80)

Amidation of Compound I-62 provided Compound I-80. $^1$H-NMR (DMSO-d$_6$) δ: 12.67 (1H, br s), 9.03 (1H, d, J=7.3 Hz), 8.23 (1H, s), 7.62-7.54 (3H, m), 7.50-7.45 (2H, m), 4.41-4.37 (1H, m), 4.32-4.28 (2H, m), 3.95 (1H, d, J=12.8 Hz), 3.64 (1H, d, J=12.2 Hz), 3.31-3.22 (2H, m), 2.76-2.62 (2H, m), 1.99-1.50 (12H, m). LC/MS: 494 [M+H].

Example 60: (cis-4-((5-(2-chlorobenzoyl)-7H-pyrrolo[2,3-d]pyrimidin-4-yl)amino) cyclohexyl)(3-hydroxyazetidin-1-yl)methanone (I-81)

Amidation of Compound I-62 provided Compound I-81. $^1$H-NMR (DMSO-d$_6$) δ: 12.68 (1H, br s), 8.98 (1H, d, J=7.3 Hz), 8.22 (1H, s), 7.61-7.54 (3H, m), 7.49-7.45 (2H, m), 5.69 (1H, d, J=6.1 Hz), 4.46-4.39 (1H, m), 4.34 (2H, t, J=7.6 Hz), 3.99 (1H, dd, J=9.5, 7.0 Hz), 3.88 (1H, dd, J=8.5, 4.3 Hz), 3.54 (1H, dd, J=9.8, 4.3 Hz), 2.38-2.31 (1H, m), 1.55-1.93 (8H, m). LC/MS: 454 [M+H].

Example 61: (cis-4-((5-(2-chlorobenzoyl)-7H-pyrrolo[2,3-d]pyrimidin-4-yl)amino) cyclohexyl)(4-methylpiperazin-1-yl)methanone (I-82)

Amidation of Compound I-62 provided Compound I-82. $^1$H-NMR (DMSO-d$_6$) δ: 12.68 (1H, br s), 9.03 (1H, d, J=7.3 Hz), 8.23 (1H, s), 7.62-7.54 (3H, m), 7.50-7.45 (2H, m), 4.42-4.37 (1H, m), 3.52-3.39 (4H, m), 2.74-2.66 (1H, m), 2.35-2.16 (7H, m), 1.94-1.89 (2H, m), 1.80-1.70 (4H, m), 1.62-1.55 (2H, m). LC/MS: 481 [M+H].

Example 62: (cis-4-((5-(2-chlorobenzoyl)-7H-pyrrolo[2,3-d]pyrimidin-4-yl)amino) cyclohexyl)((3S,5R)-3,5-dimethylpiperazin-1-yl)methanone (I-83)

Amidation of Compound I-62 provided Compound I-83. $^1$H-NMR (CDCl$_3$) δ: 9.30 (1H, d, J=6.7 Hz), 8.33 (1H, s), 7.49-7.34 (4H, m), 7.25 (1H, s), 4.56-4.42 (2H, m), 3.72 (1H, d, J=11.5 Hz), 2.84-2.57 (4H, m), 2.23-2.01 (5H, m), 1.84-1.68 (4H, m), 1.04-1.13 (6H, m). LC/MS: 495 [M+H].

Example 63: N-(trans-4-((5-(2-chlorobenzoyl)-7H-pyrrolo[2,3-d]pyrimidin-4-yl)amino) cyclohexyl) acetamide (I-84)

Acylation of Compound I-5 provided Compound I-84. $^1$H-NMR (DMSO-d$_6$) δ: 12.69 (1H, br s), 8.70 (1H, d, J=7.3 Hz), 8.24 (1H, s), 7.78 (1H, d, J=7.9 Hz), 7.61-7.53 (3H, m), 7.49-7.45 (2H, m), 4.03-3.95 (1H, m), 3.63-3.54 (1H, m), 2.15-2.10 (2H, m), 1.90-1.85 (2H, m), 1.27-1.44 (4H, m). LC/MS: 412 [M+H].

Example 64: (S)—N-(cis-4-((5-(2-chlorobenzoyl)-7H-pyrrolo[2,3-d]pyrimidin-4-yl)amino) cyclohexyl)-2-hydroxypropanamide (I-85)

Acylation of Compound I-6 provided Compound I-85. $^1$H-NMR (DMSO-d$_6$) δ: 12.71 (1H, br s), 8.96 (1H, d, J=6.7

Hz), 8.24 (1H, s), 7.62-7.53 (3H, m), 7.49-7.43 (3H, m), 5.40-5.34 (1H, m), 4.31-4.25 (1H, m), 3.99-3.93 (1H, m), 3.76-3.70 (1H, m), 1.59-1.84 (8H, m), 1.19 (3H, d, J=6.7 Hz). LC/MS: 442 [M+H].

Example 65: (R)—N-(cis-4-((5-(2-chlorobenzoyl)-7H-pyrrolo[2,3-d]pyrimidin-4-yl)amino) cyclohexyl)-2-hydroxypropanamide (I-86)

Acylation of Compound I-6 provided Compound I-86.
$^1$H-NMR (DMSO-$d_6$) δ: 12.71 (1H, s), 8.95 (1H, d, J=7.3 Hz), 8.24 (1H, s), 7.62-7.54 (3H, m), 7.49-7.43 (3H, m), 5.37 (1H, d, J=5.5 Hz), 4.31-4.25 (1H, m), 3.99-3.93 (1H, m), 3.78-3.69 (1H, m), 1.59-1.85 (8H, m), 1.19 (3H, d, J=6.7 Hz). LC/MS: 442 [M+H].

Example 66: N-(cis-4-((5-(2-chlorobenzoyl)-7H-pyrrolo[2,3-d]pyrimidin-4-yl)amino) cyclohexyl)-2-methoxyacetamide (I-87)

Acylation of Compound I-6 provided Compound I-87.
$^1$H-NMR (DMSO-$d_6$) δ: 12.71 (1H, s), 8.95 (1H, d, J=7.3 Hz), 8.24 (1H, s), 7.66 (1H, d, J=7.9 Hz), 7.62-7.54 (3H, m), 7.50-7.46 (2H, m), 4.31-4.25 (1H, m), 3.76-3.80 (3H, m), 3.28 (3H, s), 1.87-1.64 (8H, m). LC/MS: 442 [M+H].

Example 67: (2-chlorophenyl)(4-((cis-4-(3-hydroxyazetidin-1-yl)cyclohexyl)amino)-7H-pyrrolo[2,3-d]pyrimidin-5-yl)methanone (I-88)

Reductive amination of Compound I-36 and subsequent isomer separation provided Compound I-88.
$^1$H-NMR (DMSO-$d_6$) δ: 12.67 (1H, s), 8.84 (1H, d, J=7.9 Hz), 8.22 (1H, s), 7.60-7.55 (3H, m), 7.48-7.44 (2H, m), 5.22 (1H, d, J=6.1 Hz), 4.21-4.12 (2H, m), 3.49 (2H, t, J=6.7 Hz), 2.65-2.63 (2H, m), 2.13-2.10 (1H, m), 1.72-1.66 (4H, m), 1.55-1.46 (4H, m). LC/MS: 426 [M+H].

Example 68: (2-chlorophenyl)(4-((trans-4-(3-hydroxyazetidin-1-yl)cyclohexyl)amino)-7H-pyrrolo[2,3-d]pyrimidin-5-yl)methanone (I-89)

Reductive amination of Compound I-36 and subsequent isomer separation provided Compound I-89. $^1$H-NMR (DMSO-$d_6$) δ: 8.71 (1H, d, J=7.3 Hz), 8.23 (1H, s), 7.61-7.53 (3H, m), 7.48-7.45 (2H, m), 5.23 (1H, d, J=6.7 Hz), 4.12 (1H, dd, J=12.5, 6.4 Hz), 4.00-3.99 (1H, m), 3.48 (2H, t, J=6.7 Hz), 2.68 (2H, t, J=6.7 Hz), 2.07-2.03 (3H, m), 1.78 (2H, d, J=9.8 Hz), 1.31 (2H, dd, J=22.9, 9.5 Hz), 1.13-1.03 (2H, m). LC/MS: 426 [M+H].

Example 69: N-(cis-4-((5-(2-chlorobenzoyl)-7H-pyrrolo[2,3-d]pyrimidin-4-yl)amino) cyclohexyl) propionamide (I-92)

Acylation of Compound I-6 provided Compound I-92.
$^1$H-NMR (DMSO-$d_6$) δ: 12.70 (1H, s), 8.93 (1H, d, J=7.3 Hz), 8.24 (1H, s), 7.81 (1H, d, J=7.3 Hz), 7.62-7.54 (3H, m), 7.50-7.45 (2H, m), 4.27-4.22 (1H, m), 3.69-3.76 (1H, m), 2.08 (2H, q, J=7.5 Hz), 1.83-1.59 (8H, m), 0.97 (3H, t, J=7.6 Hz). LC/MS: 426 [M+H].

Example 70: N-(cis-4-((5-(2-chlorobenzoyl)-7H-pyrrolo[2,3-d]pyrimidin-4-yl)amino) cyclohexyl) isobutyramide (I-93)

Acylation of Compound I-6 provided Compound I-93.
$^1$H-NMR (DMSO-$d_6$) δ: 12.71 (1H, s), 8.93 (1H, d, J=6.7 Hz), 8.24 (1H, s), 7.76 (1H, d, J=7.3 Hz), 7.62-7.53 (3H, m), 7.50-7.46 (2H, m), 4.27-4.20 (1H, m), 3.75-3.68 (1H, m), 2.38-2.46 (1H, m), 1.56-1.87 (8H, m), 0.95 (6H, d, J=6.7 Hz). LC/MS: 440 [M+H].

Example 71: N-(cis-4-((5-(2-chlorobenzoyl)-7H-pyrrolo[2,3-d]pyrimidin-4-yl)amino) cyclohexyl) cyclopropanecarboxamide (I-94)

Acylation of Compound I-6 provided Compound I-94.
$^1$H-NMR (DMSO-$d_6$) δ: 12.70 (1H, s), 8.95 (1H, d, J=7.9 Hz), 8.24 (1H, s), 8.11 (1H, d, J=7.3 Hz), 7.62-7.54 (3H, m), 7.50-7.46 (2H, m), 4.29-4.21 (1H, m), 3.78-3.71 (1H, m), 1.84-1.61 (9H, m), 0.56-0.67 (4H, m). LC/MS: 438 [M+H].

Example 72: 4-methyl-N-(cis-4-((5-(2-methylbenzoyl)-7H-pyrrolo[2,3-d]pyrimidin-4-yl)amino)cyclohexyl)benzamide (I-95)

Acylation of Compound I-14 provided Compound I-95.
$^1$H-NMR (DMSO-$d_6$) δ: 12.60 (1H, s), 9.15 (1H, d, J=6.7 Hz), 8.27 (1H, d, J=6.7 Hz), 8.24 (1H, s), 7.76 (2H, d, J=8.5 Hz), 7.44-7.42 (2H, m), 7.37-7.28 (3H, m), 7.23 (2H, d, J=7.9 Hz), 4.32-4.29 (1H, m), 3.93-3.90 (1H, m), 2.33 (3H, s), 2.30 (3H, s), 1.98 (2H, d, J=9.2 Hz), 1.78 (6H, d, J=4.9 Hz). LC/MS: 468 [M+H].

Example 73: 3-methyl-N-(cis-4-((5-(2-methylbenzoyl)-7H-pyrrolo[2,3-d]pyrimidin-4-yl)amino)cyclohexyl)benzamide (I-96)

Acylation of Compound I-14 provided Compound I-96.
$^1$H-NMR (DMSO-$d_6$) δ: 12.60 (1H, s), 9.15 (1H, d, J=6.7 Hz), 8.30 (1H, d, J=7.3 Hz), 8.24 (1H, s), 7.65-7.62 (2H, m), 7.45-7.42 (2H, m), 7.35-7.30 (5H, m), 4.32-4.29 (1H, m), 3.93-3.90 (1H, m), 2.33 (3H, s), 2.30 (3H, s), 1.99-1.97 (2H, m), 1.79-1.78 (6H, m). LC/MS: 468 [M+H].

Example 74: 2-methyl-N-(cis-4-((5-(2-methylbenzoyl)-7H-pyrrolo[2,3-d]pyrimidin-4-yl)amino)cyclohexyl)benzamide (I-97)

Acylation of Compound I-14 provided Compound I-97.
$^1$H-NMR (DMSO-$d_6$) δ: 12.58 (1H, s), 9.08 (1H, d, J=7.3 Hz), 8.37 (1H, d, J=7.3 Hz), 8.23 (1H, s), 7.42-7.40 (2H, m), 7.35-7.16 (7H, m), 4.28-4.25 (1H, m), 3.95-3.92 (1H, m), 2.31 (3H, s), 2.27 (3H, s), 1.91-1.89 (2H, m), 1.81-1.79 (6H, m). LC/MS: 468 [M+H].

Example 75: (S)—N-(cis-4-((5-(2-chlorobenzoyl)-7H-pyrrolo[2,3-d]pyrimidin-4-yl)amino) cyclohexyl)-2-methoxypropanamide (I-98)

Acylation of Compound I-6 provided Compound I-98.
$^1$H-NMR (DMSO-$d_6$) δ: 12.71 (1H, s), 8.94 (1H, d, J=7.3 Hz), 8.24 (1H, s), 7.75 (1H, d, J=7.3 Hz), 7.62-7.53 (3H, m), 7.50-7.45 (2H, m), 4.30-4.23 (1H, m), 3.68-3.80 (2H, m), 3.20 (3H, s), 1.61-1.87 (8H, m), 1.18 (3H, d, J=6.7 Hz). LC/MS: 456 [M+H].

Example 76: (R)—N-(cis-4-((5-(2-chlorobenzoyl)-7H-pyrrolo[2,3-d]pyrimidin-4-yl)amino) cyclohexyl)-2-methoxypropanamide (I-99)

Acylation of Compound I-6 provided Compound I-99.
$^1$H-NMR (DMSO-$d_6$) δ: 12.71 (1H, s), 8.95 (1H, d, J=7.3 Hz), 8.24 (1H, s), 7.75 (1H, d, J=7.3 Hz), 7.62-7.54 (3H, m), 7.50-7.46 (2H, m), 4.30-4.23 (1H, m), 3.78-3.68 (2H, m), 3.20 (3H, s), 1.60-1.89 (8H, m), 1.18 (3H, d, J=6.7 Hz). LC/MS: 456 [M+H].

Example 77: (S)—N-(cis-4-((5-(2-chlorobenzoyl)-7H-pyrrolo[2,3-d]pyrimidin-4-yl)amino) cyclohexyl)tetrahydrofuran-2-carboxamide (I-100)

Acylation of Compound I-6 provided Compound I-100. $^1$H-NMR (DMSO-$d_6$) δ: 12.71 (1H, s), 8.95 (1H, d, J=6.7 Hz), 8.23 (1H, d, J=5.5 Hz), 7.62-7.54 (4H, m), 7.50-7.46 (2H, m), 4.19-4.30 (2H, m), 3.89-3.83 (1H, m), 3.75-3.69 (2H, m), 2.11-2.01 (1H, m), 1.87-1.63 (11H, m). LC/MS: 468 [M+H].

Example 78: (R)—N-(cis-4-((5-(2-chlorobenzoyl)-7H-pyrrolo[2,3-d]pyrimidin-4-yl)amino) cyclohexyl)tetrahydrofuran-2-carboxamide (I-101)

Acylation of Compound I-6 provided Compound I-101. $^1$H-NMR (DMSO-$d_6$) δ: 12.71 (1H, s), 8.95 (1H, d, J=7.3 Hz), 8.24 (1H, s), 7.63-7.54 (4H, m), 7.50-7.46 (2H, m), 4.30-4.19 (2H, m), 3.89-3.83 (1H, m), 3.75-3.69 (2H, m), 2.02-2.11 (1H, m), 1.87-1.63 (11H, m). LC/MS: 468 [M+H].

Example 79: N-(cis-4-((5-(2-chlorobenzoyl)-7H-pyrrolo[2,3-d]pyrimidin-4-yl)amino) cyclohexyl)-1-hydroxycyclopropane-1-carboxamide (I-102)

Acylation of Compound I-6 provided Compound I-102. $^1$H-NMR (DMSO-$d_6$) δ: 12.71 (1H, s), 8.98 (1H, d, J=7.3 Hz), 8.24 (1H, s), 7.62-7.54 (3H, m), 7.50-7.42 (3H, m), 6.29 (1H, s), 4.35-4.27 (1H, m), 3.80-3.71 (1H, m), 1.66-1.85 (8H, m), 1.01 (2H, q, J=3.9 Hz), 0.81 (2H, q, J=3.9 Hz). LC/MS: 454 [M+H].

Example 80: (S)—N-(cis-4-((5-(2-chlorobenzoyl)-7H-pyrrolo[2,3-d]pyrimidin-4-yl)amino) cyclohexyl)-2-hydroxy-N-methylpropanamide (I-106)

Acylation of Compound I-43 provided Compound I-106. $^1$H-NMR (DMSO-$d_6$) δ: 12.34 (1H, br s), 9.05 (1H, d, J=7.3 Hz), 8.22 (1H, s), 7.57-7.44 (4H, m), 7.34 (1H, s), 4.54-4.33 (3H, m), 2.86 (3H, s), 2.05-1.91 (5H, m), 1.80-1.70 (2H, m), 1.49-1.59 (2H, m), 1.20 (3H, d, J=6.1 Hz). LC/MS: 442 [M+H].

Example 81: (2-chlorophenyl)(4-((cis-4-(3-methoxyazetidin-1-yl)cyclohexyl)amino)-7H-pyrrolo[2,3-d]pyrimidin-5-yl)methanone (I-109)

Reductive amination of Compound I-36 and subsequent isomer separation provided Compound I-109. $^1$H-NMR (DMSO-$d_6$) δ: 12.69 (1H, s), 8.85 (1H, d, J=7.9 Hz), 8.22 (1H, s), 7.59-7.57 (3H, m), 7.49-7.45 (2H, m), 4.21 (1H, s), 3.95-3.90 (1H, m), 3.48 (2H, t, J=6.7 Hz), 3.14 (3H, s), 2.71 (2H, t, J=6.7 Hz), 2.14 (1H, s), 1.72-1.67 (4H, m), 1.56-1.46 (4H, m). LC/MS: 440 [M+H].

Example 82: (2-chlorophenyl)(4-((trans-4-(3-methoxyazetidin-1-yl)cyclohexyl)amino)-7H-pyrrolo[2,3-d]pyrimidin-5-yl)methanone (I-110)

Reductive amination of Compound I-36 and subsequent isomer separation provided Compound I-110. $^1$H-NMR (DMSO-$d_6$) δ: 12.69 (1H, br s), 8.72 (1H, d, J=7.3 Hz), 8.23 (1H, s), 7.59-7.55 (3H, m), 7.48-7.43 (2H, m), 4.04-3.99 (1H, m), 3.94-3.88 (1H, m), 3.49-3.43 (2H, m), 3.14 (3H, s), 2.76 (2H, t, J=6.7 Hz), 2.10-2.02 (3H, m), 1.79 (2H, d, J=10.4 Hz), 1.33-1.26 (2H, m), 1.12-1.05 (2H, m). LC/MS: 440 [M+H].

Example 83: (2-chlorophenyl)(4-((cis-4-(3-hydroxy-3-methylazetidin-1-yl)cyclohexyl) amino)-7H-pyrrolo[2,3-d]pyrimidin-5-yl)methanone (I-111)

Reductive amination of Compound I-36 and subsequent isomer separation provided Compound I-111. $^1$H-NMR (DMSO-$d_6$) δ: 12.69 (1H, s), 8.87 (1H, d, J=7.3 Hz), 8.22 (1H, s), 7.59-7.56 (3H, m), 7.49-7.45 (2H, m), 5.08 (1H, s), 4.24 (1H, s), 3.17-3.14 (2H, m), 2.81-2.78 (2H, m), 2.13 (1H, s), 1.79-1.76 (2H, m), 1.68-1.63 (2H, m), 1.55-1.53 (2H, m), 1.45-1.43 (2H, m), 1.33 (3H, s). LC/MS: 440 [M+H].

Example 84: (2-chlorophenyl)(4-((trans-4-(3-hydroxy-3-methylazetidin-1-yl)cyclohexyl) amino)-7H-pyrrolo[2,3-d]pyrimidin-5-yl)methanone (I-112)

Reductive amination of Compound I-36 and subsequent isomer separation provided Compound I-112. $^1$H-NMR (DMSO-$d_6$) δ: 12.68 (1H, br s), 8.70 (1H, d, J=7.3 Hz), 8.23 (1H, s), 7.59-7.54 (3H, m), 7.49-7.44 (2H, m), 5.09 (1H, s), 3.99 (1H, d, J=6.7 Hz), 3.16 (2H, d, J=7.3 Hz), 2.82 (2H, d, J=6.7 Hz), 2.09-2.05 (3H, m), 1.78 (2H, d, J=10.4 Hz), 1.34-1.23 (5H, m), 1.14-1.03 (2H, m). LC/MS: 440 [M+H].

Example 85: (4-((cis-4-(3-amino-3-methylazetidin-1-yl)cyclohexyl)amino)-7H-pyrrolo[2,3-d]pyrimidin-5-yl)(2-chlorophenyl)methanone (I-113)

Reductive amination of Compound I-36 with tert-butyl N-(3-methylazetidin-3-yl)carbamate and subsequent isomer separation, followed by Boc deprotection provided Compound I-113. $^1$H-NMR (DMSO-$d_6$) δ: 8.87 (1H, d, J=7.9 Hz), 8.21 (1H, s), 7.61-7.53 (3H, m), 7.49-7.44 (2H, m), 4.23 (1H, s), 3.10 (2H, d, J=7.3 Hz), 3.30-2.80 (2H, br m), 2.67 (2H, d, J=6.7 Hz), 2.11-2.09 (1H, m), 1.82-1.79 (2H, m), 1.67-1.41 (6H, m), 1.27 (3H, s). LC/MS: 439 [M+H].

Example 86: (4-((trans-4-(3-amino-3-methylazetidin-1-yl)cyclohexyl)amino)-7H-pyrrolo[2,3-d]pyrimidin-5-yl)(2-chlorophenyl)methanone (I-114)

Reductive amination of Compound I-36 with tert-butyl N-(3-methylazetidin-3-yl)carbamate and subsequent isomer separation, followed by Boc deprotection provided Compound I-114. $^1$H-NMR (DMSO-$d_6$) δ: 8.70 (1H, d, J=7.3 Hz), 8.22 (1H, s), 7.59-7.54 (3H, m), 7.48-7.43 (2H, m), 3.98-3.96 (1H, m), 3.11 (2H, d, J=7.3 Hz), 3.21-2.80 (2H, br m), 2.70 (2H, d, J=6.7 Hz), 2.11-1.99 (3H, m), 1.79-1.68 (2H, m), 1.33-1.23 (5H, m), 1.12-1.03 (2H, m). LC/MS: 439 [M+H].

Example 87: N-(cis-4-((5-(2-chlorobenzoyl)-7H-pyrrolo[2,3-d]pyrimidin-4-yl)amino) cyclohexyl)-2-hydroxy-2-methylpropanamide (I-115)

Acylation of Compound I-6 provided Compound I-115. $^1$H-NMR (DMSO-$d_6$) δ: 12.72 (1H, s), 8.96 (1H, d, J=7.3 Hz), 8.24 (1H, s), 7.62-7.53 (3H, m), 7.50-7.46 (2H, m), 7.29 (1H, d, J=7.3 Hz), 5.45 (1H, s), 4.31-4.25 (1H, m), 3.73-3.65 (1H, m), 1.59-1.84 (8H, m), 1.23 (6H, s). LC/MS: 456 [M+H].

Example 88: N—((S)-1-((2S,5R)-5-((5-(2-chlorobenzoyl)-7H-pyrrolo[2,3-d]pyrimidin-4-yl)amino)tetrahydro-2H-pyran-2-yl)ethyl)acetamide (I-116)

N—((S)-1-((2S,5R)-5-((5-(2-chlorobenzoyl)-7H-pyrrolo[2,3-d]pyrimidin-4-yl)amino) tetrahydro-2H-pyran-2-yl)ethyl)acetamide (I-116) was synthesized according to General Procedure A, Step 2 via halogen displacement using N-((1S)-1-((2S,5R)-5-aminotetrahydro-2H-pyran-2-yl)ethyl)acetamide. $^1$H-NMR (DMSO-d$_6$) δ: 12.53 (1H, s), 8.60 (1H, d, J=7.3 Hz), 8.25 (1H, s), 7.71 (1H, d, J=8.5 Hz), 7.61-7.54 (3H, m), 7.50-7.45 (2H, m), 4.25-4.10 (2H, m), 3.94-3.83 (1H, m), 3.31-3.28 (1H, m), 3.14-3.08 (1H, m), 2.20-2.16 (1H, m), 1.83 (3H, s), 1.70-1.42 (3H, m), 1.05 (3H, d, J=6.7 Hz). LC/MS: 442 [M+H].

Example 89: N—((S)-1-((2S,5R)-5-((5-(2-methylbenzoyl)-7H-pyrrolo[2,3-d]pyrimidin-4-yl)amino)tetrahydro-2H-pyran-2-yl)ethyl)acetamide (I-117)

N—((S)-1-((2S,5R)-5-((5-(2-methylbenzoyl)-7H-pyrrolo[2,3-d]pyrimidin-4-yl)amino) tetrahydro-2H-pyran-2-yl)ethyl)acetamide (I-117) was synthesized according to General Procedure A, Step 2 via halogen displacement using N-((1S)-1-((2S,5R)-5-aminotetrahydro-2H-pyran-2-yl)ethyl)acetamide. $^1$H-NMR (DMSO-d$_6$) δ: 8.75 (1H, d, J=6.7 Hz), 8.24 (1H, s), 7.70 (1H, d, J=9.2 Hz), 7.45-7.28 (5H, m), 4.23-4.13 (2H, m), 3.90-3.88 (1H, m), 3.31-3.29 (1H, m), 3.12-3.10 (1H, m), 2.27 (3H, s), 2.20-2.17 (1H, m), 1.84-1.82 (3H, m), 1.67-1.42 (3H, m), 1.05 (3H, d, J=6.7 Hz). LC/MS: 422 [M+H].

Example 90: N-(((2S,5R)-5-((5-(2-chlorobenzoyl)-7H-pyrrolo[2,3-d]pyrimidin-4-yl)amino)tetrahydro-2H-pyran-2-yl)methyl)acetamide (I-118)

N-(((2S,5R)-5-((5-(2-chlorobenzoyl)-7H-pyrrolo[2,3-d]pyrimidin-4-yl)amino)tetrahydro-2H-pyran-2-yl)methyl)acetamide (I-118) was synthesized according to General Procedure A, Step 2 via halogen displacement using N-(((2S,5R)-5-aminotetrahydro-2H-pyran-2-yl)methyl)acetamide. $^1$H-NMR (DMSO-d$_6$) δ: 12.75 (1H, s), 8.60 (1H, d, J=7.3 Hz), 8.26 (1H, s), 7.95 (1H, t, J=5.8 Hz), 7.61-7.45 (5H, m), 4.16-4.13 (2H, m), 3.39-3.37 (1H, m), 3.21-3.05 (3H, m), 2.19-2.16 (1H, m), 1.83 (3H, s), 1.78-1.74 (1H, m), 1.60-1.57 (1H, m), 1.44-1.35 (1H, m). LC/MS: 428 [M+H].

Example 91: N-(((2S,5R)-5-((5-(2-methylbenzoyl)-7H-pyrrolo[2,3-d]pyrimidin-4-yl)amino)tetrahydro-2H-pyran-2-yl)methyl)acetamide (I-119)

N-(((2S,5R)-5-((5-(2-methylbenzoyl)-7H-pyrrolo[2,3-d]pyrimidin-4-yl)amino)tetrahydro-2H-pyran-2-yl)methyl)acetamide (I-119) was synthesized according to General Procedure A, Step 2 via halogen displacement using N-(((2S,5R)-5-aminotetrahydro-2H-pyran-2-yl)methyl)acetamide. $^1$H-NMR (DMSO-d$_6$) δ: 8.75 (1H, d, J=6.7 Hz), 8.24 (1H, s), 7.95 (1H, t, J=5.8 Hz), 7.45-7.28 (5H, m), 4.18-4.17 (2H, m), 3.21-3.05 (4H, m), 2.27 (3H, s), 2.19-2.16 (1H, m), 1.83 (3H, s), 1.77-1.74 (1H, m), 1.62-1.54 (1H, m), 1.42-1.36 (1H, m). LC/MS: 408 [M+H].

Example 92: N-(3-(4-((cis-4-aminocyclohexyl)amino)-7H-pyrrolo[2,3-d]pyrimidine-5-carbonyl)phenyl)methanesulfonamide (I-120)

Step 1: (4-chloro-7H-pyrrolo[2,3-d]pyrimidin-5-yl)-(3-nitrophenyl)methanone (120a)

(4-chloro-7H-pyrrolo[2,3-d]pyrimidin-5-yl)-(3-nitrophenyl)methanone (120a) was synthesized according to General Procedure A, Step 1. $^1$H-NMR (DMSO-D$_6$) δ: 13.45 (1H, s), 8.77 (1H, s), 8.56 (1H, s), 8.52 (1H, d, J=7.6 Hz), 8.33 (1H, s), 8.29 (1H, d, J=7.6 Hz), 7.86 (1H, t, J=7.6 Hz).

Step 2: tert-butyl N-(cis-4-((5-(3-nitrobenzoyl)-7H-pyrrolo[2,3-d]pyrimidin-4-yl)amino)-cyclohexyl)-carbamate (120b)

tert-butyl N-(cis-4-((5-(3-nitrobenzoyl)-7H-pyrrolo[2,3-d]pyrimidin-4-yl)amino)-cyclohexyl)-carbamate (120b) was synthesized according to General Procedure A, Step 2 via halogen displacement using tert-butyl (cis-4-aminocyclohexyl)carbamate. LC/MS: 481 [M+H].

Step 3: tert-butyl N-(cis-4-((5-(3-aminobenzoyl)-7H-pyrrolo[2,3-d]pyrimidin-4-yl)amino)-cyclohexyl)carbamate (120c)

Reduction of the nitro group using Palladium on Carbon (Pd/C) and ammonium formate provided tert-butyl N-(cis-4-((5-(3-aminobenzoyl)-7H-pyrrolo[2,3-d]pyrimidin-4-yl)amino)-cyclohexyl)carbamate (120c). LC/MS: 451 [M+H].

Step 4. N-(3-(4-((cis-4-aminocyclohexyl)amino)-7H-pyrrolo[2,3-d]pyrimidine-5-carbonyl)phenyl)methanesulfonamide (I-120)

Sulfonylation of 120c followed by a Boc deprotection of Boc provided Compound I-120. $^1$H-NMR (DMSO-d$_6$) δ: 10.13 (1H, s), 8.40 (1H, s), 8.16-7.98 (4H, m), 7.70-7.42 (3H, m), 4.29 (1H, br s), 3.25 (1H, br s), 3.10 (3H, s), 2.33-2.23 (8H, m). LC/MS: 429 [M+H].

Example 93: N-(3-(4-((cis-4-aminocyclohexyl)amino)-7H-pyrrolo[2,3-d]pyrimidine-5-carbonyl)phenyl)benzenesulfonamide (I-121)

Phenylsulfonylation of tert-butyl N-(cis-4-((5-(3-aminobenzoyl)-7H-pyrrolo[2,3-d]pyrimidin-4-yl)amino)-cyclohexyl)carbamate followed by Boc deprotection provided Compound I-121. $^1$H-NMR (DMSO-d$_6$) δ: 10.74 (1H, s), 8.40 (1H, s), 8.15-8.02 (3H, br m), 7.86-7.40 (10H, m), 4.27 (1H, br s), 3.24 (1H, br s), 2.05-1.68 (8H, m). LC/MS: 491 [M+H].

Example 93: Intermediate methyl 2-chloro-4-phenoxybenzoate (4-1)

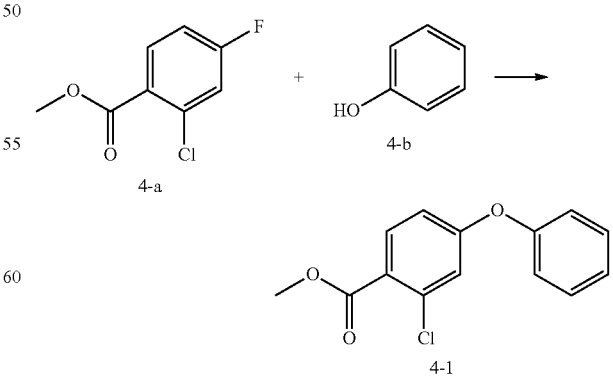

To a stirred solution of methyl 2-chloro-4-fluorobenzoate (4-a, 7.35 g, 39.0 mmol) and phenol (4-b, 4.40 g, 46.8 mmol)

in DMF (100 mL) was added Cs₂CO₃ (19.0 g, 58.5 mmol) at room temperature. The reaction mixture was stirred at 90° C. for 3 h and then extracted with Et₂O. The extract was washed with water and brine, dried over Na₂SO₄, and concentrated under reduced pressure. The residue was purified by column chromatography over SiO₂ with n-hexane-EtOAc to give methyl 2-chloro-4-phenoxybenzoate (4-1, 9.58 g, 94%) as a colorless oil. ¹H-NMR (400 MHz, CDCl₃) δ: 7.87 (1H, d, J=8.5 Hz), 7.43-7.39 (2H, m), 7.22 (1H, t, J=7.3 Hz), 7.07-7.05 (2H, m), 7.01 (1H, d, J=2.4 Hz), 6.88 (1H, dd, J=8.5, 2.4 Hz), 3.91 (3H, s). LC/MS: 263 [M+H].

Example 94: Intermediate N-((1S)-1-((2S,5R)-5-aminotetrahydro-2H-pyran-2-yl)ethyl)-acetamide hydrochloride (5-1)

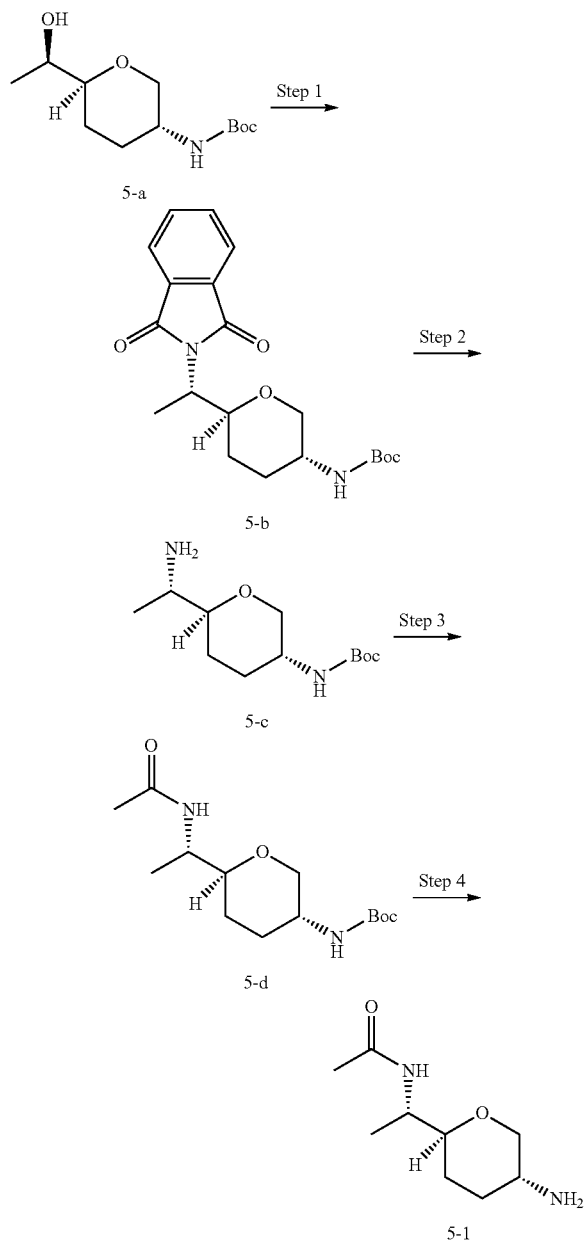

Step 1. tert-butyl N-((3R,6S)-6-((1S)-1-(1,3-dioxoisoindolin-2-yl)-ethyl)tetrahydro-2H-pyran-3-yl)carbamate (5-b)

To a stirred solution of tert-butyl N-((3R,6S)-6-((1R)-1-hydroxyethyl) tetrahydro-pyran-3-yl)carbamate (5-a, 9.96 g, 40.6 mmol), phthalimide (7.19 g, 48.7 mmol), and PPh₃ (12.77 g, 48.7 mmol) in THF (100 mL) was added dropwise diethyl azodicarboxylate (2.2M in toluene, 22.1 mL, 48.7 mmol) at 0° C. The resulting mixture was stirred for 3 h at room temperature and under reduced pressure. Addition of Et₂O to the mixture gave a precipitate which was removed by filtration. The filtrate was concentrated under reduced pressure and the resulting residue was purified by column chromatography over SiO₂ eluting with n-hexane-EtOAc to provide tert-butyl N-((3R,6S)-6-((1S)-1-(1,3-dioxoisoindolin-2-yl)ethyl)tetrahydro-2H-pyran-3-yl)-carbamate (5-b, 13.82 g, 91%). ¹H-NMR (400 MHz, CDCl₃) δ: 7.87-7.77 (2H, m), 7.72-7.68 (2H, m), 4.30-4.19 (2H, m), 3.92-3.87 (2H, m), 3.59-3.57 (1H, m), 2.88 (1H, t, J=10.4 Hz), 2.17-2.15 (1H, m), 1.94-1.91 (1H, m), 1.46-1.29 (14H, m). LC/MS: 375 [M+H].

Step 2. tert-butyl N-((3R,6S)-6-((1S)-1-aminoethyl)tetrahydro-2H-pyran-3-yl)carbamate (5-c)

The mixture of tert-butyl N-((3R,6S)-6-((1S)-1-(1,3-dioxoisoindolin-2-yl)ethyl)-tetrahydro-2H-pyran-3-yl)carbamate (5-b, 13.82 g, 36.9 mmol) and hydrazine monohydrate (5.4 mL, 110.7 mmol) in EtOH (200 mL) was stirred under reflux for 3 h and then cooled to room temperature. After the resulting solid was removed by filtration, the filtrate was concentrated under reduced pressure. To the resulting residue was added EtOAc and the resulting solid was again removed. This was repeated until no precipitate came out of the solution. Concentration under reduced pressure provided tert-butyl N-((3R,6S)-6-((1S)-1-aminoethyl)tetrahydro-2H-pyran-3-yl)carbamate (5-c, 7.54 g, 83%) which was used in the next step without further purification. LC/MS: 245 [M+H].

Step 3. tert-butyl N-((3R,6S)-6-((1S)-1-acetamidoethyl)-tetrahydro-pyran-3-yl)carbamate (5-d)

To a stirred solution of tert-butyl N-((3R,6S)-6-((1S)-1-aminoethyl)-tetrahydro-2H-pyran-3-yl)-carbamate (5-c, 7.54 g, 30.9 mmol) and Et₃N (8.6 mL, 61.7 mmol) in DMF (30 mL) was added acetic anhydride (Ac₂O, 4.3 mL, 46.3 mL) at room temperature. After stirring for 1 h at room temperature, the reaction mixture was quenched with saturated aqueous NaHCO₃ and then concentration in vacuo. The resulting residue was extracted with CH₂C₁₂, washed with H₂O, dried over Na₂SO₄, filtered, and concentrated under reduced pressure. The resulting residue was purified by column chromatography over SiO₂ and eluting with n-hexane-EtOAc to provide tert-butyl N-((3R,6S)-6-((1S)-1-acetamidoethyl)-tetrahydro-pyran-3-yl)carbamate (5-d) which was used in the next step without further purification. ¹H-NMR (CDCl₃) δ: 5.77-5.74 (1H, m), 4.28 (1H, d, J=7.9 Hz), 4.10-4.07 (1H, m), 4.03-3.96 (1H, m), 3.61-3.52 (1H, m), 3.19 (1H, d, J=11.0 Hz), 2.98-2.96 (1H, m), 2.08-2.06 (1H, m), 1.99 (3H, s), 1.64-1.24 (12H, m), 1.18 (3H, d, J=6.7 Hz). LC/MS: 287 [M+H].

Step 4. N-((1S)-1-((2S,5R)-5-aminotetrahydro-2H-pyran-2-yl)ethyl)-acetamide hydrochloride (5-1)

To a stirred solution of tert-butyl N-((3R,6S)-6-((1S)-1-acetamidoethyl)-tetra-hydro-2H-pyran-3-yl)carbamate (5-d, 30.9 mmol) in DCM (40 mL) was added 4N HCl in dioxane (40 mL) at room temperature and the reaction mixture was stirred at room temperature for 1 h. The resulting mixture was concentrated in vacuo. The resulting solid was washed with EtOAc under sonication and then collected by filtration to give N-((1S)-1-((2S,5R)-5-aminotetrahydro-2H-pyran-2-yl)ethyl)acetamide hydrochloride (5-1, 6.87 g, over 2 steps) as a colorless solid. LC/MS: 187 [M+H].

Example 95: N—((S)-1-((2S,5R)-5-((5-(2-chloro-4-phenoxybenzoyl)-7H-pyrrolo[2,3-d]pyrimidin-4-yl)amino)tetrahydro-2H-pyran-2-yl)ethyl)acetamide (I-122)

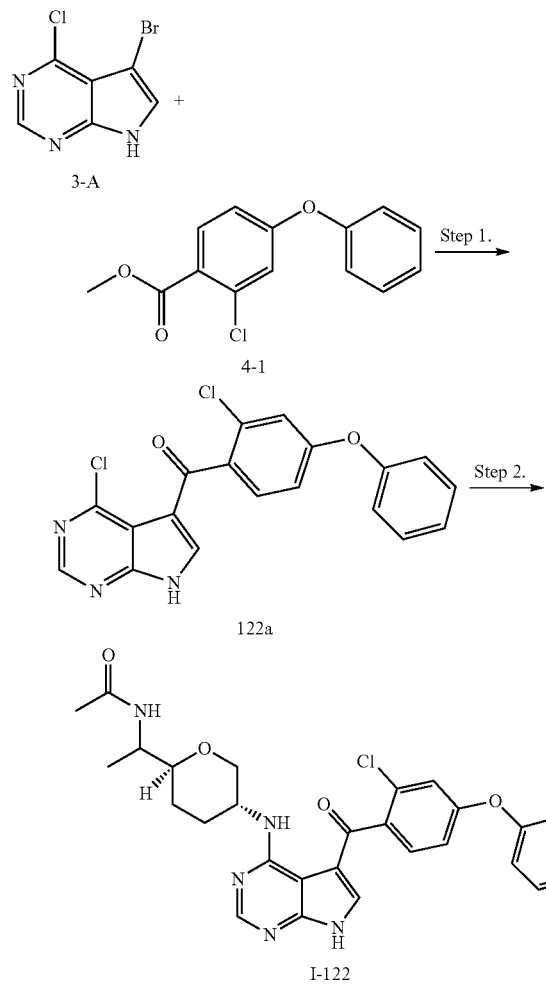

Step 1. (2-chloro-4-phenoxy-phenyl)-(4-chloro-7H-pyrrolo-[2,3-d]pyrimidin-5-yl)methanone (122a)

To a stirred solution of 3-bromo-4-chloro-7H-pyrrolo[2,3-d]pyrimidine (3-A, 6.90 g, 29.7 mmol) in THF (200 mL) was added dropwise n-BuLi (2.69M in hexane, 23.2 mL, 62.3 mmol) at −78° C. under an atmosphere of nitrogen (N$_2$). The reaction mixture was stirred at −78° C. for 50 min and methyl 2-chloro-4-phenoxybenzoate (4-1, 8.19 g, 31.2 mmol) was then added at the same temperature. After stirring at −78° C. for 50 min, the reaction mixture was quenched with 1N HCl (65 mL), warmed to room temperature, and extracted with EtOAc. The extract was washed with brine, dried over Na$_2$SO$_4$, filtered, and concentrated under reduced pressure. The resulting residue was purified by column chromatography over SiO$_2$ eluting with n-hexane-EtOAc to give (2-chloro-4-phenoxy-phenyl)-(4-chloro-7H-pyrrolo[2,3-d]pyrimidin-5-yl)methanone (122a, 4.73 g, 41%) as a colorless solid. $^1$H-NMR (400 MHz, CDCl$_3$/CD$_3$OD=9/1) δ: 8.69 (1H, d, J=1.8 Hz), 7.71 (1H, d, J=1.8 Hz), 7.50 (1H, dd, J=8.5, 1.8 Hz), 7.46-7.41 (2H, m), 7.27-7.21 (1H, m), 7.13-7.09 (2H, m), 7.07-7.05 (1H, m), 6.96-6.93 (1H, m), 3.40 (1H, br s). LC/MS: 386 [M+H, $^{35}$Cl+$^{35}$Cl], 384 [M+H, $^{35}$Cl+$^{37}$Cl].

Step 2. N—((S)-1-((2S,5R)-5-((5-(2-chloro-4-phenoxybenzoyl)-7H-pyrrolo[2,3-d]pyrimidin-4-yl)amino)tetrahydro-2H-pyran-2-yl)ethyl)acetamide (I-122)

The mixture of (2-chloro-4-phenoxy-phenyl)-(4-chloro-7H-pyrrolo[2,3-d]pyrimidin-5-yl)-methanone (122a, 1.0 g, 2.60 mmol), N-((1S)-1-((2S,5R)-5-aminotetrahydro-2H-pyran-2-yl)ethyl)acetamide hydrochloride (5-1, 638 mg, 2.86 mmol), and DIPEA (1.359 mL, 7.80 mmol) in IPA (10 mL) was stirred at 160° C. for 1 h under microwave irradiation and the resulting mixture was concentrated under reduced pressure. The resulting residue was purified by column chromatography over NH$_2$—SiO$_2$ eluting with CH$_2$Cl$_2$-MeOH to give N—((S)-1-((2S,5R)-5-((5-(2-chloro-4-phenoxybenzoyl)-7H-pyrrolo[2,3-d]pyrimidin-4-yl)amino)tetrahydro-2H-pyran-2-yl)ethyl)acetamide (I-122, 638 mg, 2.86 mmol) as a colorless solid. $^1$H-NMR (DMSO-d$_6$) δ: 12.76 (1H, s), 8.58 (1H, d, J=7.3 Hz), 8.25 (1H, s), 7.70 (1H, d, J=8.5 Hz), 7.64 (1H, s), 7.57 (1H, d, J=7.9 Hz), 7.49-7.47 (2H, m), 7.27-7.25 (1H, m), 7.19-7.18 (3H, m), 7.03-7.01 (1H, m), 4.21-4.14 (2H, m), 3.90-3.88 (1H, m), 3.31-3.30 (1H, m), 3.12-3.09 (1H, m), 2.19-2.16 (1H, m), 1.83 (3H, s), 1.68-1.42 (3H, m), 1.05 (3H, d, J=6.7 Hz). LC/MS: 536 [M+H, $^{37}$Cl], 534 [M+H, $^{35}$Cl].

Example 96: (2-chloro-4-phenoxyphenyl)(4-(((3R,6S)-6-(hydroxymethyl)tetrahydro-2H-pyran-3-yl)amino)-7H-pyrrolo[2,3-d]pyrimidin-5-yl)methanone (I-123)

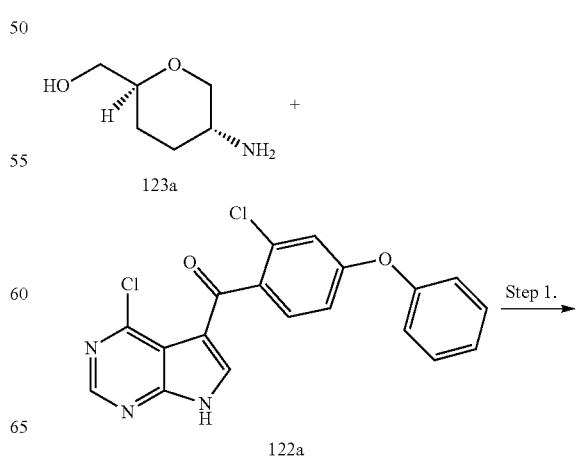

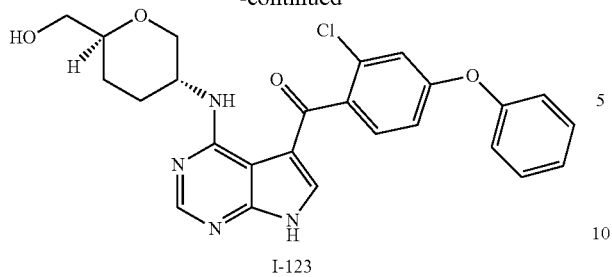

I-123

The mixture of (2-chloro-4-phenoxy-phenyl)-(4-chloro-7H-pyrrolo[2,3-d]-pyrimidin-5-yl)methanone (122a, 200 mg, 0.52 mmol), ((2S,5R)-5-aminotetrahydro-2H-pyran-2-yl)-methanol (123a, 72 mg, 0.54 mmol), and DIPEA (272 µL, 1.56 mmol) in IPA (4 mL) was stirred at 160° C. for 1 h under microwave irradiation and then concentrated under reduced pressure. The resulting residue was purified by column chromatography over $NH_2$—$SiO_2$ eluting with $CH_2C_{12}$-MeOH to give (2-chloro-4-phenoxyphenyl)(4-(((3R,6S)-6-(hydroxymethyl)tetrahydro-2H-pyran-3-yl) amino)-7H-pyrrolo[2,3-d]pyrimidin-5-yl)methanone (I-123, 175 mg, 70%) as a colorless solid. $^1$H NMR (400 MHz, DMSO-$d_6$) δ: 12.75 (1H, brs), 8.60 (1H, d, J=6.7 Hz), 8.25 (1H, d, J=1.8 Hz), 7.64 (1H, d, J=1.8 Hz), 7.49-7.48 (2H, m), 7.27-7.25 (1H, m), 7.20-7.18 (3H, m), 7.04-7.01 (1H, m), 4.68-4.67 (1H, m), 4.17-4.15 (2H, m), 3.43-3.32 (3H, m), 3.14-3.11 (1H, m), 2.21-2.18 (1H, m), 1.80-1.77 (1H, m), 1.58-1.55 (1H, m), 1.41-1.38 (1H, m). LC/MS: 481 [M+H, $^{37}$Cl], 479 [M+H, $^{35}$Cl].

Example 97: Intermediate-N-(((2S,5R)-5-aminotetrahydro-2H-pyran-2-yl)methyl)acetamide hydrochloride (6-1)

Step 1. tert-butyl N-((3R,6S)-6-((1,3-dioxoisoindolin-2-yl)methyl)-tetrahydro-2H-pyran-3-yl)carbamate (6-b)

tert-butyl N-((3R,6S)-6-((1,3-dioxoisoindolin-2-yl)methyl)tetrahydro-2H-pyran-3-yl)carbamate (6-b, 2.5 g, 81%) was synthesized according to the procedure described above for Step 1 in Example 94 from tert-butyl N-((3R,6S)-6-(hydroxymethyl)tetrahydro-2H-pyran-3-yl)carbamate (6-a, 2.0 g, 8.6 mmol). LC/MS: 305 [M-tBu+2H].

Step 2. tert-butyl N-((3R,6S)-6-(aminomethyl)tetrahydro-2H-pyran-3-yl)carbamate (6-c)

tert-butyl N-((3R,6S)-6-(aminomethyl)tetrahydro-2H-pyran-3-yl)carbamate (6-c, 1.6 g, quantitative) was synthesized according to the procedure described above for Step 2 in Example 94 from tert-butyl N-((3R,6S)-6-((1,3-dioxoisoindolin-2-yl)methyl)tetrahydro-2H-pyran-3-yl)carbamate (6-b, 2.5 g, 7.0 mmol). LC/MS: 231 [M+H].

Step 3. tert-butyl N-((3R,6S)-6-(acetamidomethyl)tetrahydro-2H-pyran-3-yl)carbamate (6-d)

tert-butyl N-((3R,6S)-6-(acetamidomethyl)tetrahydro-2H-pyran-3-yl)carbamate (845 mg, 44%) was synthesized according to the procedure described above for Step 3 in Example 94 from tert-butyl N-((3R,6S)-6-(aminomethyl)-tetrahydro-2H-pyran-3-yl)carbamate (1.6 g, 7.0 mmol). $^1$H-NMR (CDCl$_3$) δ: 5.90 (1H, br s), 4.26 (1H, br s), 4.08-4.06 (1H, m), 3.61-3.58 (2H, m), 3.33-3.31 (1H, m), 3.01-2.98 (2H, m), 2.08-2.05 (1H, m), 1.99 (3H, s), 1.44-1.19 (13H, m). LC/MS: 273 [M+H].

Step 4. N-(((2S,5R)-5-aminotetrahydro-2H-pyran-2-yl)methyl)acetamide hydrochloride (6-1)

N-(((2S,5R)-5-aminotetrahydro-2H-pyran-2-yl)methyl) acetamide hydrochloride (607 mg, 98%) was synthesized according to the procedure described above for Step 4 in Example 94 from tert-butyl N-((3R,6S)-6-(acetamidomethyl)tetrahydro-2H-pyran-3-yl)carbamate (845 mg, 3.1 mmol). $^1$H-NMR (DMSO-$d_6$) δ: 8.30 (3H, br s), 8.00 (1H, t, J=5.5 Hz), 4.03-4.00 (1H, m), 3.28-3.24 (2H, m), 3.13-

2.99 (3H, m), 2.08-2.05 (1H, m), 1.82-1.78 (3H, m), 1.70-1.66 (1H, m), 1.57-1.51 (1H, m), 1.26-1.17 (1H, m). LC/MS: 173 [M+H].

Example 98: N-(((2S,5R)-5-((5-(2-chloro-4-phenoxybenzoyl)-7H-pyrrolo[2,3-d]pyrimidin-4-yl)amino)tetrahydro-2H-pyran-2-yl)methyl)acetamide (I-127)

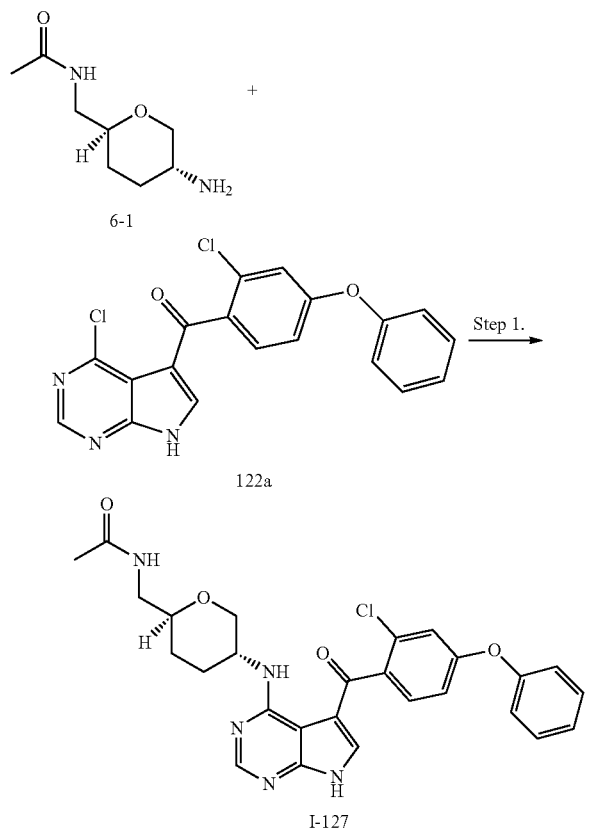

N-(((2S,5R)-5-((5-(2-chloro-4-phenoxybenzoyl)-7H-pyrrolo[2,3-d]pyrimidin-4-yl)amino)tetrahydro-2H-pyran-2-yl)methyl)acetamide (I-127, 88 mg, 61%) was synthesized according to the procedure described herein above for Example 96 from N-(((2S,5R)-5-aminotetrahydro-2H-pyran-2-yl)methyl)acetamide hydrochloride (6-1, 100 mg, 0.26 mmol). $^1$H-NMR (DMSO-$d_6$) δ: 12.63 (1H, br s), 8.59 (1H, d, J=6.7 Hz), 8.26 (1H, s), 7.95 (1H, t, J=5.8 Hz), 7.64 (1H, s), 7.58 (1H, d, J=8.5 Hz), 7.51-7.45 (2H, m), 7.27-7.25 (1H, m), 7.19-7.18 (3H, m), 7.02 (1H, dd, J=8.5, 2.4 Hz), 4.20-4.10 (2H, m), 3.22-3.04 (4H, m), 2.21-2.12 (1H, m), 1.85-1.73 (4H, m), 1.64-1.50 (1H, m), 1.45-1.33 (1H, m). LC/MS: 522 [M+H, $^{37}$Cl], 520 [M+H, $^{35}$Cl].

Example 99: General Procedure B

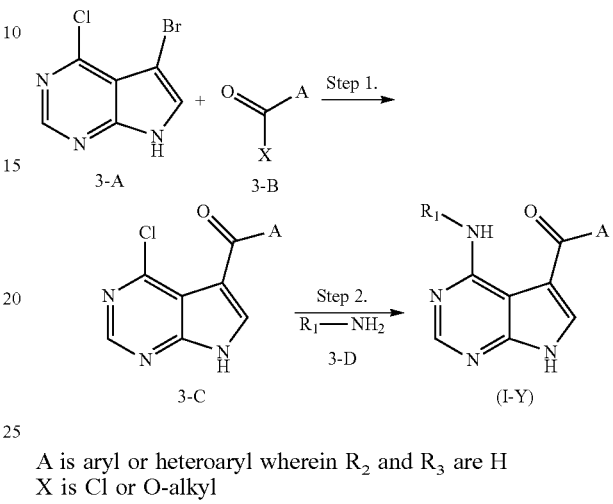

A is aryl or heteroaryl wherein $R_2$ and $R_3$ are H
X is Cl or O-alkyl

Step 1. Intermediate 3-C

To a stirred solution of 3-bromo-4-chloro-7H-pyrrolo[2,3-d]pyrimidine (3-A) in THF was added n-BuLi solution (in hexane, 2-3 eq.) dropwise at −78° C. and under inert atmosphere. The reaction mixture was stirred at −78° C. for 0.5-2 hrs and an ester or acid chloride (3-B, 1-2 eq.) was then added at −78° C. After stirring at −78° C. for 0.5-2 hrs, the reaction mixture was quenched with 1N HCl aqueous. Work-up and/or purification provided the corresponding aryl- or heteroaryl-(4-chloro-7H-pyrrolo[2,3-d]pyrimidin-5-yl)methanone (3-C).

Step 2. Compounds of Formula I-Y

A mixture of 3-C, a primary amine (3-D, 1-4 eq.), and optionally a base (e.g., TEA, DIPEA, pyridine, and/or $K_2CO_3$ (1-5 eq.)) in a solvent (e.g., DMF, NMP, IPA, n-BuOH or neat) was heated (70-160° C.) for 5-50 hrs or heated (100-220° C.) under microwave radiation for 0.5-5 hrs. Work-up and/or purification provided a compound of Formula (I) (aryl- or heteroaryl-[4-(substituted-amino)]-7H-pyrrolo[2,3-d]pyrimidin-5-yl]methanone (I-Y)).

The compounds of Formula (I) in Table 2 below were made according to General Procedure B using the applicable aryl or heteroaryl ester or acid chloride and amine.

TABLE 2

| Cmpd No. | $^1$H NMR and/or LC/MS data |
|---|---|
| I-124 | $^1$H NMR (300 MHz, DMSO-$d_6$) δ: 12.71 (1H, brs), 8.57 (1H, d, J = 6.9 Hz), 8.23 (1H, s,), 7.61 (1H, s), 7.55 (1H, d, J = 8.4 Hz), 7.46 (2H, t, J = 8.0 Hz), 7.30-7.00 (4H, m), 6.99 (1H, dd, J = 8.7, 2.1 Hz), 4.70-4.60 (1H, m), 4.20-3.90 (2H, m), 3.45-3.30 (1H, m), 3.10 (1H, t, J = 11.6 Hz), 2.16 (1H, d, J = 10.5 Hz), 1.76 (1H, d, J = 12.6 Hz), 1.65-1.45 (1H, m), 1.45-1.25 (1H, m), 1.20-1.05 (1H, m), 1.05-0.90 (1H, m). LC/MS: 481 [M + H, $^{37}$Cl], 479 [M + H, $^{35}$Cl]. |
| I-125 | $^1$H NMR (300 MHz, DMSO-$d_6$) δ: 12.63 (1H, br s), 9.19 (1H, d, J = 8.1 Hz), 8.20 (1H, s), 7.60-7.55 (2H, m), 7.46 (2H, t, J = 8.0 Hz), 7.26-7.10 (4H, m), 7.01 (1H, dd, J = 8.7, 2.4 Hz), 4.65-4.60 (1H, m), 4.35-4.25 (1H, m), 4.05-3.85 (1H, m), 3.62 (1H, d, J = 10.5 Hz), 3.60-3.25 (3H, m), 1.95-1.80 (2H, m), 1.65-1.50 (2H, m). LC/MS: 481 [M + H, $^{37}$Cl], 479 [M + H, $^{35}$Cl]. |

TABLE 2-continued

| Cmpd No. | ¹H NMR and/or LC/MS data |
|---|---|
| I-126 | ¹H NMR (300 MHz, DMSO-$d_6$) δ: 12.69 (1H, br s), 9.19 (1H, d, J = 7.8 Hz), 8.21 (1H, s), 7.62-7.54 (2H, m), 7.46 (2H, t, J = 8.0 Hz), 7.26-7.01 (4H, m), 7.01 (1H, dd, J = 8.4, 2.4 Hz), 4.64-4.60 (1H, m), 4.31 (1H, d, J = 7.5 Hz), 3.91 (1H, d, J = 11.7 Hz), 3.62 (1H, d, J = 10.2 Hz), 3.47-3.25 (3H, m), 2.01-1.75 (2H, m), 1.65-1.45 (2H, m). LC/MS: 481 [M + H, $^{37}$Cl], 479 [M + H, $^{35}$Cl]. |
| I-129 | ¹H-NMR (DMSO-$d_6$) δ: 12.61 (1H, s), 8.89 (0.65H, d, J = 7.9 Hz), 8.43 (0.35H, d, J = 7.3 Hz), 8.20 (0.65H, s), 8.21 (0.35H, s), 7.98 (0.35H, s), 8.01 (0.65H, s), 7.82-7.84 (1H, m), 7.14-7.15 (1H, m), 4.38-4.39 (0.65H, m), 3.96-4.00 (0.35H, m), 2.43 (1.05H, s), 2.45 (1.95H, s), 2.06-2.09 (0.65H, m), 1.03-1.81 (8.35H, m), 0.84-0.95 (3H, m). LC/MS: 355 [M + H]. (diastereo mixture: 65/35) |
| I-130 | ¹H-NMR (DMSO-$d_6$) δ: 8.36 (1H, s), 8.06-8.01 (4H, m), 7.89 (2H, d, J = 7.9 Hz), 7.49 (2H, t, J = 7.6 Hz), 7.27 (1H, t, J = 7.0 Hz), 7.17 (2H, d, J = 7.9 Hz), 7.12 (2H, d, J = 7.9 Hz), 4.27-4.23 (1H, m), 3.24-3.18 (1H, m), 2.00-1.71 (8H, m). LC/MS: 428 [M + H]. |
| I-131 | ¹H-NMR (DMSO-$d_6$) δ: 8.37 (1H, s), 8.10-8.02 (4H, m), 7.60-7.58 (2H, m), 7.47-7.43 (2H, m), 7.35-7.32 (2H, m), 7.21 (1H, t, J = 7.3 Hz), 7.13 (2H, d, J = 7.9 Hz), 4.27-4.25 (1H, m), 3.23-3.20 (1H, m), 1.98-1.69 (8H, m). LC/MS: 428 [M + H]. |
| I-133 | ¹H-NMR (DMSO-$d_6$) δ: 12.62 (1H, s), 8.95 (1H, d, J = 7.3 Hz), 8.21 (1H, s), 7.76 (1H, s), 7.46 (1H, t, J = 7.9 Hz), 7.36 (1H, d, J = 7.9 Hz), 7.29 (1H, s), 7.21 (1H, d, J = 7.3 Hz), 6.96-6.93 (1H, m), 4.23-4.19 (1H, m), 3.83 (3H, m), 3.45-3.37 (1H, m), 1.88-1.80 (2H, m), 1.73-1.59 (6H, m), 1.38 (9H, s). LC/MS: 466 [M + H]. |
| I-134 | ¹H-NMR (DMSO-$d_6$) δ: 12.57 (1H, s), 9.03 (1H, d, J = 7.3 Hz), 8.21 (1H, s), 7.41 (1H, s), 7.24 (1H, d, J = 8.5 Hz), 7.01-6.95 (3H, m), 4.24-4.20 (1H, m), 3.76 (3H, s), 3.44-3.40 (1H, m), 2.19 (3H, s), 1.86-1.79 (2H, m), 1.74-1.59 (6H, m), 1.38 (9H, s). LC/MS: 480 [M + H]. |
| I-142 | ¹H-NMR (DMSO-$d_6$) δ: 12.67 (1H, s), 8.65 (1H, d, J = 7.3 Hz), 8.23 (1H, s), 7.85-7.80 (3H, m), 7.50-7.46 (2H, m), 7.25 (1H, t, J = 7.3 Hz), 7.17-7.14 (2H, m), 7.10-7.07 (2H, m), 4.59 (1H, d, J = 5.5 Hz), 4.17-4.12 (2H, m), 3.53-3.45 (1H, m), 3.11-3.04 (2H, m), 2.20-2.16 (1H, m), 1.94-1.89 (1H, m), 1.57-1.35 (2H, m), 1.08 (3H, d, J = 6.1 Hz). LC/MS: 459 [M + H]. |
| I-146 | ¹H-NMR (DMSO-$d_6$) δ: 12.67 (1H, br s), 8.66 (1H, d, J = 7.3 Hz), 8.24 (1H, s), 7.86-7.80 (3H, m), 7.51-7.45 (2H, m), 7.28-7.23 (1H, m), 7.18-7.14 (2H, m), 7.11-7.06 (2H, m), 4.66 (1H, t, J = 5.8 Hz), 4.18-4.09 (2H, m), 3.45-3.35 (2H, m), 3.10 (1H, t, J = 11.3 Hz), 2.20-2.13 (1H, m), 1.81-1.74 (1H, m), 1.62-1.50 (1H, m), 1.44-1.31 (1H, m). LC/MS: 445 [M + H]. |
| I-147 | ¹H-NMR (CDCl$_3$) δ: 8.80 (1H, d, J = 7.3 Hz), 8.37 (1H, s), 7.80 (2H, d, J = 8.5 Hz), 7.58 (1H, s), 7.42 (2H, t, J = 8.2 Hz), 7.25-7.19 (1H, m), 7.13-7.06 (4H, m), 4.42-4.28 (2H, m), 3.27 (1H, t, J = 10.4 Hz), 3.21-3.15 (1H, m), 2.55 (1H, br s), 2.38-2.31 (1H, m), 1.84-1.51 (4H, m), 1.21 (6H, d, J = 10.4 Hz). LC/MS: 473 [M + H]. |
| I-149 | ¹H-NMR (DMSO-$d_6$) δ: 12.70 (1H, s), 8.65 (1H, d, J = 7.3 Hz), 8.50 (1H, d, J = 3.1 Hz), 8.48-8.46 (1H, m), 8.24 (1H, s), 7.87-7.82 (3H, m), 7.64-7.61 (1H, m), 7.51 (1H, dd, J = 8.2, 4.6 Hz), 7.16 (2H, d, J = 8.5 Hz), 4.60 (1H, d, J = 4.9 Hz), 4.17-4.11 (2H, m), 3.52-3.46 (1H, m), 3.11-3.04 (2H, m), 2.20-2.15 (1H, m), 1.94-1.90 (1H, m), 1.58-1.48 (1H, m), 1.45-1.35 (1H, m), 1.08 (3H, d, J = 6.7 Hz). LC/MS: 460 [M + H]. |
| I-150 | ¹H-NMR (DMSO-$d_6$) δ: 12.76 (1H, s), 8.58 (1H, d, J = 7.3 Hz), 8.25 (1H, s), 7.64 (1H, s), 7.58 (1H, d, J = 8.5 Hz), 7.51-7.46 (2H, m), 7.28-7.24 (1H, m), 7.20-7.17 (3H, m), 7.02 (1H, dd, J = 8.2, 2.1 Hz), 4.60 (1H, d, J = 5.5 Hz), 4.19-4.10 (2H, m), 3.51-3.46 (1H, m), 3.13-3.06 (2H, m), 2.22-2.17 (1H, m), 1.95-1.90 (1H, m), 1.59-1.50 (1H, m), 1.46-1.36 (1H, m), 1.08 (3H, d, J = 6.7 Hz). LC/MS: 493 [M + H]. |
| I-151 | ¹H-NMR (DMSO-$d_6$) δ: 12.72 (1H, s), 8.92 (1H, d, J = 7.3 Hz), 8.23 (1H, s), 7.90 (1H, d, J = 7.3 Hz), 7.62 (1H, s), 7.59 (1H, d, J = 8.5 Hz), 7.51-7.46 (2H, m), 7.28-7.24 (1H, m), 7.20-7.17 (3H, m), 7.03 (1H, dd, J = 8.2, 2.1 Hz), 4.26-4.22 (1H, m), 3.75-3.70 (1H, m), 1.81 (3H, s), 1.84-1.57 (8H, m). LC/MS: 504 [M + H]. |
| I-152 | ¹H-NMR (DMSO-$d_6$) δ: 12.64 (1H, s), 8.97 (1H, d, J = 6.7 Hz), 8.22 (1H, s), 7.88-7.83 (3H, m), 7.78 (1H, s), 7.34-7.29 (2H, m), 7.24-7.20 (2H, m), 7.10-7.06 (2H, m), 4.23-4.20 (1H, m), 3.73-3.69 (1H, m), 1.85-1.57 (8H, m), 1.80 (3H, s). LC/MS: 488 [M + H]. |
| I-153 | ¹H-NMR (DMSO-$d_6$) δ: 12.66 (1H, s), 8.98 (1H, d, J = 7.3 Hz), 8.23 (1H, s), 7.90-7.86 (3H, m), 7.81 (1H, s), 7.70 (1H, t, J = 7.9 Hz), 7.60 (1H, d, J = 7.9 Hz), 7.50 (1H, s), 7.47-7.44 (1H, m), 7.21-7.17 (2H, m), 4.24-4.20 (1H, m), 3.74-3.69 (1H, m), 1.80 (3H, s), 1.87-1.55 (8H, m). LC/MS: 538 [M + H]. |
| I-155 | ¹H-NMR (DMSO-$d_6$) δ: 12.67 (1H, s), 8.93 (1H, d, J = 7.3 Hz), 8.23 (1H, s), 7.86-7.84 (2H, m), 7.82-7.80 (1H, m), 7.49-7.46 (2H, m), 7.27-7.23 (1H, m), 7.17-7.14 (2H, m), 7.10-7.08 (2H, m), 4.24-4.21 (1H, m), 3.89-3.87 (1H, m), 3.69-3.64 (1H, m), 3.59-3.54 (1H, m), 3.42-3.38 (1H, m), 2.05-1.99 (1H, m), 1.83-1.81 (1H, m), 1.74-1.56 (2H, m). LC/MS: 415 [M + H]. |
| I-156 | ¹H-NMR (DMSO-$d_6$) δ: 12.67 (1H, s), 8.88 (1H, d, J = 7.3 Hz), 8.24 (1H, s), 7.87-7.84 (2H, m), 7.81 (1H, s), 7.51-7.45 (2H, m), 7.27-7.24 (1H, m), 7.17-7.14 (2H, m), 7.10-7.08 (2H, m), 4.30-4.27 (1H, m), 3.91-3.89 (2H, m), 3.54-3.48 (2H, m), 2.02-2.00 (1H, m), 1.56-1.51 (2H, m). LC/MS: 415 [M + H]. |
| I-157 | ¹H-NMR (CDCl$_3$) δ: 13.03 (1H, br s), 8.94 (1H, d, J = 7.3 Hz), 8.38 (1H, s), 7.80 (2H, d, J = 8.5 Hz), 7.64 (1H, s), 7.46-7.39 (2H, m), 7.22 (1H, t, J = 7.3 Hz), 7.10 (4H, t, J = 9.2 Hz), 6.61 (1H, d, J = 3.1 Hz), 5.91 (1H, d, J = 3.1 Hz), 4.45-4.34 (2H, m), 3.93-3.87 (1H, m), 3.33 (1H, t, J = 10.4 Hz), 2.42-2.30 (2H, m), 1.85-1.64 (2H, m). LC/MS: 458 [M + H]. |

TABLE 2-continued

| Cmpd No. | $^1$H NMR and/or LC/MS data |
|---|---|
| I-158 | $^1$H-NMR (DMSO-d$_6$) δ: 12.66 (1H, s), 9.16 (1H, s), 8.83 (1H, d, J = 7.3 Hz), 8.24 (1H, s), 7.87-7.84 (2H, m), 7.81 (1H, s), 7.50-7.46 (2H, m), 7.27-7.24 (1H, m), 7.17-7.16 (2H, m), 7.10-7.08 (2H, m), 4.12-4.07 (1H, m), 3.13-3.07 (1H, m), 2.23-2.16 (4H, m), 1.74-1.68 (2H, m), 1.54-1.47 (2H, m). LC/MS: 481 [M + H]. |
| I-159 | $^1$H-NMR (DMSO-d$_6$) δ: 12.13 (1H, s), 8.83 (1H, d, J = 7.3 Hz), 8.24 (1H, s), 7.86-7.84 (2H, m), 7.82-7.79 (1H, m), 7.50-7.46 (2H, m), 7.27-7.25 (1H, m), 7.17-7.15 (2H, m), 7.10-7.08 (2H, m), 4.13-4.05 (1H, m), 3.34 (3H, s), 3.01 (1H, s), 2.20-2.14 (4H, m), 1.75-1.66 (2H, m), 1.54-1.45 (2H, m). LC/MS: 495 [M + H]. |
| I-160 | $^1$H-NMR (CDCl$_3$) δ: 13.32 (1H, br s), 8.89 (1H, d, J = 7.3 Hz), 8.36 (1H, s), 7.83-7.78 (2H, m), 7.64 (1H, s), 7.45-7.39 (2H, m), 7.22 (1H, t, J = 7.3 Hz), 7.13-7.06 (4H, m), 4.41-4.29 (2H, m), 3.70-3.63 (1H, m), 3.30-3.21 (1H, m), 3.18-3.11 (1H, m), 2.37-2.29 (1H, m), 1.84-1.65 (3H, m), 1.61-1.49 (1H, m), 1.19 (3H, d, J = 6.7 Hz). LCMS: 459 [M + H]. |
| I-161 | $^1$H-NMR (DMSO-d$_6$) δ: 12.65 (1H, s), 8.97 (1H, d, J = 7.3 Hz), 8.22 (1H, s), 7.88-7.85 (3H, m), 7.79 (1H, s), 7.53-7.50 (2H, m), 7.19-7.18 (2H, m), 7.14-7.13 (2H, m), 4.23-4.20 (1H, m), 3.72-3.70 (1H, m), 1.88-1.55 (11H, m). LC/MS: 504 [M + H]. (Synthesized from [4-(4-chlorophenoxy)phenyl]-(4-chloro-7H-pyrrolo[2,3-d]pyrimidin-5-yl)methanone, LC/MS: 384 [M + H].) |
| I-162 | $^1$H-NMR (DMSO-d$_6$) δ: 12.63 (1H, s), 8.97 (1H, d, J = 7.3 Hz), 8.22 (1H, s), 7.88-7.82 (3H, m), 7.78 (1H, s), 7.28 (2H, d, J = 8.5 Hz), 7.05 (4H, d, J = 8.5 Hz), 4.22-4.19 (1H, m), 3.72-3.70 (1H, m), 2.33 (3H, s), 1.87-1.53 (11H, m). LC/MS: 484 [M + H]. (Synthesized from (4-chloro-7H-pyrrolo[2,3-d]pyrimidin-5-yl)-(4-(4-methylphenoxy)phenyl)methanone LC/MS: 364 [M + H]) |
| I-163 | $^1$H-NMR (DMSO-d$_6$) δ: 12.58 (1H, s), 8.98 (1H, d, J = 6.7 Hz), 8.21 (1H, s), 7.87 (1H, d, J = 7.3 Hz), 7.79-7.77 (3H, m), 7.09 (2H, d, J = 9.2 Hz), 6.01-5.97 (1H, m), 5.87-5.85 (1H, m), 5.05-5.02 (1H, m), 4.22-4.20 (1H, m), 3.72-3.71 (1H, m), 2.13-1.91 (3H, m), 1.80-1.57 (14H, m). LC/MS: 474 [M + H]. (Synthesized from methyl 4-hydroxybenzoate and 3-bromocyclohexene LC/MS: 233 [M + H] and (4-chloro-7H-pyrrolo[2,3-d]pyrimidin-5-yl)-(4-cyclohex-2-en-1-yloxyphenyl)methanone LC/MS: 354 [M + H].) |
| I-164 | $^1$H-NMR (DMSO-d$_6$) δ: 12.78 (1H, s), 8.82 (1H, d, J = 7.3 Hz), 8.24 (1H, s), 8.10 (1H, d, J = 7.9 Hz), 7.90 (1H, d, J = 7.3 Hz), 7.82 (1H, s), 7.50-7.48 (2H, m), 7.31-7.26 (3H, m), 7.11 (1H, d, J = 7.9 Hz), 4.24-4.21 (1H, m), 3.74-3.71 (1H, m), 1.81-1.58 (11H, m). LC/MS: 505 [M + H]. (Synthesized from (2-chloro-6-phenoxy-3-pyridyl)-(4-chloro-7H-pyrrolo[2,3-d]pyrimidin-5-yl)methanone LC/MS: 385 [M + H].) |
| I-165 | $^1$H-NMR (CDCl$_3$) δ: 8.98 (1H, d, J = 7.9 Hz), 8.34 (1H, s), 7.81 (2H, d, J = 8.8 Hz), 7.59 (1H, s), 7.42 (2H, t, J = 7.9 Hz), 7.24-7.19 (1H, m), 7.13-7.06 (4H, m), 4.19-4.07 (1H, m), 3.52 (2H, d, J = 6.1 Hz), 2.30-2.23 (2H, m), 1.96-1.38 (6H, m), 1.27-1.15 (2H, m). LC/MS: 443 [M + H]. |
| I-168 | $^1$H-NMR (DMSO-d$_6$) δ: 12.62 (1H, s), 8.75 (1H, d, J = 7.3 Hz), 8.22 (1H, s), 7.85-7.81 (2H, m), 7.78 (1H, s), 7.50-7.46 (2H, m), 7.25 (1H, t, J = 7.3 Hz), 7.16 (2H, d, J = 7.9 Hz), 7.10-7.06 (2H, m), 4.60 (1H, d, J = 4.3 Hz), 4.02-3.97 (1H, m), 3.54-3.50 (1H, m), 2.09-2.03 (2H, m), 1.89-1.85 (2H, m), 1.38-1.29 (4H, m). LC/MS: 429 [M + H]. |
| I-169 | $^1$H-NMR (DMSO-d$_6$) δ: 12.70 (1H, s), 8.69 (1H, d, J = 7.9 Hz), 8.23 (1H, s), 7.60-7.58 (1H, m), 7.57 (1H, d, J = 7.3 Hz), 7.50-7.46 (2H, m), 7.26 (1H, t, J = 7.6 Hz), 7.20-7.17 (3H, m), 7.02 (1H, dd, J = 8.2, 2.1 Hz), 4.60 (1H, d, J = 4.3 Hz), 4.03-3.98 (1H, m), 3.55-3.49 (1H, m), 2.10-2.05 (2H, m), 1.90-1.85 (2H, m), 1.40-1.28 (4H, m). LC/MS: 463 [M + H]. |
| I-171 | $^1$H-NMR (DMSO-d$_6$) δ: 12.70 (1H, s), 8.67 (1H, d, J = 6.7 Hz), 8.24-8.22 (1H, m), 8.24 (1H, s), 7.95-7.91 (1H, m), 7.88-7.83 (3H, m), 7.27 (2H, d, J = 7.9 Hz), 7.24-7.20 (1H, m), 7.15 (1H, d, J = 7.9 Hz), 4.60 (1H, d, J = 5.5 Hz), 4.18-4.12 (2H, m), 3.52-3.47 (1H, m), 3.12-3.05 (2H, m), 2.21-2.16 (1H, m), 1.95-1.90 (1H, m), 1.59-1.49 (1H, m), 1.46-1.36 (1H, m), 1.08 (3H, d, J = 5.5 Hz). LC/MS: 460 [M + H]. |
| I-172 | $^1$H-NMR (DMSO-d$_6$) δ: 12.71 (1H, s), 8.66 (1H, d, J = 7.3 Hz), 8.24 (1H, s), 7.98 (1H, t, J = 7.9 Hz), 7.91-7.84 (3H, m), 7.35-7.31 (3H, m), 7.15 (1H, d, J = 7.9 Hz), 4.60 (1H, d, J = 5.5 Hz), 4.18-4.12 (2H, m), 3.52-3.47 (1H, m), 3.12-3.05 (2H, m), 2.21-2.16 (1H, m), 1.95-1.90 (1H, m), 1.59-1.49 (1H, m), 1.46-1.36 (1H, m), 1.08 (3H, d, J = 6.1 Hz). LC/MS: 494 [M + H]. |
| I-173 | $^1$H-NMR (DMSO-d$_6$) δ: 12.77 (1H, s), 8.92 (1H, d, J = 6.7 Hz), 8.27 (1H, s), 7.65 (1H, s), 7.58 (1H, d, J = 8.5 Hz), 7.50-7.46 (2H, m), 7.28-7.24 (1H, m), 7.20-7.17 (3H, m), 7.03 (1H, dd, J = 8.2, 2.1 Hz), 4.73-4.66 (1H, m), 3.96-3.90 (2H, m), 3.83-3.76 (1H, m), 3.68 (1H, dd, J = 8.9, 3.4 Hz), 2.39-2.30 (1H, m), 1.94-1.85 (1H, m). LC/MS: 435 [M + H]. |
| I-174 | $^1$H-NMR (DMSO-d$_6$) δ: 12.77 (1H, s), 8.92 (1H, d, J = 6.7 Hz), 8.27 (1H, s), 7.65 (1H, s), 7.58 (1H, d, J = 8.5 Hz), 7.51-7.45 (2H, m), 7.26 (1H, t, J = 7.6 Hz), 7.20-7.17 (3H, m), 7.02 (1H, dd, J = 8.5, 2.4 Hz), 4.73-4.66 (1H, m), 3.96-3.90 (2H, m), 3.82-3.76 (1H, m), 3.66-3.70 (1H, m), 2.39-2.30 (1H, m), 1.93-1.86 (1H, m). LC/MS: 435 [M + H]. |
| I-179 | $^1$H-NMR (DMSO-d$_6$) δ: 12.71 (1H, s), 8.71 (1H, d, J = 7.3 Hz), 8.23 (1H, s), 7.60-7.58 (2H, m), 7.49-7.47 (2H, m), 7.27-7.25 (1H, m), 7.20-7.18 (3H, m), 7.02 (1H, dd, J = 8.5, 2.4 Hz), 4.55 (1H, d, J = 5.5 Hz), 4.35 (1H, d, J = 3.1 Hz), 4.13-4.00 (1H, m), 3.76-3.74 (1H, m), 3.54-3.52 (1H, m), 3.17 (3H, d, J = 5.5 Hz), 1.95-1.92 (1H, m), 1.78-1.74 (2H, m). LC/MS: 479 [M + H]. Racemic mixture. |

TABLE 2-continued

| Cmpd No. | $^1$H NMR and/or LC/MS data |
|---|---|
| I-180 | $^1$H-NMR (DMSO-$d_6$) δ: 12.71 (1H, s), 8.71 (1H, d, J = 7.9 Hz), 8.23 (1H, s), 7.59-7.56 (2H, m), 7.50-7.46 (2H, m), 7.26-7.25 (1H, m), 7.19-7.18 (3H, m), 7.02 (1H, dd, J = 8.5, 2.4 Hz), 4.43-4.40 (3H, m), 3.84-3.83 (1H, m), 3.60-3.59 (1H, m), 2.04-2.01 (2H, m), 1.73-1.57 (3H, m), 1.35-1.33 (1H, m). LC/MS: 479 [M + H]. Racemic mixture. |
| I-184 | $^1$H-NMR (CDCl$_3$) δ: 9.14 (1H, d, J = 7.3 Hz), 8.36 (1H, s), 7.82-7.78 (2H, m), 7.60 (1H, s), 7.45-7.39 (2H, m), 7.24-7.18 (1H, m), 7.13-7.06 (4H, m), 4.74-4.60 (2H, m), 4.21 (1H, br s), 2.39-2.24 (2H, m), 2.18-1.99 (2H, m), 1.79-1.67 (1H, m), 1.62-1.47 (1H, m), 1.45 (9H, s). LC/MS: 514 [M + H]. |
| I-185 | $^1$H-NMR (CDCl$_3$) δ: 9.34 (1H, d, J = 5.5 Hz), 8.36 (1H, s), 7.81 (2H, d, J = 8.5 Hz), 7.62 (1H, s), 7.42 (2H, t, J = 7.9 Hz), 7.21 (1H, t, J = 7.3 Hz), 7.13-7.06 (4H, m), 4.92 (1H, br s), 4.81-4.71 (1H, m), 4.33 (1H, br s), 2.62-2.38 (4H, m), 1.45 (9H, s). LC/MS: 500 [M + H]. |
| I-186 | $^1$H-NMR (CDCl$_3$) δ: 9.19 (1H, d, J = 7.3 Hz), 8.36 (1H, s), 7.81 (2H, d, J = 8.5 Hz), 7.62 (1H, s), 7.45-7.40 (2H, m), 7.22 (1H, t, J = 7.3 Hz), 7.14-7.06 (4H, m), 4.76 (1H, d, J = 6.7 Hz), 4.53-4.40 (1H, m), 4.06-3.93 (1H, m), 3.05-2.93 (2H, m), 2.03-1.91 (2H, m), 1.45 (9H, s). LC/MS: 500 [M + H]. |
| I-187 | $^1$H-NMR (CDCl$_3$) δ: 12.64 (1H, s), 9.01 (1H, d, J = 7.3 Hz), 8.21 (1H, s), 7.85 (2H, dt, J = 9.2, 2.3 Hz), 7.80 (1H, s), 7.51-7.45 (2H, m), 7.28-7.23 (1H, m), 7.19-7.15 (2H, m), 7.12-7.07 (2H, m), 4.69-4.62 (2H, m), 3.51 (2H, dd, J = 6.7, 5.5 Hz), 2.41-2.21 (3H, m), 2.07-1.98 (2H, m). LC/MS: 415 [M + H]. |
| I-188 | $^1$H-NMR (DMSO-$d_6$) δ: 12.78 (1H, s), 8.58 (1H, d, J = 7.3 Hz), 8.25 (1H, s), 7.64 (1H, s), 7.58 (1H, d, J = 8.5 Hz), 7.49-7.47 (2H, m), 7.27-7.25 (1H, m), 7.19-7.18 (3H, m), 7.03-7.01 (1H, m), 4.29 (1H, s), 4.22-4.19 (1H, m), 4.13-4.11 (1H, m), 3.13-3.07 (2H, m), 2.22-2.19 (1H, m), 1.88-1.84 (1H, m), 1.55-1.46 (2H, m), 1.11 (3H, s), 1.06 (3H, s). LC/MS: 507 [M + H]. |
| I-198 | $^1$H-NMR (DMSO-$d_6$) δ: 11.88 (1H, br s), 8.66 (1H, d, J = 7.3 Hz), 8.24 (1H, s), 7.86-7.81 (3H, m), 7.71 (1H, d, J = 8.5 Hz), 7.48 (2H, m), 7.28-7.24 (1H, m), 7.19-7.16 (2H, m), 7.09-7.08 (2H, m), 4.21-4.09 (2H, m), 3.93-3.83 (1H, m), 3.29-3.29 (1H, m), 3.10-3.08 (1H, m), 2.18-2.15 (1H, m), 1.83 (3H, s), 1.67-1.44 (3H, m), 1.05 (3H, d, J = 6.7 Hz). LC/MS: 500 [M + H]. |
| I-200 | $^1$H-NMR (DMSO-$d_6$) δ: 12.69 (1H, s), 8.70 (1H, d, J = 7.3 Hz), 8.22 (1H, s), 7.59-7.56 (2H, m), 7.49-7.47 (2H, m), 7.27-7.25 (1H, m), 7.20-7.18 (3H, m), 7.03-7.01 (1H, m), 4.18 (1H, s), 4.00-3.99 (1H, m), 1.82-1.81 (2H, m), 1.72-1.60 (4H, m), 1.46-1.40 (2H, m), 1.14 (3H, s). LC/MS: 477 [M + H]. |
| I-201 | $^1$H-NMR (DMSO-$d_6$) δ: 12.71 (1H, s), 8.92 (1H, d, J = 7.9 Hz), 8.22 (1H, s), 7.60-7.57 (2H, m), 7.49-7.47 (2H, m), 7.26-7.24 (1H, m), 7.19-7.17 (3H, m), 7.03-7.01 (1H, m), 4.25 (1H, s), 4.24-4.22 (1H, m), 2.00-1.97 (2H, m), 1.66-1.64 (2H, m), 1.51-1.49 (4H, m), 1.14 (3H, s). LC/MS: 477 [M + H]. |
| I-204 | $^1$H-NMR (DMSO-$d_6$) δ: 8.72 (1H, d, J = 7.3 Hz), 8.24 (1H, s), 7.71 (1H, d, J = 8.5 Hz), 7.52 (1H, s), 7.47-7.42 (3H, m), 7.22-7.20 (1H, m), 7.13-7.11 (2H, m), 6.98 (1H, d, J = 2.4 Hz), 6.85 (1H, dd, J = 7.9, 2.4 Hz), 4.22-4.10 (2H, m), 3.90-3.88 (1H, m), 3.32-3.29 (1H, m), 3.12-3.09 (1H, m), 2.28 (3H, s), 2.19-2.16 (1H, m), 1.83 (3H, s), 1.67-1.42 (3H, m), 1.05 (3H, d, J = 6.7 Hz). LC/MS: 514 [M + H]. |
| I-205 | $^1$H-NMR (DMSO-$d_6$) δ: 12.69 (1H, s), 8.66 (1H, d, J = 7.3 Hz), 8.24 (1H, s), 7.96 (1H, t, J = 5.5 Hz), 7.85-7.83 (3H, m), 7.51-7.45 (2H, m), 7.28-7.24 (1H, m), 7.17-7.16 (2H, m), 7.10-7.07 (2H, m), 4.15-4.13 (2H, m), 3.21-3.04 (4H, m), 2.15 (1H, m), 1.82 (3H, s), 1.77-1.73 (1H, m), 1.57-1.53 (1H, m), 1.41-1.35 (1H, m). LC/MS: 486 [M + H]. |
| I-207 | $^1$H-NMR (DMSO-$d_6$) δ: 12.73 (1H, br s), 8.96 (1H, d, J = 7.3 Hz), 8.22 (1H, s), 7.63-7.57 (2H, m), 7.52-7.46 (2H, m), 7.29-7.16 (4H, m), 7.03 (1H, dd, J = 8.5, 1.8 Hz), 4.69-4.61 (2H, m), 3.51 (2H, t, J = 6.1 Hz), 2.41-1.98 (5H, m). LC/MS: 449 [M + H]. |
| I-209 | $^1$H-NMR (DMSO-$d_6$) δ: 12.89 (1H, s), 8.94 (1H, s), 8.30 (1H, s), 7.89-7.85 (3H, m), 7.50-7.47 (2H, m), 7.28-7.26 (2H, m), 7.18-7.16 (2H, m), 7.10-7.09 (2H, m), 4.18-4.14 (2H, m), 4.01-3.99 (1H, m), 3.88-3.85 (1H, m), 3.40-3.37 (1H, m), 3.16-3.14 (1H, m), 2.18-2.16 (1H, m), 1.66-1.47 (3H, m), 1.22-1.21 (3H, m), 1.10-1.09 (3H, m). LC/MS: 530 [M + H]. |
| I-211 | $^1$H-NMR (DMSO-$d_6$) δ: 12.78 (1H, br s), 8.80 (1H, br s), 8.26 (1H, s), 7.85-7.83 (3H, m), 7.60-7.59 (1H, m), 7.49-7.47 (2H, m), 7.26-7.25 (1H, m), 7.17-7.15 (2H, m), 7.09-7.08 (2H, m), 4.15-4.13 (2H, m), 3.98 (1H, q, J = 6.7 Hz), 3.45-3.42 (1H, m), 3.20-3.13 (2H, m), 2.17-2.15 (1H, m), 1.77-1.73 (1H, m), 1.57-1.54 (1H, m), 1.42-1.39 (1H, m), 1.21 (3H, d, J = 6.7 Hz). LC/MS: 516 [M + H]. |
| I-212 | $^1$H-NMR (CDCl$_3$) δ: 9.20 (1H, d, J = 8.5 Hz), 8.29-8.25 (1H, m), 7.47-7.40 (3H, m), 7.33-7.21 (3H, m), 7.13-7.07 (3H, m), 7.00-6.95 (1H, m), 4.53 (1H, br s), 3.94 (1H, br s), 3.81-3.73 (1H, m), 2.36-2.29 (1H, m), 2.21-2.13 (2H, m), 1.95-1.40 (15H, m), 1.13 (3H, d, J = 6.1 Hz). LC/MS: 590 [M + H]. |
| I-214 | $^1$H-NMR (CDCl$_3$) δ: 9.30 (1H, d, J = 7.9 Hz), 8.32-8.24 (1H, m), 7.47-6.95 (10H, m), 5.68 (1H, d, J = 7.9 Hz), 4.47 (1H, s), 3.98 (1H, br s), 3.82-3.76 (1H, m), 2.40-2.32 (2H, m), 2.19-13 (1H, m), 1.93-1.41 (15H, m), 1.15 (3H, d, J = 6.1 Hz). LC/MS: 604 [M + H]. (Synthesized by method described herein for Compound I-181) |
| I-215 | $^1$H-NMR (DMSO-$d_6$) δ: 12.78 (1H, s), 8.79 (1H, s), 8.27 (1H, s), 7.86-7.83 (3H, m), 7.49-7.47 (2H, m), 7.26-7.24 (2H, m), 7.17-7.15 (2H, m), 7.10-7.08 (2H, m), 4.18-4.14 (2H, m), 3.98-3.97 (1H, m), 3.88-3.85 (1H, m), 3.40-3.37 (1H, m), 3.15-3.12 (1H, m), 2.15 (1H, s), 1.63-1.49 (3H, m), 1.24 (3H, d, J = 6.7 Hz), 1.10 (3H, d, J = 6.7 Hz). LC/MS: 530 [M + H]. |
| I-217 | $^1$H-NMR (DMSO-$d_6$) δ: 12.82 (1H, br s), 8.85 (1H, br s), 8.28 (1H, s), 7.86-7.84 (3H, m), 7.60-7.58 (1H, m), 7.49-7.47 (2H, m), 7.27-7.25 (1H, m), 7.16-7.09 (4H, m), 4.16-4.14 (2H, m), 3.99-3.97 (1H, m), 3.44-3.41 (1H, m), 3.29-3.23 (1H, m), 3.15-3.12 |

TABLE 2-continued

| Cmpd No. | ¹H NMR and/or LC/MS data |
| --- | --- |
| | (2H, m), 2.17-2.14 (1H, m), 1.78-1.74 (1H, m), 1.60-1.57 (1H, m), 1.42-1.39 (1H, m), 1.22 (3H, d, J = 6.7 Hz). LC/MS: 516 [M + H]. |

Example 100: 2-(4-methylpiperazin-1-yl)-N-(cis-4-((5-(3-methylthiophene-2-carbonyl)-7H-pyrrolo[2,3-d]pyrimidin-4-yl)amino)cyclohexyl)acetamide (I-128)

2-(4-Methylpiperazin-1-yl)-N-(cis-4-((5-(3-methylthiophene-2-carbonyl)-7H-pyrrolo[2,3-d]pyrimidin-4-yl)amino)cyclohexyl)acetamide (I-128) was made according to General Procedure B from (4-chloro-7H-pyrrolo[2,3-d]pyrimidin-5-yl)-(3-methyl-2-thienyl)methanone (128a) and N-(cis-4-aminocyclohexyl)-2-(4-methylpiperazin-1-yl)-acetamide (128b). ¹H-NMR (DMSO-$d_6$) δ: 12.64 (1H, br s), 8.76 (1H, d, J=7.3 Hz), 8.22 (1H, s), 8.01 (1H, s), 7.83 (1H, d, J=4.9 Hz), 7.57 (1H, d, J=7.9 Hz), 7.15 (1H, d, J=4.9 Hz), 4.22-4.24 (1H, m), 3.76-3.79 (1H, m), 2.90 (2H, s), 2.35-2.41 (11H, m), 1.64-1.76 (8H, m), 2.07 (3H, s). LC/MS: 496 [M+H].

(4-chloro-7H-pyrrolo[2,3-d]pyrimidin-5-yl)-(3-methyl-2-thienyl)methanone (128a) was synthesized from 3-methyl-thiophen-2-carbonyl chloride. ¹H-NMR (DMSO-$d_6$) δ: 13.24 (1H, s), 8.73 (1H, s), 8.31 (1H, s), 7.88 (1H, d, J=4.9 Hz), 7.17 (1H, d, J=4.9 Hz), 2.45 (3H, s). LC/MS: 278 [M+H].

Condensation of 4-methylpiperazin-1-yl)acetic acid and tert-butyl N-(cis-4-aminocyclohexyl)carbamate followed by Boc deprotection provided tert-butyl N-(cis-4-((2-(4-methylpiperazin-1-yl)acetyl)amino)cyclohexyl)carbamate. ¹H-NMR (CDCl₃) δ: 7.25 (1H, br s), 4.56 (1H, br s), 3.93-3.94 (1H, m), 3.63 (1H, s), 2.99 (2H, s), 2.47-2.57 (8H, m), 2.32 (3H, s), 1.42-1.82 (17H, m). LC/MS: 355 [M+H]. Subsequent Boc deprotection provided N-(cis-4-aminocyclohexyl)-2-(4-methylpiperazin-1-yl)-acetamide(128b). LC/MS: 255 [M+H].

Example 101: 2-(4-methylpiperazin-1-yl)-N-(cis-4-((5-(2-methylthiophene-3-carbonyl)-7H-pyrrolo[2,3-d]pyrimidin-4-yl)amino)cyclohexyl)acetamide (I-132)

2-(4-methylpiperazin-1-yl)-N-(cis-4-((5-(2-methylthiophene-3-carbonyl)-7H-pyrrolo[2,3-d]pyrimidin-4-yl)amino)cyclohexyl)acetamide (I-132) was synthesized from N-methoxy-N,2-dimethyl-thiophene-3-carboxamide (132a) and (4-chloro-7H-pyrrolo[2,3-d]pyrimidin-5-yl)-(2-methyl-3-thienyl)methanone (132b). ¹H-NMR (DMSO-$d_6$) δ: 12.60 (1H, s), 9.04 (1H, d, J=7.3 Hz), 8.21 (1H, s), 7.69 (1H, s), 7.58 (1H, d, J=7.9 Hz), 7.42 (1H, d, J=5.5 Hz), 7.32 (1H, d, J=5.5 Hz), 4.24-4.26 (1H, m), 3.76-3.79 (1H, m), 2.91 (2H, s), 2.57 (3H, s), 2.33-2.42 (8H, m), 2.11 (3H, s), 1.63-1.81 (8H, m). LC/MS: 496 [M+H].

N-methoxy-N,2-dimethyl-thiophene-3-carboxamide (132a) was synthesized from 2-methylthiophen-3-carboxylic acid by condensation reaction. ¹H-NMR (CDCl₃) δ: 7.12 (1H, d, J=4.9 Hz), 7.02 (1H, dd, J=4.9, 1.2 Hz), 3.56 (3H, s), 3.32 (3H, s), 2.57 (3H, d, J=1.2 Hz). LC/MS: 186 [M+H]. (4-chloro-7H-pyrrolo[2,3-d]pyrimidin-5-yl)-(2-methyl-3-thienyl)methanone (132b) was synthesized from the Weinreb amide. LC/MS: 278 [M+H].

Example 102: (4-((cis-4-aminocyclohexyl)amino)-7H-pyrrolo[2,3-d]pyrimidin-5-yl)(3-methoxyphenyl)methanone (I-135)

Boc deprotection of Compound I-133 provided (4-((cis-4-aminocyclohexyl)amino)-7H-pyrrolo[2,3-d]pyrimidin-5-yl)(3-methoxyphenyl)methanone (I-135). ¹H-NMR (DMSO-$d_6$) δ: 13.31 (1H, br s), 8.37 (1H, s), 8.10-8.01 (4H, m), 7.50 (1H, t, J=7.9 Hz), 7.39 (1H, d, J=7.9 Hz), 7.32 (1H, s), 7.27-7.24 (1H, m), 4.29-4.25 (1H, m), 3.84 (3H, s), 3.24-3.20 (1H, m), 1.99-1.70 (8H, m). LC/MS: 366 [M+H].

Example 103: (4-((cis-4-aminocyclohexyl)amino)-7H-pyrrolo[2,3-d]pyrimidin-5-yl)(5-methoxy-2-methylphenyl)methanone (I-136)

Boc deprotection of Compound I-134 provided (4-((cis-4-aminocyclohexyl)amino)-7H-pyrrolo[2,3-d]pyrimidin-5-yl)(5-methoxy-2-methylphenyl)methanone (I-136). ¹H-NMR (DMSO-$d_6$) δ: 8.36 (1H, s), 8.08-8.06 (3H, m), 7.67 (1H, br s), 7.28 (1H, d, J=8.5 Hz), 7.04 (1H, dd, J=8.2, 2.7 Hz), 7.00-7.00 (1H, m), 4.29-4.27 (1H, m), 3.76 (3H, s), 3.24-3.21 (1H, m), 2.21 (3H, s), 1.99-1.73 (8H, m). LC/MS: 380 [M+H].

Example 104: (4-((cis-4-aminocyclohexyl)amino)-7H-pyrrolo[2,3-d]pyrimidin-5-yl)(2-chloro-5-methoxyphenyl)methanone (I-137)

(4-chloro-7H-pyrrolo[2,3-d]pyrimidin-5-yl)-(2-chloro-5-methoxyphenyl)methanone was synthesized from methyl 2-chloro-5-methoxybenzoate, then tert-butyl N-(cis-4-aminocyclohexyl)carbamate was introduced and the Boc group was deprotected to provide I-137 according to General Procedure B followed by Boc deprotection. ¹H-NMR (DMSO-$d_6$) δ: 8.33 (1H, s), 8.07-7.97 (3H, m), 7.71 (1H, s), 7.51 (1H, d, J=8.5 Hz), 7.16-7.15 (1H, m), 7.13 (1H, d, J=3.1 Hz), 4.29-4.26 (1H, m), 3.80 (3H, s), 3.24-3.21 (1H, m), 1.95-1.72 (8H, m). LC/MS: 400 [M+H].

Example 105: (4-((cis-4-aminocyclohexyl)amino)-7H-pyrrolo[2,3-d]pyrimidin-5-yl)(4-fluoro-3-methoxyphenyl)methanone (I-138)

(4-chloro-7H-pyrrolo[2,3-d]pyrimidin-5-yl)-(4-fluoro-3-methoxyphenyl)methanone was synthesized from methyl 4-fluoro-3-methoxybenzoate, then tert-butyl N-(cis-4-aminocyclohexyl)carbamate was introduced and the Boc group was deprotected to provide I-138 according to General Procedure B followed by Boc deprotection. ¹H-NMR (DMSO-$d_6$) δ: 8.33 (1H, s), 8.04-7.97 (4H, m), 7.55 (1H, dd, J=8.5, 1.8 Hz), 7.44-7.38 (2H, m), 4.27-4.24 (1H, m), 3.93 (3H, s), 3.22-3.19 (1H, m), 1.99-1.68 (8H, m). LC/MS: 384 [M+H].

Example 106: N-(cis-4-((5-(4-phenoxybenzoyl)-7H-pyrrolo[2,3-d]pyrimidin-4-yl)amino)cyclohexyl)acetamide (I-139)

Acylation of Compound I-130 provided N-(cis-4-((5-(4-phenoxybenzoyl)-7H-pyrrolo[2,3-d]pyrimidin-4-yl)amino)

cyclohexyl)acetamide (I-139). $^1$H-NMR (DMSO-d$_6$) δ: 12.62 (1H, br s), 8.98 (1H, d, J=6.7 Hz), 8.22 (1H, s), 7.89-7.83 (3H, m), 7.80 (1H, s), 7.51-7.46 (2H, m), 7.28-7.23 (1H, m), 7.18-7.14 (2H, m), 7.12-7.07 (2H, m), 4.21 (1H, s), 3.67-3.74 (1H, m), 1.85-1.57 (11H, m). LC/MS: 470 [M+H].

Example 107: N-(cis-4-((5-(3-phenoxybenzoyl)-7H-pyrrolo[2,3-d]pyrimidin-4-yl)amino)cyclohexyl) acetamide (I-140)

Acylation of Compound I-131 provided N-(cis-4-((5-(3-phenoxybenzoyl)-7H-pyrrolo[2,3-d]pyrimidin-4-yl)amino) cyclohexyl)acetamide (I-140). $^1$H-NMR (DMSO-d$_6$) δ: 12.68 (1H, br s), 8.93-8.89 (1H, m), 8.22 (1H, s), 7.87 (1H, d, J=7.3 Hz), 7.78 (1H, s), 7.57-7.55 (2H, m), 7.47-7.42 (2H, m), 7.32-7.28 (2H, m), 7.22-7.18 (1H, m), 7.15-7.11 (2H, m), 4.22-4.17 (1H, m), 3.75-3.68 (1H, m), 1.81-1.55 (11H, m). LC/MS: 470 [M+H].

Example 108: (4-((cis-4-aminocyclohexyl)amino)-7H-pyrrolo[2,3-d]pyrimidin-5-yl)(2-chloro-4-phenoxyphenyl)methanone (I-141)

S$_N$Ar reaction with (2-chloro-4-phenoxy-phenyl)-(4-chloro-7H-pyrrolo-[2,3-d]pyrimidin-5-yl)methanone and tert-butyl N-(cis-4-aminocyclohexyl)carbamate followed by subsequent Boc deprotection provided (4-((cis-4-aminocyclohexyl)amino)-7H-pyrrolo[2,3-d]pyrimidin-5-yl)(2-chloro-4-phenoxyphenyl)methanone (I-141). $^1$H-NMR (DMSO-d$_6$) δ: 8.32 (1H, s), 8.04-7.95 (4H, m), 7.76 (1H, s), 7.60 (1H, d, J=8.5 Hz), 7.49 (2H, dd, J=8.5, 7.3 Hz), 7.27 (1H, t, J=7.3 Hz), 7.22 (1H, d, J=2.4 Hz), 7.20-7.17 (2H, m), 7.04 (1H, dd, J=8.2, 2.1 Hz), 4.28-4.25 (1H, m), 3.24-3.19 (1H, m), 1.97-1.70 (8H, m). LC/MS: 462 [M+H].

Example 109: (4-((cis-4-aminocyclohexyl)amino)-7H-pyrrolo[2,3-d]pyrimidin-5-yl)(4-(2-methoxyethoxy)phenyl)methanone (I-143)

(4-((cis-4-aminocyclohexyl)amino)-7H-pyrrolo[2,3-d] pyrimidin-5-yl)(4-(2-methoxyethoxy)phenyl)methanone (I-143) was synthesized from (4-chloro-7H-pyrrolo[2,3-d] pyrimidin-5-yl)-(3-(2-methoxyethoxy)phenyl)methanone and tert-butyl N-(cis-4-aminocyclohexyl) carbamate according to General Procedure B followed by Boc deprotection. $^1$H-NMR (DMSO-d$_6$) δ: 8.34 (1H, s), 7.98-7.94 (4H, m), 7.84 (2H, d, J=8.5 Hz), 7.12 (2H, d, J=8.5 Hz), 4.25-4.20 (3H, m), 3.72-3.69 (2H, m), 3.33 (3H, s), 3.23-3.18 (1H, m), 1.98-1.69 (8H, m). LC/MS: 410 [M+H].

Example 110: Compound 144: rac-(4-((cis-6-(hydroxymethyl)tetrahydro-2H-pyran-3-yl)amino)-7H-pyrrolo[2,3-d]pyrimidin-5-yl)(4-phenoxyphenyl) methanone (I-144)

Step 1. 6-((tert-butyl(diphenyl)-silyl)oxymethyl) tetrahydro-2H-pyran-3-one (144a)

Hydroboration of tert-butyl-(3,4-dihydro-2H-pyran-2-yl-methoxy)-diphenylsilane followed by oxidation of the secondary alcohol using Dess-Martin periodinane provided 6-((tert-butyl(diphenyl)-silyl)oxymethyl)tetrahydro-2H-pyran-3-one (144a). $^1$H-NMR (CDCl$_3$) δ: 7.70-7.65 (4H, m), 7.46-7.36 (6H, m), 4.14 (1H, d, J=16.5 Hz), 3.94 (1H, d, J=16.5 Hz), 3.84-3.77 (2H, m), 3.71-3.65 (1H, m), 2.65-2.57 (1H, m), 2.50-2.41 (1H, m), 2.15-2.08 (1H, m), 1.99-1.88 (1H, m), 1.07 (9H, s).

Step 2. rac-tert-butyl N-[cis-6-(hydroxymethyl)tetrahydro-pyran-3-yl] carbamate (144b) and rac-tert-butyl N-(trans-6-(hydroxymethyl)tetrahydro-2H-pyran-3-yl)carbamate (144c)

Reductive amination of Intermediate 144a using ammonium acetate/sodium triacetoxyborohydride followed by Boc protection of the generated amino group, and removal of TBDPS group provided intermediates 144b and 144c.

rac-tert-butyl N-[cis-6-(hydroxymethyl)tetrahydro-pyran-3-yl]carbamate (144b): $^1$H-NMR (CDCl$_3$) δ: 5.20-5.14 (0.8H, m), 3.89 (1H, d, J=12.2 Hz), 3.76-3.70 (1H, m), 3.65-3.43 (5H, m), 2.06-1.92 (2H, m), 1.78-1.68 (1H, m), 1.59-1.41 (10H, m).

rac-tert-butyl N-(trans-6-(hydroxymethyl)tetrahydro-2H-pyran-3-yl)carbamate (144c): $^1$H-NMR (CDCl$_3$) δ: 4.35-4.25 (1H, m), 4.15-4.09 (1H, m), 3.65-3.44 (4H, m), 3.40-3.33 (1H, m), 3.02 (1H, t, J=10.7 Hz), 2.15-2.06 (2H, m), 1.66-1.58 (1H, m), 1.52-1.40 (9H, m), 1.35-1.24 (1H, m).

Step 3. rac-(4-((cis-6-(hydroxymethyl)tetrahydro-2H-pyran-3-yl)amino)-7H-pyrrolo[2,3-d]pyrimidin-5-yl)(4-phenoxyphenyl)methanone (I-144)

rac-(4-((cis-6-(hydroxymethyl)tetrahydro-2H-pyran-3-yl) amino)-7H-pyrrolo[2,3-d]pyrimidin-5-yl)(4-phenoxyphenyl)methanone (I-144) was synthesized according to General Procedure B from rac-tert-butyl N-(cis-6-(hydroxymethyl)tetrahydro-pyran-3-yl)carbamate 144c (after Boc deprotection) and (4-chloro-7H-pyrrolo[2,3-d] pyrimidin-5-yl)-(4-phenoxy-phenyl)methanone. $^1$H-NMR (DMSO-d$_6$) δ: 12.62 (1H, br s), 9.23 (1H, d, J=7.9 Hz), 8.22 (1H, s), 7.86-7.83 (2H, m), 7.79 (1H, s), 7.50-7.45 (2H, m), 7.27-7.22 (1H, m), 7.18-7.15 (2H, m), 7.12-7.08 (2H, m), 4.65 (1H, t, J=5.8 Hz), 4.33-4.28 (1H, m), 3.95-3.89 (1H, m), 3.66-3.61 (1H, m), 3.49-3.37 (2H, m), 1.97-1.82 (2H, m), 1.62-1.56 (2H, m). LC/MS: 445 [M+H].

Example 111: rac-(4-((trans-6-(hydroxymethyl)tetrahydro-2H-pyran-3-yl)amino)-7H-pyrrolo[2,3-d]pyrimidin-5-yl)(4-phenoxyphenyl)methanone (I-145)

rac-(4-((trans-6-(hydroxymethyl)tetrahydro-2H-pyran-3-yl)amino)-7H-pyrrolo[2,3-d]pyrimidin-5-yl)(4-phenoxyphenyl)methanone (I-145) was synthesized according to General Procedure B from rac-tert-butyl N-(trans-6-(hydroxymethyl)tetrahydro-pyran-3-yl)carbamate 144c (after Boc deprotection and (4-chloro-7H-pyrrolo[2,3-d]pyrimidin-5-yl)-(4-phenoxy-phenyl)methanone. $^1$H-NMR (DMSO-d$_6$) δ: 12.67 (1H, br s), 8.66 (1H, d, J=7.3 Hz), 8.24 (1H, s), 7.86-7.80 (3H, m), 7.51-7.45 (2H, m), 7.28-7.23 (1H, m), 7.18-7.14 (2H, m), 7.11-7.06 (2H, m), 4.66 (1H, t, J=5.8 Hz), 4.18-4.09 (2H, m), 3.45-3.35 (2H, m), 3.10 (1H, t, J=11.3 Hz), 2.20-2.13 (1H, m), 1.81-1.74 (1H, m), 1.62-1.50 (1H, m), 1.44-1.31 (1H, m). LC/MS: 445 [M+H].

Example 112: (4-((cis-4-aminocyclohexyl)amino)-7H-pyrrolo[2,3-d]pyrimidin-5-yl)(4-(3-fluorophenoxy)phenyl)methanone (I-148)

(4-((cis-4-aminocyclohexyl)amino)-7H-pyrrolo[2,3-d] pyrimidin-5-yl)(4-(3-fluorophenoxy)phenyl)methanone (I-148) was synthesized according to General Procedure B from ethyl 4-(3-fluorophenoxy)benzoate and tert-butyl N-(4-aminocyclo-hexyl)carbamate followed by Boc deprotection. $^1$H-NMR (DMSO-$d_6$) δ: 8.38 (1H, s), 8.09 (4H, s), 7.92 (2H, d, J=8.5 Hz), 7.52 (1H, q, J=7.7 Hz), 7.20 (2H, d, J=8.5 Hz), 7.13-7.05 (2H, m), 7.01-6.98 (1H, m), 4.29-4.24 (1H, m), 3.25-3.19 (1H, m), 2.00-1.71 (8H, m). LC/MS: 446 [M+H].

Example 113: (4-((cis-4-aminocyclohexyl)amino)-7H-pyrrolo[2,3-d]pyrimidin-5-yl)(4-(benzyloxy)phenyl)methanone (I-154)

(4-((cis-4-aminocyclohexyl)amino)-7H-pyrrolo[2,3-d]pyrimidin-5-yl)(4-(benzyloxy)phenyl)methanone (I-154) was synthesized from (4-benzyloxyphenyl)-(4-chloro-7H-pyrrolo[2,3-d]pyrimidin-5-yl)methanone (154a) and tert-butyl N-(4-aminocyclo-hexyl)carbamate according to General Procedure B followed by Boc deprotection. $^1$H-NMR (DMSO-$d_6$) δ: 8.35 (1H, s), 8.02-7.99 (4H, m), 7.86 (2H, d, J=9.2 Hz), 7.50-7.49 (2H, m), 7.44-7.41 (2H, m), 7.38-7.35 (1H, m), 7.19 (2H, d, J=6.7 Hz), 5.24 (2H, s), 4.25-4.23 (1H, m), 3.18-3.15 (1H, m), 1.99-1.71 (8H, m). LC/MS: 442 [M+H].

(4-benzyloxyphenyl)-(4-chloro-7H-pyrrolo[2,3-d]pyrimidin-5-yl)methanone (154a): $^1$H-NMR (DMSO-$d_6$) δ: 13.21 (1H, s), 8.72 (1H, s), 8.14 (1H, s), 7.86 (2H, d, J=9.2 Hz), 7.51-7.33 (5H, m), 7.16 (2H, d, J=9.2 Hz), 5.23 (2H, s). LC/MS: 364 [M+H].

Example 114: (4-(((3R,6S)-6-((S)-1-aminoethyl)tetrahydro-2H-pyran-3-yl)amino)-7H-pyrrolo[2,3-d]pyrimidin-5-yl)(2-chloro-4-phenoxyphenyl)methanone (I-166)

Removal of the phthaloyl group from 2-((S)-1-((2S,5R)-5-((5-(2-chloro-4-phenoxybenzoyl)-7H-pyrrolo[2,3-d]pyrimidin-4-yl)amino)tetrahydro-2H-pyran-2-yl)ethyl)isoindoline-1,3-dione (166a) provided (((3R,6S)-6-((S)-1-aminoethyl)tetrahydro-2H-pyran-3-yl)amino)-7H-pyrrolo[2,3-d]pyrimidin-5-yl)(2-chloro-4-phenoxyphenyl)methanone (I-166). $^1$H-NMR (DMSO-$d_6$) δ: 8.60 (1H, d, J=7.3 Hz), 8.22 (1H, s), 7.58 (1H, s), 7.55 (1H, d, J=8.5 Hz), 7.49-7.46 (2H, m), 7.26-7.24 (1H, m), 7.19-7.17 (3H, m), 7.02-7.00 (1H, m), 4.22-4.18 (1H, m), 4.12-4.09 (1H, m), 3.13-3.03 (2H, m), 2.79-2.77 (1H, m), 2.19-2.16 (1H, m), 1.80-1.76 (1H, m), 1.56-1.42 (2H, m), 0.98 (3H, q, J=6.7 Hz). LC/MS: 492 [M+H].

2-((S)-1-((2S,5R)-5-((5-(2-chloro-4-phenoxybenzoyl)-7H-pyrrolo[2,3-d]pyrimidin-4-yl)amino)tetrahydro-2H-pyran-2-yl)ethyl)isoindoline-1,3-dione (166a) was synthesized according to General Procedure A from (2-chloro-4-phenoxy-phenyl)-(4-chloro-7H-pyrrolo[2,3-d]-pyrimidin-5-yl)methanone and 2-((S)-1-((2S,5R)-5-aminotetrahydro-2H-pyran-2-yl)ethyl)isoindoline-1,3-dione (166b). $^1$H-NMR (DMSO-$d_6$) δ: 8.57 (1H, d, J=7.3 Hz), 8.21 (1H, s), 7.88-7.83 (4H, m), 7.62 (1H, s), 7.56 (1H, d, J=8.5 Hz), 7.49-7.47 (2H, m), 7.26-7.24 (1H, m), 7.19-7.18 (3H, m), 7.02-7.00 (1H, m), 4.21-4.04 (3H, m), 3.93-3.90 (1H, m), 3.00-2.98 (1H, m), 2.22-2.19 (1H, m), 2.02-2.00 (1H, m), 1.71-1.57 (1H, m), 1.53-1.39 (4H, m). LC/MS: 622 [M+H].

Boc deprotection of N-((3R,6S)-6-((1S)-1-(1,3-dioxoisoindolin-2-yl)ethyl)-tetrahydro-2H-pyran-3-yl)carbamate provided 2-((S)-1-((2S,5R)-5-aminotetrahydro-2H-pyran-2-yl)ethyl)isoindoline-1,3-dione 166b. LC/MS: 275 [M+H].

Example 115: (2-chloro-4-phenoxyphenyl)(4-(((3R, 6S)-6-((S)-1-(dimethylamino)ethyl) tetrahydro-2H-pyran-3-yl)amino)-7H-pyrrolo[2,3-d]pyrimidin-5-yl)methanone (I-167)

Reductive methylation of Compound I-166 with formaline/sodium triacetoxyborohydride provided (2-chloro-4-phenoxyphenyl)(4-(((3R,6S)-6-((S)-1-(dimethylamino)ethyl)tetrahydro-2H-pyran-3-yl)amino)-7H-pyrrolo[2,3-d]pyrimidin-5-yl)methanone (I-167). $^1$H-NMR (DMSO-$d_6$) δ: 12.62 (1H, br s), 8.59 (1H, d, J=7.3 Hz), 8.25 (1H, s), 7.62 (1H, s), 7.57 (1H, d, J=8.5 Hz), 7.49-7.47 (2H, m), 7.27-7.25 (1H, m), 7.19-7.18 (3H, m), 7.03-7.01 (1H, m), 4.18-4.10 (2H, m), 3.39-3.37 (2H, m), 3.10-3.08 (1H, m), 2.21-2.17 (7H, m), 1.66-1.52 (3H, m), 0.93-0.92 (3H, m). LC/MS: 520 [M+H].

Example 116: 2-(dimethylamino)-N-(cis-4-((5-(4-phenoxybenzoyl)-7H-pyrrolo[2,3-d]pyrimidin-4-yl)amino)cyclohexyl)acetamide (I-170)

Acylation of Compound I-130 provided 2-(dimethylamino)-N-(cis-4-((5-(4-phenoxybenzoyl)-7H-pyrrolo[2,3-d]pyrimidin-4-yl)amino)cyclohexyl)acetamide (I-170). $^1$H-NMR (DMSO-$d_6$) δ: 12.65 (1H, s), 8.99 (1H, d, J=7.3 Hz), 8.22 (1H, s), 7.85 (2H, d, J=8.5 Hz), 7.80 (1H, s), 7.61 (1H, d, J=7.3 Hz), 7.48 (2H, t, J=7.9 Hz), 7.25 (1H, t, J=7.3 Hz), 7.16 (2H, d, J=7.9 Hz), 7.10 (2H, d, J=8.5 Hz), 4.26-4.22 (1H, m), 3.78-3.74 (1H, m), 2.85 (2H, s), 2.19 (6H, s), 1.84-1.59 (8H, m). LC/MS: 513 [M+H].

Example 117: (2S,5R)—N-((2R,3R)-1,3-dihydroxybutan-2-yl)-5-((5-(4-phenoxybenzoyl)-7H-pyrrolo[2,3-d]pyrimidin-4-yl)amino)tetrahydro-2H-pyran-2-carboxamide (I-175)

Condensation of (2S,5R)-5-((5-(4-phenoxybenzoyl)-7H-pyrrolo[2,3-d]pyrimidin-4-yl)amino)tetrahydro-2H-pyran-2-carboxylic acid (LC/MS: 459 [M+H]) and (2R,3R)-2-aminobutane-1,3-diol provided (2S,5R)—N-((2R,3R)-1,3-dihydroxybutan-2-yl)-5-((5-(4-phenoxybenzoyl)-7H-pyrrolo[2,3-d]pyrimidin-4-yl)amino) tetrahydro-2H-pyran-2-carboxamide (I-175). $^1$H-NMR (DMSO-$d_6$) δ: 12.71 (1H, s), 8.71 (1H, d, J=7.3 Hz), 8.25 (1H, s), 7.87-7.82 (3H, m), 7.51-7.45 (2H, m), 7.25 (1H, t, J=7.3 Hz), 7.18-7.14 (2H, m), 7.09 (2H, d, J=8.5 Hz), 6.95 (1H, d, J=8.5 Hz), 4.82 (1H, d, J=4.9 Hz), 4.72 (1H, t, J=5.5 Hz), 4.28-4.17 (2H, m), 3.98-3.86 (2H, m), 3.65-3.58 (1H, m), 3.44-3.22 (3H, m), 2.23-2.10 (2H, m), 1.74-1.46 (2H, m), 1.02 (3H, d, J=6.7 Hz). LC/MS: 546 [M+H].

Example 118: (2S,5R)—N—((R)-2,3-dihydroxypropyl)-5-((5-(4-phenoxybenzoyl)-7H-pyrrolo[2,3-d]pyrimidin-4-yl)amino)tetrahydro-2H-pyran-2-carboxamide (I-176)

Condensation of (R)-3-aminopropane-1,2-diol and (2S,5R)-5-((5-(4-phenoxybenzoyl)-7H-pyrrolo[2,3-d]pyrimidin-4-yl)amino)tetrahydro-2H-pyran-2-carboxylic acid and the applicable amine provided (2S,5R)—N—((R)-2,3-dihydroxypropyl)-5-((5-(4-phenoxybenzoyl)-7H-pyrrolo[2,3-d]pyrimidin-4-yl)amino)tetrahydro-2H-pyran-2-carboxamide (I-176). $^1$H-NMR (CDCl$_3$) δ: 12.70 (1H, s), 8.71 (1H, d, J=7.3 Hz), 8.25 (1H, s), 7.87-7.82 (3H, m), 7.54-7.45 (3H, m), 7.28-7.23 (1H, m), 7.19-7.14 (2H, m), 7.11-7.07 (2H, m), 4.87 (1H, d, J=5.5 Hz), 4.60 (1H, t, J=5.8 Hz), 4.27-4.14 (2H, m), 3.88 (1H, dd, J=11.0, 2.4 Hz), 3.55-3.47 (1H, m), 3.36-3.21 (4H, m), 3.07-3.00 (1H, m), 2.23-2.06 (2H, m), 1.73-1.47 (2H, m). LC/MS: 532 [M+H].

Example 119: (2-chloro-4-phenoxyphenyl)(4-((trans-4-((dimethylamino)methyl)-4-hydroxycyclohexyl)amino)-7H-pyrrolo[2,3-d]pyrimidin-5-yl)methanone (I-177)

(2-chloro-4-phenoxyphenyl)(4-((trans-4-((dimethylamino)methyl)-4-hydroxycyclohexyl)amino)-7H-pyrrolo[2,3-d]pyrimidin-5-yl)methanone (I-177) was synthesized from 4-amino-1-((dimethylamino)methyl)cyclohexan-1-ol (177a) and (2-chloro-4-phenoxy-phenyl)-(4-chloro-7H-pyrrolo[2,3-d]pyrimidin-5-yl)-methanone according to General Procedure B.

Synthesis of 177a

Cbz deprotection of benzyl N-(4-((dimethylamino)methyl)-4-hydroxy-cyclohexyl)carbamate (177b) provided 4-amino-1-((dimethylamino)methyl)cyclohexan-1-ol (177a).

Synthesis of 177b

Benzyl N-(4-((dimethylamino)methyl)-4-hydroxy-cyclohexyl)carbamate (177b, cis stereoisomer) was synthesized from benzyl N-(1-oxaspiro[2.5]octan-6-yl)carbamate (cis/trans mixture) and dimethylamine followed by stereoisomer separation (isomer A, B; configurations are unknown). Cbz group of isomer A (given trans configuration for differentiation purposes only) was removed. $^1$H-NMR (DMSO-d$_6$) δ: 12.69 (1H, s), 8.71 (1H, d, J=7.3 Hz), 8.22 (1H, s), 7.59-7.58 (2H, m), 7.50-7.47 (2H, m), 7.27-7.24 (1H, m), 7.20-7.18 (3H, m), 7.02 (1H, dd, J=8.5, 2.4 Hz), 4.04-3.97 (2H, m), 2.30-2.25 (9H, m), 1.85-1.83 (2H, m), 1.68-1.65 (4H, m), 1.45-1.42 (2H, m). LC/MS: 520 [M+H].

Example 120: (2-chloro-4-phenoxyphenyl)(4-((cis-4-((dimethylamino)methyl)-4-hydroxycyclohexyl)amino)-7H-pyrrolo[2,3-d]pyrimidin-5-yl)methanone (I-178)

Cbz group of isomer B from Example 119 above (given cis configuration for differentiation purposes only) was removed. (2-chloro-4-phenoxyphenyl)(4-((cis-4-((dimethylamino)methyl)-4-hydroxycyclohexyl)amino)-7H-pyrrolo[2,3-d]pyrimidin-5-yl)methanone (I-178) was synthesized from the resultant cis amine and (2-chloro-4-phenoxy-phenyl)-(4-chloro-7H-pyrrolo[2,3-d]pyrimidin-5-yl)-methanone according to General Procedure B. $^1$H-NMR (DMSO-d$_6$) δ: 12.70 (1H, s), 8.89 (1H, d, J=7.3 Hz), 8.23 (1H, s), 7.60-7.59 (2H, m), 7.50-7.46 (2H, m), 7.27-7.23 (1H, m), 7.20-7.17 (3H, m), 7.02 (1H, dd, J=8.5, 2.4 Hz), 4.22-4.05 (2H, m), 2.30-2.23 (9H, m), 2.00-1.95 (2H, m), 1.75-1.73 (2H, m), 1.48-1.46 (4H, m). LC/MS: 520 [M+H].

Example 121: N-(cis-4-((5-(2-chloro-4-phenoxybenzoyl)-7H-pyrrolo[2,3-d]pyrimidin-4-yl)amino)cyclohexyl)-2-(dimethylamino)acetamide (I-181)

Acylation of Compound I-141 provided N-(cis-4-((5-(2-chloro-4-phenoxybenzoyl)-7H-pyrrolo[2,3-d]pyrimidin-4-yl)amino)cyclohexyl)-2-(dimethylamino)acetamide (I-181). $^1$H-NMR (DMSO-d$_6$) δ: 12.73 (1H, s), 8.95 (1H, d, J=7.3 Hz), 8.24 (1H, s), 7.63-7.59 (3H, m), 7.48 (2H, t, J=7.6 Hz), 7.26 (1H, t, J=7.3 Hz), 7.21-7.18 (3H, m), 7.03 (1H, dd, J=8.5, 2.4 Hz), 4.29-4.25 (1H, m), 3.79-3.74 (1H, m), 2.86 (2H, s), 2.19 (6H, s), 1.81-1.60 (8H, m). LC/MS: 547 [M+H].

Example 122: (2-chloro-4-(3-fluorophenoxy)phenyl)(4-(((3R,6S)-6-((R)-1-hydroxyethyl) tetrahydro-2H-pyran-3-yl)amino)-7H-pyrrolo[2,3-d]pyrimidin-5-yl)methanone (I-182)

(2-chloro-4-(3-fluorophenoxy)phenyl)(4-(((3R,6S)-6-((R)-1-hydroxyethyl) tetrahydro-2H-pyran-3-yl)amino)-7H-pyrrolo[2,3-d]pyrimidin-5-yl)methanone (I-182) was synthesized from according to General Procedure B using chloro-7H-pyrrolo[2,3-d]pyrimidin-5-yl)methanone and the applicable amine. $^1$H-NMR (DMSO-d$_6$) δ: 12.78 (1H, s), 8.58 (1H, d, J=7.3 Hz), 8.25 (1H, s), 7.68 (1H, s), 7.60 (1H, d, J=8.5 Hz), 7.50 (1H, q, J=7.9 Hz), 7.31 (1H, d, J=2.4 Hz), 7.13-7.05 (3H, m), 7.02 (1H, dd, J=7.9, 1.8 Hz), 4.60 (1H, d, J=5.5 Hz), 4.19-4.10 (2H, m), 3.53-3.46 (1H, m), 3.13-3.06 (2H, m), 2.22-2.17 (1H, m), 1.95-1.90 (1H, m), 1.59-1.49 (1H, m), 1.46-1.36 (1H, m), 1.08 (3H, d, J=6.1 Hz). LC/MS: 511 [M+H].

(2-chloro-4-(3-fluorophenoxy)phenyl)-(4-chloro-7H-pyrrolo[2,3-d]pyrimidin-5-yl)methanone was synthesized from methyl 2-chloro-4-(3-fluorophenoxy)benzoate. Methyl 2-chloro-4-(3-fluorophenoxy)benzoate was synthesized from methyl 2-chloro-4-fluorobenzoate and 3-fluorophenol.

Example 123: (2-chloro-4-(3-chlorophenoxy)phenyl)(4-(((3R,6S)-6-((R)-1-hydroxyethyl) tetrahydro-2H-pyran-3-yl)amino)-7H-pyrrolo[2,3-d]pyrimidin-5-yl)methanone (I-183)

(2-chloro-4-(3-chlorophenoxy)phenyl)(4-(((3R,6S)-6-((R)-1-hydroxyethyl) tetrahydro-2H-pyran-3-yl)amino)-7H-pyrrolo[2,3-d]pyrimidin-5-yl)methanone (I-183) was synthesized according to General Procedure B from (2-chloro-4-(3-chlorophenoxy)phenyl)-(4-chloro-7H-pyrrolo[2,3-d]pyrimidin-5-yl)methanone and the applicable amine. $^1$H-NMR (DMSO-d$_6$) δ: 12.78 (1H, s), 8.58 (1H, d, J=7.3 Hz), 8.25 (1H, s), 7.68 (1H, d, J=2.4 Hz), 7.60 (1H, d, J=8.5 Hz), 7.48 (1H, t, J=8.2 Hz), 7.32-7.29 (3H, m), 7.17-7.14 (1H, m), 7.10 (1H, dd, J=8.2, 2.1 Hz), 4.60 (1H, d, J=5.5 Hz), 4.19-4.10 (2H, m), 3.53-3.46 (1H, m), 3.13-3.06 (2H, m), 2.22-2.18 (1H, m), 1.95-1.90 (1H, m), 1.60-1.49 (1H, m), 1.46-1.36 (1H, m), 1.08 (3H, d, J=6.1 Hz). LC/MS: 527 [M+H].

(2-chloro-4-(3-chlorophenoxy)phenyl)-(4-chloro-7H-pyrrolo[2,3-d]pyrimidin-5-yl)methanone was synthesized from methyl 2-chloro-4-(3-chlorophenoxy)benzoate. Methyl 2-chloro-4-(3-chlorophenoxy)benzoate was synthesized from methyl 2-chloro-4-fluorobenzoate and 3-chlorophenol.

Example 124: (4-(((1R,3R)-3-aminocyclopentyl)amino)-7H-pyrrolo[2,3-d]pyrimidin-5-yl)(4-phenoxyphenyl)methanone (I-189)

Deprotection of Compound I-184 provided (4-(((1R,3R)-3-aminocyclopentyl)amino)-7H-pyrrolo[2,3-d]pyrimidin-5-yl)(4-phenoxyphenyl)methanone (I-189). $^1$H-NMR (DMSO-d$_6$) δ: 13.35 (1H, br s), 9.75 (1H, br s), 8.39 (1H, s), 8.16 (3H, br s), 8.04 (1H, br s), 7.90-7.84 (2H, m), 7.52-7.46 (2H, m), 7.27 (1H, t, J=7.3 Hz), 7.17 (2H, d, J=7.9 Hz), 7.13-7.08 (2H, m), 4.73-4.63 (1H, m), 3.80-3.69 (1H, m), 2.40-2.32 (1H, m), 2.27-2.15 (2H, m), 2.11-2.03 (1H, m), 1.79-1.66 (2H, m). LC/MS: 414 [M+H].

Example 125: (4-((cis-3-aminocyclobutyl)amino)-7H-pyrrolo[2,3-d]pyrimidin-5-yl)(4-phenoxyphenyl)methanone (I-190)

Deprotection of Compound I-186 provided (4-((cis-3-aminocyclobutyl)amino)-7H-pyrrolo[2,3-d]pyrimidin-5-yl)(4-phenoxyphenyl)methanone (I-190). $^1$H-NMR (DMSO-$d_6$) δ: 13.13 (1H, br s), 9.52 (1H, br s), 8.33 (1H, s), 8.17 (3H, br s), 7.99 (1H, s), 7.90-7.85 (2H, m), 7.52-7.46 (2H, m), 7.30-7.25 (1H, m), 7.19-7.15 (2H, m), 7.13-7.09 (2H, m), 4.55-4.43 (1H, m), 3.60-3.47 (1H, m), 2.86-2.77 (2H, m), 2.27-2.16 (2H, m). LC/MS: 400 [M+H].

Example 126: (4-((trans-3-aminocyclobutyl)amino)-7H-pyrrolo[2,3-d]pyrimidin-5-yl)(4-phenoxyphenyl)methanone (I-191)

Deprotection of Compound I-185 provided (4-((trans-3-aminocyclobutyl)amino)-7H-pyrrolo[2,3-d]pyrimidin-5-yl)(4-phenoxyphenyl)methanone (I-191). $^1$H-NMR (DMSO-$d_6$) δ: 13.09 (1H, br s), 8.34 (1H, s), 8.31-8.22 (3H, br m), 7.98 (1H, br s), 7.88 (2H, d, J=9.2 Hz), 7.52-7.47 (2H, m), 7.29-7.24 (1H, m), 7.19-7.15 (2H, m), 7.13-7.09 (2H, m), 4.86-4.75 (1H, m), 4.06-3.61 (1H, m), 2.71-2.60 (2H, m), 2.48-2.39 (2H, m). LC/MS: 400 [M+H].

Example 127: Compound 192: N-((1R,3R)-3-((5-(4-phenoxybenzoyl)-7H-pyrrolo[2,3-d]pyrimidin-4-yl)amino)cyclopentyl)acetamide (I-192)

Acylation of Compound I-189 gave N-((1R,3R)-3-((5-(4-phenoxybenzoyl)-7H-pyrrolo[2,3-d]pyrimidin-4-yl)amino)cyclopentyl)acetamide (I-192). $^1$H-NMR (CDCl$_3$) δ: 9.17 (1H, d, J=7.3 Hz), 8.34 (1H, s), 7.82-7.77 (2H, m), 7.60 (1H, s), 7.46-7.38 (2H, m), 7.21 (1H, t, J=7.3 Hz), 7.14-7.04 (4H, m), 5.73 (1H, d, J=7.3 Hz), 4.76-4.63 (1H, m), 4.54-4.43 (1H, m), 2.42-2.28 (2H, m), 2.20-2.00 (2H, m), 1.98 (3H, s), 1.83-1.70 (1H, m), 1.62-1.49 (1H, m). LC/MS: 456 [M+H].

Example 128: (S)—N-(cis-4-((5-(2-chloro-4-phenoxybenzoyl)-7H-pyrrolo[2,3-d]pyrimidin-4-yl)amino)cyclohexyl)-2-hydroxypropanamide (I-193)

Acylation of Compound I-141 provided (S)—N-(cis-4-((5-(2-chloro-4-phenoxybenzoyl)-7H-pyrrolo[2,3-d]pyrimidin-4-yl)amino)cyclohexyl)-2-hydroxypropanamide (I-193). $^1$H-NMR (DMSO-$d_6$) δ: 12.74 (1H, s), 8.95 (1H, d, J=7.3 Hz), 8.24 (1H, s), 7.63 (1H, s), 7.60 (1H, d, J=8.5 Hz), 7.51-7.43 (3H, m), 7.27-7.24 (1H, m), 7.21-7.17 (3H, m), 7.03 (1H, dd, J=8.5, 2.4 Hz), 5.39 (1H, d, J=5.5 Hz), 4.31-4.24 (1H, m), 4.00-3.93 (1H, m), 3.77-3.69 (1H, m), 1.59-1.83 (8H, m), 1.19 (3H, d, J=6.7 Hz). LC/MS: 534 [M+H].

Example 129: N-(cis-4-((5-(2-chloro-4-phenoxybenzoyl)-7H-pyrrolo[2,3-d]pyrimidin-4-yl)amino)cyclohexyl)-2-hydroxy-2-methylpropanamide (I-194)

Acylation of compound I-141 gave N-(cis-4-((5-(2-chloro-4-phenoxybenzoyl)-7H-pyrrolo[2,3-d]pyrimidin-4-yl)amino)cyclohexyl)-2-hydroxy-2-methylpropanamide (I-194). $^1$H-NMR (DMSO-$d_6$) δ: 12.74 (1H, s), 8.96 (1H, d, J=7.3 Hz), 8.24 (1H, s), 7.64 (1H, s), 7.61 (1H, d, J=8.5 Hz), 7.50-7.46 (2H, m), 7.29-7.24 (2H, m), 7.21-7.17 (3H, m), 7.03 (1H, dd, J=8.5, 2.4 Hz), 5.46 (1H, s), 4.32-4.25 (1H, m), 3.74-3.65 (1H, m), 1.60-1.83 (8H, m), 1.24 (6H, s). LC/MS: 548 [M+H].

Example 130: N—((R)-1-((2S,5R)-5-((5-(2-chloro-4-phenoxybenzoyl)-7H-pyrrolo[2,3-d]pyrimidin-4-yl)amino)tetrahydro-2H-pyran-2-yl)ethyl)acetamide (I-195)

N—((R)-1-((2S,5R)-5-((5-(2-chloro-4-phenoxybenzoyl)-7H-pyrrolo[2,3-d]pyrimidin-4-yl)amino)tetrahydro-2H-pyran-2-yl)ethyl)acetamide (I-195) was synthesized according to General Procedure B from N-((1R)-1-((2S,5R)-5-aminotetrahydro-2H-pyran-2-yl)ethyl)acetamide hydrochloride salt (195a) and (2-chloro-4-phenoxy-phenyl)-(4-chloro-7H-pyrrolo[2,3-d]-pyrimidin-5-yl)methanone. $^1$H-NMR (DMSO-$d_6$) δ: 12.77 (1H, s), 8.59 (1H, d, J=6.7 Hz), 8.25 (1H, s), 7.80 (1H, d, J=8.5 Hz), 7.64 (1H, s), 7.57 (1H, d, J=8.5 Hz), 7.51-7.45 (2H, m), 7.28-7.23 (1H, m), 7.20-7.17 (3H, m), 7.02 (1H, dd, J=8.2, 2.1 Hz), 4.22-4.10 (2H, m), 3.82-3.76 (1H, m), 3.25-3.18 (1H, m), 3.15-3.08 (1H, m), 2.22-2.15 (1H, m), 1.82-1.75 (4H, m), 1.60-1.41 (2H, m), 1.05 (3H, d, J=6.7 Hz). LC/MS: 534 [M+H].

Synthesis of N-((1R)-1-((2S,5R)-5-aminotetrahydro-2H-pyran-2-yl)ethyl)acetamide hydrochloride salt (195a)

tert-butyl N-((3R,6S)-6-((1R)-1-azidoethyl)tetrahydro-2H-pyran-3-yl)carbamate was synthesized from tert-butyl N-((3R,6S)-6-((1S)-1-hydroxyethyl)tetrahydro-2H-pyran-3-yl)carbamate under Mitsunobu conditions using DPPA. LC/MS: 215 [M-t-Bu+2H]. Reduction of the Azide group via hydrogenation (LC/MS: 245 [M+H]) followed by acetylation provided tert-butyl N-((3R,6S)-6-((1R)-1-acetamidoethyl)tetrahydro-2H-pyran-3-yl)carbamate. $^1$H-NMR (CDCl$_3$) δ: 5.85 (1H, br s), 4.24 (1H, br s), 4.10-4.07 (1H, m), 4.04-3.96 (1H, m), 3.59-3.56 (1H, m), 3.27-3.25 (1H, m), 2.97-2.95 (1H, m), 2.12-2.06 (1H, m), 1.98 (3H, s), 1.50-1.47 (10H, m), 1.32-1.19 (2H, m), 1.09 (3H, d, J=6.7 Hz). LC/MS: 287 [M+H].

Boc deprotection of tert-butyl N-((3R,6S)-6-((1R)-1-acetamidoethyl)tetrahydro-2H-pyran-3-yl)carbamate provided N-((1R)-1-((2S,5R)-5-aminotetrahydro-2H-pyran-2-yl)ethyl)acetamide hydrochloride salt (195a). $^1$H-NMR (DMSO-$d_6$) δ: 8.21 (3H, br s), 7.81 (1H, d, J=8.5 Hz), 4.05-4.02 (1H, m), 3.74-3.70 (1H, m), 3.32-3.20 (1H, m), 3.09-3.01 (2H, m), 2.08-2.05 (1H, m), 1.79 (3H, s), 1.69-1.65 (1H, m), 1.55-1.50 (1H, m), 1.33-1.28 (1H, m), 1.01 (3H, d, J=6.7 Hz). LC/MS: 187 [M+H].

Example 131: N-(cis-3-((5-(4-phenoxybenzoyl)-7H-pyrrolo[2,3-d]pyrimidin-4-yl)amino) cyclobutyl)acetamide (I-196)

Acylation of Compound I-190 gave N-(cis-3-((5-(4-phenoxybenzoyl)-7H-pyrrolo[2,3-d]pyrimidin-4-yl)amino)cyclobutyl)acetamide (I-196). $^1$H-NMR (DMSO-$d_6$) δ: 12.70 (1H, br s), 8.98 (1H, d, J=6.1 Hz), 8.23 (1H, s), 8.21 (1H, d, J=7.9 Hz), 7.88-7.81 (3H, m), 7.51-7.46 (2H, m), 7.29-7.24 (1H, m), 7.19-7.15 (2H, m), 7.09 (2H, d, J=8.5 Hz), 4.42-

4.30 (1H, m), 4.10-3.98 (1H, m), 2.77-2.67 (2H, m), 1.94-1.84 (2H, m), 1.78 (3H, s). LC/MS: 442 [M+H].

Example 132: (4-(((3R,6S)-6-((R)-1-hydroxyethyl)tetrahydro-2H-pyran-3-yl)amino)-7H-pyrrolo[2,3-d]pyrimidin-5-yl)(2-methyl-4-phenoxyphenyl)methanone (I-197)

(4-(((3R,6S)-6-((R)-1-hydroxyethyl)tetrahydro-2H-pyran-3-yl)amino)-7H-pyrrolo[2,3-d]pyrimidin-5-yl)(2-methyl-4-phenoxyphenyl)methanone (I-197) was synthesized according to General Procedure B from (4-chloro-7H-pyrrolo[2,3-d]pyrimidin-5-yl)-(2-methyl-4-phenoxyphenyl)-methanone and the applicable amine. $^1$H-NMR (DMSO-d$_6$) δ: 8.72 (1H, d, J=7.3 Hz), 8.24 (1H, s), 7.51 (1H, s), 7.47-7.43 (3H, m), 7.21 (1H, t, J=7.6 Hz), 7.12 (2H, d, J=7.9 Hz), 6.98 (1H, d, J=2.4 Hz), 6.85 (1H, dd, J=7.9, 2.4 Hz), 4.61 (1H, d, J=5.5 Hz), 4.19-4.09 (2H, m), 3.53-3.46 (1H, m), 3.13-3.05 (2H, m), 2.28 (3H, s), 2.21-2.17 (1H, m), 1.95-1.90 (1H, m), 1.59-1.49 (1H, m), 1.46-1.36 (1H, m), 1.08 (3H, d, J=6.1 Hz). LC/MS: 473 [M+H].

Example 133: N-(trans-3-((5-(4-phenoxybenzoyl)-7H-pyrrolo[2,3-d]pyrimidin-4-yl)amino)cyclobutyl)acetamide (I-199)

Acylation of Compound I-191 provided N-(trans-3-((5-(4-phenoxybenzoyl)-7H-pyrrolo[2,3-d]pyrimidin-4-yl)amino)cyclobutyl)acetamide (I-199). $^1$H-NMR (DMSO-d$_6$) δ: 13.13 (1H, br s), 8.37-8.32 (2H, m), 8.00 (1H, br s), 7.92-7.87 (2H, m), 7.52-7.46 (2H, m), 7.29-7.24 (1H, m), 7.19-7.15 (2H, m), 7.11 (2H, d, J=8.5 Hz), 4.57 (1H, br s), 4.40-4.30 (1H, m), 2.48-2.39 (2H, m), 2.38-2.28 (2H, m), 1.82 (3H, s). LC/MS: 442 [M+H].

Example 134: (S)-2-hydroxy-N-(cis-4-((5-(4-phenoxybenzoyl)-7H-pyrrolo[2,3-d]pyrimidin-4-yl)amino)cyclohexyl)propanamide (I-202)

Acylation of Compound I-130 provided (S)-2-hydroxy-N-(cis-4-((5-(4-phenoxybenzoyl)-7H-pyrrolo[2,3-d]pyrimidin-4-yl)amino)cyclohexyl)propanamide (I-202). $^1$H-NMR (DMSO-d$_6$) δ: 12.65 (1H, s), 9.00 (1H, d, J=7.3 Hz), 8.22 (1H, s), 7.87-7.84 (2H, m), 7.80 (1H, s), 7.50-7.46 (3H, m), 7.25 (1H, t, J=7.3 Hz), 7.18-7.15 (2H, m), 7.09 (2H, d, J=8.5 Hz), 5.38 (1H, d, J=5.5 Hz), 4.27-4.22 (1H, m), 4.00-3.93 (1H, m), 3.75-3.69 (1H, m), 1.83-1.63 (8H, m), 1.19 (3H, d, J=6.7 Hz). LC/MS: 500 [M+H].

Example 135: 2-hydroxy-2-methyl-N-(cis-4-((5-(4-phenoxybenzoyl)-7H-pyrrolo[2,3-d]pyrimidin-4-yl)amino)cyclohexyl)propanamide (I-203)

Acylation of Compound I-130 provided 2-hydroxy-2-methyl-N-(cis-4-((5-(4-phenoxybenzoyl)-7H-pyrrolo[2,3-d]pyrimidin-4-yl)amino)cyclohexyl)propanamide (I-203). $^1$H-NMR (DMSO-d$_6$) δ: 12.65 (1H, s), 9.00 (1H, d, J=7.3 Hz), 8.23 (1H, s), 7.87-7.84 (2H, m), 7.80 (1H, s), 7.50-7.46 (2H, m), 7.32 (1H, d, J=7.9 Hz), 7.25 (1H, t, J=7.3 Hz), 7.18-7.15 (2H, m), 7.11-7.08 (2H, m), 5.44 (1H, s), 4.27-4.23 (1H, m), 3.71-3.67 (1H, m), 1.81-1.63 (8H, m), 1.24 (6H, s). LC/MS: 514 [M+H].

Example 136: (R)-2-hydroxy-N-(cis-4-((5-(4-phenoxybenzoyl)-7H-pyrrolo[2,3-d]pyrimidin-4-yl)amino)cyclohexyl)propanamide (I-206)

Acylation of Compound I-130 provided (R)-2-hydroxy-N-(cis-4-((5-(4-phenoxybenzoyl)-7H-pyrrolo[2,3-d]pyrimidin-4-yl)amino)cyclohexyl)propanamide (I-206). $^1$H-NMR (DMSO-d$_6$) δ: 12.65 (1H, s), 9.00 (1H, d, J=7.9 Hz), 8.22 (1H, s), 7.86 (2H, d, J=8.5 Hz), 7.80 (1H, s), 7.50-7.46 (3H, m), 7.25 (1H, t, J=7.6 Hz), 7.17-7.15 (2H, m), 7.11-7.08 (2H, m), 5.38 (1H, d, J=5.5 Hz), 4.26-4.23 (1H, m), 3.99-3.93 (1H, m), 3.75-3.70 (1H, m), 1.83-1.63 (8H, m), 1.19 (3H, d, J=6.7 Hz). LC/MS: 500 [M+H].

Example 137: (S)—N—((S)-1-((2S,5R)-5-((5-(2-chloro-4-phenoxybenzoyl)-7H-pyrrolo[2,3-d]pyrimidin-4-yl)amino)tetrahydro-2H-pyran-2-yl)ethyl)-2-hydroxypropanamide (I-208)

(S)—N—((S)-1-((2S,5R)-5-((5-(2-chloro-4-phenoxybenzoyl)-7H-pyrrolo[2,3-d]pyrimidin-4-yl)amino)tetrahydro-2H-pyran-2-yl)ethyl)-2-hydroxypropanamide (I-208) was synthesized according to General Procedure B from (S)—N—((S)-1-((2S,5R)-5-aminotetrahydro-2H-pyran-2-yl)ethyl)-2-hydroxypropanamide (208a). $^1$H-NMR (DMSO-d$_6$) δ: 12.94 (1H, br s), 8.80 (1H, br s), 8.30 (1H, s), 7.71 (1H, s), 7.58 (1H, d, J=8.5 Hz), 7.50-7.47 (2H, m), 7.27-7.26 (2H, m), 7.20-7.19 (3H, m), 7.04-7.02 (1H, m), 4.19-4.14 (2H, m), 4.01-3.99 (1H, m), 3.88-3.86 (1H, m), 3.41-3.38 (1H, m), 3.18-3.15 (1H, m), 2.19-2.17 (1H, m), 1.65-1.52 (3H, m), 1.22 (3H, d, J=6.7 Hz), 1.10 (3H, d, J=6.7 Hz). LC/MS: 564 [M+H].

Synthesis of (S)—N—((S)-1-((2S,5R)-5-aminotetrahydro-2H-pyran-2-yl)ethyl)-2-hydroxypropanamide (208a)

Boc deprotection of tert-butyl N-((3R,6S)-6-((1S)-1-(((2S)-2-hydroxy-propanoyl)amino)ethyl)tetrahydro-2H-pyran-3-yl)carbamate (208b) provided amine 208a. LC/MS: 217 [M+H].

Synthesis of tert-butyl N-((3R,6S)-6-((1S)-1-(((2S)-2-hydroxy-propanoyl)amino) ethyl)tetrahydro-2H-pyran-3-yl)carbamate (208b)

Acylation of tert-butyl N-((3R,6S)-6-((1S)-1-aminoethyl)tetrahydro-2H-pyran-3-yl)carbamate with (2S)-2-hydroxypropanoic acid provided tert-butyl N-((3R,6S)-6-((1S)-1-(((2S)-2-hydroxy-propanoyl)amino)ethyl)tetrahydro-2H-pyran-3-yl)carbamate (208b). $^1$H-NMR (CDCl$_3$) δ: 6.55 (1H, d, J=8.5 Hz), 4.26-4.18 (2H, m), 4.09-4.07 (1H, m), 4.04-3.96 (1H, m), 3.52-3.49 (1H, m), 3.24-3.20 (1H, m), 3.00-2.92 (2H, m), 2.08-2.06 (1H, m), 1.47-1.43 (13H, m), 1.32-1.26 (2H, m), 1.20 (3H, d, J=7.3 Hz). LC/MS: 317 [M+H].

Example 138: (S)—N-(((2S,5R)-5-((5-(2-chloro-4-phenoxybenzoyl)-7H-pyrrolo[2,3-d]pyrimidin-4-yl)amino)tetrahydro-2H-pyran-2-yl)methyl)-2-hydroxypropanamide (I-210)

Acylation of tert-Butyl N-((3R,6S)-6-(aminomethyl)tetrahydro-2H-pyran-3-yl)carbamate with (2S)-2-hydroxypropanoic acid provided tert-butyl N-((3R,6S)-6-((((2S)-2-hydroxypropanoyl)-amino)methyl)tetrahydro-2H-pyran-3-yl)carbamate (210a). LC/MS: 303 [M+H].

Boc deprotection of 210a provided (S)—N-(((2S,5R)-5-aminotetrahydro-2H-pyran-2-yl)methyl)-2-hydroxypropanamide (210b). LC/MS: 203 [M+H].

(S)—N-(((2S,5R)-5-((5-(2-chloro-4-phenoxybenzoyl)-7H-pyrrolo[2,3-d]pyrimidin-4-yl)amino)tetrahydro-2H-pyran-2-yl)methyl)-2-hydroxypropanamide (I-210) was synthesized according to General Procedure B from (S)—N-(((2S,5R)-5-aminotetrahydro-2H-pyran-2-yl)methyl)-2-hydroxypropanamide (210b) and (2-chloro-4-phenoxy-phenyl)-(4-chloro-7H-pyrrolo[2,3-d]pyrimidin-5-yl)-methanone. $^1$H-NMR (DMSO-$d_6$) δ: 12.92 (1H, br s), 8.78 (1H, br s), 8.31-8.28 (1H, m), 7.70 (1H, s), 7.59-7.57 (2H, m), 7.50-7.48 (2H, m), 7.27-7.26 (1H, m), 7.20-7.18 (3H, m), 7.02 (1H, dd, J=8.2, 2.1 Hz), 4.18-4.16 (2H, m), 4.04-3.96 (1H, m), 3.45 (1H, s), 3.17-3.15 (3H, m), 2.19-2.16 (1H, m), 1.78-1.75 (1H, m), 1.61-1.58 (1H, m), 1.43-1.40 (1H, m), 1.22-1.21 (3H, m). LC/MS: 550 [M+H].

Example 139: (R)—N—((S)-1-((2S,5R)-5-((5-(2-chloro-4-phenoxybenzoyl)-7H-pyrrolo[2,3-d]pyrimidin-4-yl)amino)tetrahydro-2H-pyran-2-yl)ethyl)-2-hydroxypropanamide (I-213)

Acylation of tert-butyl N-((3R,6S)-6-((1S)-1-aminoethyl)tetrahydro-2H-pyran-3-yl)carbamate with (2R)-2-hydroxypropanoic acid provided tert-butyl N-((3R,6S)-6-((1S)-1-(((2R)-2-hydroxy-propanoyl)amino)ethyl)tetrahydro-2H-pyran-3-yl)carbamate (213a). LC/MS: 317 [M+H].

Boc deprotection of tert-butyl N-((3R,6S)-6-((1S)-1-(((2R)-2-hydroxy-propanoyl)amino)ethyl)tetrahydro-2H-pyran-3-yl)carbamate (213a) provided (R)—N—((S)-1-((2S,5R)-5-aminotetrahydro-2H-pyran-2-yl)ethyl)-2-hydroxypropanamide (213b) LC/MS: 217 [M+H].

(R)—N—((S)-1-((2S,5R)-5-((5-(2-chloro-4-phenoxybenzoyl)-7H-pyrrolo[2,3-d]pyrimidin-4-yl)amino)tetrahydro-2H-pyran-2-yl)ethyl)-2-hydroxypropanamide (I-213) was synthesized according to General Procedure B from (R)—N—((S)-1-((2S,5R)-5-aminotetrahydro-2H-pyran-2-yl)ethyl)-2-hydroxypropanamide (213b) and (2-chloro-4-phenoxy-phenyl)-(4-chloro-7H-pyrrolo[2,3-d]pyrimidin-5-yl)methanone. $^1$H-NMR (DMSO-$d_6$) δ: 12.92 (1H, br s), 8.79 (1H, br s), 8.30 (1H, s), 7.70 (1H, s), 7.58 (1H, d, J=7.9 Hz), 7.49-7.47 (2H, m), 7.25-7.21 (5H, m), 7.03-7.01 (1H, m), 4.19-4.14 (2H, m), 3.98-3.97 (1H, m), 3.88-3.85 (1H, m), 3.41-3.38 (1H, m), 3.18-3.15 (1H, m), 2.21-2.18 (1H, m), 1.69-1.45 (3H, m), 1.24 (3H, d, J=6.7 Hz), 1.10 (3H, d, J=6.7 Hz). LC/MS: 564 [M+H].

Example 140: (R)—N-(((2S,5R)-5-((5-(2-chloro-4-phenoxybenzoyl)-7H-pyrrolo[2,3-d]pyrimidin-4-yl)amino)tetrahydro-2H-pyran-2-yl)methyl)-2-hydroxypropanamide (I-216)

Acylation of tert-Butyl N-((3R,6S)-6-(aminomethyl)tetrahydro-2H-pyran-3-yl)carbamate with (2R)-2-hydroxypropanoic acid provided tert-butyl N-((3R,6S)-6-((((2R)-2-hydroxypropanoyl)-amino)methyl)tetrahydro-2H-pyran-3-yl)carbamate (216a). LC/MS: 303 [M+H].

Boc deprotection of tert-butyl N-((3R,6S)-6-((((2R)-2-hydroxypropanoyl)-amino)methyl)tetrahydro-2H-pyran-3-yl)carbamate (216a) provided (R)—N-(((2S,5R)-5-aminotetrahydro-2H-pyran-2-yl)methyl)-2-hydroxypropanamide (216b) LC/MS: 203 [M+H].

(R)—N-(((2S,5R)-5-((5-(2-chloro-4-phenoxybenzoyl)-7H-pyrrolo[2,3-d]pyrimidin-4-yl)amino)tetrahydro-2H-pyran-2-yl)methyl)-2-hydroxypropanamide (I-216) was synthesized according to General Procedure B from (R)—N-(((2S,5R)-5-aminotetrahydro-2H-pyran-2-yl)methyl)-2-hydroxypropanamide (216b) and (2-chloro-4-phenoxy-phenyl)-(4-chloro-7H-pyrrolo[2,3-d]pyrimidin-5-yl)methanone. $^1$H-NMR (DMSO-$d_6$) δ: 12.89 (1H, br s), 8.75 (1H, br s), 8.29 (1H, s), 7.69 (1H, s), 7.60-7.58 (2H, m), 7.49-7.47 (2H, m), 7.27-7.25 (1H, m), 7.19-7.18 (3H, m), 7.03-7.02 (1H, m), 4.18-4.15 (2H, m), 3.98 (1H, q, J=6.5 Hz), 3.46-3.44 (1H, m), 3.27-3.25 (1H, m), 3.15-3.13 (2H, m), 2.20-2.17 (1H, m), 1.78-1.75 (1H, m), 1.61-1.58 (1H, m), 1.42-1.40 (1H, m), 1.22 (3H, d, J=6.7 Hz). LC/MS: 550 [M+H].

Example 141: General Procedure C

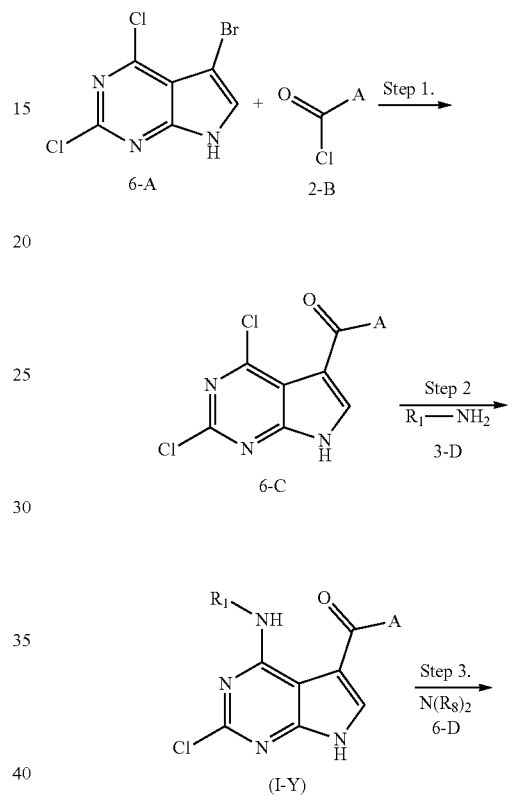

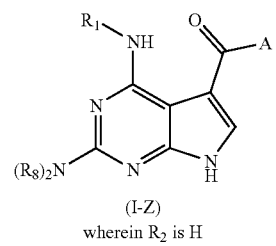

A is aryl or heteroaryl

Step 1. Intermediate 6-C

A mixture of 2,4-dichloro-7H-pyrrolo[2,3-d]pyrimidine (6-A, 2.00 g, 10.6 mmol), an aroyl chloride or heteroaroyl chloride (2-B, 1-3 eq.), and $AlCl_3$ (2-5 eq.) in nitrobenzene was heated at 70-90° C. for 1-6 hrs. Work-up and/or purification provided the corresponding aryl- or heteroaryl-(2,4-dichloro-7H-pyrrolo[2,3-d]pyrimidin-5-yl)methanone (6-C).

Step 2. Intermediate I-Y

A mixture of 6-C (1.00 g, 3.27 mmol), a primary amine (3-D, 1-4 eq.), and optionally a base (e.g., TEA, DIPEA, pyridine, and/or K₂CO₃ (1-5 eq.)) in a solvent (e.g., DMF, NMP, IPA, n-BuOH or neat) was heated (70-160° C.) for 5-50 hrs or heated (100-220° C.) under microwave radiation for 0.5-5 hrs. Work-up and/or purification provided the corresponding aryl- or heteroaryl-(4-substituted-amino-2-chloro-7H-pyrrolo[2,3-d]pyrimidin-5-yl)-methanone (I-Y).

Step 3. Compounds of Formula I-Z

A mixture of I-Y (70 mg, 0.145 mmol), a primary amine (6-D, 1-4 eq.), and optionally a base (e.g., TEA, DIPEA, pyridine, and/or K₂CO₃ (1-5 eq.)) in a solvent (e.g., DMF, NMP, IPA, n-BuOH or neat) was heated (70-160° C.) for 5-50 hrs or heated (100-220° C.) under microwave radiation for 0.5-5 hrs. Work-up and/or purification provided a compound of Formula (I) (aryl- or heteroaryl-(2-substituted-amino-4-substituted-amino-7H-pyrrolo[2,3-d]pyrimidin-5-yl)methanone (I-Z)).

The compounds of Formula (I) in Table 3 below were made according to General Procedure C.

TABLE 3

| Cmpd No. | $^1$H NMR and/or LC/MS data |
|---|---|
| I-226 | $^1$H-NMR (CDCl₃) δ: 12.73-12.90 (1H, m), 9.27-9.30 (1H, m), 8.38 (1H, d, J = 8.5 Hz), 7.79 (2H, d, J = 7.6 Hz), 7.60-7.63 (2H, m), 7.53 (2H, t, J = 7.6 Hz), 4.78-4.85 (1H, m), 3.85 (1H, dd, J = 11.3, 6.4 Hz), 3.61-3.71 (1H, m), 3.35-3.57 (2H, m), 2.31-2.40 (1H, m), 2.05-2.15 (1H, m), 1.46 (9H, s). MS (ESI) m/z: 408 [M + H]⁺. |
| I-230 | $^1$H-NMR (DMSO-d₆) δ: 12.67 (1H, s), 8.82 (1H, t, J = 5.5 Hz), 8.24 (1H, s), 7.78 (2H, d, J = 7.3 Hz), 7.74 (1H, s), 7.65 (1H, t, J = 7.3 Hz), 7.55 (2H, t, J = 7.6 Hz), 3.52 (2H, q, J = 6.5 Hz), 3.29-3.39 (4H, m), 2.20 (2H, t, J = 7.9 Hz), 1.78-1.95 (4H, m). MS (ESI) m/z: 364 [M + H]⁺. |

Example 142: (4-((cis-4-aminocyclohexyl)amino)-2-((1-methylpiperidin-4-yl)amino)-7H-pyrrolo[2,3-d]pyrimidin-5-yl)(o-tolyl)methanone (I-218)

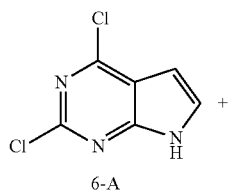

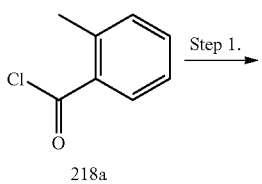

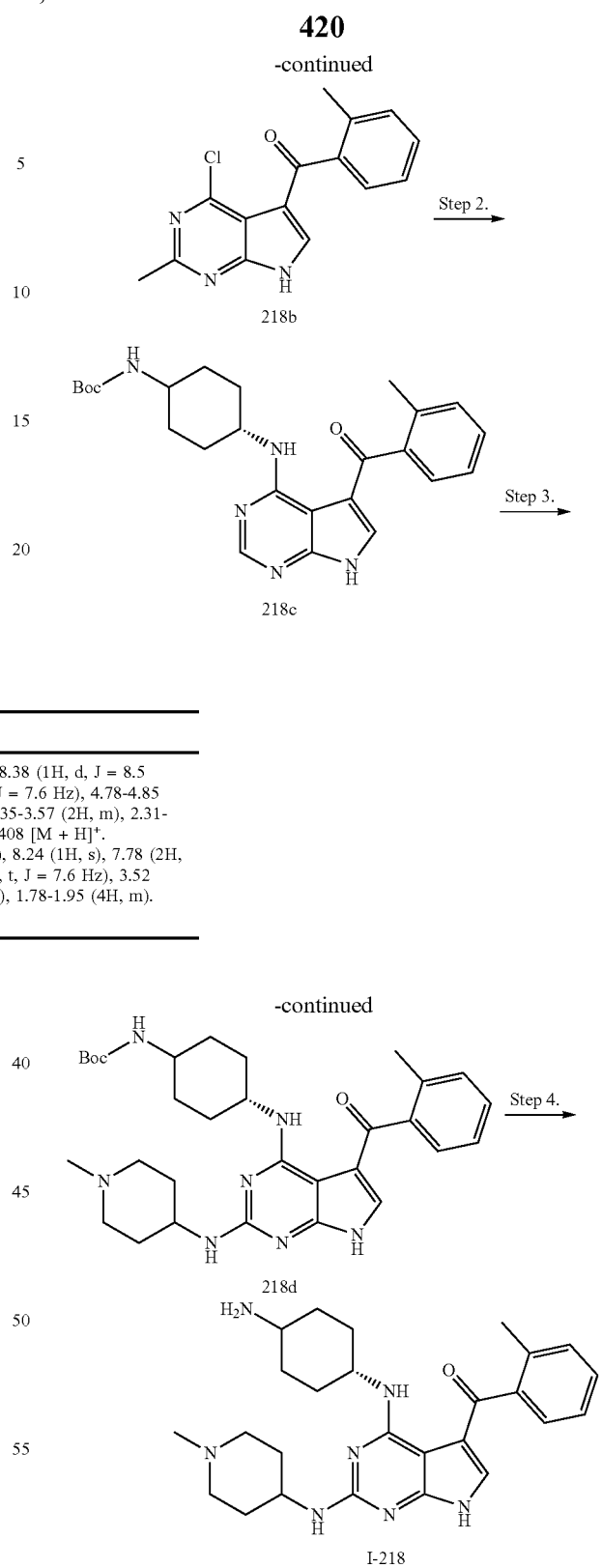

Step 1. (2,4-dichloro-7H-pyrrolo[2,3-d]pyrimidin-5-yl)-(o-tolyl)methanone (218 b)

The mixture of 2,4-dichloro-7H-pyrrolo[2,3-d]pyrimidine (6-A, 2.00 g, 10.6 mmol), 2-methylbenzoyl chloride (218a, 2.00 mL, 15.3 mmol), AlCl$_3$ (5.00 g, 37.5 mmol) and nitrobenzene (30 mL) was heated at 70° C. for 3 hrs. The resultant mixture was poured into ice and extracted with EtOAc. The extract was washed with water and brine, then dried over anhydrous Na$_2$SO$_4$, filtered and concentrated in vacuo. EtOAc and hexane was added to the residue and precipitate was collected by filtration to give (2,4-dichloro-7H-pyrrolo[2,3-d]pyrimidin-5-yl)-(o-tolyl)-methanone (218b, 2.20 g, 7.18 mmol, 68%). LC/MS: 306 [M+H].

Step 2. tert-butyl N-(cis-4-((2-chloro-5-(2-methylbenzoyl)-7H-pyrrolo[2,3-d]pyrimidin-4-yl)amino) cyclohexyl)carbamate (218c)

The mixture of (2,4-dichloro-7H-pyrrolo[2,3-d]pyrimidin-5-yl)-(o-tolyl)-methanone (218b, 1.00 g, 3.27 mmol), tert-butyl N-(cis-4-aminocyclohexyl)carbamate (909 mg, 4.25 mmol), DIPEA (850 μL, 4.97 mmol) and IPA (15 mL) was stirred at 160° C. for 1 h under microwave irradiation. The resultant mixture was diluted with chloroform and purified by column chromatography over SiO$_2$ eluting with CHCl$_3$-MeOH to give tert-butyl N-(cis-4-((2-chloro-5-(2-methylbenzoyl)-7H-pyrrolo[2, 3-d]pyrimidin-4-yl)amino) cyclohexyl)carbamate (218c, 1.40 g, 2.89 mmol, 89%) as colorless solid. LC/MS: 484 [M+H].

Step 3. tert-butyl N-(cis-4-((5-(2-methylbenzoyl)-2-((1-methyl-4-piperidyl)amino)-7H-pyrrolo[2,3-d] pyrimidin-4-yl)amino)cyclohexyl)carbamate (218d)

The mixture of tert-butyl N-(cis-4-((2-chloro-5-(2-methylbenzoyl)-7H-pyrrolo[2,3-d]pyrimidin-4-yl)amino)cyclohexyl)carbamate (218c, 70 mg, 0.145 mmol) and 1-methylpiperidin-4-amine (1 mL) was stirred at 160° C. for 1 h under microwave irradiation. The resultant mixture was poured into water, extracted with CHCl$_3$, dried over anhydrous Na$_2$SO$_4$, filtered, and concentrated in vacuo. The resulting residue was purified by column chromatography over SiO$_2$ eluting with CHCl$_3$-MeOH to give tert-butyl N-(cis-4-((5-(2-methylbenzoyl)-2-((1-methyl-4-piperidyl) amino)-7H-pyrrrol[2,3-d]pyrimidin-4-yl)amino)cyclohexyl)carbamate (218d, 68 mg, 0.121 mmol, 84%) as yellow oil. LC/MS: 562 [M+H].

Step 4. (4-((cis-4-aminocyclohexyl)amino)-2-((1-methyl-4-piperidyl)amino)-7H-pyrrolo[2,3-d]pyrimidin-5-yl)-(o-tolyl)methanone (I-218)

The mixture of tert-butyl N-(cis-4-((5-(2-methylbenzoyl)-2-((1-methyl-4-piperidyl)amino)-7H-pyrrolo[2,3-d]pyrimidin-4-yl)amino)cyclohexyl)carbamate (218d, 65 mg, 0.116 mmol) and dichloromethane (5 mL) was treated with TFA (2 mL) at ambient temperature and stirred for 1 hr. The mixture was concentrated in vacuo and the residue was purified by column chromatography over SiO$_2$ with CHCl$_3$-MeOH. Then the product was lyophilized to give (4-((cis-4-aminocyclohexyl)amino)-2-((1-methyl-4-piperidyl)amino)-7H-pyrrolo[2,3-d]pyrimidin-5-yl)-(o-tolyl)methanone (15 mg, 0.0325 mmol, 28%) as pale yellow solid. $^1$H-NMR (400 MHz, CD$_3$OD) δ: 7.42-7.26 (5H, m), 4.39-4.35 (1H, m), 3.85-3.79 (1H, m), 2.87-2.81 (3H, m), 2.33 (3H, s), 2.29 (3H, s), 2.25-2.15 (2H, m), 2.08-1.97 (4H, m), 1.84-1.57 (8H, m). LC/MS: 462 [M+H].

Example 143: (2-amino-4-(cis-4-aminocyclohexyl) amino)-7H-pyrrolo[2,3-d]pyrimidin-5-yl)(o-tolyl) methanone (I-219)

(2-amino-4-(cis-4-aminocyclohexyl)amino)-7H-pyrrolo[2,3-d]pyrimidin-5-yl)(o-tolyl)methanone (I-219) was synthesized according to General Procedure C from 4-methoxybenzyl amine (LC/MS: 585 [M+H]) followed by simultaneous Boc and benzyl deprotection. $^1$H-NMR (CD$_3$OD) δ: 7.42-7.26 (5H, m), 4.39-4.35 (1H, m), 2.80-2.74 (1H, m), 2.33 (3H, s), 2.01-1.94 (2H, m), 1.84-1.58 (6H, m). LC/MS: 365 [M+H].

Example 144: (4-((cis-4-aminocyclohexyl)amino)-2-(methylamino)-7H-pyrrolo[2,3-d]pyrimidin-5-yl)(o-tolyl)methanone (I-220)

(4-((cis-4-aminocyclohexyl)amino)-2-(methylamino)-7H-pyrrolo[2,3-d]pyrimidin-5-yl)(o-tolyl)methanone (I-220) was synthesized according to General Procedure C from N-methylamine (LC/MS: 479 [M+H]) followed by Boc deprotection. $^1$H-NMR (CDCl$_3$) δ: 9.10 (1H, d, J=7.8 Hz), 7.33-7.28 (2H, m), 7.23-7.17 (2H, m), 6.85 (1H, s), 4.73-4.69 (1H, m), 4.37-4.30 (1H, m), 2.92 (3H, d, J=5.1 Hz), 2.80-274 (1H, m), 2.32 (3H, s), 1.97-1.92 (2H, m), 1.77-1.54 (6H, m). LC/MS: 379 [M+H].

Example 145: (4-((cis-4-aminocyclohexyl)amino)-2-(4-methylpiperazin-1-yl)-7H-pyrrolo[2,3-d]pyrimidin-5-yl)(o-tolyl)methanone (I-221)

(4-((cis-4-aminocyclohexyl)amino)-2-(4-methylpiperazin-1-yl)-7H-pyrrolo[2,3-d]pyrimidin-5-yl)(o-tolyl)methanone (I-221) was synthesized according to General Procedure C from N-methylpiperazine followed by Boc deprotection. $^1$H-NMR (CD$_3$OD) δ: 9.06 (1H, d, J=6.7 Hz), 7.00-7.42 (5H, m), 4.38-4.42 (1H, m), 3.79-3.82 (4H, m), 2.82-2.89 (1H, m), 2.48-2.51 (4H, m), 2.34 (3H, s), 2.33 (3H, s), 2.02-2.06 (2H, m), 1.62-1.87 (6H, m). MS (ESI) m/z: 448 [M+H]$^+$.

Example 146: N-(cis-4-((5-(2-chlorobenzoyl)-7H-pyrrolo[2,3-d]pyrimidin-4-yl)amino) cyclohexyl)-2-(4-methylpiperazin-1-yl)acetamide (I-222)

Acylation of Compound I-6 gave N-(cis-4-((5-(2-chlorobenzoyl)-7H-pyrrolo[2,3-d]pyrimidin-4-yl)amino)cyclohexyl)-2-(4-methylpiperazin-1-yl)acetamide (I-222). $^1$H-NMR (DMSO-d$_6$) δ: 9.01 (1H, d, J=7.9 Hz), 8.23 (1H, s), 7.53-7.62 (4H, m), 7.45-7.49 (2H, m), 4.30 (1H, br s), 3.73-3.83 (1H, m), 3.57 (1H, s), 2.89 (2H, s), 2.16-2.49 (8H, m), 2.02 (3H, s), 1.60-1.84 (8H, m). MS (ESI) m/z: 510 [M+H]$^+$.

Example 147: rac-(4-(3-aminopyrrolidin-1-yl)-7H-pyrrolo[2,3-d]pyrimidin-5-yl) (phenyl)methanone (I-223)

rac-(4-(3-aminopyrrolidin-1-yl)-7H-pyrrolo[2,3-d]pyrimidin-5-yl) (phenyl)methanone (I-223) was synthesized according to General Procedure C from tert-butyl pyrrolidin-3-ylcarbamate followed by Boc deprotection. $^1$H-NMR (DMSO-d$_6$) δ: 8.16 (1H, s), 7.93 (2H, dd, J=7.6, 1.2 Hz), 7.68 (1H, t, J=7.6 Hz), 7.56 (2H, t, J=7.6 Hz), 7.44 (1H, s), 3.66-3.71 (1H, m), 3.62 (1H, dd, J=11.3, 5.8 Hz), 3.50-3.56 (1H, m), 3.29-3.33 (1H, m), 3.19 (1H, dd, J=11.0, 4.9 Hz), 1.79-1.87 (1H, m), 1.48-1.56 (1H, m). MS (ESI) m/z: 308 [M+H]$^+$.

Example 148: rac-N-(1-(5-benzoyl-7H-pyrrolo[2,3-d]pyrimidin-4-yl)pyrrolidin-3-yl)-2-(tetrahydro-2H-pyran-4-yl)acetamide (I-224)

Acylation of Compound I-223 provided rac-N-(1-(5-benzoyl-7H-pyrrolo[2,3-d]pyrimidin-4-yl)pyrrolidin-3-yl)-2-

(tetrahydro-2H-pyran-4-yl)acetamide (I-224). ¹H-NMR (DMSO-d₆) δ: 12.34 (1H, s), 8.19 (1H, s), 7.97 (1H, d, J=6.1 Hz), 7.90 (2H, d, J=7.6 Hz), 7.68 (1H, t, J=7.6 Hz), 7.57 (2H, t, J=7.6 Hz), 7.45 (1H, d, J=1.8 Hz), 4.03-4.07 (1H, m), 3.55-3.77 (5H, m), 3.44 (1H, dd, J=11.6, 4.3 Hz), 3.08-3.18 (2H, m), 1.93-1.98 (1H, m), 1.89 (2H, d, J=10.0 Hz), 1.69-1.78 (2H, m), 1.36-1.39 (1H, m), 1.21-1.25 (1H, m), 0.93-1.11 (2H, m). MS (ESI) m/z: 434 [M+H]⁺.

Example 149: rac-N-(1-(5-benzoyl-7H-pyrrolo[2,3-d]pyrimidin-4-yl)pyrrolidin-3-yl)-3-methoxypropanamide (I-225)

Acylation of Compound I-223 provided rac-N-(1-(5-benzoyl-7H-pyrrolo[2,3-d]pyrimidin-4-yl)pyrrolidin-3-yl)-3-methoxypropanamide (I-225). ¹H-NMR (DMSO-d₆) δ: 12.73 (1H, br s), 9.05 (1H, dd, J=14.3, 6.4 Hz), 8.28 (1H, d, J=1.8 Hz), 7.77-7.79 (3H, m), 7.65 (1H, t, J=7.6 Hz), 7.55 (2H, t, J=7.6 Hz), 4.61-4.76 (1H, m), 3.90 (0.5H, dd, J=10.4, 6.1 Hz), 3.65-3.73 (1.5H, m), 3.45-3.57 (4H, m), 3.35-3.39 (1H, m), 3.20 (1.5H, s), 3.18 (1.5H, s), 2.46-2.54 (2H, m), 2.21-2.38 (1H, m), 1.90-2.09 (1H, m). MS (ESI) m/z: 394 [M+H]⁺.

Example 150: rac-phenyl(4-(pyrrolidin-3-ylamino)-7H-pyrrolo[2,3-d]pyrimidin-5-yl)methanone (I-227)

rac-phenyl(4-(pyrrolidin-3-ylamino)-7H-pyrrolo[2,3-d]pyrimidin-5-yl)methanone (I-227) was synthesized according to General Procedure C followed by Boc deprotection. ¹H-NMR (DMSO-d₆) δ: 13.01 (1H, br s), 9.14-9.25 (3H, m), 8.36 (1H, s), 7.89 (1H, s), 7.80 (2H, dd, J=7.6, 1.2 Hz), 7.68 (1H, t, J=7.6 Hz), 7.57 (2H, t, J=7.6 Hz), 4.73-4.81 (1H, m), 3.58-3.63 (1H, m), 3.37-3.45 (1H, m), 3.28-3.36 (1H, m), 3.18-3.25 (1H, m), 2.39-2.47 (1H, m), 2.00-2.09 (1H, m).

Example 151: Compound 228: rac-1-(3-((5-benzoyl-7H-pyrrolo[2,3-d]pyrimidin-4-yl)amino)pyrrolidin-1-yl)-2-(tetrahydro-2H-pyran-4-yl)ethan-1-one (I-228)

Acylation of Compound I-227 provided rac-1-(3-((5-benzoyl-7H-pyrrolo[2,3-d]pyrimidin-4-yl)amino)pyrrolidin-1-yl)-2-(tetrahydro-2H-pyran-4-yl)ethan-1-one (I-228). ¹H-NMR (DMSO-d₆) δ: 12.73 (1H, br s), 9.05 (1H, dd, J=11.0, 6.7 Hz), 8.28 (1H, d, J=4.3 Hz), 7.76-7.78 (3H, m), 7.65 (1H, t, J=7.6 Hz), 7.55 (2H, t, J=7.6 Hz), 4.62-4.75 (1H, m), 3.62-3.86 (4H, m), 3.40-3.57 (2H, m), 3.33-3.30 (1H, m), 3.15-3.27 (2H, m), 1.85-2.34 (5H, m), 1.51-1.60 (2H, m), 1.10-1.24 (2H, m). MS (ESI) m/z: 434 [M+H]⁺.

Example 152: rac-1-(3-((5-benzoyl-7H-pyrrolo[2,3-d]pyrimidin-4-yl)amino)pyrrolidin-1-yl)-3-methoxypropan-1-one (I-229)

Acylation of Compound I-227 provided rac-1-(3-((5-benzoyl-7H-pyrrolo[2,3-d]pyrimidin-4-yl)amino)pyrrolidin-1-yl)-3-methoxypropan-1-one (I-229). ¹H-NMR (DMSO-d₆) δ: 12.73 (1H, br s), 9.05 (1H, dd, J=14.3, 6.4 Hz), 8.28 (1H, d, J=1.8 Hz), 7.77-7.79 (3H, m), 7.65 (1H, t, J=7.6 Hz), 7.55 (2H, t, J=7.6 Hz), 4.61-4.76 (1H, m), 3.90 (0.5H, dd, J=10.4, 6.1 Hz), 3.65-3.73 (1.5H, m), 3.45-3.57 (4H, m), 3.35-3.39 (1H, m), 3.20 (1.5H, s), 3.18 (1.5H, s), 2.46-2.54 (2H, m), 2.21-2.38 (1H, m), 1.90-2.09 (1H, m). MS (ESI) m/z: 394 [M+H]⁺.

General Procedure D

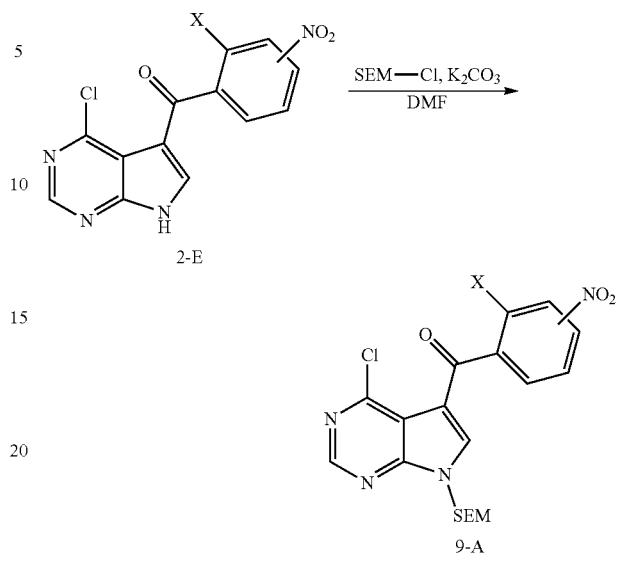

To a solution of pyrrolo[2,3-d]pyrimidine (8-A)(1 eq.) in DMF (1 mL/0.28 mmol) at room temperature was added potassium carbonate (2 eq.) and SEM-Cl (1.2 eq.). The reaction mixture was stirred at room temperature for 3 hours. The reaction mixture was then poured into 1:1 water/EtOAc and partitioned. The aqueous layer was extracted with EtOAc. The combined organic layers were washed with brine, dried over MgSO₄, filtered and concentrated to dryness. The residue was purified by flash chromatography on silica gel eluting with 30-100% EtOAc/hexanes to afford the product.

General Procedure E

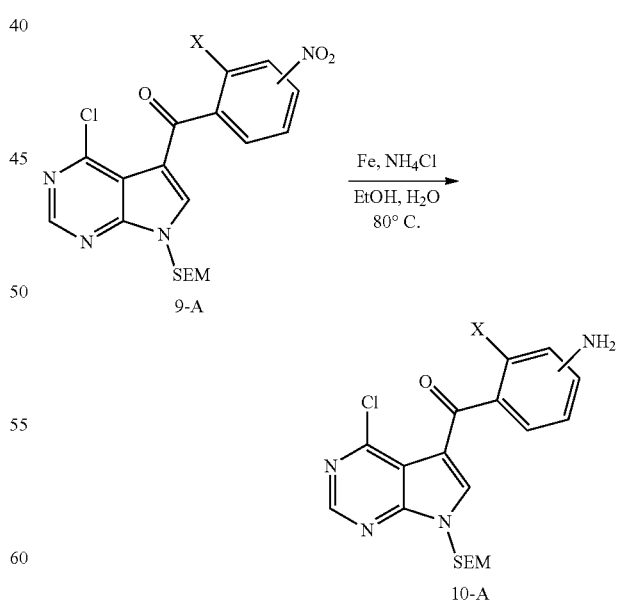

A suspension of the arylnitro compound (9-A) (1 eq.), ammonium chloride (10 eq. and iron (5 eq) in EtOH (1 mL/0.12 mmol) and water (1 mL/0.25 mmol) was heated to 80° C. for 2 hours. Upon cooling to room temperature, methanol was added, the reaction mixture was vigorously stirred for 30 min, filtered through Celite and washed with methanol and EtOAc. The filtrate was concentrated to dryness. The residue was triturated in water and the solids were collected by filtration, dried under high vacuum to afford the corresponding arylamine.

General Procedure F

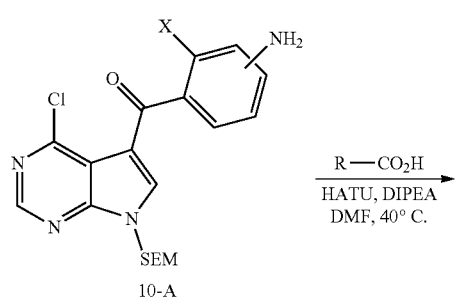

10-A

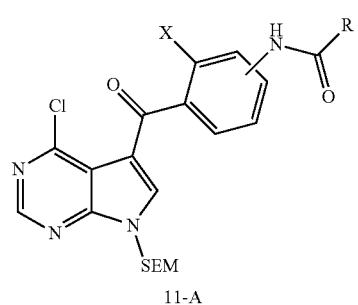

11-A

To a solution of the arylamine (10-A) (1 eq.) in DMF (2 mL/0.16 mmol) were added carboxylic acid (1.5 eq.), HATU (1.2 eq.) and DIPEA (2.5 eq.) and the reaction mixture was allowed to stir at room temperature for 18 hours or heated to 40-50° C. for 3-90 hours. Upon cooling to room temperature, the reaction mixture diluted with aqueous saturated NaHCO₃ and ethyl acetate. The layers were partitioned and the aqueous layer was extracted with ethyl acetate. The combined organic layer were washed with brine, dried over magnesium sulfate, filtered and concentrated to dryness under reduced pressure. The crude product was adsorbed onto silica gel for purification by ISCO CombiFlash (eluted with 0-10% MeOH/DCM or EtOAc/hexanes) or purified by reverse phase $C_{18}$ column chromatography (10-95% acetonitrile in water, 0.1% formic acid) to yield the amide product (11-A).

General Procedure G

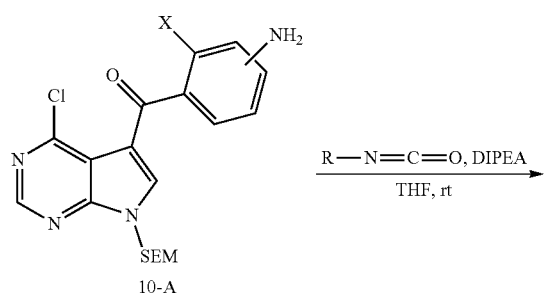

10-A

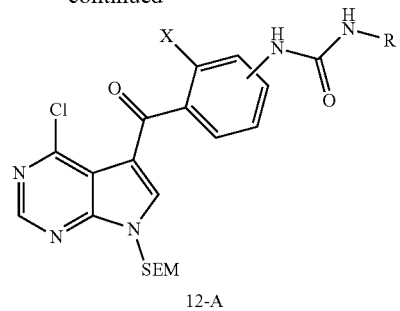

12-A

To a solution of the arylamine (1 eq.) in THF (2 mL/0.343 mmol) were added isocyanate (1.2 eq.) and DIPEA (2.5 eq.). The reaction mixture was allowed to stir at room temperature for 18 hours. The volatiles were removed under reduced pressure and the residue was adsorbed in silica gel purification by ISCO CombiFlash eluting with EtOAc/hexanes to yield the urea product.

General Procedure H

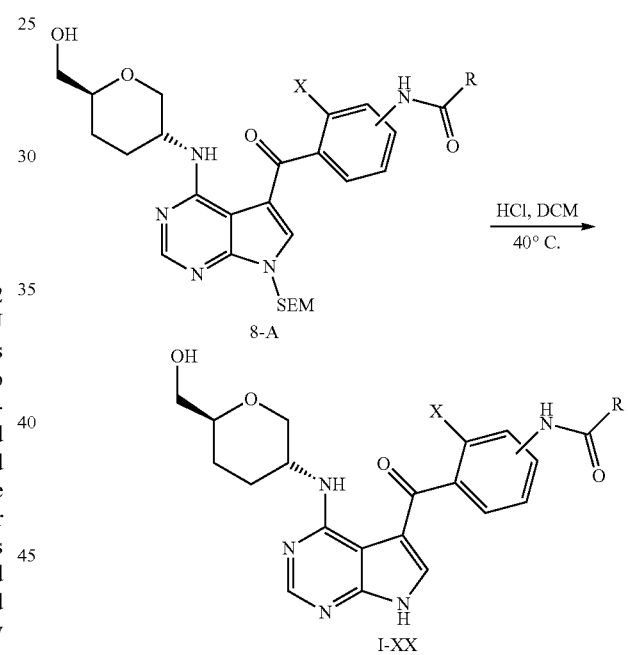

To a solution of SEM-protected substrate (8-A) (1 eq.) in DCM (1 mL/0.044 mmol) was added a solution of HCl (4N in dioxane, 60-81 eq.). The mixture was heated to 40° C. for 18 hours and concentrated to dryness under reduced pressure. The residue was diluted with 10 mL of DCM/MeOH/NH₄OH (90:9:1) and adsorbed onto silica gel for purification by flash chromatography on silica gel eluting with MeOH/DCM (9:1) and DCM/MeOH/NH₄₀H (90:9:1) to yield the deprotected product.

Example 153: Synthesis of N-(4-chloro-3-(4-(((3R,6S)-6-(hydroxymethyl) tetrahydro-2H-pyran-3-yl)amino)-7H-pyrrolo[2,3-d]pyrimidine-5-carbonyl)phenyl)benzamide (I-601)

N-(4-Chloro-3-(4-(((3R,6S)-6-(hydroxymethyl)tetrahydro-2H-pyran-3-yl)amino)-7H-pyrrolo[2,3-d]pyrimidine- 5-carbonyl)phenyl)benzamide was synthesized according to General Scheme 4, General Procedures A, D, E, F, H. $^1$H NMR (DMSO-d$_6$, 400 mHz): δ 12.79 (s; 1H); 10.50 (s; 1H); 8.59 (d; J=7.06 Hz; 1H); 8.26 (s; 1H); 8.01 (d; J=2.53 Hz; 1H); 7.93-7.97 (m; 3H); 7.53-7.63 (m; 5H); 4.66 (t; J=5.58 Hz; 1H); 4.14-4.19 (m; 2H); 3.34-3.44 (m; 3H); 3.14 (t; J=11.24 Hz; 1H); 2.18-2.22 (m; 1H); 1.77-1.81 (m; 1H); 1.57-1.61 (m; 1H); 1.37-1.43 (m; 1H). LCMS [M+H]$^+$: 506.2

Example 154: Synthesis of N-(4-chloro-3-(4-(((3R,6S)-6-(hydroxymethyl)tetrahydro-2H-pyran-3-yl) amino)-7H-pyrrolo[2,3-d]pyrimidine-5-carbonyl) phenyl)-2-phenylacetamide (I-602)

N-(4-Chloro-3-(4-(((3R,6S)-6-(hydroxymethyl)tetrahydro-2H-pyran-3-yl)amino)-7H-pyrrolo[2,3-d]pyrimidine-5-carbonyl)phenyl)-2-phenylacetamide was synthesized according to General Scheme 4, General Procedures A, D, E, F, H. $^1$H NMR (DMSO-d$_6$, 400 mHz): δ 12.75 (s; 1H); 10.46 (s; 1H); 8.56 (d; J=7.05 Hz; 1H); 8.25 (s; 1H); 7.81 (d; J=2.54 Hz; 1H); 7.70 (dd; J=8.80; 2.56 Hz; 1H); 7.58 (s; 1H); 7.52 (d; J=8.78 Hz; 1H); 7.32 (d; J=4.37 Hz; 4H); 7.23-7.26 (m; 1H); 4.66 (t; J=5.15 Hz; 1H); 4.12-4.18 (m; 2H); 3.65 (s; 2H); 3.34-3.41 (m; 3H); 3.12 (t; J=11.05 Hz; 1H); 2.17-2.21 (m; 1H); 1.76-1.80 (m; 1H); 1.56-1.60 (m; 1H); 1.36-1.42 (m; 1H). LCMS [M+H]$^+$: 520.2.

Example 155: Synthesis of N-(4-chloro-3-(4-(((3R,6S)-6-(hydroxymethyl)tetrahydro-2H-pyran-3-yl) amino)-7H-pyrrolo[2,3-d]pyrimidine-5-carbonyl) phenyl)tetrahydro-2H-pyran-4-carboxamide (I-603)

N-(4-Chloro-3-(4-(((3R,6S)-6-(hydroxymethyl)tetrahydro-2H-pyran-3-yl)amino)-7H-pyrrolo[2,3-d]pyrimidine-5-carbonyl)phenyl)tetrahydro-2H-pyran-4-carboxamide was synthesized according to General Scheme 4, General Procedures A, D, E, F, H. $^1$H NMR (DMSO-d$_6$, 400 mHz): δ 10.22 (s; 1H); 8.56-8.58 (m; 1H); 8.24 (s; 1H); 7.83 (d; J=2.52 Hz; 1H); 7.71 (dd; J=8.79; 2.55 Hz; 1H); 7.56 (s; 1H); 7.50 (d; J=8.77 Hz; 1H); 4.60-4.71 (m; 1H); 4.10-4.18 (m; 2H); 3.88-3.92 (m; 2H); 3.36-3.41 (m; 5H); 3.09-3.16 (m; 1H); 2.52-2.63 (m; 1H); 2.16-2.21 (m; 1H); 1.54-1.77 (m; 6H); 1.33-1.43 (m; 1H). NH of indole not observed. 0.2 equiv. of formic acid (8.36 ppm) observed. LCMS [M+H]$^+$: 514.2.

Example 156: Synthesis of N-(4-chloro-3-(4-(((3R,6S)-6-(hydroxymethyl)tetrahydro-2H-pyran-3-yl) amino)-7H-pyrrolo[2,3-d]pyrimidine-5-carbonyl) phenyl)thiazole-5-carboxamide (I-604)

N-(4-Chloro-3-(4-(((3R,6S)-6-(hydroxymethyl)tetrahydro-2H-pyran-3-yl)amino)-7H-pyrrolo[2,3-d]pyrimidine-5-carbonyl)phenyl)thiazole-5-carboxamide was synthesized according to General Scheme 4, General Procedures A, D, E, F, H. $^1$H NMR (DMSO-d$_6$, 400 mHz): δ 12.83 (s; 1H); 10.71 (s; 1H); 9.33 (s; 1H); 8.70 (s; 1H); 8.61 (d; J=6.93 Hz; 1H); 8.27 (s; 1H); 7.92 (d; J=2.53 Hz; 1H); 7.89 (dd; J=8.75; 2.59 Hz; 1H); 7.64 (s; 1H); 7.61 (d; J=8.73 Hz; 1H); 4.13-4.19 (m; 2H); 3.39-3.46 (m; 5H); 3.14 (t; J=11.03 Hz; 1H); 2.18-2.22 (m; 1H); 1.76-1.80 (m; 1H); 1.57-1.63 (m; 1H); 1.37-1.43 (m; 1H). OH of alcohol not observed. LCMS [M+H]$^+$: 513.1.

Example 157: Synthesis of N-(4-chloro-3-(4-(((3R,6S)-6-(hydroxymethyl)tetrahydro-2H-pyran-3-yl) amino)-7H-pyrrolo[2,3-d]pyrimidine-5-carbonyl) phenyl)-1-phenylcyclopropane-1-carboxamide (I-605)

N-(4-Chloro-3-(4-(((3R,6S)-6-(hydroxymethyl)tetrahydro-2H-pyran-3-yl)amino)-7H-pyrrolo[2,3-d]pyrimidine-5-carbonyl)phenyl)-1-phenylcyclopropane-1-carboxamide was synthesized according to General Scheme 4, General Procedures A, D, E, F, H. $^1$H NMR (DMSO-d$_6$, 400 mHz): δ 12.75 (s; 1H); 9.32 (s; 1H); 8.55 (d; J=7.12 Hz; 1H); 8.24 (s; 1H); 7.74-7.76 (m; 2H); 7.55 (s; 1H); 7.47-7.49 (m; 1H); 7.33-7.40 (m; 4H); 7.26-7.30 (m; 1H); 4.65 (t; J=5.58 Hz; 1H); 4.12-4.16 (m; 2H); 3.36-3.44 (m; 3H); 3.11 (t; J=11.35 Hz; 1H); 2.16-2.20 (m; 1H); 1.76-1.80 (m; 1H); 1.54-1.58 (m; 1H); 1.37-1.47 (m; 3H); 1.10-1.13 (m; 2H). LCMS [M+H]$^+$: 546.2.

Example 158: Synthesis of N-(4-chloro-3-(4-(((3R,6S)-6-(hydroxymethyl)tetrahydro-2H-pyran-3-yl) amino)-7H-pyrrolo[2,3-d]pyrimidine-5-carbonyl) phenyl)-5,6,7,8-tetrahydroisoquinoline-3-carboxamide (I-606)

N-(4-Chloro-3-(4-(((3R,6S)-6-(hydroxymethyl)tetrahydro-2H-pyran-3-yl)amino)-7H-pyrrolo[2,3-d]pyrimidine-5-carbonyl)phenyl)-5,6,7,8-tetrahydroisoquinoline-3-carboxamide was synthesized according to General Scheme 4, General Procedures A, D, E, F, H. $^1$H NMR (DMSO-d$_6$, 400 mHz): δ 12.79 (s; 1H); 10.88 (s; 1H); 8.61 (d; J=7.06 Hz; 1H); 8.41 (s; 1H); 8.26 (s; 1H); 8.11-8.15 (m; 2H); 7.85 (s; 1H); 7.63 (s; 1H); 7.57 (d; J=8.58 Hz; 1H); 4.66 (t; J=5.51 Hz; 1H); 4.14-4.19 (m; 2H); 3.35-3.42 (m; 3H); 3.14 (t; J=11.12 Hz; 1H); 2.81-2.83 (m; 4H); 2.18-2.22 (m; 1H); 1.76-1.80 (m; 5H); 1.57-1.63 (m; 1H); 1.37-1.41 (m; 1H). LCMS [M+H]$^+$: 561.3.

Example 159: Synthesis of N-(4-chloro-3-(4-(((3R,6S)-6-(hydroxymethyl)tetrahydro-2H-pyran-3-yl) amino)-7H-pyrrolo[2,3-d]pyrimidine-5-carbonyl) phenyl)isoquinoline-1-carboxamide (I-607)

N-(4-Chloro-3-(4-(((3R,6S)-6-(hydroxymethyl)tetrahydro-2H-pyran-3-yl)amino)-7H-pyrrolo[2,3-d]pyrimidine-5-carbonyl)phenyl)isoquinoline-1-carboxamide was synthesized according to General Scheme 4, General Procedures A, D, E, F, H. $^1$H NMR (DMSO-d$_6$, 400 mHz): δ 12.86 (s; 1H); 11.19 (s; 1H); 8.92 (d; J=8.63 Hz; 1H); 8.71 (d; J=5.58 Hz; 1H); 8.67 (d; J=7.07 Hz; 1H); 8.33 (s; 1H); 8.21 (d; J=2.55 Hz; 1H); 8.18 (s; 1H); 8.16 (d; J=2.20 Hz; 1H); 8.12 (dd; J=8.80; 2.56 Hz; 1H); 7.93 (t; J=7.59 Hz; 1H); 7.83 (t; J=7.81 Hz; 1H); 7.74 (s; 1H); 7.69 (d; J=8.78 Hz; 1H); 4.73 (t; J=5.52 Hz; 1H); 4.20-4.26 (m; 2H); 3.41-3.51 (m; 3H); 3.21 (t; J=11.10 Hz; 1H); 2.25-2.29 (m; 1H); 1.83-1.87 (m; 1H); 1.65-1.69 (m; 1H); 1.44-1.50 (m; 1H). LCMS [M+H]$^+$: 557.2.

Example 160: Synthesis of 1-(4-chloro-3-(4-(((3R,6S)-6-(hydroxymethyl)tetrahydro-2H-pyran-3-yl) amino)-7H-pyrrolo[2,3-d]pyrimidine-5-carbonyl) phenyl)-3-phenylurea (I-608)

1-(4-Chloro-3-(4-(((3R,6S)-6-(hydroxymethyl)tetrahydro-2H-pyran-3-yl)amino)-7H-pyrrolo[2,3-d]pyrimidine-5-carbonyl)phenyl)-3-phenylurea was synthesized according to General Scheme 4, General Procedures A, D, E, F, G.

¹H NMR (DMSO-d₆, 400 mHz): δ 12.74 (br s; 1H); 9.38 (s; 1H); 9.19 (s; 1H); 8.60 (d; J=7.05 Hz; 1H); 8.25 (s; 1H); 7.70 (d; J=2.59 Hz; 1H); 7.57-7.60 (m; 2H); 7.44-7.48 (m; 3H); 7.24-7.28 (m; 2H); 6.96 (t; J=7.37 Hz; 1H); 4.66 (t; J=5.36 Hz; 1H); 4.12-4.19 (m; 2H); 3.35-3.42 (m; 3H); 3.11-3.17 (m; 1H); 2.17-2.22 (m; 1H); 1.76-1.80 (m; 1H); 1.53-1.64 (m; 1H); 1.32-1.43 (m; 1H). Contained 0.2 equiv. of formic acid. LCMS [M+H]⁺: 521.1.

Example 161: Synthesis of 1-(4-chloro-3-(4-(((3R, 6S)-6-(hydroxymethyl)tetrahydro-2H-pyran-3-yl) amino)-7H-pyrrolo[2,3-d]pyrimidine-5-carbonyl) phenyl)-3-(pyridin-3-yl)urea (I-609)

1-(4-Chloro-3-(4-(((3R,6S)-6-(hydroxymethyl)tetrahydro-2H-pyran-3-yl)amino)-7H-pyrrolo[2,3-d]pyrimidine-5-carbonyl)phenyl)-3-(pyridin-3-yl)urea was synthesized according to General Scheme 4, General Procedures A, D, E, F, G. ¹H NMR (DMSO-d₆, 400 mHz): δ 12.76 (br s; 1H); 9.56 (s; 1H); 9.44 (s; 1H); 8.59-8.62 (m; 2H); 8.25 (s; 1H); 8.18 (dd; J=4.67; 1.43 Hz; 1H); 7.92 (ddd; J=8.36; 2.58; 1.46 Hz; 1H); 7.70 (d; J=2.59 Hz; 1H); 7.59-7.62 (m; 2H); 7.49 (d; J=8.77 Hz; 1H); 7.30 (dd; J=8.34; 4.67 Hz; 1H); 4.66 (s; 1H); 4.12-4.19 (m; 2H); 3.37-3.45 (m; 3H); 3.10-3.16 (m; 1H); 2.18-2.22 (m; 1H); 1.77-1.81 (m; 1H); 1.54-1.64 (m; 1H); 1.33-1.43 (m; 1H). LCMS [M+H]⁺: 522.2.

Example 162: Synthesis of 3-chloro-4-(4-(((3R,6S)-6-(hydroxymethyl)tetrahydro-2H-pyran-3-yl)amino)-7H-pyrrolo[2,3-d]pyrimidine-5-carbonyl)-N-phenylbenzamide (I-236)

3-Chloro-4-(4-(((3R,6S)-6-(hydroxymethyl)tetrahydro-2H-pyran-3-yl)amino)-7H-pyrrolo[2,3-d]pyrimidine-5-carbonyl)-N-phenylbenzamide was synthesized according to General Scheme 5, using aniline as the amine. ¹H NMR (DMSO-d₆, 400 mHz): δ 12.80 (br s; 1H); 10.45 (s; 1H); 8.56 (d; J=7.03 Hz; 1H); 8.27 (s; 1H); 8.17 (d; J=1.53 Hz; 1H); 8.04 (dd; J=7.92; 1.59 Hz; 1H); 7.79 (d; J=8.03 Hz; 2H); 7.74 (d; J=7.89 Hz; 1H); 7.59 (s; 1H); 7.39 (t; J=7.77 Hz; 2H); 7.12-7.16 (m; 1H); 4.66 (t; J=5.42 Hz; 1H); 4.08-4.17 (m; 2H); 3.40-3.49 (m; 3H); 3.11-3.18 (m; 1H); 2.17-2.22 (m; 1H); 1.78-1.88 (m; 1H); 1.52-1.65 (m; 1H); 1.32-1.45 (m; 1H). LCMS [M+H]⁺: 506.2.

Example 163: Synthesis of 3-chloro-4-(4-(((3R,6S)-6-(hydroxymethyl)tetrahydro-2H-pyran-3-yl)amino)-7H-pyrrolo[2,3-d]pyrimidine-5-carbonyl)-N-(2-methoxyethyl) benzamide (I-610)

3-Chloro-4-(4-(((3R,6S)-6-(hydroxymethyl)tetrahydro-2H-pyran-3-yl)amino)-7H-pyrrolo[2,3-d]pyrimidine-5-carbonyl)-N-(2-methoxyethyl)benzamide was synthesized according to General Scheme 5 using 2-methoxyethylamine. ¹H NMR (DMSO-d₆, 400 mHz): δ 12.78 (s; 1H); 8.78-8.80 (m; 1H); 8.55 (d; J=7.09 Hz; 1H); 8.26 (s; 1H); 8.05 (d; J=1.51 Hz; 1H); 7.93 (dd; J=7.92; 1.56 Hz; 1H); 7.66 (d; J=7.91 Hz; 1H); 7.58 (s; 1H); 4.66 (t; J=5.57 Hz; 1H); 4.15-4.17 (m; 2H); 3.35-3.50 (m; 7H); 3.28 (s; 3H); 3.13 (t; J=11.33 Hz; 1H); 2.18 (s; 1H); 1.78 (d; J=12.89 Hz; 1H); 1.58 (d; J=12.92 Hz; 1H); 1.38 (d; J=13.18 Hz; 1H). LCMS [M+H]⁺: 488.2.

Example 164: Synthesis of (3-chloro-4-(4-(((3R, 6S)-6-(hydroxymethyl)tetrahydro-2H-pyran-3-yl) amino)-7H-pyrrolo[2,3-d]pyrimidine-5-carbonyl) phenyl)(morpholino) methanone (I-611)

(3-Chloro-4-(4-(((3R,6S)-6-(hydroxymethyl)tetrahydro-2H-pyran-3-yl)amino)-7H-pyrrolo[2,3-d]pyrimidine-5-carbonyl)phenyl)(morpholino)methanone was synthesized according to General Scheme 5, using morpholine as the amine. ¹H NMR (DMSO-d₆, 400 mHz): δ 12.80 (s; 1H); 8.56 (d; J=7.11 Hz; 1H); 8.26 (s; 1H); 7.66 (s; 1H); 7.63 (s; 1H); 7.62 (d; J=6.31 Hz; 1H); 7.46 (dd; J=7.74; 1.45 Hz; 1H); 4.66 (t; J=5.58 Hz; 1H); 4.16 (d; J=9.36 Hz; 2H); 3.58-3.69 (m; 6H); 3.34-3.44 (m; 5H); 3.13 (t; J=11.37 Hz; 1H); 2.17-2.20 (m; 1H); 1.77-1.81 (m; 1H); 1.55-1.59 (m; 1H); 1.36-1.39 (m; 1H). LCMS [M+H]⁺: 500.2.

Example 165: Synthesis of (4-chloro-3-(4-(((3R, 6S)-6-(hydroxymethyl)tetrahydro-2H-pyran-3-yl) amino)-7H-pyrrolo[2,3-d]pyrimidine-5-carbonyl) phenyl)(morpholino) methanone (I-612)

(4-Chloro-3-(4-(((3R,6S)-6-(hydroxymethyl)tetrahydro-2H-pyran-3-yl)amino)-7H-pyrrolo[2,3-d]pyrimidine-5-carbonyl)phenyl)(morpholino)methanone was synthesized according to General Scheme 5, using morpholine as the amine. ¹H NMR (DMSO-d₆, 400 mHz): δ 12.77 (br s; 1H); 8.55 (d; J=7.06 Hz; 1H); 8.25 (s; 1H); 7.57-7.69 (m; 4H); 4.66 (s; 1H); 4.16 (m; 2H); 3.32-3.57 (m; 11H); 3.12 (t; J=11.26 Hz; 1H); 2.19 (d; J=11.57 Hz; 1H); 1.76-1.79 (m; 1H); 1.52-1.61 (m; 1H); 1.38 (q; J=11.99 Hz; 1H). LCMS [M+H]⁺: 500.2, 502.2.

Example 166: Synthesis of 3-chloro-4-(4-(((3R,6S)-6-(hydroxymethyl)tetrahydro-2H-pyran-3-yl)amino)-7H-pyrrolo[2,3-d]pyrimidine-5-carbonyl)-N-(2-morpholinoethyl) benzamide (I-613)

3-Chloro-4-(4-(((3R,6S)-6-(hydroxymethyl)tetrahydro-2H-pyran-3-yl)amino)-7H-pyrrolo[2,3-d]pyrimidine-5-carbonyl)-N-(2-morpholinoethyl)benzamide was synthesized according to General Scheme 5, using 2-morpholinoethan-1-amine. ¹H NMR (DMSO-d₆, 400 mHz): δ 12.78 (s; 1H); 8.67-8.70 (m, 1H); 8.55 (d; J=7.05 Hz; 1H); 8.26 (s; 1H); 8.02 (d; J=1.52 Hz; 1H); 7.90 (dd; J=7.94; 1.56 Hz; 1H); 7.66 (d; J=7.91 Hz; 1H); 7.55 (s; 1H); 4.66 (t; J=5.58 Hz; 1H); 4.14-4.18 (m; 2H); 3.58 (t; J=4.51 Hz; 4H); 3.34-3.45 (m; 6H); 3.13 (t; J=11.30 Hz; 1H); 2.39-2.46 (m; 5H); 2.16-2.21 (m; 1H); 1.77-1.80 (m; 1H); 1.55-1.59 (m; 1H); 1.36-1.41 (m; 1H). LCMS [M+H]⁺: 543.3.

Example 167: Synthesis of 3-chloro-N-(3-cyanophenyl)-4-(4-(((3R,6S)-6-(hydroxymethyl) tetrahydro-2H-pyran-3-yl)amino)-7H-pyrrolo[2,3-d]pyrimidine-5-carbonyl)benzamide (I-614)

3-Chloro-N-(3-cyanophenyl)-4-(4-(((3R,6S)-6-(hydroxymethyl)tetrahydro-2H-pyran-3-yl)amino)-7H-pyrrolo[2,3-d]pyrimidine-5-carbonyl)benzamide was synthesized according to General Scheme 5, using 3-aminobenzonitrile. ¹H NMR (DMSO-d₆, 400 mHz): δ 12.74-12.89 (bs; 1H); 10.76 (s; 1H); 8.55 (d; J=7.05 Hz; 1H); 8.26-8.28 (m; 2H); 8.18 (d; J=1.57 Hz; 1H); 8.03-8.08 (m; 2H); 7.76 (d; J=7.91 Hz; 1H); 7.62 (d; J=4.90 Hz; 2H); 7.59 (s; 1H); 4.64-4.67 (m; 1H); 4.15-4.19 (m; 2H); 3.35-3.44 (m; 3H); 3.10-3.16 (m; 1H); 2.15-2.22 (m; 1H); 1.76-1.81 (m; 1H); 1.52-1.64 (m; 1H); 1.33-1.44 (m; 1H). LCMS [M+H]⁺: 531.2.

Example 168: Synthesis of 3-chloro-4-(4-(((3R,6S)-6-(hydroxymethyl)tetrahydro-2H-pyran-3-yl)amino)-7H-pyrrolo[2,3-d]pyrimidine-5-carbonyl)-N-(pyridin-3-yl)benzamide (I-256)

3-Chloro-4-(4-(((3R,6S)-6-(hydroxymethyl)tetrahydro-2H-pyran-3-yl)amino)-7H-pyrrolo[2,3-d]pyrimidine-5-carbonyl)-N-(pyridin-3-yl)benzamide was synthesized according to General Scheme 5, using pyridine-3-amine. ¹H NMR (DMSO-d₆, 400 mHz): δ 12.79 (br s; 1H); 10.66 (s; 1H); 8.95 (s; 1H); 8.55 (d; J=7.01 Hz; 1H); 8.36 (dd; J=4.66; 1.81 Hz; 1H); 8.27 (s; 1H); 8.19-8.22 (m; 2H); 8.03-8.06 (m; 1H); 7.75-7.78 (m; 1H); 7.60 (s; 1H); 7.43 (dd; J=8.30; 4.69 Hz); 1H); 4.66 (t; J=5.50 Hz; 1H); 4.11-4.29 (m; 2H); 3.33-3.42 (m; 3H); 3.10-3.17 (m; 1H); 2.16-2.23 (m; 1H); 1.76-1.81 (m; 1H); 1.54-1.64 (m; 1H); 1.33-1.44 (m; 1H). LCMS [M+H]⁺: 507.2.

Example 169: Synthesis of (2-chloro-4-(1,2,3,4-tetrahydroisoquinoline-2-carbonyl)phenyl)(4-(((3R,6S)-6-(hydroxymethyl)tetrahydro-2H-pyran-3-yl)amino)-7H-pyrrolo[2,3-d]pyrimidin-5-yl)methanone (I-615)

(2-Chloro-4-(1,2,3,4-tetrahydroisoquinoline-2-carbonyl)phenyl)(4-(((3R,6S)-6-(hydroxymethyl)tetrahydro-2H-pyran-3-yl)amino)-7H-pyrrolo[2,3-d]pyrimidin-5-yl)methanone was synthesized according to General Scheme 5, using 1,2,3,4-tetrahydroisoquinoline. ¹H NMR (DMSO-d₆, 400 mHz): δ 8.57-8.59 (m; 1H); 8.24-8.26 (m; 1H); 7.63-7.70 (m; 3H); 7.49-7.53 (m; 1H); 7.10-7.29 (m; 4H); 4.78-4.79 (m; 1H); 4.62-4.67 (m; 2H); 4.13-4.19 (m; 2H); 3.82-3.89 (m; 1H); 3.61-3.64 (m; 1H); 3.40-3.44 (m; 3H); 3.10-3.16 (m; 1H); 2.85-2.91 (m; 2H); 2.16-2.21 (m; 1H); 1.77-1.80 (m; 1H); 1.53-1.60 (m; 1H); 1.36-1.44 (m; 1H). NH of indole not observed. LCMS [M+H]⁺: 546.02.

Example 170: Synthesis of (3-chloro-4-(4-(((3R,6S)-6-(hydroxymethyl)tetrahydro-2H-pyran-3-yl)amino)-7H-pyrrolo[2,3-d]pyrimidine-5-carbonyl)phenyl)(4-(pyridin-2-yl)piperazin-1-yl)methanone (I-616)

(3-Chloro-4-(4-(((3R,6S)-6-(hydroxymethyl)tetrahydro-2H-pyran-3-yl)amino)-7H-pyrrolo[2,3-d]pyrimidine-5-carbonyl)phenyl)(4-(pyridin-2-yl)piperazin-1-yl)methanone was synthesized according to General Scheme 5, using 1-(pyridin-2-yl)piperazine. ¹H NMR (DMSO-d₆, 400 mHz): δ 12.82 (s; 1H); 8.57 (d; J=7.09 Hz; 1H); 8.27 (s; 1H); 8.13-8.14 (m; 1H); 7.68 (s; 1H); 7.66 (d; J=1.43 Hz; 1H); 7.64 (d; J=7.72 Hz; 1H); 7.55-7.59 (m; 1H); 7.50 (dd; J=7.75; 1.44 Hz; 1H); 6.87 (d; J=8.63 Hz; 1H); 6.68 (dd; J=7.05; 4.93 Hz; 1H); 4.66 (t; J=5.58 Hz; 1H); 4.12-4.19 (m; 2H); 3.44-3.78 (m; 8H); 3.34-3.42 (m; 3H); 3.13 (t; J=11.28 Hz; 1H); 2.18-2.22 (m; 1H); 1.76-1.80 (m; 1H); 1.56-1.60 (m; 1H); 1.37-1.43 (m; 1H). LCMS [M+H]⁺: 576.3.

Example 171: Synthesis of (3-chloro-4-(4-(((3R,6S)-6-(hydroxymethyl)tetrahydro-2H-pyran-3-yl)amino)-7H-pyrrolo[2,3-d]pyrimidine-5-carbonyl)phenyl)(piperidin-1-yl)methanone (I-617)

(3-Chloro-4-(4-(((3R,6S)-6-(hydroxymethyl)tetrahydro-2H-pyran-3-yl)amino)-7H-pyrrolo[2,3-d]pyrimidine-5-carbonyl)phenyl)(piperidin-1-yl)methanone was synthesized according to General Scheme 5, using piperidine. ¹H NMR (DMSO-d₆, 400 mHz): δ 12.79 (s; 1H); 8.57 (d; J=7.10 Hz; 1H); 8.26 (s; 1H); 7.67 (s; 1H); 7.61 (d; J=7.73 Hz; 1H); 7.57 (d; J=1.40 Hz; 1H); 7.42 (dd; J=7.73; 1.46 Hz; 1H); 4.66 (t; J=5.59 Hz; 1H); 4.12-4.17 (m; 2H); 3.53-3.63 (m; 2H); 3.34-3.44 (m; 5H); 3.13 (t; J=11.27 Hz; 1H); 2.17-2.21 (m; 1H); 1.77-1.81 (m; 1H); 1.49-1.62 (m; 7H); 1.36-1.42 (m; 1H). LCMS [M+H]⁺: 498.2.

Example 172: Synthesis of N-benzyl-3-chloro-4-(4-(((3R,6S)-6-(hydroxymethyl) tetrahydro-2H-pyran-3-yl)amino)-7H-pyrrolo[2,3-d]pyrimidine-5-carbonyl)benzamide (I-618)

N-Benzyl-3-chloro-4-(4-(((3R,6S)-6-(hydroxymethyl)tetrahydro-2H-pyran-3-yl)amino)-7H-pyrrolo[2,3-d]pyrimidine-5-carbonyl)benzamide was synthesized according to General Scheme 5, using benzylamine. ¹H NMR (DMSO-d₆, 400 mHz): δ 12.80 (s; 1H); 9.30 (t; J=5.94 Hz; 1H); 8.55 (d; J=7.09 Hz; 1H); 8.26 (s; 1H); 8.09 (d; J=1.52 Hz; 1H); 7.97 (dd; J=7.93; 1.56 Hz; 1H); 7.68 (d; J=7.91 Hz; 1H); 7.59 (s; 1H); 7.34-7.35 (m; 4H); 7.25-7.28 (m; 1H); 4.66 (t; J=5.58 Hz; 1H); 4.52 (d; J=5.87 Hz; 2H); 4.16 (d; J=9.29 Hz; 2H); 3.36-3.44 (m; 3H); 3.13 (t; J=11.36 Hz; 1H); 2.17-2.21 (m; 1H); 1.76-1.80 (m; 1H); 1.56-1.60 (m; 1H); 1.35-1.41 (m; 1H). LCMS [M+H]⁺: 520.2.

Example 173: Synthesis of 3-chloro-4-(4-(((3R,6S)-6-(hydroxymethyl)tetrahydro-2H-pyran-3-yl)amino)-7H-pyrrolo[2,3-d]pyrimidine-5-carbonyl)-N-(1-methyl-1H-pyrazol-4-yl)benzamide (I-619)

3-Chloro-4-(4-(((3R,6S)-6-(hydroxymethyl)tetrahydro-2H-pyran-3-yl)amino)-7H-pyrrolo[2,3-d]pyrimidine-5-carbonyl)-N-(1-methyl-1H-pyrazol-4-yl)benzamide was synthesized according to General Scheme 5, using 1-methyl-1H-pyrazol-4-amine. ¹H NMR (DMSO-d₆, 400 mHz): δ 10.67 (s; 1H); 8.56 (d; J=7.08 Hz; 1H); 8.26 (s; 1H); 8.14 (d; J=1.56 Hz; 1H); 8.07 (s; 1H); 8.02 (dd; J=7.93; 1.59 Hz; 1H); 7.73 (d; J=7.93 Hz; 1H); 7.60 (s; 2H); 4.66 (t; J=5.47 Hz; 1H); 4.15-4.19 (m; 2H); 3.84 (s; 3H); 3.35-3.43 (m; 3H); 3.10-3.17 (m; 1H); 2.17-2.22 (m; 1H); 1.76-1.81 (m; 1H); 1.55-1.61 (m; 1H); 1.36-1.43 (m; 1H), NH of indole not observed. LCMS [M+H]⁺: 510.2.

Example 174: Synthesis of 3-chloro-4-(4-(((3R,6S)-6-(hydroxymethyl)tetrahydro-2H-pyran-3-yl)amino)-7H-pyrrolo[2,3-d]pyrimidine-5-carbonyl)-N-(pyridin-4-yl)benzamide (I-246)

3-Chloro-4-(4-(((3R,6S)-6-(hydroxymethyl)tetrahydro-2H-pyran-3-yl)amino)-7H-pyrrolo[2,3-d]pyrimidine-5-carbonyl)-N-(pyridin-4-yl)benzamide was synthesized according to General Scheme 5, using pyridine-4-amine. ¹H NMR (DMSO-d₆, 400 mHz): δ 10.83 (s; 1H); 8.55 (d; J=7.11 Hz; 1H); 8.52 (dd; J=5.29; 1.46 Hz; 2H); 8.26 (s; 1H); 8.18 (d; J=1.57 Hz; 1H); 8.04 (dd; J=7.91; 1.60 Hz; 1H); 7.81 (dd; J=5.19; 1.53 Hz; 2H); 7.76 (d; J=7.91 Hz; 1H); 7.57 (s; 1H); 4.15-4.19 (m; 2H); 3.36-3.44 (m; 3H); 3.10-3.16 (m; 1H); 2.18-2.22 (m; 1H); 1.77-1.81 (m; 1H); 1.56-1.60 (m; 1H); 1.37-1.43 (m; 1H). NH of indole and OH not observed. Contained formic acid at 8.38 ppm (0.4 eq.). LCMS [M+H]⁺: 507.2.

Example 175: Synthesis of (3-chloro-4-(4-(((3R,6S)-6-(hydroxymethyl)tetrahydro-2H-pyran-3-yl)amino)-7H-pyrrolo[2,3-d]pyrimidine-5-carbonyl)phenyl)(4-methylpiperazin-1-yl)methanone (I-620)

(3-Chloro-4-(4-(((3R,6S)-6-(hydroxymethyl)tetrahydro-2H-pyran-3-yl)amino)-7H-pyrrolo[2,3-d]pyrimidine-5-carbonyl)phenyl)(4-methylpiperazin-1-yl)methanone was synthesized according to General Scheme 5, using 1-methylpiperazine. ¹H NMR (DMSO-d₆, 400 mHz): δ 12.79 (s; 1H); 8.56 (d; J=7.10 Hz; 1H); 8.26 (s; 1H); 7.67 (s; 1H); 7.58-7.61 (m; 2H); 7.43 (dd; J=7.73; 1.47 Hz; 1H); 4.65

(t; J=5.58 Hz; 1H); 4.12-4.17 (m; 2H); 3.56-3.66 (m; 2H); 3.33-3.45 (m; 5H); 3.13 (t; J=11.35 Hz; 1H); 2.28-2.39 (m; 4H); 2.21 (s; 3H); 2.17-2.19 (m; 1H); 1.77-1.80 (m; 1H); 1.56-1.60 (m; 1H); 1.36-1.42 (m; 1H). LCMS [M+H]$^+$: 514.3.

Example 176: Synthesis of 3-chloro-4-(4-(((3R,6S)-6-(hydroxymethyl)tetrahydro-2H-pyran-3-yl)amino)-7H-pyrrolo[2,3-d]pyrimidine-5-carbonyl)-N-(2-oxaspiro[3.3]heptan-6-yl)benzamide (I-621)

3-Chloro-4-(4-(((3R,6S)-6-(hydroxymethyl)tetrahydro-2H-pyran-3-yl)amino)-7H-pyrrolo[2,3-d]pyrimidine-5-carbonyl)-N-(2-oxaspiro[3.3]heptan-6-yl)benzamide was synthesized according to General Scheme 5, using 2-oxa-6-azaspiro[3.3]heptane. $^1$H NMR (DMSO-d$_6$, 400 mHz): δ 12.78 (s; 1H); 8.81 (d; J=7.16 Hz; 1H); 8.55 (d; J=7.05 Hz; 1H); 8.26 (s; 1H); 8.02 (d; J=1.52 Hz; 1H); 7.90 (dd; J=7.94; 1.56 Hz; 1H); 7.66 (d; J=7.91 Hz; 1H); 7.55 (s; 1H); 4.63-4.66 (m; 3H); 4.52 (s; 2H); 4.21-4.27 (m; 1H); 4.14-4.18 (m; 2H); 3.33-3.43 (m; 3H); 3.12 (t; J=11.30 Hz; 1H); 2.57-2.62 (m; 2H); 2.26 (t; J=10.09 Hz; 2H); 2.16-2.21 (m; 1H); 1.77-1.80 (m; 1H); 1.55-1.59 (m; 1H); 1.36-1.41 (m; 1H). LCMS [M+H]$^+$: 526.3.

Example 177: Synthesis of (4-chloro-3-(4-(((3R,6S)-6-(hydroxymethyl)tetrahydro-2H-pyran-3-yl)amino)-7H-pyrrolo[2,3-d]pyrimidine-5-carbonyl)phenyl)(4-methylpiperazin-1-yl)methanone (I-622)

(4-Chloro-3-(4-(((3R,6S)-6-(hydroxymethyl)tetrahydro-2H-pyran-3-yl)amino)-7H-pyrrolo[2,3-d]pyrimidine-5-carbonyl)phenyl)(4-methylpiperazin-1-yl)methanone was prepared according to General Scheme 5, using 1-methylpiperazine. $^1$H NMR (DMSO-d$_6$, 400 mHz): δ 8.53 (d; J=7.11 Hz; 1H); 8.28 (s; 1.3H); 8.24 (s; 1H); 7.65 (d; J=8.84 Hz; 1H); 7.60 (s; 1H); 7.53 (m; 2H); 4.14 (m; 2H); 3.57 (br s; 2H); 3.32-3.42 (m; 5H); 3.10 (t; J=11.34 Hz; 1H); 2.29 (br s; 6H); 2.16 (s; 3H); 1.77 (d; J=13.06 Hz; 1H); 1.51-1.58 (m; 1H); 1.32-1.40 (m; 1H). LCMS [M+H]$^+$: 513.3, 515.3.

Example 178: Synthesis of (4-chloro-3-(4-(((3R,6S)-6-(hydroxymethyl)tetrahydro-2H-pyran-3-yl)amino)-7H-pyrrolo[2,3-d]pyrimidine-5-carbonyl)phenyl)(piperidin-1-yl)methanone (I-623)

(4-Chloro-3-(4-(((3R,6S)-6-(hydroxymethyl)tetrahydro-2H-pyran-3-yl)amino)-7H-pyrrolo[2,3-d]pyrimidine-5-carbonyl)phenyl)(piperidin-1-yl)methanone was prepared according to General Scheme 5, using piperidine. $^1$H NMR (DMSO-d$_6$, 400 mHz): δ 8.55 (d; J=7.12 Hz; 1H); 8.35 (s; 0.3H); 8.25 (s; 1H); 7.66 (d; J=8.77 Hz; 1H); 7.59 (s; 1H); 7.52-7.54 (m; 2H); 4.66 (br s; 1H); 4.16 (m; 2H); 3.8 (m, 2H); 3.6 (m, 6H); 3.12 (t; J=11.31 Hz; 1H); 2.19 (d; J=11.68 Hz; 1H); 1.78 (d; J=13.20 Hz; 1H); 1.59 (br s; 8H). LCMS [M+H]$^+$: 498.3, 500.3.

Example 179: Synthesis of 4-chloro-3-(4-(((3R,6S)-6-(hydroxymethyl)tetrahydro-2H-pyran-3-yl)amino)-7H-pyrrolo[2,3-d]pyrimidine-5-carbonyl)-N-(2-methoxyethyl) benzamide (I-624)

4-Chloro-3-(4-(((3R,6S)-6-(hydroxymethyl)tetrahydro-2H-pyran-3-yl)amino)-7H-pyrrolo[2,3-d]pyrimidine-5-carbonyl)-N-(2-methoxyethyl)benzamide was prepared according to General Scheme 5, using 2-methoxyethan-1-amine. $^1$H NMR (DMSO-d$_6$, 400 mHz): δ 8.67 (s; 1H); 8.56 (d; J=7.05 Hz; 1H); 8.35 (s; 0.1H); 8.26 (s; 1H); 8.00-8.02 (m; 2H); 7.70 (d; J=9.04 Hz; 1H); 7.61 (s; 1H); 4.66 (s; 1H); 4.16 (m; 2H); 3.40-3.44 (m; 5H); 3.35 (m; 2H); 3.25 (s; 3H); 3.12 (t; J=11.56 Hz; 1H); 2.19 (s; 1H); 1.79 (d; J=13.13 Hz; 1H); 1.53-1.62 (m; 1H); 1.34-1.43 (m; 1H). LCMS [M+H]$^+$: 488.2, 490.2.

Example 180: Synthesis of (4-chloro-3-(4-(((3R,6S)-6-(hydroxymethyl)tetrahydro-2H-pyran-3-yl)amino)-7H-pyrrolo[2,3-d]pyrimidine-5-carbonyl)phenyl)(3,4-dihydroisoquinolin-2(1H)-yl)methanone (I-625)

(4-Chloro-3-(4-(((3R,6S)-6-(hydroxymethyl)tetrahydro-2H-pyran-3-yl)amino)-7H-pyrrolo[2,3-d]pyrimidine-5-carbonyl)phenyl)(3,4-dihydroisoquinolin-2(1H)-yl)methanone was prepared according to General Scheme 5, using 1,2,3,4-tetrahydroisoquinoline. $^1$H NMR (DMSO-d$_6$, 400 mHz): δ 8.48 (d; J=7.03 Hz; 1H); 8.26 (s; 1.3H); 7.66 (d; J=8.51 Hz; 1H); 7.58 (m; 3H); 7.19 (s; 4H); 4.72 (s; 2H); 4.20 (s; 2H); 3.74 (s; 2H); 3.43 (t; J=6.82 Hz; 1H); 3.35 (m; 2H); 3.14 (m; 2H); 2.85 (m; 2H); 2.20 (d; J=11.69 Hz; 1H); 1.79 (d; J=13.23 Hz; 1H); 1.52-1.61 (m; 1H); 1.42 (t; J=12.35 Hz; 1H). LCMS [M+H]$^+$: 546.3, 548.25.

Example 181: Synthesis of 4-chloro-3-(4-(((3R,6S)-6-(hydroxymethyl)tetrahydro-2H-pyran-3-yl)amino)-7H-pyrrolo[2,3-d]pyrimidine-5-carbonyl)-N-(2-morpholinoethyl) benzamide (I-626)

4-Chloro-3-(4-(((3R,6S)-6-(hydroxymethyl)tetrahydro-2H-pyran-3-yl)amino)-7H-pyrrolo[2,3-d]pyrimidine-5-carbonyl)-N-(2-morpholinoethyl)benzamide was prepared according to General Scheme 5, using 2-morpholinoethan-1-amine. $^1$H NMR (DMSO-d$_6$, 400 mHz): δ 8.56 (d; J=6.97 Hz; 2H); 8.34 (s; 1H); 8.26 (s; 1.3H); 7.98-8.00 (m; 2H); 7.70 (d; J=8.96 Hz; 1H); 7.60 (s; 1H); 4.16 (d; J=9.22 Hz; 2H); 3.55 (t; J=4.54 Hz; 4H); 3.33-3.43 (m; 6H); 3.12 (t; J=11.57 Hz; 1H); 2.44 (t; J=6.91 Hz; 2H); 2.39 (m; 4H); 2.19 (d; J=11.85 Hz; 1H); 1.79 (d; J=13.00 Hz; 1H); 1.53-1.59 (m; 1H); 1.34-1.40 (m; 1H). LCMS [M+H]$^+$: 543.3, 545.3.

Example 182: Synthesis of (4-chloro-3-(4-(((3R,6S)-6-(hydroxymethyl)tetrahydro-2H-pyran-3-yl)amino)-7H-pyrrolo[2,3-d]pyrimidine-5-carbonyl)phenyl)(4-(pyridin-2-yl)piperazin-1-yl)methanone (I-627)

(4-Chloro-3-(4-(((3R,6S)-6-(hydroxymethyl)tetrahydro-2H-pyran-3-yl)amino)-7H-pyrrolo[2,3-d]pyrimidine-5-carbonyl)phenyl)(4-(pyridin-2-yl)piperazin-1-yl)methanone was prepared according to General Scheme 5, using 1-(pyridin-2-yl)piperazine. $^1$H NMR (DMSO-d$_6$, 400 mHz): δ 8.55 (d; J=7.05 Hz; 1H); 8.34 (s; 0.4H); 8.25 (s; 1H); 8.12 (d; J=4.91 Hz; 1H); 7.52-7.69 (m; 5H); 6.84 (d; J=8.62 Hz; 1H); 6.66 (dd; J=7.09; 4.93 Hz; 1H); 4.15 (d; J=9.32 Hz; 2H); 3.34-3.57 (br m; 12H); 3.12 (t; J=11.30 Hz; 1H); 2.19 (d; J=11.63 Hz; 1H); 1.78 (d; J=13.12 Hz; 1H); 1.52-1.61 (m; 1H); 1.33-1.42 (m; 1H). LCMS [M+H]$^+$: 576.3, 578.3.

Example 183: Synthesis of N-benzyl-4-chloro-3-(4-(((3R,6S)-6-(hydroxymethyl) tetrahydro-2H-pyran-3-yl)amino)-7H-pyrrolo[2,3-d]pyrimidine-5-carbonyl)benzamide (I-628)

N-Benzyl-4-chloro-3-(4-(((3R,6S)-6-(hydroxymethyl)tetrahydro-2H-pyran-3-yl)amino)-7H-pyrrolo[2,3-d]pyrimidine-5-carbonyl)benzamide was prepared according to General Scheme 5, using benzylamine. $^1$H NMR (DMSO-d$_6$, 400 mHz): δ 9.17 (t; J=5.91 Hz; 1H); 8.56 (d; J=7.05 Hz; 1H); 8.32 (s; 0.2H); 8.25 (s; 1H); 8.03-8.05 (m; 2H); 7.72 (d; J=8.45 Hz; 1H); 7.63 (s; 1H); 7.31 (d; J=4.43 Hz; 4H); 7.24 (d; J=5.57 Hz; 1H); 4.66 (br s; 1H); 4.47 (d; J=5.85 Hz; 2H); 4.15 (d; J=9.12 Hz; 2H); 3.33-3.41 (m; 3H); 3.12 (t; J=11.58 Hz; 1H); 2.19 (d; J=11.63 Hz; 1H); 1.78 (d; J=13.16 Hz; 1H); 1.56 (dd; J=14.28; 11.21 Hz; 1H); 1.34-1.40 (m; 1H). LCMS [M+H]$^+$: 520.2, 523.3.

Example 184: Synthesis of 4-chloro-3-(4-(((3R,6S)-6-(hydroxymethyl)tetrahydro-2H-pyran-3-yl)amino)-7H-pyrrolo[2,3-d]pyrimidine-5-carbonyl)-N-(1-methyl-1H-pyrazol-4-yl)benzamide (I-629)

4-Chloro-3-(4-(((3R,6S)-6-(hydroxymethyl)tetrahydro-2H-pyran-3-yl)amino)-7H-pyrrolo[2,3-d]pyrimidine-5-carbonyl)-N-(1-methyl-1H-pyrazol-4-yl)benzamide was prepared according to General Scheme 5, using 1-methyl-1H-pyrazol-4-amine. $^1$H NMR (DMSO-d$_6$, 400 mHz): δ 12.85 (br s; 1H); 10.52 (s; 1H); 8.58 (d; J=7.03 Hz; 1H); 8.37 (s; 0.1H); 8.26 (s; 1H); 8.08-8.11 (m; 2H); 8.02 (s; 1H); 7.76 (d; J=8.20 Hz; 1H); 7.65 (s; 1H); 7.54 (s; 1H); 4.66 (s; 1H); 4.17 (d; J=9.13 Hz; 2H); 3.82 (s; 3H); 3.32-3.41 (m; 3H); 3.13 (t; J=11.60 Hz; 1H); 2.20 (d; J=11.64 Hz; 1H); 1.79 (d; J=13.12 Hz; 1H); 1.53-1.62 (m; 1H); 1.39-1.41 (br m; 1H). LCMS [M+H]$^+$: 510.2, 512.2.

Example 185: Synthesis of 4-chloro-N-(3-cyanophenyl)-3-(4-(((3R,6S)-6-(hydroxymethyl) tetrahydro-2H-pyran-3-yl)amino)-7H-pyrrolo[2,3-d]pyrimidine-5-carbonyl)benzamide (I-630)

4-Chloro-N-(3-cyanophenyl)-3-(4-(((3R,6S)-6-(hydroxymethyl)tetrahydro-2H-pyran-3-yl)amino)-7H-pyrrolo[2,3-d]pyrimidine-5-carbonyl)benzamide was prepared according to General Scheme 5, using 3-aminobenzonitrile. $^1$H NMR (DMSO-d$_6$, 400 mHz): δ 10.61 (s; 1H); 8.58 (d; J=7.05 Hz; 1H); 8.39 (s; 0.2H); 8.24 (m; 2H); 8.10-8.17 (m; 2H); 8.01-8.04 (m; 1H); 7.80 (m; 1H); 7.65 (m; 1H); 7.58 (m; 2H); 4.66 (s; 1H); 4.17 (d; J=9.29 Hz; 2H); 3.36-3.42 (m; 3H); 3.13 (t; J=11.56 Hz; 1H); 2.20 (d; J=11.65 Hz; 1H); 1.79 (d; J=13.07 Hz; 1H); 1.53-1.62 (m; 1H); 1.34-1.43 (m; 1H). LCMS [M+H]$^+$: 531.2, 533.2.

Example 186: Synthesis of 4-chloro-3-(4-(((3R,6S)-6-(hydroxymethyl)tetrahydro-2H-pyran-3-yl)amino)-7H-pyrrolo[2,3-d]pyrimidine-5-carbonyl)-N-phenylbenzamide (I-631)

4-Chloro-3-(4-(((3R,6S)-6-(hydroxymethyl)tetrahydro-2H-pyran-3-yl)amino)-7H-pyrrolo[2,3-d]pyrimidine-5-carbonyl)-N-phenylbenzamide was prepared according to General Scheme 5, using aniline. $^1$H NMR (DMSO-d$_6$, 400 mHz): δ 10.31 (s; 1H); 8.59 (d; J=7.06 Hz; 1H); 8.41 (s; 0.2H); 8.26 (s; 1H); 8.09-8.16 (m; 2H); 7.76 (m; 3H); 7.64 (s; 1H); 7.35 (m; 2H); 7.11 (t; J=7.39 Hz; 1H); 4.66 (s; 1H); 4.17 (m; 2H); 3.33-3.41 (m; 3H); 3.13 (t; J=11.53 Hz; 1H); 2.20 (d; J=11.72 Hz; 1H); 1.79 (d; J=11.57 Hz; 1H); 1.53-1.62 (m; 1H); 1.39 (q; J=12.08 Hz; 1H). LCMS [M+H]$^+$: 506.2, 508.2.

General Procedure I

General procedure for the saponification of a benzoic ester

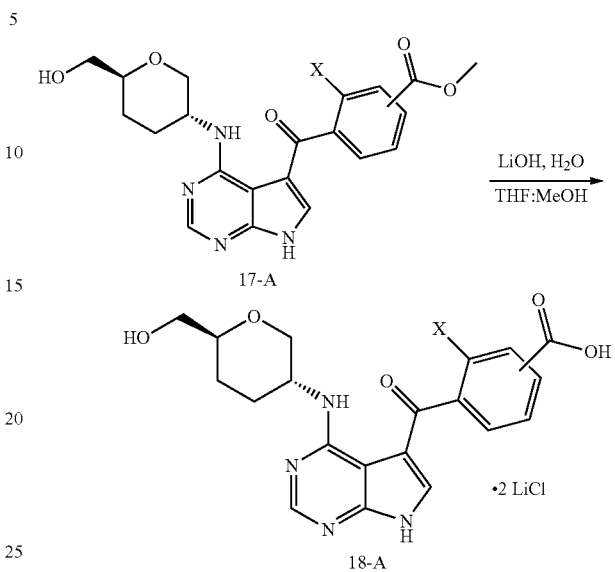

The benzoic ester substrate (17-A) (1 eq.) were suspended in THF (1 mL/0.2 mmol) and methanol (1 mL/0.2 mmol). A solution of 1N lithium hydroxide was then added (2 eq.) and left to stir at room temperature overnight. The reaction crude was neutralized with a 1N aqueous solution of HCl and was concentrated to dryness. The crude product was used as is without further purification.

Example 187: Synthesis of (4-(((3R,6S)-6-(hydroxymethyl)tetrahydro-2H-pyran-3-yl)amino)-7H-pyrrolo[2,3-d]pyrimidin-5-yl)(4-(morpholine-4-carbonyl)phenyl) methanone (I-632)

(4-(((3R,6S)-6-(Hydroxymethyl)tetrahydro-2H-pyran-3-yl)amino)-7H-pyrrolo[2,3-d]pyrimidin-5-yl)(4-(morpholine-4-carbonyl)phenyl)methanone was synthesized according to General Scheme 6. $^1$H NMR (DMSO-d$_6$, 400 mHz): δ 12.74 (s; 1H); 8.66 (d; J=7.13 Hz; 1H); 8.25 (s; 1H); 7.81-7.83 (m; 3H); 7.55 (d; J=7.88 Hz; 2H); 4.65 (t; J=5.51 Hz; 1H); 4.12-4.17 (m; 2H); 3.55-3.68 (m; 7H); 3.35-3.45 (m; 5H); 3.11 (t; J=11.26 Hz; 1H); 2.15-2.20 (m; 1H); 1.77-1.80 (m; 1H); 1.53-1.59 (m; 1H); 1.36-1.42 (m; 1H). LCMS [M+H]$^+$: 466.1.

Example 188: Synthesis of 4-(4-(((3R,6S)-6-(hydroxymethyl)tetrahydro-2H-pyran-3-yl)amino)-7H-pyrrolo[2,3-d]pyrimidine-5-carbonyl)-N-(1-methyl-1H-pyrazol-4-yl)benzamide (I-633)

4-(4-(((3R,6S)-6-(Hydroxymethyl)tetrahydro-2H-pyran-3-yl)amino)-7H-pyrrolo[2,3-d]pyrimidine-5-carbonyl)-N-(1-methyl-1H-pyrazol-4-yl)benzamide was synthesized according to General Scheme 6. $^1$H NMR (DMSO-d$_6$, 400 mHz): δ 12.76 (br s; 1H); 10.62 (s; 1H); 8.69 (d; J=7.17 Hz; 1H); 8.25 (s; 1H); 8.17 (s; 1H); 8.09 (d; J=8.10 Hz; 2H); 8.07 (s; 1H); 7.90 (d; J=8.09 Hz; 2H); 7.79 (s; 1H); 7.60 (s; 1H); 4.65 (s; 1H); 4.11-4.21 (m; 2H); 3.84 (s; 3H); 3.38-3.45 (m; 1H); 3.30-3.35 (m; 6H); 3.12 (t; J=11.19 Hz; 1H); 2.13-2.23 (m; 1H); 1.74-1.82 (m; 1H); 1.51-1.63 (m; 1H); 1.31-1.44 (m; 1H). LCMS [M+H]$^+$: 476.2.

Example 189: Synthesis of 3-(4-(((3R,6S)-6-(hydroxymethyl)tetrahydro-2H-pyran-3-yl)amino)-7H-pyrrolo[2,3-d]pyrimidine-5-carbonyl)-N-phenylbenzamide (I-634)

3-(4-(((3R,6S)-6-(Hydroxymethyl)tetrahydro-2H-pyran-3-yl)amino)-7H-pyrrolo[2,3-d]pyrimidine-5-carbonyl)-N-phenylbenzamide was synthesized according to General Scheme 6. $^1$H NMR (DMSO-$d_6$, 400 mHz): δ 12.76 (s; 1H); 10.37 (s; 1H); 8.70 (d; J=7.11 Hz; 1H); 8.35 (s; 1H); 8.26 (s; 1H); 8.20 (d; J=7.86 Hz; 1H); 7.99 (d; J=7.69 Hz; 1H); 7.89 (s; 1H); 7.78 (d; J=8.06 Hz; 2H); 7.71 (t; J=7.73 Hz; 1H); 7.36 (t; J=7.79 Hz; 2H); 7.12 (t; J=7.39 Hz; 1H); 4.13-4.19 (m; 2H); 3.29-3.45 (m; 5H); 3.12 (t; J=11.03 Hz; 1H); 2.16-2.21 (m; 1H); 1.76-1.81 (m; 1H); 1.52-1.59 (m; 1H); 1.34-1.43 (m; 1H). LCMS [M+H]$^+$: 472.2.

Example 190: Synthesis of (4-(((3R,6S)-6-(hydroxymethyl)tetrahydro-2H-pyran-3-yl)amino)-7H-pyrrolo[2,3-d]pyrimidin-5-yl)(3-(morpholine-4-carbonyl)phenyl) methanone (I-635)

(4-(((3R,6S)-6-(Hydroxymethyl)tetrahydro-2H-pyran-3-yl)amino)-7H-pyrrolo[2,3-d]pyrimidin-5-yl)(3-(morpholine-4-carbonyl)phenyl)methanone was synthesized according to General Scheme 6. $^1$H NMR (DMSO-$d_6$, 400 mHz): δ 12.72 (s; 1H); 8.65 (d; J=7.24 Hz; 1H); 8.26 (s; 1H); 7.86 (dt; J=7.46; 1.57 Hz; 1H); 7.78 (s; 1H); 7.76 (t; J=1.65 Hz; 1H); 7.68 (dt; J=7.65; 1.51 Hz; 1H); 7.63 (t; J=7.54 Hz; 1H); 4.67 (t; J=5.53 Hz; 1H); 4.13-4.21 (m; 2H); 3.50-3.71 (m; 7H); 3.35-3.49 (m; 5H); 3.12 (t; J=11.32 Hz; 1H); 2.16-2.23 (m; 1H); 1.77-1.83 (m; 1H); 1.51-1.63 (m; 1H); 1.35-1.45 (m; 1H). LCMS [M+H]$^+$: 466.2.

Example 191: Synthesis of 4-(4-(((3R,6S)-6-(hydroxymethyl)tetrahydro-2H-pyran-3-yl)amino)-7H-pyrrolo[2,3-d]pyrimidine-5-carbonyl)-N-(2-methoxyethyl)benzamide (I-636)

4-(4-(((3R,6S)-6-(Hydroxymethyl)tetrahydro-2H-pyran-3-yl)amino)-7H-pyrrolo[2,3-d]pyrimidine-5-carbonyl)-N-(2-methoxyethyl)benzamide was synthesized according to General Scheme 6. $^1$H NMR (DMSO-$d_6$, 400 mHz): δ 8.67-8.72 (m; 2H); 8.24 (s; 1H); 7.98-8.00 (m; 2H); 7.82-7.84 (m; 2H); 7.76 (s; 1H); 4.65 (t; J=5.48 Hz; 1H); 4.11-4.17 (m; 2H); 3.58-3.61 (m; 1H); 3.38-3.50 (m; 6H); 3.28 (s; 3H); 3.11 (t; J=11.28 Hz; 1H); 2.15-2.21 (m; 1H); 1.75-1.81 (m; 2H); 1.54-1.61 (m; 1H); 1.33-1.43 (m; 1H). LCMS [M+H]$^+$: 454.2.

Example 192: Synthesis of 3-(4-(((3R,6S)-6-(hydroxymethyl)tetrahydro-2H-pyran-3-yl)amino)-7H-pyrrolo[2,3-d]pyrimidine-5-carbonyl)-N-(2-methoxyethyl)benzamide (I-637)

3-(4-(((3R,6S)-6-(Hydroxymethyl)tetrahydro-2H-pyran-3-yl)amino)-7H-pyrrolo[2,3-d]pyrimidine-5-carbonyl)-N-(2-methoxyethyl)benzamide was synthesized according to General Scheme 6. $^1$H NMR (DMSO-$d_6$, 400 mHz): δ 12.73 (br s; 1H); 8.66-8.71 (m; 2H); 8.25 (s; 1H); 8.22-8.23 (m; 1H); 8.08-8.11 (m; 1H); 7.91-7.93 (m; 1H); 7.80 (s; 1H); 7.63 (t; J=7.73 Hz; 1H); 4.65 (t; J=5.55 Hz; 1H); 4.11-4.18 (m; 2H); 3.37-3.49 (m; 8H); 3.27 (s; 3H); 3.11 (t; J=11.22 Hz; 1H); 2.14-2.22 (m; 1H); 1.74-1.82 (m; 1H); 1.51-1.61 (m; 1H); 1.32-1.44 (m; 1H). LCMS [M+H]$^+$: 454.2.

Example 193: Synthesis of 3-(4-(((3R,6S)-6-(hydroxymethyl)tetrahydro-2H-pyran-3-yl)amino)-7H-pyrrolo[2,3-d]pyrimidine-5-carbonyl)-N-(1-methyl-1H-pyrazol-4-yl)benzamide (I-638)

3-(4-(((3R,6S)-6-(Hydroxymethyl)tetrahydro-2H-pyran-3-yl)amino)-7H-pyrrolo[2,3-d]pyrimidine-5-carbonyl)-N-(1-methyl-1H-pyrazol-4-yl)benzamide was synthesized according to General Scheme 6. $^1$H NMR (DMSO-$d_6$, 400 mHz): δ 12.76 (s; 1H); 10.56 (s; 1H); 8.68 (d; J=7.22 Hz; 1H); 8.34 (t; J=1.66 Hz; 1H); 8.24-8.25 (m; 1H); 8.20 (dt; J=7.82; 1.40 Hz; 1H); 8.05 (s; 1H); 7.96 (dt; J=7.69; 1.35 Hz; 1H); 7.86 (s; 1H); 7.69 (t; J=7.74 Hz; 1H); 7.58 (d; J=0.72 Hz; 1H); 4.66 (t; J=5.45 Hz; 1H); 4.13-4.21 (m; 3H); 3.83 (s; 3H); 3.38-3.45 (m; 2H); 3.34-3.37 (m; 3H); 3.11 (t; J=11.07 Hz; 2H); 2.16-2.19 (m; 2H); 1.77-1.80 (m; 2H); 1.52-1.62 (m; 2H); 1.34-1.44 (m; 2H). LCMS [M+H]$^+$: 476.2.

Example 194: Synthesis of 4-(4-(((3R,6S)-6-(hydroxymethyl)tetrahydro-2H-pyran-3-yl)amino)-7H-pyrrolo[2,3-d]pyrimidine-5-carbonyl)-N-phenylbenzamide (I-231)

4-(4-(((3R,6S)-6-(Hydroxymethyl)tetrahydro-2H-pyran-3-yl)amino)-7H-pyrrolo[2,3-d]pyrimidine-5-carbonyl)-N-phenylbenzamide was synthesized according to General Scheme 6. $^1$H NMR (DMSO-$d_6$, 400 mHz): δ 12.80 (s; 1H); 10.46 (s; 1H); 8.74 (d; J=7.15 Hz; 1H); 8.30 (s; 1H); 8.15 (d; J=8.03 Hz; 2H); 7.95 (d; J=8.03 Hz; 2H); 7.86 (s; 1H); 7.83 (d; J=5.06 Hz; 2H); 7.42 (t; J=7.77 Hz; 2H); 7.17 (t; J=7.37 Hz; 1H); 4.70 (t; J=5.53 Hz; 1H); 4.16-4.23 (m; 2H); 3.42-3.47 (m; 1H); 3.37-3.41 (m; 2H); 3.16 (t; J=11.18 Hz; 1H); 2.19-2.25 (m; 1H); 1.81-1.85 (m; 1H); 1.60-1.66 (m; 1H); 1.38-1.47 (m; 1H). LCMS [M+H]$^+$: 472.2.

Example 195: Synthesis of N-(3-chloro-4-(4-(((3R,6S)-6-(hydroxymethyl)tetrahydro-2H-pyran-3-yl)amino)-7H-pyrrolo[2,3-d]pyrimidine-5-carbonyl)phenyl)benzamide (I-276)

Step 1: Synthesis of (2-chloro-4-nitrophenyl)(4-chloro-7H-pyrrolo[2,3-d]pyrimidin-5-yl)methanone (2-Chloro-4-nitrophenyl)(4-chloro-7H-pyrrolo[2,3-d]pyrimidin-5-yl)methanone was synthesized according General Procedure A, step 1, using 4-chloro-7H-pyrrolo[2,3-d]pyrimidine and 2-chloro-4-nitrobenzoyl chloride. LCMS [M+H]$^+$: 337.9.

Step 2: Synthesis of (2-chloro-4-nitrophenyl)(4-chloro-7-((2-(trimethylsilyl)ethoxy) methyl)-7H-pyrrolo[2,3-d]pyrimidin-5-yl)methanone Protection of the nitrogen was achieved according to General Procedure A, step 1 LCMS [M+H]$^+$: 467.0.

Step 2: Synthesis of (2-chloro-4-nitrophenyl)(4-(((3R,6S)-6-(hydroxymethyl)tetrahydro-2H-pyran-3-yl)amino)-7-((2-(trimethylsilyl)ethoxy)methyl)-7H-pyrrolo[2,3-d]pyrimidin-5-yl)methanone The chloride displacement was done according to General Procedure A, step 2, with ((2S,5R)-5-aminotetrahydro-2H-pyran-2-yl)methanol. LCMS [M+H]$^+$: 562.2

Step 3: Synthesis of (4-(((3R,6S)-6-(((tert-butyldimethylsilyl)oxy)methyl)tetrahydro-2H-pyran-3-yl)amino)-7-((2-(trimethylsilyl)ethoxy)methyl)-7H-pyrrolo[2,3-d]pyrimidin-5-yl)(2-chloro-4-nitrophenyl)methanone To a solution of (2-chloro-4-nitrophenyl)(4-(((3R,6S)-6-(hydroxymethyl) tetrahydro-2H-pyran-3-yl)amino)-7-((2-(trimethylsilyl)ethoxy)methyl)-7H-pyrrrol[2,3-d]pyrimidin-5-yl)methanone (1260 mg, 2.242 mmol) in DMF (12 mL) were added TBDMS-Cl (405 mg, 2.69 mmol) and imidazole (305 mg, 4.483 mmol). The reaction mixture was stirred at room temperature for 18 hours. The reaction mixture was diluted with EtOAc (50 mL) and aqueous saturated NH$_4$Cl (60 mL). The layers were partitioned and the aqueous layer was extracted with EtOAc (40 mL). The combined organic layers were washed with aqueous saturated NaHCO$_3$ (60 mL), water (60 mL) and brine. The n it was dried over MgSO$_4$, filtered and concentrated to dryness to afford 1600 mg of the desired material which was used in the subsequent step without further purification.

Step 4: Synthesis of (4-Amino-2-chlorophenyl)(4-(((3R,6S)-6-(((tert-butyldimethylsilyl) oxy) methyl)tetrahydro-2H-pyran-3-yl)amino)-7-((2-(trimethylsilyl)ethoxy)methyl)-7H-pyrrolo[2,3-d]pyrimidin-5-yl)methanone Sylilation was achieved under standard conditions. LCMS [M+H]: 646.4.
General Procedure J
A general method for amide formation using an acyl chloride with silyl-protected aniline substrate followed by desilylation

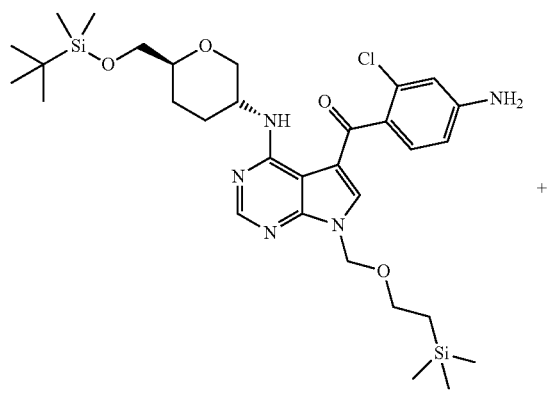

23-A

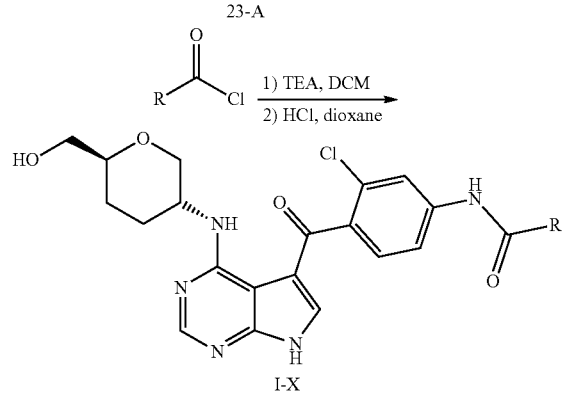

I-X

A solution of (4-amino-2-chlorophenyl)(4-(((3R,6S)-6-(((tert-butyldimethylsilyl) oxy)methyl)-tetrahydro-2H-pyran-3-yl)amino)-7-((2-(trimethylsilyl)ethoxy)methyl)-7H-pyrrolo[2,3-d]pyrimidin-5-yl)methanone (23-A) (1 eq) in DCM (1 mL/0.05 mmol) is treated with corresponding acyl chloride (1.5 eq) and triethylamine (3 eq) at room temperature for 3 h. The mixture is then concentrated and 4M HCl in dioxane (2 mL/0.05 mmol) is added. The mixture is stirred at 40° C. overnight then concentrated and the residue purified by preparative reverse phase HPLC (gradient from 30% to 95% of acetonitrile+0.1% formic acid).

Step 5: Synthesis of N-(3-chloro-4-(4-(((3R,6S)-6-(hydroxymethyl)tetrahydro-2H-pyran-3-yl)amino)-7H-pyrrolo[2,3-d]pyrimidine-5-carbonyl)phenyl)benzamide (I-276)

N-(3-Chloro-4-(4-(((3R,6S)-6-(hydroxymethyl)tetrahydro-2H-pyran-3-yl)amino)-7H-pyrrolo[2,3-d]pyrimidine-5-carbonyl)phenyl)benzamide was synthesized according to General Scheme 7, using benzoyl chloride. $^1$H NMR (DMSO-d$_6$, 400 MHz): δ 12.90 (bs, 1H), 10.62 (s, 1), 8.85 (bs, 1H), 8.29 (s, 1H), 8.13 (d, J=1.8 Hz, 1H), 7.99-7.97 (m, 2H), 7.87 (dd, J=8.4 Hz, J=1.8 Hz, 1H), 7.65-7.55 (m, 5H), 4.18-4.10 (m, 2H), 3.45-3.33 (m, 3H), 3.18-3.13 (m, 1H), 2.22-2.19 (m, 1H), 1.81-1.75 (m, 1H), 1.66-1.56 (m, 1H), 1.44-1.34 (m, 1H). LCMS [M+H]$^+$: 506.2.

Example 196: Synthesis of N-(3-chloro-4-(4-(((3R,6S)-6-(hydroxymethyl)tetrahydro-2H-pyran-3-yl)amino)-7H-pyrrolo[2,3-d]pyrimidine-5-carbonyl)phenyl)-2-phenylacetamide (I-639)

N-(3-Chloro-4-(4-(((3R,6S)-6-(hydroxymethyl)tetrahydro-2H-pyran-3-yl)amino)-7H-pyrrolo[2,3-d]pyrimidine-5-carbonyl)phenyl)-2-phenylacetamide was synthesized according to General Scheme 7, using 2-phenylacetyl chloride. $^1$H NMR (DMSO-d$_6$, 400 mHz): δ 12.70 (bs, 1H), 10.63 (s, 1H), 8.60 (d, J=7.2 Hz, 1H), 8.23 (s, 1H), 7.95 (d, J=1.8 Hz, 1H), 7.59 (dd, J=8.4 Hz, J=1.8 Hz, 1H), 7.54 (s, 1H), 7.51 (d, J=8.4 Hz, 1H), 7.35-7.32 (m, 3H), 7.28-7.25 (m, 1H), 4.66 (bs, 1H), 4.19-4.10 (m, 2H), 3.70 (s, 2H), 3.43-3.40 (m, 1H), 3.45-3.31 (m, 3H), 3.14-3.08 (m, 1H), 2.19-2.16 (m, 1H), 1.79-1.76 (m, 1H), 1.62-1.52 (m, 1H), 1.43-1.32 (m, 1H). LCMS [M+H]$^+$: 520.1.

Example 197: Synthesis of N-(3-chloro-4-(4-(((3R,6S)-6-(hydroxymethyl)tetrahydro-2H-pyran-3-yl)amino)-7H-pyrrolo[2,3-d]pyrimidine-5-carbonyl)phenyl)-1-phenylcyclopropane-1-carboxamide (I-640)

N-(3-Chloro-4-(4-(((3R,6S)-6-(hydroxymethyl)tetrahydro-2H-pyran-3-yl)amino)-7H-pyrrolo[2,3-d]pyrimidine-5-carbonyl)phenyl)-1-phenylcyclopropane-1-carboxamide was synthesized according to General Scheme 7, using 1-phenylcyclopropane-1-carbonyl chloride. $^1$H NMR (DMSO-d$_6$, 400 mHz): δ 9.58 (s, 1H), 8.60 (d, J=7.0 Hz, 1H), 8.22 (s, 1H), 7.91 (d, J=2.0 Hz, 1H), 7.65 (dd, J=8.4 Hz, J=1.8 Hz, 1H), 7.51 (s, 1H), 7.46 (d, J=8.4 Hz, 1H), 7.42-7.35 (m, 4H), 7.32-7.28 (m, 1H), 4.65 (bs, 1H), 4.18-4.10 (m, 2H), 3.44-3.33 (m, 7H) 3.14-3.08 (m, 1H), 2.19-2.16 (m, 1H), 1.79-1.76 (m, 1H), 1.62-1.52 (m, 1H), 1.48 (dd, J=6.8 Hz, J=4.5 Hz, 2H), 1.42-1.32 (m, 1H), 1.16 (dd, J=6.8 Hz, J=4.5 Hz, 2H). LCMS [M+H]$^+$: 546.3.

Example 198: Synthesis of 2-(benzyloxy)-N-(3-chloro-4-(4-(((3R,6S)-6-(hydroxymethyl)tetrahydro-2H-pyran-3-yl)amino)-7H-pyrrolo[2,3-d]pyrimidine-5-carbonyl)phenyl) acetamide (I-641)

2-(Benzyloxy)-N-(3-chloro-4-(4-(((3R,6S)-6-(hydroxymethyl)tetrahydro-2H-pyran-3-yl)amino)-7H-pyrrolo[2,3-d]pyrimidine-5-carbonyl)phenyl)acetamide was synthesized according to General Scheme 7, using 2-(benzyloxy)acetyl chloride. $^1$H NMR (DMSO-$d_6$, 400 mHz): δ 12.73 (bs, 1H), 10.24 (s, 1H), 8.62 (d, J=7.0 Hz, 1H), 8.24 (s, 1H), 8.00 (d, J=1.8 Hz, 1H), 7.70 (dd, J=8.4 Hz, J=1.8 Hz, 1H), 7.55 (s, 1H), 7.53 (d, J=8.4 Hz, 1H), 7.43-7.37 (m, 3H), 7.34-7.31 (m, 1H), 4.64 (s, 2H), 4.15 (bs, 4H), 4.06-3.88 (m, 1H), 3.57-3.51 (m, 3H), 3.46-3.33 (m, 11H+$H_2O$), 3.15-3.09 (m, 1H), 2.20-2.17 (m, 1H), 1.91-1.80 (m, 1H), 1.63-1.50 (m, 1H), 1.44-1.31 (m, 1H). LCMS [M+H]$^+$: 550.2.

Example 199: Synthesis of N-(3-(4-(((3R,6S)-6-(hydroxymethyl)tetrahydro-2H-pyran-3-yl)amino)-7H-pyrrolo[2,3-d]pyrimidine-5-carbonyl)phenyl) benzamide (I-642)

N-(3-(4-(((3R,6S)-6-(Hydroxymethyl)tetrahydro-2H-pyran-3-yl)amino)-7H-pyrrolo[2,3-d]pyrimidine-5-carbonyl)phenyl)benzamide was prepared according to General Scheme 8 and using benzoic acid. $^1$H NMR (DMSO-$d_6$, 400 mHz): d 12.71 (s, 1H); 10.45 (s, 1H); 8.72 (d; J=6.93 Hz; 1H); 8.23 (s; 2H); 8.03 (d; J=6.49 Hz; 1H); 7.97 (d; J=7.51 Hz; 2H); 7.83 (s; 1H); 7.51-7.60 (m; 5H); 4.64 (t; J=5.34 Hz; 1H); 4.14 (d; J=9.29 Hz; 2H); 3.35-3.43 (m; 3H); 3.11 (t; J=11.33 Hz; 1H); 2.15-2.18 (m; 1H); 1.75-1.78 (m; 1H); 1.52-1.61 (m; 1H); 1.32-1.41 (m; 1H). LCMS [M+H]$^+$: 472.2.

Example 200: Synthesis of N-(3-(4-(((3R,6S)-6-(hydroxymethyl)tetrahydro-2H-pyran-3-yl)amino)-7H-pyrrolo[2,3-d]pyrimidine-5-carbonyl)phenyl) picolinamide (I-643)

N-(3-(4-(((3R,6S)-6-(Hydroxymethyl)tetrahydro-2H-pyran-3-yl)amino)-7H-pyrrolo[2,3-d]pyrimidine-5-carbonyl)phenyl)picolinamide was prepared according to General Scheme 8 and using 2-picolinic acid. $^1$H NMR (DMSO-$d_6$, 400 mHz): δ 12.75 (s; 1H); 10.94 (s; 1H); 8.77 (m; 2H); 8.38 (s; 1H); 8.25 (s; 1H); 8.15-8.19 (m; 3H); 8.07-8.11 (m; 1H); 7.89 (s; 1H); 7.68-7.71 (m; 1H); 7.54 (m; 2H); 4.15 (d; J=9.34 Hz; 2H); 3.13 (t; J=11.53 Hz; 1H); 2.18 (s; 1H); 1.78 (d; J=13.08 Hz; 1H); 1.59 (d; J=12.82 Hz; 1H); 1.39 (d; J=12.79 Hz; 1H). LCMS [M+H]$^+$: 472.1.

Example 201: Synthesis of N-(3-(4-(((3R,6S)-6-(hydroxymethyl)tetrahydro-2H-pyran-3-yl)amino)-7H-pyrrolo[2,3-d]pyrimidine-5-carbonyl)phenyl) tetrahydro-2H-pyran-4-carboxamide (I-644)

N-(3-(4-(((3R,6S)-6-(Hydroxymethyl)tetrahydro-2H-pyran-3-yl)amino)-7H-pyrrolo[2,3-d]pyrimidine-5-carbonyl)phenyl)tetrahydro-2H-pyran-4-carboxamide was prepared according to General Scheme 8 and using tetrahydro-2H-pyran-4-carboxylic acid. $^1$H NMR (DMSO-$d_6$, 400 mHz): δ 12.70 (s; 1H); 10.12 (s; 1H); 8.70 (d; J=7.05 Hz; 1H); 8.24 (s; 1H); 8.08 (s; 1H); 7.78-7.81 (m; 2H); 7.45-7.49 (m; 2H); 4.65 (t; J=5.56 Hz; 1H); 4.14 (d; J=9.28 Hz; 2H); 3.91 (d; J=11.26 Hz; 2H); 3.11 (t; J=11.56 Hz; 1H); 2.60 (s; 1H); 2.17 (s; 1H); 1.65-1.71 (m; 4H); 1.40 (s; 1H). LCMS [M+H]$^+$: 480.3.

Example 202: Synthesis of N-(3-(4-(((3R,6S)-6-(hydroxymethyl)tetrahydro-2H-pyran-3-yl)amino)-7H-pyrrolo[2,3-d]pyrimidine-5-carbonyl)phenyl)-2-methoxyacetamide (I-645)

N-(3-(4-(((3R,6S)-6-(Hydroxymethyl)tetrahydro-2H-pyran-3-yl)amino)-7H-pyrrolo[2,3-d]pyrimidine-5-carbonyl)phenyl)-2-methoxyacetamide was prepared according to General Scheme 8 and using 2-methoxyacetic acid. $^1$H NMR (DMSO-$d_6$, 400 mHz): δ 12.71 (s; 1H); 10.01 (s; 1H); 8.71 (d; J=7.08 Hz; 1H); 8.24 (s; 1H); 8.13 (s; 1H); 7.89-7.92 (m; 1H); 7.80 (s; 1H); 7.48 (m; 2H); 4.65 (t; J=5.58 Hz; 1H); 4.14 (m; 2H); 4.03 (s; 2H); 3.11 (t; J=11.53 Hz; 1H); 2.17 (m; 1H); 1.78 (m; 1H); 1.57 (m; 1H); 1.33-1.43 (m; 1H). LCMS [M+H]$^+$: 440.2.

General Procedure K

A general procedure for arylamine formation

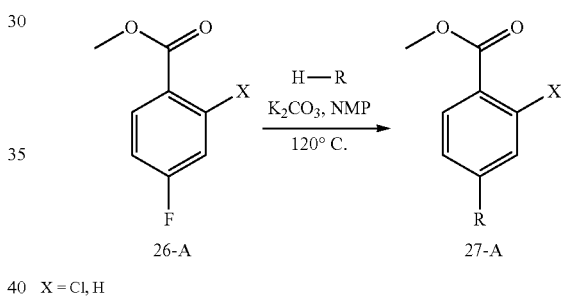

X = Cl, H

The arylfluoride substrate (26-A) (1 eq.) was diluted in NMP (1 mL/1.32 mmol). Cyclic amine (1.1 eq.) and potassium carbonate (2 eq.) were added and the mixture was stirred at 120° C. overnight. The reaction mixture was allowed to cool to room temperature and was diluted with water. The crude mixture was extracted with ethyl acetate (×3) and the combined organics were washed with water (×2). Organics were dried over magnesium sulfate, filtered and concentrated to dryness. The product was purified by silica gel chromatography (0-50% ethyl acetate in hexanes).

General Procedure L

A general procedure for phenol alkylation

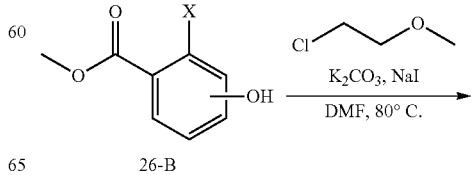

-continued

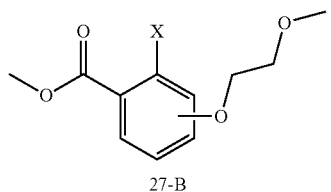

X = Cl, H

A mixture of phenol (26-B) (1 eq.), 1-chloro-2-methoxyethane (1.5 eq.), potassium carbonate (2 eq.) and sodium iodide (0.2 eq.) in DMF (1 mL/0.45 mmol) is heated overnight at 80° C. The reaction mixture is then cooled to room temperature and poured in water, stirred for 15 min and filtered then dried under high vacuum. The product was used as is without further purification.

General Procedure M

A general procedure for ketone formation through aryllithium attack on an ester

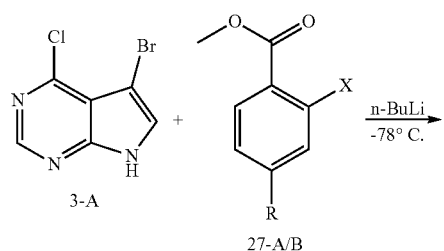

X = Cl, H

5-Bromo-4-chloro-7H-pyrrolo[2,3-d]pyrimidine (3-A) (1 eq.) was diluted in dry THF (1 mL/0.21 mmol) and was cooled to −78° C. n-BuLi (2.1 eq.) was added dropwise and the temperature was monitored with an internal thermocouple to ensure the reaction temperature never rose above −60° C. The reaction mixture was stirred for 1 hour before the substituted methyl benzoate (27-A/B) (1.05 eq.) in dry THF (1 mL/0.9 mmol) was added dropwise with the internal temperature never exceeding −60° C. The mixture was stirred at −78° C. for 1 hour then quenched with saturated aqueous Ammonium chloride solution and extracted with ethyl acetate (×3). The combined organic layers were washed with sodium bicarbonate and dried over magnesium sulfate, filtered and concentrated. The resulting residue was purified by silica gel column chromatography (10-100% ethyl acetate in hexanes).

Example 203: Synthesis of (2-chloro-4-morpholinophenyl)(4-(((3R,6S)-6-(hydroxymethyl)tetrahydro-2H-pyran-3-yl)amino)-7H-pyrrolo[2,3-d]pyrimidin-5-yl)methanone (I-311i)

(2-Chloro-4-morpholinophenyl)(4-(((3R,6S)-6-(hydroxymethyl)tetrahydro-2H-pyran-3-yl)amino)-7H-pyrrolo[2,3-d]pyrimidin-5-yl)methanone was synthesized according to General Scheme 9, using ((2S,5R)-5-aminotetrahydro-2H-pyran-2-yl)methanol. $^1$H NMR (DMSO-$d_6$, 400 mHz): δ 12.61 (s; 1H); 8.65 (d; J=6.98 Hz; 1H); 8.23 (s; 1H); 7.50 (s; 1H); 7.43 (d; J=8.54 Hz; 1H); 7.07 (s; 1H); 6.96 (d; J=8.68 Hz; 1H); 4.65 (t; J=5.29 Hz; 1H); 4.10-4.15 (m; 2H); 3.73-3.75 (m; 4H); 3.38-3.43 (m; 3H); 3.26-3.27 (m; 4H); 3.11 (t; J=11.29 Hz; 1H); 2.15-2.20 (m; 1H); 1.76-1.79 (m; 1H); 1.49-1.60 (m; 1H); 1.33-1.43 (m; 1H). LCMS [M+H]$^+$: 472.

Example 204: Synthesis of (2-chloro-4-(piperidin-1-yl)phenyl)(4-(((3R,6S)-6-(hydroxymethyl)tetrahydro-2H-pyran-3-yl)amino)-7H-pyrrolo[2,3-d]pyrimidin-5-yl)methanone (I-646)

(2-Chloro-4-(piperidin-1-yl)phenyl)(4-(((3R,6S)-6-(hydroxymethyl)tetrahydro-2H-pyran-3-yl)amino)-7H-pyrrolo[2,3-d]pyrimidin-5-yl)methanone was synthesized according to General Scheme 9, using ((2S,5R)-5-aminotetrahydro-2H-pyran-2-yl)methanol. $^1$H NMR (DMSO-$d_6$, 400 mHz): δ 12.60 (s; 1H); 8.66 (d; J=7.11 Hz; 1H); 8.22 (s; 1H); 7.51 (s; 1H); 7.38 (d; J=8.66 Hz; 1H); 7.01 (d; J=2.36 Hz; 1H); 6.91 (dd; J=8.75; 2.40 Hz; 1H); 4.66 (t; J=5.54 Hz; 1H); 4.12-4.18 (m; 2H); 3.36-3.42 (m; 3H); 3.30-3.32 (m; 4H); 3.11 (t; J=11.42 Hz; 1H); 2.16-2.20 (m; 1H); 1.74-1.79 (m; 1H); 1.51-1.58 (m; 8H); 1.33-1.43 (m; 1H). LCMS [M+H]$^+$: 470.

Example 205: Synthesis of (2-chloro-4-(2-oxa-6-azaspiro[3.3]heptan-6-yl)phenyl)(4-(((3R,6S)-6-(hydroxymethyl)tetrahydro-2H-pyran-3-yl)amino)-7H-pyrrolo[2,3-d]pyrimidin-5-yl)methanone (I-647)

(2-Chloro-4-(2-oxa-6-azaspiro[3.3]heptan-6-yl)phenyl)(4-(((3R,6S)-6-(hydroxymethyl)tetrahydro-2H-pyran-3-yl)amino)-7H-pyrrolo[2,3-d]pyrimidin-5-yl)methanone was synthesized according to General Scheme 9, using 2-oxa-6-azaspiro[3.3]heptane, and ((2S,5R)-5-aminotetrahydro-2H-pyran-2-yl)methanol. $^1$H NMR (DMSO-$d_6$, 400 mHz): δ 12.59 (s; 1H); 8.65 (d; J=7.08 Hz; 1H); 8.22 (s; 1H); 7.44 (s; 1H); 7.39 (d; J=8.37 Hz; 1H); 6.54 (d; J=2.18 Hz; 1H); 6.41 (dd; J=8.42; 2.21 Hz; 1H); 4.73 (s; 4H); 4.65 (t; J=5.57 Hz; 1H); 4.11-4.17 (m; 2H); 4.10 (s; 4H); 3.35-3.44 (m; 3H); 3.10 (t; J=11.53 Hz; 1H); 2.15-2.19 (m; 1H); 1.76-1.80 (m; 1H); 1.51-1.61 (m; 1H); 1.32-1.42 (m; 1H). LCMS [M+H]$^+$: 484.

Example 206: Synthesis of (4-(((3R,6S)-6-(hydroxymethyl)tetrahydro-2H-pyran-3-yl)amino)-7H-pyrrolo[2,3-d]pyrimidin-5-yl)(4-(2-methoxyethoxy)phenyl)methanone (I-318i)

(4-(((3R,6S)-6-(Hydroxymethyl)tetrahydro-2H-pyran-3-yl)amino)-7H-pyrrolo[2,3-d]pyrimidin-5-yl)(4-(2-methoxyethoxy)phenyl)methanone was prepared according to General Scheme 9, using methyl 4-hydroxybenzoate and ((2S, 5R)-5-aminotetrahydro-2H-pyran-2-yl)methanol. $^1$H NMR (DMSO-$d_6$, 400 mHz): δ 12.63 (bs, 1H), 8.66 (d, J=7.2 Hz, 1H), 8.23 (s, 1H), 7.79 (d, J=8.8 Hz, 2H), 7.76 (s, 1H), 7.08

(d, J=8.8 Hz, 2H), 4.65 (bs, 1H), 4.22-4.19 (m, 2H), 4.16-4.11 (m, 2H), 3.71-3.69 (m, 2H), 3.42-3.39 (m, 1H), 3.36-3.30 (m, 4H+H2O), 3.13-3.07 (m, 1H), 2.18-2.15 (m, 1H), 1.79-1.76 (m, 1H), 1.61-1.51 (m, 1H), 1.42-1.32 (m, 1H). LCMS [M+H+]: 427.30.

Example 207: Synthesis of (2-chloro-4-(2-methoxyethoxy)phenyl)(4-(((3R,6S)-6-(hydroxymethyl)tetrahydro-2H-pyran-3-yl)amino)-7H-pyrrolo[2,3-d]pyrimidin-5-yl)methanone (I-317i)

(2-Chloro-4-(2-methoxyethoxy)phenyl)(4-(((3R,6S)-6-(hydroxymethyl)tetrahydro-2H-pyran-3-yl)amino)-7H-pyrrolo[2,3-d]pyrimidin-5-yl)methanone was prepared according to General Scheme 9, using methyl 2-chloro-4-hydroxybenzoate and ((2S,5R)-5-aminotetrahydro-2H-pyran-2-yl)methanol. $^1$H NMR (DMSO-$d_6$, 400 mHz): δ 12.70 (bs, 1H), 8.61 (d, J=7.0 Hz, 1H), 8.21 (s, 1H), 7.48 (s, 1H), 7.47 (d, J=8.6 Hz, 1H), 7.16 (d, J=2.3 Hz, 1H), 7.00 (dd, J=8.4, 2.3 Hz, 1H), 4.45 (bs, 1H), 4.20-4.17 (m, 2H), 4.17-4.11 (m, 2H), 3.68-3.65 (m, 2H), 3.48-3.33 (m, 3H), 3.30 (m, 3H), 3.13-3.07 (m, 1H), 2.18-2.15 (m, 1H), 1.79-1.76 (m, 1H), 1.60-1.50 (m, 1H), 1.40-1.34 (m, 1H). Presence of formic acid at 8.42 mm (0.2 equivalents). LCMS [M+H+]: 461.20.

Example 208: Synthesis of (2-chloro-5-(2-methoxyethoxy)phenyl)(4-(((3R,6S)-6-(hydroxymethyl)tetrahydro-2H-pyran-3-yl)amino)-7H-pyrrolo[2,3-d]pyrimidin-5-yl)methanone (I-648)

(2-Chloro-5-(2-methoxyethoxy)phenyl)(4-(((3R,6S)-6-(hydroxymethyl)tetrahydro-2H-pyran-3-yl)amino)-7H-pyrrolo[2,3-d]pyrimidin-5-yl)methanone was prepared according to General Scheme 9, using methyl methyl 2-chloro-5-hydroxybenzoate and ((2S,5R)-5-aminotetrahydro-2H-pyran-2-yl)methanol. $^1$H NMR (DMSO-$d_6$, 400 mHz): δ 12.73 (bs, 1H), 8.57 (d, J=7.4 Hz, 1H), 8.23 (s, 1H), 7.51 (s, 1H), 7.44 (d, J=8.6 Hz, 1H), 7.12-7.07 (m, 2H), 4.64 (bs, 1H), 4.15-4.10 (m, 4H), 3.63-3.61 (m, 2H), 3.45-3.31 (m, 3H), 3.27 (m, 3H), 3.12-3.07 (m, 1H), 2.18-2.15 (m, 1H), 1.78-1.74 (m, 1H), 1.60-1.51 (m, 1H), 1.41-1.32 (m, 1H). Presence of formic acid at 8.37 ppm (0.08 equivalents). LCMS [M+H$^+$]: 461.20.

Example 209: Synthesis of (4-(((3R,6S)-6-(hydroxymethyl)tetrahydro-2H-pyran-3-yl)amino)-7H-pyrrolo[2,3-d]pyrimidin-5-yl)(3-(2-methoxyethoxy)phenyl)methanone (I-649)

(4-(((3R,6S)-6-(Hydroxymethyl)tetrahydro-2H-pyran-3-yl)amino)-7H-pyrrolo[2,3-d]pyrimidin-5-yl)(3-(2-methoxyethoxy)phenyl)methanone was prepared according to General Scheme 9, using methyl 3-hydroxybenzoate and ((2S,5R)-5-aminotetrahydro-2H-pyran-2-yl)methanol. $^1$H NMR (DMSO-$d_6$, 400 mHz): δ 12.67 (bs, 1H), 8.68 (d, J=7.2 Hz, 1H), 8.24 (s, 1H), 7.77 (s, 1H), 7.44 (t, J=7.6 Hz, 1H), 7.33 (d, J=7.6 Hz, 1H), 7.28 (m, 1H), 7.20 (dd, J=8.2 Hz, J=2.0 Hz, 1H), 4.65 (bs, 1H), 4.19-4.11 (m, 4H), 3.69-3.67 (m, 2H), 3.44-3.40 (m, 1H), 3.35-3.27 (m, 6H), 3.13-3.08 (m, 1H), 2.19-2.16 (m, 1H), 1.79-1.76 (m, 1H), 1.61-1.51 (m, 1H), 1.44-1.33 (m, 1H). Presence of formic acid at 8.37 ppm (0.1 equivalents). LCMS [M+H+]: 427.20.

Example 210: Synthesis of (2-chloro-4-(phenylamino)phenyl)(4-(((3R,6S)-6-(hydroxymethyl)tetrahydro-2H-pyran-3-yl)amino)-7H-pyrrolo[2,3-d]pyrimidin-5-yl)methanone (I-650)

Step 1: Synthesis of (4-(((3R,6S)-6-(((tert-butyldimethylsilyl)oxy)methyl)tetrahydro-2H-pyran-3-yl)amino)-7-((2-(trimethylsilyl)ethoxy)methyl)-7H-pyrrolo[2,3-d]pyrimidin-5-yl)(2-chloro-4-(phenylamino)phenyl)methanone and (2-chloro-4-(phenylamino)phenyl)(4-(((3R,6S)-6-(hydroxymethyl)tetrahydro-2H-pyran-3-yl)amino)-7-((2-(trimethylsilyl)ethoxy)methyl)-7H-pyrrolo[2,3-d]pyrimidin-5-yl)methanone (4-Amino-2-chlorophenyl)(4-(((3R,6S)-6-(((tert-butyldimethylsilyl)oxy)methyl)tetrahydro-2H-pyran-3-yl)amino)-7-((2-(trimethylsilyl)-ethoxy)methyl)-7H-pyrrolo[2,3-d]pyrimidin-5-yl)methanone (200 mg, 0.309 mmol) was dissolved in dioxane (2 mL). Bromobenzene (36 μL, 0.34 mmol) and sodium tert-butoxide (42 mg, 0.43 mmol) were added. The crude was degassed with argon and Pd$_2$(dba)$_3$ (6 mg, 0.006 mmol) and BINAP (14 mg, 0.022 mmol) were added. The reaction was then capped and heated to 100° C. for 3 hours. After cooling to room temperature the crude was diluted in water and ethyl acetate. The biphasic mixture was extracted with ethyl acetate (×2). The combined organics were dried over MgSO$_4$, filtered and concentrated. The residue was purified by silica gel column chromatography eluting a gradient of 0% to 100% ethyl acetate in hexanes. Combined both products to get 150 mg of yellow oil.

Step 2. Synthesis of (2-Chloro-4-(phenylamino)phenyl)(4-(((3R,6S)-6-(hydroxymethyl)tetrahydro-2H-pyran-3-yl)amino)-7H-pyrrolo[2, 3-d]pyrimidin-5-yl)methanone (I-650)

Deprotection of the silyl groups was achieved using General Procedure H. $^1$H NMR (DMSO-$d_6$, 400 mHz): δ 12.64 (s; 1H); 8.75 (s; 1H); 8.66 (d; J=7.13 Hz; 1H); 8.23 (s; 1H); 7.59 (s; 1H); 7.43 (d; J=8.43 Hz; 1H); 7.32-7.37 (m; 2H); 7.20 (dd; J=7.97; 1.21 Hz; 2H); 7.09 (d; J=2.16 Hz; 1H); 6.99-7.04 (m; 2H); 4.65 (t; J=5.58 Hz; 1H); 4.08-4.17 (m; 2H); 3.39-3.45 (m; 1H); 3.34-3.38 (m; 2H); 3.11 (t; J=11.42 Hz; 1H); 2.16-2.20 (m; 1H); 1.76-1.80 (m; 1H); 1.52-1.62 (m; 1H); 1.33-1.43 (m; 1H). LCMS [M+H]$^+$: 478.
General Procedure N
One general procedure for formation of a diaryl ether is described

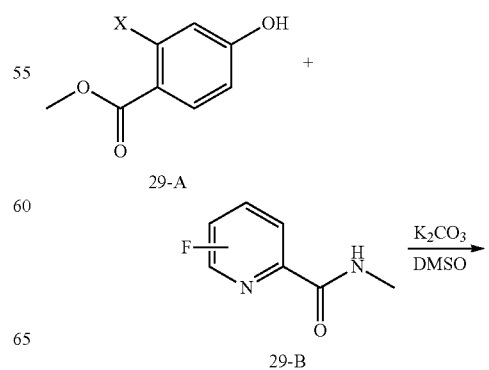

-continued

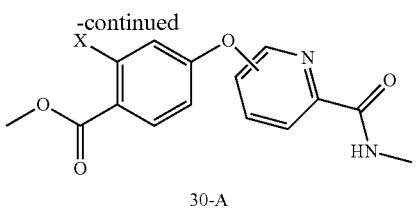

30-A

Fluoropyridine substrate (29-B) (1 eq.), methyl-hydroxybenzoate (29-A) (1 eq.) and potassium carbonate (1 eq.) were dissolved in DMSO (1 mL/0.3 mmol). The mixture was stirred at 120° C. under argon atmosphere overnight. After cooled, the reaction mixture was diluted in water and extracted several times with ethyl acetate. Combined organics were washed with water and dried over magnesium sulfate and concentrated under reduced pressure. The product was purified by column chromatography (0-100% ethyl acetate in hexanes).

Example 211: Synthesis of 6-(4-(4-(((3R,6S)-6-(hydroxymethyl)tetrahydro-2H-pyran-3-yl)amino)-7H-pyrrolo[2,3-d]pyrimidine-5-carbonyl)phenoxy)-N-methylpicolinamide (I-320)

6-(4-(4-(((3R,6S)-6-(Hydroxymethyl)tetrahydro-2H-pyran-3-yl)amino)-7H-pyrrolo[2,3-d]pyrimidine-5-carbonyl)phenoxy)-N-methylpicolinamide was synthesized according to General Scheme 11, using 6-fluoro-N-methylpicolinamide and methyl-4-hydroxy-benzoate. $^1$H NMR (DMSO-$d_6$, 400 mHz): δ 8.61 (d; J=7.13 Hz; 1H); 8.15-8.17 (m; 2H); 8.02 (dd; J=8.22; 7.41 Hz; 1H); 7.78-7.82 (m; 4H); 7.22 (t; J=8.83 Hz; 3H); 4.53-4.66 (m; 1H); 4.06-4.12 (m; 2H); 3.32-3.42 (m; 3H); 3.04 (t; J=11.35 Hz; 1H); 2.72 (d; J=4.81 Hz; 3H); 2.08-2.13 (m; 1H); LCMS [M+H]: 503.1.

Example 212: Synthesis of 6-(3-chloro-4-(4-(((3R,6S)-6-(hydroxymethyl)tetrahydro-2H-pyran-3-yl)amino)-7H-pyrrolo[2,3-d]pyrimidine-5-carbonyl)phenoxy)-N-methyl picolinamide (I-319)

6-(3-Chloro-4-(4-(((3R,6S)-6-(hydroxymethyl)tetrahydro-2H-pyran-3-yl)amino)-7H-pyrrolo[2,3-d]pyrimidine-5-carbonyl)phenoxy)-N-methylpicolinamide was synthesized according to General Scheme 11, using 6-fluoro-N-methylpicolinamide and methyl 2-chloro-4-hydroxybenzoate. $^1$H NMR (DMSO-$d_6$, 400 mHz): δ 12.72 (br s; 1H); 8.54 (d; J=7.11 Hz; 1H); 8.23 (q; J=4.87 Hz; 1H); 8.19 (s; 1H); 8.03 (dd; J=8.21; 7.43 Hz; 1H); 7.79 (dd; J=7.41; 0.80 Hz; 1H); 7.64 (s; 1H); 7.56 (d; J=8.41 Hz; 1H); 7.41 (d; J=2.28 Hz; 1H); 7.25 (dd; J=8.19; 0.81 Hz; 1H); 7.18 (dd; J=8.40; 2.30 Hz; 1H); 4.57-4.60 (m; 1H); 4.05-4.12 (m; 2H); 3.27-3.35 (m; 3H); 3.06 (t; J=11.29 Hz; 1H); 2.73 (d; J=4.83 Hz; 3H); 2.11-2.14 (m; 1H); 1.71-1.74 (m; 1H); 1.45-1.58 (m; 1H); 1.27-1.37 (m; 1H). LCMS [M+H]: 537.2.

Example 213: Synthesis of 5-(3-chloro-4-(4-(((3R,6S)-6-(hydroxymethyl)tetrahydro-2H-pyran-3-yl)amino)-7H-pyrrolo[2,3-d]pyrimidine-5-carbonyl)phenoxy)-N-methyl picolinamide (I-651)

5-(3-Chloro-4-(4-(((3R,6S)-6-(hydroxymethyl)tetrahydro-2H-pyran-3-yl)amino)-7H-pyrrolo[2,3-d]pyrimidine-5-carbonyl)phenoxy)-N-methylpicolinamide was synthesized according to General Scheme 11, using 5-fluoro-N-methylpicolinamide and methyl 2-chloro-4-hydroxybenzoate. $^1$H NMR (DMSO-$d_6$, 400 mHz): δ 12.73 (br s; 1H); 8.62-8.66 (m; 1H); 8.52 (d; J=7.11 Hz; 1H); 8.47 (d; J=2.78 Hz; 1H); 8.19 (s; 1H); 8.01 (d; J=8.64 Hz; 1H); 7.66 (dd; J=8.63; 2.81 Hz; 1H); 7.61 (s; 1H); 7.57 (d; J=8.42 Hz; 1H); 7.38 (d; J=2.34 Hz; 1H); 7.15 (dd; J=8.42; 2.36 Hz; 1H); 4.57-4.60 (m; 1H); 4.03-4.12 (m; 2H); 3.28-3.37 (m; 3H); 3.06 (t; J=11.30 Hz; 1H); 2.76 (d; J=4.81 Hz; 3H); 2.10-2.16 (m; 1H); 1.70-1.73 (m; 1H); 1.46-1.56 (m; 1H); 1.26-1.38 (m; 1H). LCMS [M+H]: 537.1.

Example 214: Synthesis of N-(4-(4-(((3R,6S)-6-(hydroxymethyl)tetrahydro-2H-pyran-3-yl)amino)-7H-pyrrolo[2,3-d]pyrimidine-5-carbonyl)benzyl)-2-methoxybenzamide (I-652)

Step 1: Synthesis of methyl 4-((2-methoxybenzamido)methyl)benzoate (652a)

The compound was prepared according to General Procedure F, using methyl 4-(aminomethyl)benzoate hydrochloride and 2-methoxybenzoic acid. LCMS [M+H]: 300.1.

Step 2: Synthesis of N-(4-(4-chloro-7H-pyrrolo[2,3-d]pyrimidine-5-carbonyl)benzyl)-2-methoxybenzamide (652b)

N-(4-(4-Chloro-7H-pyrrolo[2,3-d]pyrimidine-5-carbonyl)benzyl)-2-methoxybenzamide was prepared according to General Procedure M, using methyl 4-((2-methoxybenzamido)methyl) benzoate and 3-A. After 1 h at −78° C., the reaction mixture was allowed to warm up to 0° C. over 1 h. LCMS [M+H]: 421.1.

Step 3: Synthesis of N-(4-(4-(((3R,6S)-6-(hydroxymethyl)tetrahydro-2H-pyran-3-yl)amino)-7H-pyrrolo[2,3-d]pyrimidine-5-carbonyl)benzyl)-2-methoxybenzamide (I-652)

N-(4-(4-(((3R,6S)-6-(Hydroxymethyl)tetrahydro-2H-pyran-3-yl)amino)-7H-pyrrolo[2,3-d]pyrimidine-5-carbonyl)benzyl)-2-methoxybenzamide was prepared according to General Scheme 12, General Procedure A, step 2, with ((2S,5R)-5-aminotetrahydro-2H-pyran-2-yl)methanol. After removal of solvents, the residue was diluted with EtOAc (30 mL) and water (20 mL). The layers were partitioned and the organic layer was washed with water (20 mL) and brine, dried over MgSO$_4$, filtered and concentrated to dryness. The residue was purified by reverse phase $C_{18}$ using Isco CombiFlash (30 g column, loaded with DMSO) eluting with 5-80% CH$_3$CN/water (+0.1% formic acid) over 20 minutes. $^1$H NMR (DMSO-$d_6$, 400 mHz): δ 12.66 (s; 1H); 8.80-8.83 (m; 1H); 8.71-8.73 (m; 1H); 8.23 (s; 1H); 7.75-7.78 (m; 4H); 7.47-7.51 (m; 3H); 7.17 (d; J=8.35 Hz; 1H); 7.03-7.07 (m; 1H); 4.65 (t; J=5.56 Hz; 1H); 4.60 (d; J=6.13 Hz; 2H); 4.09-4.18 (m; 2H); 3.92 (s; 3H); 3.26-3.36 (m; 3H); 3.08-3.14 (m; 1H); 2.13-2.20 (m; 1H); 1.74-1.81 (m; 1H); 1.50-1.60 (m; 1H); 1.32-1.43 (m; 1H). LCMS [M+H]: 516.3.

Step 1: Synthesis of tert-butyl (racemic)-3-((5-(2-chloro-4-phenoxybenzoyl)-7H-pyrrolo[2,3-d]pyrimidin-4-yl)amino)piperidine-1-carboxylate (37-A)

The intermediate 37-A was prepared according General Procedure A, using 3-amino-N-Boc-piperidine and (2-chloro-4-phenoxyphenyl)(4-chloro-7H-pyrrolo[2,3-d]pyrimidin-5-yl)methanone (36-A). LCMS [M+H]+: 548.1.

Step 1': Synthesis of tert-butyl (racemic)-2-(((5-(2-chloro-4-phenoxybenzoyl)-7H-pyrrolo[2,3-d]pyrimidin-4-yl)amino)methyl)pyrrolidine-1-carboxylate (37-B)

The intermediate 37-B was prepared according General Procedure A, using tert-butyl 2-(aminomethyl)pyrrolidine-1-carboxylate and (2-chloro-4-phenoxyphenyl)(4-chloro-7H-pyrrolo[2,3-d]pyrimidin-5-yl)methanone. LCMS [M+H]+: 548.1.

General Procedure O
One general procedure for Boc-deprotection is described.

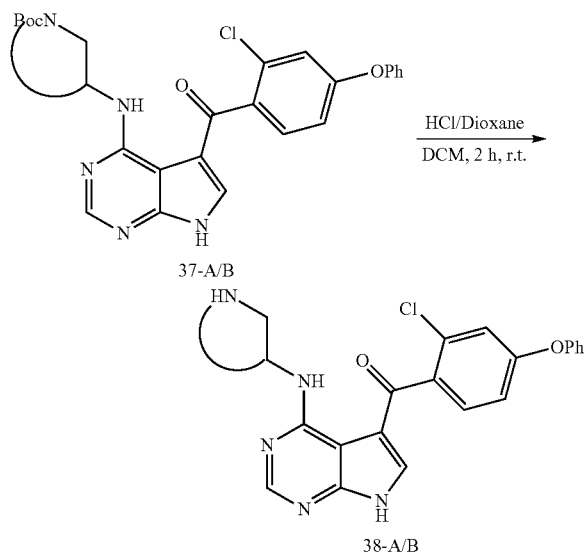

Boc-protected amine (37-A/B) (1.0 equiv) was dissolved in DCM (1.0 mL/mmol) and a 4.0M HCl/Dioxane solution (4.0 equiv) was added. Mixture was stirred at room temperature for 2.0 h, then concentrated under vacuum. A 1:10 solution of aqueous ammonia in EtOH was added until complete dissolution of the residue. The residue was absorbed onto silica and purified by normal phase column chromatography to give the purified amine product.

Step 2: Synthesis of (racemic)-(2-chloro-4-phenoxyphenyl)(4-(piperidin-3-ylamino)-7H-pyrrolo[2,3-d]pyrimidin-5-yl)methanone (38-A)

Intermediate 37-A was BOC-deprotected according to General Scheme 13 General Procedure O. LCMS [M+H]+: 448.10.

Step 2': Synthesis of (racemic)-(2-chloro-4-phenoxyphenyl)(4-((pyrrolidin-2-ylmethyl)amino)-7H-pyrrolo[2,3-d]pyrimidin-5-yl)methanone (38-B)

Intermediate 37-B was BOC-deprotected according to General Scheme 13 General Procedure O. LCMS [M+H]+: 448.10.

Example 215: Synthesis of (racemic)-1-(3-((5-(2-chloro-4-phenoxybenzoyl)-7H-pyrrolo[2,3-d]pyrimidin-4-yl)amino)piperidin-1-yl)but-2-yn-1-one (I-324r)

(racemic)-1-(3-((5-(2-Chloro-4-phenoxybenzoyl)-7H-pyrrolo[2,3-d]pyrimidin-4-yl)amino)piperidin-1-yl)but-2-yn-1-one was prepared according to General Scheme 13 and General Scheme 5, step 3, using (racemic)-(2-chloro-4-phenoxyphenyl)(4-(piperidin-3-ylamino)-7H-pyrrolo[2,3-d]pyrimidin-5-yl)methanone and 2-butynoic acid. $^1$H NMR (CDCl$_3$, 400 mHz, 3:2 amide rotamer/conformer ratio, asterisks denote minor rotamer/conformer peaks): δ 9.11 (d, J=7.0 Hz, 1H), 9.07* (d, J=7.6 Hz, 1H), 8.37 (s, 1H), 8.30* (s, 1H), 7.41-7.45 (m, 3H), 7.37 (d, J=7.6 Hz, 1H), 7.23 (t, J=7.5 Hz, 1H), 7.11 (s, 1H), 7.07-7.08 (m, 2H), 6.95-6.99 (m, 1H), 4.24-4.39 (m, 2H), 3.97-4.02* (m, 1H), 3.81-3.87 (m, 1H), 3.73 (dd, J=13.0, 7.4 Hz, 1H), 3.41-3.56 (m, 1H), 3.34* (dd, J=12.6, 8.0 Hz, 1H), 2.14-2.25 (m, 1H), 1.60-2.10 (m, 3H), 2.01* (s, 3H), 1.80 (s, 3H). LCMS [M+H]+: 514.10.

Example 216: Synthesis of (racemic)-1-(2-(((5-(2-chloro-4-phenoxybenzoyl)-7H-pyrrolo[2,3-d]pyrimidin-4-yl)amino)methyl)pyrrolidin-1-yl)but-2-yn-1-one (I-328r)

(racemic)-1-(2-(((5-(2-Chloro-4-phenoxybenzoyl)-7H-pyrrolo[2,3-d]pyrimidin-4-yl)amino)methyl)pyrrolidin-1-yl)but-2-yn-1-one was prepared according to General Scheme 13 and General Scheme 5, step 3, using (racemic)-(2-chloro-4-phenoxyphenyl)(4-((pyrrolidin-2-ylmethyl)amino)-7H-pyrrolo[2,3-d]pyrimidin-5-yl)methanone and 2-butynoic acid. $^1$H NMR (CDCl$_3$, 400 mHz, 2:1 amide rotamer ratio, asterisks denote minor rotamer peaks): δ 9.17 (t, J=6.2 Hz, 1H), 9.01* (t, J=5.9 Hz, 1H), 8.34 (s, 1H), 7.34-7.47 (m, 4H), 7.20-7.26 (m, 1H), 7.12 (s, 1H), 7.08-7.09 (m, 2H), 6.97 (dd, J=8.4, 2.3 Hz, 1H), 4.40-4.54 (m, 1H), 3.98-4.10 (m, 1H), 3.69-3.88 (m, 2H), 3.49-3.66 (m, 1H) 1.92-2.17 (4H, m), 1.98* (3H, s), 1.89 (3H, s). LCMS [M+H]+: 514.10.

Example 217: Synthesis of (racemic)-1-(3-((5-(2-chloro-4-phenoxybenzoyl)-7H-pyrrolo[2,3-d]pyrimidin-4-yl)amino)piperidin-1-yl)prop-2-en-1-one (I-321r)

(racemic)-1-(3-((5-(2-Chloro-4-phenoxybenzoyl)-7H-pyrrolo[2,3-d]pyrimidin-4-yl)amino)piperidin-1-yl)prop-2-en-1-one was prepared according to General Scheme 13 and General Scheme 5, step 3, using (racemic)-(2-chloro-4-phenoxyphenyl)(4-(piperidin-3-ylamino)-7H-pyrrolo[2,3-d]pyrimidin-5-yl)methanone and acrylic acid. $^1$H NMR 400 MHz (DMSO-d$_6$, 3:2 amide rotamer ratio, asterisks denote minor rotamer peaks): δ 12.8 (br s, 1H); 8.85 (d, J=7.3 Hz, 1H); 8.27 (br s, 1H); 7.62 (s, 1H); 7.55 (d, J=8.4 Hz, 1H); 7.48 (t, J=7.6 Hz, 2H); 7.25 (t, J=7.3 Hz, 1H); 7.17-7.19 (m, 3H); 7.02 (d, J=8.4 Hz, 1H); *6.77-6.84 (m, 1H); 6.56-6.64 (m, 1H); 5.93-6.05 (m, 1H); *5.60-5.65 (m, 1H); 5.46-5.51 (m, 1H); 4.17-4.25 (m, 1H); *4.00-4.06 (m, 1H); 3.89-3.95 (m, 1H); 3.45-3.71 (m, 2H); 3.20-3.30 (m, 1H); 2.01-2.10 (m, 1H); 1.72-1.85 (m, 2H); 1.53-1.63 (m, 1H). LCMS [M+H]+: 502.10.

Example 218: Synthesis of (racemic)-1-(2-(((5-(2-chloro-4-phenoxybenzoyl)-7H-pyrrolo[2,3-d]pyrimidin-4-yl)amino)methyl)pyrrolidin-1-yl)prop-2-en-1-one (I-325r)

(racemic)-1-(2-(((5-(2-Chloro-4-phenoxybenzoyl)-7H-pyrrolo[2,3-d]pyrimidin-4-yl)amino)methyl)pyrrolidin-1-yl)prop-2-en-1-one was prepared according to General Scheme 13 and General Scheme 5, step 3, using (racemic)-(2-chloro-4-phenoxyphenyl)(4-((pyrrolidin-2-ylmethyl)amino)-7H-pyrrolo[2,3-d]pyrimidin-5-yl)methanone and acrylic acid. ¹H NMR 400 MHz (DMSO-d₆, 5:4 amide rotamer ratio, asterisks denote minor rotamer peaks): δ 12.76 (br s, 1H); 8.88 (t, J=6.1 Hz, 1H); 8.75-8.80* (m, 1H); 8.31 (s, 1H); 8.24* (s, 1H); 7.64 (dd, J=6.5, 2.9 Hz, 1H); 7.57 (dd, J=8.5, 3.7 Hz, 1H); 7.48 (t, J=7.8 Hz, 2H); 7.26 (t, J=7.4 Hz, 1H); 7.20 (s, 1H); 7.19 (d, J=5.0 Hz, 2H); 7.08 (dd, J=16.6, 10.3 Hz, 1H); 7.03 (dd, J=8.3, 2.3 Hz, 1H); 6.60* (dd, J=16.8, 10.3 Hz, 1H); 6.14 (ddd, J=16.7, 3.8, 2.5 Hz, 1H); 5.65 (td, J=9.9, 2.5 Hz, 1H); 4.31-4.36 (m, 1H); 4.24-4.29* (m, 1H); 3.95-4.01 (m, 1H); 3.68-3.82 (m, 1H); 3.55-3.67 (m, 1H); 3.39-3.49 (m, 2H); 3.39-3.49* (m, 1H); 1.86-2.03 (m, 3H); 1.81-1.89 (m, 1H). LCMS [M+H]⁺: 502.10.

General Procedure P

One general procedure for vinysulfonamide formation.

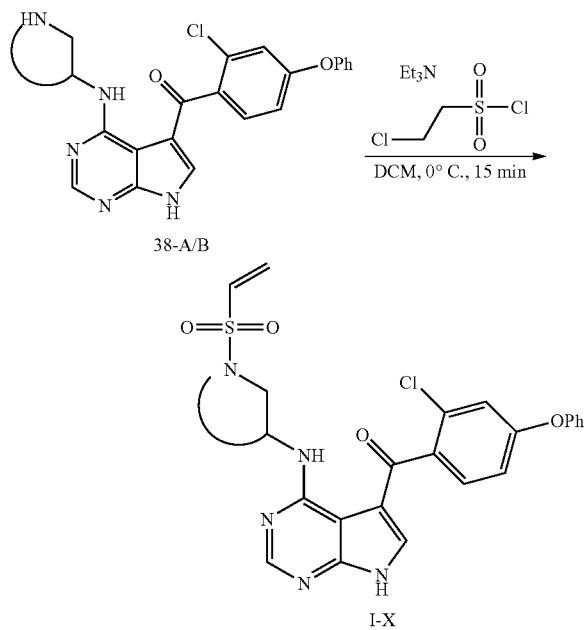

A solution of 2-chloroethanesulfonyl chloride (1.0 equiv) and Et₃N (1.0 equiv) in DCM (18 mL/mmol) cooled to 0° C. was added dropwise to a suspension of secondary amine (38-A/B) (1.0 equiv) and Et₃N (1.0 equiv) in DCM (18 mL/mmol), also cooled to 0° C. After 15 minutes, the reaction mixture was washed with saturated aqueous NaHCO₃ (twice), dried over MgSO₄ and concentrated under vacuum. The residue was purified by normal phase chromatography (75%-100% EtOAc/hexanes).

Example 219: Synthesis of (racemic)-(2-chloro-4-phenoxyphenyl)(4-((1-(vinylsulfonyl)piperidin-3-yl)amino)-7H-pyrrolo[2,3-d]pyrimidin-5-yl)methanone (I-322r)

(racemic)-(2-Chloro-4-phenoxyphenyl)(4-((1-(vinylsulfonyl)piperidin-3-yl)amino)-7H-pyrrolo[2,3-d]pyrimidin-5-yl)methanone was prepared according to General Scheme 13 and General Procedure P, using (racemic)-(2-chloro-4-phenoxyphenyl)(4-(piperidin-3-ylamino)-7H-pyrrolo[2, 3-d]pyrimidin-5-yl)methanone. ¹H NMR 400 MHz (DMSO-d₆): δ 12.75 (br s, 1H); 8.84 (d, J=7.4 Hz, 1H); 8.26 (s, 1H); 7.63 (d, J=8.5 Hz, 1H); 7.46 (s, 2H); 7.24 (t, J=7.4 Hz, 1H); 7.18 (s, 1H); 7.17 (d, J=6.1 Hz, 2H); 7.01 (dd, J=8.5, 2.4 Hz, 1H); 6.79 (dd, J=16.5, 10.0 Hz, 1H); 6.10 (d, J=4.5 Hz, 1H); 6.07 (d, J=11.0 Hz, 1H); 4.24-4.33 (m, 1H); 3.55 (d, J=11.2 Hz, 2H); 3.18-3.23 (m, 1H); 2.88-2.99 (m, 2H); 1.83-1.97 (m, 2H); 1.56-1.72 (m, 2H). LCMS [M+H]⁺: 538.10.

Example 220: Synthesis of (racemic)-(2-chloro-4-phenoxyphenyl)(4-(((1-(vinylsulfonyl)pyrrolidin-2-yl)methyl)amino)-7H-pyrrolo[2,3-d]pyrimidin-5-yl)methanone (I-326r)

(racemic)-(2-Chloro-4-phenoxyphenyl)(4-(((1-(vinylsulfonyl)pyrrolidin-2-yl)methyl)amino)-7H-pyrrolo[2,3-d]pyrimidin-5-yl)methanone was prepared according to General Scheme 13 and General Procedure P, using (racemic)-(2-chloro-4-phenoxyphenyl)(4-((pyrrolidin-2-ylmethyl)amino)-7H-pyrrolo[2,3-d]pyrimidin-5-yl)methanone. ¹H NMR 400 MHz (DMSO-d₆): δ 12.75 (s, 1H); 8.85 (dd, J=6.7, 4.7 Hz, 1H); 8.25 (s, 1H); 7.63 (d, J=2.7 Hz, 1H); 7.58 (d, J=8.5 Hz, 1H); 7.48 (dd, J=8.4, 7.3 Hz, 2H); 7.25 (t, J=7.4 Hz, 1H); 7.20 (s, 1H); 7.18 (d, J=6.1 Hz, 2H); 7.03 (dd, J=8.4, 2.3 Hz, 1H); 6.93 (dd, J=16.5, 10.0 Hz, 1H); 6.52 (s, 1H); 6.15 (d, J=10.2 Hz, 1H); 6.12 (d, J=3.7 Hz, 1H); 3.95-4.01 (m, 1H); 3.86-3.90 (m, 1H); 3.54-3.60 (m, 1H); 3.19-3.27 (m, 2H); 1.88-1.96 (m, 2H); 1.81-1.85 (m, 1H); 1.73-1.77 (m, 1H). LCMS [M+H]⁺: 538.10.

Example 221: Synthesis of (racemic)-(2-chloro-4-phenoxyphenyl)(4-((6-(hydroxymethyl)-1-(methylsulfonyl)piperidin-3-yl)amino)-7H-pyrrolo[2,3-d]pyrimidin-5-yl)methanone (I-653)

Step 1: Synthesis of rac-methyl-2-((tert-butoxycarbonyl)amino)-6-(dimethyl(oxo)-16-sulfaneylidene)-5-oxohexanoate (653b)

To a solution of trimethylsulfonium iodide (4.5 g, 21 mmol) in dry DMSO (20 mL) is added tBuOK (2.1 g, 18 mmol) and the mixture is stirred for 1 h at RT. rac-1-(tert-butyl) 2-methyl 5-oxopyrrolidine-1,2-dicarboxylate (653a) (5 g, 21 mmol) is then added and the mixture is stirred at room temperature for 3 h. The mixture is then quenched by addition of water and extracted with EtOAc. Combined organic phases are dried over MgSO₄, filtered and concentrated. Purification by chromatography (DCM/MeOH 9/1) yielded the title compound. ¹H NMR (CDCl₃): δ 5.44 (d, J=7.4 Hz, 1H), 4.38 (s, 1H), 4.29-4.24 (m, 1H), 3.73 (s, 3H), 3.39-3.38 (m, 6H), 2.33-2.19 (m, 2H), 2.14-2.04 (m, 1H), 1.98-1.89 (m, 1H), 1.42 (s, 9H).

Step 2: Synthesis of rac-1-(tert-butyl) 2-methyl 5-oxopiperidine-1,2-dicarboxylate (653c)

A solution of methyl rac-2-((tert-butoxycarbonyl)amino)-6-(dimethyl(oxo)-16-sulfaneylidene)-5-oxohexanoate (2.7 g, 8.0 mmol) and [Ir(COD)Cl]₂ (54 mg, 0.1 mmol) in DCE (80 mL) is degassed by bubbling argon for 20 min. The mixture is then heated at reflux for 2 h. The mixture is then concentrated and then purified by normal phase chromatography (gradient from 100% hexane to 100% EtOAc). ¹H NMR (CDCl₃, 400 mHz): δ 4.82 (t, J=6.7 Hz, 0.5H), 4.58 (t, J=7.0 Hz, 0.5H), 4.43-4.27 (m, 1H), 3.95-3.85 (m, 1H), 3.77 (s, 1H), 2.51-2.28 (m, 3H), 2.21-2.04 (m, 1H), 1.46-1.43 (m, 9H).

Step 3: Synthesis of rac-1-(tert-butyl) 2-methyl 5-hydroxypiperidine-1,2-dicarboxylate (653 d)

To a solution of rac-1-(tert-butyl) 2-methyl 5-oxopiperidine-1,2-dicarboxylate (5.9 g, 22.9 mmol) in THF (200 mL)

at −45° C. is added a solution of L-Selectride (1.0M, 27.5 mL, 37.5 mmol). The mixture is stirred for 1 h at −45° C. then quenched with saturated aqueous NH₄Cl. The aqueous phase is extracted with EtOAc. Combined organic phases are dried over MgSO₄, filtered and concentrated. The crude is purified by chromatography (gradient from 100% hexane to 100% EtOAc). LCMS [M+Na]⁺: 282.1.

Step 4: Synthesis of rac-1-(tert-butyl) 2-methyl 5-((methyl sulfonyl)oxy)piperidine-1,2-dicarboxylate (653e)

A solution of rac-1-(tert-butyl) 2-methyl 5-hydroxypiperidine-1,2-dicarboxylate (2.4 g, 9.3 mmol), methanesulfonyl chloride (788 µL, 10.2 mmol) and triethylamine (1.9 mL, 13.9 mmol) in DCM (50 mL) is stirred for 3 h at room temperature. The mixture is then washed twice with a sat. aq. sol. of NaHCO₃, twice with HCl 1M and once with water, dried over MgSO₄, filtered and concentrated. The crude is used as is in the next step.

Step 5: Synthesis of rac-1-(tert-butyl) 2-methyl 5-azidopiperidine-1,2-dicarboxylate (653f)

A solution of rac-1-(tert-butyl) 2-methyl 5-((methyl sulfonyl)oxy)piperidine-1,2-dicarboxylate (2.70 g, 8.0 mmol) and sodium azide (3.12 g, 48.0 mmol) in DMF (20 mL) is stirred overnight at 80° C. After cooling to room temperature the mixture is diluted in water and extracted with EtOAc. Combined organic phases are washed with 1M HCl, brine, dried over MgSO₄, filtered and concentrated. LCMS [M+Na]⁺: 307.1.

Step 6: Synthesis of rac-tert-butyl 5-azido-2-(hydroxymethyl)piperidine-1-carboxylate (653g)

To a solution of rac-1-(tert-butyl) 2-methyl 5-azidopiperidine-1,2-dicarboxylate (2.1 g, 7.4 mmol) in THF (70 mL) is added ethanol (1.3 mL, 22.2 mmol) and lithium borohydride (2M, 11.1 mL, 22.2 mmol) and the mixture is stirred overnight at room temperature. The mixture is then quenched with sat. aq. NaHCO₃ and extracted with EtOAc. Combined organic phases are dried over MgSO₄, filtered and concentrated. The crude is purified by chromatography (gradient from DCM to DCM/MeOH 9/1). LCMS [M+Na]⁺: 279.0.

Step 7: Synthesis of rac-tert-butyl-5-azido-2-(((tert-butyldiphenyl silyl)oxy)methyl) piperidine-1-carboxylate (653h)

A mixture of rac-tert-butyl-5-azido-2-(hydroxymethyl)piperidine-1-carboxylate (700 mg, 2.73 mmol), TBDPSCl (781 µL, 3.00 mmol) and imidazole (242 mg, 3.55 mmol) in DMF (10 mL) is stirred overnight at room temperature. The mixture is then diluted in water and extracted with EtOAc. Combined organic phases are washed with brine, dried over MgSO₄, filtered and concentrated. The crude is purified by chromatography (gradient from hexane to hexane/EtOAc 1/1). LCMS [M+H-Boc]⁺: 395.2.

Step 8: Synthesis of rac-5-azido-2-(((tert-butyldiphenylsilyl)oxy)methyl)piperidin-1-ium 2,2,2-trifluoroacetate (653i)

To a solution of rac-tert-butyl-5-azido-2-(((tert-butyldiphenylsilyl)oxy)methyl)piperidine-1-carboxylate (1.07 g, 2.17 mmol) in DCM (18 mL) is added TFA (2 mL) and the mixture is stirred for 1 h at RT. The mixture is then concentrated to dryness, co-evaporated with DCM and the crude is brought on to the next step without further purification. LCMS [M+H]: 395.2.

Step 9: Synthesis of rac-5-azido-2-(((tert-butyldiphenylsilyl)oxy)methyl)-1-(methylsulfonyl) piperidine (653j)

To a solution of rac-5-azido-2-(((tert-butyldiphenyl silyl)oxy)methyl)piperidine (150 mg, 0.38 mmol) and triethylamine (264.9 µL, 1.90 mmol) in DCM (3.75 mL) at 0° C. is added methanesulfonyl chloride (32.4 µL, 0.42 mmol). The mixture is stirred for 2 h at 0° C. then concentrated and the crude is purified by chromatography (gradient from 100% hexanes to 50% EtOAc/hexanes). LCMS [M+Na]: 495.1.

Step 10: Synthesis of rac-6-(((tert-butyldiphenylsilyl)oxy)methyl)-1-(methylsulfonyl) piperidin-3-amine (653k)

To a solution of azide (653j) in methanol (0.1M) is added Pd(OH)₂/C (10% w/w) and the mixture is stirred under hydrogen atmosphere at room temperature and atmospheric pressure. The mixture is then filtered through Celite and concentrated. The crude is used as is without further purification. LCMS [M+H]: 447.2.

Step 11: Synthesis of rac-(4-((6-(((tert-butyldiphenylsilyl)oxy)methyl)-1-(methylsulfonyl)piperidin-3-yl)amino)-7H-pyrrolo[2,3-d]pyrimidin-5-yl)(2-chloro-4-phenoxyphenyl)methanone (653l)

rac-(4-((6-(((Tert-butyldiphenylsilyl)oxy)methyl)-1-(methylsulfonyl)piperidin-3-yl)amino)-7H-pyrrolo[2,3-d]pyrimidin-5-yl)(2-chloro-4-phenoxyphenyl)methanone was prepared according to General Procedure A, using rac-6-(((tert-butyldiphenylsilyl)oxy)methyl)-1-(methylsulfonyl) piperidin-3-amine with 36-A. LCMS [M+H]: 794.3.

Step 12

Synthesis of rac-(2-chloro-4-phenoxyphenyl)(4-((6-(hydroxymethyl)-1-(methylsulfonyl)piperidin-3-yl)amino)-7H-pyrrolo[2,3-d]pyrimidin-5-yl)methanone (I-653) rac-(4-((6-(((Tert-butyldiphenylsilyl)oxy)methyl)-1-(methylsulfonyl) piperidin-3-yl)amino)-7H-pyrrolo[2,3-d]pyrimidin-5-yl)(2-chloro-4-phenoxyphenyl)methanone in methanolic HCl solution (1.25M) was stirred at room temperature for 2 hours then concentrated to dryness and purified by RP chromatography (gradient from 30% to 90% MeCN+0.1% formic acid in water. Two distinct isomers were observed but kept together. ¹H NMR (DMSO-d₆, 400 MHz): mixture of cis and trans isomers: δ 9.14 (d, J=7.2 Hz, 0.5H), 8.69 (d, J=7.2 Hz, 0.5H), 8.27 (s, 1H), 7.64 (s, 1H), 7.59-7.53 (m, 1H), 7.50-7.46 (m, 1H), 7.28-7.23 (m, 1H), 7.19-7.17 (m, 1H), 7.04-7.01 (m, 1H), 4.95 (bs, 1H), 4.34-4.32 (m, 0.5H), 4.12-3.99 (m, 1.5H), 3.90-3.84 (m, 1.5H), 3.69-3.58 (m, 2H), 3.28-3.25 (m, 1H), 3.04 (s, 1.5H), 3.59-2.84 (m, 2H), 2.07-1.61 (m, 4H). LCMS [M+H]: 556.1.

Example 222: Synthesis of rac-(2-chloro-4-phenoxyphenyl)(4-((6-(hydroxymethyl)piperidin-3-yl)amino)-7H-pyrrolo[2,3-d]pyrimidin-5-yl)methanone (I-343r)

Step 1: Synthesis of rac-tert-butyl-5-amino-2-(hydroxymethyl)piperidine-1-carboxylate (343ra)

Analogous to the preparation of 653k, a solution of azide (653g) in methanol (0.1M) is added Pd(OH)₂/C (10% w/w)

and the mixture is stirred under hydrogen atmosphere at room temperature and atmospheric pressure. The mixture is then filtered through Celite and concentrated. The crude is used as is without further purification. LCMS [M+H]: 231.2.

Step 2: Synthesis of rac-tert-butyl-5-((5-(2-chloro-4-phenoxybenzoyl)-7H-pyrrolo[2,3-d]pyrimidin-4-yl)amino)-2-(hydroxymethyl)-piperidine-1-carboxylate (343rb)

rac-Tert-butyl-5-((5-(2-chloro-4-phenoxybenzoyl)-7H-pyrrolo[2,3-d]pyrimidin-4-yl)amino)-2-(hydroxymethyl)-piperidine-1-carboxylate was prepared according General Procedure A, using rac-tert-butyl-5-amino-2-(hydroxymethyl)piperidine-1-carboxylate with 36-A. LCMS [M+H]: 578.3.

Step 3: Synthesis of rac-(2-chloro-4-phenoxyphenyl)(4-((6-(hydroxymethyl)piperidin-3-yl)amino)-7H-pyrrolo[2,3-d]pyrimidin-5-yl)methanone (I-343r)

A solution of tert-butyl rac-5-((5-(2-chloro-4-phenoxybenzoyl)-7H-pyrrolo[2,3-d]pyrimidin-4-yl)amino)-2-(hydroxymethyl)piperidine-1-carboxylate (113 mg, 0.19 mmol) in DCM (3 mL) is treated with trifluoroacetic acid (3 mL) for 1 h. The mixture is then concentrated to dryness and purified by preparative HPLC (gradient from 20% to 95% of acetonitrile+0.1% formic acid). $^1$H NMR (DMSO-$d_6$, 400 mHz): δ 8.94 (d, J=6.3 Hz, 0.5H), 8.65 (d, J=7.0 Hz, 0.5H), 8.21 (d, J=5.9 Hz, 1H), 7.61 (d, J=7.4 Hz, 1H), 7.51-7.42 (m, 3H), 7.21-7.19 (m, 1H), 7.15-7.11 (m, 3H), 6.98-6.95 (m, 1H), 5.26 (bs, 0.5H), 5.06 (bs, 0.5H), 4.25-4.30 (m, 1H), 3.54-3.33 (m, 3H), 3.03-2.96 (m, 1.5H), 2.80-2.60 (m, 0.5H), 2.11-2.10 (m, 0.5H), 1.86-1.81 (m, 1.5H), 1.67-1.62 (m, 1.5H), 1.45-1.42 (m, 0.5H). LCMS [M+H]: 478.2.

Example 223: Synthesis of rac-1-(5-((5-(2-chloro-4-phenoxybenzoyl)-7H-pyrrolo[2,3-d]pyrimidin-4-yl)amino)-2-(hydroxymethyl)-piperidin-1-yl)ethan-1-one (I-654)

A mixture of rac-(2-chloro-4-phenoxyphenyl)(4-((6-(hydroxymethyl)piperidin-3-yl)amino)-7H-pyrrolo[2,3-d]pyrimidin-5-yl)methanone (I-343r) (30 mg, 0.063 mmol), sodium acetate (5.7 mg, 0.069 mmol), EDCI (12.6 mg, 0.066 mmol), HOAt (9.0 mg, 0.066 mmol) and DIPEA (32.8 μL, 0.19 mmol) in DCM (0.5 mL) is stirred at RT for 24 h. The mixture is then concentrated to dryness and purified by RP (gradient from 35% to 90% MeCN+0.1% formic acid). $^1$H NMR (DMSO-$d_6$, 400 mHz): (mixture of cis/trans, presence of rotamers) δ 9.09-9.04 (m, 1H), 8.74-8.69 (m, 1H), 8.44 (s, 1H), 8.26-8.23 (m, 1H), 7.61-7.54 (m, 3H), 7.50-7.46 (m, 3H), 7.27-7.24 (m, 1H), 7.20-7.18 (m, 3H), 7.03-7.01 (m, 1H), 4.98-4.66 (m, 2H), 4.63-4.31 (m, 2H), 4.20-3.89 (m, 3H), 3.75-3.70 (m, 1H), 3.64-3.13 (m, 18H+H$_2$O), 2.94-2.84 (m, 1H), 2.45-2.39 (m, 1H), 2.12-1.52 (m, 10H). LCMS [M+H]: 520.2.

Example 224: Synthesis of (2-chloro-4-phenoxyphenyl)(4-(((3R,5S)-5-(hydroxymethyl) pyrrolidin-3-yl)amino)-7H-pyrrolo[2,3-d]pyrimidin-5-yl)methanone (I-345e)

Step 1: Synthesis of tert-butyl (2S,4R)-4-((5-(2-chloro-4-phenoxybenzoyl)-7H-pyrrolo[2,3-d]pyrimidin-4-yl)amino)-2-(hydroxymethyl)pyrrolidine-1-carboxylate (345ea)

Tert-butyl (2S,4R)-4-((5-(2-chloro-4-phenoxybenzoyl)-7H-pyrrolo[2,3-d]pyrimidin-4-yl)amino)-2-(hydroxymethyl)pyrrolidine-1-carboxylate was prepared according to Procedure A using tert-butyl (2S,4R)-4-amino-2-(hydroxymethyl)pyrrolidine-1-carboxylate and 36-A. LCMS [M+H]$^+$: 564.3, 566.3.

Step 2: Synthesis of (2-chloro-4-phenoxyphenyl)(4-(((3R,5S)-5-(hydroxymethyl)pyrrolidin-3-yl)amino)-7H-pyrrolo[2,3-d]pyrimidin-5-yl)methanone (I-345e)

(2-Chloro-4-phenoxyphenyl)(4-(((3R,5S)-5-(hydroxymethyl)pyrrolidin-3-yl)amino)-7H-pyrrolo[2,3-d]pyrimidin-5-yl)methanone was prepared according to General Scheme 15. To a solution of tert-butyl (2S,4R)-4-((5-(2-chloro-4-phenoxybenzoyl)-7H-pyrrolo[2,3-d]pyrimidin-4-yl)amino)-2-(hydroxymethyl)-pyrrolidine-1-carboxylate (42 mg, 0.0746 mmol) in DCM (2 mL) was added TFA (1 mL) and the solution stirred 2 h at room temperature. The reaction mixture was concentrated under reduced pressure and the residue co-distilled with MeCN. The residue was dissolved in water and lyophilized affording (2-chloro-4-phenoxyphenyl)(4-(((3R,5S)-5-(hydroxymethyl)pyrrolidin-3-yl)amino)-7H-pyrrolo[2,3-d]pyrimidin-5-yl)methanone as the trifluoroacetate salt (50.5 mg, 0.073 mmol, 98%). $^1$H NMR (DMSO-$d_6$, 400 mHz): δ 12.89 (s; 1H); 9.38 (s; 1H); 8.92 (d; J=5.85 Hz; 1H); 8.70 (s; 1H); 8.32 (s; 0.7H); 7.72 (s; 1H); 7.55 (d; J=8.47 Hz; 1H); 7.49 (m; 2H); 7.26 (t; J=7.40 Hz; 1H); 7.18-7.22 (m; 3H); 7.03 (dd; J=8.46; 2.37 Hz; 1H); 4.75-4.79 (m; 1H); 3.90 (t; J=7.26 Hz; 1H); 3.74 (dd; J=11.75; 3.80 Hz; 1H); 3.66 (dd; J=11.53; 5.78 Hz; 1H); 3.60 (dd; J=11.88; 7.00 Hz; 1H); 3.24-3.31 (m; 1H); 2.22 (d; J=7.77 Hz; 1H); 2.16 (s; 1H). LCMS [M+H]$^+$: 464.20, 466.2.

Example 225: Synthesis of (2-chloro-4-phenoxyphenyl)(4-(((3R,5S)-5-(hydroxymethyl)-1-methylpyrrolidin-3-yl)amino)-7H-pyrrolo[2,3-d]pyrimidin-5-yl)methanone (I-342e)

(2-Chloro-4-phenoxyphenyl)(4-(((3R,5S)-5-(hydroxymethyl)pyrrolidin-3-yl)amino)-7H-pyrrolo[2,3-d]pyrimidin-5-yl)methanone trifluoroacetate (68.8 mg, 0.1045 mmol) was suspended in concentrated ammonium hydroxide solution, water was added and the mixture lyophilized. The solid residue was dissolved in 2,2,2-trifluoroethanol (2.6 mL). Paraformaldehyde (25.1 mg, 0.8311 mmol) and sodium borohydride (5.5 mg, 0.1463 mmol) were added and the mixture stirred at room temperature overnight. MeOH (1 mL) was added and the mixture stirred 30 min at RT. The solution was concentrated under reduced pressure. The residue was dissolved in water (1 mL) and DMSO (0.5 mL), filtered through a Teflon filter and purified by preparative HPLC, 10% MeCN (5 min), 5% to 80% MeCN (30 min) in water, the tubes containing the product were lyophilized affording (2-chloro-4-phenoxyphenyl)(4-(((3R,5S)-5-(hydroxymethyl)-1-methylpyrrolidin-3-yl)amino)-7H-pyrrolo[2,3-d]pyrimidin-5-yl)methanone (18 mg, 0.0344 mmol, 33%). $^1$H NMR (DMSO-$d_6$, 400 mHz): δ 8.84 (d; J=6.81 Hz; 1H); 8.25 (s; 2H); 7.62 (s; 1H); 7.58 (d; J=8.45 Hz; 1H); 7.46-7.50 (m; 2H); 7.26 (t; J=7.34 Hz; 1H); 7.18-7.20 (m; 3H); 7.02 (dd; J=8.46; 2.36 Hz; 1H); 4.50-4.54 (m; 1H); 3.45-3.49 (m; 2H); 3.33 (m; 2H); 2.34 (s; 3H); 2.21 (t; J=8.54 Hz; 1H); 2.13 (dt; J=13.03; 8.02 Hz; 1H); 1.76-1.83 (m; 1H). LCMS [M+H]$^+$: 478.25, 480.20.

Example 226: Synthesis of 1-((2S,4R)-4-((5-(2-chloro-4-phenoxybenzoyl)-7H-pyrrolo[2,3-d]pyrimidin-4-yl)amino)-2-(hydroxymethyl)pyrrolidin-1-yl)ethan-1-one (I-655)

1-((2S,4R)-4-((5-(2-Chloro-4-phenoxybenzoyl)-7H-pyrrolo[2,3-d]pyrimidin-4-yl)amino)-2-(hydroxymethyl)pyrrolidin-1-yl)ethan-1-one was prepared according to General Scheme 15. A solution of (2-chloro-4-phenoxyphenyl)(4-(((3R,5S)-5-(hydroxymethyl)pyrrolidin-3-yl)amino)-7H-pyrrolo[2,3-d]pyrimidin-5-yl)methanone (30 mg, 0.0434 mmol) was dissolved in 0.3 mL 1N HCl and 5 mL water and lyophilized. The product was dissolved in DMF (0.4 mL). DIPEA (16.61 ml, 0.0954 mmol) was added and the solution was stirred 30 min at room temperature. AcONa (3.7 mg, 0.0455 mmol), HOAt (5.9 mg, 0.0434 mmol) and EDCI (8.3 mg, 0.0434 mmol) were added at room temperature and the reaction mixture stirred overnight. The crude was diluted with DMF, water was added and the solution concentrated under reduced pressure. The residue was dissolved in water (1 mL) and DMSO (0.5 mL), filtered through a Teflon filter and purified by preparative HPLC, 10% MeCN (5 min), 5% to 80% MeCN (30 min) in water. 1-((2S,4R)-4-((5-(2-chloro-4-phenoxybenzoyl)-7H-pyrrolo[2,3-d]pyrimidin-4-yl)amino)-2-(hydroxymethyl) pyrrolidin-1-yl)ethan-1-one (23.5 mg, 0.0452 mmol, 46%) was isolated as a white solid after lyophilization. $^1$H NMR (DMSO-$d_6$, 400 mHz): δ 8.88 (t; J=6.02 Hz; 1H); 8.44 (s; 0.3H); 8.27 (d; J=3.14 Hz; 1H); 7.62 (d; J=3.06 Hz; 1H); 7.57 (dd; J=8.46; 1.82 Hz; 1H); 7.46-7.50 (m; 2H); 7.25 (t; J=7.40 Hz; 1H); 7.18-7.20 (m; 3H); 7.02 (dd; J=8.45; 2.37 Hz; 1H); 4.78-4.87 (m; 1.7H); 4.10 (d; J=6.86 Hz; 1H); 3.94 (dd; J=10.29; 6.78 Hz; 0.7H); 3.64 (t; J=6.50 Hz; 0.3H); 2.33-2.37 (m; 3.3H); 2.03 (s; 1H); 1.97-2.00 (m; 1H); 1.95 (s; 2H). LCMS [M+H]$^+$: 506.2, 508.2.

Example 227: Synthesis of (2-chloro-4-phenoxyphenyl)(4-(((3R,5S)-5-(hydroxymethyl)-1-(methylsulfonyl)pyrrolidin-3-yl)amino)-7H-pyrrolo[2,3-d]pyrimidin-5-yl)methanone (I-656)

Step 1: Synthesis of tert-butyl (2S,4R)-4-azido-2-(((tert-butyldiphenylsilyl)oxy)methyl) pyrrolidine-1-carboxylate (656a)

To a solution of tert-butyl (2S,4R)-4-azido-2-(hydroxymethyl)pyrrolidine-1-carboxylate (see J. Org. Chem. 2003, 68, 4439-4445 for preparation procedures) (400 mg, 1.65 mmol) in DMF (8.2 mL), TBDPSCl (472 mL, 1.82 mmol) and imidazole (123.6 mg, 1.82 mmol) were added and the reaction mixture was stirred overnight at room temperature. The crude mixture was diluted with EtOAc, washed with water and brine, dried over anhydrous sodium sulfate and concentrated to dryness. The crude mixture was purified by flash chromatography, ISCO, 12 g column, (EtOAc/hexanes mixture) 0% EtOAc (3 min), 0% to 5% EtOAc (12 min, 5% EtOAc (3 min) affording tert-butyl (2S,4R)-4-azido-2-(((tert-butyldiphenylsilyl)oxy)methyl)pyrrolidine-1-carboxylate (570 mg, 1.1858 mmol, 72%) as a transparent oil. $^1$H NMR (CDCl$_3$, 400 mHz): δ 7.72 (dd; J=7.39; 1.88 Hz; 1H); 7.62-7.64 (m; 2H); 7.36-7.43 (m; 5H); 3.96-4.17 (m; 2H); 3.49-3.75 (m; 2H); 2.24 (t; J=46.59 Hz; 1H); 1.59 (s; 1H); 1.48 (s; 2H); 1.07 (s; 4H); 1.05 (s; 5H). LCMS Step 2: Synthesis of (2S,4R)-4-azido-2-(((tert-butyldiphenylsilyl)oxy)methyl)pyrrolidine (656b)

To a solution of tert-butyl (2S,4R)-4-azido-2-(((tert-butyldiphenylsilyl)oxy)methyl)pyrrolidine-1-carboxylate (42 mg, 0.0746 mmol) in DCM (2 mL) was added TFA (1 mL) and the solution stirred 2 h at room temperature. The reaction mixture was concentrated under reduced pressure and the residue codestilled with MeCN. The residue was suspended in EtOAc, washed with saturated sodium bicarbonate, dried over anhydrous sodium sulfate and concentrated under reduced pressure affording (2S,4R)-4-azido-2-(((tert-butyldiphenylsilyl)oxy)methyl)pyrrolidine as the TFA salt (50.5 mg, 0.073 mmol, 98%). LCMS 381.3 [M+H]$^+$.

Step 3: Synthesis of (2S,4R)-4-azido-2-(((tert-butyldiphenylsilyl)oxy)methyl)-1-(methylsulfonyl)pyrrolidine (656c)

(2S,4R)-4-Azido-2-(((tert-butyldiphenylsilyl)oxy)methyl)pyrrolidine (70 mg, 0.18 mmol) was dissolved in 0.5 mL of dry dichloromethane, cooled to 0° C., DIPEA (128 mL, 0.74 mmol) was added followed by methanesulfonyl chloride (15.7 mL, 22.42 mmol). The reaction mixture was stirred at room temperature under N$_2$ for about 8 hours and diluted with dichloromethane. The reaction mixture was washed with 1N HCl, saturated aqueous Na$_2$CO$_3$ and water. The organic phase was dried over anhydrous sodium sulfate and concentrated under reduced pressure affording (2S,4R)-4-azido-2-(((tert-butyldiphenylsilyl)oxy)methyl)-1-(methylsulfonyl) pyrrolidine (42.3 mg, 0.0922 mmol, 50%) as a white solid. $^1$H NMR (CDCl$_3$, 400 mHz): δ 7.66 (m; 4H); 7.37-7.46 (m; 6H); 4.21 (t; J=4.01 Hz; 1H); 3.81-3.87 (m; 3H); 3.46-3.55 (m; 2H); 2.84 (s; 3H); 2.30-2.36 (m; 1H); 2.21 (m; 1H); 1.08 (s; 9H). LCMS 481.2 [M+Na]$^+$.

Step 4: Synthesis of (3R,5S)-5-(((Tert-butyldiphenylsilyl)oxy)methyl)-1-(methylsulfonyl) pyrrolidin-3-amine (656d)

A mixture of (2S,4R)-4-azido-2-(((tert-butyldiphenylsilyl)oxy)methyl)-1-(methylsulfonyl) pyrrolidine (42.3 mg, 0.09 mmol) and 10% palladium on carbon (5 mg) in methanol (10 mL) was stirred under 1 atm of hydrogen at room temperature for 16 h. The catalyst was filtered off through a Teflon filter and the filtrate afforded (3R,5S)-5-(((tert-butyldiphenylsilyl)oxy)methyl)-1-(methylsulfonyl) pyrrolidin-3-amine (39 mg, 0.0901 mmol, 98%) as an oil after evaporation. LCMS 433.2 [M+H]$^+$.

Step 5: Synthesis of (4-(((3R,5S)-5-(((tert-butyldiphenylsilyl)oxy)methyl)-1-(methylsulfonyl)pyrrolidin-3-yl)amino)-7H-pyrrolo[2,3-d]pyrimidin-5-yl)(2-chloro-4-phenoxyphenyl)methanone (656e)

(4-(((3R,5S)-5-(((Tert-butyldiphenylsilyl)oxy)methyl)-1-(methylsulfonyl) pyrrolidine-3-yl)amino)-7H-pyrrolo[2,3-d]pyrimidin-5-yl)(2-chloro-4-phenoxyphenyl) methanone was prepared according General Procedure A with (3R,5S)-5-(((tert-butyl diphenylsilyl)oxy)methyl)-1-(methylsulfonyl)pyrrolidin-3-amine (656d) and 36-A. LCMS 780.3, 782.3 [M+H]$^+$.

Step 6: Synthesis of (2-chloro-4-phenoxyphenyl)(4-(((3R,5S)-5-(hydroxymethyl)-1-(methylsulfonyl) pyrrolidin-3-yl)amino)-7H-pyrrolo[2,3-d]pyrimidin-5-yl)methanone (I-656)

(2-Chloro-4-phenoxyphenyl)(4-(((3R,5S)-5-(hydroxymethyl)-1-(methylsulfonyl)pyrrolidin-3-yl)amino)-7H-pyrrolo[2,3-d]pyrimidin-5-yl)methanone was prepared according to General Scheme 16. A solution of (4-(((3R,5S)-5-(((tert-butyldiphenylsilyl)oxy)methyl)-1-methylpyrrolidin-3-yl)amino)-7H-pyrrolo[2,3-d]pyrimidin-5-yl)(2-chloro-4-phenoxyphenyl)methanone (83.4 mg, 0.116 mmol) in 1.25N HCl in MeOH was stirred overnight at room temperature.

The reaction mixture was concentrated under reduced pressure and the residue purified by preparative HPLC (5% to 80% MeCN in water, 0.1% TFA, 30 min) affording (4-(((3R,5S)-5-(((tert-butyldiphenylsilyl)oxy)methyl)-1-(methylsulfonyl)pyrrolidin-3-yl)amino)-7H-pyrrolo[2,3-d]pyrimidin-5-yl)(2-chloro-4-phenoxyphenyl)methanone (11.9 mg, 0.022 mmol, 32%) as a white solid after lyophilization. $^1$H NMR (DMSO-$d_6$, 400 mHz): δ 8.87 (d; J=6.13 Hz; 1H); 8.37 (s; 0.2H); 8.30 (s; 1H); 7.67 (s; 1H); 7.56 (d; J=8.46 Hz; 1H); 7.48 (m; 2H); 7.25 (t; J=7.40 Hz; 1H); 7.19 (m; 3H); 7.03 (dd; J=8.45; 2.37 Hz; 1H); 4.96 (br s; 1H); 4.70 (d; J=6.59 Hz; 1H); 3.86 (s; 1H); 3.72 (dd; J=10.15; 5.62 Hz; 1H); 3.61 (d; J=8.71 Hz; 1H); 3.46 (t; J=8.81 Hz; 1H); 3.30-3.32 (m; 1H); 2.89 (s; 3H); 2.36-2.42 (m; 1H); 2.11-2.18 (m; 1H). LCMS [M+H]$^+$: 542.2, 544.2.

Example 228: Synthesis of (2-chloro-4-phenoxyphenyl)(4-((((3R,5S)-5-(hydroxymethyl)pyrrolidin-3-yl)methyl)amino)-7H-pyrrolo[2,3-d]pyrimidin-5-yl)methanone (I-369e)

Step 1: Synthesis of 1-(tert-butyl) 2-methyl (2S,4S)-4-((methyl sulfonyl)oxy)pyrrolidine-1,2-dicarboxylate (369ea)

To a solution of 1-(tert-butyl) 2-methyl (2S,4S)-4-hydroxypyrrolidine-1,2-dicarboxylate (10 g, 40.766 mmol) in DCM (100 mL) at 0° C. was added MsCl (3.8 mL, 49.096 mmol) followed by slow addition of DIPEA (8.5 mL, 48.801 mmol). After the addition, the reaction mixture was allowed to warm up to rt and stirred for 5 hours. The reaction mixture was poured into a cooled aqueous saturated NH$_4$Cl (250 mL). The layers were partitioned and the aqueous layer was extracted with DCM (80 mL). The combined organic layers were washed with aqueous saturated NaHCO$_3$ (250 mL), water (250 mL) and brine. It was dried over MgSO$_4$, filtered and concentrated to dryness to afford 13 g of the desired product as a yellow oil which was used as such in the subsequent step without further purification.

Step 2: Synthesis of tert-butyl (2S,4S)-2-(hydroxymethyl)-4-((methylsulfonyl)oxy) pyrrolidine-1-carboxylate (369eb)

To a solution of 1-(tert-butyl) 2-methyl (2S,4S)-4-((methylsulfonyl)oxy)pyrrolidine-1,2-dicarboxylate (500 mg, 1.546 mmol) in THF (125 mL) at 0° C. was added LiBH$_4$ (2M, 39 mL, 78.0 mmol) followed by slow addition of methanol (3.13 mL, 77.27 mmol). The reaction mixture was allowed to warm up slowly to rt and stirred at rt for 18 h. Acetone (10 mL) was added slowly, stirred for 1 h, then the mixture was poured into a cooled aqueous saturated NH$_4$Cl (300 mL). The mixture was extracted with EtOAc (2×80 mL). The combined organic layers were washed with water (100 mL) and brine, dried over MgSO$_4$, filtered and concentrated to dryness to afford 11.37 g of the desired product as a colorless solid which was used as such in the subsequent step without further purification. LCMS [M+Na]$^+$: 318.1.

Step 3: Synthesis of tert-butyl (2S,4S)-2-(((tert-butyldiphenylsilyl)oxy)methyl)-4-((methylsulfonyl)oxy)-pyrrolidine-1-carboxylate (369ec)

To a solution of tert-butyl (2S,4S)-2-(hydroxymethyl)-4-((methylsulfonyl)oxy)pyrrolidine-1-carboxylate (11.37 g, 35.16 mmol) in DCM (100 mL) at rt were added imidazole (4.8 g, 70.505 mmol) and TBDPS-Cl (11.0 mL, 42.30 mmol). The reaction mixture was stirred at rt for 18 hours. The mixture was diluted with water (100 mL) and DCM (50 mL). The layers were partitioned and DCM layer was washed with brine, dried over MgSO$_4$, filtered and concentrated to dryness to afford 18.5 g of the desired product as a colorless gum which was used as such in the subsequent step without further purification. LCMS [M+Na]$^+$: 556.3.

Step 4: Synthesis of tert-butyl (2S,4S)-2-(((tert-butyldiphenylsilyl)oxy)methyl)-4-((methylsulfonyl)oxy)-pyrrolidine-1-carboxylate (369ed)

To a solution of tert-butyl (2S,4S)-2-(((tert-butyldiphenylsilyl)oxy)methyl)-4-((methylsulfonyl)oxy)pyrrolidine-1-carboxylate (18 g, 33.723 mmol) in DMF (100 mL) at rt was added sodium cyanide (2 g, 40.808 mmol). The reaction mixture was heated to 80° C. for 18 hours. Upon cooling to rt, the reaction mixture was diluted with EtOAc (30 mL) and water (30 mL). The layers were partitioned and the aqueous layer was extracted with EtOAc (15 mL). The combined organic layers were washed with brine, dried over MgSO$_4$, filtered and concentrated to dryness. The residue was purified by flash chromatography on silica gel eluting with 10 and 15% EtOAc/hexanes to afford 6 g of the desired material as a colorless gum. LCMS [M+Na]$^+$: 487.3.

Step 5: Synthesis of tert-butyl (2S,4S)-4-(aminomethyl)-2-(((tert-butyldiphenylsilyl) oxy)methyl)pyrrolidine-1-carboxylate (369ee)

To a solution of tert-butyl (2S,4S)-2-(((tert-butyldiphenylsilyl)oxy)methyl)-4-((methylsulfonyl)oxy)pyrrolidine-1-carboxylate (220 mg, 0.473 mmol) in ethanol (3 mL) at 0° C. was added nickel chloride (II) (62 mg, 0.478 mmol) followed by portion wise addition of NaBH$_4$ (68 mg, 1.798 mmol). The reaction mixture was allowed to stir at rt for 6 hours. TLC showed complete reaction. The mixture was cooled to 0° C. and 10% NH$_4$OH (20 mL) was added slowly, extracted with EtOAc (2×25 mL). The combined organic layers were washed with water (2×20 mL) and brine (20 mL), dried over MgSO$_4$, filtered and concentrated to dryness to afford 200 mg of the desired product as a light yellow oil. The crude material was used as such in the subsequent step without further purification. LCMS [M+Na]$^+$: 491.3.

Step 6: Synthesis of tert-butyl (2S,4S)-2-(((tert-butyldiphenylsilyl)oxy)methyl)-4-(((5-(2-chloro-4-phenoxybenzoyl)-7H-pyrrolo[2,3-d]pyrimidin-4-yl)amino)methyl)pyrrolidine-1-carboxylate (369ef)

Prepared according to General Procedure A using tert-butyl (2S,4S)-4-(aminomethyl)-2-(((tert-butyldiphenylsilyl)oxy)methyl)pyrrolidine-1-carboxylate and 36-A. LCMS [M+H]$^+$: 816.3.

Step 7: Synthesis of (2-chloro-4-phenoxyphenyl)(4-((((3R,5S)-5-(hydroxymethyl)pyrrolidin-3-yl)methyl)amino)-7H-pyrrolo[2,3-d]pyrimidin-5-yl)methanone (I-369e)

(2-Chloro-4-phenoxyphenyl)(4-((((3R,5S)-5-(hydroxymethyl)pyrrolidin-3-yl)methyl)amino)-7H-pyrrolo[2,3-d]pyrimidin-5-yl)methanone was prepared according to General Scheme 1, using General Procedure. Product was isolated as a formate salt after reverse phase purification (Biotage C18, 5-80% CH$_3$CN/H$_2$O +0.1% formic acid). $^1$H NMR (DMSO-$d_6$, 400 mHz): δ 8.84 (t; J=5.66 Hz; 1H); 8.35 (s; 1H); 8.24

(s; 1H); 7.63 (s; 1H); 7.58 (d; J=8.46 Hz; 1H); 7.48 (t; J=7.82 Hz; 2H); 7.25 (t; J=7.40 Hz; 1H); 7.18-7.20 (m; 3H); 7.02 (dd; J=8.45; 2.37 Hz; 1H); 3.55-3.60 (m; 2H); 3.40-3.48 (m; 4H); 3.22 (dd; J=11.02; 7.02 Hz; 1H); 2.82 (dd; J=10.96; 7.04 Hz; 1H); 2.54-2.60 (m; 1H); 1.73-1.78 (m; 2H). NH of indole not observed. LCMS [M+H]$^+$: 478.1.

Example 229: Synthesis of (2-chloro-4-phenoxyphenyl)(4-((((3S,5S)-5-(hydroxymethyl)-1-methylpyrrolidin-3-yl)methyl)amino)-7H-pyrrolo[2,3-d]pyrimidin-5-yl)methanone (I-370e)

To a solution of (2-chloro-4-phenoxyphenyl)(4-((((3R,5S)-5-(hydroxymethyl)pyrrolidin-3-yl)methyl)amino)-7H-pyrrolo[2,3-d]pyrimidin-5-yl)methanone (500 mg, 1.372 mmol) in 2,2,2-trifluoroethanol (5 mL) at rt were added paraformaldehyde (330 mg, 10.989 mmol) and sodium borohydride (73 mg, 1.930 mmol). The reaction mixture was stirred at rt for 18 hours. LCMS showed complete reaction. The reaction mixture was diluted with (1:1) aqueous sat. NaHCO$_3$/water (30 mL) and EtOAc (30 mL). The layers were partitioned and the aqueous layer was extracted with EtOAc (20 mL). The combined organic layers were washed with brine, dried over MgSO$_4$, filtered and concentrated to dryness. The residue was purified by reverse phase C$_{18}$ ISCO CombiFlash (13 g column) eluting with 5-80% CH$_3$CN/water (0.1% formic acid) over 25 minutes. The product fractions were combined and concentrated to dryness. The residue was freeze dried to afford 22 mg of the title compound as a colorless powder. $^1$H NMR (DMSO-d$_6$, 400 mHz): δ 8.79 (t; J=5.41 Hz; 1H); 8.24 (s; 2H); 7.62 (s; 1H); 7.58 (d; J=8.46 Hz; 1H); 7.48 (dd; J=8.45; 7.27 Hz; 2H); 7.25 (t; J=7.39 Hz; 1H); 7.18-7.20 (m; 3H); 7.02 (dd; J=8.44; 2.37 Hz; 1H); 3.55 (t; J=6.31 Hz; 2H); 3.43 (dd; J=10.90; 4.63 Hz; 1H); 3.30 (dd; J=10.90; 5.90 Hz; 1H); 3.17 (t; J=7.86 Hz; 1H); 2.41-2.46 (m; 2H); 2.33 (s; 3H); 2.13 (t; J=9.33 Hz; 1H); 1.77-1.82 (m; 1H); 1.67-1.72 (m; 1H). LCMS [M+H]$^+$: 492.3.

Example 230: Synthesis of (4-((((3S,5S)-1-benzyl-5-(hydroxymethyl)pyrrolidin-3-yl)methyl)amino)-7H-pyrrolo[2,3-d]pyrimidin-5-yl)(2-chloro-4-phenoxyphenyl)methanone (I-657)

Step 1: Synthesis of (3R,5S)-5-(((tert-butyldiphenylsilyl)oxy)methyl)pyrrolidine-3-carbonitrile (657a)

Tert-butyl (2S,4R)-2-(((tert-butyldiphenylsilyl)oxy)methyl)-4-cyanopyrrolidine-1-carboxylate (3 g, 4.639 mmol) in DCM (30 mL) at 0° C. was added TFA (10 mL, 130.591 mmol). The reaction mixture was allowed to stir at rt for 3 hours. Toluene (15 mL) was added and the volatiles were removed under reduced pressure. The residue was dissolved in EtOAc (40 mL) and aqueous sat. NaHCO$_3$ (50 mL) was added (pH ~8). The layers were partitioned and the aqueous layer was extracted with EtOAc (30 mL). The combined organic layers were washed with brine, dried over MgSO$_4$, filtered and concentrated to dryness under reduced pressure to 1.7 g of the desired product as a red oil. This crude material was used as such in the subsequent step without further purification. LCMS [M+H]$^+$: 365.3.

Step 2: Synthesis of (3R,5S)-1-benzyl-5-(((tert-butyldiphenylsilyl)oxy)methyl)pyrrolidine-3-carbonitrile (657b)

To a solution of (3R,5S)-5-(((tert-butyldiphenylsilyl)oxy)methyl)pyrrolidine-3-carbonitrile (500 mg, 1.372 mmol) in acetonitrile (5 mL) at rt were added potassium carbonate (569 mg, 4.117 mmol) and benzyl bromide (0.163 mL, 1.370 mmol). The reaction mixture was stirred at rt for 18 hours. LCMS showed complete reaction. The reaction mixture was diluted with water (30 mL) and EtOAc (30 mL). The layers were partitioned and the aqueous layer was extracted with EtOAc (20 mL). The combined organic layers were washed with brine, dried over MgSO$_4$, filtered and concentrated to dryness. The residue was purified by ISCO CombiFlash (24 g column) eluting with 0-50% EtOAc/hexanes to afford 480 mg of the desired product as a colorless oil. LCMS [M+H]$^+$: 455.1.

Step 3: Synthesis of (((3S,5S)-1-benzyl-5-(((tert-butyldiphenylsilyl)oxy)methyl)pyrrolidin-3-yl)methanamine (657c)

To a solution of (3R,5S)-1-benzyl-5-(((tert-butyldiphenylsilyl)oxy)methyl)pyrrolidine-3-carbonitrile (480 mg, 1.056 mmol) in ethanol (4 mL) at 0° C. was added nickel chloride (II) (137 mg, 1.057 mmol) followed by portion wise addition of NaBH$_4$ (152 mg, 4.018 mmol). The reaction mixture was allowed to stir at rt for 6 hours. Additional nickel chloride (II) (137 mg, 1.057 mmol) followed by portionwise addition of NaBH$_4$ (152 mg, 4.018 mmol) and the mixture was allowed to stir at rt for 18 hours. The mixture was cooled to 0° C. and 10% NH$_4$OH (20 mL) was added slowly, extracted with EtOAc (2×30 mL). The combined organic layers were washed with water (2×30 mL) and brine (30 mL), dried over MgSO$_4$, filtered and concentrated to dryness to afford 430 mg of the desired product as a light yellow oil. The crude material was used as such in the subsequent step without further purification. LCMS [M+H]$^+$: 459.3.

Step 4: Synthesis of (4-((((3S,5S)-1-benzyl-5-(((tert-butyldiphenylsilyl)oxy)methyl) pyrrolidin-3-yl)methyl)amino)-7H-pyrrolo[2,3-d]pyrimidin-5-yl)(2-chloro-4-phenoxyphenyl)methanone (657d)

According to General Procedure A, using (4-((((3S,5S)-1-benzyl-5-(((tert-butyl diphenylsilyl)oxy)methyl) pyrrolidin-3-yl)methyl)amino)-7H-pyrrolo[2,3-d]pyrimidin-5-yl) (2-chloro-4-phenoxyphenyl)methanone and ((3S,5S)-1-benzyl-5-(((tert-butyldiphenylsilyl)oxy)methyl)pyrrolidin-3-yl)methanamine. LCMS [M+H]$^+$: 806.4.

Step 5: Synthesis of (4-((((3S,5S)-1-benzyl-5-(hydroxymethyl)pyrrolidin-3-yl)methyl)amino)-7H-pyrrolo[2,3-d]pyrimidin-5-yl)(2-chloro-4-phenoxyphenyl)methanone (I-657)

(4-((((3S,5S)-1-benzyl-5-(hydroxymethyl)pyrrolidin-3-yl)methyl)amino)-7H-pyrrolo[2,3-d]pyrimidin-5-yl)(2-chloro-4-phenoxyphenyl)methanone was prepared according to General Procedure H. The product was isolated as formate salt after purification (Biotage C18, 5-85% acetonitrile in water+0.1% formic acid). $^1$H NMR (DMSO-d$_6$, 400 mHz): δ 12.71 (br s; 1H); 8.74-8.77 (m; 1H); 8.22 (s; 1H); 7.60 (s; 1H); 7.56 (d; J=8.46 Hz; 1H); 7.46-7.50 (m; 2H); 7.26-7.32 (m; 5H); 7.16-7.23 (m; 4H); 7.02 (dd; J=8.45; 2.37 Hz; 1H); 4.03-4.06 (m; 1H); 3.51-3.54 (m; 2H); 3.28-3.46 (m; 3H); 2.99 (dd; J=8.87; 6.52 Hz; 1H); 2.74-2.79 (m; 1H); 2.33-2.46 (m; 1H); 2.08-2.13 (m; 1H); 1.82-1.89 (m; 1H); 1.68-1.75 (m; 1H). Contained 0.48 eq. of formic acid at 8.14 ppm. LCMS [M+H]$^+$: 568.3.

Example 231: Synthesis of (2-chloro-4-phenoxyphenyl)(4-((((2R,5S)-5-(hydroxymethyl)tetrahydrofuran-2-yl)methyl)amino)-7H-pyrrolo[2,3-d]pyrimidin-5-yl)methanone (I-362e)

(2-Chloro-4-phenoxyphenyl)(4-((((2R,5S)-5-(hydroxymethyl)tetrahydrofuran-2-yl)methyl)amino)-7H-pyrrolo[2,3-d]pyrimidin-5-yl)methanone was prepared according to General Procedure A, using 36-A and ((2S,5R)-5-(aminomethyl)tetrahydrofuran-2-yl)methanol. $^1$H NMR (DMSO-$d_6$, 400 mHz): δ 8.82 (t; J=5.57 Hz; 1H); 8.43 (s; 0.16H); 8.22 (s; 1H); 7.6 (s, 1H), 7.57 (m; 2H); 7.48 (d; J=8.45 Hz; 1H); 7.25 (t; J=7.40 Hz; 1H); 7.18-7.20 (m; 3H); 7.03 (dd; J=8.44; 2.37 Hz; 1H); 4.61 (s; 1H); 4.10 (t; J=5.74 Hz; 1H); 3.87 (t; J=5.91 Hz; 1H); 3.61-3.72 (m; 2H); 3.37-3.47 (m; 2H); 1.86-1.95 (m; 2H); 1.63-1.69 (m; 2H). LCMS [M+H]$^+$: 479.2, 481.2.

Example 232: Synthesis of racemic-cis-(2-chloro-4-phenoxyphenyl)(4-(((6-(hydroxymethyl)piperidin-2-yl)methyl)amino)-7H-pyrrolo[2,3-d]pyrimidin-5-yl)methanone (I-359e)

Step 1: Synthesis of methyl 6-((hydroxyimino)methyl)picolinate (359ea)

To methyl 5-formylpicolinate (1.0 g, 6.055 mmol) dissolved in ethanol-water (14.4 mL, 2:1) was added hydroxylamine hydrochloride (0.463 g, 6.66 mmol) and sodium acetate (0.546 mg, 0.6661 mmol). The reaction mixture was stirred overnight at 55° C. The reaction was concentrated under reduced pressure and redissolved in EtOAc (100 mL). The organic phase was washed with water, dried over sodium sulfate, filtered and concentrated under reduced pressure. The solid residue was dissolved triturated with EtOAc, filtered and dried under reduced pressure affording methyl 6-(hydroxyimino)methyl)picolinate (990 mg, 5.495 mmol, 91%) as a beige solid. LCMS [M+H]$^+$: 181.1.

Step 2: Synthesis of racemic-cis-methyl 6-(aminomethyl)piperidine-2-carboxylate dihydrochloride (359eb)

To a suspension of methyl 6-(hydroxyimino)methyl)picolinate (200 mg, 1.161 mmol) and PtO$_2$ (26.37 mg, 0.116 mmol) in EtOH (5.8 mL), conc. HCl (0.2 mL) was added and the mixture was stirred over night under hydrogen (1 atm), the crude was filtered through Celite and concentrated under reduced pressure. The residue was dissolved in water and lyophilized affording a cis-isomer mixture of methyl 6-(aminomethyl)piperidine-2-carboxylate dihydrochloride (343 mg, 1.366 mmol, 100%) as a white solid. $^1$H NMR (D$_2$O, 400 mHz): δ 4.03 (dd; J=12.04; 3.58 Hz; 1H); 3.71 (s; 23H); 3.49 (dtd; J=12.46; 6.29; 2.93 Hz; 1H); 3.29 (dd; J=13.80; 5.98 Hz; 1H); 3.16 (dd; J=13.81; 6.76 Hz; 1H); 2.24 (d; J=10.21 Hz; 1H); 1.91-1.99 (m; 2H); 1.52-1.64 (m; 2H); 1.43 (t; J=13.38 Hz; 1H). LCMS [M+H]$^+$: 173.2.

Step 3: Synthesis of racemic-cis-1-benzyl 2-methyl 6-((((benzyloxy)carbonyl) amino) methyl)piperidine-1,2-dicarboxylate (359ec)

A cis-isomer mixture of methyl 6-(aminomethyl)piperidine-2-carboxylate dihydrochloride (300 mg, 1.195 mmol), CbzCl (374 mL, 2.63 mmol), saturated sodium bicarbonate in water (6.5 mL) and dioxane (6.5 mL) was stirred overnight at room temperature. The mixture was diluted with EtOAc, the phases separated. The aqueous phase extracted with EtOAc. The combined organic phases were combined and dried over anhydrous sodium sulfate. The solution was concentrated under reduced pressure and the residue purified by flash chromatography (ISCO, 12 g column, EtOAc in hexanes) affording a cis-isomer mixture of 1-benzyl 2-methyl 6-((((benzyloxy) carbonnyl)amino)methyl)piperidine-1,2-dicarboxylate (OS03-034A1) (543.1 mg, 1.23 mmol, 62%) as a transparent syrup. LCMS [M+H]$^+$: 441.3.

Step 4: Synthesis of racemic-cis-benzyl 2-((((benzyloxy)carbonyl)amino)methyl)-6-(hydroxymethyl) piperidine-1-carboxylate (359ed)

A solution of 2M lithium borohydride in THF (0.62 mL, 1.23 mmol) was added to a solution of a mixture of cis-isomers of 1-benzyl 2-methyl 6-((((benzyloxy)carbonnyl)amino)methyl) piperidine-1,2-dicarboxylate (543.1 mg, 1.23 mmol) in diethylether (3.5 mL) at 0° C. The reaction mixture was stirred at 0° C. 2 h. A saturated aqueous sodium bicarbonate solution was added dropwise, the mixture was stirred 1 h at room temperature. The layers were separated. The aqueous layer extracted with diethyl ether, the organic phased were combined, dried over anhydrous sodium sulfate and concentrated under reduced pressure affording a cis-isomer mixture of benzyl 2-((((benzyloxy)carbonyl)amino)methyl)-6-(hydroxymethyl)piperidine-1-carboxylate (270 mg, 0.654 mmol, 100%) as transparent syrup. LCMS [M+H]$^+$: 413.2.

Step 5: Synthesis of racemic-cis-6-(aminomethyl)piperidin-2-yl)methanol (359ee)

To a suspension of a cis-isomer mixture of benzyl 2-((((benzyloxy)carbonyl)amino)methyl)-6-(hydroxymethyl)piperidine-1-carboxylate (270 mg, 0.654 mmol) and 20% palladium hydroxide on carbon (130 mg) in MeOH (15 mL), 1N HCl (2 mL) was added and the mixture was stirred overnight under hydrogen (1 atm), the crude was filtered through Celite and concentrated under reduced pressure. The residue was dissolved in water and lyophilized affording a cis-isomer mixture of 6-(aminomethyl)piperidin-2-yl) methanol dihydrochloride (140 mg, 0.65 mmol, 100%) as a white solid. LCMS [M+H]$^+$: 145.1.

Step 6: Synthesis of racemic-cis-(2-chloro-4-phenoxyphenyl)(4-(((6-(hydroxymethyl) piperidin-2-yl)methyl)amino)-7H-pyrrolo[2,3-d]pyrimidin-5-yl)methanone (I-359e)

Racemic-cis-(2-chloro-4-phenoxyphenyl)(4-(((6-(hydroxymethyl) piperidin-2-yl)methyl)amino)-7H-pyrrolo[2,3-d]pyrimidin-5-yl)methanone was prepared according to General Procedure A, using a cis-isomer mixture of 6-(aminomethyl)piperidin-2-yl)methanol dihydrochloride and 36-A. $^1$H NMR (DMSO-$d_6$, 400 mHz): δ 8.86 (t; J=5.71 Hz; 1H); 8.32 (s; 0.1H); 8.25 (s; 2H); 7.63 (s; 1H); 7.57 (d; J=8.46 Hz; 1H); 7.46-7.50 (m; 2H); 7.26 (t; J=7.40 Hz; 1H); 7.18-7.20 (m; 3H); 7.03 (dd; J=8.45; 2.37 Hz; 1H); 3.60-3.66 (m; 1H); 3.51-3.57 (m; 1H); 3.40 (dd; J=10.64; 4.31 Hz; 1H); 3.26 (dd; J=10.64; 7.23 Hz; 1H); 2.93 (br s; 1H); 2.68 (br s; 1H); 1.77 (m; 2H); 1.55 (d; J=12.64 Hz; 1H); 1.36 (q; J=12.90 Hz; 1H); 1.18 (q; J=12.16 Hz; 1H); 1.03 (q; J=12.11 Hz; 1H). LCMS [M+H]$^+$: 492.2, 494.2.

Example 233: Synthesis of racemic-cis-(2-chloro-4-phenoxyphenyl)(4-(((6-(hydroxymethyl)-1-methylpiperidin-2-yl)methyl)amino)-7H-pyrrolo[2,3-d]pyrimidin-5-yl)methanone (I-360e)

A cis-isomer mixture of (2-chloro-4-phenoxyphenyl)(4-(((6-(hydroxymethyl)piperidin-2-yl)methyl)amino)-7H-pyrrolo[2,3-d]pyrimidin-5-yl)methanone (I-359e) (20.9 mg, 0.0421 mmol) was dissolved in 2,2,2-trifluoroethanol (1.05 mL), paraformaldehyde (10.1 mg, 0.3367 mmol) and sodium borohydride (2.2 mg, 0.0589 mmol) were added and the mixture stirred at RT overnight. MeOH (1 mL) was added and the mixture stirred 30 min at room temperature. The solution was concentrated under reduced pressure. The residue was purified by preparative HPLC 10% to 85%0 MeCN in water). The fractions containing the product were combined and lyophilized affording a mixture of (2-chloro-4-phenoxyphenyl)(4-((((2R,6S)-6-(hydroxymethyl)-1-methylpiperidin-2-yl)methyl)amino)-7H-pyrrolo[2,3-d]pyrimidin-5-yl)methanone and (2-chloro-4-phenoxyphenyl)(4-((((2S,6R)-6-(hydroxymethyl)-1-methylpiperidin-2-yl)methyl)amino)-7H-pyrrolo[2,3-d]pyrimidin-5-yl)methanone (10.1 mg, 0.0183 mmol, 43%) as a white powder. $^1$H NMR (DMSO-$d_6$, 400 mHz): δ 8.90 (t; J=4.88 Hz; 1H); 8.24 (s; 1H); 8.22 (s; 1H); 7.56-7.59 (m; 2H); 7.48 (m; 2H); 7.25 (t; J=7.39 Hz; 1H); 7.18-7.20 (m; 3H); 7.02 (dd; J=8.45; 2.37 Hz; 1H); 3.60-3.67 (m; 2H); 3.40-3.49 (m; 2H); 2.43 (s; 1H); 2.30 (s; 3H); 2.23 (s; 1H); 1.72 (s; 1H); 1.60-1.64 (m; 2H); 1.47 (d; J=13.15 Hz; 1H); 1.32 (s; 2H). LCMS [M+H]$^+$: 506.26, Example 234: BTK Kinase Activity Assay Radiometric Assay Enzyme assay using full length recombinant active form of wild-type BTK and BTK-C481S was measured as described previously (Anastassiadis T, et al., Nat. Biotechnol. 29(11):1039-45 (2011)). Compounds were tested in 10-point dose IC$_{50}$ mode with 3-fold serial dilution starting at 1 or 10 μM concentration. BTK kinase activity was assayed in a buffer solution containing 20 mM Hepes (pH 7.5), 10 mM MgCl2, 1 mM EGTA, 0.02% Brij35, 0.02 mg/ml BSA, 0.1 mM Na3VO4, 2 mM DTT, 1% DMSO. Compounds in 100% DMSO were mixed with kinase (8 nM wild-type BTK or 5 nM BTK-C481S mutant) with substrate into the kinase reaction mixture by Acoustic technology (Echo550; nanoliter range) and incubated for 20 min at room temp. The reaction was initiated by adding 10 μM ATP containing $^{33}$P-ATP into the mixture and incubated for 2 hours at room temperature. Kinase activity was detected by P81 filter-binding $^{33}$P radioisotope based radiometric method. All compounds were tested in duplicate. The raw data was fit to a 4-parameter logistic model to derive the IC$_{50}$ value for kinase activity inhibition.

Mobility Shift Assay (MSA)

Compounds were tested either in the inactive or active BTK assays on Caliper LabChip microfluidic mobility shift assay platform.

Full length unphosphorylated form of BTK expressed in Sf9 cells was employed to test inhibitory activity in the inactive BTK assay. The assay was measured in buffer solution containing 100 mM HEPES pH7.5, 0.01% Triton X-100, 0.1% BSA, 5 mM MgCl$_2$, 1 mM DTT. The enzyme and increasing concentrations of inhibitor was incubated at room temperature for 30 minutes and the kinase reaction was initiated by the addition an activation mixture diluted in assay buffer containing Srctide peptide substrate, DOPS/DOPC, PtdIns(3,4,5)P3, and ATP for final concentrations of 1 μM Srctide, 5.5 μM DOPS, 5.5 μM DOPC, 0.5 μM PtdIns(3,4,5)P3, and 16 μM ATP. The plates were incubated for 60 minutes at room temperature, and then the reaction stopped with 100 mM HEPES buffer containing 0.01% Triton and 40 mM EDTA and read on Caliper Life Sciences Labchip EZ Reader II instrument.

The active BTK assay consisted of phosphorylated form of full length BTK. The assay was performed in a buffer solution utilized in the inactive BTK assay. The enzyme inhibitor complexes was incubated for 30 minutes at the room temperature and the kinase activation reaction was initiated by the addition of 1 μM Srctide peptide substrate and 16M ATP. After incubation at room temperature for 60 minutes, the reaction was stopped and the mobility shift was measured as described above for the inactive BTK assay. The data of inactive and active BTK assays was fit to a 4 parameter logistic model to calculate the IC$_{50}$ value.

Alpha Screen Assay

Purified full-length inactive BTK (wild type and C481 mutant, N-terminal 6XHIS tagged BTK, Mwt=78.2 kDa) were activated using soluble inositol hexakisphosphate (IP6) and ATP as described (Q. Wang, E. M. Vogan, L. M. Nocka, C. E. Rosen, J. A. Zorn, S. C. Harrison J. Kuriyan, eLife 2015; 4:e06074), with minor modification. To 190 μl of 1 mM IP6 in activation buffer (25 mM Tris, pH 7.5, 150 mM NaCl, 5% glycerol) was added 10 μl of inactive BTK at 5-6 mg/ml and incubated for 10 min at room temperature followed by addition of 200 μl of 2 mM ATP in assay buffer (50 mM Tris, pH 8, 10 mM MgCl2, 1 mM EDTA, 0.1 mM NaF, 0.02 mg/ml BSA, 10% glycerol, 2 mM sodium orthovanadate, 0.25 mM DTT) for a further 10 min. The activated BTK was frozen in 50 μl aliquots (125-150 μg/ml).

BTK activity was assayed using a PLCγ2-derived biotinylated peptide substrate (biotin-EELNNQLFLY-DTHQNLR-OH) and AlphaScreen™ (Amplified Luminescent Proximity Homogeneous Assay) technology. The extent of peptide phosphorylation was determined by using acceptor beads conjugated to phosphotyrosine antibody that recognized the phosphorylated peptide and donor beads conjugated to streptavidin that binds to the biotin on the peptide. Excitation of the donor beads converted ambient oxygen to excited singlet oxygen which when in close proximity to acceptor beads, reacted with acceptor beads resulting in signal amplification.

Test inhibitors and controls were prepared in 10% DMSO at 10-fold the desired final concentration and added to each well of a reaction plate (Corning 96-well half-area solid white nonbinding surface plate) in a volume of 2.5 μl. Full-length activated BTK (wildtype or mutant C481S) diluted to 0.179 nM in assay buffer (50 mM Tris, pH 8, 10 mM MgCl2, 1 mM EDTA, 0.1 mM NaF, 0.02 mg/ml BSA, 10% glycerol, 0.2 mM Na3VO4, 0.1 mM beta-glycerophosphate, 0.25 mM DTT) was added to each well in a volume of 17.5 μl and incubated with the inhibitors for 30 min. The kinase reaction was initiated by the addition of 5 μl of biotin-PLCγ2 peptide and ATP mixture diluted in assay buffer for a final concentration in the 25 μl reaction of 150 nM and 180 μM respectively and 0.125 nM enzyme. The plate was incubated for 120 min at room temperature and the reaction stopped by the addition of 10 μl stop/detection mixture containing 35 mM EDTA, 50 ug/ml AlphaScreen™ Streptavidin Donor beads (final concentration is 500 ng/well) and AlphaScreen™ Phospho-tyrosine (P-Tyr-100) Acceptor beads (final concentration is 500 ng/well) under green light conditions. The plate was incubated overnight at room temperature in the dark and the plates read on the BMG PolarStar Omega (excitation wavelength: 640 nm, emission wavelength: 570 nm, Gain=4000). Data were archived and analyzed with a 4-parameter fit to generate $IC_{50}$ values using the CDD Vault from Collaborative Drug Discovery.

TABLE 4

Biological activity of Compounds of Formula (I) in BTK Kinase Assay Type A (MSA using active BTK), Assay Type B (MSA using active BTK), and Assay Type C (radiometric assay with active enzyme).

| Cmpd No. | BTK $IC_{50}$ (nM) | Assay type |
|---|---|---|
| I-1 | 11 | A |
| I-2 | 17 | A |
| I-3 | 19 | A |
| I-4 | 107 | A |
| I-5 | 90 | A |
| I-6 | 7.4 | A |
| I-7 | 93 | A |
| I-8 | 74 | A |
| I-9 | 6.1 | A |
| I-10 | 30 | A |
| I-11 | 151 | A |
| I-12 | 37 | A |
| I-13 | 25 | A |
| I-14 | 14 | A |
| I-15 | 8.3 | A |
| I-16 | 134 | A |
| I-17 | 80 | A |
| I-18 | 9.7 | A |
| I-19 | 9.2 | A |
| I-20 | 9.5 | A |
| I-21 | 9.7 | A |
| I-22 | 5.9 | A |
| I-23 | 5.9 | A |
| I-24 | 6.2 | A |
| I-25 | 154 | A |
| I-26 | 33 | A |
| I-27 | 46 | A |
| I-28 | 8.3 | A |
| I-29 | 9.3 | A |
| I-30 | 4.9 | A |
| I-31 | 9.0 | A |
| I-32 | 11 | A |
| I-33 | 4.2 | A |
| I-34 | 4.4 | A |
| I-35 | 150 | A |
| I-36 | 29 | A |
| I-37 | 15 | A |
| I-38 | 5.2 | A |
| I-39 | 3.0 | A |
| I-40 | 10 | A |
| I-41 | 2.6 | A |
| I-42 | 5.4 | A |
| I-43 | 2.1 | A |
| I-44 | 5.4 | A |
| I-45 | 2.6 | A |
| I-46 | 66 | A |
| I-47 | 10 | A |
| I-48 | 6.0 | A |
| I-49 | 8.6 | A |
| I-50 | 2.7 | A |
| I-51 | 1.9 | A |
| I-52 | 70 | A |
| I-53 | 76 | A |
| I-54 | 83 | A |
| I-55 | 81 | A |
| I-56 | 158 | A |
| I-57 | 63 | A |
| I-58 | 3.6 | A |
| I-59 | 6.7 | A |
| I-60 | 7.0 | A |
| I-61 | 3.4 | A |
| I-62 | 5.0 | A |
| I-63 | 3.3 | A |
| I-64 | 4.1 | A |
| I-65 | 11 | A |
| I-66 | 11 | A |
| I-67 | 5.4 | A |
| I-68 | 5.6 | A |
| I-69 | 2.2 | A |
| I-70 | 4.6 | A |
| I-71 | 19 | A |
| I-72 | 447 | A |
| I-73 | 66 | A |
| I-74 | 20 | A |
| I-75 | 12 | A |
| I-76 | 52 | A |
| I-77 | 56 | A |
| I-78 | 3.0 | A |
| I-79 | 3.7 | A |
| I-80 | 4.1 | A |
| I-81 | 5.5 | A |
| I-82 | 12 | A |
| I-83 | 19 | A |
| I-84 | 14 | A |
| I-85 | 2.3 | A |
| I-86 | 2.9 | A |
| I-87 | 4.9 | A |
| I-88 | 2.5 | A |
| I-89 | 23 | A |
| I-90 | 5.7 | A |
| I-91 | 3.5 | A |
| I-92 | 3.1 | A |
| I-93 | 3.4 | A |
| I-94 | 2.9 | A |
| I-95 | 8.1 | A |
| I-96 | 8.9 | A |
| I-97 | 7.0 | A |
| I-98 | 5.3 | A |
| I-99 | 4.8 | A |
| I-100 | 5.3 | A |
| I-101 | 5.1 | A |
| I-102 | 1.9 | A |
| I-103 | 3.5 | A |
| I-104 | 3.5 | A |
| I-105 | 7.0 | A |
| I-106 | 4.6 | B |
| I-107 | 12 | B |
| I-108 | 7.0 | B |
| I-109 | 3.2 | B |
| I-110 | 16 | B |
| I-111 | 3.0 | B |
| I-112 | 18 | B |
| I-113 | 3.6 | B |
| I-114 | 23 | B |
| I-115 | 5.8 | B |
| I-116 | 5.9 | B |
| I-117 | 5.9 | B |
| I-118 | 4.4 | B |
| I-119 | 5.1 | B |
| I-120 | 121 | B |
| I-121 | 7.3 | B |
| I-122 | 0.77 | A |
| I-123 | 0.85 | C |
| I-124 | 9.7 | C |
| I-125 | 0.56 | C |
| I-126 | 2.4 | C |
| I-127 | 1.63 | B |
| I-128 | 15 | A |
| I-129 | 34 | A |
| I-130 | 3.2 | B |
| I-131 | 3.8 | B |
| I-132 | 12 | A |
| I-133 | 188 | A |
| I-134 | 292 | A |
| I-135 | 63 | A |
| I-136 | 154 | A |
| I-137 | 95 | A |
| I-138 | 41 | A |
| I-139 | 2.3 | A |

TABLE 4-continued

Biological activity of Compounds of Formula (I) in BTK Kinase Assay Type A (MSA using active BTK), Assay Type B (MSA using active BTK), and Assay Type C (radiometric assay with active enzyme).

| Cmpd No. | BTK IC$_{50}$ (nM) | Assay type |
|---|---|---|
| I-140 | 8.0 | A |
| I-141 | 2.2 | A |
| I-142 | 6.8 | A |
| I-143 | 2359 | A |
| I-144 | 9.2 | A |
| I-145 | 7.2 | A |
| I-146 | 3.9 | A |
| I-147 | 7.5 | A |
| I-148 | 12 | A |
| I-149 | 89 | A |
| I-150 | 0.93 | A |
| I-151 | 1.3 | A |
| I-152 | 133 | A |
| I-153 | 27 | A |
| I-154 | 32 | A |
| I-155 | 9.3 | A |
| I-156 | 30 | A |
| I-157 | 4.0 | A |
| I-158 | 9.6 | A |
| I-159 | 15 | A |
| I-160 | 6.0 | A |
| I-161 | 102 | A |
| I-162 | 45 | A |
| I-163 | 29 | A |
| I-164 | 19 | A |
| I-165 | 8.4 | A |
| I-166 | 1.1 | A |
| I-167 | 1.4 | A |
| I-168 | 7.2 | A |
| I-169 | 1.7 | A |
| I-170 | 7.0 | A |
| I-171 | 39 | A |
| I-172 | 20 | A |
| I-173 | 4.3 | A |
| I-174 | 7.2 | A |
| I-175 | 3.1 | B |
| I-176 | 2.5 | B |
| I-177 | 1.7 | B |
| I-178 | 2.2 | B |
| I-179 | 1.8 | B |
| I-180 | 1.8 | B |
| I-181 | 0.98 | B |
| I-182 | 1.5 | B |
| I-183 | 2.2 | B |
| I-184 | 61 | B |
| I-185 | 57 | B |
| I-186 | 12 | B |
| I-187 | 4.2 | B |
| I-188 | 1.7 | B |
| I-189 | 17 | B |
| I-190 | 17 | B |
| I-191 | 37 | B |
| I-192 | 4.4 | B |
| I-193 | 1.2 | B |
| I-194 | 1.5 | B |
| I-195 | 2.2 | B |
| I-196 | 3.2 | B |
| I-197 | 1.6 | B |
| I-198 | 2.6 | B |
| I-199 | 6.8 | B |
| I-200 | 1.4 | B |
| I-201 | 1.5 | B |
| I-202 | 1.0 | B |
| I-203 | 1.4 | B |
| I-204 | 1.1 | B |
| I-205 | 1.6 | B |
| I-206 | 1.8 | B |
| I-207 | 4.1 | B |
| I-208 | 3.1 | B |
| I-209 | 4.0 | B |
| I-210 | 1.9 | B |
| I-211 | 2.9 | B |
| I-212 | 2.9 | B |
| I-213 | 2.5 | B |
| I-214 | 7.4 | B |
| I-215 | 3.9 | B |
| I-216 | 1.9 | B |
| I-217 | 3.2 | B |
| I-218 | 470 | A |
| I-219 | >4000 | A |
| I-220 | 14 | A |
| I-221 | >4000 | A |
| I-222 | 5.4 | A |
| I-223 | >4000 | A |
| I-224 | >4000 | A |
| I-225 | >4000 | A |
| I-226 | 364 | A |
| I-227 | >4000 | A |
| I-228 | 4300 | A |
| I-229 | 2195 | A |
| I-230 | 4000 | A |

TABLE 5a

Biological activity of Compounds of Formula (I) in BTK wild-type and BTK mutant C481S Kinase Assay (radiometric assay).

| Compound No. | BTK IC$_{50}$ (nM) | BTK-C481S IC$_{50}$ (nM) |
|---|---|---|
| I-123 | 0.85 | 0.39 |
| I-124 | 9.7 | 7.0 |
| I-125 | 0.56 | 0.37 |
| I-126 | 2.4 | 0.79 |

TABLE 5b

Biological activity of Compounds of Formula (I) in BTK wild-type and BTK mutant C481S Kinase Assay (AlphaScreen).

| Compound No. | BTK IC$_{50}$ (nM) | BTK-C481S IC$_{50}$ (nM) |
|---|---|---|
| I-601 | 20.9 | 116 |
| I-602 | 140 | 317 |
| I-603 | 466 | 1770 |
| I-604 | 304 | 731 |
| I-605 | 467 | 1860 |
| I-606 | 0.98 | 55.9 |
| I-607 | 13.8 | 216 |
| I-608 | 8.19 | 187 |
| I-609 | 114 | 519 |
| I-236 | 181 | 98.4 |
| I-610 | 491 | 1150 |
| I-611 | 1140 | 1510 |
| I-612 | 1630 | 82% @ 10 uM |
| I-613 | 87% @ 10 uM | 64% @ 10 uM |
| I-614 | 142 | 228 |
| I-256 | 156 | 317 |
| I-615 | 86.4 | 34.1 |
| I-616 | 116 | 506 |
| I-617 | 16.2 | 48.7 |
| I-618 | 87.4 | 399 |
| I-619 | 376 | 942 |
| I-246 | 103 | 514 |
| I-620 | 598 | 70% @ 10 uM |
| I-621 | 571 | 85% @ 10 uM |
| I-622 | 847 | 62% @ 10 uM |
| I-623 | 124 | 185 |
| I-624 | 1210 | 53% @ 10 uM |
| I-625 | 110 | 170 |

TABLE 5b-continued

Biological activity of Compounds of Formula (I) in BTK wild-type and BTK mutant C481S Kinase Assay (AlphaScreen).

| Compound No. | BTK IC$_{50}$ (nM) | BTK-C481S IC$_{50}$ (nM) |
|---|---|---|
| I-626 | 164 | 757 |
| I-627 | 777 | 664 |
| I-628 | 59.7 | 161 |
| I-629 | 89.5 | 804 |
| I-630 | 18.4 | 189 |
| I-631 | 52.1 | 177 |
| I-632 | 84% @ 10 uM | 66% @ 10 uM |
| I-633 | 77% @ 10 uM | 50% @ 10 uM |
| I-634 | 619.5 | 690 |
| I-635 | 73% @ 10 uM | 49% @ 10 uM |
| I-636 | 62% @ 10 uM | 41% @ 10 uM |
| I-637 | 76% @ 10 uM | 55% @ 10 uM |
| I-638 | 63% @ 10 uM | 54% @ 10 uM |
| I-231 | 318 | 248 |
| I-276 | 17.6 | 58 |
| I-639 | 14.2 | 25.6 |
| I-640 | 69.5 | 203 |
| I-641 | 8.28 | 32.6 |
| I-642 | 251 | 203 |
| I-643 | 269 | 150 |
| I-644 | 58% @ 10 uM | 44% @ 10 uM |
| I-645 | 743 | 81% @ 10 uM |
| I-311i | 867 | 81% @ 10 uM |
| I-646 | 380 | 781 |
| I-647 | 1440 | 108 |
| I-318i | 423 | 714 |
| I-317i | 40.7 | 156 |
| I-648 | 731 | 810 |
| I-649 | 959 | 82% @ 10 uM |
| I-650 | 202 | 326 |
| I-320 | 336 | 63.1 |
| I-319 | 444 | 127 |
| I-651 | 332 | 230 |
| I-652 | 177 | 497 |
| I-324r | 17.2 | 105 |
| I-328r | 0.98 | 18.4 |
| I-321r | 4.5 | 179 |
| I-325r | 0.98 | 136 |
| I-322r | 10.4 | 98.6 |
| I-326r | 4.33 | 419 |
| I-653 | 10 | 38.8 |
| I-343r | 11 | 34 |
| I-654 | 6.55 | 20.7 |
| I-345e | 10.1 | 68.2 |
| I-342e | 14.2 | 33.4 |
| I-655 | 44.5 | 52 |
| I-656 | 123 | 254 |
| I-369e | 19.8 | 137 |
| I-370e | 59.5 | 49.8 |
| I-657 | 236 | 832 |
| I-362e | 35.6 | 44.5 |
| I-359e | 29.4 | 124 |
| I-360e | 1.07 | 59.4 |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A compound of Formula (I):

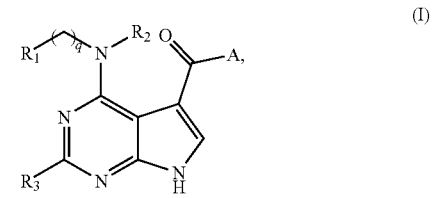

or a pharmaceutically acceptable salt, solvate, stereoisomer, or tautomer thereof, wherein:

A is $(C_6-C_{10})$ aryl or 5- or 6-membered heteroaryl comprising 1 to 3 heteroatoms selected from N, O, and S, wherein the aryl and heteroaryl are optionally substituted with one or more $R_4$;

$R_1$ is $(C_3-C_7)$ cycloalkyl or 4- to 9-membered heterocyclyl comprising 1 to 3 heteroatoms selected from N, O, and S, wherein the cycloalkyl and heterocyclyl are optionally substituted with one or more $R_5$;

$R_2$ is H or $(C_1-C_4)$ alkyl; or when q is 0, $R_1$ and $R_2$ together with the nitrogen atom to which they are attached may form a 5- or 6-membered heterocyclyl ring comprising 0 to 1 additional heteroatoms selected from N, O, and S and optionally substituted with one or more $NR_6R_7$;

$R_3$ is H or $N(R_8)_2$;

each $R_4$ is independently (i) $(C_1-C_4)$ alkyl, (ii) $(C_1-C_4)$ alkoxy optionally substituted with one or more $(C_1-C_4)$ alkoxy, (iii) halogen, (iv) $(CH_2)_nC(=O)NHR_{25}$, (v) $(CH_2)_nNHC(=O)R_{25}$, (vi) $(CH_2)_nNHC(=O)NHR_{25}$, or (vii) $C(=O)R_{25}$;

each $R_5$ is independently (i) $(C_1-C_6)$ alkyl optionally substituted with one or more $(C_1-C_4)$ alkoxy or phenyl, (ii) $(C_2-C_4)$ alkenyl optionally substituted with one or more $C(=O)(C_1-C_4)$ alkyl, (iii) $(C(R_{12})_2)_rOH$, (iv) $(C(R_{12})_2)_rNR_{13}R_{14}$, (v) $C(=O)OH$, (vi) $C(=O)O(C_1-C_4)$ alkyl, (vii) $C(=O)NR_{13}R_{15}$, (viii) $C(=O)R_{16}$, (ix) $S(O)_pR_{16}$, or (x) 5- or 6-membered heteroaryl comprising 1 to 3 heteroatoms selected from N, O, and S and optionally substituted with one or more $(C_1-C_4)$ alkyl, or (xi) two $R_5$ together with the carbon atom to which they are attached form (=O), or (xii) two $R_5$ together with the atoms to which they are attached form a bridged 3- to 6-membered heterocyclyl ring comprising 1 to 3 heteroatoms selected from N, O, and S;

$R_6$ is H or $(C_1-C_4)$ alkyl;

$R_7$ is H, $(C_1-C_4)$ alkyl, or $C(=O)R_{24}$;

each $R_8$ is independently (i) H, (ii) $(C_1-C_4)$ alkyl, or (iii) 5- or 6-membered heterocyclyl comprising 1 to 3 heteroatoms selected from N, O, and S and optionally substituted with one or more $(C_1-C_4)$ alkyl, or (iv) two $R_8$ together with the nitrogen atom to which they are attached form a 5- or 6-membered heterocyclyl ring comprising 0 to 1 additional heteroatoms selected from N, O, and S and optionally substituted with one or more $(C_1-C_4)$ alkyl;

each $R_{12}$ is independently H or $(C_1-C_6)$ alkyl;

$R_{13}$ is H or $(C_1-C_4)$ alkyl;

$R_{14}$ is (i) H, (ii) $(C_1-C_4)$ alkyl, (iii) $(C(R_{18})_2)_rC(=O)NR_{19}R_{20}$, (iv) $(CH_2)_n(C_6-C_{10})$ aryl optionally substituted with one or more $(C_1-C_4)$ alkyl or halogen, (v) $C(=O)R_2i$, (vi) $C(=O)O(C_1-C_4)$ alkyl, (vii) $S(O)_2(C_1-C_8)$ alkyl, (viii) $S(O)_2NH(C_1-C_8)$ alkyl, (ix) $S(O)_2N$ $((C_1\text{-}C_8)\text{ alkyl})_2$, or (x) $C(=O)(C_1\text{-}C_8)$ alkyl optionally substituted with one or more $R_{22}$; or $R_{13}$ and $R_{14}$ together with the nitrogen atom to which they are attached form a 4- to 6-membered heterocyclyl ring comprising 1 to 3 heteroatoms selected from N, O, and S and optionally substituted with one or more substituents selected from $(C_1\text{-}C_4)$ alkyl, $(C_1\text{-}C_4)$ alkoxy, OH, $NH_2$, and $(=O)$;

$R_{15}$ is (i) H, (ii) 5- or 6-membered heterocyclyl comprising 1 to 3 heteroatoms selected from N, O, and S, or (iii) $(C_1\text{-}C_4)$ alkyl optionally substituted with one or more substituents selected from OH, 5- or 6-membered heterocyclyl comprising 1 to 3 heteroatoms selected from N, O, and S, and 5- or 6-membered heteroaryl comprising 1 to 3 heteroatoms selected from N, O, and S; or $R_{13}$ and $R_{15}$ together with the nitrogen atom to which they are attached form a 4- to 6-membered heterocyclyl ring comprising 1 to 3 heteroatoms selected from N, O, and S and optionally substituted with one or more substituents selected from $(C_1\text{-}C_4)$ alkyl, $(C_1\text{-}C_4)$ alkoxy, and OH, or form a 5- to 8-membered bicyclic heterocyclyl ring comprising 1 to 3 heteroatoms selected from N, O, and S and optionally substituted with one or more substituents selected from $(C_1\text{-}C_4)$ alkyl, $(C_1\text{-}C_4)$ alkoxy, and OH;

$R_{16}$ is $(C_1\text{-}C_4)$ alkyl, $(C_2\text{-}C_4)$ alkenyl, $(C_2\text{-}C_4)$ alkynyl, or 3- to 6-membered heterocyclyl comprising 1 to 3 heteroatoms selected from N, O, and S, wherein the alkyl, alkenyl, and alkynyl are optionally substituted with one or more substituents selected from $(C_1\text{-}C_4)$ alkoxy, O-phenyl, halogen, CN, $NH_2$, $(C_1\text{-}C_4)$ alkylamino, di-$(C_1\text{-}C_4)$ alkylamino, and $OS(O)_2(C_1\text{-}C_4)$ alkyl, and wherein the heterocyclyl is optionally substituted with one or more $R_{23}$;

each $R_{18}$ is independently H or $(C_1\text{-}C_4)$ alkyl;

$R_{19}$ is H or $(C_1\text{-}C_4)$ alkyl;

$R_{20}$ is H or $(CH_2)_n(C_6\text{-}C_{10})$ aryl optionally substituted with one or more $(C_1\text{-}C_4)$ alkyl;

$R_{21}$ is $(C_3\text{-}C_7)$ cycloalkyl, 5- or 6-membered heterocyclyl comprising 1 to 3 heteroatoms selected from N, O, and S, $(C_6\text{-}C_{10})$ aryl, or 5- or 6-membered heteroaryl comprising 1 to 3 heteroatoms selected from N, O, and S, wherein the aryl, heteroaryl, cycloalkyl, and heterocyclyl are optionally substituted with one or more substituents selected from $(C_1\text{-}C_4)$ alkyl, $(C_1\text{-}C_4)$ alkoxy, $(C_1\text{-}C_4)$ haloalkyl, $(C_1\text{-}C_4)$ haloalkoxy, OH, and halogen;

each $R_{22}$ is independently (i) $(C_1\text{-}C_4)$ alkoxy, (ii) OH, (iii) $NH_2$, (iv) $(C_1\text{-}C_4)$ alkylamino, (v) di-$(C_1\text{-}C_4)$ alkylamino, or (vi) 5- or 6-membered heterocyclyl comprising 1 to 3 heteroatoms selected from N, O, and S and optionally substituted with one or more substituents selected from (a) $(C_1\text{-}C_4)$ alkyl, (b) $(CH_2)_x(C_6\text{-}C_{10})$ aryl, and (c) $C(=O)(C_6\text{-}C_{10})$aryl optionally substituted with one or more $(C_1\text{-}C_4)$ alkyl;

each $R_{23}$ is independently $(C_1\text{-}C_4)$ alkyl or $C(=O)(C_1\text{-}C_4)$ alkyl, or two $R_{23}$ together with the atoms to which they are attached form a 5- or 6-membered heterocyclyl ring comprising 1 to 3 heteroatoms selected from N, O, and S;

$R_{24}$ is $(C_1\text{-}C_4)$ alkyl optionally substituted with one or more substituents selected from $(C_1\text{-}C_4)$ alkoxy and 5- or 6-membered heterocyclyl comprising 1 to 3 heteroatoms selected from N, O, and S;

$R_{25}$ is $(C_1\text{-}C_4)$ alkyl optionally substituted with one or more $(C_1\text{-}C_4)$ alkoxy, $(C(R_{26})_2)_x(C_6\text{-}C_{10})$ aryl, $(C(R_{26})_2)_x$-heteroaryl, wherein the heteroaryl comprises one or two 5- or 6-membered rings and 1 to 3 heteroatoms selected from N, O, and S, or $(C(R_{26})_2)_x$-heterocyclyl, wherein the heterocyclyl comprises one or two 4- to 6-membered rings and 1 to 3 heteroatoms selected from N, O, and S, wherein the alkyl, alkoxy, aryl, heteroaryl, and heterocyclyl are optionally substituted with one or more substituents selected from $(C_1\text{-}C_4)$ alkyl, $(C_1\text{-}C_4)$ alkoxy, $(C_1\text{-}C_4)$ haloalkyl, $(C_1\text{-}C_4)$ haloalkoxy, cyano, halogen, OH, $NH_2$, $(C_6\text{-}C_{10})$ aryl, and 5- or 6-membered heteroaryl comprising 1 to 3 heteroatoms selected from N, O, and S;

each $R_{26}$ is independently H or $(C_1\text{-}C_4)$ alkyl, or two $R_{26}$ together with the atom to which they are attached form a $(C_3\text{-}C_6)$ cycloalkyl ring or 3- or 6-membered heterocyclyl ring comprising 1 to 3 heteroatoms selected from N, O, and S;

each n and each p is independently 0, 1, or 2;

each r is independently 0, 1, 2, or 3; and each q and each x is independently 0, 1, 2, or 3.

2. The compound of claim 1, wherein A is phenyl, thiophenyl, or pyridinyl optionally substituted with one or more $R_4$.

3. The compound of claim 1, wherein A is phenyl, thiophenyl, or pyridinyl substituted with one to two $R_4$.

4. The compound of claim 1, wherein A is phenyl substituted with one to two $R_4$.

5. The compound of claim 1, wherein $R_2$ is H.

6. The compound of claim 1, wherein $R_3$ is H, $NH_2$, $NHCH_3$, or 4-methylpiperazine.

7. The compound of claim 1, wherein $R_3$ is H.

8. The compound of claim 1, wherein at least one $R_4$ is $C(=O)NHR_{25}$, $NHC(=O)R_{25}$, $(CH_2)C(=O)NHR_{25}$, or $(CH_2)NHC(=O)R_{25}$.

9. The compound of claim 1, wherein $R_1$ is 4- to 7-membered heterocyclyl comprising 1 to 3 heteroatoms selected from N, O, and S optionally substituted with one to three $R_5$.

10. The compound of claim 1, wherein $R_1$ is piperidinyl, tetrahydrofuranyl, tetrahydropyranyl, pyrrolidinyl, or 1,4-dioxanyl optionally substituted with one to three $R_5$.

11. The compound of claim 1, wherein $R_1$ is tetrahydropyranyl optionally substituted with one to three $R_5$.

12. The compound of claim 1, wherein q is 0 or 1.

13. The compound of claim 1, wherein the compound is of Formula (Ia'), (Ib'), or (Ic'):

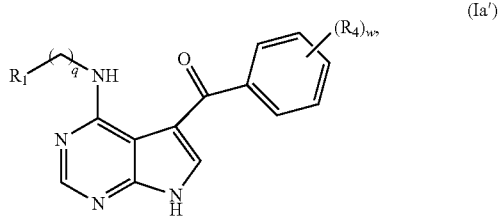

(Ia')

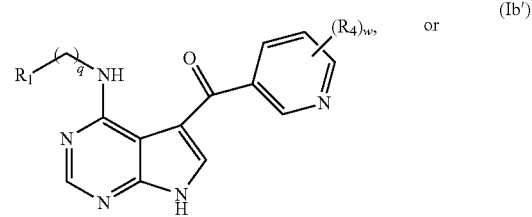

(Ib') or

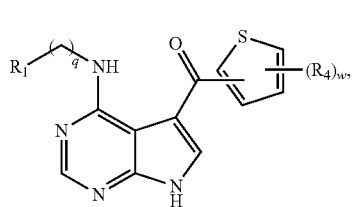
(Ic′)

or a pharmaceutically acceptable salt, solvate, stereoisomer, or tautomer thereof, wherein w is 1 or 2.

14. The compound of claim 1, wherein the compound is of Formula (Id′), (Ie′), or (If′):

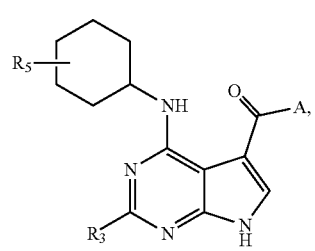
(Id′)

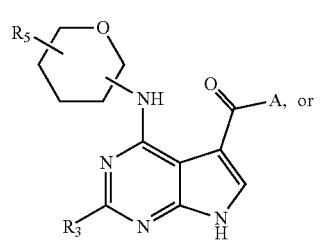
(Ie′)

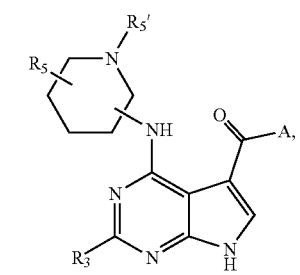
(If′)

or a pharmaceutically acceptable salt, solvate, stereoisomer, or tautomer thereof, wherein $R_5'$ is H or $R_5$.

15. The compound of claim 1, wherein the compound is of any of Formulae (Ig1)-(Ig12), (Ih1)-(Ih12), and (Ii1)-(Ii12):

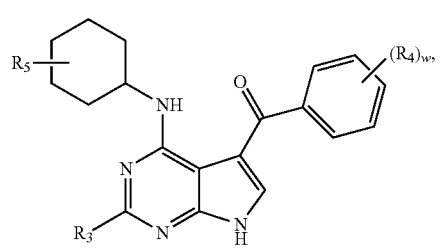
(Ig1)

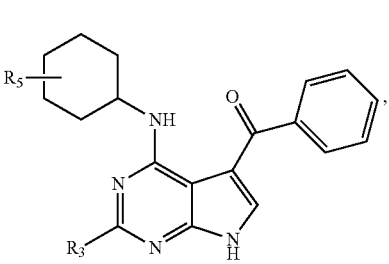
(Ig2)

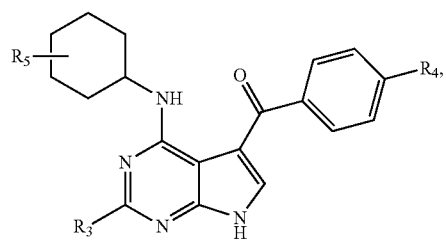
(Ig3)

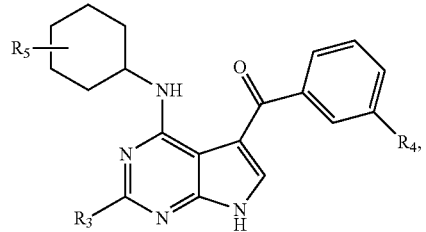
(Ig4)

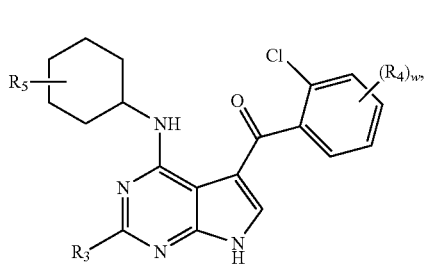
(Ig5)

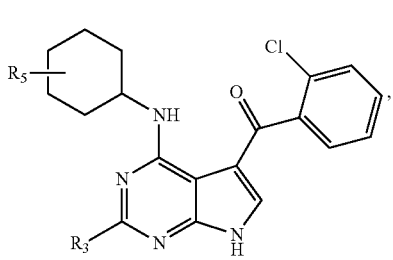
(Ig6)

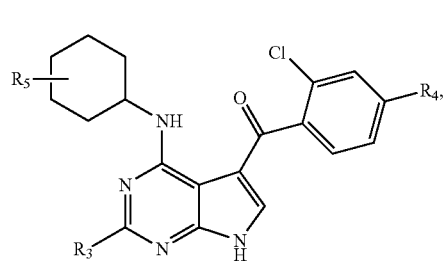
(Ig7)

477
-continued
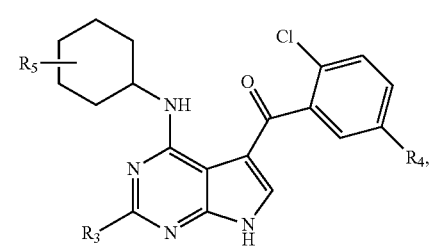
(Ig8)
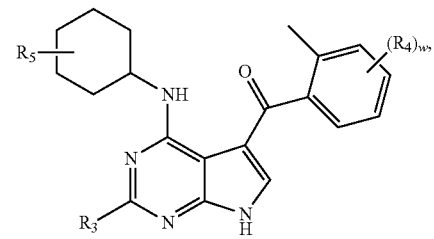
(Ig9)
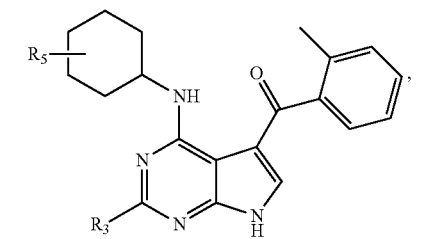
(Ig10)
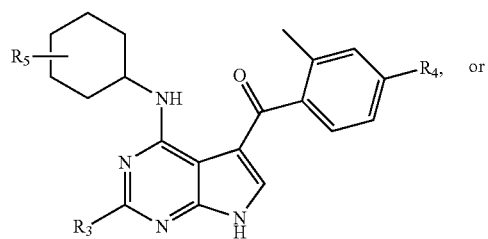
(Ig11)
or
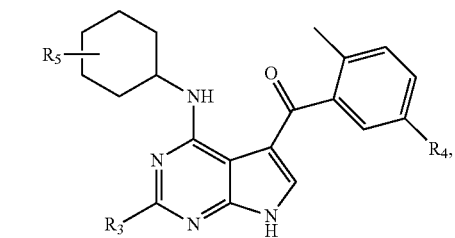
(Ig12)
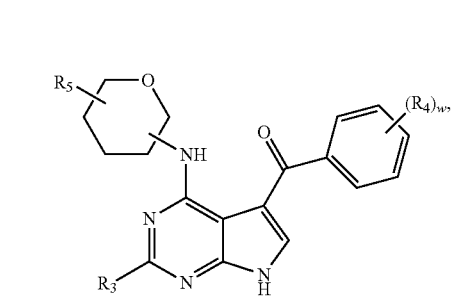
(Ih1)
478
-continued
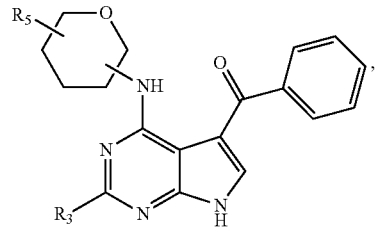
(Ih2)
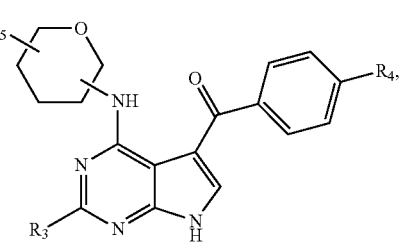
(Ih3)
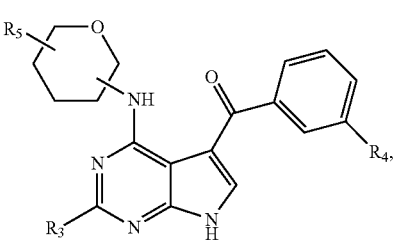
(Ih4)
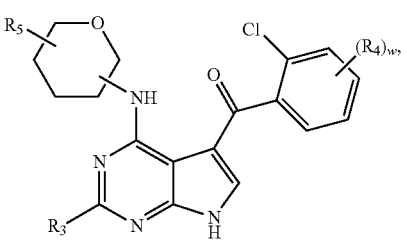
(Ih5)
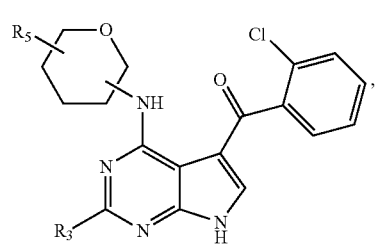
(Ih6)
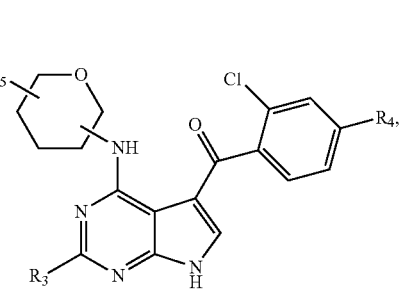
(Ih7)

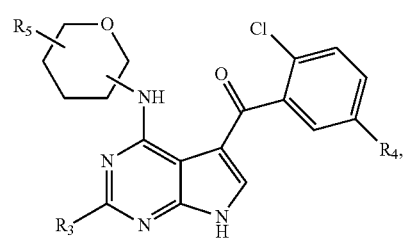
(Ih8)
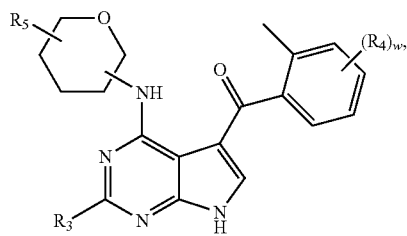
(Ih9)
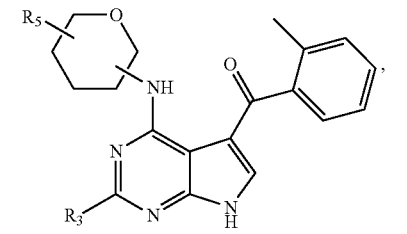
(Ih10)
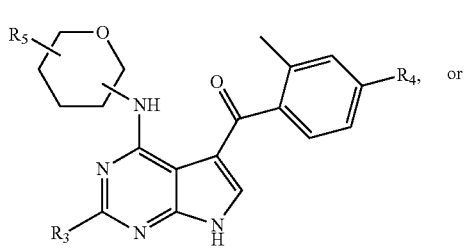
(Ih11) or
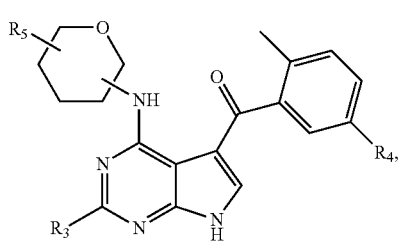
(Ih12)
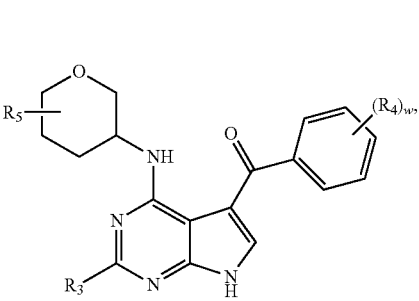
(Ii1)
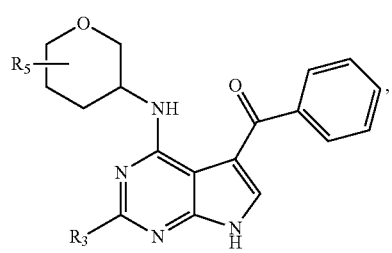
(Ii2)
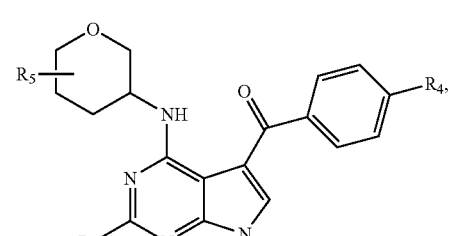
(Ii3)
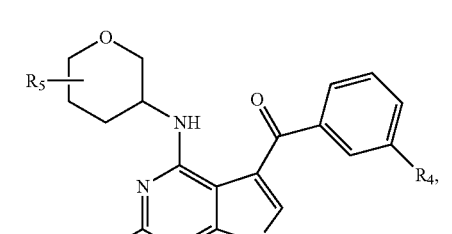
(Ii4)
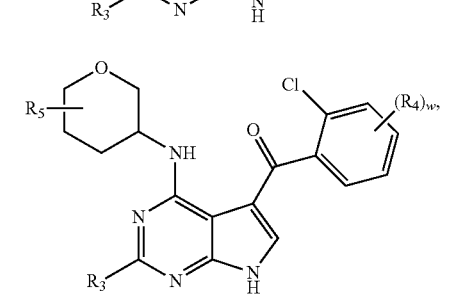
(Ii5)
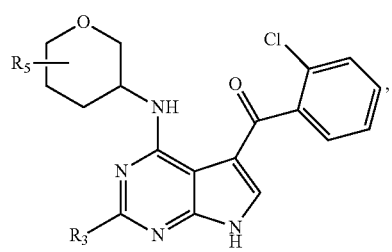
(Ii6)
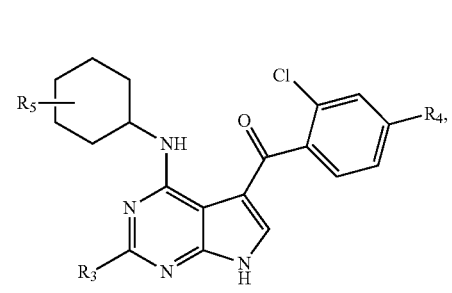
(Ii7)

-continued (Ii8)
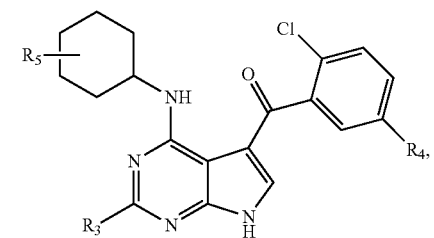

(Ii9)
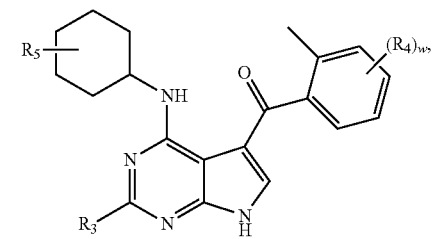

(Ii10)
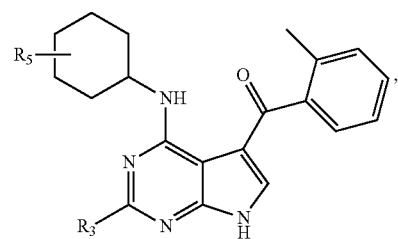

(Ii11)
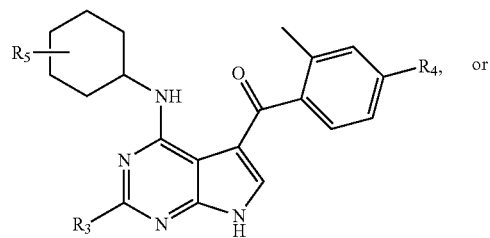 or (Ii12)
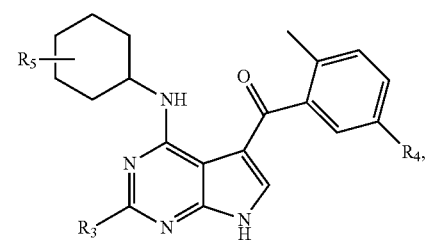

or a pharmaceutically acceptable salt, solvate, stereoisomer, or tautomer thereof, wherein w is 1 or 2.

16. A pharmaceutical composition comprising a compound of claim 1, or a pharmaceutically acceptable salt, solvate, stereoisomer, or tautomer thereof, and a pharmaceutically acceptable diluent, excipient or carrier.

17. The compound of claim 1, wherein at least one $R_4$ is NHC(=O)$R_{25}$.

18. The compound of claim 1, selected from the group consisting of:

I-271
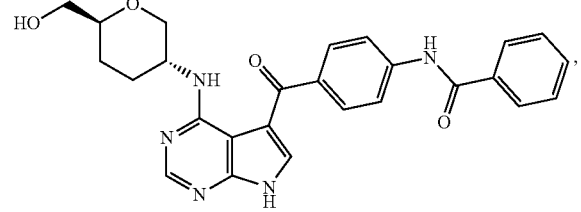

I-272
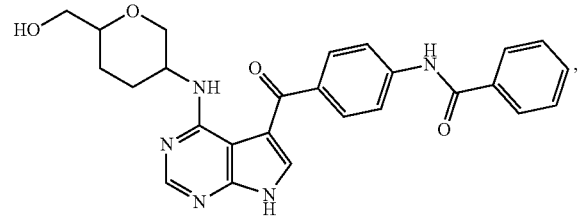

I-273
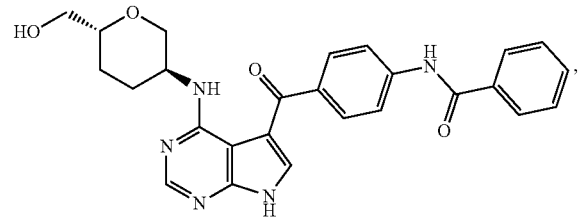

I-274
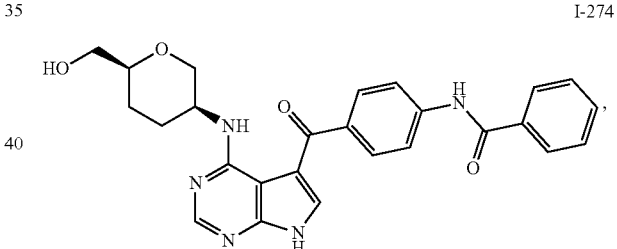

I-275
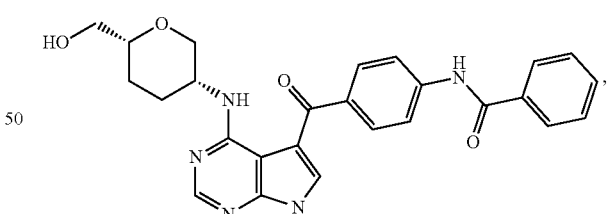

I-276
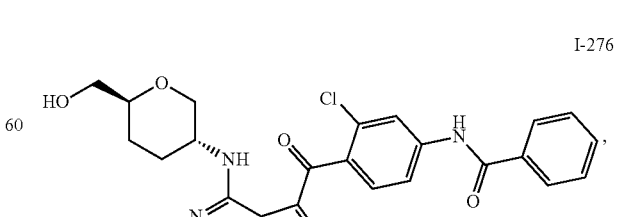

I-277
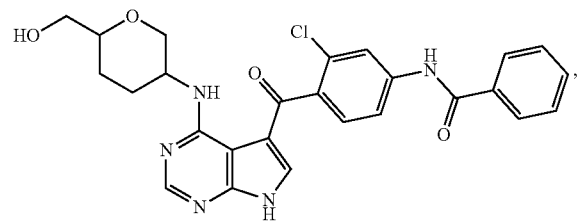
I-278
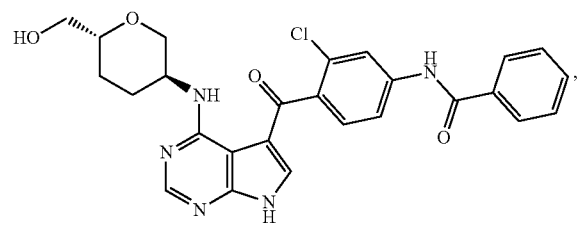
I-279
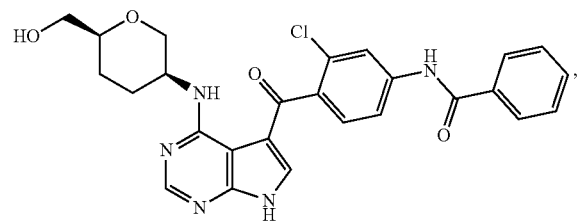
I-280
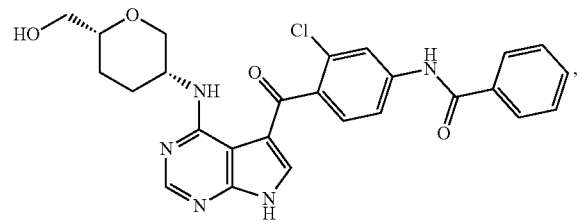
I-281
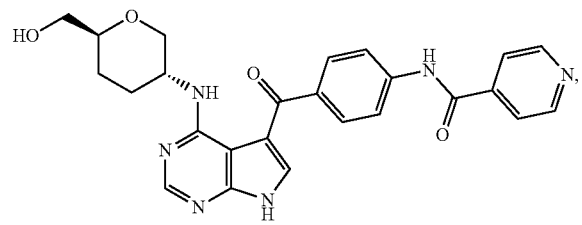
I-282
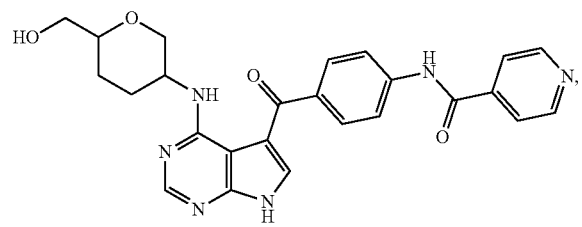
I-283
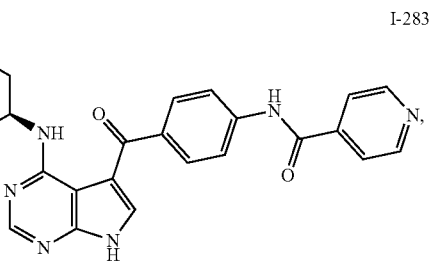
I-284
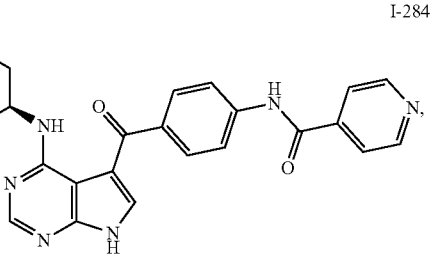
I-285
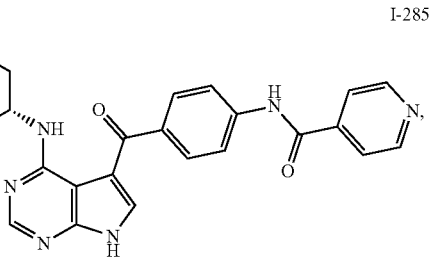
I-286
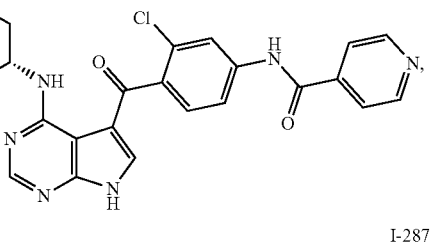
I-287
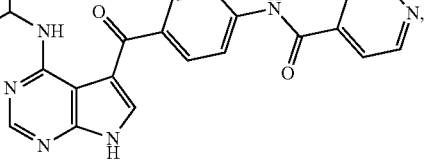
I-288
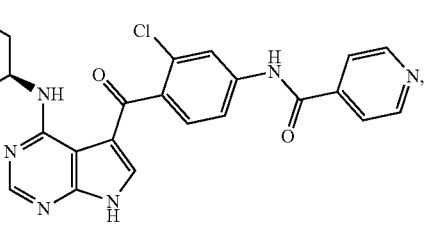

I-289

I-290

I-291

I-292

I-293

I-294

I-295

I-296

I-297

I-298

I-299

I-300

-continued

I-301

I-302

I-303

I-304

I-305

I-306

I-307

I-308

I-309

I-310

I-601

I-602

I-603
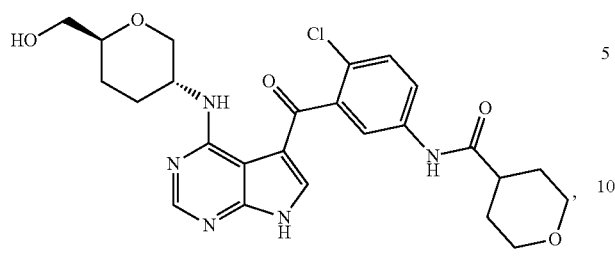
I-604
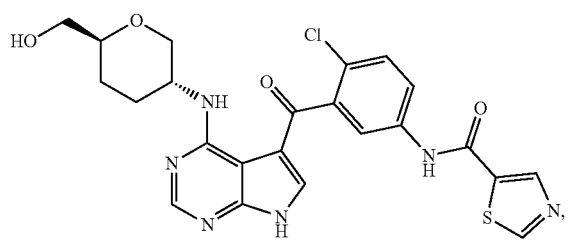
I-605
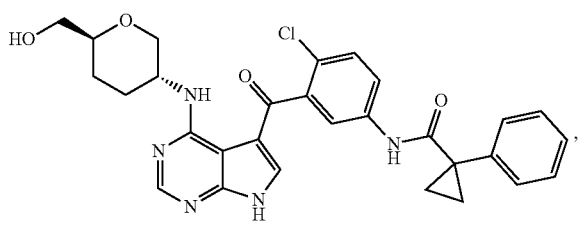
I-606
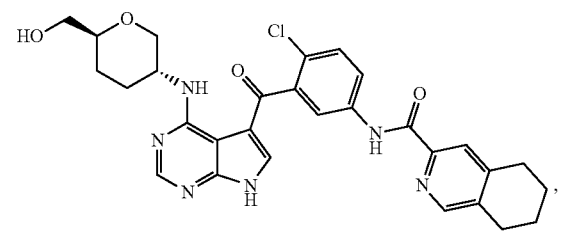 [SMILES: O=C(Nc1ccc(Cl)c(C(=O)c2c[nH]c3ncnc(N[C@@H]4CC[C@@H](CO)OC4)c23)c1)c1cc2c(cn1)CCCC2]
I-607
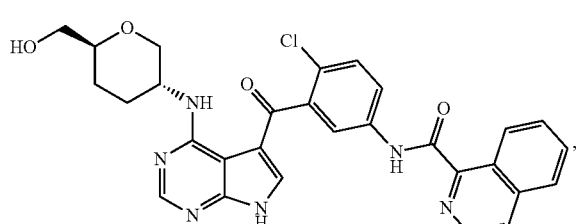
I-639
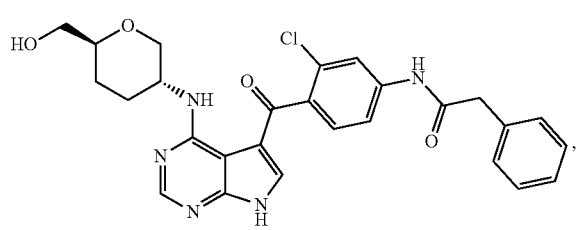
I-640
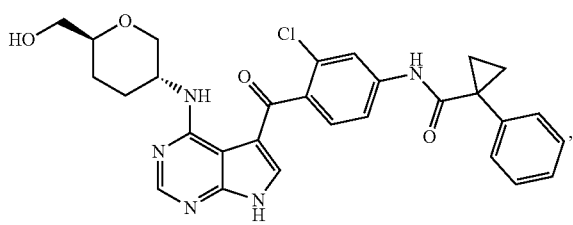
I-641
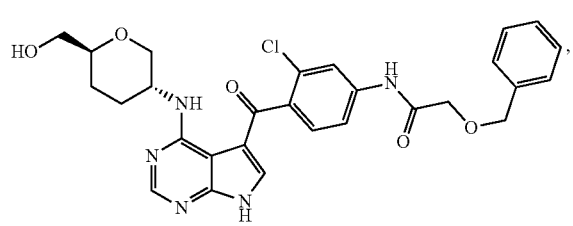
I-642
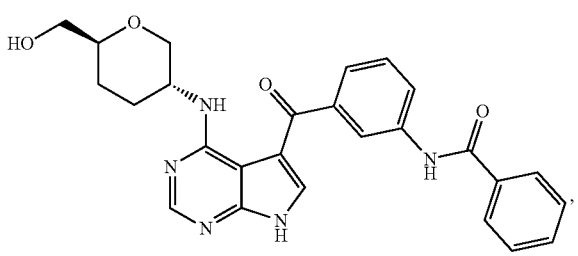
I-643
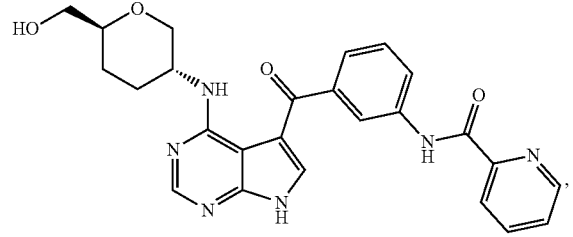
I-644
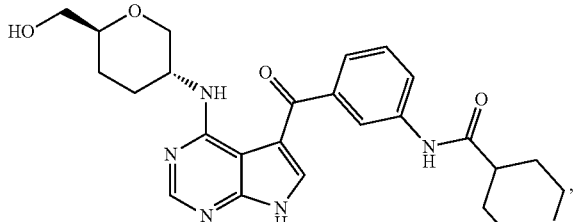
I-645
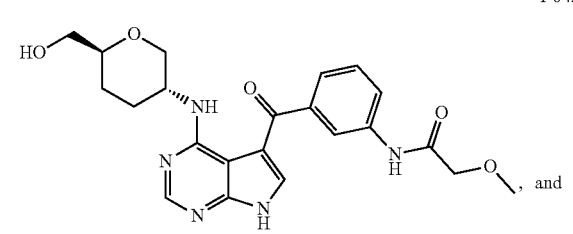
, and

I-652

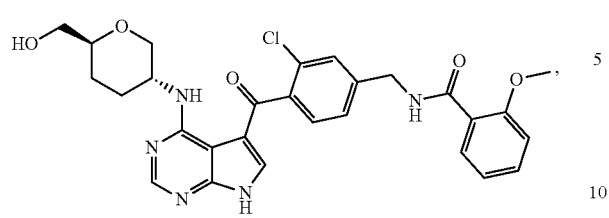

or a pharmaceutically acceptable salt, solvate, stereoisomer, or tautomer thereof.

19. The compound of claim 1, wherein the compound is:

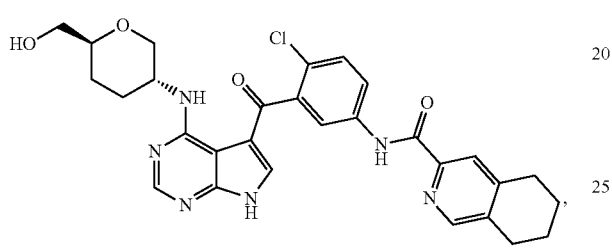

or a pharmaceutically acceptable salt, solvate, stereoisomer, or tautomer thereof.

20. A pharmaceutical composition comprising a compound of claim 18, or a pharmaceutically acceptable salt, solvate, stereoisomer, or tautomer thereof, and a pharmaceutically acceptable diluent, excipient or carrier.

21. A pharmaceutical composition comprising the compound of claim 19, or a pharmaceutically acceptable salt, solvate, stereoisomer, or tautomer thereof, and a pharmaceutically acceptable diluent, excipient or carrier.

22. The compound of claim 1, selected from the group consisting of:

I-1

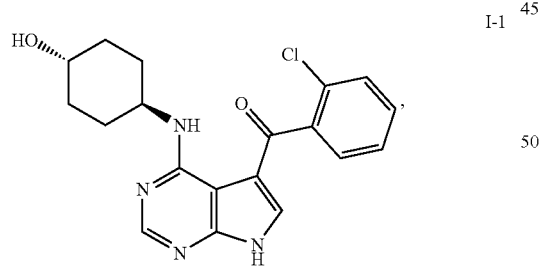

I-2

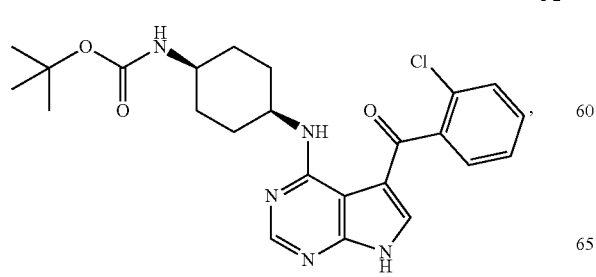

I-3

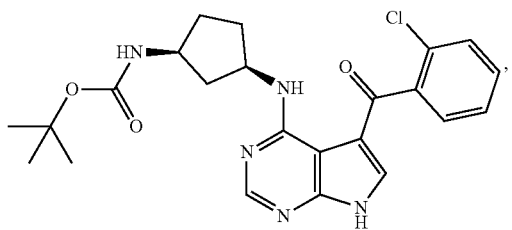

I-4

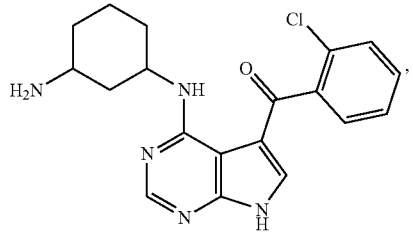

I-5

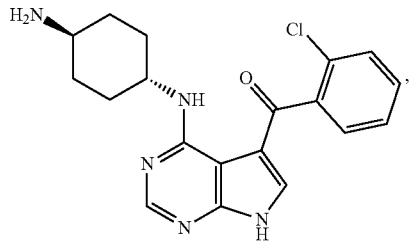

I-6

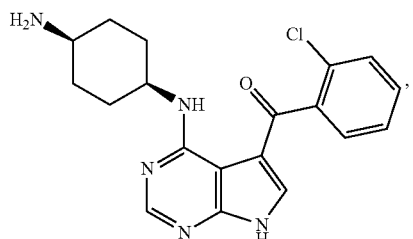

I-7

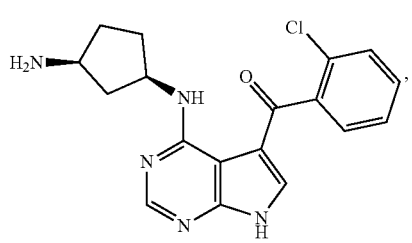

I-8

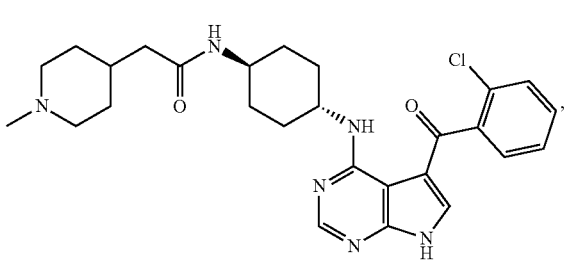

493
-continued
I-9
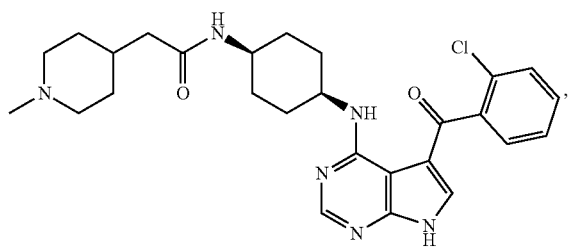
I-10
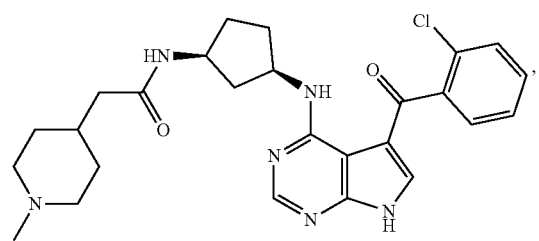
I-11
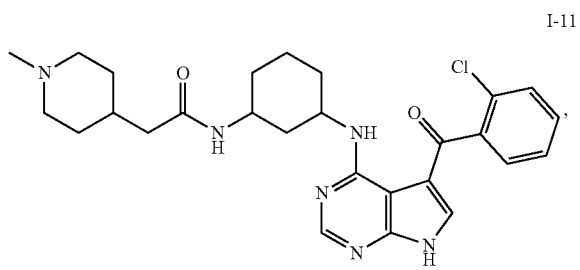
I-12
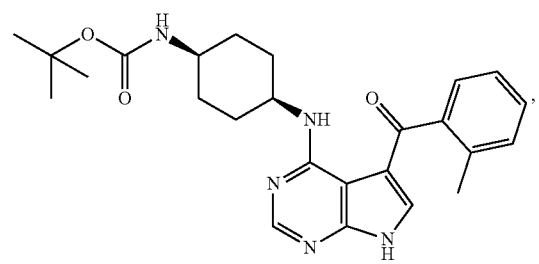
I-13
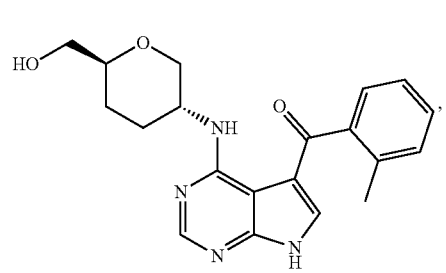
I-14
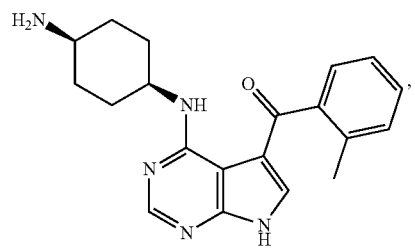
494
-continued
I-15
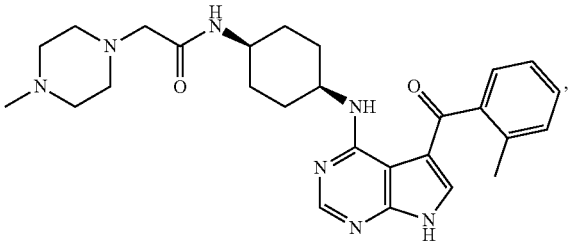
I-16
I-17
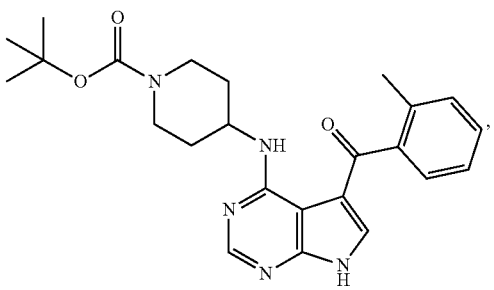
I-18
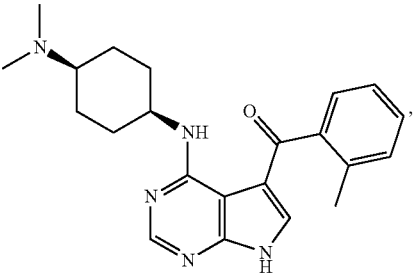
I-19
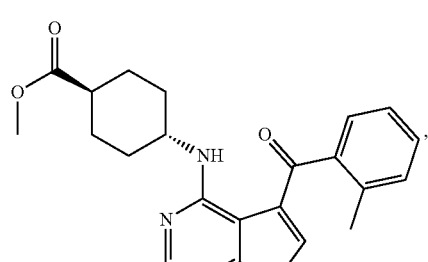
I-20

| | |
|---|---|
| I-21 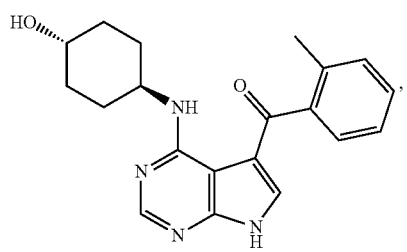 | I-27 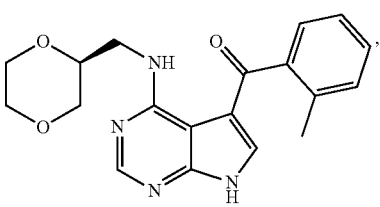 |
| I-22 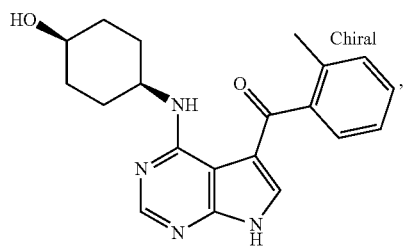 Chiral | I-28 |
| I-23 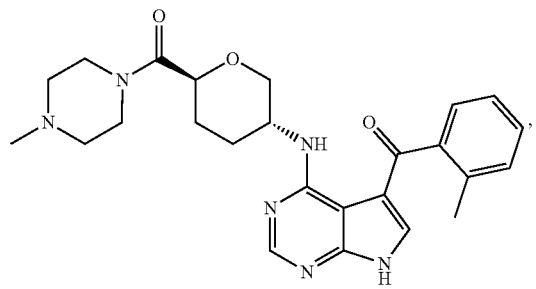 | I-29 |
| I-24 | I-30 |
| I-25 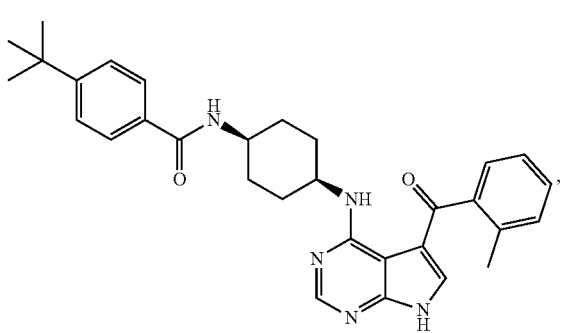 | I-31 |
| | I-32 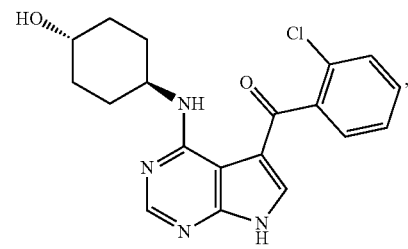 |

I-33
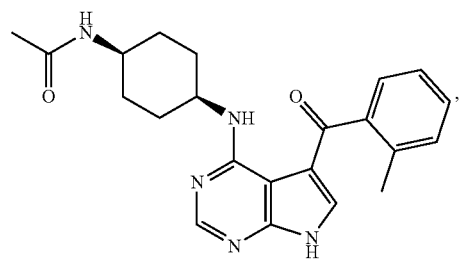
I-34
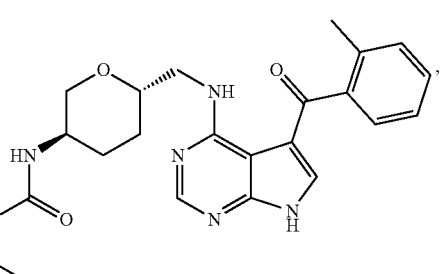
I-35
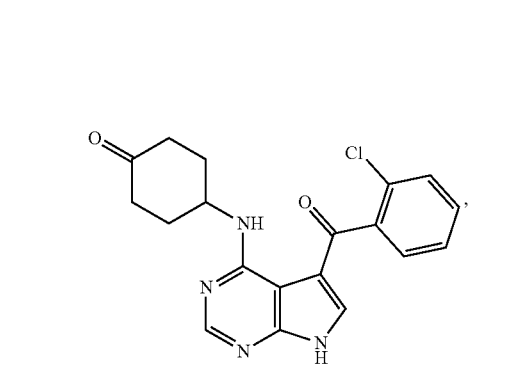
I-36
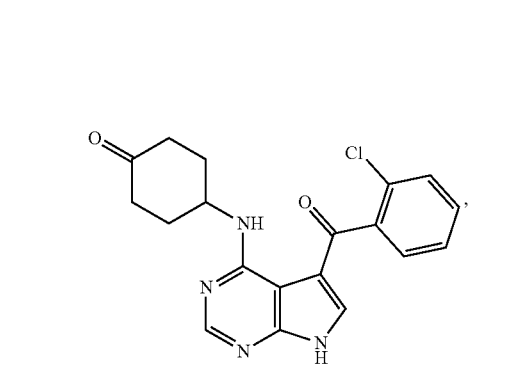
I-37
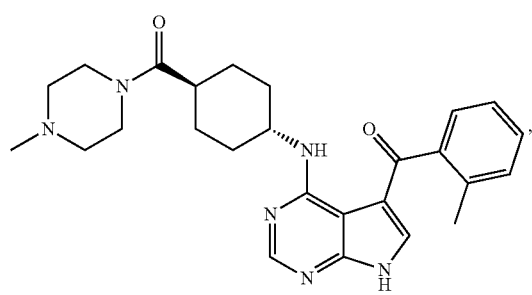
I-38
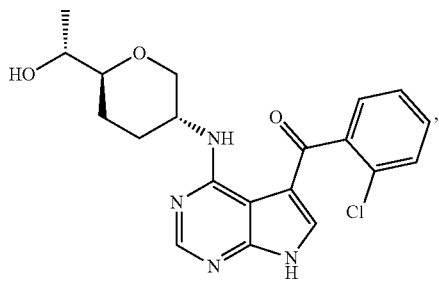
I-39
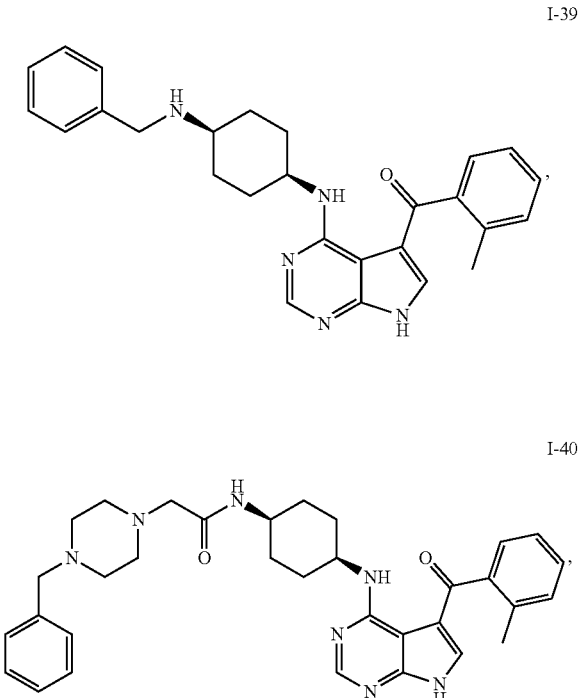
I-40
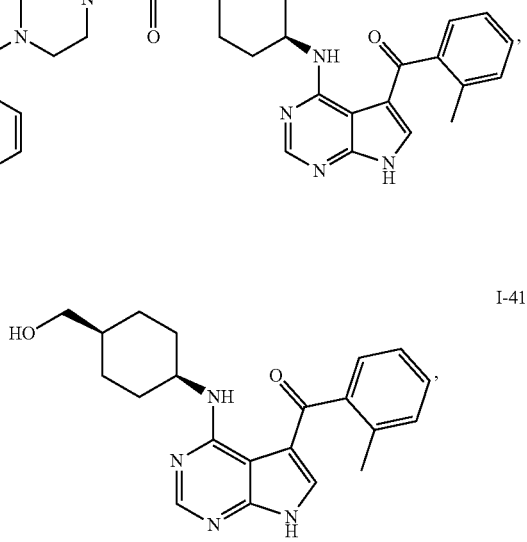
I-41
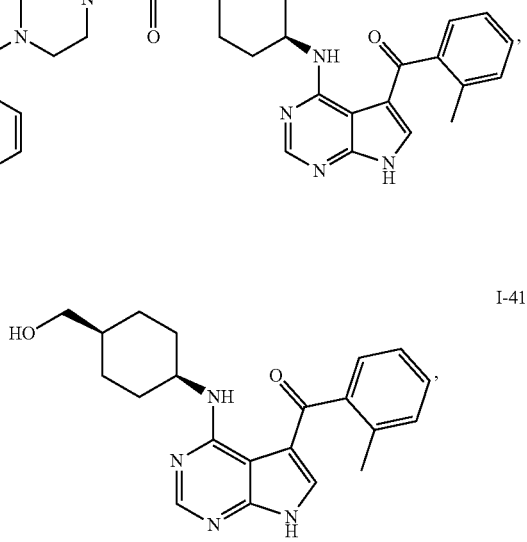
I-42
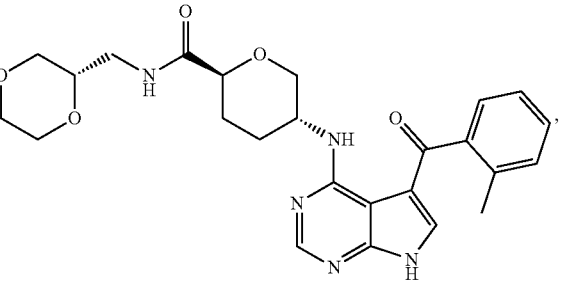

I-43
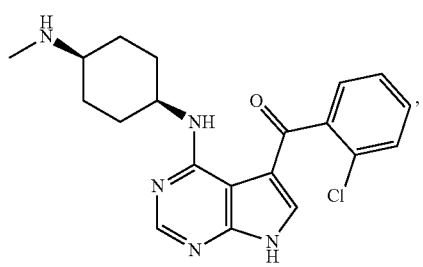
I-44
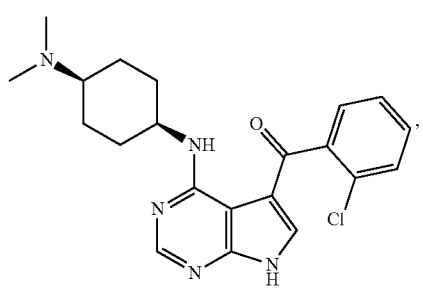
I-45
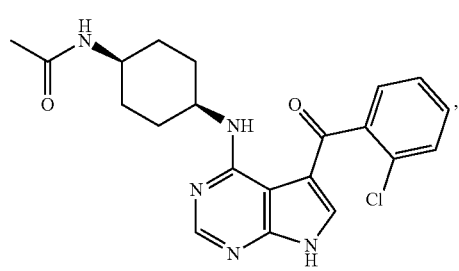
I-46
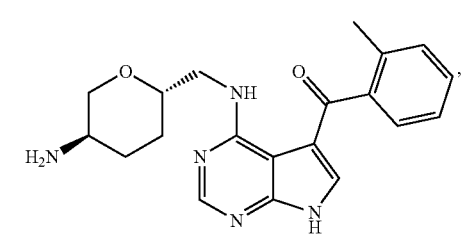
I-47
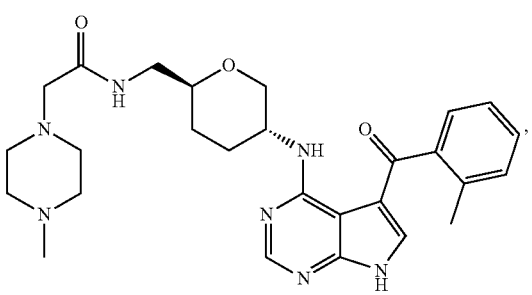
I-48
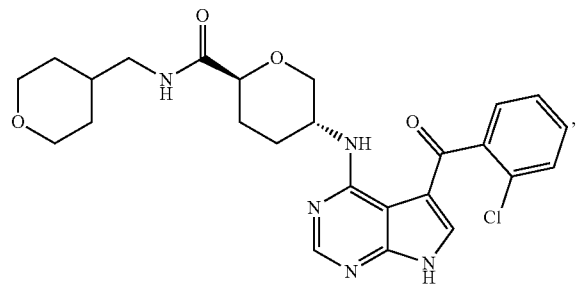
I-49
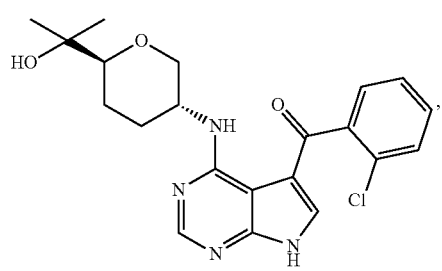
I-50
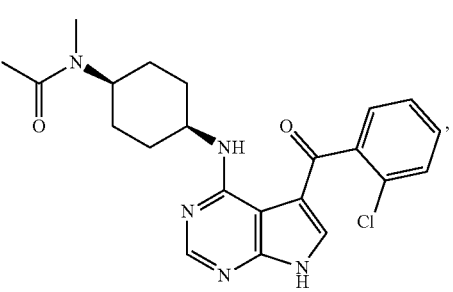
I-51
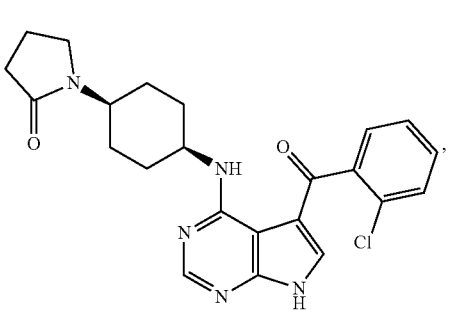
I-52
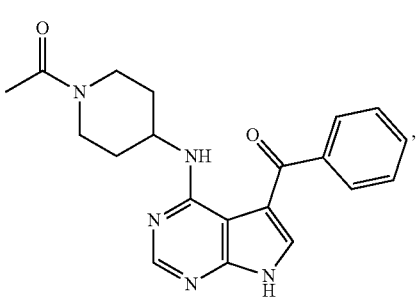

-continued
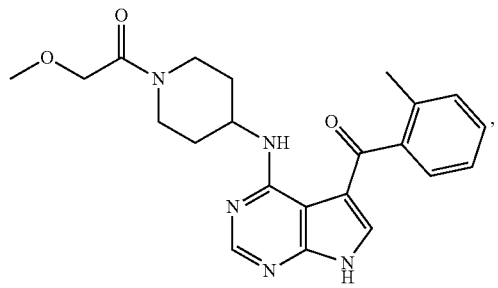
I-53
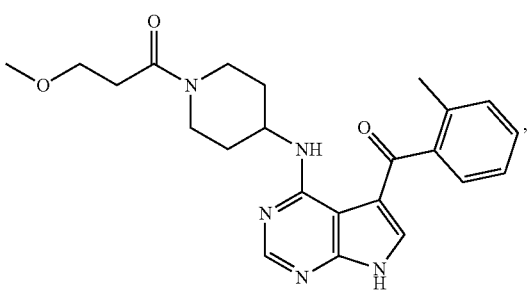
I-54
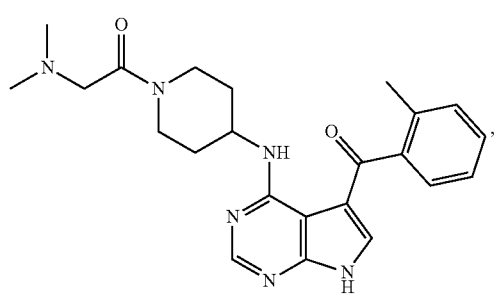
I-55
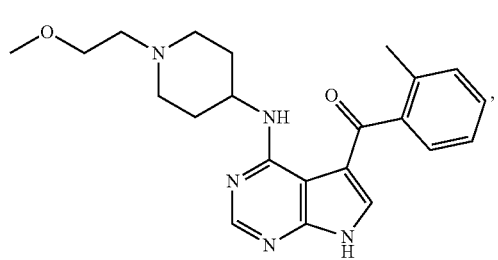
I-56
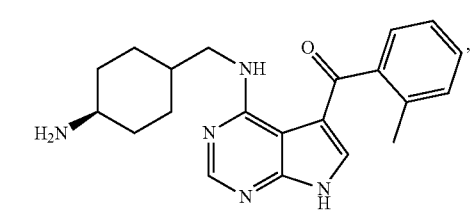
I-57
-continued
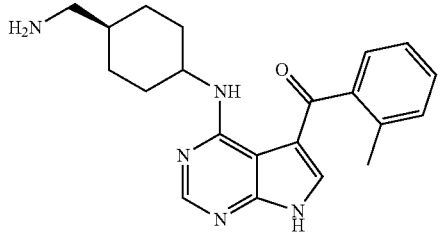
I-58
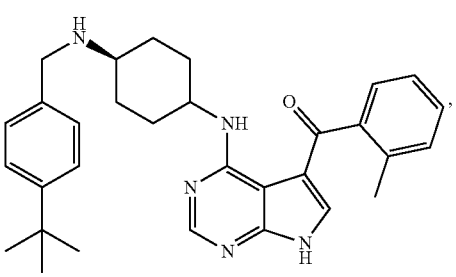
I-59
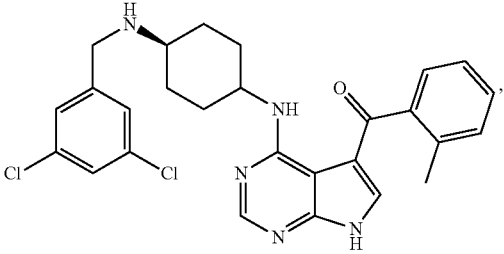
I-60
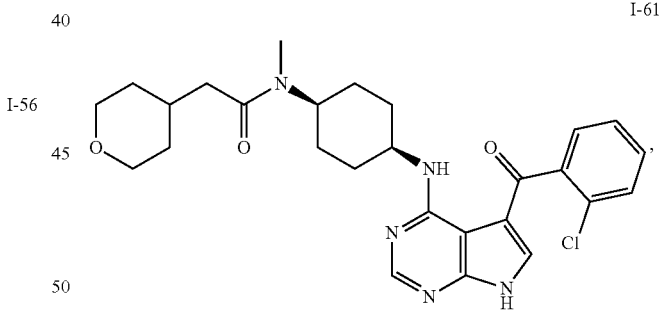
I-61
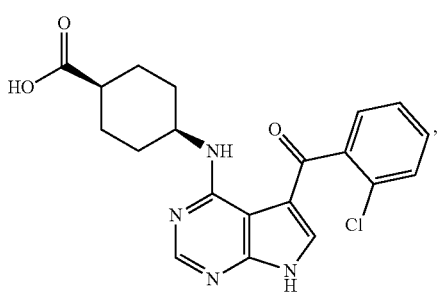
I-62

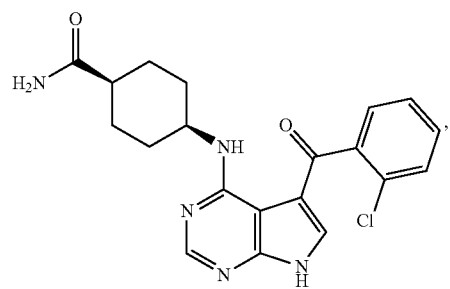

I-73
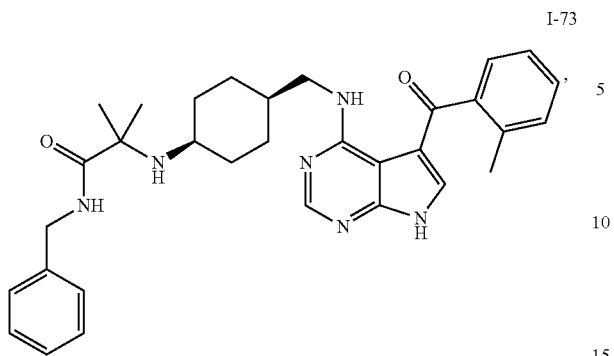
I-78
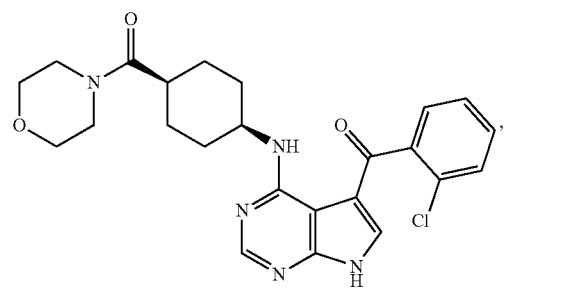
I-74
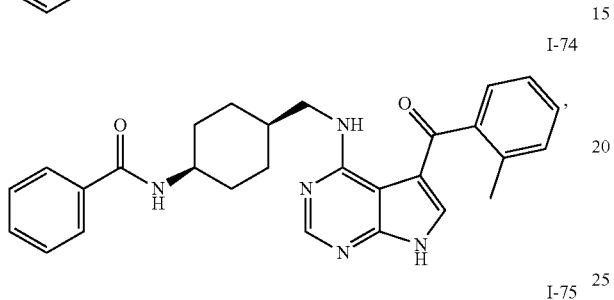
I-79
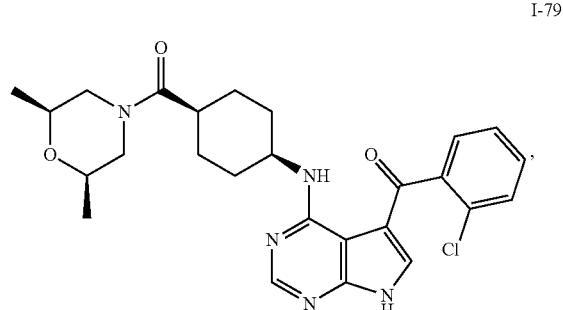
I-75
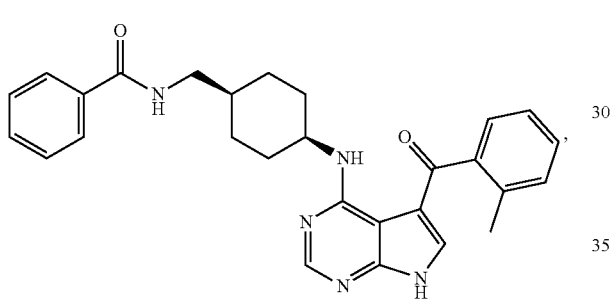
I-80
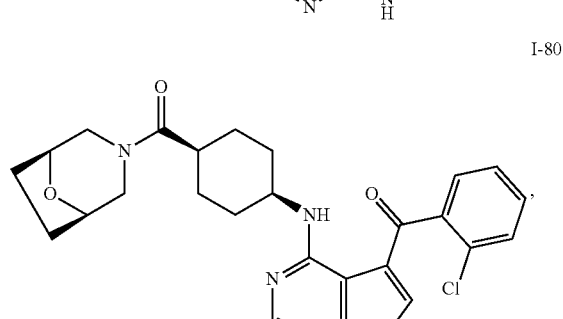
I-76
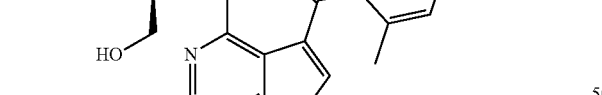
I-81
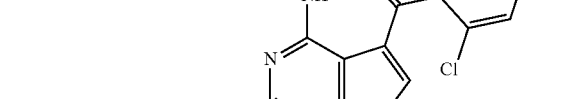
I-77
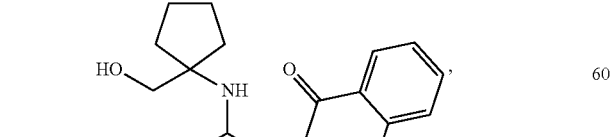
I-82
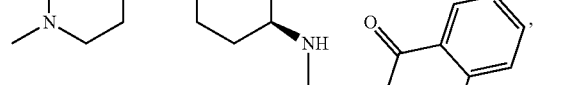

507
-continued
I-83
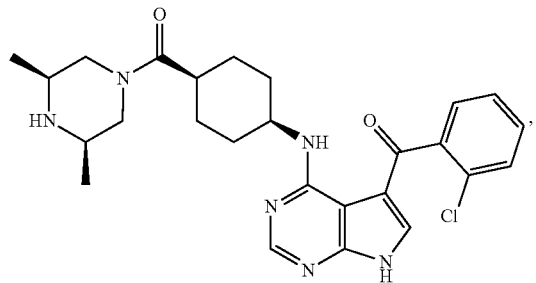
I-84
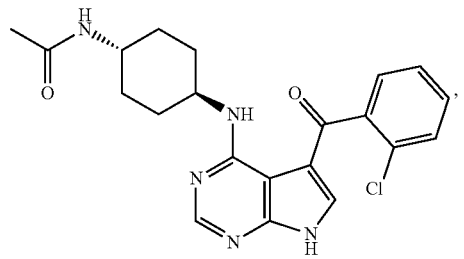
I-85
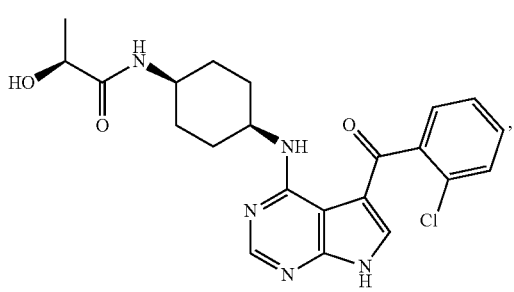
I-86
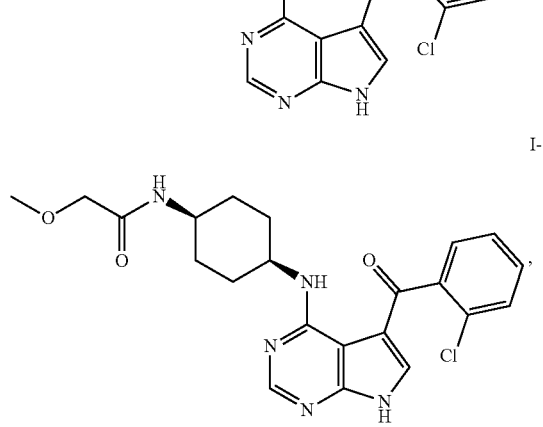
I-87
508
-continued
I-88
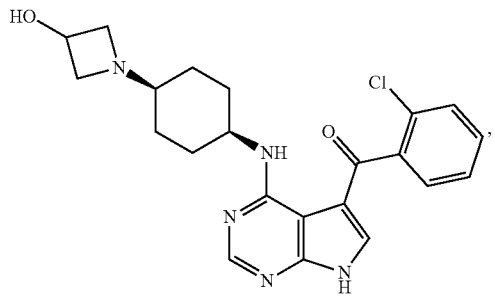
I-89
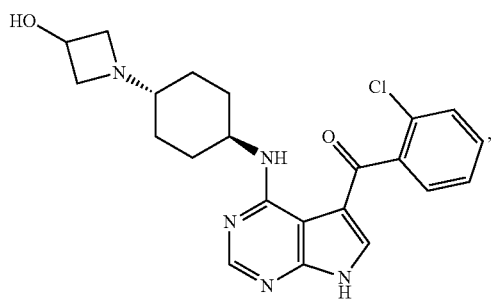
I-90
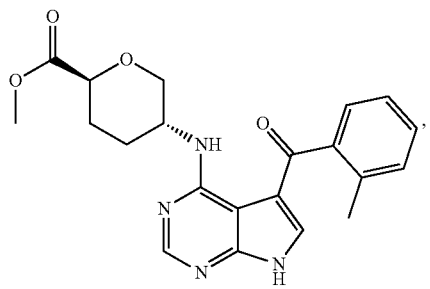
I-91
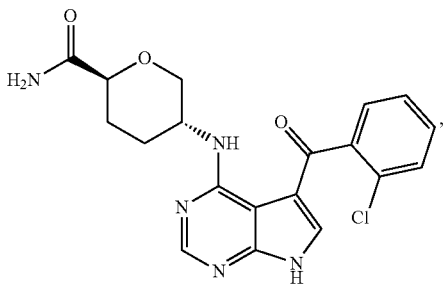
I-92

I-93
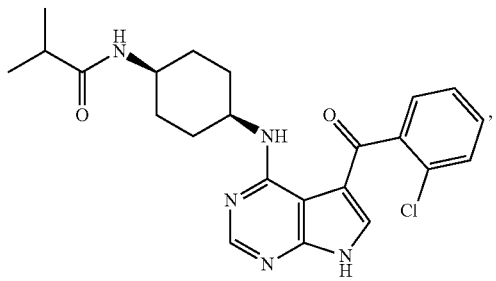
I-94
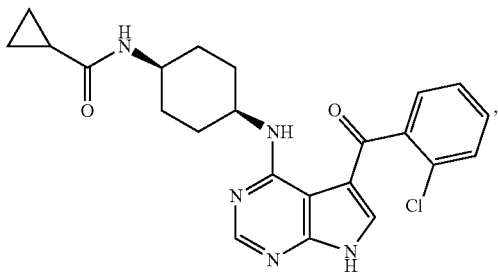
I-95
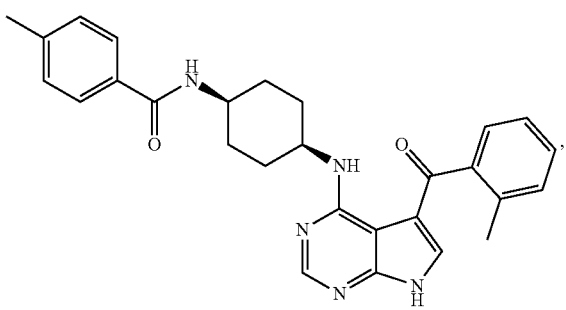
I-96
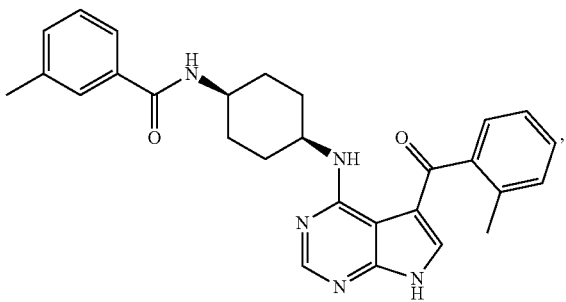
I-97
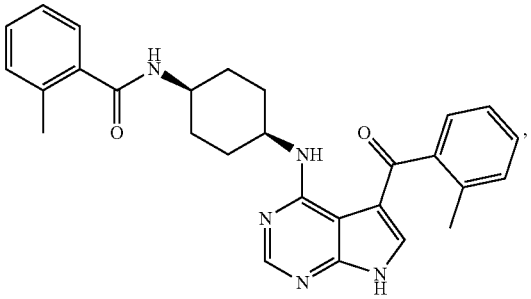
I-98
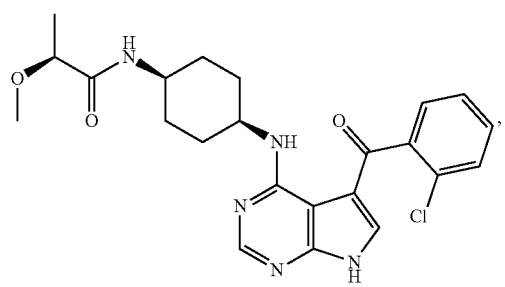
I-99
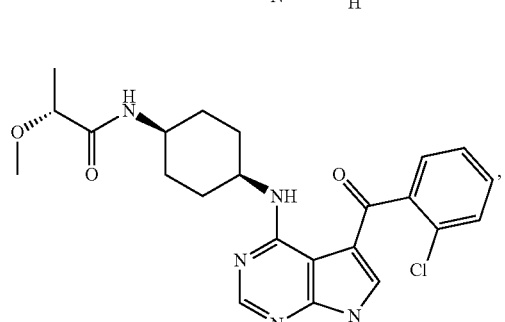
I-100
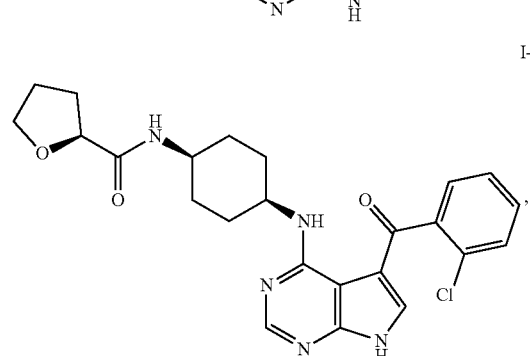
I-101
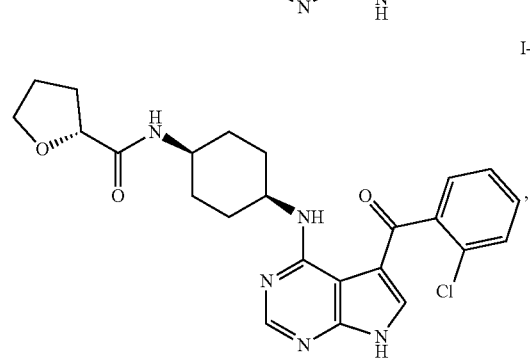
I-102
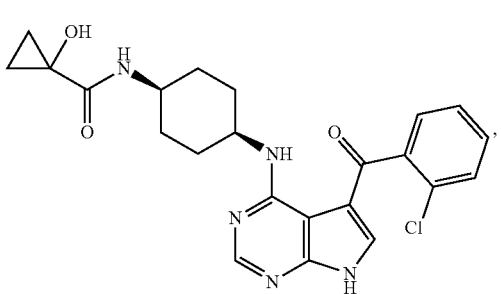

-continued
I-103
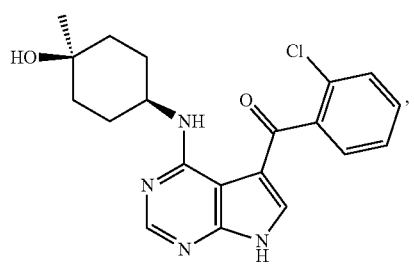
I-104
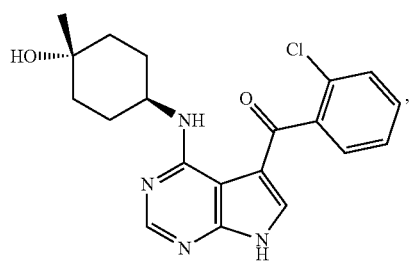
I-105
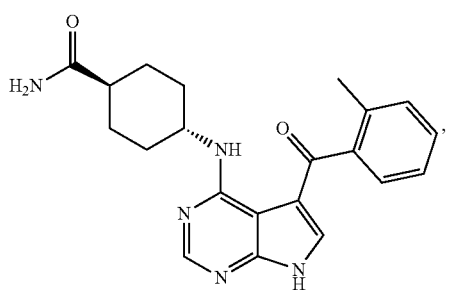
I-106
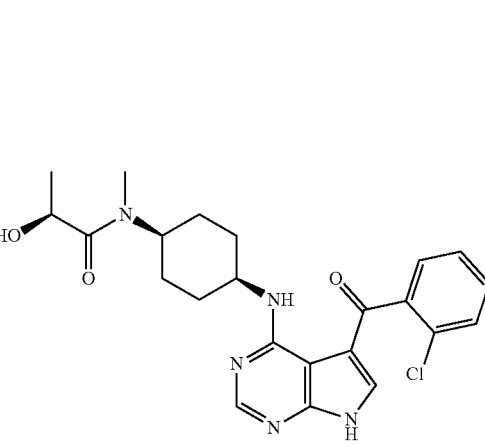
I-107
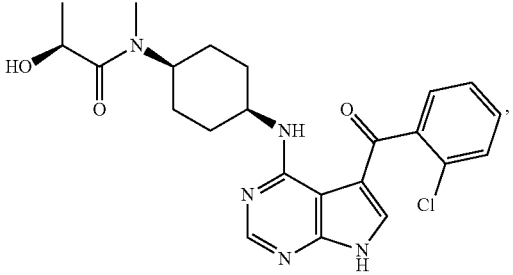
-continued
I-108
I-109
I-110
I-111
I-112

-continued
I-113
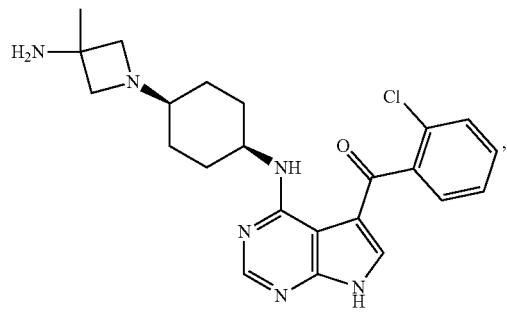
I-114
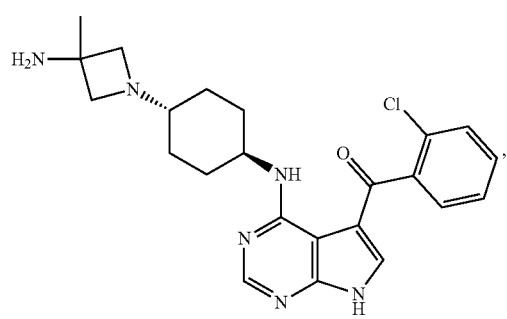
I-115
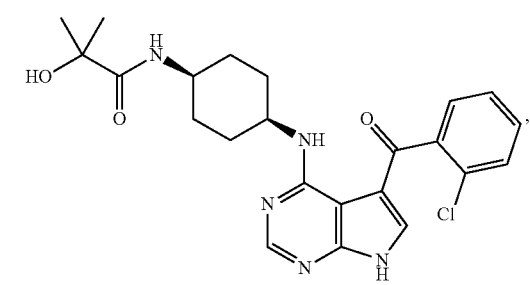
I-116
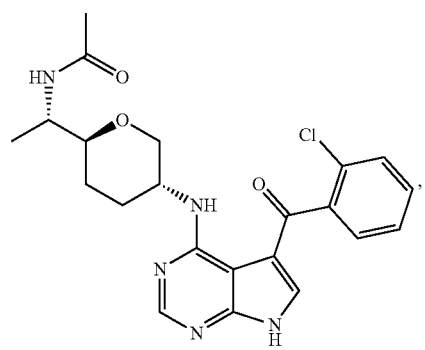
-continued
I-117
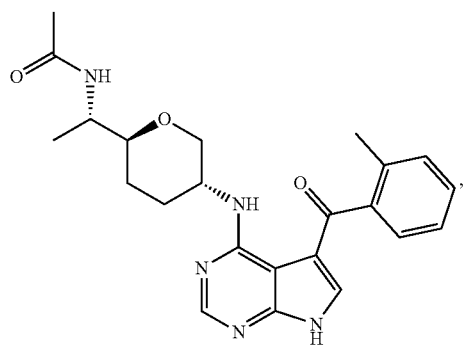
I-118
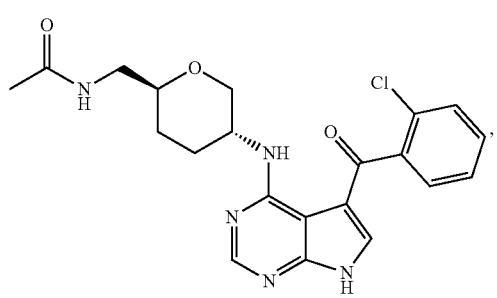
I-119
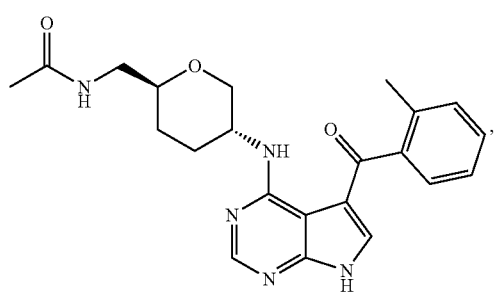
I-128
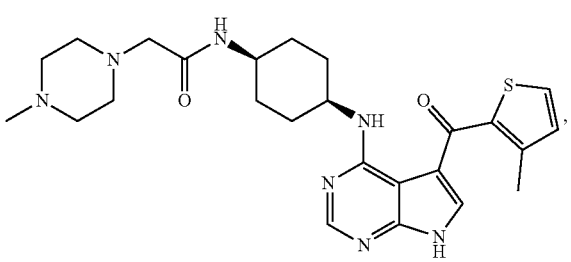
I-129
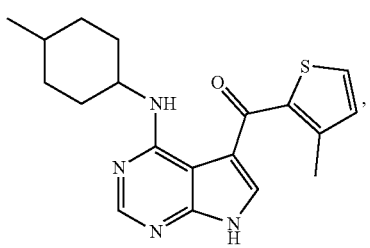

I-132
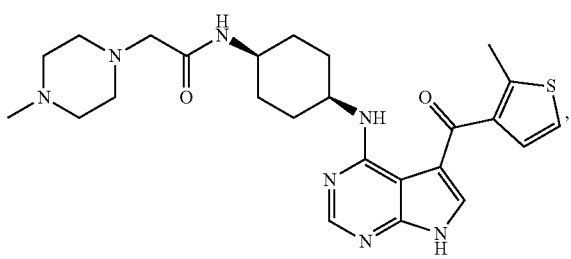
I-133
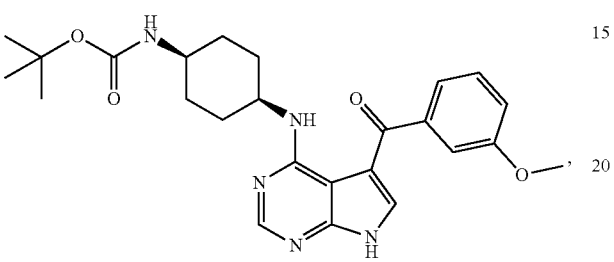
I-134
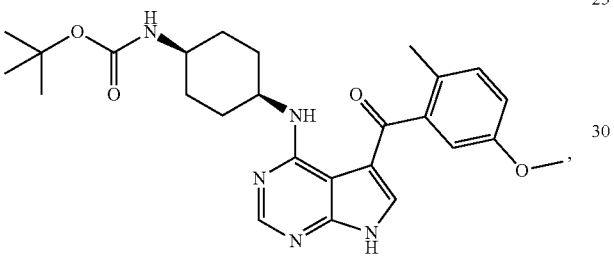
I-135
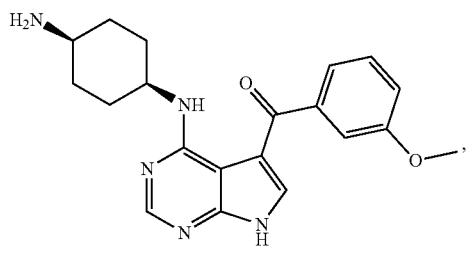
I-136
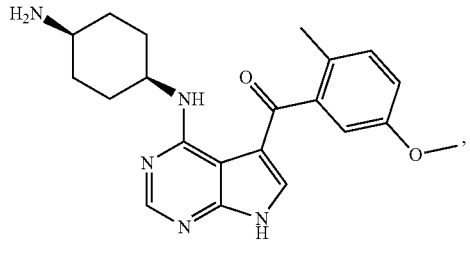
I-137
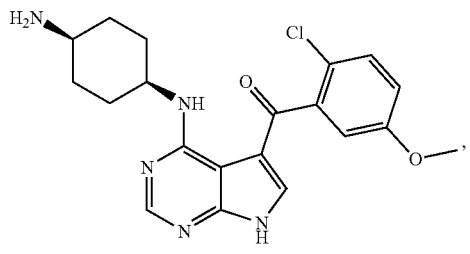
I-138
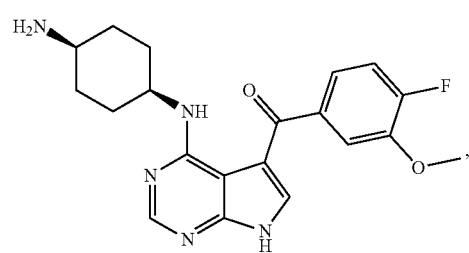
I-143
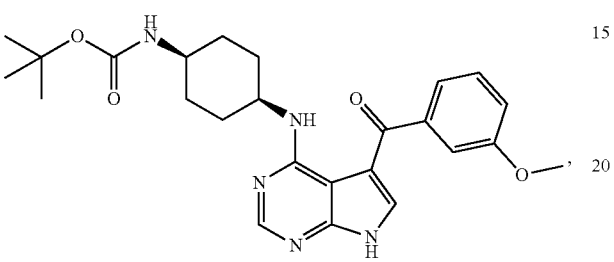
I-218
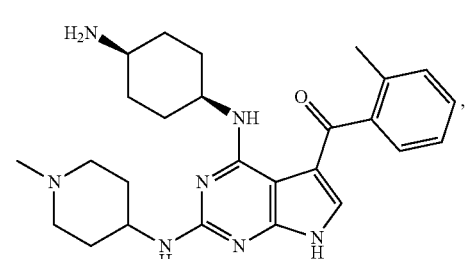
I-219
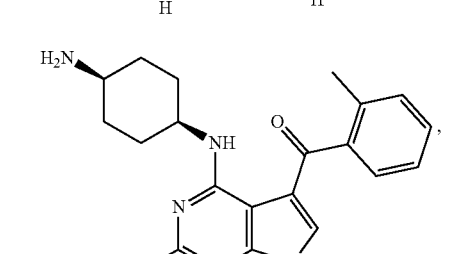
I-220
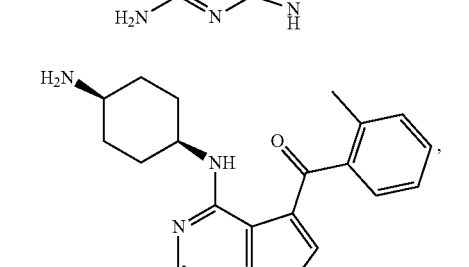
I-221
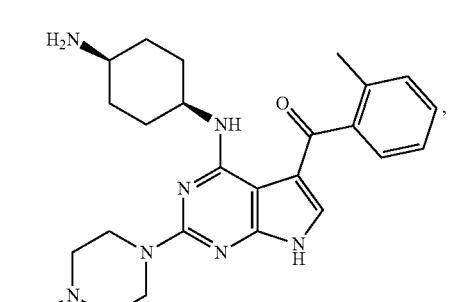

I-222
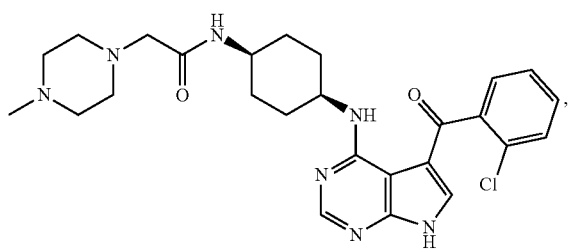
I-317
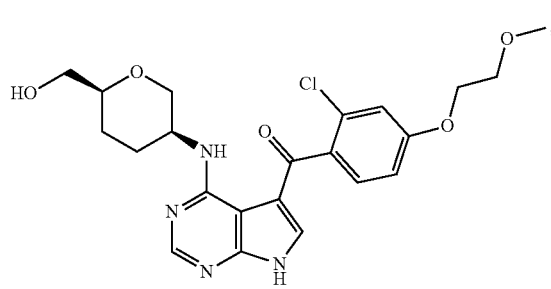
I-317i
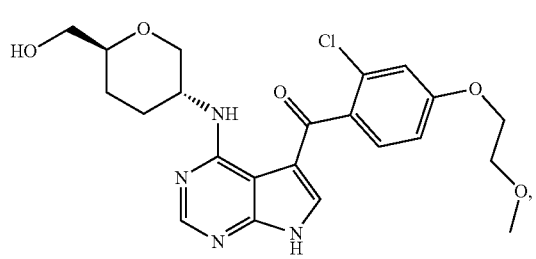
I-318
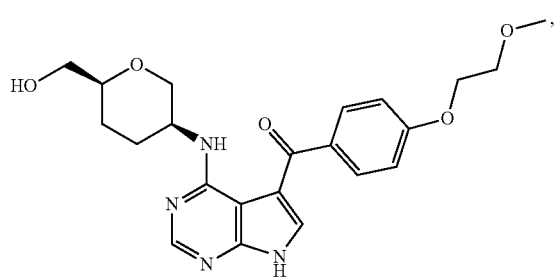
I-318i
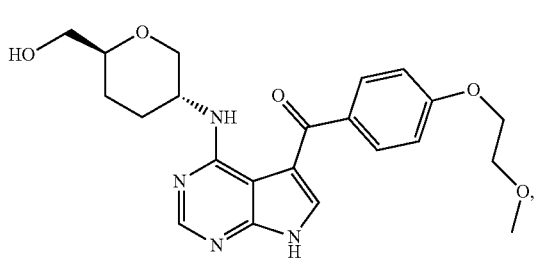
I-648
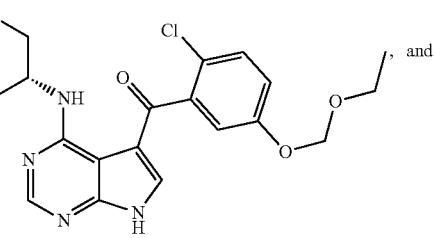
I-649
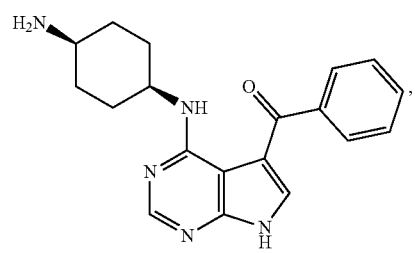
or a pharmaceutically acceptable salt, solvate, stereoisomer, or tautomer thereof.
23. The compound of claim 1, selected from the group consisting of:
I-26
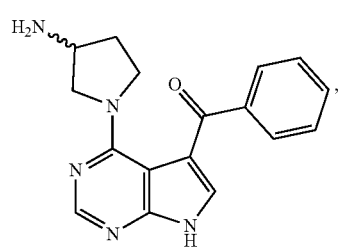
I-223
I-224
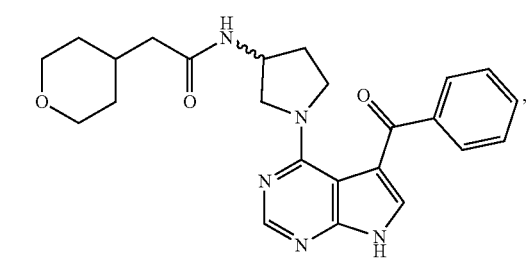

-continued
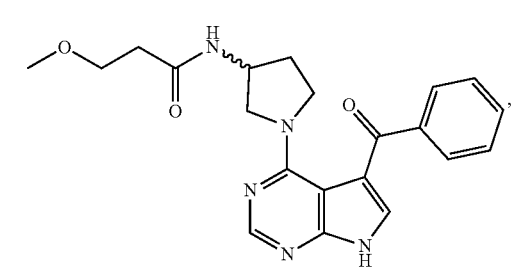
I-225
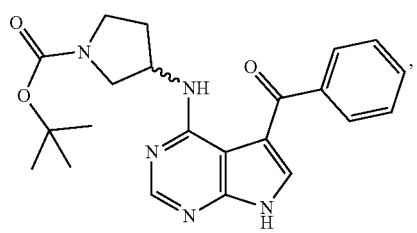
I-226
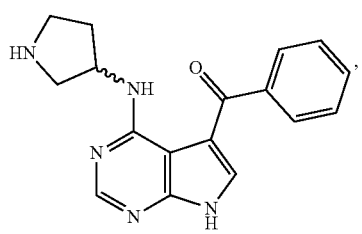
I-227
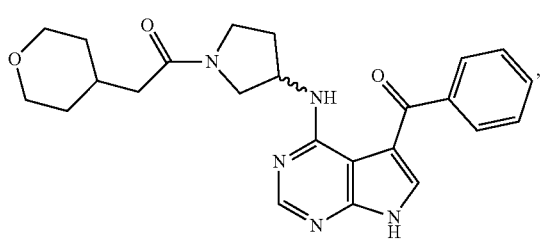
I-228
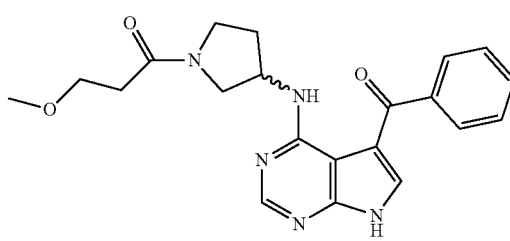
I-229, and
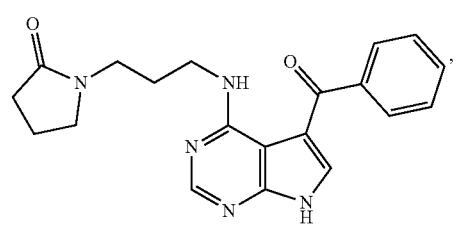
I-230
or a pharmaceutically acceptable salt, solvate, stereoisomer, or tautomer thereof.
24. The compound of claim 1, selected from the group consisting of:
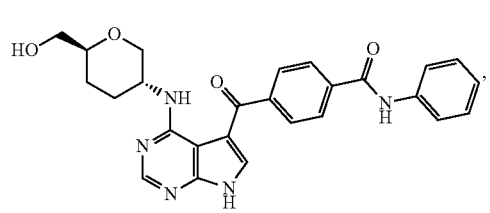
I-231
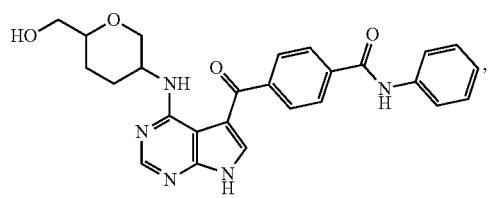
I-232
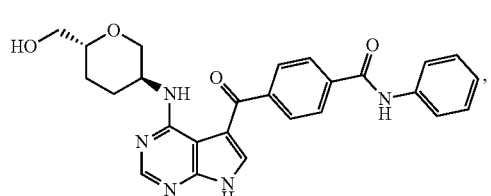
I-233
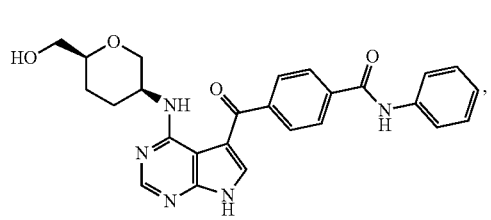
I-234
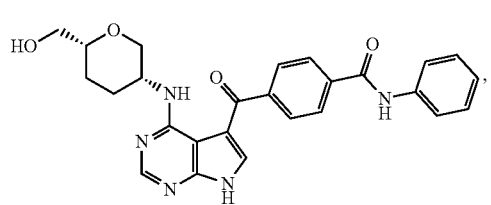
I-235
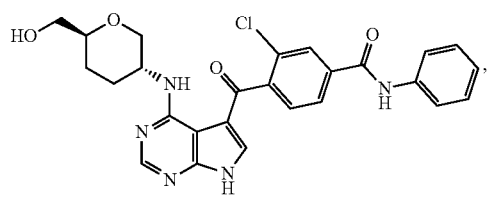
I-236
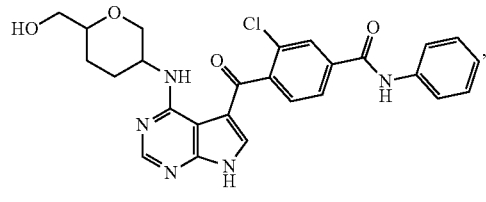
I-237
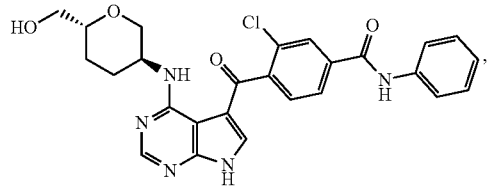
I-238

-continued
I-239
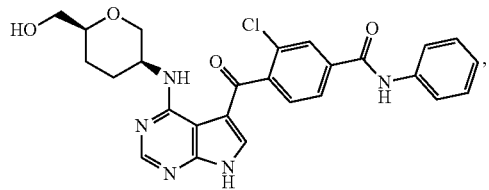
I-240
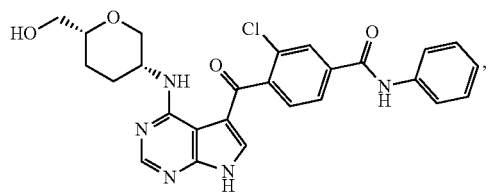
I-241
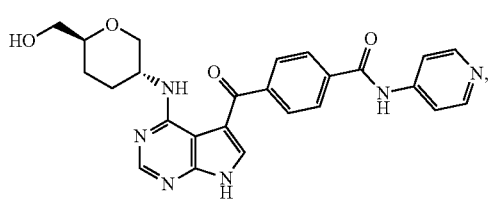
I-242
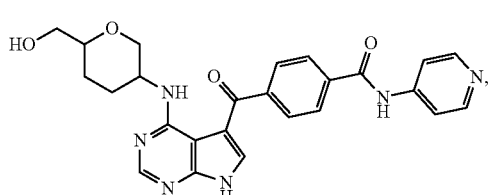
I-243
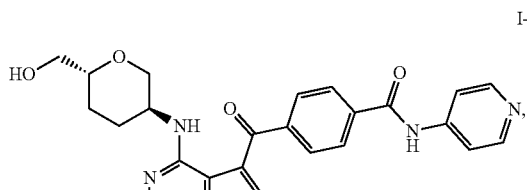
I-244
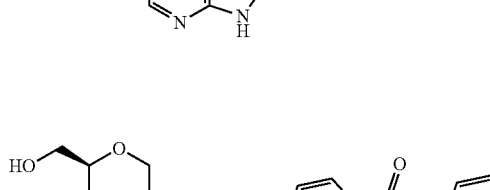
I-245
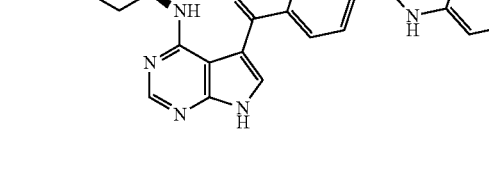
-continued
I-246
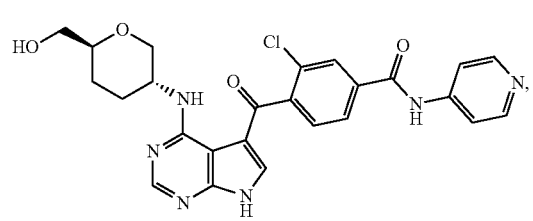
I-247
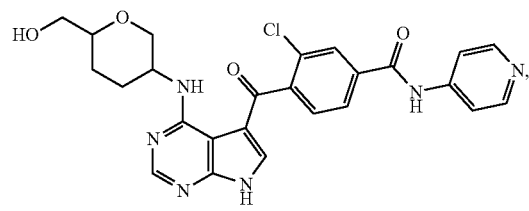
I-248
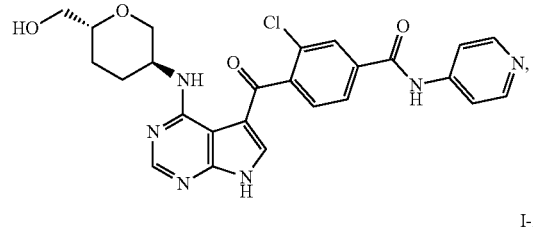
I-249
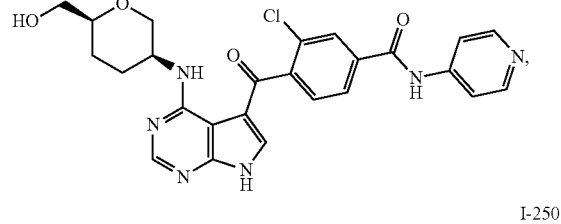
I-250
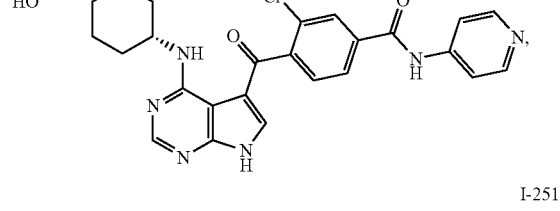
I-251
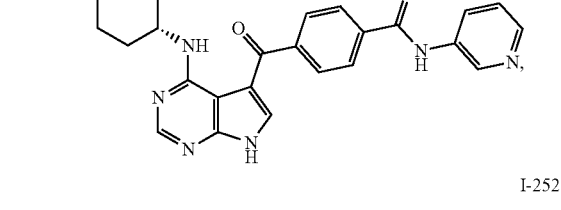
I-252

I-253
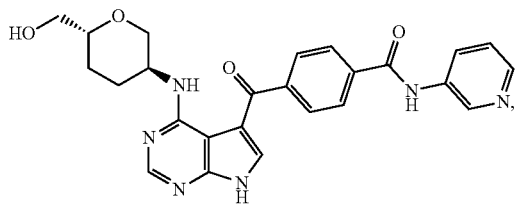
I-254
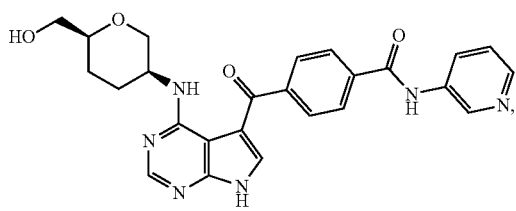
I-255
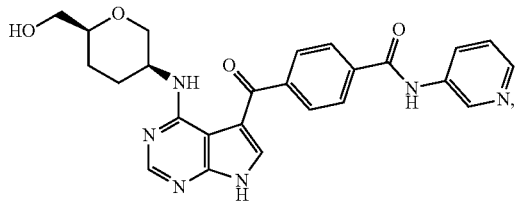
I-256
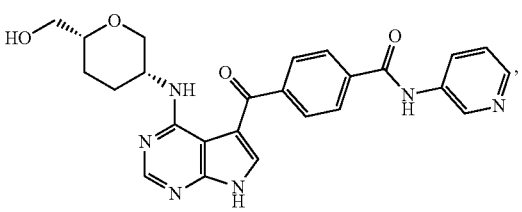
I-257
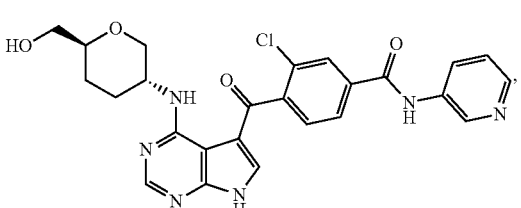
I-258
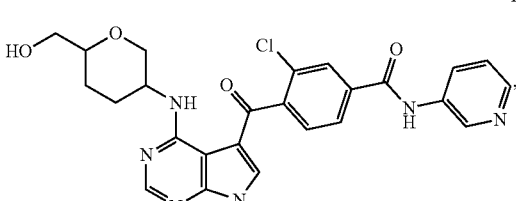
I-259
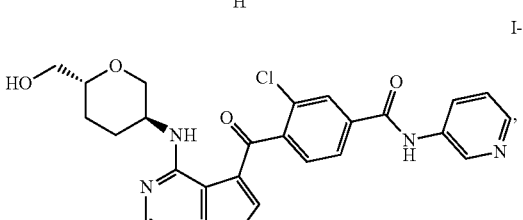
I-260
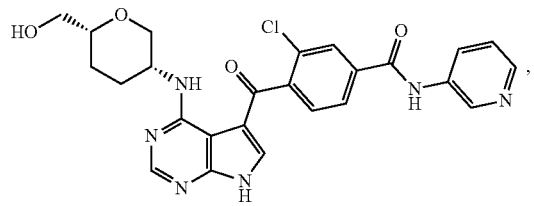
I-261
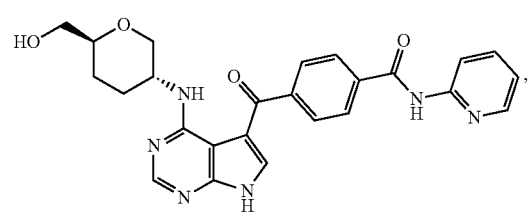
I-262
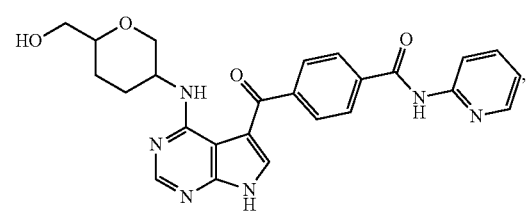
I-263
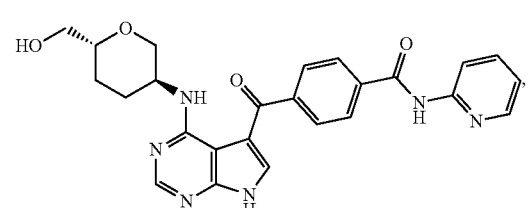
I-264
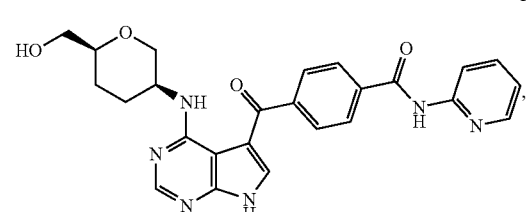
I-265
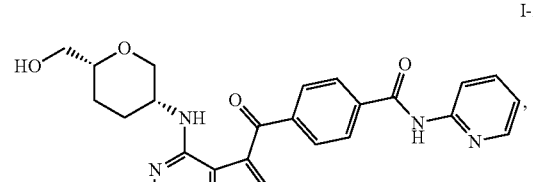
I-266
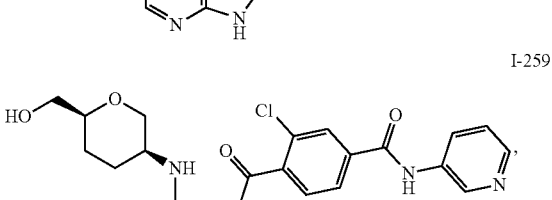

I-267
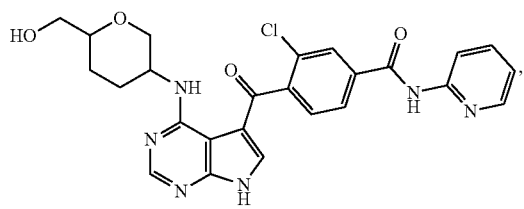
I-268
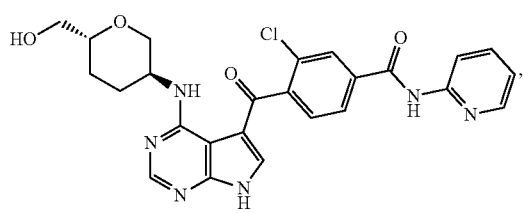
I-269
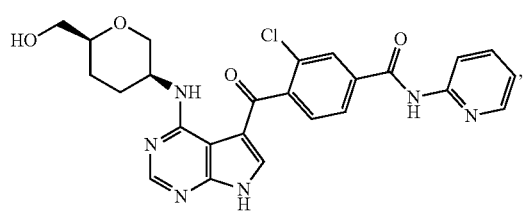
I-270
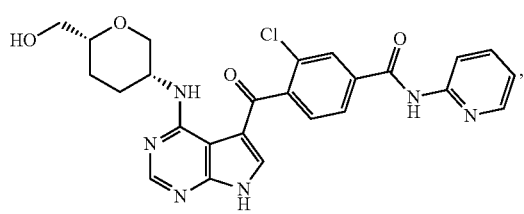
I-610
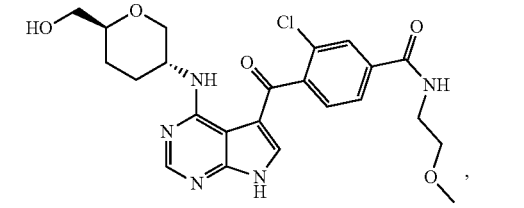
I-613
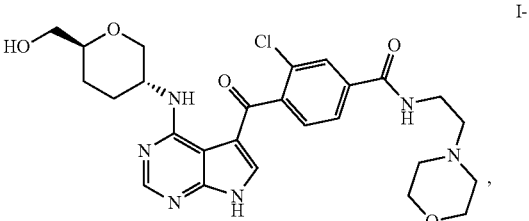
I-614
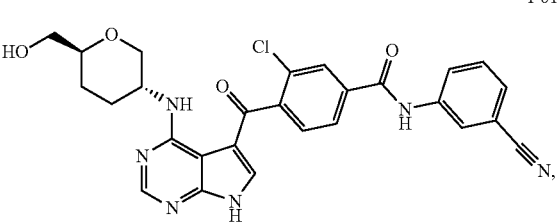
I-618
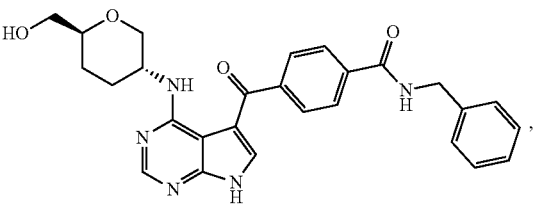
I-619
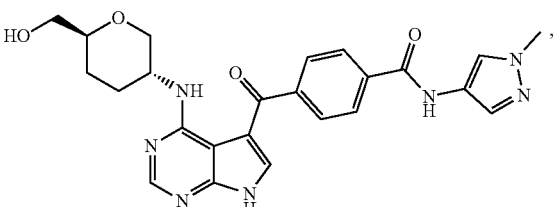
I-621
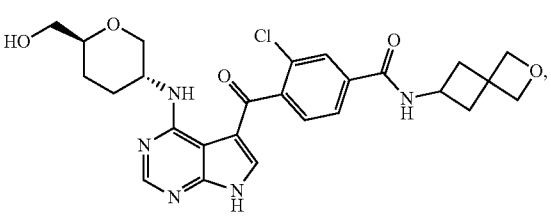
I-624
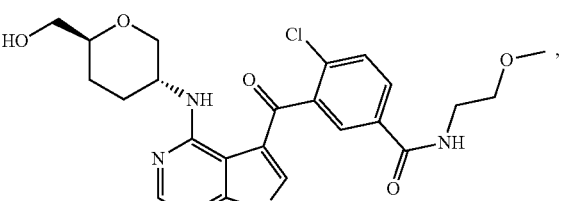
I-626
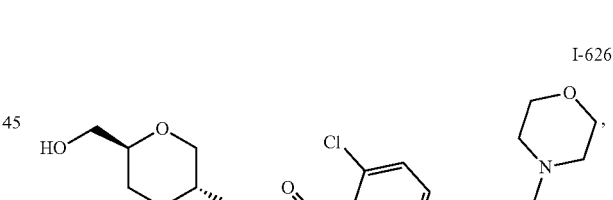
I-624
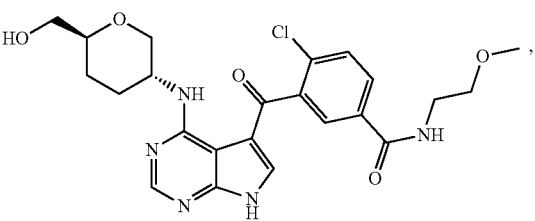

527
-continued
I-626
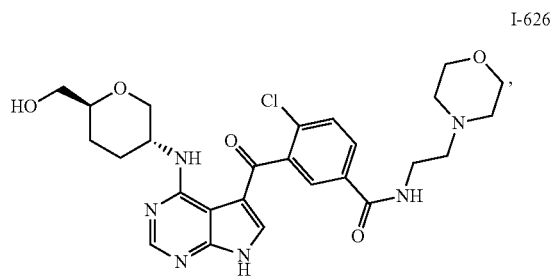
I-628
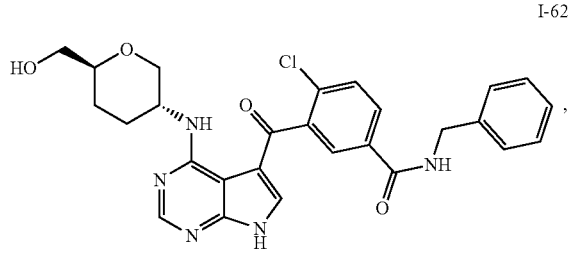
I-629
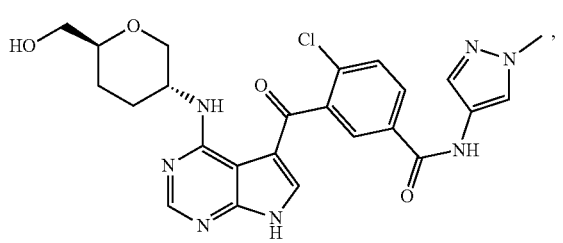
I-630
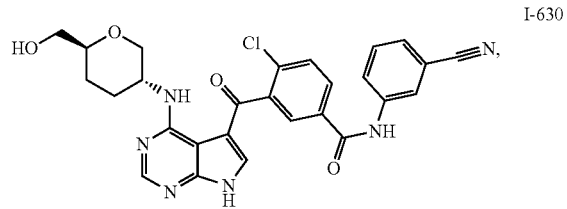
I-631
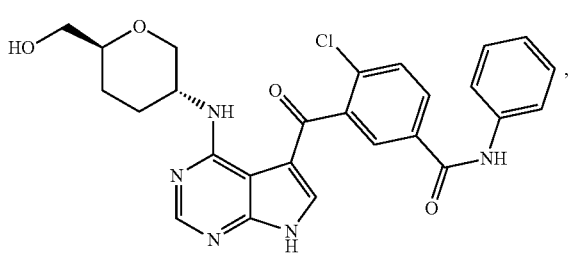
I-633
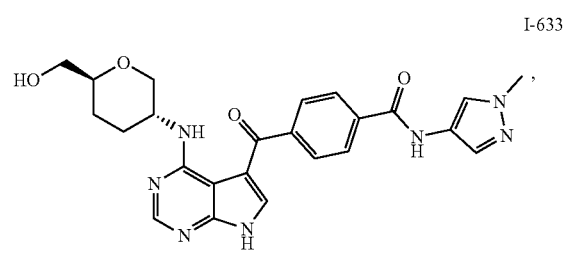
528
-continued
I-634
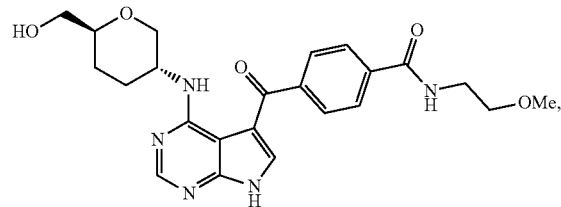
I-636
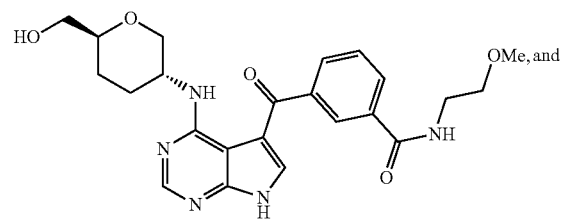
I-637
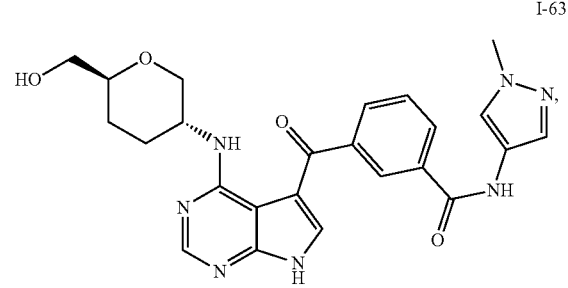
I-638
or a pharmaceutically acceptable salt, solvate, stereoisomer, or tautomer thereof.
25. The compound of claim 1, selected from the group consisting of:
I-611
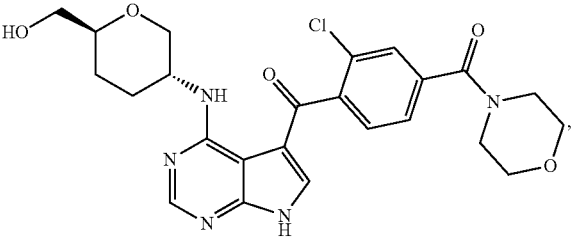

I-612
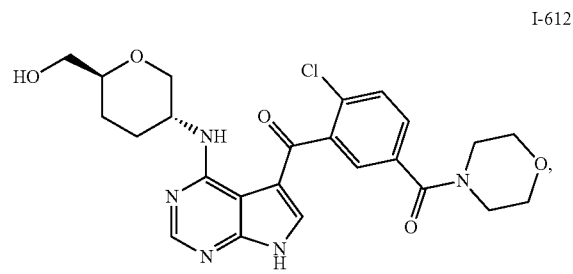
I-615
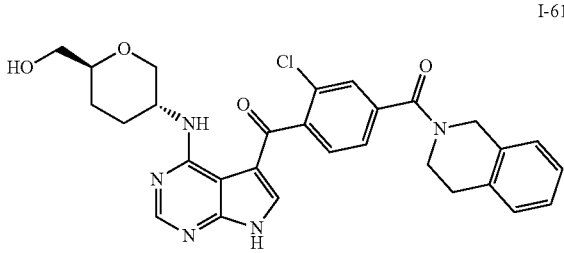
I-616
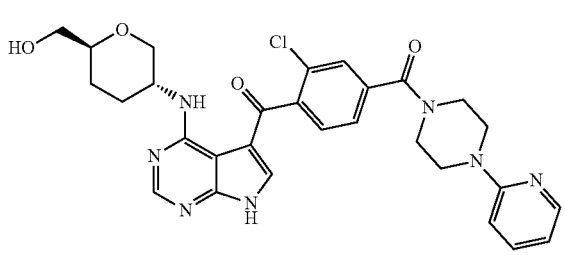
I-617
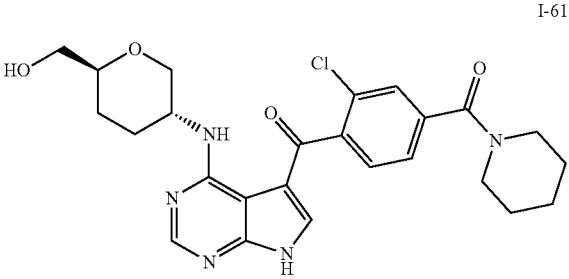
I-620
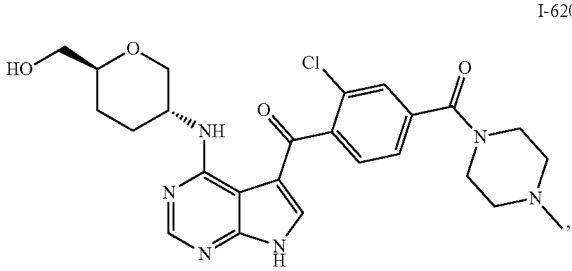 [SMILES: CN1CCN(C(=O)c2ccc(C(=O)c3c[nH]c4ncnc(N[C@@H]5CC[C@@H](CO)OC5)c34)c(Cl)c2)CC1]
I-622
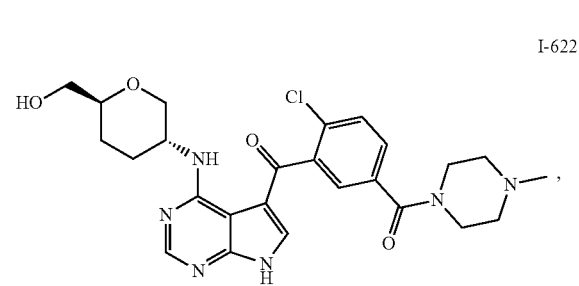
I-623
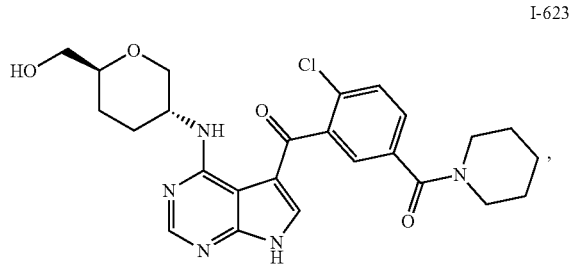
I-625
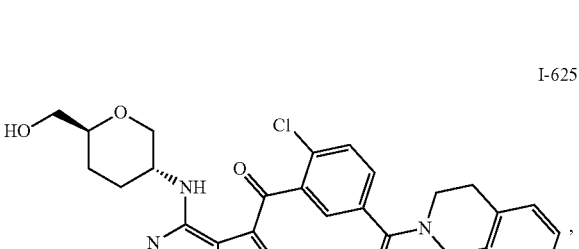
I-627
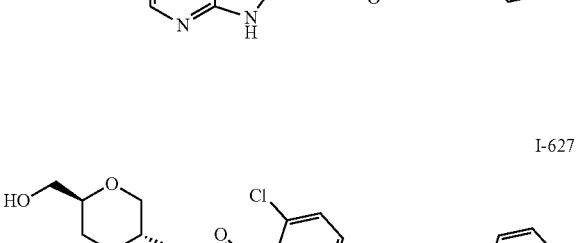
I-632
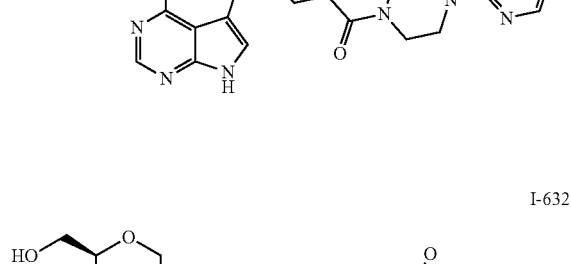
, and
I-635
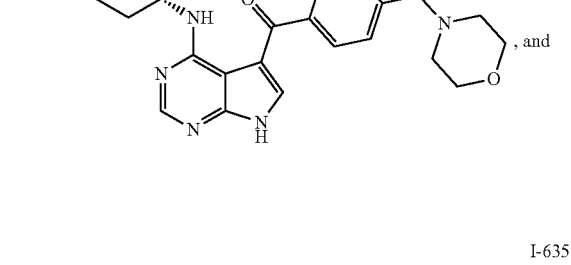
or a pharmaceutically acceptable salt, solvate, stereoisomer, or tautomer thereof.

26. The compound of claim 1, selected from the group consisting of:

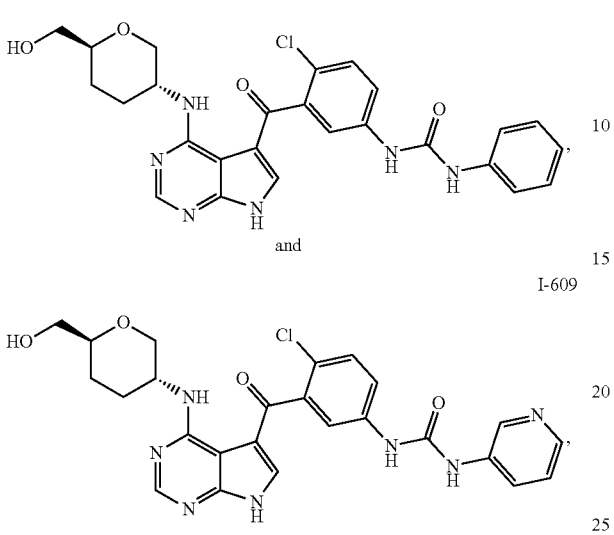

or a pharmaceutically acceptable salt, solvate, stereoisomer, or tautomer thereof.

27. A compound of Formula (I):

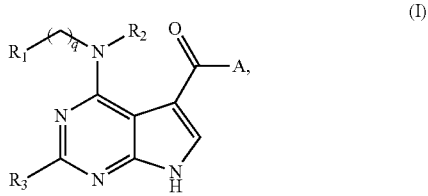

or a pharmaceutically acceptable salt, solvate, stereoisomer, or tautomer thereof, wherein:
A is $(C_6-C_{10})$ aryl or 5- or 6-membered heteroaryl comprising 1 to 3 heteroatoms selected from N, O, and S, wherein the aryl and heteroaryl are optionally substituted with one or more $R_4$;
$R_1$ is $(C_3-C_7)$ cycloalkyl or 4- to 9-membered heterocyclyl comprising 1 to 3 heteroatoms selected from N, O, and S, wherein the cycloalkyl and heterocyclyl are optionally substituted with one or more $R_5$;
$R_2$ is H or $(C_1-C_4)$ alkyl; or
when q is 0, $R_1$ and $R_2$ together with the nitrogen atom to which they are attached may form a 5- or 6-membered heterocyclyl ring comprising 0 to 1 additional heteroatoms selected from N, O, and S and optionally substituted with one or more $NR_6R_7$;
$R_3$ is H or $N(R_8)_2$;
each $R_4$ is independently $NR_9S(O)_pR_{10}$ or $NH(CH_2)_nR_{11}$;
each $R_5$ is independently (i) $(C_1-C_6)$ alkyl optionally substituted with one or more $(C_1-C_4)$ alkoxy or phenyl, (ii) $(C_2-C_4)$ alkenyl optionally substituted with one or more $C(=O)(C_1-C_4)$ alkyl, (iii) $(C(R_{12})_2)_nOH$, (iv) $(C(R_{12})_2)_nNR_{13}R_{14}$, (v) $C(=O)OH$, (vi) $C(=O)O(C_1-C_4)$, (vii) $C(=O)NR_{13}R_{15}$, (viii) $C(=O)R_{16}$, (ix) $S(O)_pR_{16}$, or (x) 5- or 6-membered heteroaryl comprising 1 to 3 heteroatoms selected from N, O, and S and optionally substituted with one or more $(C_1-C_4)$ alkyl, or (xi) two $R_5$ together with the carbon atom to which they are attached form (=O), or (xii) two $R_5$ together with the atoms to which they are attached form a bridged 3- to 6-membered heterocyclyl ring comprising 1 to 3 heteroatoms selected from N, O, and S;
$R_6$ is H or $(C_1-C_4)$ alkyl;
$R_7$ is H, $(C_1-C_4)$ alkyl, or $C(=O)R_{24}$;
each $R_8$ is independently (i) H, (ii) $(C_1-C_4)$ alkyl, or (iii) 5- or 6-membered heterocyclyl comprising 1 to 3 heteroatoms selected from N, O, and S and optionally substituted with one or more $(C_1-C_4)$ alkyl, or (iv) two $R_8$ together with the nitrogen atom to which they are attached form a 5- or 6-membered heterocyclyl ring comprising 0 to 1 additional heteroatoms selected from N, O, and S and optionally substituted with one or more $(C_1-C_4)$ alkyl;
$R_9$ is H or $(C_1-C_4)$ alkyl;
$R_{10}$ is unsubstituted $(C_1-C_4)$ alkyl or unsubstituted $(C_6-C_{10})$ aryl;
$R_{11}$ is unsubstituted $(C_3-C_7)$ cycloalkyl, $(C_4-C_7)$ cycloalkenyl, $(C_6-C_{10})$ aryl, or 5- or 6-membered heteroaryl comprising 1 to 3 heteroatoms selected from N, O, and S, wherein the aryl and heteroaryl are optionally substituted with one or more $R_{17}$;
each $R_{12}$ is independently H or $(C_1-C_6)$ alkyl;
$R_{13}$ is H or $(C_1-C_4)$ alkyl;
$R_{14}$ is (i) H, (ii) $(C_1-C_4)$ alkyl, (iii) $(C(R_{18})_2)_rC(=O)NR_{19}R_{20}$, (iv) $(CH_2)_n(C_6-C_{10})$ aryl optionally substituted with one or more $(C_1-C_4)$ alkyl or halogen, (v) $C(=O)R_{21}$, (vi) $C(=O)O(C_1-C_4)$ alkyl, (vii) $S(O)_2(C_1-C_8)$ alkyl, (viii) $S(O)_2NH(C_1-C_8)$ alkyl, (ix) $S(O)_2N((C_1-C_8)$ alkyl$)_2$, or (x) $C(=O)(C_1-C_8)$ alkyl optionally substituted with one or more $R_{22}$; or
$R_{13}$ and $R_{14}$ together with the nitrogen atom to which they are attached form a 4- to 6-membered heterocyclyl ring comprising 1 to 3 heteroatoms selected from N, O, and S and optionally substituted with one or more substituents selected from $(C_1-C_4)$ alkyl, $(C_1-C_4)$ alkoxy, OH, $NH_2$, and (=O);
$R_{15}$ is (i) H, (ii) 5- or 6-membered heterocyclyl comprising 1 to 3 heteroatoms selected from N, O, and S, or (iii) $(C_1-C_4)$ alkyl optionally substituted with one or more substituents selected from OH, 5- or 6-membered heterocyclyl comprising 1 to 3 heteroatoms selected from N, O, and S, and 5- or 6-membered heteroaryl comprising 1 to 3 heteroatoms selected from N, O, and S; or
$R_{13}$ and $R_{15}$ together with the nitrogen atom to which they are attached form a 4- to 6-membered heterocyclyl ring comprising 1 to 3 heteroatoms selected from N, O, and S and optionally substituted with one or more substituents selected from $(C_1-C_4)$ alkyl, $(C_1-C_4)$ alkoxy, and OH, or form a 5- to 8-membered bicyclic heterocyclyl ring comprising 1 to 3 heteroatoms selected from N, O, and S and optionally substituted with one or more substituents selected from $(C_1-C_4)$ alkyl, $(C_1-C_4)$ alkoxy, and OH;
$R_{16}$ is $(C_1-C_4)$ alkyl, $(C_2-C_4)$ alkenyl, $(C_2-C_4)$ alkynyl, or 3- to 6-membered heterocyclyl comprising 1 to 3 heteroatoms selected from N, O, and S, wherein the alkyl, alkenyl, and alkynyl are optionally substituted with one or more substituents selected from $(C_1-C_4)$ alkoxy, O-phenyl, halogen, CN, $NH_2$, $(C_1-C_4)$ alkylamino, di-$(C_1-C_4)$ alkylamino, and $OS(O)_2(C_1-C_4)$ alkyl, and wherein the heterocyclyl is optionally substituted with one or more $R_{23}$;

each $R_{17}$ is independently $(C_1$-$C_4)$ alkyl, $(C_1$-$C_4)$ alkoxy, $(C_1$-$C_4)$ haloalkyl, $(C_1$-$C_4)$ haloalkoxy, halogen, $C(=O)NH_2$, $C(=O)NH(C_1$-$C_4)$ alkyl, or $C(=O)N((C_1$-$C_4)$ alkyl$)_2$;

each $R_{18}$ is independently H or $(C_1$-$C_4)$ alkyl;

$R_{19}$ is H or $(C_1$-$C_4)$ alkyl;

$R_{20}$ is H or $(CH_2)_n(C_6$-$C_{10})$ aryl optionally substituted with one or more $(C_1$-$C_4)$ alkyl;

$R_{21}$ is $(C_3$-$C_7)$ cycloalkyl, 5- or 6-membered heterocyclyl comprising 1 to 3 heteroatoms selected from N, O, and S, $(C_6$-$C_{10})$ aryl, or 5- or 6-membered heteroaryl comprising 1 to 3 heteroatoms selected from N, O, and S, wherein the aryl, heteroaryl, cycloalkyl, and heterocyclyl are optionally substituted with one or more substituents selected from $(C_1$-$C_4)$ alkyl, $(C_1$-$C_4)$ alkoxy, $(C_1$-$C_4)$ haloalkyl, $(C_1$-$C_4)$ haloalkoxy, OH, and halogen;

each $R_{22}$ is independently (i) $(C_1$-$C_4)$ alkoxy, (ii) OH, (iii) $NH_2$, (iv) $(C_1$-$C_4)$ alkylamino, (v) di-$(C_1$-$C_4)$ alkylamino, or (vi) 5- or 6-membered heterocyclyl comprising 1 to 3 heteroatoms selected from N, O, and S and optionally substituted with one or more substituents selected from (a) $(C_1$-$C_4)$ alkyl, (b) $(CH_2)_x(C_6$-$C_{10})$ aryl, and (c) $C(=O)(C_6$-$C_{10})$aryl optionally substituted with one or more $(C_1$-$C_4)$ alkyl;

each $R_{23}$ is independently $(C_1$-$C_4)$ alkyl or $C(=O)(C_1$-$C_4)$ alkyl, or two $R_{23}$ together with the atoms to which they are attached form a 5- or 6-membered heterocyclyl ring comprising 1 to 3 heteroatoms selected from N, O, and S;

$R_{24}$ is $(C_1$-$C_4)$ alkyl optionally substituted with one or more substituents selected from $(C_1$-$C_4)$ alkoxy and 5- or 6-membered heterocyclyl comprising 1 to 3 heteroatoms selected from N, O, and S;

each n and each p is independently 0, 1, or 2;

each r is independently 0, 1, 2, or 3;

each q and each x is independently 0, 1, 2, or 3; and provided that when $R_4$ is $NR_9S(O)_pR_{10}$, A is optionally substituted with one additional $R_4$.

28. The compound of claim 27, wherein A is phenyl, thiophenyl, or pyridinyl optionally substituted with one or more $R_4$.

29. The compound of claim 27, wherein A is phenyl, thiophenyl, or pyridinyl substituted with one to two $R_4$.

30. The compound of claim 27, wherein A is phenyl substituted with one to two $R_4$.

31. The compound of claim 27, wherein $R_2$ is H.

32. The compound of claim 27, wherein $R_3$ is H, $NH_2$, $NHCH_3$, or 4-methylpiperazine.

33. The compound of claim 27, wherein $R_3$ is H.

34. The compound of claim 27, wherein $R_1$ is 4- to 7-membered heterocyclyl comprising 1 to 3 heteroatoms selected from N, O, and S optionally substituted with one to three $R_5$.

35. The compound of claim 27, wherein $R_1$ is piperidinyl, tetrahydrofuranyl, tetrahydropyranyl, pyrrolidinyl, or 1,4-dioxanyl optionally substituted with one to three $R_5$.

36. The compound of claim 27, wherein $R_1$ is tetrahydropyranyl optionally substituted with one to three $R_5$.

37. The compound of claim 27, wherein q is 0 or 1.

38. The compound of claim 27, selected from the group consisting of:

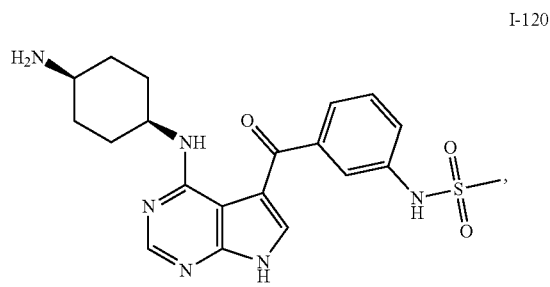

I-120

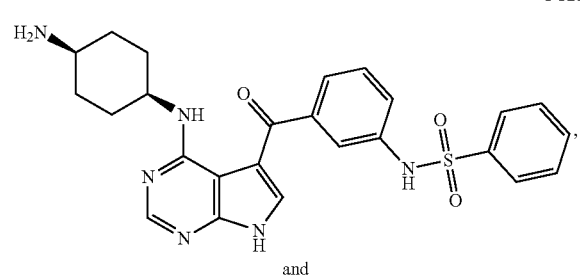

I-121 and

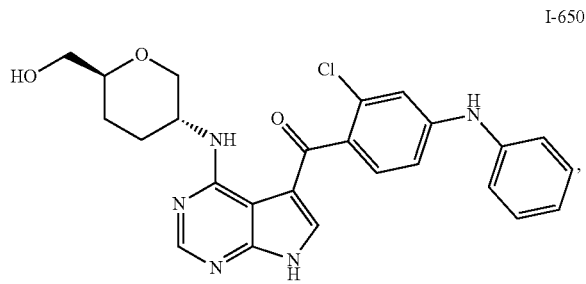

I-650 or a pharmaceutically acceptable salt, solvate, stereoisomer, or tautomer thereof.

* * * * *